United States Patent
Beirnaert

(10) Patent No.: US 11,472,871 B2
(45) Date of Patent: Oct. 18, 2022

(54) NANOBODIES AGAINST TUMOR NECROSIS FACTOR-ALPHA

(71) Applicant: Ablynx N.V., Ghent-Zwijnaarde (BE)

(72) Inventor: Els Anna Alice Beirnaert, Bellem (BE)

(73) Assignee: Ablynx N.V., Zwijnaarde (BE)

( * ) Notice: Subject to any disclaimer, the term of this patent is extended or adjusted under 35 U.S.C. 154(b) by 0 days.

(21) Appl. No.: 16/423,596

(22) Filed: May 28, 2019

(65) Prior Publication Data

US 2020/0079844 A1    Mar. 12, 2020

Related U.S. Application Data

(60) Continuation of application No. 15/644,890, filed on Jul. 10, 2017, now abandoned, which is a continuation of application No. 14/709,870, filed on May 12, 2015, now abandoned, which is a continuation of application No. 14/191,907, filed on Feb. 27, 2014, now Pat. No. 9,067,991, which is a division of application No. 11/920,677, filed as application No. PCT/EP2006/004678 on May 17, 2006, now Pat. No. 8,703,131.

(60) Provisional application No. 60/682,332, filed on May 18, 2005.

(51) Int. Cl.
| | | |
|---|---|---|
| *C07K 16/24* | (2006.01) | |
| *A61K 39/395* | (2006.01) | |
| *C07K 14/525* | (2006.01) | |
| *C07K 16/46* | (2006.01) | |
| *C07K 16/18* | (2006.01) | |
| *A61K 39/00* | (2006.01) | |

(52) U.S. Cl.
CPC .......... *C07K 16/241* (2013.01); *C07K 14/525* (2013.01); *C07K 16/18* (2013.01); *C07K 16/468* (2013.01); *A61K 2039/505* (2013.01); *C07K 2317/22* (2013.01); *C07K 2317/24* (2013.01); *C07K 2317/31* (2013.01); *C07K 2317/565* (2013.01); *C07K 2319/31* (2013.01)

(58) Field of Classification Search
CPC combination set(s) only.
See application file for complete search history.

(56) References Cited

U.S. PATENT DOCUMENTS

| | | |
|---|---|---|
| 4,722,896 A | 2/1988 | Kadish |
| 4,735,898 A | 4/1988 | Herr et al. |
| 5,530,101 A | 6/1996 | Queen et al. |
| 5,667,998 A | 9/1997 | Dougherty et al. |
| 6,262,238 B1 | 7/2001 | Steipe et al. |
| 6,670,453 B2 | 12/2003 | Frenken et al. |
| 7,084,257 B2 | 8/2006 | Deshpande et al. |
| 7,229,619 B1 | 6/2007 | Young et al. |
| 7,368,111 B2 | 5/2008 | Thompson et al. |
| 7,432,238 B2 | 10/2008 | Kisiel et al. |
| 8,097,251 B2 | 1/2012 | Muyldermans et al. |
| 8,188,223 B2 | 5/2012 | Beirnaert et al. |
| 8,282,924 B2 | 10/2012 | Rother et al. |
| 8,703,131 B2 | 4/2014 | Beirnaert |
| 9,067,991 B2 | 6/2015 | Beirnaert |
| 9,156,905 B2 | 10/2015 | Muyldermans et al. |
| 9,371,381 B2* | 6/2016 | Silence .............. C07K 16/2863 |
| 10,633,438 B2* | 4/2020 | Crowe ................... A61P 29/00 |
| 10,772,839 B2* | 9/2020 | Crowe ...................... A61P 1/00 |
| 2002/0001587 A1 | 1/2002 | Erickson et al. |
| 2002/0165387 A1 | 11/2002 | Kerr Anderson et al. |
| 2003/0099655 A1 | 5/2003 | Watkins |
| 2003/0129659 A1 | 7/2003 | Whelihan et al. |
| 2004/0071705 A1 | 4/2004 | Sato et al. |
| 2005/0054001 A1 | 3/2005 | Muyldermans |
| 2005/0271663 A1 | 12/2005 | Ignatovich et al. |
| 2006/0034845 A1 | 2/2006 | Silence et al. |
| 2006/0106203 A1 | 5/2006 | Winter et al. |
| 2006/0228355 A1 | 10/2006 | Laeremans et al. |
| 2006/0286066 A1 | 12/2006 | Basran |
| 2007/0031424 A1 | 2/2007 | Muyldermans |
| 2007/0077249 A1 | 4/2007 | Silence et al. |

(Continued)

FOREIGN PATENT DOCUMENTS

| | | |
|---|---|---|
| EP | 0486526 A1 | 5/1992 |
| EP | 93201239.6 B6 | 4/1993 |

(Continued)

OTHER PUBLICATIONS

U.S. Appl. No. 60/207,234, filed N/A, Tanha et al.
[No author listed] Anti human IgG ligand for depletion of human plasma. Biotechnol App Centre. Sep. 2003. Product sheet 101-0822-V1.0. www.bac.nl. 2 pages.
[No author listed] Anti human serum albumin ligand for depletion of human plasma. Biotechnol App Centre. Sep. 2003. Product sheet 102-0826-V1.0. www.bac.nl. 2 pages.
[No author listed] BAC invoice (redacted) for 102-0822-03 CaptureSelect anti-human IgG ligand. Invoice No. S05-0006. Invoice date: Mar. 24, 2005. 1 page.

(Continued)

*Primary Examiner* — Laura B Goddard
(74) *Attorney, Agent, or Firm* — Wolf, Greenfield & Sacks, P.C.

(57) ABSTRACT

The present invention relates to improved Nanobodies™ against Tumor Necrosis Factor-alpha (TNF-alpha), as well as to polypeptides comprising or essentially consisting of one or more of such Nanobodies. The invention also relates to nucleic acids encoding such Nanobodies and polypeptides; to methods for preparing such Nanobodies and polypeptides; to host cells expressing or capable of expressing such Nanobodies or polypeptides; to compositions comprising such Nanobodies, polypeptides, nucleic acids or host cells; and to uses of such Nanobodies, such polypeptides, such nucleic acids, such host cells or such compositions, in particular for prophylactic, therapeutic or diagnostic purposes, such as the prophylactic, therapeutic or diagnostic purposes.

6 Claims, 49 Drawing Sheets

Figure 3:
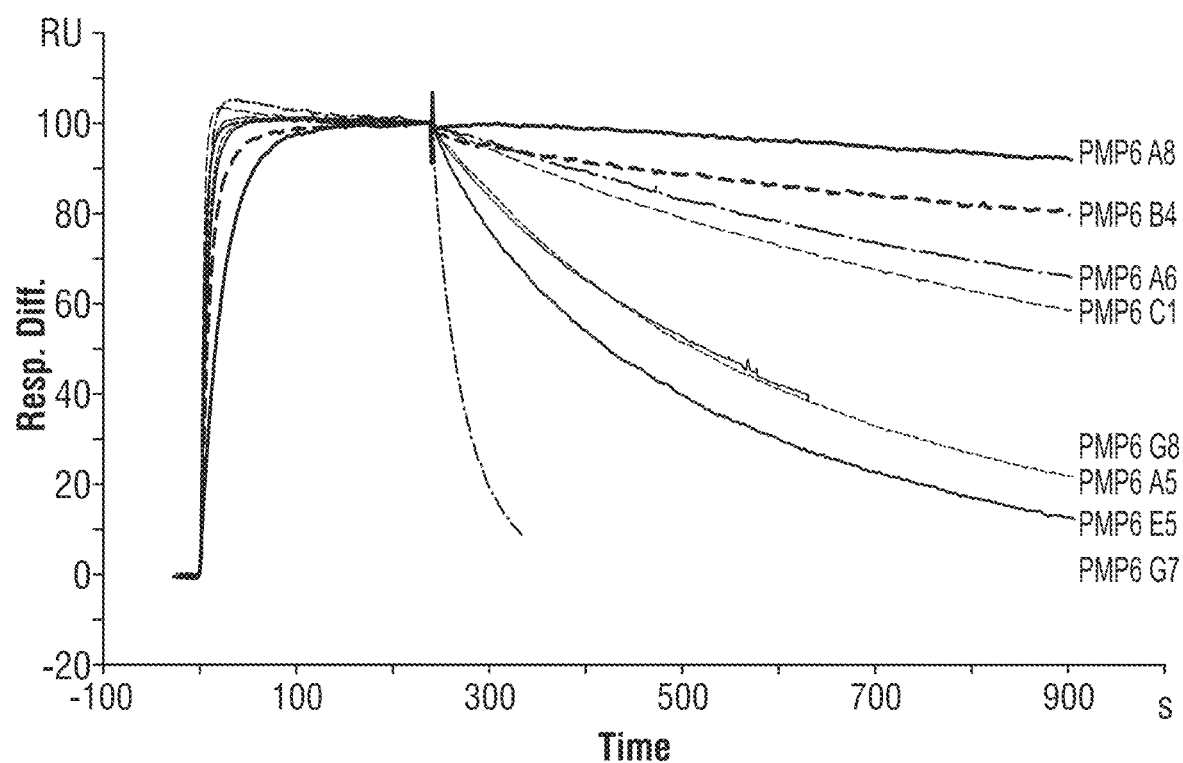

Specification includes a Sequence Listing.

(56) References Cited

U.S. PATENT DOCUMENTS

| | | |
|---|---|---|
| 2007/0178082 A1 | 8/2007 | Silence et al. |
| 2007/0237769 A1 | 10/2007 | Silence et al. |
| 2007/0269422 A1 | 11/2007 | Beirnaert et al. |
| 2008/0008713 A1 | 1/2008 | Brewis |
| 2009/0022721 A1 | 1/2009 | Silence et al. |
| 2009/0028880 A1 | 1/2009 | Beirnaert et al. |
| 2009/0148434 A1 | 6/2009 | Tomlinson et al. |
| 2010/0047241 A1 | 2/2010 | Muyldermans |
| 2010/0081792 A1 | 4/2010 | Grant et al. |
| 2010/0297111 A1 | 11/2010 | Beirnaert |
| 2011/0251373 A1 | 10/2011 | Muyldermans |
| 2012/0172578 A1 | 7/2012 | Muyldermans |
| 2013/0209481 A1 | 8/2013 | Zhou et al. |
| 2014/0335101 A1 | 11/2014 | Beirnaert |
| 2015/0353635 A1 | 12/2015 | Beirnaert |
| 2016/0052999 A1 | 2/2016 | Muyldermans et al. |
| 2017/0342146 A1 | 11/2017 | Beirnaert |

FOREIGN PATENT DOCUMENTS

| | | |
|---|---|---|
| EP | 0 584 421 A1 | 3/1994 |
| EP | 98300525.7 B7 | 1/1998 |
| EP | 1 399 484 B1 | 3/2004 |
| GB | 115841.9 A | 6/2001 |
| JP | 62-175426 A | 8/1987 |
| JP | 6-502526 A | 3/1994 |
| RU | 2004117915 A | 5/2005 |
| WO | WO 1991/13804 A1 | 9/1991 |
| WO | WO 1992/01787 A1 | 2/1992 |
| WO | WO 1994/04678 A1 | 3/1994 |
| WO | WO 1994/13804 A1 | 6/1994 |
| WO | WO 1994/25591 A1 | 11/1994 |
| WO | WO 1999/20749 A2 | 4/1999 |
| WO | WO 1999/37681 A2 | 7/1999 |
| WO | WO 1999/42077 A2 | 8/1999 |
| WO | WO 2000/09757 A1 | 2/2000 |
| WO | WO 2000/73430 A2 | 12/2000 |
| WO | WO 2001/44301 A1 | 6/2001 |
| WO | WO 2001/45746 A2 | 6/2001 |
| WO | WO 2001/90190 A2 | 11/2001 |
| WO | WO 2002/48193 A2 | 6/2002 |
| WO | WO 2003/002609 A2 | 1/2003 |
| WO | WO 2003/035694 A2 | 5/2003 |
| WO | WO 2003/042247 A2 | 5/2003 |
| WO | WO 2003/050531 A2 | 6/2003 |
| WO | WO 2004/001064 A2 | 12/2003 |
| WO | WO 2004/003019 A2 | 1/2004 |
| WO | WO 2004/003019 A3 | 1/2004 |
| WO | WO 2004/041862 A2 | 5/2004 |
| WO | WO 2005/035572 A2 | 4/2005 |
| WO | WO 2006/030220 A1 | 3/2006 |
| WO | WO 2006/038027 A2 | 4/2006 |
| WO | WO 2006/059106 A2 | 6/2006 |
| WO | WO 2007/049017 A2 | 5/2007 |
| WO | WO 2008/149144 A2 | 12/2008 |
| WO | WO 2008/149146 A2 | 12/2008 |
| WO | WO 2008/149147 A2 | 12/2008 |
| WO | WO 2008/149148 A2 | 12/2008 |
| WO | WO 2009/068627 A2 | 6/2009 |
| WO | WO 2010/009391 A1 | 1/2010 |
| WO | WO 2016/156465 | * 10/2016 |

OTHER PUBLICATIONS

[No Author Listed] Single-domain antibody. Wikipedia. Last accessed on Jul. 22, 2016 from https://en.wikipedia.org/wiki/Single-domain_antibody.

[No Author Listed]Fundamental Immunology, William E. Paul, MD, Ed. 3$^{rd}$ ed. 1993, p. 242.

Ameloot et al., Heterotrimers formed by tumor necrosis factors of different species or muteins. J Biol Chem. Jul. 20, 2001;276(29):27098-103. Epub May 22, 2001.

Anker et al., $V_H$ and $V_L$ region structure of antibodies that recognize the (NANP)3 dodecapeptide sequence in the circumsporozoite protein of Plasmodium falciparum. Eur J Immunol. Dec. 1990;20(12):2757-61.

Arbabi Ghahroudi et al., Selection and identification of single domain antibody fragments from camel heavy-chain antibodies. FEBS Lett. Sep. 15, 1997;414(3):521-6.

Babu et al., Omalizumab, a novel anti-IgE therapy in allergic disorders. Expert Opin Biol Ther. Nov. 2001;1(6):1049-58.

Black et al., Development of hydrophobicity parameters to analyze proteins which bear post-pr cotranslational modifications. Anal Biochem. Feb. 15, 1991;193(1):72-82.

Bodtger et al., The safety and efficacy of subcutaneous birch pollen immunotherapy—a one-year, randomized, double-blind, placebo-controlled study. Allergy. Apr. 2002;57(4):297-305.

Borrebaeck et al., Kinetic analysis of recombinant antibody-antigen interactions: relation between structural domains and antigen binding. Biotechnology (N Y). 1992 un;10(6):697-8.

Brorson et al., Mutational analysis of avidity and fine specificity of anti-levan antibodies. J Immunol. Dec. 15, 1999;163(12):6694-701.

Brummell et al., Probing the combining site of an anti-carbohydrate antibody by saturation-mutagenesis: role of the heavy-chain CDR3 residues. Biochemistry. Feb. 2, 1993;32(4):1180-7. Abstract only.

Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.

Burks et al., In vitro scanning saturation mutagenesis of an antibody binding pocket. Proc Natl Acad Sci U S A. Jan. 21, 1997;94(2):412-7.

Caldas et al., Humanization of the anti-CD18 antibody 6.7: an unexpected effect of a framework residue in binding to antigen. Mol Immunol. May 2003;39(15):941-52.

Carter et al., Structure of serum albumin. Adv Protein Chem. 1994;45:153-203.

Casset et al., A peptide mimetic of an anti-CD4 monoclonal antibody by rational design. Biochem Biophys Res Commun. Jul. 18, 2003;307(1):198-205.

Chavez et al., Antibody as an immunological probe for studying the refolding of bovine serum albumin. An immunochemical approach to the identification of possible nucleation sites. J Biol Chem. Nov. 25, 1978;253(22):8081-6.

Chen et al., Selection and analysis of an optimized anti-VEGF antibody: crystal structure of an affinity-matured Fab in complex with antigen. J Mol Biol. Nov. 5, 1999;293(4):865-81.

Chien et al., Significant structural and functional change of an antigen-binding site by a distant amino acid substitution: proposal of a structural mechanism. Proc Natl Acad Sci U S A. Jul. 1989;86(14):5532-6.

Chothia et al., Domain association in immunoglobulin molecules. The packing of variable domains. J Mol Biol. Dec. 5, 1985;186(3):651-63.

Chukwuocha et al., Isolation, characterization and sequence analysis of five IgG monoclonal anti-beta 2-glycoprotein-1 and anti-prothrombin antigen-binding fragments generated by phage display. J Immunol. Oct. 15, 1999;163(8):4604-11.

Colman, Effects of amino acid sequence changes on antibody-antigen interactions. Res in Immunol. 1994;145:33-36.

Conrath et al., Antigen binding and solubility effects upon the veneering of a camel VHH in framework-2 to mimic a VH. J Mol Biol. Jul. 1, 2005;350(1):112-25.

Conrath et al., Beta-lactamase inhibitors derived from single-domain antibody fragments elicited in the camelidae. Antimicrob Agents Chemother. Oct. 2001;45(10):2807-12.

Conrath et al., Camel single-domain antibodies as modular building units in bispecific and bivalent antibody constructs. J Biol Chem. Mar. 9, 2001;276(10):7346-50. Epub Oct. 25, 2000.

Coppieters et al., Formatted anti-TNF-alpha nanobodies show superior efficacy in a collagen-induced arthritis model in mice. Arthritis Rheum. Sep. 2005;52(9):Supp. S362-3. Abstract 922.

Coppieters et al., Formatted anti-tumor necrosis factor alpha VHH proteins derived from camelids show superior potency and targeting

(56) References Cited

OTHER PUBLICATIONS to inflamed joints in a murine model of collagen-induced arthritis. Arthritis Rheum. Jun. 2006;54(6):1856-66.
Cortez-Retamozo et al., Efficient cancer therapy with a nanobody-based conjugate. Cancer Res. Apr. 15, 2004;64(8):2853-7.
Davies et al, Single antibody domains as small recognition units: design and in vitro antigen selection of camelized, human VH domains with improved protein stability. Protein Eng. Jun. 1996;9(6):531-7.
De Pascalis et al., Grafting of "abbreviated" complementarity-determining regions containing specificity-determining residues essential for ligand contact to engineer a less immunogenic humanized monoclonal antibody. J Immunol. Sep. 15, 2002;169(6):3076-84.
Dennis et al., Albumin binding as a general strategy for improving the pharmacokinetics of proteins. J Biol Chem. Sep. 20, 2002;277(38):35035-43. Epub Jul. 15, 2002.
Desmyter et al., Antigen specificity and high affinity binding provided by one single loop of a camel single-domain antibody. J Biol Chem. Jul. 13, 2001;276(28):26285-90. Epub May 7, 2001.
Desmyter et al., Crystal structure of a camel single-domain VH antibody fragment in complex with lysozyme. Nat Struct Biol. Sep. 1996;3(9):803-11.
Dimasi et al., Characterization of engineered hepatitis C virus NS3 protease inhibitors affinity selected from human pancreatic secretory trypsin inhibitor and minibody repertoires. J Virol. Oct. 1997;71(10):7461-9.
Dufner et al., Harnessing phage and ribosome display for antibody optimisation. Trends Biotechnol. Nov. 2006;24(11):523-9. Epub Sep. 26, 2006.
Dumoulin et al., Single-domain antibody fragments with high conformational stability. Protein Sci. Mar. 2002;11(3):500-15.
Eck et al., The structure of tumor necrosis factor-alpha at 2.6 A resolution. Implications for receptor binding. J Biol Chem. Oct. 15, 1989;264(29):17595-605.
Fan et al., Three-dimensional structure of an Fv from a human IgM immunoglobulin. J Mol Biol. Nov. 5, 1992;228(1):188-207.
Ferguson et al., Immunoregulatory properties of antigenic fragments from bovine serum albumin. Cell Immunol. May 1983;78(1):1-12.
GenBank Submission; NIH/NCBI, Accession No. AJ401076; Harmsen et al.; May 22, 2010.
GenBank Submission; NIH/NCBI, Accession No. AJ401077; Harmsen et al.; May 22, 2010.
Georgiou et al., The promise and challenge of high-throughput sequencing of the antibody repertoire. Nat Biotechnol. Feb. 2014;32(2):158-68. doi: 10.1038/nbt.2782. Epub Jan. 19, 2014.
Giusti et al., Somatic diversification of S107 from an antiphosphocholine to an anti-DNA autoantibody is due to a single base change in its heavy chain variable region. Proc Natl Acad Sci U S A. May 1987;84(9):2926-30.
Gordon et al., A pilot study of treatment of active ulcerative colitis with natalizumab, a humanized monoclonal antibody to alpha-4 integrin. Aliment Pharmacol Ther. Apr. 2002;16(4):699-705.
Hamers-Casterman et al., Naturally occurring antibodies devoid of light chains. Nature. Jun. 3, 1993;363(6428):446-8.
Hanauer et al., Maintenance infliximab for Crohn's disease: the ACCENT I randomised trial. Lancet. May 4, 2002;359(9317):1541-9.
Harmsen et al., Llama heavy-chain V regions consist of at least four distinct subfamilies revealing novel sequence features. Mol Immunol. Aug. 2000;37(10):579-90.
Harmsen et al., Properties, production, and applications of camelid single-domain antibody fragments. Appl Microbiol Biotechnol. Nov. 2007;77(1):13-22. Epub Aug. 18, 2007.
Hasemann et al., Mutational analysis of arsonate binding by a CRIA+ antibody. VH and VL junctional diversity are essential for binding activity. J Biol Chem. Apr. 25, 1991;266(12):7626-32.
Hoefman et al., Pre-Clinical Intravenous Serum Pharmacokinetics of Albumin Binding and Non-Half-Life Extended Nanobodies®. Antibodies. 2015;4:141-156.
Holm et al., Functional mapping and single chain construction of the anti-cytokeratin 8 monoclonal antibody TS1. Mol Immunol. Feb. 2007;44(6):1075-84. Epub Sep. 20, 2006.
Holt et al., Anti-serum albumin domain antibodies for extending the half-lives of short lived drugs. Protein Eng Des Sel. May 2008;21(5):283-8. doi: 10.1093/protein/gzm067. Epub Apr. 2, 2008.
Hommes et al., Infliximab treatment for Crohn's disease: one-year experience in a Dutch academic hospital. Inflamm Bowel Dis. Mar. 2002;8(2):81-6.
Hoogenboom et al., Multi-subunit proteins on the surface of filamentous phage: methodologies for displaying antibody (Fab) heavy and light chains. Nucleic Acids Res. Aug. 11, 1991;19(15):4133-7.
Hu et al., Comparison of the inhibition mechanisms of adalimumab and infliximab in treating tumor necrosis factor α-associated diseases from a molecular view. J Biol Chem. Sep. 20, 2013;288(38):27059-67. doi: 10.1074/jbc.M113.491530. Epub Aug. 13, 2013.
Ibragimova et al., Stability of the beta-sheet of the WW domain: A molecular dynamics simulation study. Biophys J. Oct. 1999;77(4):2191-8.
Janeway et al., Immunobiology, $3^{rd}$ Ed. Garland Press, 1997, p. 3:7-3:11.
Jang et al., The structural basis for DNA binding by an anti-DNA autoantibody. Mol Immunol. Dec. 1998;35(18):1207-17.
Jones et al., Replacing the complementarity-determining regions in a human antibody with those from a mouse. Lett Nature. 1986;321:522-25.
Klooster et al., Improved anti-IgG and HAS affinity ligands: clinical application of VHH antibody technology. J Immunol Methods. Jul. 31, 2007;324(1-2):1-12. Epub May 11, 2007.
Klostermann et al., The thylakoid membrane protein ALB3 associates with the cpSecY-translocase in *Arabidopsis thaliana*. Biochem J. Dec. 15, 2002;368(Pt 3):777-81.
Kobayashi et al., Tryptophan H33 plays an important role in pyrimidine (6-4) pyrimidone photoproduct binding by a high-affinity antibody. Protein Eng. Oct. 1999;12(10):879-84.
Krauss et al., Impact of antibody framework residue VH-71 on the stability of a humanised anti-MUC1 scFv and derived immunoenzyme. Br J Cancer. May 4, 2004;90(9):1863-70.
Kumar et al., Molecular cloning and expression of the Fabs of human autoantibodies in *Escherichia coli*. Determination of the heavy or light chain contribution to the anti-DNA/-cardiolipin activity of the Fab. J Biol Chem. Nov. 10, 2000;275(45):35129-36.
Lauwereys et al., Potent enzyme inhibitors derived from dromedary heavy-chain antibodies. EMBO J. Jul. 1, 1998;17(13):3512-20.
Lazar et al., Transforming growth factor alpha: mutation of aspartic acid 47 and leucine 48 results in different biological activities. Mol Cell Biol. Mar. 1988;8(3):1247-52.
Lefranc et al., IMGT unique numbering for immunoglobulin and T cell receptor variable domains and Ig superfamily V-like domains. Dev Comp Immunol. Jan. 2003;27(1):55-77.
Liang et al., Structural basis for treating tumor necrosis factor α (TNFα)-associated diseases with the therapeutic antibody infliximab. J Biol Chem. May 10, 2013;288(19):13799-807. doi: 10.1074/jbc.M112.433961. Epub Mar. 15, 2013.
Lin et al., Structure-function relationships in glucagon: properties of highly purified des-His-1-, monoiodo-, and (des-Asn-28, Thr-29)(homoserine lactone-27)-glucagon. Biochemistry. Apr. 22, 1975;14(8):1559-63.
López-Requena et al., Gangliosides, Ab1 and Ab2 antibodies II. Light versus heavy chain: An idiotype-anti-idiotype case study. Mol Immunol. Feb. 2007;44(5):1015-28. Epub Apr. 18, 2006.
Maccallum et al., Antibody-antigen interactions: contact analysis and binding site topography. J Mol Biol. Oct. 11, 1996;262(5):732-45.
Mariuzza et al., The structural basis of antigen-antibody recognition. Annu Rev Biophys Biophys Chem. 1987;16:139-59.
Mulydermans et al., Recognition of antigens by single-domain antibody fragments: the superfluous luxury of paired domains. Trends Biochem Sci. Apr. 2001;26(4):230-5.
Mulydermans et al., Unique single-domain antigen binding fragments derived from naturally occurring camel heavy-chain antibodies. J Mol Recognit. Mar.-Apr. 1999;12(2):131-40.

(56) References Cited

OTHER PUBLICATIONS

Mulydermans, Single domain camel antibodies: current status. J Biotechnol. Jun. 2001;74(4):277-302.

Nargessi et al., Solid-phase fluoroimmunoassay of human albumin in biological fluids. Clin Chim Acta. Nov. 1, 1978;89(3):455-60.

Nguyen et al., Camel heavy-chain antibodies: diverse germline V(H)H and specific mechanisms enlarge the antigen-binding repertoire. EMBO J. Mar. 1, 2000;19(5):921-30.

Nguyen, Thesis, Generation of heavy chain antibodies in camelids. Free University of Brussels, Faculty of Science, Inst. for Molecular Biology and Biotechnology, Lab. of Ultrastructure, (Submitted Aug. 2001).

Nuttall et al., Immunoglobulin VH domains and beyond: design and selection of single-domain binding and targeting reagents. Curr Pharm Biotechnol. Nov. 2000;1(3):253-63.

Pakula et al., Genetic analysis of protein stability and function. Annu Rev Genet. 1989;23:289-310. Summary only.

Pessi et al., A designed metal-binding protein with a novel fold. Nature. Mar. 25, 1993;362(6418):367-9.

Portolano et al., Lack of promiscuity in autoantigen-specific H and L chain combinations as revealed by human H and L chain "roulette". J Immunol. Feb. 1, 1993;150(3):880-7.

Quiocho, Protein engineering. Making of the minibody. Nature. Mar. 25, 1993;362(6418):293-4.

Rahbarizadeh et al., Production of novel recombinant single-domain antibodies against tandem repeat region of MUC1 mucin. Hybrid Hybridomics. Jun. 2004;23(3):151-9.

Reiter et al., An antibody single-domain phage display library of a native heavy chain variable region: isolation of functional single-domain VH molecules with a unique interface. J Mol Biol. Jul. 16, 1999;290(3):685-98.

Riechmann et al., Single domain antibodies: comparison of camel VH and camelised human VH domains. J Immunol Methods. Dec. 10, 1999;231(1-2):25-38.

Riechmann, Rearrangement of the former VL interface in the solution structure of a camelised, single antibody VH domain. J Mol Biol. Jun. 28, 1996;259(5):957-69.

Roitt et al., Immunology. MIR. Moscow. 2000; p. 150. Russian with English Translation.

Roovers et al., Efficient inhibition of EGFR signaling and of tumour growth by antagonistic anti-EFGR Nanobodies. Cancer Immunol Immunother. Mar. 2007;56(3):303-317.

Rudikoff et al., Single amino acid substitution altering antigen-binding specificity. Proc Natl Acad Sci U S A. Mar. 1982;79(6):1979-83.

Sandborn et al., Antitumor necrosis factor therapy for inflammatory bowel disease: a review of agents, pharmacology, clinical results, and safety. Inflamm Bowel Dis. May 1999;5(2):119-33.

Schildbach et al., Modulation of antibody affinity by a non-contact residue. Protein Sci. Feb. 1993;2(2):206-14.

Schwartz et al., A superactive insulin: [B10-aspartic acid]insulin(human). Proc Natl Acad Sci U S A. Sep. 1987;84(18):6408-11.

Shealy et al., Characterization of golimumab, a human monoclonal antibody specific for human tumor necrosis factor α. MAbs. Jul.-Aug. 2010;2(4):428-39. Epub Jul. 1, 2010.

Sheikh et al., Enhanced recognition of reactive oxygen species damaged human serum albumin by circulating systemic lupus erythematosus autoantibodies. Autoimmunity. Nov. 2007;40(7):512-20.

Shimamoto et al., Inhibition of Helicobacter pylori infection by orally administered yolk-derived anti-Helicobacter pylori antibody. Hepatogastroenterology. May-Jun. 2002;49(45):709-14. Database BIOSIS Abstract. Accession No. PREV200200382020 and full text.

Skurkovich et al., Treatment of corneal transplant rejection in humans with anti-interferon-gamma antibodies. Am J Ophthalmol. Jun. 2002;133(6):829-30.

Smith et al., Prolonged in vivo residence times of antibody fragments associated with albumin. Bioconjug Chem. Sep.-Oct. 2001;12(5):750-6.

Smith-Gill et al., Contributions of immunoglobulin heavy and light chains to antibody specificity for lysozyme and two haptens. J Immunol. Dec. 15, 1987;139(12):4135-44.

Sollinger et al., Basiliximab versus antithymocyte globulin for prevention of acute renal allograft rejection. Transplantation. Dec. 27, 2001;72(12):1915-9.

Song et al., Light chain of natural antibody plays a dominant role in protein antigen binding. Biochem Biophys Res Commun. Feb. 16, 2000;268(2):390-4.

Spinelli et al., The crystal structure of a llama heavy chain variable domain. Nat Struct Biol. Sep. 1996;3(9):752-7.

Stancovski et al., Mechanistic aspects of the opposing effects of monoclonal antibodies to the ERBB2 receptor on tumor growth. Proc Natl Acad Sci U S A. Oct. 1, 1991;88(19):8691-5.

Tang et al., Stabilization of leucine zipper coiled coils by introduction of trifluoroleucine. Abst Pap Am Chem. 1999;S218:U138-U138. Abstract 416.

Tanha et al., Selection by phage display of llama conventional V(H) fragments with heavy chain antibody V(H)H properties. J Immunol Methods. May 1, 2002;263(1-2):97-109.

Teitelbaum et al., A mAb recognizing a surface antigen of *Mycobacterium tuberculosis* enhances host survival. Proc Natl Acad Sci U S A. Dec. 22, 1998;95(26):15688-93.

Vajdos et al., Comprehensive functional maps of the antigen-binding site of an anti-ErbB2 antibody obtained with shotgun scanning mutagenesis. J Mol Biol. Jul. 5, 2002;320(2):415-28.

Van Der Linden et al., Comparison of physical chemical properties of llama VHH antibody fragments and mouse monoclonal antibodies. Biochim Biophys Acta. Apr. 12, 1999;1431(1):37-46.

Van Hest et al., Efficient introduction of alkene functionality into proteins in vivo. FEBS Lett. May 22, 1998;428(1-2):68-70.

Vincke et al., General strategy to humanize a camelid single-domain antibody and identification of a universal humanized nanobody scaffold. J Biol Chem. Jan. 30, 2009;284(5):3273-84. Epub Nov. 14, 2008.

Vu et al., Comparison of llama VH sequences from conventional and heavy chain antibodies. Mol Immunol. Nov.-Dec. 1997;34(16-17):1121-31.

Ward et al., Binding activities of a repertoire of single immunoglobulin variable domains secreted from *Escherichia coli*. Nature. Oct. 12, 1989;341(6242):544-6.

Winkler et al., Changing the antigen binding specificity by single point mutations of an anti-p24 (HIV-1) antibody. J Immunol. Oct. 15, 2000;165(8):4505-14.

Worledge et al., Oral administration of avian tumor necrosis factor antibodies effectively treats experimental colitis in rats. Dig Dis Sci. Dec. 2000;45(12):2298-305.

Wu et al., Humanization of a murine monoclonal antibody by simultaneous optimization of framework and CDR residues. J Mol Biol. Nov. 19, 1999;294(1):151-62.

Wunder et al., Albumin-based drug delivery as novel therapeutic approach for rheumatoid arthritis. J Immunol. May 1, 2003;170(9):4793-801.

Zhang et al., Site-directed mutational analysis of human tumor necrosis factor-alpha receptor binding site and structure-functional relationship. J Biol Chem. Nov. 25, 1992;267(33):24069-75.

Diamond et al., Somatic mutation of the T15 heavy chain gives rise to an antibody with autoantibody specificity. Proc Natl Acad Sci U S A. Sep. 1984;81(18):5841-4. doi: 10.1073/pnas.81.18.5841.

Jespers et al., Guiding the selection of human antibodies from phage display repertoires to a single epitope of an antigen. Biotechnology (N Y). Sep. 1994;12(9):899-903. doi: 10.1038/nbt0994-899.

Kolker, Antibodies and the written description requirement of 35 U.S.C.112(a). Sep. 17, 2020. 36 pages.

Nagahira et al., Epitope mapping of monoclonal antibodies to tumor necrosis factor-alpha by synthetic peptide approach. Immunol Lett. May 1995;46(1-2):135-41. doi: 10.1016/0165-2478(95)00031-y.

Ohno et al., Antigen-binding specificities of antibodies are primarily determined by seven residues of VH. Proc Natl Acad Sci U S A. May 1985;82(9):2945-9. doi: 10.1073/pnas.82.9.2945.

Saerens et al., Single domain antibodies derived from dromedary lymph node and peripheral blood lymphocytes sensing conformational

(56) References Cited

OTHER PUBLICATIONS variants of prostate-specific antigen. J Biol Chem. Dec. 10, 2004;279(50):51965-72. Epub Sep. 30, 2004.

Tomlinson et al., The repertoire of human germline VH sequences reveals about fifty groups of VH segments with different hypervariable loops. J Mol Biol. Oct. 5, 1992;227(3):776-98. doi: 10.1016/0022-2836(92)90223-7.

Yarilin et al., V-domains of immunoglobulins. Antigen-binding sites. Moskva, Medicina. 1999:172-174.

Zarebski et al., Llama single domain antibodies as a tool for molecular mimicry. J Mol Biol. Jun. 17, 2005;349(4):814-24. doi: 10.1016/j.jmb.2005.03.072. Epub Apr. 21, 2005.

U.S. Appl. No. 15/644,890, filed Jul. 10, 2017, Beirnaert.

U.S. Appl. No. 14/807,951, filed Jul. 24, 2015, Muyldermans.

EP 02772097.8, Jan. 26, 2006, *European Exam Report.

EP 06 00 6277, Sep. 19, 2006, *European Search Report.

PCT/EP02/07804, Jul. 29, 2003, *International Search Report.

PCT/EP2006/004679, Oct. 4, 2006, *International Search Report.

PCT/EP2006/.04678, Jan. 4, 2007, *International Search Report and Written Opinion.

PCT/EP2006/04678, Nov. 29, 2007, *International Preliminary Report on Patentability.

Eastwood et al., Monoclonal antibody TGN1412 trial failure explained by species differences in CD28 expression on CD4+ effector memory T-cells. Br J Pharmacol. Oct. 2010;161(3):512-26. doi: 10.1111/j.1476-5381.2010.00922.x.

Edwards et al., The remarkable flexibility of the human antibody repertoire; isolation of over one thousand different antibodies to a single protein, BLyS. J Mol Biol. Nov. 14, 2003;334(1):103-18. doi: 10.1016/j.jmb.2003.09.054.

Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.

Alfaleh et al., Phage Display Derived Monoclonal Antibodies: From Bench to Bedside. Front Immunol. Aug. 28, 2020;11:1986. doi: 10.3389/fimmu.2020.01986.

Ladner et al., Mapping the epitopes of antibodies. Biotechnol Genet Eng Rev. 2007;24:1-30. doi: 10-1080/02648725.2007.10648092. 30 pages.

Lu et al., A fully human recombinant IgG-like bispecific antibody to both the epidermal growth factor receptor and the insulin-like growth factor receptor for enhanced antitumor activity. J Biol Chem. May 20, 2005;280(20):19665-72. doi: 10.1075/jbc.M500815200. Epub Mar. 9, 2005.

* cited by examiner

```
PMP1C2    qvqlvesggg lvqpggslrl scaasGFTFS D.....YWMY wvrqapgkgl  class I
PMP1G11   qvqlqesggg mvqpggslrl scaasGFDFG V.....SWMY wvrqapgkgl
PMP1H6    evqlvesggg lvqpggslrl scatsGFDFS V.....SWMY wvrqapgkgl
PMP3D10   qvqlvesggg lvqaggslsl scaasGRSFT G.....YYMG wfrqapgker  class III
PMP5F10   evqlvesggg lvqaggslsl scsasGRSLS N.....YYMG wfrqapgker
PMP1G5    qvqlvesggg lvqaggslrl scaasGRTFS EPSGYTYTIG wfrqapgker  class II
PMP1H2    qvkleesggg lvqpgdslrl scaasGRTFS DYSGYTYTVG wfrqapgker
PMP3G2    avqlvesggg lvqpgdslrl scaasGRTFS DYSGYTYTVG wfrqapgker
PMP1D2    avqlvdsggg lvqaggslrl scaasGRTFS AHSV..YTMG wfrqapgker  class IIb PMP1C2    ewvseINTNG LITKYPDSVK Grftisrdna kntlylqmns lkpedtalyy
PMP1G11   ewvseINTNG LITKYPDSVK Grftisrdna kttlylqmns lkpedtalyy
PMP1H6    ewvseINTNG LITKYVDSVK Grftisrdna kntlylqmds lipedtalyy
PMP3D10   qllasISWRG DNTYYKESVK Grftisrdda kntiylqmns lkpedtavyy
PMP5F10   ellgnISWRG YNIYYKDSVK Grftisrdda kntiylqmnr lkpedtavyy
PMP1G5    efvarIYWSS GLTYYADSVK Grftisrdia kntvdllmns lkpedtavyy
PMP1H2    efvarIYWSS GNTYYADSVK Grftisrdia kntvdllmnn lepedtavyy
PMP3G2    efvarIYWSS GNTYYADSVK Grftisrdia kntvdllmnn lepedtavyy
PMP1D2    efvarIYWSS ANTYYADSVK Grftisrdna kntvdllmnc lkpedtavyy PMP1C2    carS......    ...PSGFNrg qgtqvtvss  (SEQ ID NO: 52)
PMP1G11   carS......    ...PSGSFrg qgtqvtvss  (SEQ ID NO: 53)
PMP1H6    carS......    ...PSGSFrg qgtqvtvss  (SEQ ID NO: 54)
PMP3D10   caaS.ILPLS    DDPGWNTNwg qgtqvtvss  (SEQ ID NO: 59)
PMP5F10   caaS.ILPLS    DDPGWNTYwg qgtqvtvss  (SEQ ID NO: 60)
PMP1G5    caaRDGIPTS    RSVGSYNYwg qgtqvtvss  (SEQ ID NO: 55)
PMP1H2    caaRDGIPTS    RSVESYNYwg qgtqvtvss  (SEQ ID NO: 56)
PMP3G2    caaRDGIPTS    RSVESYNYwg qgtqvtvss  (SEQ ID NO: 57)
PMP1D2    caaRDGIPTS    RSVEAYNYwg qgtqvtvss  (SEQ ID NO: 58)
```

Figure 1

```
Hum+, Rhe+, Mou+ > PMP6G8   avqlvesggg lvqpggslrl tctasGFTFR SFGMSwvrqa pgkdqewvsa A
Hum+, Rhe+, Mou- > PMP6A5   qvqlaesggg lvqpggslrl tctasGFTFG SFGMSwvrqa pgeqlewvsa
Hum+, Rhe+, Mou+ > PMP6A6   avqlvesggg lvqpgnslrl scaasGFTFR SFGMSwvrqa pgkepewvss B
Hum+, Rhe+, Mou+ > PMP6C1   avqlvdsggg lvqpggslrl scaasGFSFG SFGMSwvrqy pgkepewvss
Hum+, Rhe+, Mou+ > PMP6A8   avqlvesggg lvqgggslrl acaasERIFD LNLMGwvrqg pgnerelvat C
Hum+, Rhe+, Mou+ > PMP6B4   evqlvesggg lvqeggslrl acaasERIWD INLLGwyrqg pgnerelvat
Hum+, Rhe-, Mou+ > PMP6G7   qvqlvesggg lvqpggslrl scaasGFTFS NYWMYwvrva pgkglerisr D PMP6G8          ISADSSTKNY ADSVKGrfti srdnakkmly lemnslkped tavyycviGR
PMP6A5          ISADSSDKRY ADSVKGrfti srdnakkmly lemnslksed tavyycviGR
PMP6A6          ISGSGSDTLY ADSVKGrfti srdnakttly lqmnslkped tavyyctiGG
PMP6C1          INGRGDDTRY ADSVKGrfsi srdnakntly lqmnslkped taeyyctiGR
PMP6A8          ITVG.DSTNY ADSVKGrfti smdytkqtvy lhmnslrped tglyyckiRR
PMP6B4          ITVG.DSTSY ADSVKGrfti srdydkntly lqmnslrped tglyyckiRR
PMP6G7          ISTGGGYSYY ADSVKGrfti srdnakntly lqmnslkped talyycakDR PMP6G8          GSPs......  ..spgtqvtv ss (SEQ ID NO: 65)
PMP6A5          GSPa......  ..sqgtqvtv ss (SEQ ID NO: 66)
PMP6A6          SLSRs.....  ..sqgtqvtv ss (SEQ ID NO: 63)
PMP6C1          SVSRS.....  .rtgtqvtv  ss (SEQ ID NO: 64)
PMP6A8          TWHSEL....  .wgqgtqvtv ss (SEQ ID NO: 61)
PMP6B4          TWHSEL....  .wgqgtqvtv ss (SEQ ID NO: 62)
PMP6G7          EAQVDTLDFD  Yrgqgtqvtv ss (SEQ ID NO: 67)
```

Figure 2

Figure 15:
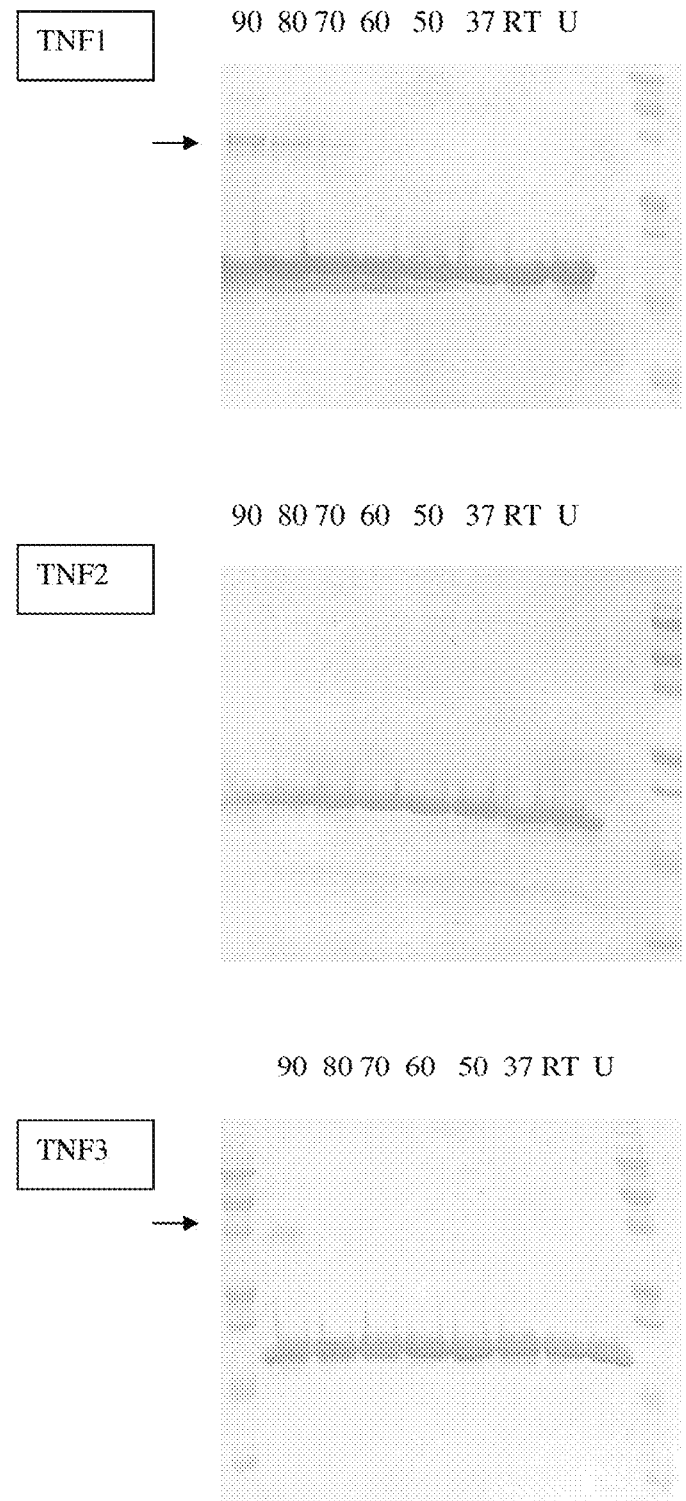

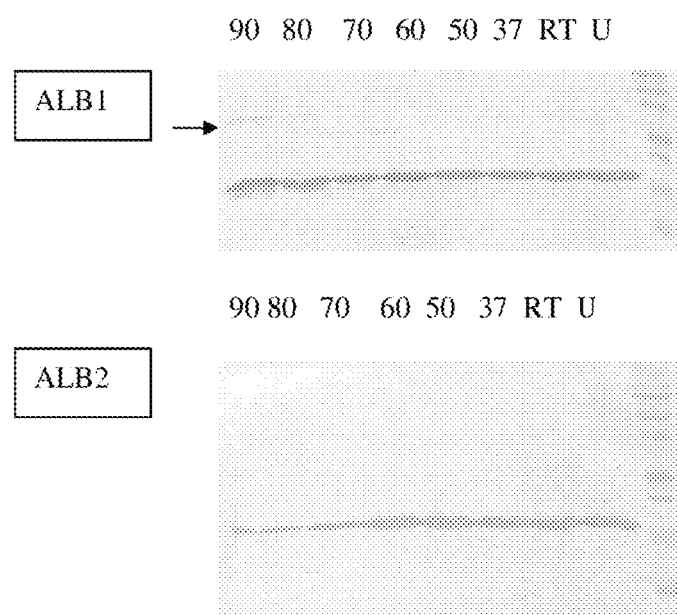
Figure 15 - continued

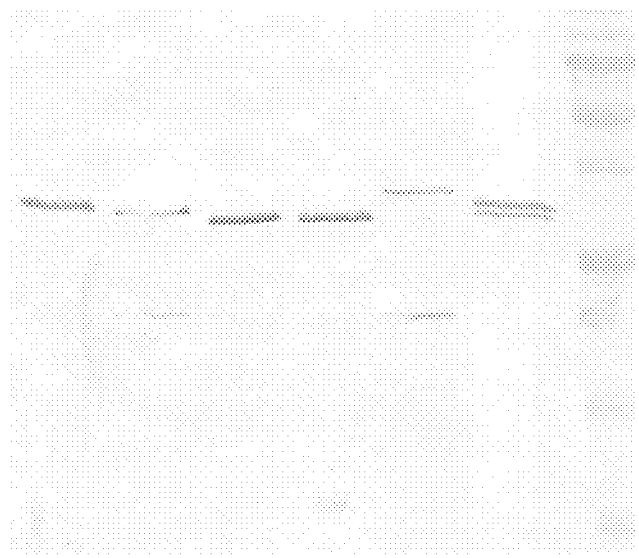
Figure 19

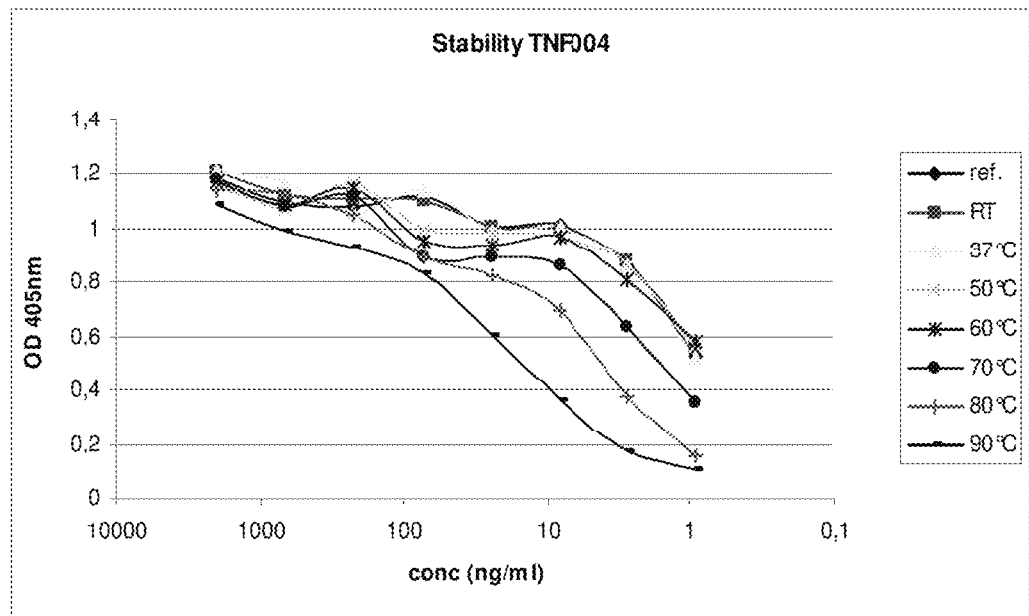
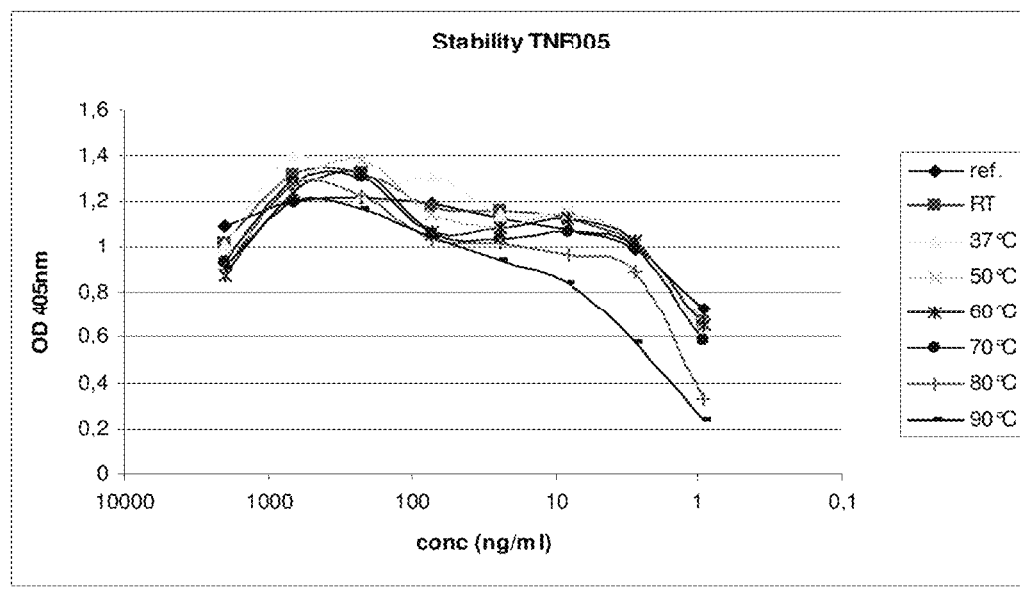
Figure 21

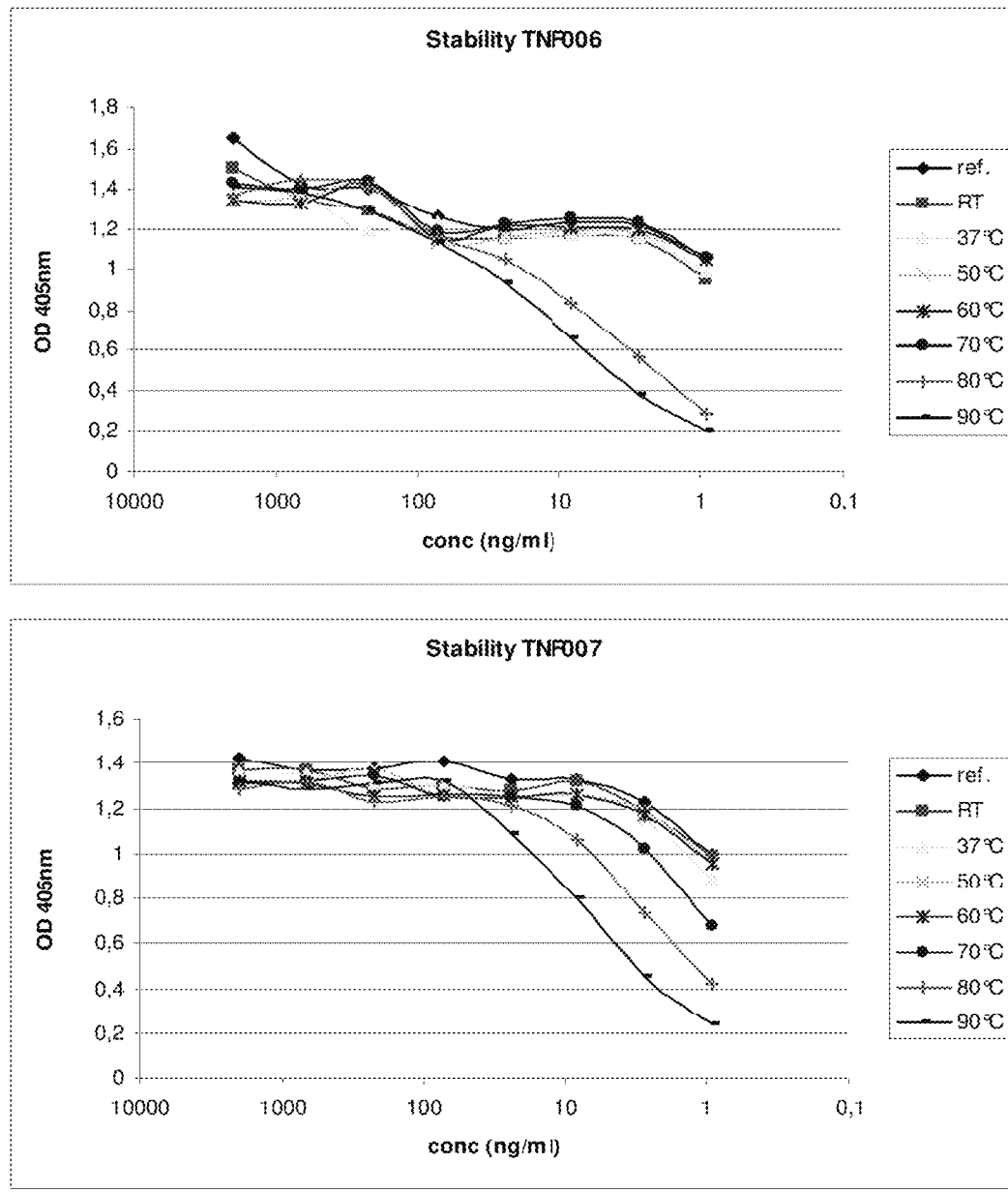
Figure 21 - continued

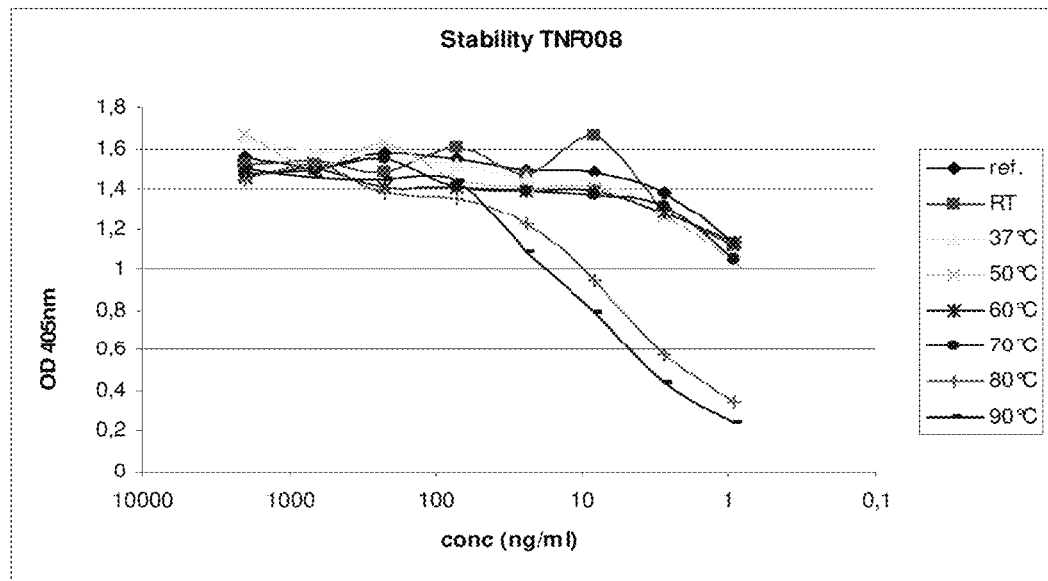
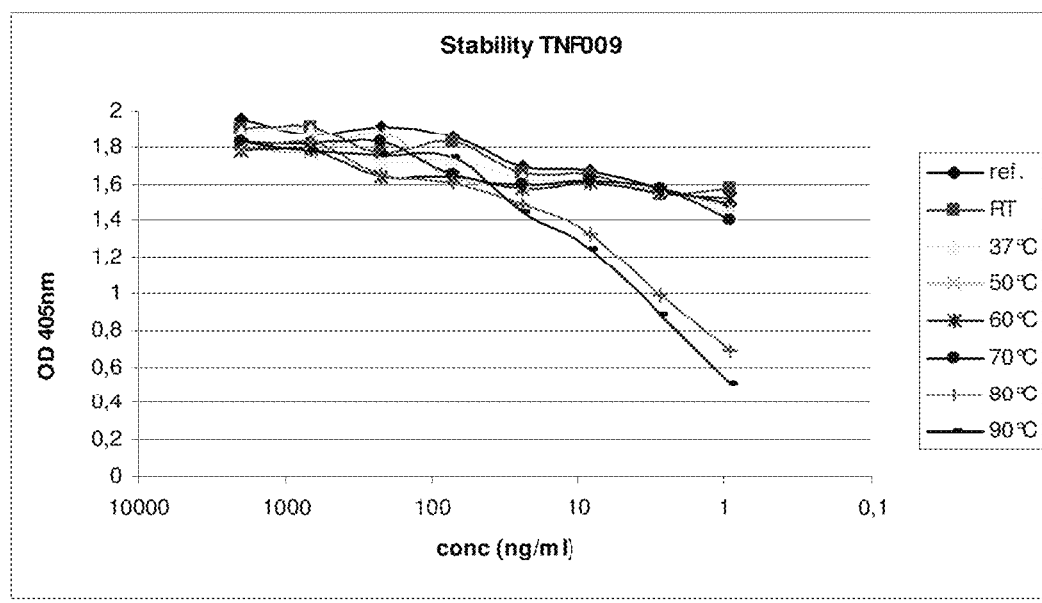
Figure 21 - continued

```
TNF1:
DP51    EVQLVESGGGLVQPGGSLRLSCAASGFTFS SYSMN WVRQAPGKGLEWVS YISSSSSTIYY
DP53    EVQLVESGGGLVQPGGSLRLSCAASGFTFS SYWMH WVRQAPGKGLVWVS RINSDGSSTSY
TNF1    QVQLVESGGGLVQPGGSLRLSCAASGFTFS DYWMY WVRQAPGKGLEWVS EINTNGLITKY
TNF13   EVQLVESGGGLVQPGGSLRLSCAASGFTFS DYWMY WVRQAPGKGLEWVS EINTNGLITKY
TNF14   EVQLVESGGGLVQPGGSLRLSCAASGFTFS DYWMY WVRQAPGKGLEWVS EINTNGLITKY
        ****************************   *  * **********  ***      *       *

DP51    ADSVKG RFTISRDNAKNSLYLQMNSLRDEDTAVYYCAR ------ WGQGTLVTVSS (SEQ ID NO: 472)
DP53    ADSVKG RFTISRDNAKNTLYLQMNSLRAEDTAVYYCAR ------ WGQGTLVTVSS (SEQ ID NO: 473)
TNF1    PDSVKG RFTISRDNAKNTLYLQMNSLKPEDTALYYCAR SPSGFN RGQGTQVTVSS (SEQ ID NO: 52)
TNF13   PDSVKG RFTISRDNAKNTLYLQMNSLKPEDTAVYYCAR SPSGFN RGQGTQVTVSS (SEQ ID NO: 76)
TNF14   PDSVKG RFTISRDNAKNTLYLQMNSLKPEDTALYYCAR SPSGFN RGQGTLVTVSS (SEQ ID NO: 77)
        *****  ************ ********   **** *****         **** *****
```

Figure 22

```
TNF2:    (From top to bottom, SEQ ID NOs: 474, 55, 78, 79, 80, 81, 82)
DP54    EVQLVESGGGLVQPGGSLRLSCAASGFTFS ------SYWMS WVRQAPGKGLEWVANIKQDGSEKYY
TNF2    QVQLVESGGGLVQAGGSLRLSCAASGRTFS EPSGYTYTIG WFRQAPGKEREFVARIYWSSGLTYY
TNF15   EVQLVESGGGLVQPGGSLRLSCAASGRTFS EPSGYTYTIG WFRQAPGKGREFVARIYWSSGLTYY
TNF16   EVQLVESGGGLVQPGGSLRLSCAASGFTFS EPSGYTYTIG WFRQAPGKGREFVARIYWSSGLTYY
TNF17   EVQLVESGGGLVQPGGSLRLSCAASGRTFS EPSGYTYTIG WFRQAPGKGREFVARIYWSSGLTYY
TNF18   EVQLVESGGGLVQPGGSLRLSCAASGRTFS EPSGYTYTIG WFRQAPGKGREFVARIYWSSGLTYY
TNF19   EVQLVESGGGLVQPGGSLRLSCAASGRTFS EPSGYTYTIG WFRQAPGKGREFVARIYWSSGLTYY
        ***********  *************** ***          *   * ****** *  ** *   **

DP54    VDSVKG RFTISRDNAKNSLYLQMNSLRAEDTAVYYCAR ----------------- WGQGTLVTVSS
TNF2    ADSVKG RFTISRDIAKNTVDLLMNSLKPEDTAVYYCAA RDGIPTSRSVGSYNY WGQGTQVTVSS
TNF15   ADSVKG RFTISRDIAKNTVDLQMNSLKPEDTAVYYCAA RDGIPTSRSVGSYNY WGQGTQVTVSS
TNF16   ADSVKG RFTISRDIAKNTVDLQMNSLKPEDTAVYYCAA RDGIPTSRSVGSYNY WGQGTQVTVSS
TNF17   ADSVKG RFTISRDIAKNTVDLQMNSLKPEDTAVYYCAA RDGIPTSRSVGSYNY WGQGTQVTVSS
TNF18   ADSVKG RFTISRDIAKNTVDLQMNSLRPEDTAVYYCAA RDGIPTSRSVGSYNY WGQGTQVTVSS
TNF19   ADSVKG RFTISRDIAKNTVDLQMNSLKPEDTAVYYCAA RDGIPTSRSVGSYNY WGQGTLVTVSS
        *****  *******  ***   *  ****  ********                ****  *****
```

Figure 23

```
TNF3:    (From top to bottom, SEQ ID NOs: 475, 60, 83, 84, 85, 86)
DP29    EVQLVESGGGLVQPGGSLRLSCAASGFTFS DHYMDWVRQAPGKGLEWVG RTRNKANSYTTEYAAS
TNF3    EVQLVESGGGLVQAGGSLSLSCSASGRSLS NYYMGWFRQAPGKERELLG NI--SWRGYNIYYKDS
TNF20   EVQLVESGGGLVQPGGSLRLSCAASGRSLS NYYMGWFRQAPGKGRELLG NI--SWRGYNIYYKDS
TNF21   EVQLVESGGGLVQPGGSLRLSCAASGFTFS NYYMGWFRQAPGKGRELLG NI--SWRGYNIYYKDS
TNF22   EVQLVESGGGLVQPGGSLRLSCAASGRSLS NYYMGWFRQAPGKGRELLG NI--SWRGYNIYYKDS
TNF23   EVQLVESGGGLVQPGGSLRLSCAASGRSLS NYYMGWFRQAPGKGRELLG NI--SWRGYNIYYKDS
        ************  ***  ***  ***   * ** ******* **** *     *  * * *  *

DP29    VKG RFTISRDDSKNSLYLQMNSLKTEDTAVYYCAR---------------- WGQGTLVTVSS
TNF3    VKG RFTISRDDAKNTIYLQMNRLKPEDTAVYYCAA SILPLSDDPGWNTY WGQGTQVTVSS
TNF20   VKG RFTISRDDSKNTIYLQMNSLKPEDTAVYYCAA SILPLSDDPGWNTY WGQGTQVTVSS
TNF21   VKG RFTISRDDSKNTIYLQMNSLKPEDTAVYYCAA SILPLSDDPGWNTY WGQGTQVTVSS
TNF22   VKG RFTISRDDSKNTIYLQMNSLKTEDTAVYYCAA SILPLSDDPGWNTY WGQGTQVTVSS
TNF23   VKG RFTISRDDSKNTIYLQMNSLKPEDTAVYYCAA SILPLSDDPGWNTY WGQGTLVTVSS
        ***  ********  **  *****  **  ********                  ****  *****
```

Figure 24

ALB1:
```
DP51  EVQLVESGGGLVQPGGSLRLSCAASGFTFS SYSMN WVRQAPGKGLEWVS YISSSSSTIYYADSVKG
DP53  EVQLVESGGGLVQPGGSLRLSCAASGFTFS SYWMH WVRQAPGKGLVWVS RINSDGSSTSYADSVKG
ALB1  AVQLVESGGGLVQPGNSLRLSCAASGFTFR SFGMS WVRQAPGKEPEWVS SISGSGSDTLYADSVKG
ALB3  EVQLVESGGGLVQPGGSLRLSCAASGFTFR SFGMS WVRQAPGKEPEWVS SISGSGSDTLYADSVKG
ALB4  EVQLVESGGGLVQPGGSLRLSCAASGFTFS SFGMS WVRQAPGKEPEWVS SISGSGSDTLYADSVKG
ALB5  EVQLVESGGGLVQPGGSLRLSCAASGFTFR SFGMS WVRQAPGKGLEWVS SISGSGSDTLYADSVKG
      **************  *************    *     ********   ***   **  * *******

DP51  RFTISRDNAKNSLYLQMNSLRDEDTAVYYCAR ------ WGQGTLVTVSS (SEQ ID NO: 472)
DP53  RFTISRDNAKNTLYLQMNSLRAEDTAVYYCAR ------ WGQGTLVTVSS (SEQ ID NO: 473)
ALB1  RFTISRDNAKTTLYLQMNSLKPEDTAVYYCTI GGSLSR SSQGTQVTVSS (SEQ ID NO: 63)
ALB3  RFTISRDNAKTTLYLQMNSLKPEDTAVYYCTI GGSLSR SSQGTQVTVSS (SEQ ID NO: 87)
ALB4  RFTISRDNAKTTLYLQMNSLKPEDTAVYYCTI GGSLSR SSQGTQVTVSS (SEQ ID NO: 88)
ALB5  RFTISRDNAKTTLYLQMNSLKPEDTAVYYCTI GGSLSR SSQGTQVTVSS (SEQ ID NO: 89)
      *********  ********  *******            *********
```

Figure 25

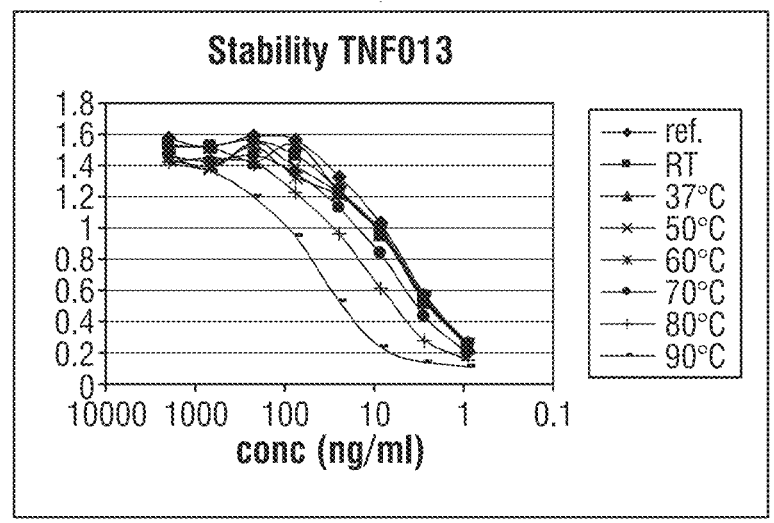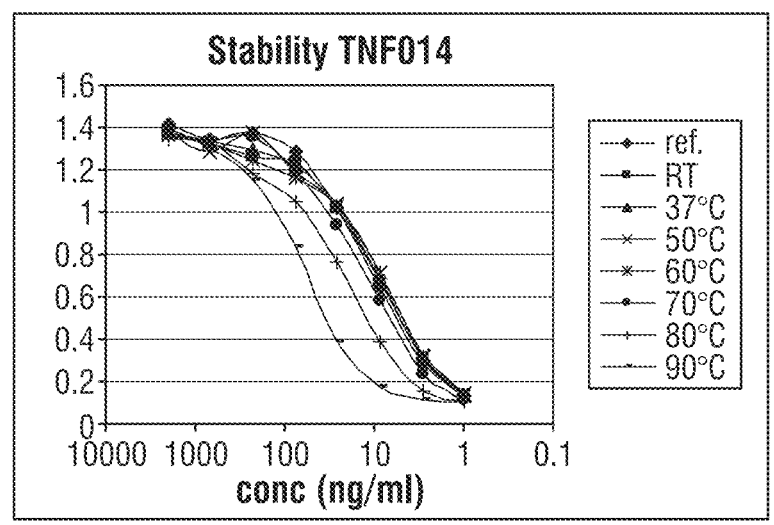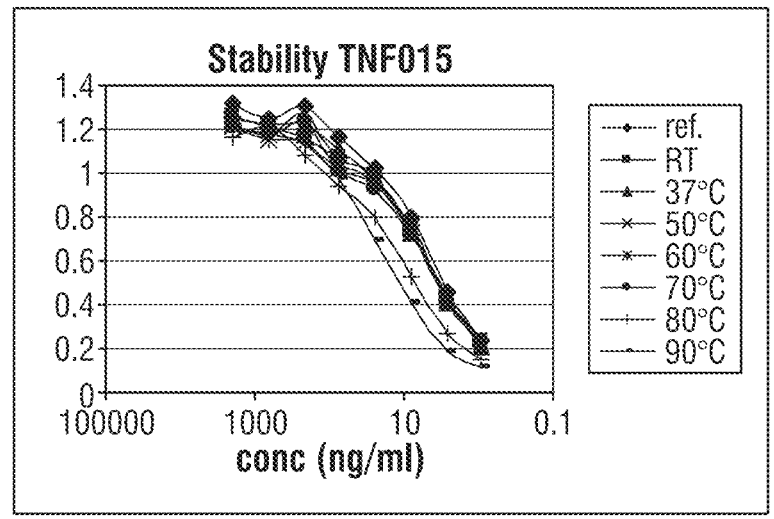
Figure 30

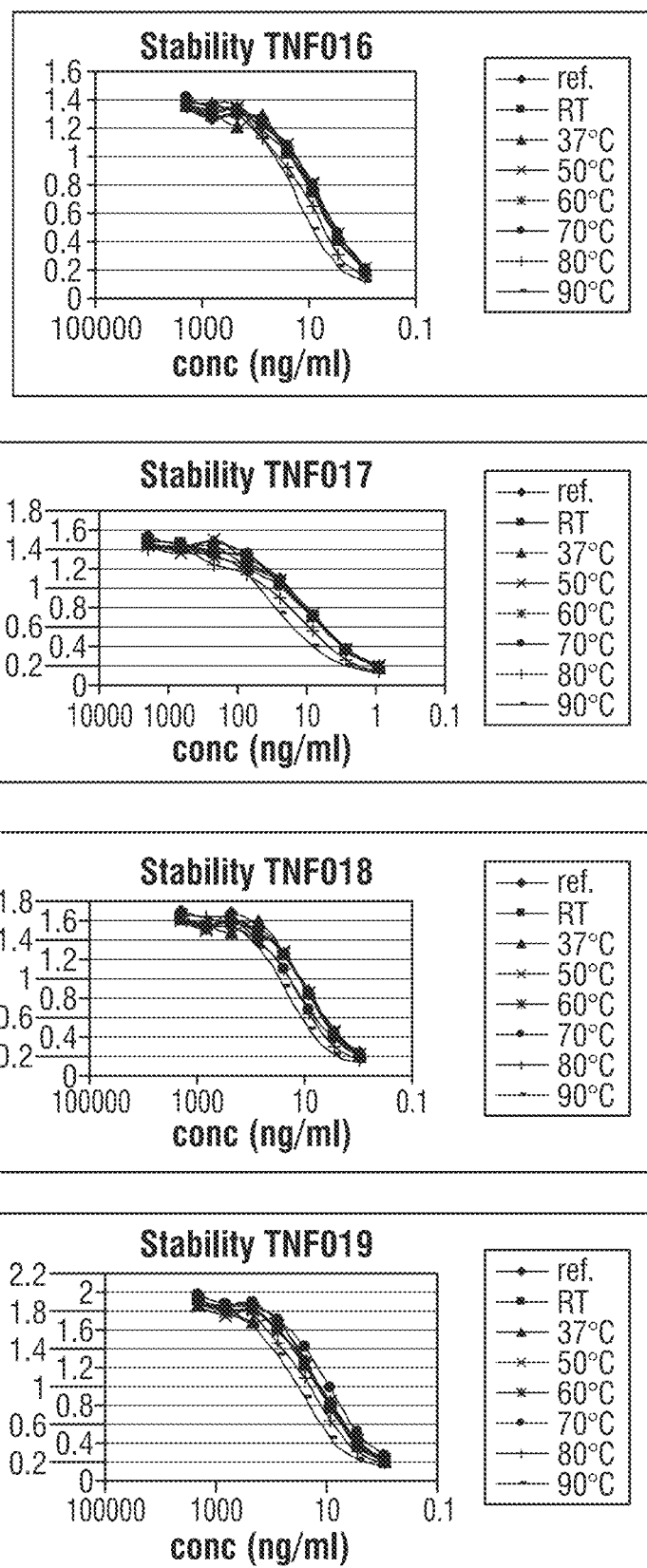
Figure 30 - continued

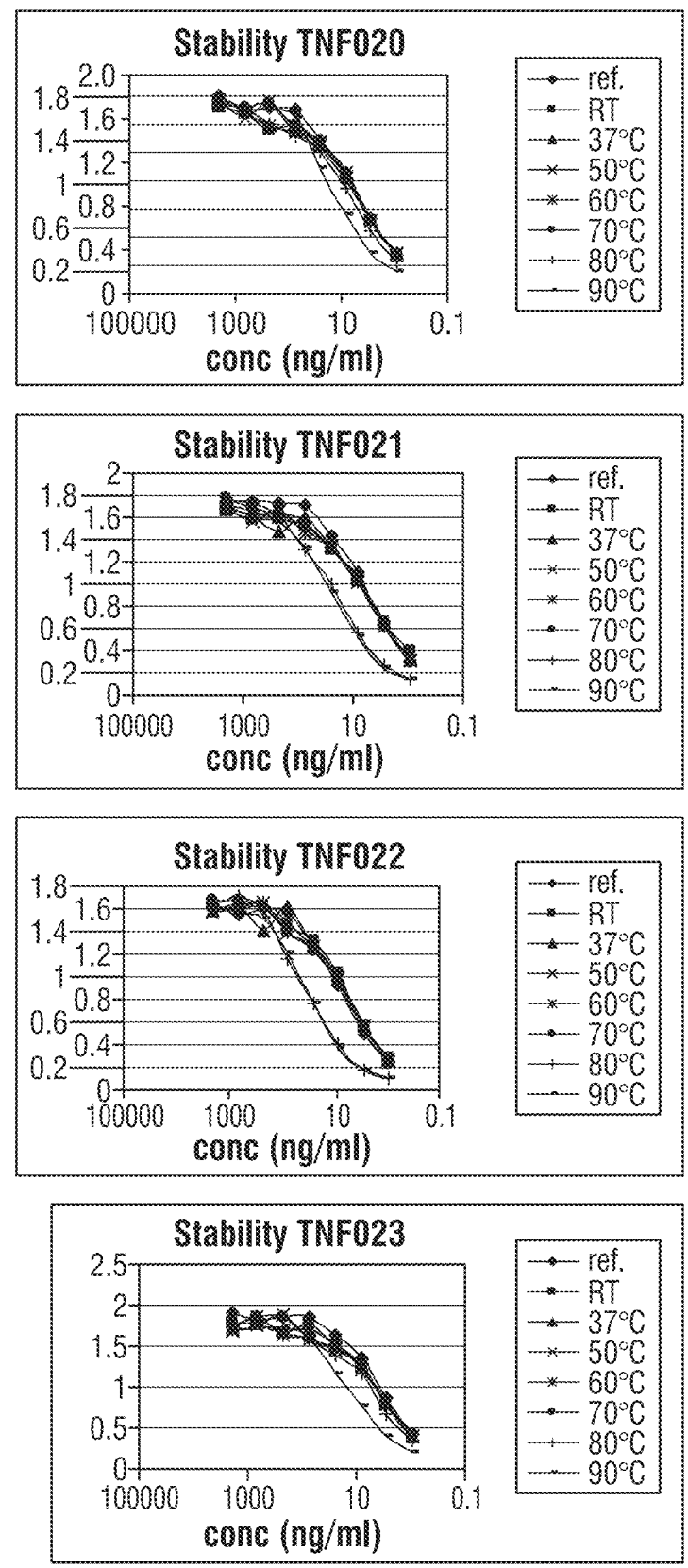
Figure 30 - continued

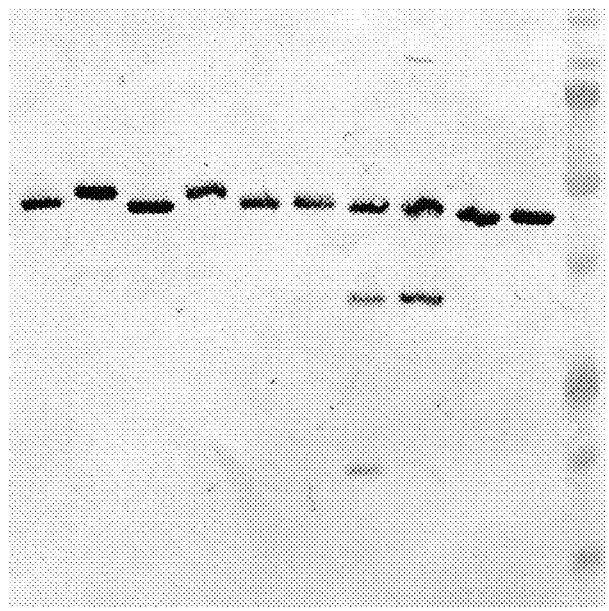
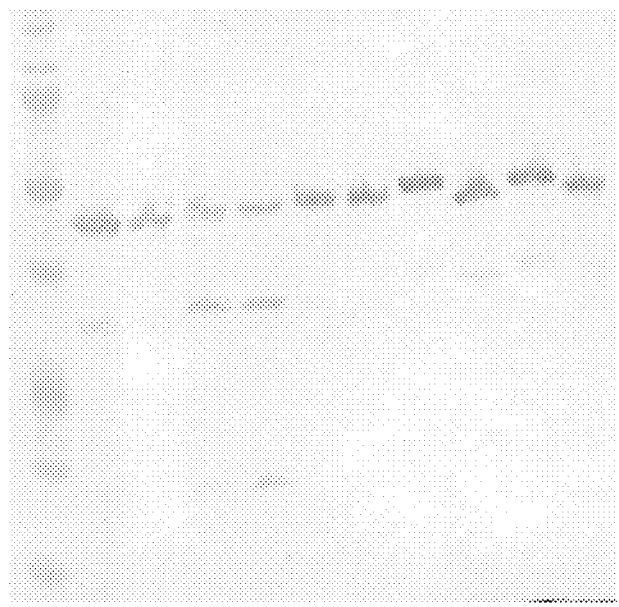
Figure 32

TNF1:
```
DP51   EVQLVESGGGLVQPGGSLRLSCAASGFTFS SYSMN WVRQAPGKGLEWVS YISSSSSTIYY
DP53   EVQLVESGGGLVQPGGSLRLSCAASGFTFS SYWMH WVRQAPGKGLVWVS RINSDGSSTSY
TNF1   QVQLVESGGGLVQPGGSLRLSCAASGFTFS DYWMY WVRQAPGKGLEWVS EINTNGLITKY
TNF13  EVQLVESGGGLVQPGGSLRLSCAASGFTFS DYWMY WVRQAPGKGLEWVS EINTNGLITKY
TNF14  EVQLVESGGGLVQPGGSLRLSCAASGFTFS DYWMY WVRQAPGKGLEWVS EINTNGLITKY
TNF29  EVQLVESGGGLVQPGGSLRLSCAASGFTFS DYWMY WVRQAPGKGLEWVS EINTNGLITKY
TNF30  EVQLVESGGGLVQPGGSLRLSCAASGFTFS DYWMY WVRQAPGKGLEWVS EINTNGLITKY
         e

DP51   ADSVKG RFTISRDNAKNSLYLQMNSLRDEDTAVYYCAR ------ WGQGTLVTVSS (SEQ ID NO: 472)
DP53   ADSVKG RFTISRDNAKNTLYLQMNSLRAEDTAVYYCAR ------ WGQGTLVTVSS (SEQ ID NO: 473)
TNF1   PDSVKG RFTISRDNAKNTLYLQMNSLKPEDTALYYCAR SPSGFN RGQGTQVTVSS (SEQ ID NO: 52)
TNF13  PDSVKG RFTISRDNAKNTLYLQMNSLKPEDTAVYYCAR SPSGFN RGQGTQVTVSS (SEQ ID NO: 76)
TNF14  PDSVKG RFTISRDNAKNTLYLQMNSLKPEDTALYYCAR SPSGFN RGQGTLVTVSS (SEQ ID NO: 77)
TNF29  PDSVKG RFTISRDNAKNTLYLQMNSLKPEDTAVYYCAR SPSGFN RGQGTLVTVSS (SEQ ID NO: 95)
TNF30  PDSVKG RFTISRDNAKNTLYLQMNSLRPEDTAVYYCAR SPSGFN RGQGTLVTVSS (SEQ ID NO: 96)
                                ii    b                    e
```

Figure 34

TNF2: (From top to bottom, SEQ ID NOs: 474, 55, 78, 79, 80, 81, 82, 97, 98)
```
DP54   EVQLVESGGGLVQPGGSLRLSCAASGFTFS -----SYWMS WVRQAPGKGLEWVA NIKQDGSEKYY
TNF2   QVQLVESGGGLVQAGGSLRLSCAASGRTFS EPSGYTYTIG WFRQAPGKEREFVAR IYWSSGLTYY
TNF15  EVQLVESGGGLVQPGGSLRLSCAASGRTFS EPSGYTYTIG WFRQAPGKGREFVAR IYWSSGLTYY
TNF16  EVQLVESGGGLVQPGGSLRLSCAASGFTFS EPSGYTYTIG WFRQAPGKGREFVAR IYWSSGLTYY
TNF17  EVQLVESGGGLVQPGGSLRLSCAASGRTFS EPSGYTYTIG WFRQAPGKGREFVAR IYWSSGLTYY
TNF18  EVQLVESGGGLVQPGGSLRLSCAASGRTFS EPSGYTYTIG WFRQAPGKGREFVAR IYWSSGLTYY
TNF19  EVQLVESGGGLVQPGGSLRLSCAASGRTFS EPSGYTYTIG WFRQAFGKGREFVAR IYWSSGLTYY
TNF31  EVQLVESGGGLVQPGGSLRLSCAASGFTFS EPSGYTYTIG WFRQAPGKGREFVAR IYWSSGLTYY
TNF32  EVQLVESGGGLVQPGGSLRLSCAASGFTFS EPSGYTYTIG WFRQAPGKGREFVAR IYWSSGLTYY
         e          i         e                b       ei b DP54   VDSVKG RFTISRDNAKNSLYLQMNSLRAEDTAVYYCAR ------------------ WGQGTLVTVSS
TNF2   ADSVKG RFTISRDIAKNTVDLLMNSLKPEDTAVYYCAA RDGIPTSRSVGSYNY WGQGTQVTVSS
TNF15  ADSVKG RFTISRDIAKNTVDLQMNSLKPEDTAVYYCAA RDGIPTSRSVGSYNY WGQGTQVTVSS
TNF16  ADSVKG RFTISRDIAKNTVDLQMNSLKPEDTAVYYCAA RDGIPTSRSVGSYNY WGQGTQVTVSS
TNF17  ADSVKG RFTISRDIAKNTVDLQMNSLKPEDTAVYYCAA RDGIPTSRSVGSYNY WGQGTQVTVSS
TNF18  ADSVKG RFTISRDIAKNTVDLQMNSLRPEDTAVYYCAA RDGIPTSRSVGSYNY WGQGTQVTVSS
TNF19  ADSVKG RFTISRDIAKNTVDLQMNSLKPEDTAVYYCAA RDGIPTSRSVGSYNY WGQGTLVTVSS
TNF31  ADSVKG RFTISRDIAKNTVDLQMNSLRPEDTAVYYCAA RDGIPTSRSVGSYNY WGQGTQVTVSS
TNF32  ADSVKG RFTISRDIAKNTVDLQMNSLRPEDTAVYYCAA RDGIPTSRSVGSYNY WGQGTLVTVSS
           e    bbb b    ii        b                          e
```

Figure 35

TNF3:      (From top to bottom, SEQ ID NOs: 475, 60, 83, 84, 85, 86, 99)
DP29    EVQLVESGGGLVQPGGSLRLSCAASGFTFS DHYMD WVRQAPGKGLEWVG RTRNKANSYTTEYAAS
TNF3    EVQLVESGGGLVQAGGSLSLSCSASGRSLS NYYMG WFRQAPGKERELLG NI--SWRGYNIYYKDS
TNF20   EVQLVESGGGLVQPGGSLRLSCAASGRSLS NYYMG WFRQAPGKGRELLG NI--SWRGYNIYYKDS
TNF21   EVQLVESGGGLVQPGGSLRLSCAASGFTFS NYYMG WFRQAPGKGRELLG NI--SWRGYNIYYKDS
TNF22   EVQLVESGGGLVQPGGSLRLSCAASGRSLS NYYMG WFRQAPGKGRELLG NI--SWRGYNIYYKDS
TNF23   EVQLVESGGGLVQPGGSLRLSCAASGRSLS NYYMG WFRQAPGKGRELLG NI--SWRGYNIYYKDS
TNF33   EVQLVESGGGLVQPGGSLRLSCAASGRSLS NYYMG WFRQAPGKGRELLG NI--SWRGYNIYYKDS
                  i    i   i    ebi          b          ei bb DP29    VKG RFTISRDDSKNSLYLQMNSLKTEDTAVYYCAR --------------- WGQGTLVTVSS
TNF3    VKG RFTISRDDAKNTIYLQMNRLKPEDTAVYYCAA SILPLSDDPGWNTY WGQGTQVTVSS
TNF20   VKG RFTISRDDSKNTIYLQMNSLKPEDTAVYYCAA SILPLSDDPGWNTY WGQGTQVTVSS
TNF21   VKG RFTISRDDSKNTIYLQMNSLRPEDTAVYYCAA SILPLSDDPGWNTY WGQGTQVTVSS
TNF22   VKG RFTISRDDSKNTIYLQMNSLKTEDTAVYYCAA SILPLSDDPGWNTY WGQGTQVTVSS
TNF23   VKG RFTISRDDSKNTIYLQMNSLKPEDTAVYYCAA SILPLSDDPGWNTY WGQGTLVTVSS
TNF33   VKG RFTISRDDSKNTIYLQMNSLRPEDTAVYYCAA SILPLSDDPGWNTY WGQGTLVTVSS
              c   bb    i ii            b                   c

Figure 36

ALB1:
DP51    EVQLVESGGGLVQPGGSLRLSCAASGFTFS SYSMN WVRQAPGKGLEWVS YISSSSSTIYYADSVKG
DP53    EVQLVESGGGLVQPGGSLRLSCAASGFTFS SYWMH WVRQAPGKGLVWVS RINSDGSSTSYADSVKG
ALB1    AVQLVESGGGLVQPGNSLRLSCAASGFTFR SFGMS WVRQAPGKEPEWVS SISGSGSDTLYADSVKG
ALB3    EVQLVESGGGLVQPGGSLRLSCAASGFTFR SFGMS WVRQAPGKEPEWVS SISGSGSDTLYADSVKG
ALB4    EVQLVESGGGLVQPGGSLRLSCAASGFTFS SFGMS WVRQAPGKEPEWVS SISGSGSDTLYADSVKG
ALB5    EVQLVESGGGLVQPGGSLRLSCAASGFTFR SFGMS WVRQAPGKGLEWVS SISGSGSDTLYADSVKG
ALB6    EVQLVESGGGLVQPGNSLRLSCAASGFTFR SFGMS WVRQAPGKGLEWVS SISGSGSDTLYADSVKG
ALB7    EVQLVESGGGLVQPGNSLRLSCAASGFTFR SFGMS WVRQAPGKGLEWVS SISGSGSDTLYADSVKG
ALB8    EVQLVESGGGLVQPGNSLRLSCAASGFTFS SFGMS WVRQAPGKGLEWVS SISGSGSDTLYADSVKG
ALB9    EVQLVESGGGLVQPGNSLRLSCAASGFTFS SFGMS WVRQAPGKGLEWVS SISGSGSDTLYADSVKG
ALB10   EVQLVESGGGLVQPGNSLRLSCAASGFTFS SFGMS WVRQAPGKGLEWVS SISGSGSDTLYADSVKG
              e              i              i                 ei

DP51    RFTISRDNAKNSLYLQMNSLRDEDTAVYYCAR ------ WGQGTLVTVSS (SEQ ID NO: 472)
DP53    RFTISRDNAKNTLYLQMNSLRAEDTAVYYCAR ------ WGQGTLVTVSS (SEQ ID NO: 473)
ALB1    RFTISRDNAKTTLYLQMNSLKPEDTAVYYCTI GGSLSR SSQGTQVTVSS (SEQ ID NO: 370)
ALB3    RFTISRDNAKTTLYLQMNSLKPEDTAVYYCTI GGSLSR SSQGTQVTVSS (SEQ ID NO: 87)
ALB4    RFTISRDNAKTTLYLQMNSLKPEDTAVYYCTI GGSLSR SSQGTQVTVSS (SEQ ID NO: 88)
ALB5    RFTISRDNAKTTLYLQMNSLKPEDTAVYYCTI GGSLSR SSQGTQVTVSS (SEQ ID NO: 89)
ALB6    RFTISRDNAKTTLYLQMNSLKPEDTAVYYCTI GGSLSR SSQGTLVTVSS (SEQ ID NO: 100)
ALB7    RFTISRDNAKTTLYLQMNSLRPEDTAVYYCTI GGSLSR SSQGTLVTVSS (SEQ ID NO: 101)
ALB8    RFTISRDNAKTTLYLQMNSLRPEDTAVYYCTI GGSLSR SSQGTLVTVSS (SEQ ID NO: 102)
ALB9    RFTISRDNAKNTLYLQMNSLRPEDTAVYYCTI GGSLSR SSQGTLVTVSS (SEQ ID NO: 103)
ALB10   RFTISRDNAKNTLYLQMNSLRPEDTAVYYCTI GGSLSR SGQGTLVTVSS (SEQ ID NO: 104)
              i       ii      bb         ib   i

Figure 37

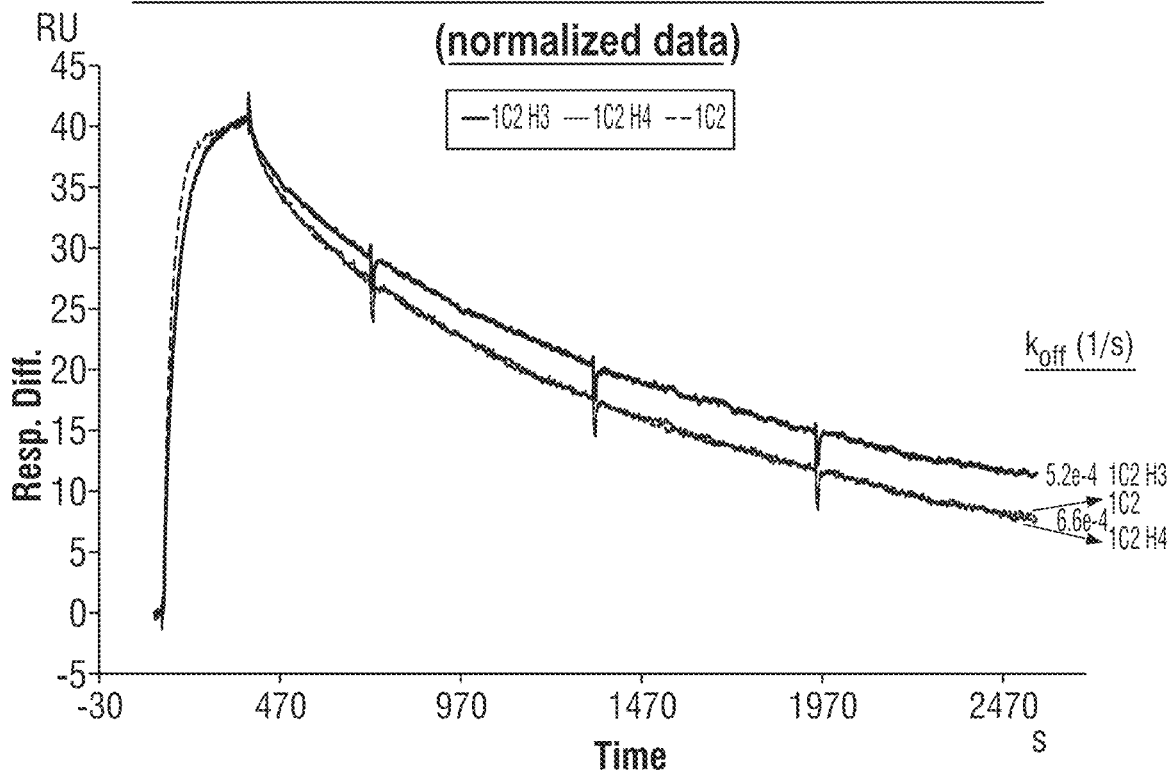
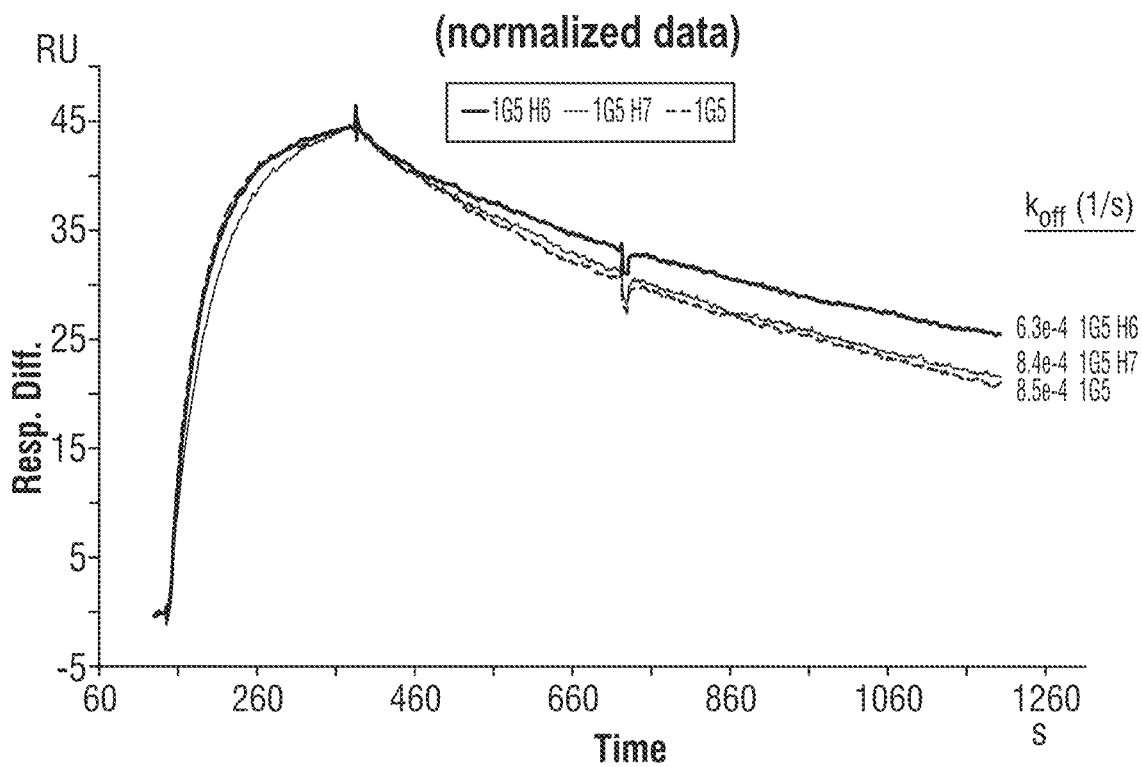
Figure 40

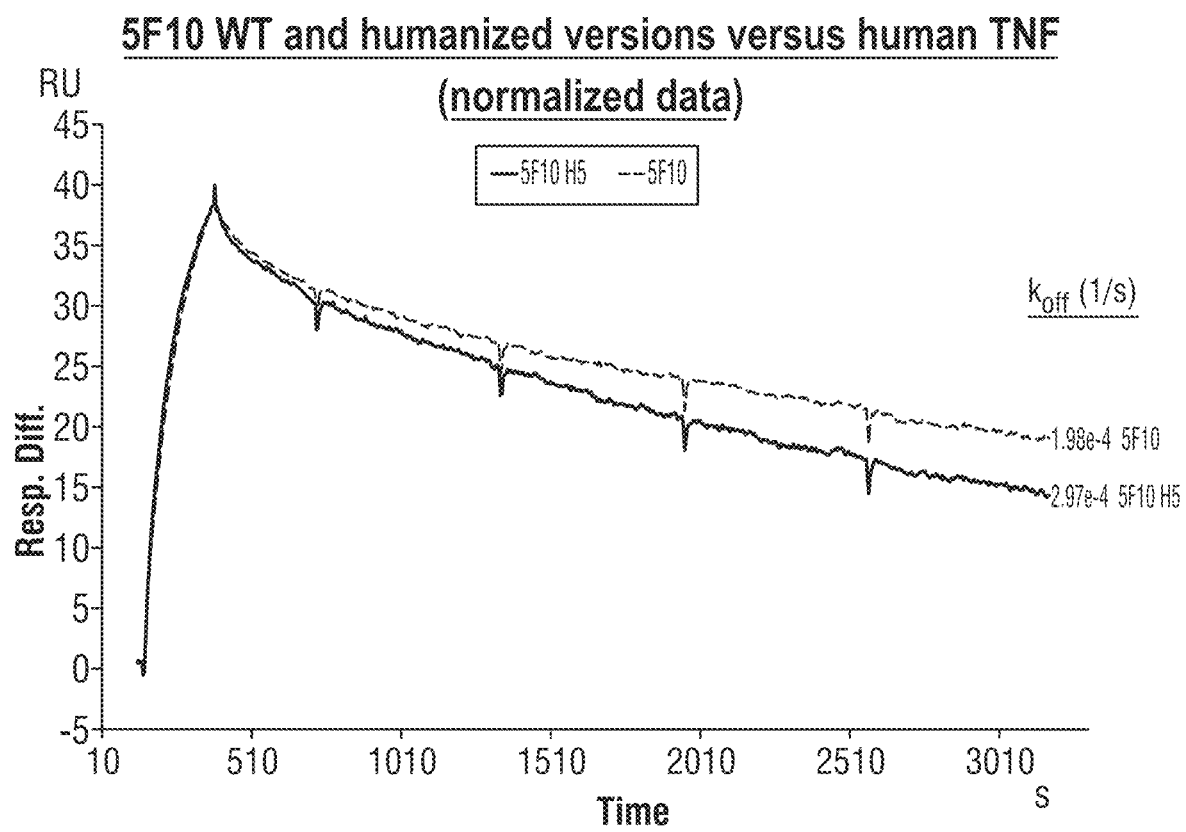
Figure 40 - continued

```
                    1                                                    50
PMP1C2+M13rev  (1)  QVQLV SGGGLVQ GGSLRLSCAA GF FS      RQAPG  L
       VHH1A   (1)  QVQL  SGGGLVQ GGSLRLSCAT SGFDFSVS      RQAPG  L
       VHH3E   (1)  QVQL  SGGGLVQ GGSLRLSCA SG  S  SGYT  GWFRQAPG E
       VHH3G   (1)  QVQL  SGGGLVQAGGSLRLSCAVSG  FSA S--V  GWFRQAPG E
    Consensus  (1)  QVQLQESGGGLVQPGGSLRLSCAASGRTFSDHW   YTMYWVRQAPGKGR
                    51                                                  100
PMP1C2+M13rev (46)   V EINTN   I KYP SVKGRF  SRD AKNT L    LKPEDTA  Y
       VHH1A  (46)   V EINTN   I KYV SVKGRF  SRD AKNT L MD LKPEDTA  Y
       VHH3E  (51)   V  I    G T Y  SVKGRFAISRDIAKN  DLTM NL PEDTA  Y
       VHH3G  (49)   V  I   A T Y  SVKGRF  SRD AKNT DLL   KPEDTA  Y
    Consensus (51)  EFVARIYWSSLNTYYADSVKGRFTISRDNAKNTLYLQMNSLKPEDTALYY
                    101                      129
PMP1C2+M13rev (96)  CA      -SP-- C -NRG  T  T  SS (SEQ ID NO: 52)
       VHH1A  (96)  CA      -SP-- CS- RGQ T V SS (SEQ ID NO: 483)
       VHH3E (101)  CAA          N     GQ T  T SS (SEQ ID NO: 484)
       VHH3G  (99)  CAA          O     GQ T  T SS (SEQ ID NO: 485)
    Consensus (101) CARRDGIPTSRSVSSYNYWGQGTQVTVSS (SEQ ID NO: 486)
```

Figure 61

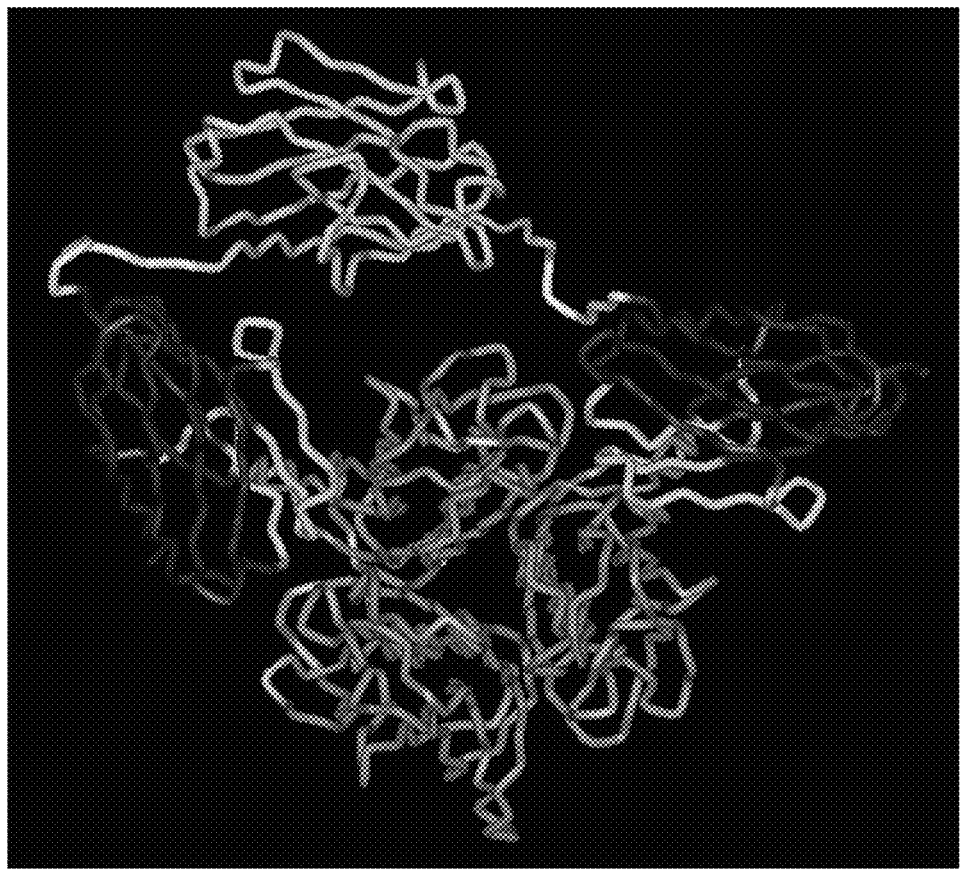

Figure 62

US 11,472,871 B2

NANOBODIES AGAINST TUMOR NECROSIS FACTOR-ALPHA

RELATED APPLICATIONS

This application is a continuation of U.S. application Ser. No. 15/644,890, filed Jul. 10, 2017, which is a continuation of U.S. application Ser. No. 14/709,870, which is a continuation of U.S. application Ser. No. 14/191,907, filed Feb. 27, 2014 and now issued as U.S. Pat. No. 9,067,991, which is a divisional of U.S. application Ser. No. 11/920,677, filed Jul. 30, 2010 and now issued as U.S. Pat. No. 8,703,131, which is a national stage filing under 35 U.S.C. § 371 of international application PCT/EP2006/004678, filed May 17, 2006, and claims the benefit under 35 U.S.C. § 119(e) of U.S. provisional application Ser. No. 60/682,332, filed May 18, 2005, the disclosures of each of which are incorporated by reference herein in their entirities.

INCORPORATION BY REFERENCE

This application contains a Sequence Listing which has been filed electronically in ASCII and is hereby incorporated by reference in its entirety. This ASCII copy, created on Jun. 30, 2021, is named A084870008US06-SUBSEQ-CRP and is 225,035 bytes in size.

The present invention relates to improved Nanobodies™ against Tumor Necrosis Factor-alpha (TNF-alpha), as well as to polypeptides comprising or essentially consisting of one or more of such Nanobodies. [Note: Nanobody™, Nanobodies™ and Nanoclone™ are trademarks of Ablynx N.V.]

The invention also relates to nucleic acids encoding such Nanobodies and polypeptides; to methods for preparing such Nanobodies and polypeptides; to host cells expressing or capable of expressing such Nanobodies or polypeptides; to compositions comprising such Nanobodies, polypeptides, nucleic acids or host cells; and to uses of such Nanobodies, such polypeptides, such nucleic acids, such host cells or such compositions, in particular for prophylactic, therapeutic or diagnostic purposes, such as the prophylactic, therapeutic or diagnostic purposes mentioned below.

Other aspects, embodiments, advantages and applications of the invention will become clear from the further description hereinbelow.

WO 04/041862 by applicant relates to Nanobodies against TNF-alpha and to the preparation and use thereof, in particular for the prevention and/or treatment of diseases and disorders associated with and/or mediated by TNF-alpha, such as inflammation, rheumatoid arthritis, Crohn's disease, ulcerative colitis, inflammatory bowel syndrome, multiple sclerosis, addison's disease, autoimmune hepatitis, autoimmune parotitis, diabetes type 1, epididymitis, glomerulonephritis, Graves' disease, Guillain-Barre syndrome, Hashimoto's disease, hemolytic anemia, systemic lupus erythematosus, male infertility, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, and vasculitis.

The anti-TNF Nanobodies according to WO 04/041862 may be humanized and may be monovalent or multivalent, the latter of which leads to increased affinity for TNF. The anti-TNF Nanobodies™ according to WO 04/041862 may also be multispecific, and may in particular be in the form of a multispecific construct comprising two or more Nanobodies against TNF and a further Nanobody directed against a serum protein such as human serum albumin, which leads to an increased half-life in vivo.

WO 04/041862 also relates to methods for the preparation of the anti-TNF Nanobodies, to nucleic acids or constructs encoding the anti-TNF Nanobodies, as well as to pharmaceutical compositions comprising the anti-TNF Nanobodies, which may be suitable for intravenous, subcutaneous, oral, sublingual, topical, nasal, vaginal or rectal administration, or for administration by inhalation. The anti-TNF Nanobodies according to WO 04/041862 may also be used for diagnostic purposes, optionally in the form of a kit-of-parts.

EP 0 486 526 describes TNF-alpha binding ligands against a specific epitope of TNF. Among the binding ligands, single domain antibodies ("dAbs") are mentioned.

Reiter et al., *J. Mol. Biol.* (1999), 290, 685-698 describe single domain antibodies against TNF-alpha obtained from a randomized phage display library that was generated starting from a VH domain scaffold from a mouse hybridoma.

WO 00/29004 describes murine single domain antibodies ("microbodies") against TNF-alpha.

WO 04/003019 inter alia describes ligands comprising a first binding domain against TNF-alpha and a second binding domain against a serum protein such as serum albumin.

It is a general object of the present invention to provide Nanobodies against TNF-alpha, in particular against human TNF-alpha.

In particular, it is an object of the present invention to provide Nanobodies against TNF-alpha, in particular against human TNF-alpha, and to provide proteins or polypeptides comprising the same, that are suitable for therapeutic and/or diagnostic use, and in particular for the prevention, treatment and/or diagnosis of one or more diseases and disorders associated with and/or mediated by TNF-alpha such as those mentioned above, and/or that can be used in the preparation of a pharmaceutical composition for the prevention and/or treatment of one or more diseases associated with and/or mediated by TNF-alpha, such as those mentioned above.

More in particular, it is an object of the invention to provide Nanobodies against TNF-alpha, and to provide proteins and polypeptides comprising the same, that are either an alternative to the Nanobodies and polypeptides against TNF-alpha described in WO 04/041862 and/or that have one or more improved properties or characteristics, compared to the Nanobodies and polypeptides against TNF-alpha described in WO 04/041862.

More in particular, it is an object of the invention to provide Nanobodies against TNF-alpha, and to provide proteins or polypeptides comprising the same, that are improved compared to the Nanobodies and polypeptides against TNF-alpha described in WO 04/041862 with respect to one or more of the following properties or characteristics:
  increased affinity for TNF-alpha, either in a monovalent format, in a multivalent format (for example in a bivalent format) and/or in a multispecific format (for example one of the multispecific formats described in WO 04/041862 or hereinbelow);
  better suitability for formatting in a multivalent format (for example in a bivalent format);
  better suitability for formatting in a multispecific format (for example one of the multispecific formats described in WO 04/041862 or hereinbelow);
  improved suitability or susceptibility for "humanizing" substitutions (as defined herein); and/or
  less immunogenicity, either in a monovalent format, in a multivalent format (for example in a bivalent format) and/or in a multispecific format (for example one of the multispecific formats described in WO 04/041862 or hereinbelow) in a monovalent format;

increased stability, either in a monovalent format, in a multivalent format (for example in a bivalent format) and/or in a multispecific format (for example one of the multispecific formats described in WO 04/041862 or hereinbelow) in a monovalent format;

increased specificity towards TNF-alpha, either in a monovalent format, in a multivalent format (for example in a bivalent format) and/or in a multispecific format (for example one of the multispecific formats described in WO 04/041862 or hereinbelow) in a monovalent format;

decreased or where desired increased cross-reactivity with TNF-alpha from different species;

and/or one or more other improved properties desirable for pharmaceutical use (including prophylactic use and/or therapeutic use) and/or for diagnostic use (including but not limited to use for imaging purposes), either in a monovalent format, in a multivalent format (for example in a bivalent format) and/or in a multispecific format (for example one of the multispecific formats described in WO 04/041862 or hereinbelow).

These objects are achieved by the Nanobodies, proteins and polypeptides described herein. These Nanobodies are also referred to herein as "Nanobodies of the invention"; and these proteins and polypeptides are also collectively referred to herein "polypeptides of the invention".

Since the Nanobodies and polypeptides described herein are mainly intended for therapeutic and/or diagnostic use, they are directed against (as defined herein) human TNF-alpha. It is however not excluded (but also not required) that Nanobodies and polypeptides described herein show cross-reactivity with TNF-alpha from one or more other species of warm-blooded animals, for example with TNF-alpha from one or more other species of primates and/or with TNF-alpha from one or more species of animals that are often used in animal models for diseases (for example mouse, rat, rabbit, pig or dog), and in particular in animal models for diseases and disorders associated with TNF-alpha (such as the species and animal models mentioned herein). In this respect, it will be clear to the skilled person that such cross-reactivity, when present, may have advantages from a drug development point of view, since it allows the Nanobodies and polypeptides against human TNF-alpha to be tested in such disease models.

The present invention is in its broadest sense also not particularly limited to or defined by a specific antigenic determinant, epitope, part, domain, subunit or confirmation (where applicable) of TNF-alpha against which the Nanobodies and polypeptides of the invention are directed.

However, in a preferred embodiment, the Nanobodies, proteins or polypeptides described herein are directed against and/or can bind to an epitope of TNF-alpha that lies in and/or forms part of the TNF receptor binding site(s) (e.g. the binding sites for the TNF-RI, THF-RII, also known as p55 or p75). As is well known in the art, a TNF trimer comprises three receptor binding sites, which are essentially equivalent and which are formed by/at the interface of two TNF monomers within the TNF trimer. For example, the Nanobodies, proteins or polypeptides described herein are preferably directed against and/or can bind to an epitope of TNF-alpha that comprises the following amino acid residues of TNF-alpha: Gln at position 88, Lys at position 90, and/or Glu at position 146).

In particular, the Nanobodies, proteins or polypeptides described herein are directed against and/or can bind to an epitope of the TNF-alpha trimer, which lies in and/or forms part of the TNF receptor binding site(s). For example, the Nanobodies, proteins or polypeptides described herein may be directed against and/or can bind to an epitope of the TNF-alpha trimer that comprises the following amino acid residues: Gln at position 88 and Lys at position 90 on a first TNF monomer (referred to herein as "monomer A"), and Glu at position 146 on a second TNF monomer (referred to herein as "monomer B") (in which Monomer A and Monomer B together, in the TNF trimer, form the TNF receptor binding site(s)).

More particularly, the Nanobodies, proteins or polypeptides described herein may be directed against and/or can bind to an epitope of the TNF-alpha trimer that comprises the aforementioned amino acids (Gln at position 88 in monomer A; Lys at position 90 in monomer A and Glu at position 146 in monomer B), and in addition at least one, preferably two or more, more preferably 5 or more, and preferably all or essentially all, of the following amino acid residues of TNF-alpha monomer A: Gly at position 24, Gln at position 25, Thr at position 72, His at position 73, Val at position 74, Leu at position 75, Thr at position 77, Thr at position 79, Be at position 83, Thr at position 89, Val at position 91. Asn at position 92, Ile at position 97, Arg at position 131, Glu at position 135, Ile at position 136, Asn at position 137, Arg at position 138, Pro at position 139, Asp at position 140 and the following residues in monomer B: Pro at position 20, Arg at position 32, Lys at position 65, Lys at position 112, Tyr at position 115, Ala at position 145, Ser at position 147.

Alternatively, the Nanobodies, proteins or polypeptides described herein may be directed against and/or can bind to an epitope of TNF-alpha that comprises the aforementioned amino acids (Gln at position 88 in monomer A; Lys at position 90 in monomer A and Glu at position 146 in monomer B), and in addition at least one, preferably two or more, more preferably 5 or more and preferably all or essentially all, of the following amino acid residues of TNF-alpha monomer A: Leu at position 75, Thr at position 77, Thr at position 79, Be at position 80, Ser at position 81, Tyr at position 87, Thr at position 89, Val at position 91, Asn at position 92, Ser at position 95, Be at position 97, Glu at position 135, Ile at position 136, Asn at position 137 and the following residues in monomer B: Ala at position 33, Ala at position 145, Ser at position 147.

Such epitope can be delineated from structural analysis of the nanobody crystallized in complex with the TNF molecule, or from other approaches such as epitope mapping via pepscan analysis.

By comparison, from crystallographic data (not shown), it can be seen that the Nanobody 3E from WO 04/041862 binds to a different epitope (i.e. an epitope comprising Tyr at position 141, Asp at position 140, Gln at position 67, Gly at position 24 and Glu at position 23) than the preferred epitope of the invention.

Thus, in another aspect, the present invention relates to an immunoglobulin variable domain (or a suitable fragment thereof) that can bind to an epitope of TNF-alpha that lies in and/or forms part of the TNF receptor binding site, and preferably to an epitope that comprises at least one, preferably two or more, and preferably all, of the following amino acid residues of TNF-alpha: Gln at position 88; Lys at position 90 and Glu at position 146. Such an immunoglobulin variable domain is preferably a heavy chain variable domain or a light chain variable domain, and in particular a heavy chain variable domain, which may be any mammalian heavy chain variable domain, including but not limited to human heavy chain variable domains, mouse heavy chain variable domains and Camelid heavy chain variable domains (such as the heavy chain variable domains from Camelid 4-chain immunoglobulins or the heavy chain variable domains (VHH domains) from so-called heavy chain antibodies). The immunoglobulin variable domain is preferably a domain antibody or single domain antibody or suitable for use as a (single) domain antibody. Most preferably, the immunoglobulin variable domain is a Nanobody (as defined herein), and some preferred, but non-limiting examples of Nanobodies that are suitable for use in this aspect of the invention are PMP1C2 (TNF1, SEQ ID NO:52) and PMP5F10 (TNF3, SEQ ID NO: 60), as well as humanized and other variants thereof (as further described herein).

The aforementioned immunoglobulin variable domain may also be humanized (as for example, and without limitation) described herein with respect to Nanobodies. The invention also relates to proteins and polypeptides that comprise or essentially consist of such immunoglobulin variable domains, which may for example be as defined herein. Alternatively, such variable domains may form part of ScFv constructs, dual-specific constructs, chimeric antibody or antibody structures and other immunoglobulin constructs, as for example reviewed by Hoogenboom (Nature Biotechnology (1997), 15:125-126). Preferably, however, the immunoglobulin variable domains directed against the above epitope are Nanobodies, in which case the proteins and polypeptides comprising such Nanobodies may be as further described herein.

Thus, some preferred aspects of the invention relate to:
I) A Nanobody which is directed against the same epitope on the trimer of TNF-alpha as Nanobody TNF1 (SEQ ID NO: 52).
II) A Nanobody which is directed against the same epitope on the trimer of TNF-alpha as Nanobody TNF3 (SEQ ID NO: 60).
III) A Nanobody which is directed against an epitope of the trimer of TNF-alpha that at least comprises the following amino acid residues: Gln at position 88 in monomer A; Lys at position 90 in monomer A and Glu at position 146 in monomer B.
IV) A Nanobody which is directed against an epitope of the trimer of TNF-alpha that comprises the following amino acid residues: Gln at position 88 in monomer A; Lys at position 90 in monomer A and Glu at position 146 in monomer B; and that further comprises at least comprises at least one, preferably two or more, more preferably 5 or more, and preferably all or essentially all, of the following amino acid residues of TNF-alpha monomer A: Gly at position 24, Gln at position 25, Thr at position 72, His at position 73, Val at position 74, Leu at position 75, Thr at position 77, Thr at position 79, Ile at position 83, Thr at position 89, Val at position 91. Asn at position 92, Be at position 97, Arg at position 131, Glu at position 135, Ile at position 136, Asn at position 137, Arg at position 138, Pro at position 139, Asp at position 140 and the following residues in monomer B: Pro at position 20, Arg at position 32, Lys at position 65, Lys at position 112, Tyr at position 115, Ala at position 145, Ser at position 147.
V) A Nanobody which is directed against an epitope of the trimer of TNF-alpha that comprises the following amino acid residues: Gln at position 88 in monomer A; Lys at position 90 in monomer A and Glu at position 146 in monomer B; and that further comprises at least one, preferably two or more, more preferably 5 or more, and preferably all or essentially all, of the following amino acid residues of TNF-alpha monomer A Leu at position 75, Thr at position 77, Thr at position 79, Ile at position 80, Ser at position 81, Tyr at position 87, Thr at position 89, Val at position 91, Asn at position 92, Ser at position 95, Be at position 97, Glu at position 135, Ile at position 136, Asn at position 137 and the following residues in monomer B: Ala at position 33, Ala at position 145, Ser at position 147.

A Nanobody in accordance with any of I) to V) above, which has a $K_{off}$ rate for TNF of better than $2.10^{-3}$ (1/s), preferably better than $1.10^{-3}$.

A Nanobody in accordance with any one of I) to V) above, which has an EC50 value in the cell-based assay using KYM cells described in Example 1, under 3), of WO 04/041862 that is better than the EC50 value of Nanobody VHH 3E (SEQ ID NO:4) of WO 04/041862 in the same assay; or a humanized variant of such a Nanobody.

A Nanobody in accordance with any one of I) to V) above, which has an EC50 value in the cell-based assay using KYM cells described in Example 1, under 3), of WO 04/041862 that is better than 12 nM; or a humanized variant of such a Nanobody.

A Nanobody in accordance with any one of I) to V) above, which has an EC50 value in the cell-based assay using KYM cells described in Example 1, under 3), of WO 04/041862 that is better than 5 nM; or a humanized variant of such a Nanobody.

A Nanobody in accordance with any one of I) to V) above, which has an EC50 value in the cell-based assay using KYM cells described in Example 1, under 3), of WO 04/041862 that is better than 3 nM; or a humanized variant of such a Nanobody.

A Nanobody in accordance with any one of I) to V) above, which is a humanized Nanobody.

and some preferred aspects of this embodiment relate to:
A Nanobody in accordance with any one of I) to V) above, which is a GLEW-class Nanobody.
A Nanobody in accordance with any one of I) to V) above, which is a humanized GLEW-class Nanobody.
A Nanobody in accordance with any one of I) to V) above, which contains an arginine residue (R) at position 103.
A Nanobody in accordance with any one of I) to V) above, which contains an arginine residue (R) at position 103, and which is humanized
A Nanobody in accordance with any one of I) to V) above, which is a GLEW-class Nanobody, and which contains an arginine residue (R) at position 103, and which is humanized.
A Nanobody in accordance with any one of I) to V) above, which contains a leucine residue (L) at position 108.
A Nanobody in accordance with any one of I) to V) above, which has at least 80%, preferably at least 90%, more preferably at least 95%, even more preferably at least 99% sequence identity (as defined herein) with one of the amino acid sequences of SEQ ID NO's 52 (TNF1), 76 (TNF13), 77 (TNF14), 95 (TNF29) or 96 (TNF30)
A Nanobody in accordance with any one of I) to V) above, in which
a) CDR1 comprises:
the amino acid sequence DYWMY (SEQ ID NO: 164); or
an amino acid sequence that has at least 80%, preferably at least 90%, more preferably at least 95%, even more preferably at least 99% sequence identity with the amino acid sequence DYWMY (SEQ ID NO: 164); or
an amino acid sequences that has 2 or only 1 amino acid difference(s) with the amino acid sequence DYWMY (SEQ ID NO: 164);
and
b) CDR2 comprises:
the amino acid sequence EINTNGLITKYPDSVKG (SEQ ID NO: 232); or
an amino acid sequence that has at least 80%, preferably at least 90%, more preferably at least 95%, even more preferably at least 99% sequence identity with the amino acid sequence EINTNGLITKYPDSVKG (SEQ ID NO: 232); or
an amino acid sequences that has 2 or only 1 amino acid difference(s) with the amino acid sequence EINTNGLITKYPDSVKG (SEQ ID NO: 232);
and
c) CDR3 comprises:
the amino acid sequence SPSGFN (SEQ ID NO: 300); or
an amino acid sequence that has at least 80%, preferably at least 90%, more preferably at least 95%, even more preferably at least 99% sequence identity with the amino acid sequence SPSGFN (SEQ ID NO: 300); or
an amino acid sequences that has 2 or only 1 amino acid difference(s) with the amino acid sequence SPSGFN (SEQ ID NO: 300).

A Nanobody in accordance with any one of I) to V) above, in which CDR1 comprises the amino acid sequence DYWMY (SEQ ID NO: 164).

A Nanobody in accordance with any one of I) to V) above, in which CDR2 comprises the amino acid sequence EINTNGLITKYPDSVKG (SEQ ID NO: 232).

A Nanobody in accordance with any one of I) to V) above, in which CDR3 comprises the amino acid sequence SPSGFN (SEQ ID NO: 300).

A Nanobody in accordance with any one of I) to V) above, in which:
CDR1 comprises the amino acid sequence DYWMY (SEQ ID NO: 164); and CDR3 comprises the amino acid sequence SPSGFN (SEQ ID NO: 300); or
CDR1 comprises the amino acid sequence DYWMY (SEQ ID NO: 164); and CDR2 comprises the amino acid sequence EINTNGLITKYPDSVKG (SEQ ID NO: 232); or
CDR2 comprises the amino acid sequence EINTNGLITKYPDSVKG (SEQ ID NO: 232); and CDR3 comprises the amino acid sequence SPSGFN (SEQ ID NO: 300)

A Nanobody in accordance with any one of I) to V) above, in which CDR1 comprises the amino acid sequence DYWMY (SEQ ID NO: 164); and CDR3 comprises the amino acid sequence SPSGFN (SEQ ID NO: 300).

A Nanobody in accordance with any one of I) to V) above, in which CDR1 comprises the amino acid sequence DYWMY (SEQ ID NO: 164); CDR2 comprises the amino acid sequence EINTNGLITKYPDSVKG (SEQ ID NO: 232) and CDR3 comprises the amino acid sequence SPSGFN (SEQ ID NO: 300).

A Nanobody in accordance with any one of I) to V) above, in which
a) CDR1 is:
the amino acid sequence DYWMY (SEQ ID NO: 164); or
an amino acid sequence that has at least 80%, preferably at least 90%, more preferably at least 95%, even more preferably at least 99% sequence identity with the amino acid sequence DYWMY (SEQ ID NO: 164); or
an amino acid sequences that has 2 or only 1 amino acid difference with the amino acid sequence DYWMY (SEQ ID NO: 164);
and in which:
b) CDR2 is:
the amino acid sequence EINTNGLITKYPDSVKG (SEQ ID NO: 232); or
an amino acid sequence that has at least 80%, preferably at least 90%, more preferably at least 95%, even more preferably at least 99% sequence identity with the amino acid sequence EINTNGLITKYPDSVKG (SEQ ID NO: 232); or
an amino acid sequences that has 2 or only 1 amino acid difference(s) with the amino acid sequence EINTNGLITKYPDSVKG (SEQ ID NO: 232);
and in which
c) CDR3 is:
the amino acid sequence SPSGFN (SEQ ID NO: 300); or
an amino acid sequence that has at least 80%, preferably at least 90%, more preferably at least 95%, even more preferably at least 99% sequence identity with the amino acid sequence SPSGFN(SEQ ID NO: 300); or
an amino acid sequences that has 2 or only 1 amino acid difference with the amino acid sequence SPSGFN (SEQ ID NO: 300).

A Nanobody in accordance with any one of I) to V) above, in which CDR1 is the amino acid sequence DYWMY (SEQ ID NO: 164).

A Nanobody in accordance with any one of I) to V) above, in which CDR2 is the amino acid sequence EINTNGLITKYPDSVKG (SEQ ID NO: 232).

A Nanobody in accordance with any one of I) to V) above, in which CDR3 is the amino acid sequence SPSGFN (SEQ OD NO: 300)

A Nanobody in accordance with any one of I) to V) above, in which:
CDR1 is the amino acid sequence DYWMY (SEQ ID NO: 164); and CDR3 is the amino acid sequence SPSGFN (SEQ ID NO: 300); or
CDR1 is the amino acid sequence DYWMY (SEQ ID NO: 164); and CDR2 is the amino acid sequence EINTNGLITKYPDSVKG (SEQ ID NO:232); or
CDR2 is the amino acid sequence EINTNGLIT-KYPDSVKG (SEQ ID NO: 232); and CDR3 is the amino acid sequence SPSGFN (SEQ ID NO: 300)

A Nanobody in accordance with any one of I) to V) above, in which CDR1 is the amino acid sequence DYWMY (SEQ ID NO: 164); and CDR3 is the amino acid sequence SPSGFN (SEQ ID NO: 300).

A Nanobody in accordance with any one of I) to V) above, in which CDR1 is the amino acid sequence DYWMY (SEQ ID NO: 164); CDR2 is the amino acid sequence EINTNGLITKYPDSVKG (SEQ ID NO: 232) and CDR3 is the amino acid sequence SPSGFN (SEQ ID NO: 300).

A Nanobody in accordance with any one of I) to V) above, in which
any amino acid substitution is preferably a conservative amino acid substitution; and/or said amino acid sequence preferably only contains amino acid substitutions, and no amino acid deletions or insertions, compared to the above amino acid sequence(s).

and some other preferred aspects of this embodiment relate to:

A Nanobody in accordance with any one of I) to V) above, which is a KERE-class Nanobody A Nanobody in accordance with any one of I) to V) above, which is a humanized KERE-class Nanobody A Nanobody in accordance with any one of I) to V) above, which has at least 80%, preferably at least 90%, more preferably at least 95%, even more preferably at least 99% sequence identity (as defined herein) with one of the amino acid sequences of SEQ ID NO's 50 (TNF3), 83 (TNF20), 85 (TNF21), 85 (TNF22), 96 (TNF23) or 98 (TNF33).

A Nanobody in accordance with any one of I) to V) above, in which a) CDR1 is:
  the amino acid sequence NYYMG (SEQ ID NO: 172); or
  an amino acid sequence that has at least 80%, preferably at least 90%, more preferably at least 95%, even more preferably at least 99% sequence identity with the amino acid sequence NYYMG (SEQ ID NO: 172); or
  an amino acid sequences that has 2 or only 1 amino acid difference with the amino acid sequence NYYMG (SEQ ID NO: 172);
and
b) CDR2 is:
  the amino acid sequence NISWRGYNIYYKDSVKG (SEQ ID NO: 240); or
  an amino acid sequence that has at least 80%, preferably at least 90%, more preferably at least 95%, even more preferably at least 99% sequence identity with the amino acid sequence NISWRGY-NIYYKDSVKG (SEQ ID NO: 240); or an amino acid sequences that has 2 or only 1 amino acid difference(s) with the amino acid sequence NISWRGYNIYYKDSVKG;
and
c) CDR3 is:
  the amino acid sequence SILPLSDDPGWNTY (SEQ ID NO: 308); or
  an amino acid sequence that has at least 80%, preferably at least 90%, more preferably at least 95%, even more preferably at least 99% sequence identity with the amino acid sequence SILPLSDDPGWNTY (SEQ ID NO: 308); or
  an amino acid sequences that has 2 or only 1 amino acid difference with the amino acid sequence SIL-PLSDDPGWNTY (SEQ ID NO: 308).

A Nanobody in accordance with any one of I) to V) above, in which CDR1 is the amino acid sequence NYYMG (SEQ ID NO: 172).

A Nanobody in accordance with any one of I) to V) above, in which CDR2 is the amino acid sequence NISWRGY-NIYYKDSVKG (SEQ ID NO: 240).

A Nanobody in accordance with any one of I) to V) above, in which CDR3 is the amino acid sequence SIL-PLSDDPGWNTY (SEQ ID NO: 308).

A Nanobody in accordance with any one of I) to V) above, in which:
  CDR1 is the amino acid sequence NYYMG (SEQ ID NO: 172); and CDR3 is the amino acid sequence SILPLSDDPGWNTY (SEQ ID NO: 308); or
  CDR1 is the amino acid sequence NYYMG (SEQ ID NO: 172); and CDR2 is the amino acid sequence NISWRGYNIYYKDSVKG (SEQ ID NO: 240); or
  CDR2 is the amino acid sequence NISWRGY-NIYYKDSVKG (SEQ ID NO: 240); and CDR3 is the amino acid sequence SILPLSDDPGWNTY (SEQ ID NO: 308).

A Nanobody in accordance with any one of I) to V) above, in which CDR1 is the amino acid sequence NYYMG (SEQ ID NO: 172); CDR2 is the amino acid sequence SILPLSDDPGWNTY (SEQ ID NO: 308) and CDR3 is the amino acid sequence ILPLSDDPGWNTY (SEQ ID NO: 436).

A Nanobody in accordance with any one of I) to V) above, in which
  any amino acid substitution is preferably a conservative amino acid substitution; and/or
  said amino acid sequence preferably only contains amino acid substitutions, and no amino acid deletions or insertions, compared to the above amino acid sequence(s).

and with yet some other particularly preferred aspects being:

VI) A protein or polypeptide, which comprises a or essentially consists a Nanobody in accordance with any one of I) to V) above.

VII) A protein or polypeptide, which comprises or essentially consists of at least one Nanobody in accordance with any one of I) to V) above.

VIII) A protein or polypeptide, which comprises two Nanobodies in accordance with any one of I) to V) above.

IX) A protein or polypeptide, which comprises two Nanobodies in accordance with any one of I) to V) above, and which is such that said protein or polypeptide, upon binding to a TNF trimer, is capable inhibiting or reducing the TNF receptor crosslinking that is mediated by said TNF trimer and/or the signal transduction that is mediated by such receptor crosslinking.

X) A protein or polypeptide, which comprises two Nanobodies in accordance with any one of I) to V) above, and which is capable of intramolecular binding to at least two TNF receptor binding sites on a TNF trimer.

XI) A protein or polypeptide, which comprises two Nanobodies in accordance with any one of I) to V) above, linked via a suitable linker.

XII) A protein or polypeptide, which comprises two Nanobodies in accordance with any one of I) to V) above, linked via a suitable linker, and which is pegylated.

XIII) A protein or polypeptide which comprises two Nanobodies in accordance with any one of I) to V) above, and which further comprises at least one Nanobody directed against human serum albumin.

XIV) A protein or polypeptide which comprises two Nanobodies in accordance with any one of I) to V) above, and which further comprises at least one Nanobody directed against human serum albumin, and which is such that said protein or polypeptide, upon binding to a TNF trimer, is capable inhibiting or reducing the TNF receptor crosslinking that is mediated by said TNF trimer and/or the signal transduction that is mediated by such receptor crosslinking.

XV) A protein or polypeptide which comprises two Nanobodies in accordance with any one of I) to V) above, and which further comprises at least one Nanobody directed against human serum albumin and which is capable of intramolecular binding to at least two TNF receptor binding sites on a TNF trimer.

XVI) A protein or polypeptide which comprises two Nanobodies in accordance with any one of I) to V) above, and which further comprises one Nanobody directed against human serum albumin, in which each of the two Nanobodies in accordance with any one of I) to V) above is linked, optionally via a suitable linker, to the one Nanobody directed against human serum albumin.

XVII) A protein or polypeptide which comprises two Nanobodies in accordance with any one of I) to V) above, and which further comprises one Nanobody directed against human serum albumin, in which each of the two Nanobodies in accordance with any one of I) to V) above is linked, optionally via a suitable linker, to the one Nanobody directed against human serum albumin, and which is such that said protein or polypeptide, upon binding to a TNF trimer, is capable inhibiting or reducing the TNF receptor crosslinking that is mediated by said TNF trimer and/or the signal transduction that is mediated by such receptor crosslinking.

XVIII) A protein or polypeptide which comprises two Nanobodies in accordance with any one of I) to V) above, and which further comprises one Nanobody directed against human serum albumin, in which each of the two Nanobodies in accordance with any one of I) to V) above is linked, optionally via a suitable linker, to the one Nanobody directed against human serum albumin, and which is capable of intramolecular binding to at least two TNF receptor binding sites on a TNF trimer.

A protein or polypeptide in accordance with any one of VI) to XVIII) above, in which the at least one Nanobody directed against human serum albumin is a humanized Nanobody.

A protein or polypeptide in accordance with any one of VI) to XVIII) above, in which the at least one Nanobody directed against human serum albumin is a humanized variant of the Nanobody ALB 1 (SEQ ID NO: 63).

A protein or polypeptide in accordance with any one of VI) to XVIII) above, in which the at least one Nanobody directed against human serum albumin is a chosen from the group consisting of ALB 3 (SEQ ID NO: 87), ALB 4 (SEQ ID NO: 88), ALB 5 (SEQ ID NO: 89), ALB 6 (SEQ ID NO: 100), ALB 7 (SEQ ID NO: 101), ALB 8 (SEQ ID NO: 102) ALB 9 (SEQ ID NO: 103) and ALB 10 (SEQ ID NO: 104).

A protein or polypeptide in accordance with any one of VI) to XVIII) above, in which the at least one Nanobody directed against human serum albumin is ALB 8.

A protein or polypeptide in accordance with any one of VI) to XVIII) above, which comprises or essentially consists of two humanized Nanobodies in accordance with any one of I) to V) above, and one humanized variant of the Nanobody ALB 1 (SEQ ID NO: 63).

It should be noted that when a Nanobody is mentioned above as being "in accordance with any one of I) to V) above", it is at least according to one of I) to V), may be according to two or more of I) to V), and may also include any one or more of the other aspects that are indicated as being "in accordance with any one of I) to V) above. Similarly, when a protein or polypeptide is mentioned above as being "in accordance with any one of VI) to XVIII) above", it is at least according to one of VI) to XVIII), may be according to two or more of VI) to XVIII), and may also include any one or more of the other aspects that are indicated as being "in accordance with any one of VI) to XVIII) above.

It is also within the scope of the invention that, where applicable, a Nanobody or polypeptide of the invention can bind to two or more antigenic determinants, epitopes, parts, domains, subunits or confirmations of TNF-alpha. In such a case, the antigenic determinants, epitopes, parts, domains or subunits of TNF-alpha to which the Nanobodies and/or polypeptides of the invention bind may be the essentially same (for example, if TNF-alpha contains repeated structural motifs or is present as a multimer) or may be different (and in the latter case, the Nanobodies and polypeptides of the invention may bind to such different antigenic determinants, epitopes, parts, domains, subunits of TNF-alpha with an affinity and/or specificity which may be the same or different). Also, for example, when TNF-alpha exists in an activated conformation and in an inactive conformation, the Nanobodies and polypeptides of the invention may bind to either one of these conformation, or may bind to both these conformations (i.e. with an affinity and/or specificity which may be the same or different). Also, for example, the Nanobodies and polypeptides of the invention may bind to a conformation of TNF-alpha in which it is bound to a pertinent ligand, may bind to a conformation of TNF-alpha in which it not bound to a pertinent ligand, or may bind to both such conformations (again with an affinity and/or specificity which may be the same or different).

It is also expected that the Nanobodies and polypeptides of the invention will generally bind to all naturally occurring or synthetic analogs, variants, mutants, alleles, parts and fragments of TNF-alpha, or at least to those analogs, variants, mutants, alleles, parts and fragments of TNF-alpha that contain one or more antigenic determinants or epitopes that are essentially the same as the antigenic determinant(s) or epitope(s) to which the Nanobodies and polypeptides of the invention bind in TNF-alpha (e.g. in wild-type TNF-alpha). Again, in such a case, the Nanobodies and polypeptides of the invention may bind to such analogs, variants, mutants, alleles, parts and fragments with an affinity and/or specificity that are the same as, or that different from (i.e. higher than or lower than), the affinity and specificity with which the Nanobodies of the invention bind to (wild-type) TNF-alpha. It is also included within the scope of the invention that the Nanobodies and polypeptides of the invention bind to some analogs, variants, mutants, alleles, parts and fragments of TNF-alpha, but not to others.

Generally, the Nanobodies and polypeptides of the invention will at least bind to those forms (including monomeric, multimeric and associated forms) that are the most relevant from a biological and/or therapeutic point of view, as will be clear to the skilled person.

Also, as TNF-alpha exists in a monomeric form and in multimeric forms, and in particular in trimeric form, it is within the scope of the invention that the Nanobodies and polypeptides of the invention only bind to TNF-alpha in monomeric form, or that the Nanobodies and polypeptides of the invention in addition also bind to one or more of such multimeric forms, such as the trimeric form of TNF; or may only bind to such a multimeric (e.g. trimeric) form. Thus, generally, when in this description reference is made to a Nanobody, protein or polypeptide that is directed to TNF-alpha, it should be understood that this also comprises Nanobodies directed against TNF-alpha in its trimeric form (including but not limited to Nanobodies against the receptor binding sites (e.g. the binding sites for the TNF-RI, THF-RII, also known as p55 or p'75) of such a trimer). In all these cases, the Nanobodies and polypeptides of the invention may bind to such multimers or associated protein complexes with an affinity and/or specificity that may be the same as or different from (i.e. higher than or lower than) the affinity and/or specificity with which the Nanobodies and polypeptides of the invention bind to TNF-alpha in its monomeric and non-associated state.

Also, generally, polypeptides of the invention that contain two or more Nanobodies directed against TNF-alpha may bind with higher avidity than the corresponding monomeric Nanobody or Nanobodies.

For example, and without limitation, a multivalent (as defined herein) protein or polypeptide that contains two or more Nanobodies that are directed against different epitopes of TNF-alpha multivalent (as defined herein) protein or polypeptide that contains two or more Nanobodies that are directed against different epitopes of TNF-alpha may bind to TNF-alpha with higher avidity than the corresponding monomers.

More importantly, a multivalent (as defined herein) protein or polypeptide that contains two or more Nanobodies that are directed against TNF-alpha may (and usually will) bind with higher avidity to a multimer of TNF-alpha than to a monomer of TNF-alpha, and will usually also bind with higher avidity than the corresponding monomeric Nanobodies. In such a multivalent protein or polypeptide, the two or more Nanobodies may for example be directed against the same epitopes, substantially equivalent epitopes, or different epitopes. In one embodiment of such a multivalent protein or polypeptide, the two or more Nanobodies may be the same (and therefore be directed against the same epitope).

The latter is of particular importance, as it is known that the primary mode of signal transduction by TNF involves crosslinking by TNF receptors by a trimer of TNF molecules, which contains three receptor binding sites (see for example Peppel et al., *J. Exp. Med.*, 174 (1991), 1483-1489; Engelmann et al., *J. Biol. Chem.*, 265 (1990), 14497; Smith and Baglioni, *J. Biol. Chem.*, 264 (1989), 14646). For example, as described by Peppel et al., an engineered monovalent extracellular domain of the TNF receptor—which was only capable of blocking a single receptor binding site on a TNF trimer—was unable to prevent cross-linking of the TNF receptors by the remaining two receptor binding sites; whereas an engineered protein that comprises two such extracellular domains—thus being capable of blocking two receptor binding sites—provided a striking efficacy compared to the monovalent extracellular domain.

In the present invention, it has been found that monovalent Nanobodies are capable of binding to TNF alpha in such a way that the activity of TNF is reduced, both in in vitro models, in cellular models and in ex vivo models (see the Experimental Section below). Although the invention is not limited to any specific mechanism, explanation or hypothesis, it is assumed that because of their small size and high affinity for TNF-alpha, two or three monovalent Nanobodies of the invention are capable of simultaneously occupying two or three different receptor binding sites on the TNF trimer, thus preventing the trimer to initiate receptor cross-linking and thereby to initiate signal transduction (however, other mechanisms of action are not excluded: for example, depending on the epitope against which it is directed, a Nanobody of the invention may also inhibit the association of TNF into the trimeric state).

It should also be noted that, in addition or as an alternative to binding to two or more receptor binding sites on a single TNF-trimer, the proteins or polypeptides of the present invention that comprises or essentially consists of two or more immunoglobulin variable domains (or suitable fragments thereof) that are directed against epitopes of TNF-alpha may bind (e.g. intermolecularly) epitopes on two separate TNF-alpha molecules (e.g. two separate trimers).

However, according to one particularly preferred embodiment, the invention relates to a protein or polypeptide that comprises or essentially consists of two or more immunoglobulin variable domains (or suitable fragments thereof) that are each directed against epitopes on TNF-alpha (and in particular of the TNF-alpha trimer) that lie in and/or form part of the receptor binding site(s) of the TNF trimer, such that said polypeptide, upon binding to a TNF trimer, is capable inhibiting or reducing the TNF receptor crosslinking that is mediated by said TNF trimer and/or the signal transduction that is mediated by such receptor crosslinking.

In particular, according to this preferred embodiment, the invention relates to a protein polypeptide that comprises or essentially consist of two or more immunoglobulin variable domains (or suitable fragments thereof) that are each directed against epitopes on TNF-alpha (and in particular of the TNF-alpha trimer) that lie in and/or form part of the receptor binding site(s) of the TNF-trimer, wherein said immunoglobulin variable domains are linked to each other in such a way that the protein or polypeptide is capable of simultaneously binding to two or more receptor binding sites on a single TNF trimer (in other words, is capable of intramolecular binding to at least two TNF receptor binding sites on a TNF trimer). In this embodiment, the two or more immunoglobulin variable domains are preferably as defined above and are most preferably Nanobodies (so that the protein or polypeptide is a multivalent Nanobody construct, as further described herein). Also, in this embodiment, the two or more immunoglobulin variable domains may be the same or different; and may directed against different epitopes within the TNF receptor binding site(s), but are preferably directed against the same epitope.

In one preferred aspect of this embodiment, the two or more immunoglobulin variable domains are directed against epitopes of the TNF-alpha trimer, which epitopes lie in and/or form part of the TNF receptor binding site(s). For example, the two or more immunoglobulin variable domains are preferably directed against and/or can bind to an epitope of the TNF-alpha trimer that comprises the following amino acid residues: Gln at position 88 and Lys at position 90 on a first TNF monomer (referred to herein as "monomer A"), and Glu at position 146 on a second TNF monomer (referred to herein as "monomer B") (in which Monomer A and Monomer B together, in the TNF trimer, form the TNF receptor binding site(s)).

As further described below in more details with respect to Nanobodies, in such a protein or polypeptide, the at least two immunoglobulin variable domains are preferably linked in such a way that the distance between the N-terminus and the C-terminus of the two immunoglobulin variable domains present in such a protein or polypeptide is preferably at least 50 Angstroms, and more preferably in the region of 55-200 Angstroms, and more preferably in the region of Angstroms, and in particular in the region of 65-150 Angstroms.

In a particularly preferred aspect of this embodiment, these two or more immunoglobulin sequences are Nanobodies, and are preferably chosen from the Nanobodies described herein. Some particularly preferred Nanobodies for use in this embodiment of the invention are PMP1C2 (TNF1, SEQ ID NO:52) and/or PMP5F10 (TNF3, SEQ ID NO: 60), as well as humanized and other variants thereof (as described herein); with PMP1C2 (TNF1, SEQ ID NO:52) and its humanized variants being particularly preferred.

Accordingly, the present embodiment will now be described in more detail with reference to Nanobodies. However, it will be clear to the skilled person that the teaching herein may be applied analogously to immunoglobulin variable domains.

In this embodiment of the invention, the two or more immunoglobulin sequences will usually be linked via one or more suitable linkers, which linkers are such that each immunoglobulin sequence can bind to a different receptor binding site on the same TNF trimer. Suitable linkers will inter alia depend on (the distance between) the epitopes on the TNF trimer to which the immunoglobulin sequences bind, and will be clear to the skilled person based on the disclosure herein, optionally after some limited degree of routine experimentation. For example, when the two or more immunoglobulin sequences are (single) domain antibodies or Nanobodies, suitable linkers may be chosen from the linkers described herein, but with a linker length that is such that the two or more (single) domain antibodies or Nanobodies can each bind to a different receptor binding site on the same TNF trimer.

Also, when the two or more immunoglobulin sequences that bind to the receptor binding sites of TNF-alpha are (single) domain antibodies or Nanobodies, they may also be linked to each other via a third (single) domain antibody or Nanobody (in which the two or more immunoglobulin sequences may be linked directly to the third (single) domain antibody/Nanobody or via suitable linkers). Such a third (single) domain antibody or Nanobody may for example be a (single) domain antibody or Nanobody that provides for an increased half-life, as further described herein. For example, the latter (single) domain antibody or Nanobody may be a (single) domain antibody or Nanobody that is capable of binding to a (human) serum protein such as (human) serum albumin, as further described herein.

Alternatively, the two or more immunoglobulin sequences that bind to the receptor binding site(s) of TNF-alpha may be linked in series (either directly or via a suitable linker) and the third (single) domain antibody or Nanobody (which may provide for increased half-life, as described above) may be connected directly or via a linker to one of these two or more aforementioned immunoglobulin sequences. Some non-limiting examples of such constructs are the constructs of SEQ ID NOS: 93 or 94.

In particular, it has been found in the invention (see the crystallography data referred to herein) that, when the Nanobodies present in a multivalent or multispecific protein or polypeptide of the invention bind to the particular epitope described above (which is the epitope of TNF1 and its humanized variants, as well as of TNF3 and its humanized variants) then preferably, the two (or more) anti-TNF Nanobodies present in such a protein or polypeptide should be linked in such a way that the distance between the N-terminus and the C-terminus of two anti-TNF Nanobodies present in such a protein or polypeptide should preferably be at least 50 Angstroms, and more preferably in the region of 55-200 Angstroms, and in particular in the region of 65-150 Angstroms (with the upper limit being less critical, and being chosen for reasons of convenience, e.g. with a view to expression/production of the protein); or more generally that said distance should be such that it allows the protein or polypeptide to undergo intramolecular binding to the TNF-trimer (i.e. instead of intermolecular binding). The distance between the N-terminus and the C-terminus of two anti-TNF Nanobodies can be determined by any suitable means, such as by crystallography or molecular modelling (as described herein). These techniques generally also make it possible to determine whether a specific multivalent or multispecific protein or polypeptide is capable of providing intramolecular modelling. Alternatively, the present invention also provides a simple experiment using size-exclusion chromatography (as described by Santora et al., Anal. Biochem., 299: 119-129) that can be used to determine whether a given protein or polypeptide of the invention will (predominantly) provide intramolecular binding to a TNF-trimer or (predominantly) intermolecular binding between two or more TNF-trimers. Thus, in one particular embodiment of the invention, a protein or polypeptide of the invention is preferably such that in this experiment, it predominantly or essentially exclusively leads to intramolecular binding However, as emphasized above, it should be noted that proteins or polypeptides of the invention that operate via intermolecular binding of separate TNF-alpha molecules (e.g. trimers) are also within the scope of the present invention.

Thus, in another preferred aspect, the invention provides for a multivalent or multispecific protein or polypeptide that comprises at least two Nanobodies against TNF-alpha (and in particular of the TNF-alpha trimer), in which said Nanobodies are preferably directed to essentially the same epitope as Nanobody PMP1C2 (as mentioned herein), and in which said at least two Nanobodies are linked in such a way that the distance the distance between the N-terminus and the C-terminus of the at least two anti-TNF Nanobodies is such that the protein or polypeptide is capable of undergoing intramolecular binding (as described herein) with a TNF-trimer. Preferably, in such a protein or polypeptide, the distance between the N-terminus and the C-terminus of two anti-TNF Nanobodies is at least 50 Angstroms, and more preferably in the region of 55-200 Angstroms, and in particular in the region of 65-150 Angstroms.

In such a preferred protein or polypeptide, the two or more Nanobodies may be linked in any suitable fashion, as long as the preferred distance between the N-terminus and the C-terminus of the at least two anti-TNF Nanobodies can be achieved, and/or as long as the protein or polypeptide is capable of undergoing intramolecular binding (as described herein) with a TNF-trimer.

For example, in its simplest form, the at least two Nanobodies are directly linked via a suitable linker or spacer that provides for the preferred distance between the N-terminus and the C-terminus of the at least two anti-TNF Nanobodies and which may allow the protein or polypeptide to undergo intramolecular binding (as described herein) with a TNF-trimer. Suitable linkers are described herein, and may—for example and without limitation—comprise an amino acid sequence, which amino acid sequence preferably has a length of 14 amino acids, more preferably at least 17 amino acids, such as about 20-40 amino acid sequence (which, using an average distance of 3.5 Angstrom for one amino acid, corresponds to linker lengths of 49 Angstroms, 59.5 Angstroms and about 70 Angstroms, respectively; with the maximum amount of amino acids being calculated in the same way based on the distances mentioned above). Preferably, such an amino acid sequence should also be such that it allows the protein or polypeptide to undergo intramolecular binding (as described herein) with a TNF-trimer.

Thus, in another preferred aspect, the invention provides for a multivalent or multispecific protein or polypeptide that comprises at least two Nanobodies against TNF-alpha (and in particular of the TNF-alpha trimer), in which said Nanobodies are preferably directed to essentially the same epitope as Nanobody PMP1C2 (as mentioned herein), and in which said at least two Nanobodies are directly linked to each other using a suitable linker or spacer such that the distance the distance between the N-terminus and the C-terminus of the at least two anti-TNF Nanobodies is such that the protein or polypeptide is capable of undergoing intramolecular binding (as described herein) with a TNF-trimer. Preferably, in such a protein or polypeptide, the distance between the N-terminus and the C-terminus of two anti-TNF Nanobodies (and thereby the preferred length of the linker or spacer) is at least 50 Angstroms, and more preferably in the region of 55-200 Angstroms, and in particular in the region of 65-150 Angstroms.

More preferably, in this preferred aspect, the linker or spacer is an amino acid sequence that comprises at least 14, preferably at least 17, more preferably at least 20 amino acids (with a non-critical upper limit chosen for reasons of convenience being abut 50, and preferably about 40 amino acids). In one preferred, but non-limiting embodiment, the linker essentially consists of glycine and serine residues (as further described below). For example, one suitable linker is the GS30 linker described herein, which comprises 30 amino acid residues.

In another embodiment, the at least two Nanobodies against TNF-alpha are linked to each other via another moiety (optionally via one or two linkers), such as another protein or polypeptide. In this embodiment, it may be desirable to have the preferred distance (i.e. as mentioned above) between the N-terminus and the C-terminus of the at least two anti-TNF Nanobodies, for example such that the protein or polypeptide can still undergo intramolecular binding (as described herein) with a TNF-trimer. In this embodiment, the at least two Nanobodies may be linked directly to the other moiety, or using a suitable linker or spacer, again as long as the preferred distance and/or desired intramolecular binding can still be achieved. The moiety may be any suitable moiety which does not detract (too much) from the binding of the protein or polypeptide to TNF and/or from the further desired biological or pharmacological properties of the protein or polypeptide. As such, the moiety may be essentially inactive or may be biologically active, and as such may or may not improve the desired properties of the protein or polypeptide and/or may confer one or more additional desired properties to the protein or polypeptide. For example, and without limitation, the moiety may improve the half-life of the protein or polypeptide, and/or may reduce its immunogenicity or improve any other desired property. In one preferred embodiment, the moiety may be another Nanobody (including but not limited to a third Nanobody against TNF-alpha, although this is not necessary and usually less preferred), and in particular another Nanobody that improves the half-life of the protein or polypeptide, such as a Nanobody that is directed against a serum protein, for example against human serum albumin. Examples of such proteins and polypeptides are described herein.

Thus, in one embodiment, the invention relates to a multivalent multispecific construct comprising two or more immunoglobulin sequences (or suitable fragments thereof) that are each directed against epitopes on TNF-alpha (e.g. of the TNF-alpha trimer) that lie in and/or form part of the receptor binding site, and that are linked to each other via at least one immunoglobulin sequence that provides for increased half-life (and optionally via one or more suitable linkers), such that said polypeptide, upon binding to a TNF trimer, is capable inhibiting or reducing the TNF receptor crosslinking and/or the signal transduction that is mediated by said TNF trimer. Such a polypeptide may be such such that said firstmentioned two or more immunoglobulin sequences can each bind to a different receptor binding site on a TNF trimer.

In particular, in this embodiment, the polypeptide may comprise a trivalent bispecific Nanobody, that comprises two Nanobodies that are each directed against epitopes on TNF-alpha (and in particular of the TNF-alpha trimer) that lie in and/or form part of the receptor binding site, in which said Nanobodies are linked to each other via a third Nanobody that provides for an increased half-life (e.g. a Nanobody that is directed to a serum protein such as human serum albumin), in which each of the firstmentioned two Nanobodies may be directly linked to said third Nanobody or via one or more suitable linkers, such that said polypeptide, upon binding to a TNF trimer, is capable inhibiting or reducing the TNF receptor crosslinking and/or the signal transduction that is mediated by said TNF trimer. Such a polypeptide may be such that said firstmentioned two Nanobodies can each bind to a different receptor binding site on a TNF trimer. Again, some particularly preferred Nanobodies for use in this embodiment of the invention are PMP1C2 (TNF1, SEQ ID NO:52) and/or PMP5F10 (TNF3, SEQ ID NO: 60), as well as humanized and other variants thereof (as described herein); with PMP1C2 (TNF1, SEQ ID NO:52) and its humanized variants being particularly preferred; and the Nanobodies directed against human serum albumin described herein. Some preferred, but non-limiting constructs of this embodiment of the invention are TNF 24 (SEQ ID NO: 90), TNF 26 (SEQ ID NO: 92), TNF 27 (SEQ ID NO: 93), TNF 28 (SEQ ID NO: 94), TNF 60 (SEQ ID NO: 417) and TNF 62 (SEQ ID NO:418), of which TNF 60 (SEQ ID NO: 417) is particularly preferred.

Thus, some preferred aspects of this embodiment of the invention relate to:

XIX) A protein or polypeptide that comprises or essentially consists of two or more immunoglobulin variable domains (or suitable fragments thereof) that are each directed against epitopes on TNF-alpha (and in particular of the TNF-alpha trimer) that lie in and/or form part of the receptor binding site(s) of the TNF trimer, such that said polypeptide, upon binding to a TNF trimer, is capable inhibiting or reducing the TNF receptor crosslinking that is mediated by said TNF trimer and/or the signal transduction that is mediated by such receptor crosslinking.

XX) A protein or polypeptide that comprises or essentially consists of two or more immunoglobulin variable domains (or suitable fragments thereof) that are each directed against epitopes on TNF-alpha (and in particular of the TNF-alpha trimer) that lie in and/or form part of the receptor binding site(s) of the TNF trimer, such that said polypeptide is capable intramolecular binding to at least two TNF receptor binding sites on a TNF trimer.

A protein or polypeptide in accordance with any one of XIX) to XX) above, in which said immunoglobulin variable domains are linked to each other in such a way that the protein or polypeptide is capable of simultaneously binding to two or more receptor binding sites on a single TNF trimer.

A protein or polypeptide in accordance with any one of XIX) to XX) above, in which said immunoglobulin variable domains are capable of binding to the same epitope as Nanobody TNF1 (SEQ ID NO: 52).

A protein or polypeptide in accordance with any one of XIX) to XX) above, in which said immunoglobulin variable domains are capable of binding against the epitope within the TNF receptor binding site of the TNF trimer that at least comprises the following amino acid residues: Gln at position 88 in monomer A; Lys at position 90 in monomer A and Glu at position 146 in monomer B.

A protein or polypeptide in accordance with any one of XIX) to XX) above, in which said immunoglobulin variable domains are capable of binding against the epitope within the TNF receptor binding site of the TNF trimer that at least comprises the following amino acid residues: Gln at position 88 in monomer A; Lys at position 90 in monomer A and Glu at position 146 in monomer B; and that further comprises at least one, preferably two or more, more preferably 5 or more, and preferably all or essentially all, of the following amino acid residues of TNF-alpha monomer A: Gly at position 24, Gln at position 25, Thr at position 72, His at position 73, Val at position 74, Leu at position 75, Thr at position 77, Thr at position 79, Be at position 83, Thr at position 89, Val at position 91. Asn at position 92, Ile at position 97, Arg at position 131, Glu at position 135, Ile at position 136, Asn at position 137, Arg at position 138, Pro at position 139, Asp at position 140 and the following residues in monomer B: Pro at position 20, Arg at position 32, Lys at position 65, Lys at position 112, Tyr at position 115, Ala at position 145, Ser at position 147.

A protein or polypeptide in accordance with any one of XIX) to XX) above, in which said immunoglobulin variable domains are capable of binding against the epitope within the TNF receptor binding site of the TNF trimer that at least comprises the following amino acid residues: Gln at position 88 in monomer A; Lys at position 90 in monomer A and Glu at position 146 in monomer B; and that further comprises at least one, preferably two or more, more preferably 5 or more, and preferably all or essentially all, of the following amino acid residues of TNF-alpha monomer A Leu at position 75, Thr at position 77, Thr at position 79, Ile at position 80, Ser at position 81, Tyr at position 87, Thr at position 89, Val at position 91, Asn at position 92, Ser at position 95, Be at position 97, Glu at position 135, Ile at position 136, Asn at position 137 and the following residues in monomer B: Ala at position 33, Ala at position 145, Ser at position 147.

A protein or polypeptide in accordance with any one of XIX) to XX) above, in which the at least two immunoglobulin variable domains are linked in such a way that the distance between the N-terminus of the first immunoglobulin variable domain and the C-terminus of the second immunoglobulin variable domain present in such a protein or polypeptide is at least 50 Angstroms.

A protein or polypeptide in accordance with any one of XIX) to XX) above, in which the distance between the N-terminus of the first immunoglobulin variable domain and the C-terminus of the second immunoglobulin variable domain is between 55-200 Angstroms A protein or polypeptide in accordance with any one of XIX) to XX) above, in which the distance between the N-terminus of the first immunoglobulin variable domain and the C-terminus of the second immunoglobulin variable domain is between 65-150 Angstroms A protein or polypeptide in accordance with any one of XIX) to XX) above, in which the first and second immunoglobulin variable domain are linked to each other via a linker or spacer.

A protein or polypeptide in accordance with any one of XIX) to XX) above, in which the linker or spacer is an amino acid sequence.

A protein or polypeptide in accordance with any one of XIX) to XX) above, in which the linker or spacer is comprises at least 14 amino acid residues.

A protein or polypeptide in accordance with any one of XIX) to XX) above, in which the linker or spacer is comprises at least 17-50 amino acid residues.

A protein or polypeptide in accordance with any one of XIX) to XX) above, in which the linker or spacer essentially consists of glycine and serine residues.

A protein or polypeptide in accordance with any one of XIX) to XX) above, in which the linker or spacer is GS30 (SEQ ID NO: 69).

A protein or polypeptide in accordance with any one of XIX) to XX) above, in which the first and second immunoglobulin variable domain are linked to each other via another moiety.

A protein or polypeptide in accordance with any one of XIX) to XX) above, in which said other moiety is a protein or polypeptide moiety.

A protein or polypeptide in accordance with any one of XIX) to XX) above, in which said other moiety confers at least one desired property to the protein or polypeptide, or improves at least one desired property of the protein or polypeptide.

A protein or polypeptide in accordance with any one of XIX) to XX) above, in which said other moiety improves the half-life of the protein or polypeptide and/or reduces the immunogenicity of the protein or polypeptide.

A protein or polypeptide in accordance with any one of XIX) to XX) above, in which each of the first and second immunoglobulin variable domain are linked to said other moiety via a linker or spacer.

A protein or polypeptide in accordance with any one of XIX) to XX) above, in which the linker or spacer is an amino acid sequence.

A protein or polypeptide in accordance with any one of XIX) to XX) above, in which the linker or spacer essentially consists of glycine and serine residues.

A protein or polypeptide in accordance with any one of XIX) to XX) above, in which the said other moiety is a Nanobody.

A protein or polypeptide in accordance with any one of XIX) to XX) above, in which the other moiety is a Nanobody directed against human serum albumin.

A protein or polypeptide in accordance with any one of XIX) to XX) above, in which the at least one Nanobody directed against human serum albumin is a humanized Nanobody.

A protein or polypeptide in accordance with any one of XIX) to XX) above, in which the at least one Nanobody directed against human serum albumin is a humanized variant of the Nanobody ALB 1 (SEQ ID NO: 63).

A protein or polypeptide in accordance with any one of XIX) to XX) above, in which the at least one Nanobody directed against human serum albumin is a chosen from the group consisting of ALB 3 (SEQ ID NO: 87), ALB 4 (SEQ ID NO: 88), ALB 5 (SEQ ID NO: 89), ALB 6 (SEQ ID NO: 100), ALB 7 (SEQ ID NO: 101), ALB 8 (SEQ ID NO: 102) ALB 9 (SEQ ID NO: 103) and ALB 10 (SEQ ID NO: 104).

A protein or polypeptide in accordance with any one of XIX) to XX) above, in which the at least one Nanobody directed against human serum albumin is ALB 8.

A protein or polypeptide in accordance with any one of XIX) to XX) above, in which the first and second immunoglobulin variable domains are Nanobodies.

A protein or polypeptide in accordance with any one of XIX) to XX) above, in which the first and second immunoglobulin variable domains are Nanobodies with a $K_{off}$ rate for TNF of better than $2.10^{-3}$ (1/s), preferably better than $1.10^{-3}$ (1/s); or a humanized variant of such a Nanobody.

A protein or polypeptide in accordance with any one of XIX) to XX) above, in which the first and second immunoglobulin variable domains are Nanobodies with an EC50 value in the cell-based assay using KYM cells described in Example 1, under 3), of WO 04/041862 that is better than the EC50 value of Nanobody VHH 3E (SEQ ID NO:4) of WO 04/041862 in the same assay; or a humanized variant of such a Nanobody.

A protein or polypeptide in accordance with any one of XIX) to XX) above, in which the first and second immunoglobulin variable domains are Nanobodies with an EC50 value in the cell-based assay using KYM cells described in Example 1, under 3), of WO 04/041862 that is better than 12 nM; or a humanized variant of such a Nanobody.

A protein or polypeptide in accordance with any one of XIX) to XX) above, in which the first and second immunoglobulin variable domains are Nanobodies with an EC50 value in the cell-based assay using KYM cells described in Example 1, under 3), of WO 04/041862 that is better than 5 nM; or a humanized variant of such a Nanobody.

A protein or polypeptide in accordance with any one of XIX) to XX) above, in which the first and second immunoglobulin variable domains are Nanobodies with an EC50 value in the cell-based assay using KYM cells described in Example 1, under 3), of WO 04/041862 that is better than 3 nM; or a humanized variant of such a Nanobody.

A protein or polypeptide in accordance with any one of XIX) to XX) above, in which the first and second immunoglobulin variable domains are Nanobodies in accordance with any one of XIX) to XX) above, which are humanized;

with some particularly preferred aspects of this embodiment being:

A protein or polypeptide in accordance with any one of XIX) to XX) above, in which the first and second immunoglobulin variable domains are GLEW-class Nanobodies.

A protein or polypeptide in accordance with any one of XIX) to XX) above, in which the first and second immunoglobulin variable domains are Nanobodies with an arginine residue (R) at position 103.

A protein or polypeptide in accordance with any one of XIX) to XX) above, in which the first and second immunoglobulin variable domains are GLEW-class Nanobodies with an arginine residue (R) at position 103.

A protein or polypeptide in accordance with any one of XIX) to XX) above, in which the first and second immunoglobulin variable domains are Nanobodies with at least 80%, preferably at least 90%, more preferably at least 95%, even more preferably at least 99% sequence identity (as defined herein) with one of the amino acid sequences of SEQ ID NO's 52 (TNF1), 76 (TNF13), 77 (TNF14), 95 (TNF29) or 96 (TNF30)

A protein or polypeptide in accordance with any one of XIX) to XX) above, in which the first and second immunoglobulin variable domains are Nanobodies as described for the proteins or polypeptides in accordance with any one of XIX) to XX) in which:

a) CDR1 comprises:
the amino acid sequence DYWMY (SEQ ID NO: 164); or
an amino acid sequence that has at least 80%, preferably at least 90%, more preferably at least 95%, even more preferably at least 99% sequence identity with the amino acid sequence DYWMY (SEQ ID NO: 164); or
an amino acid sequences that has 2 or only 1 amino acid difference(s) with the amino acid sequence DYWMY (SEQ ID NO: 164);
and
b) CDR2 comprises:
the amino acid sequence EINTNGLITKYPDSVKG (SEQ ID NO: 233); or
an amino acid sequence that has at least 80%, preferably at least 90%, more preferably at least 95%, even more preferably at least 99% sequence identity with the amino acid sequence EINTNGLITKYPDSVKG (SEQ ID NO: 233); or
an amino acid sequences that has 2 or only 1 amino acid difference(s) with the amino acid sequence EINTNGLITKYPDSVKG (SEQ ID NO: 233);
and
c) CDR3 comprises:
the amino acid sequence SPSGFN (SEQ ID NO: 300); or
an amino acid sequence that has at least 80%, preferably at least 90%, more preferably at least 95%, even more preferably at least 99% sequence identity with the amino acid sequence SPSGFN (SEQ ID NO: 300); or
an amino acid sequences that has 2 or only 1 amino acid difference(s) with the amino acid sequence SPSGFN (SEQ ID NO: 300).

A protein or polypeptide in accordance with any one of XIX) to XX) above, in which the first and second immunoglobulin variable domains are Nanobodies as described for the proteins or polypeptides in accordance with any one of XIX) to XX) in which CDR1 comprises the amino acid sequence DYWMY (SEQ ID NO: 164).

A protein or polypeptide in accordance with any one of XIX) to XX), in which the first and second immunoglobulin variable domains are Nanobodies as described for the proteins or polypeptides in accordance with any one of XIX) to XX) in which CDR2 comprises the amino acid sequence EINTNGLITKYPDSVKG (SEQ ID NO: 233).

A protein or polypeptide in accordance with any one of XIX) to XX), in which the first and second immunoglobulin variable domains are Nanobodies as described for the proteins or polypeptides in accordance with any one of XIX) to XX) in which CDR3 comprises the amino acid sequence SPSGFN (SEQ ID NO: 300)

A protein or polypeptide in accordance with any one of XIX) to XX), in which the first and second immunoglobulin variable domains are Nanobodies as described for the proteins or polypeptides in accordance with any one of XIX) to XX) in which:

CDR1 comprises the amino acid sequence DYWMY (SEQ ID NO: 164); and CDR3 comprises the amino acid sequence SPSGFN (SEQ ID NO: 300); or CDR1 comprises the amino acid sequence DYWMY (SEQ ID NO: 164); and CDR2 comprises the amino acid sequence EINTNGLITKYPDSVKG (SEQ ID NO: 233); or CDR2 comprises the amino acid sequence EINTNGLITKYPDSVKG (SEQ ID NO: 233); and CDR3 comprises the amino acid sequence SPSGFN (SEQ ID NO: 300)

A protein or polypeptide in accordance with any one of XIX) to XX), in which the first and second immunoglobulin variable domains are Nanobodies as described for the proteins or polypeptides in accordance with any one of XIX) to XX) in which CDR1 comprises the amino acid sequence DYWMY (SEQ ID NO: 164); and CDR3 comprises the amino acid sequence SPSGFN (SEQ ID NO: 300).

A protein or polypeptide in accordance with any one of XIX) to XX), in which the first and second immunoglobulin variable domains are Nanobodies as described for the proteins or polypeptides in accordance with any one of XIX) to XX) in which CDR1 comprises the amino acid sequence DYWMY (SEQ ID NO: 164); CDR2 comprises the amino acid sequence EINTNGLITKYPDSVKG (SEQ ID NO: 233) and CDR3 comprises the amino acid sequence SPSGFN (SEQ ID NO: 300).

A protein or polypeptide in accordance with any one of XIX) to XX), in which the first and second immunoglobulin variable domains are Nanobodies as described for the proteins or polypeptides in accordance with any one of XIX) to XX) in which a) CDR1 is:
  the amino acid sequence DYWMY (SEQ ID NO: 164); or
  an amino acid sequence that has at least 80%, preferably at least 90%, more preferably at least 95%, even more preferably at least 99% sequence identity with the amino acid sequence DYWMY (SEQ ID NO: 164); or
  an amino acid sequences that has 2 or only 1 amino acid difference with the amino acid sequence DYWMY (SEQ ID NO: 164);
and in which:
b) CDR2 is:
  the amino acid sequence EINTNGLITKYPDSVKG (SEQ ID NO: 233); or
  an amino acid sequence that has at least 80%, preferably at least 90%, more preferably at least 95%, even more preferably at least 99% sequence identity with the amino acid sequence EINTNGLITKYPDSVKG (SEQ ID NO: 233); or
  an amino acid sequences that has 2 or only 1 amino acid difference(s) with the amino acid sequence EINTNGLITKYPDSVKG (SEQ ID NO: 233);
and in which
c) CDR3 is:
  the amino acid sequence SPSGFN (SEQ ID NO: 300); or
  an amino acid sequence that has at least 80%, preferably at least 90%, more preferably at least 95%, even more preferably at least 99% sequence identity with the amino acid sequence SPSGFN (SEQ ID NO: 300); or
  an amino acid sequences that has 2 or only 1 amino acid difference with the amino acid sequence SPSGFN (SEQ ID NO: 300).

A protein or polypeptide in accordance with any one of XIX) to XX), in which the first and second immunoglobulin variable domains are Nanobodies as described for the proteins or polypeptides in accordance with any one of XIX) to XX) in which CDR1 is the amino acid sequence DYWMY (SEQ ID NO: 164).

A protein or polypeptide in accordance with any one of XIX) to XX), in which the first and second immunoglobulin variable domains are Nanobodies as described for the proteins or polypeptides in accordance with any one of XIX) to XX) in which CDR2 is the amino acid sequence EINTNGLITKYPDSVKG (SEQ ID NO: 233).

A protein or polypeptide in accordance with any one of XIX) to XX), in which the first and second immunoglobulin variable domains are Nanobodies as described for the proteins or polypeptides in accordance with any one of XIX) to XX) in which CDR3 is the amino acid sequence SPSGFN (SEQ ID NO: 300)

A protein or polypeptide in accordance with any one of XIX) to XX), in which the first and second immunoglobulin variable domains are Nanobodies as described for the proteins or polypeptides in accordance with any one of XIX) to XX) in which:
  CDR1 is the amino acid sequence DYWMY (SEQ ID NO: 164); and CDR3 is the amino acid sequence SPSGFN (SEQ ID NO: 300); or
  CDR1 is the amino acid sequence DYWMY (SEQ ID NO: 164); and CDR2 is the amino acid sequence EINTNGLITKYPDSVKG (SEQ ID NO: 233); or
  CDR2 is the amino acid sequence EINTNGLITKYPDSVKG (SEQ ID NO: 233); and CDR3 is the amino acid sequence SPSGFN (SEQ ID NO: 300)

A protein or polypeptide in accordance with any one of XIX) to XX), in which the first and second immunoglobulin variable domains are Nanobodies as described for the proteins or polypeptides in accordance with any one of XIX) to XX) in which CDR1 is the amino acid sequence DYWMY (SEQ ID NO: 164); and CDR3 is the amino acid sequence SPSGFN (SEQ ID NO: 300).

A protein or polypeptide in accordance with any one of XIX) to XX), in which the first and second immunoglobulin variable domains are Nanobodies as described for the proteins or polypeptides in accordance with any one of XIX) to XX) in which CDR1 is the amino acid sequence DYWMY (SEQ ID NO: 164); CDR2 is the amino acid sequence EINTNGLITKYPDSVKG (SEQ ID NO:233) and CDR3 is the amino acid sequence SPSGFN (SEQ ID NO: 300).

A protein or polypeptide in accordance with any one of XIX) to XX), in which the first and second immunoglobulin variable domains are Nanobodies as described for the proteins or polypeptides in accordance with any one of XIX) to XX) in which
  any amino acid substitution is preferably a conservative amino acid substitution; and/or
  said amino acid sequence preferably only contains amino acid substitutions, and no amino acid deletions or insertions, compared to the above amino acid sequence(s).

A protein or polypeptide in accordance with any one of XIX) to XX), in which the first and second immunoglobulin variable domains are chosen from the group consisting of the Nanobody TNF 1 (SEQ ID NO: 52) and humanized variants of the Nanobody TNF 1 (SEQ ID NO: 52).

A protein or polypeptide in accordance with any one of XIX) to XX), in which the first and second immunoglobulin variable domains are chosen from the group consisting of TNF 13 (SEQ ID NO: 76), TNF 14 (SEQ ID NO: 77), TNF 29 (SEQ ID NO: 95) and TNF 30 (SEQ ID NO:96).

A protein or polypeptide in accordance with any one of XIX) to XX), in which the first and second immunoglobulin variable domains are TNF 30 (SEQ ID NO:96);

and with some particularly preferred aspects of this embodiment being:

A protein or polypeptide in accordance with any one of XIX) to XX), in which the first and second immunoglobulin variable domains are KERE-class Nanobodies.

A protein or polypeptide in accordance with any one of XIX) to XX), in which the first and second immunoglobulin variable domains are Nanobodies with at least 80%, preferably at least 90%, more preferably at least 95%, even more preferably at least 99% sequence identity (as defined herein) with one of the amino acid sequences of SEQ ID NO's 50 (TNF3), 83 (TNF20), 85 (TNF21), 85 (TNF22), 96 (TNF23) or 98 (TNF33).

A protein or polypeptide in accordance with any one of XIX) to XX), in which the first and second immunoglobulin variable domains are Nanobodies as described for the proteins or polypeptides in accordance with any one of XIX) to XX) in which:
a) CDR1 comprises:
  the amino acid sequence NYYMG (SEQ ID NO: 172); or
  an amino acid sequence that has at least 80%, preferably at least 90%, more preferably at least 95%, even more preferably at least 99% sequence identity with the amino acid sequence NYYMG (SEQ ID NO: 172); or
  an amino acid sequences that has 2 or only 1 amino acid difference with the amino acid sequence NYYMG (SEQ ID NO: 172);
and
b) CDR2 comprises:
  the amino acid sequence NISWRGYNIYYKDSVKG (SEQ ID NO: 240); or
  an amino acid sequence that has at least 80%, preferably at least 90%, more preferably at least 95%, even more preferably at least 99% sequence identity with the amino acid sequence NISWRGYNIYYKDSVKG (SEQ ID NO: 240); or
  an amino acid sequences that has 2 or only 1 amino acid difference(s) with the amino acid sequence NISWRGYNIYYKDSVKG (SEQ ID NO: 240);
and
c) CDR3 comprises:
  the amino acid sequence SILPLSDDPGWNTY (SEQ ID NO: 308); or
  an amino acid sequence that has at least 80%, preferably at least 90%, more preferably at least 95%, even more preferably at least 99% sequence identity with the amino acid sequence SILPLSDDPGWNTY (SEQ ID NO: 308); or
  an amino acid sequences that has 2 or only 1 amino acid difference with the amino acid sequence SILPLSDDPGWNTY (SEQ ID NO: 308).

A protein or polypeptide in accordance with any one of XIX) to XX), in which the first and second immunoglobulin variable domains are Nanobodies as described for the proteins or polypeptides in accordance with any one of XIX) to XX) in which CDR1 comprises the amino acid sequence NYYMG (SEQ ID NO: 172).

A protein or polypeptide in accordance with any one of XIX) to XX), in which the first and second immunoglobulin variable domains are Nanobodies as described for the proteins or polypeptides in accordance with any one of XIX) to XX) in which CDR2 comprises the amino acid sequence NISWRGYNIYYKDSVKG (SEQ ID NO: 240).

A protein or polypeptide in accordance with any one of XIX) to XX), in which the first and second immunoglobulin variable domains are Nanobodies as described for the proteins or polypeptides in accordance with any one of XIX) to XX) in which CDR3 comprises the amino acid sequence SILPLSDDPGWNTY (SEQ ID NO: 308).

A protein or polypeptide in accordance with any one of XIX) to XX), in which the first and second immunoglobulin variable domains are Nanobodies as described for the proteins or polypeptides in accordance with any one of XIX) to XX), in which:
  CDR1 comprises the amino acid sequence NYYMG (SEQ ID NO: 172); and CDR3 comprises the amino acid sequence SILPLSDDPGWNTY (SEQ ID NO: 308); or
  CDR1 comprises the amino acid sequence NYYMG (SEQ ID NO: 172); and CDR2 comprises the amino acid sequence NISWRGYNIYYKDSVKG (SEQ ID NO: 240); or
  CDR2 comprises the amino acid sequence NISWRGYNIYYKDSVKG (SEQ ID NO: 240); and CDR3 comprises the amino acid sequence SILPLSDDPGWNTY (SEQ ID NO: 308).

A protein or polypeptide in accordance with any one of XIX) to XX), in which the first and second immunoglobulin variable domains are Nanobodies as described for the proteins or polypeptides in accordance with any one of XIX) to XX), in which CDR1 comprises the amino acid sequence NYYMG (SEQ ID NO: 172); CDR2 comprises the amino acid sequence SILPLSDDPGWNTY (SEQ ID NO: 308) and CDR3 comprises the amino acid sequence ILPLSDDPGWNTY (SEQ ID NO: 436).

A protein or polypeptide in accordance with any one of XIX) to XX), in which the first and second immunoglobulin variable domains are Nanobodies as described for the proteins or polypeptides in accordance with any one of XIX) to XX), in which
a) CDR1 is:
  the amino acid sequence NYYMG (SEQ ID NO: 172); or
  an amino acid sequence that has at least 80%, preferably at least 90%, more preferably at least 95%, even more preferably at least 99% sequence identity with the amino acid sequence NYYMG (SEQ ID NO: 172); or
  an amino acid sequences that has 2 or only 1 amino acid difference with the amino acid sequence NYYMG (SEQ ID NO: 172);
and
b) CDR2 is:
  the amino acid sequence NISWRGYNIYYKDSVKG (SEQ ID NO: 240); or
  an amino acid sequence that has at least 80%, preferably at least 90%, more preferably at least 95%, even more preferably at least 99% sequence identity with the amino acid sequence NISWRGY-NIYYKDSVKG (SEQ ID NO: 240); or
an amino acid sequences that has 2 or only 1 amino acid difference(s) with the amino acid sequence NISWRGYNIYYKDSVKG (SEQ ID NO: 240);
and
c) CDR3 is:
the amino acid sequence SILPLSDDPGWNTY (SEQ ID NO: 308); or
an amino acid sequence that has at least 80%, preferably at least 90%, more preferably at least 95%, even more preferably at least 99% sequence identity with the amino acid sequence SILPLSDDPGWNTY (SEQ ID NO: 308); or
an amino acid sequences that has 2 or only 1 amino acid difference with the amino acid sequence SIL-PLSDDPGWNTY (SEQ ID NO: 308).

A protein or polypeptide in accordance with any one of XIX) to XX), in which the first and second immunoglobulin variable domains are Nanobodies as described for the proteins or polypeptides in accordance with any one of XIX) to XX), in which CDR1 is the amino acid sequence NYYMG (SEQ ID NO: 172).

A protein or polypeptide in accordance with any one of XIX) to XX), in which the first and second immunoglobulin variable domains are Nanobodies as described for the proteins or polypeptides in accordance with any one of XIX) to XX), in which CDR2 is the amino acid sequence NISWRGYNIYYKDSVKG (SEQ ID NO: 240).

A protein or polypeptide in accordance with any one of XIX) to XX), in which the first and second immunoglobulin variable domains are Nanobodies as described for the proteins or polypeptides in accordance with any one of XIX) to XX), in which CDR3 is the amino acid sequence SILPLSDDPGWNTY (SEQ ID NO: 308).

A protein or polypeptide in accordance with any one of XIX) to XX), in which the first and second immunoglobulin variable domains are Nanobodies as described for the proteins or polypeptides in accordance with any one of XIX) to XX), in which:
CDR1 is the amino acid sequence NYYMG (SEQ ID NO: 172); and CDR3 is the amino acid sequence SILPLSDDPGWNTY (SEQ ID NO: 308); or
CDR1 is the amino acid sequence NYYMG (SEQ ID NO: 172); and CDR2 is the amino acid sequence NISWRGYNIYYKDSVKG (SEQ ID NO: 240); or
CDR2 is the amino acid sequence NISWRGY-NIYYKDSVKG (SEQ ID NO: 240); and CDR3 is the amino acid sequence SILPLSDDPGWNTY (SEQ ID NO: 308).

A protein or polypeptide in accordance with any one of XIX) to XX), in which the first and second immunoglobulin variable domains are Nanobodies as described for the proteins or polypeptides in accordance with any one of XIX) to XX), in which CDR1 is the amino acid sequence NYYMG (SEQ ID NO: 172); CDR2 is the amino acid sequence SILPLSDDPGWNTY (SEQ ID NO: 308) and CDR3 is the amino acid sequence ILPLSDDPGWNTY (SEQ ID NO: 436).

A protein or polypeptide in accordance with any one of XIX) to XX), in which the first and second immunoglobulin variable domains are Nanobodies as described for the proteins or polypeptides in accordance with any one of XIX) to XX), in which
any amino acid substitution is preferably a conservative amino acid substitution; and/or
said amino acid sequence preferably only contains amino acid substitutions, and no amino acid deletions or insertions, compared to the above amino acid sequence(s).

A protein or polypeptide in accordance with any one of XIX) to XX), in which the first and second immunoglobulin variable domains are chosen from the group consisting of the Nanobody TNF 3 (SEQ ID NO: 60) and humanized variants of the Nanobody TNF 3 (SEQ ID NO: 60).

A protein or polypeptide in accordance with any one of XIX) to XX), in which the first and second immunoglobulin variable domains are chosen from the group consisting of TNF20 (SEQ ID NO:83), TNF21 (SEQ ID NO: 84), TNF 22 (SEQ ID NO: 85), TNF23 (SEQ ID NO: 86) or TNF33 (SEQ ID NO: 99).

It should be noted that when a protein or polypeptide is mentioned above as being "in accordance with any one of XIX) to XX) above", it is at least according to one of XIX) to XX), and may be according to both XIX) and XX), and may also include any one or more of the other aspects that are indicated as being "in accordance with any one of XIX) to XX) above".

However, it should be noted that the invention is not limited to any specific mechanism of action or hypothesis. In particular, it has been found that the monovalent Nanobodies of the invention may be also active in the assays and models described herein, which confirms that intramolecular binding of he TNF trimer, although preferred in one specific embodiment of the invention, is not required to obtain the desired action and effect of the Nanobodies, proteins and polypeptides described herein. Similarly, it is also encompassed within the scope of the invention that the proteins and polypeptides described herein achieve their desired action via any appropriate mechanism (i.e. by intramolecular binding, intermolecular binding or even by binding to monomeric TNF, thus inhibiting the formation of TNF trimers).

It is also within the scope of the invention to use parts, fragments, analogs, mutants, variants, alleles and/or derivatives of the Nanobodies and polypeptides of the invention, and/or to use proteins or polypeptides comprising or essentially consisting of the same, as long as these are suitable for the uses envisaged herein. Such parts, fragments, analogs, mutants, variants, alleles, derivatives, proteins and/or polypeptides will be described in the further description herein.

In another aspect, the invention relates to a Nanobody (as defined herein), against TNF-alpha, which consist of 4 framework regions (FR1 to FR4 respectively) and 3 complementarity determining regions (CDR1 to CDR3 respectively), in which:
(i) CDR1 is an amino acid sequence chosen from the group consisting of the CDR1 sequences of SEQ ID NOS: 15 to 21 or from the group consisting of the CDR1 sequences of SEQ ID NOS: 164 to 197;
or from the group consisting of amino acid sequences that have at least 80%, preferably at least 90%, more preferably at least 95%, even more preferably at least 99% sequence identity (as defined herein) with at least one of the CDR1 sequences from the group consisting of SEQ ID NOS: 15 to 21 or with at least one of the CDR1 sequences from the group consisting of SEQ ID NOS: 164 to 197, in which (1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);

and/or from the group consisting of amino acid sequences that have 2 or only 1 "amino acid difference(s)" (as defined herein) with at least one of the CDR1 sequences from the group consisting of SEQ ID NOS: 15 to 21 or with at least one of the CDR1 sequences from the group consisting of SEQ ID NOS: 164 to 197, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);

and in which:
(ii) CDR2 is an amino acid sequence chosen from the group consisting of the CDR2 sequences of SEQ ID NOS: 22 to 28 or from the group consisting of the CDR2 sequences of SEQ ID NOS: 232 to 265;
or from the group consisting of amino acid sequences that have at least 80%, preferably at least 90%, more preferably at least 95%, even more preferably at least 99% sequence identity (as defined herein) with at least one of the CDR2 sequences from the group consisting of SEQ ID NOS: 22 to 28 or with at least one of the CDR2 sequences from the group consisting of SEQ ID NOS: 232 to 265, in which
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);
and/or from the group consisting of amino acid sequences that have 3, 2 or only 1 "amino acid difference(s)" (as defined herein) with at least one of the CDR2 sequences from the group consisting of SEQ ID NOS: 22 to 28 or with at least one of the CDR2 sequences from the group consisting of SEQ ID NOS: 232 to 265, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);
and in which:
(iii) CDR3 is an amino acid sequence chosen from the group consisting of the CDR3 sequences of SEQ ID NOS: 29 to 33 or from the group consisting of the CDR3 sequences of SEQ ID NOS: 300-333;
or from the group consisting of amino acid sequences that have at least 80%, preferably at least 90%, more preferably at least 95%, even more preferably at least 99% sequence identity (as defined herein) with at least one of the CDR3 sequences from the group consisting of SEQ ID NOS: 29 to 33 or with at least one of the CDR3 sequences from the group consisting of SEQ ID NOS: 300-333, in which:

(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);
and/or from the group consisting of amino acid sequences that have 3, 2 or only 1 "amino acid difference(s)" (as defined herein) or with at least one of the CDR3 sequences from the group consisting of SEQ ID NOS: 300-333, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);
or from the group consisting of the CDR3 sequences of SEQ ID NOS: 34 and 35 or from the group consisting of amino acid sequences that have at least 80%, preferably at least 90%, more preferably at least 95%, even more preferably at least 99% sequence identity (as defined herein) with at least one of the CDR3 sequences of SEQ ID NOS: 34 and 35, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);
and/or from the group consisting of amino acid sequences that have 3, 2 or only 1 "amino acid difference(s)" (as defined herein) with at least one of the CDR3 sequences of SEQ ID NOS: 34 and 35, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s).

The Nanobodies against TNF-alpha as described above and as further described hereinbelow are also referred to herein as Nanobodies of the invention.

Of the Nanobodies of the invention, Nanobodies comprising one or more of the CDR's explicitly listed above are particularly preferred; Nanobodies comprising two or more of the CDR's explicitly listed above are more particularly preferred; and Nanobodies comprising three of the CDR's explicitly listed above are most particularly preferred.

Some particularly preferred, but non-limiting combinations of CDR sequences can be seen in Table I below, which lists the CDR's and framework sequences that are present in a number of preferred (but non-limiting) Nanobodies of the invention. As will be clear to the skilled person, a combination of CDR1, CDR2 and CDR3 sequences that occur in the same clone (i.e. CDR1, CDR2 and CDR3 sequences which are mentioned on the same line in Table I) will usually be preferred (although the invention in its broadest sense is not limited thereto, and also comprises other suitable combinations of the CDR sequences mentioned in Table I).

Also, in the Nanobodies of the invention that comprise the combinations of CDR's mentioned in Table I, each CDR can be replaced by a CDR chosen from the group consisting of amino acid sequences that have at least 80%, preferably at least 90%, more preferably at least 95%, even more preferably at least 99% sequence identity (as defined herein) with the mentioned CDR's; in which (1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);

and/or chosen from the group consisting of amino acid sequences that have 3, 2 or only 1 (as indicated in the preceding paragraph) "amino acid difference(s)" (as defined herein) with the mentioned CDR(s) one of the above amino acid sequences, in which:

(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s).

However, as will be clear to the skilled person, the (combinations of) CDR sequences mentioned in Table I will generally be preferred.

TABLE I

Preferred combinations of framework and CDR sequences

| Clone | ID | FR1 | ID | CDR1 | ID | FR2 | ID | CDR2 |
|---|---|---|---|---|---|---|---|---|
| PMP1C2 (TNF1) | 130 | QVQLVESGGGLVQPGGSLRLSCAASGFTFS | 164 | DYWMY | 198 | WVRQAPGKGLEWVS | 232 | EINTNGLITKYPDSVKG |
| PMP1G11 | 131 | QVQLQESGGGMVQPGGSLRLSCAASGFDFG | 165 | VSWMY | 199 | WVRQAPGKGLEWVS | 233 | EINTNGLITKYPDSVKG |
| PMP1H6 | 132 | EVQLVESGGGLVQPGGSLRLSCATSGFDFS | 166 | VSWMY | 200 | WVRQAPGKGLEWVS | 234 | EINTNGLITKYVDSVKG |
| PMP1G5 (TNF2) | 133 | QVQLVESGGGLVQAGGSLRLSCAASGRTFS | 167 | EPSGYTYTIG | 201 | WFRQAPGKEREFVA | 235 | RIYWSSGLTYYADSVKG |
| PMP1H2 | 134 | QVKLEESGGGLVQPGDSLRLSCAASGRTFS | 168 | DYSGYTYTVG | 202 | WFRQAPGKEREFVA | 236 | RIYWSSGNTYYADSVKG |
| PMP3G2 | 135 | AVQLVESGGGLVQPGDSLRLSCAASGRTFS | 169 | DYSGYTYTVG | 203 | WFRQAPGKEREFVA | 237 | RIYWSSGNTYYADSVKG |
| PMP1D2 | 136 | AVQLVDSGGGLVQAGGSLRLSCAASGRTFS | 170 | AHSVYTMG | 204 | WFRQAPGKEREFVA | 238 | RIYWSSANTYYADSVKG |
| PMP3D10 | 137 | QVQLVESGGGLVQAGGSLSLSCAASGRSFT | 171 | GYYMG | 205 | WFRQAPGKERQLLA | 239 | SISWRGDNTYYKESVKG |
| PMP5F10 (TNF3) | 138 | EVQLVESGGGLVQAGGSLSLSCSASGRSLS | 172 | NYYMG | 206 | WFRQAPGKERELLG | 240 | NISWRGYNIYYKDSVKG |
| NC55TNF_S1C4 | 139 | EVQLVESGGGLVQAGDSLRLSCAASQIIFG | 173 | SHVAA | 207 | WFRQAPGREREFVA | 241 | EIRPSGDFGPEGEFEHVTASLKG |
| NC55TNF_S1C3 | 140 | EVQLVESGGGLVQPGGSLRLSCKNAGSTSN | 174 | AYATG | 208 | WFRRAPGKEREFVA | 242 | GIQWSGGDAFYRNSVKG |
| NC55TNF_S2C1 | 141 | EVQLVESGGDLVQPGGSLRLSCAVSGQLFS | 175 | TNDVG | 209 | WYRRAPGKQRELVA | 243 | TITDDGTTDYGDDVKG |
| NC55TNF_S2C5 | 142 | EVQLVESGGGLVQPGGSLRLSCVVSGFTFS | 176 | TTSMT | 210 | WVRQAPGKFEEWVS | 244 | FINSDGSSTTYADSVKG |
| NC55TNF_S3C7 | 143 | EVQLVESGGGTVQAGDSLRLSCAASGRSFS | 177 | SVAMG | 211 | WFRQAPGKQREFLA | 245 | GVGYDGSSIRYAESVKG |
| NC55TNF_S3C1 | 144 | TNF-ALPHAVESGGGLMQPGGSLKLSCAASGFMFS | 178 | DSAMG | 212 | WFRQAPGKEREFVA | 246 | TISWNGGSSSYADFVKG |
| NC55TNF_BMP1B2 | 145 | EVQLVESGGGLVQAGGSLRLSCAASGRTFG | 179 | TYAMG | 213 | WFRQAPGKEREFVA | 247 | AISWGGGSIVYAESAKG |
| NC55TNF_BMP1D2 | 146 | EVQLVESGGELVQAGGSLKLSCTASGRNFV | 180 | TYAMS | 214 | WFRRAPGKEREFVA | 248 | SISWSGDTTYYSNSVKG |
| NC55TNF_BMP1E2 | 147 | EVQLVESGGRLVQPGGSLRLSCKNAGSTSN | 181 | AYATG | 215 | WFRRAPGKEREFVA | 249 | GIQWSGGDAFYRNSVKG |
| NC55TNF_BMP1G2 | 148 | EVQLVESGGGLVQPGGSLRLSCAASATISS | 182 | IVMLG | 216 | WYRQAPGKQREWVA | 250 | SITIGSRTNYADSVKG |

TABLE I-continued

Preferred combinations of framework and CDR sequences

| Clone | ID FR1 | ID CDR1 | ID FR2 | ID CDR2 |
|---|---|---|---|---|
| NC55TNF_BMP2A2 | 149 EVQLVESGGGLVQAGGSLRLSCAASGQTSS | 183 SYDMG | 217 WFRQAPGEGREFVA | 251 RISGSDGSTYYSDRAKD |
| NC55TNF_BMP2C2 | 150 EVQLVESGGGLVQPGGSLRLSCAASGSTFS | 184 TYDMS | 218 WVRQAPGKGLEWVS | 252 GIDSGGGSPMYVDSVKG |
| NC55TNF_BMP2F2 | 151 EVQLVESGGGLVQAGDSLRLSCEASERSSN | 185 RYNMA | 219 WFRQAPGEEREFLA | 253 RVDVSGGNTLYGDSVKD |
| NC55TNF_NC10 | 152 EVQLVESGGGLVQPGGSLRLSCVCVSSGCT | 186 FSAYSMT | 220 WVRQAPGKAEEWVS | 254 FINSDGSTTYADSVNG |
| NC55TNF_NC11 | 153 EVQLVESGGGLVQAGDSLTLSCASSGRGFY | 187 KNAMG | 221 WFRQPPGKEREFVA | 255 SIKWNGNNTYYADSVRG |
| NC55TNF_NC1 | 154 EVQLVESGGGLVQPGGSLRLSCVFSGFAFS | 188 ASSMA | 222 WVRQAPGKYEEWVS | 256 FINSDGSTTYADSVQG |
| NC55TNF_NC2 | 155 EVQLVESGGGLVQAGGSLRLSCAASGRTFS | 189 SYAMG | 223 WFRQAPGKEREFVA | 257 AISWSGTITNYADSVKG |
| NC55TNF_NC3 | 156 EVQLVESGGGLVQPGGSLRLSCVVSGFTFS | 190 ATSMT | 224 WVRQAPGKAEEWVS | 258 FINSDGSTTYADSVKG |
| NC55TNF_NC5 | 157 EVQLVESGGGLVQAGGSLRLSCAASGGAFS | 191 NYDVG | 225 WFRQAPGEGREIVA | 259 RISGSGDSTYSSNRAKG |
| NC55TNF_NC6 | 158 EVQLVESGGGLVQPGGSLRLSCECVSSGCT | 192 FSAYSMT | 226 WVRQAPGKAEEFVS | 260 FINSDGSTTYANSVNG |
| NC55TNF_NC7 | 159 QVQLVESGGGLVQAGGSLRLSCTASGQTSS | 193 TADMG | 227 WFRQPPGKGREFVA | 261 RISGIDGTTYYDEPVKG |
| NC55TNF_NC8 | 160 EVQLVESGGGLVQPGGSLRLSCVVSGFTFS | 194 TTSMT | 228 WVRQAPGKFEEWVS | 262 FINSDGSTTYADSVKG |
| NC55TNF_S2C2 | 161 EVQLVESGGGLVQPGGSLRLSCVASASGVK | 195 VNDMG | 229 WYRQAPGKERELVA | 263 TITDDGRTNYEDFAKG |
| NC55TNF_S1C6 | 162 EVQLVESGGGLVQAGGSLRLSCAASGRSFG | 196 SVAMG | 230 WFRQAPGKEREFVA | 264 AIGYDGNSIRYGDSVKG |
| NC55TNF_S3C2 | 163 EVQLVESGGGLVQAGASLRLSCTTSTRTN | 197 DRFNMA | 231 WFHQAPGKDREFVS | 265 RIDVAGYNTAYGDFVKG |

| Clone | ID FR3 | ID CDR3 | ID FR4 |
|---|---|---|---|
| PMP1C2 (TNF1) | 266 RFTISRDNAKNTLYLQMNSLKPEDTALYYCAR | 300 SPSGFN | 334 RGQGTQVTVSS |
| PMP1G11 | 267 RFTISRDNAKTTLYLQMNSLKPEDTALYYCAR | 301 SPSGSF | 335 RGQGTQVTVSS |
| PMP1H6 | 268 RFTISRDNAKNTLYLQMDSLIPEDTALYYCAR | 302 SPSGSF | 336 RGQGTQVTVSS |
| PMP1G5 (TNF2) | 269 RFTISRDIAKNTVDLLMNSLKPEDTAVYYCAA | 303 RDGIPTSRSVGSYNY | 337 WGQGTQVTVSS |
| PMP1H2 | 270 RFTISRDIAKNTVDLLMNNLEPEDTAVYYCAA | 304 RDGIPTSRSVESYNY | 338 WGQGTQVTVSS |
| PMP3G2 | 271 RFTISRDIAKNTVDLLMNNLEPEDTAVYYCAA | 305 RDGIPTSRSVESYNY | 339 WGQGTQVTVSS |
| PMP1D2 | 272 RFTISRDNAKNTVDLLMNCLKPEDTAVYYCAA | 306 RDGIPTSRSVEAYNY | 340 WGQGTQVTVSS |
| PMP3D10 | 273 RFTISRDDAKNTIYLQMNSLKPEDTAVYYCAA | 307 SILPLSDDPGWNTN | 341 WGQGTQVTVSS |
| PMP5F10 (TNF3) | 274 RFTISRDDAKNTIYLQMNRLKPEDTAVYYCAA | 308 SILPLSDDPGWNTY | 342 WGQGTQVTVSS |

TABLE I-continued

Preferred combinations of framework and CDR sequences

| | | | |
|---|---|---|---|
| NC55TNF_S1C4 | 275 RFTIAKNSVDNTVYLQM NSLKPEDTAVYYCAA | 309 APYRGGRDYR WEYEYEY | 343 WGQG TQVTV SS |
| NC55TNF_S1C3 | 276 RFRITRDPDNTVYLQMN DLKPEDTAIYYCAQ | 310 KLSPYYNDFD SSNYEY | 344 WGQG TQVTV SS |
| NC55TNF_S2C1 | 277 RFVISREGEMVYLEMNS LKPEDTAVYYCNI | 311 NRLRSTWGIR YDV | 345 WGQG TQVTV SS |
| NC55TNF_S2C5 | 278 RFTISRDNAKNTLYLQMN SLKPEDTAMYYCGR | 312 RGYGRD | 346 RSKGI QVTVAS |
| NC55TNF_S3C7 | 279 RFTIARGNRESTVFLQM ENLKPEDTAVYFCTA | 313 EPIGAYEGLW TY | 347 WGQG TQVTV SS |
| NC55TNF_S3C1 | 280 RFTISRDNAKNTVYLQMNG LTPQDTAIYYCAG | 314 SYSNGNPHRFS QYQY | 348 WGQG TQVTV SS |
| NC55TNF_BMP1B2 | 281 RFTISRDNAKXTMYLQMDS LKPEDTAVYYCAA | 315 ANNIATLRQGS | 349 WGQG TQVTV SS |
| NC55TNF_BMP1D2 | 282 RFTVSRDNGKNTAYLRMN SLKPEDTADYYCAV | 316 VQVIDPSWSGV NLDDYDY | 350 LGSGT QVTVSS |
| NC55TNF_BMP1E2 | 283 RFRITRDPDNTVYLQMNDL KPEDTAIYYCAQ | 317 KLSPYYNDFDS SNYEY | 351 WGQG TQVTV SS |
| NC55TNF_BMP1G2 | 284 RFTISRDNAKNTVYLQMNS LKPEDTAVYFCNA | 318 VPPRDDY | 352 WGQG TQVTV SS |
| NC55TNF_BMP2A2 | 285 RFTISRDNTKNMVYLQMD RLKPDDTAVYYCRV | 319 PRYENQWSSY DY | 353 WGQG TQVTV SS |
| NC55TNF_BMP2C2 | 286 RFTVSRDNAKNTLYLQMN SLKPEDTAVYYCAK | 320 FSTGADGGSW YWSYGMDS | 354 WGKGT QVTVSS |
| NC55TNF_BMP2F2 | 287 RFTVSRINGKNAMYLQMNNL KPEDTAIYYCAA | 321 GGWGTTQYDY DY | 355 WGQG TQVTV SS |
| NC55TNF_NC10 | 288 RFKISRDNAKKTLYLQMNSL GPEDTAMYYCQR | 322 RGYALD | 356 RGQGT QVTVSS |
| NC55TNF_NC11 | 289 RFTISRGNAKNTENTVSLQM NSLKPEDTADYYCAA | 323 DSSHYSYVYSK AYEYDY | 357 WGQG TQVTV SS |
| NC55TNF_NC1 | 290 RFTISRDNAKNTLYLQMNSL KSEDTAMYYCGR | 324 RGYGRD | 358 RSQGI QVTVSS |
| NC55TNF_NC2 | 291 RFTISRDNGKNTVHLQMNSL KPEDTAVYHCAV | 325 VQPYSGGDYY TGVEEYDY | 359 WGXG TQVTV SS |
| NC55TNF_NC3 | 292 RFTISRDNAKNTLYLQMDDL QSEDTAMYYCGR | 326 RGYGRD | 360 RSRGI QVTVSS |
| NC55TNF_NC5 | 293 RFTISRDNAKNTVYLQMNSL KREDTAVYYCRA | 327 ARYNGTWSSN DY | 361 WGQG TQVTV SS |
| NC55TNF_NC6 | 294 RFKISRDNAKKTLYLQMNSL GPEDTAMYYCQR | 328 RGYALD | 362 RGQGTQ VTVSS |
| NC55TNF_NC7 | 295 RFTISRDKAQNTVYLQMDSL KPEDTAVYYCRS | 329 PRYADQW SAYDY | 363 WGQGTQ VTVSS |

TABLE I-continued

Preferred combinations of framework and CDR sequences

| | | | |
|---|---|---|---|
| NC55TNF_NC8 | 296 RFTISRDNAKNTLYLQMNSL KPEDTAMYYCGR | 330 RGYGRD | 364 RSKGIQV TVSS |
| NC55TNF_S2C2 | 297 RFTISRDNAKNTVYLQMNSL LPEDTAVYYCNA | 331 RTYWAHL PTY | 365 WGQGTQ VTVSS |
| NC55TNF_S1C6 | 298 RFTISRDNIKNTMYLEMENL NADDTARYLCAA | 332 EPLARYE GLWTY | 366 WGQGTQ VTVSS |
| NC55TNF_S3C2 | 299 RFTVSRDSAENTVVLQMNSL RPEDTGVYYCAA | 333 GGWGISQ SDYDL | 367 WGQGTQ VTVSS |

Notes to Table I:
ID refers to the SEQ ID NO's in the attached sequence listing
For CDR1: SEQ ID NO: 164 corresponds to SEQ ID NO: 15, SEQ ID NO: 167 corresponds to SEQ ID NO: 16; SEQ ID NO: 172 corresponds to SEQ ID NO: 17, SEQ ID NOS: 165 and 166 correspond to SEQ ID NO: 18, SEQ ID NO: 170 corresponds to SEQ ID NO: 19, SEQ ID NO: 171 corresponds to SEQ ID NO: 20, and SEQ ID NOS: 168 and 169 correspond to SEQ ID NO: 21.
For CDR2: SEQ ID NOS: 232 and 233 correspond to SEQ ID NO: 22, SEQ ID NO: 235 corresponds to SEQ ID NO: 23, SEQ ID NO: 240 corresponds to SEQ ID NO: 24, SEQ ID NO: 234 corresponds to SEQ ID NO: 25, SEQ ID NOS: 236 and 237 correspond to SEQ ID NO: 26, SEQ ID NO: 238 corresponds to SEQ ID NO: 27, and SEQ ID NO: 239 corresponds to SEQ ID NO: 28.
For CDR3: SEQ ID NO: 303 corresponds to SEQ ID NO: 29, SEQ ID NO: 308 corresponds to SEQ ID NO: 30, SEQ ID NO: 306 corresponds to SEQ ID NO: 31, SEQ ID NO: 307 corresponds to SEQ ID NO: 32, SEQ ID NOS: 304 and 305 corresponds to SEQ ID NO: 33, SEQ ID NO: 300 corresponds to SEQ ID NO: 34, and SEQ ID NOS: 301 and 302 correspond to SEQ ID NO: 35.

Thus, in the Nanobodies of the invention, at least one of the CDR1, CDR2 and CDR3 sequences present is suitably chosen from the group consisting of the CDR1, CDR2 and CDR3 sequences, respectively, listed in Table I; or from the group of CDR1, CDR2 and CDR3 sequences, respectively, that have at least 80%, preferably at least 90%, more preferably at least 95%, even more preferably at least 99% "sequence identity" (as defined herein) with at least one of the CDR1, CDR2 and CDR3 sequences, respectively, listed in Table I; and/or from the group consisting of the CDR1, CDR2 and CDR3 sequences, respectively, that have 3, 2 or only 1 "amino acid difference(s)" (as defined herein) with at least one of the CDR1, CDR2 and CDR3 sequences, respectively, listed in Table I. In this context, by "suitably chosen" is meant that, as applicable, a CDR1 sequence is chosen from suitable CDR1 sequences (i.e. as defined herein), a CDR2 sequence is chosen from suitable CDR2 sequences (i.e. as defined herein) and a CDR3 sequence is chosen from suitable CDR3 sequences (i.e. as defined herein), respectively.

In particular, in the Nanobodies of the invention, at least the CDR3 sequence present is suitably chosen from the group consisting of the CDR3 sequences listed in Table I or from the group of CDR3 sequences that have at least 80%, preferably at least 90%, more preferably at least 95%, even more preferably at least 99% sequence identity with at least one of the CDR3 sequences listed in Table I; and/or from the group consisting of the CDR3 sequences that have 3, 2 or only 1 amino acid difference(s) with at least one of the CDR3 sequences listed in Table I.

Preferably, in the Nanobodies of the invention, at least two of the CDR1, CDR2 and CDR3 sequences present are suitably chosen from the group consisting of the CDR1, CDR2 and CDR3 sequences, respectively, listed in Table I or from the group consisting of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table I; and/or from the group consisting of the CDR1, CDR2 and CDR3 sequences, respectively, that have 3, 2 or only 1 "amino acid difference(s)" with at least one of the CDR1, CDR2 and CDR3 sequences, respectively, listed in Table I.

In particular, in the Nanobodies of the invention, at least the CDR3 sequence present is suitably chosen from the group consisting of the CDR3 sequences listed in Table I or from the group of CDR3 sequences that have at least 80%, preferably at least 90%, more preferably at least 95%, even more preferably at least 99% sequence identity with at least one of the CDR3 sequences listed in Table I, respectively; and at least one of the CDR1 and CDR2 sequences present is suitably chosen from the group consisting of the CDR1 and CDR2 sequences, respectively, listed in Table I or from the group of CDR1 and CDR2 sequences, respectively, that have at least 80%, preferably at least 90%, more preferably at least 95%, even more preferably at least 99% sequence identity with at least one of the CDR1 and CDR2 sequences, respectively, listed in Table I; and/or from the group consisting of the CDR1 and CDR2 sequences, respectively, that have 3, 2 or only 1 amino acid difference(s) with at least one of the CDR1 and CDR2 sequences, respectively, listed in Table I.

Most preferably, in the Nanobodies of the invention, all three CDR1, CDR2 and CDR3 sequences present are suitably chosen from the group consisting of the CDR1, CDR2 and CDR3 sequences, respectively, listed in Table I or from the group of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table I; and/or from the group consisting of the CDR1, CDR2 and CDR3 sequences, respectively, that have 3, 2 or only 1 amino acid difference(s) with at least one of the CDR1, CDR2 and CDR3 sequences, respectively, listed in Table I.

Even more preferably, in the Nanobodies of the invention, at least one of the CDR1, CDR2 and CDR3 sequences present is suitably chosen from the group consisting of the CDR1, CDR2 and CDR3 sequences, respectively, listed in Table I. Preferably, in this embodiment, at least one or preferably both of the other two CDR sequences present are suitably chosen from CDR sequences that that have at least 80%, preferably at least 90%, more preferably at least 95%, even more preferably at least 99% sequence identity with at least one of the corresponding CDR sequences, respectively, listed in Table I; and/or from the group consisting of the CDR sequences that have 3, 2 or only 1 amino acid difference(s) with at least one of the corresponding sequences, respectively, listed in Table I.

In particular, in the Nanobodies of the invention, at least the CDR3 sequence present is suitably chosen from the group consisting of the CDR3 listed in Table I. Preferably, in this embodiment, at least one and preferably both of the CDR1 and CDR2 sequences present are suitably chosen from the groups of CDR1 and CDR2 sequences, respectively, that that have at least 80%, preferably at least 90%, more preferably at least 95%, even more preferably at least 99% sequence identity with the CDR1 and CDR2 sequences, respectively, listed in listed in Table I; and/or from the group consisting of the CDR1 and CDR2 sequences, respectively, that have 3, 2 or only 1 amino acid difference(s) with at least one of the CDR1 and CDR2 sequences, respectively, listed in Table I.

Even more preferably, in the Nanobodies of the invention, at least two of the CDR1, CDR2 and CDR3 sequences present are suitably chosen from the group consisting of the CDR1, CDR2 and CDR3 sequences, respectively, listed in Table I. Preferably, in this embodiment, the remaining CDR sequence present are suitably chosen from the group of CDR sequences that that have at least 80%, preferably at least 90%, more preferably at least 95%, even more preferably at least 99% sequence identity with at least one of the corresponding CDR sequences listed in Table I; and/or from the group consisting of CDR sequences that have 3, 2 or only 1 amino acid difference(s) with at least one of the corresponding sequences listed in Table I.

In particular, in the Nanobodies of the invention, at least the CDR3 sequence is suitably chosen from the group consisting of the CDR3 sequences listed in Table I, and either the CDR1 sequence or the CDR2 sequence is suitably chosen from the group consisting of the CDR1 and CDR2 sequences, respectively, listed in Table I. Preferably, in this embodiment, the remaining CDR sequence present are suitably chosen from the group of CDR sequences that that have at least 80%, preferably at least 90%, more preferably at least 95%, even more preferably at least 99% sequence identity with at least one of the corresponding CDR sequences listed in Table I; and/or from the group consisting of CDR sequences that have 3, 2 or only 1 amino acid difference(s) with the corresponding CDR sequences listed in Table I.

Even more preferably, in the Nanobodies of the invention, all three CDR1, CDR2 and CDR3 sequences present are suitably chosen from the group consisting of the CDR1, CDR2 and CDR3 sequences, respectively, listed in Table I.

Also, generally, the combinations of CDR's listed in Table I (i.e. those mentioned on the same line in Table I) are preferred. Thus, it is generally preferred that, when a CDR in a Nanobody of the invention is a CDR sequence mentioned in Table I or is suitably chosen from the group of CDR sequences that have at least 80%, preferably at least 90%, more preferably at least 95%, even more preferably at least 99% sequence identity with a CDR sequence listed in Table I; and/or from the group consisting of CDR sequences that have 3, 2 or only 1 amino acid difference(s) with a CDR sequence listed in Table I, that at least one and preferably both of the other CDR's are suitably chosen from the CDR sequences that belong to the same combination in Table I (i.e. mentioned on the same line in Table I) or are suitably chosen from the group of CDR sequences that have at least 80%, preferably at least 90%, more preferably at least 95%, even more preferably at least 99% sequence identity with the CDR sequence(s) belonging to the same combination and/or from the group consisting of CDR sequences that have 3, 2 or only 1 amino acid difference(s) with the CDR sequence(s) belonging to the same combination. The other preferences indicated in the above paragraphs also apply to the combinations of CDR's mentioned in Table I.

Thus, by means of non-limiting examples, a Nanobody of the invention can for example comprise a CDR1 sequence that has more than 80% sequence identity with one of the CDR1 sequences mentioned in Table I, a CDR2 sequence that has 3, 2 or 1 amino acid difference with one of the CDR2 sequences mentioned in Table I (but belonging to a different combination), and a CDR3 sequence.

Some preferred Nanobodies of the invention may for example comprise: (1) a CDR1 sequence that has more than 80% sequence identity with one of the CDR1 sequences mentioned in Table I; a CDR2 sequence that has 3, 2 or 1 amino acid difference with one of the CDR2 sequences mentioned in Table I (but belonging to a different combination); and a CDR3 sequence that has more than 80% sequence identity with one of the CDR3 sequences mentioned in Table I (but belonging to a different combination); or (2) a CDR1 sequence that has more than 80% sequence identity with one of the CDR1 sequences mentioned in Table I; a CDR2 sequence, and one of the CDR3 sequences listed in Table I; or (3) a CDR1 sequence; a CDR2 sequence that has more than 80% sequence identity with one of the CDR2 sequence listed in Table I; and a CDR3 sequence that has 3, 2 or 1 amino acid differences with the CDR3 sequence mentioned in Table I that belongs to the same combination as the CDR2 sequence.

Some particularly preferred Nanobodies of the invention may for example comprise: (1) a CDR1 sequence that has more than 80% sequence identity with one of the CDR1 sequences mentioned in Table I; a CDR2 sequence that has 3, 2 or 1 amino acid difference with the CDR2 sequence mentioned in Table I that belongs to the same combination; and a CDR3 sequence that has more than 80% sequence identity with the CDR3 sequence mentioned in Table I that belongs to the same combination; (2) a CDR1 sequence; a CDR2 listed in Table I and a CDR3 sequence listed in Table I (in which the CDR2 sequence and CDR3 sequence may belong to different combinations).

Some even more preferred Nanobodies of the invention may for example comprise: (1) a CDR1 sequence that has more than 80% sequence identity with one of the CDR1 sequences mentioned in Table I; the CDR2 sequence listed in Table I that belongs to the same combination; and a CDR3 sequence mentioned in Table I that belongs to a different combination; or (2) a CDR1 sequence mentioned in Table I; a CDR2 sequence that has 3, 2 or 1 amino acid differences with the CDR2 sequence mentioned in Table I that belongs to the same combination; and more than 80% sequence identity with the CDR3 sequence listed in Table I that belongs to same different combination.

Particularly preferred Nanobodies of the invention may for example comprise a CDR1 sequence mentioned in Table I, a CDR2 sequence that has more than 80% sequence identity with the CDR2 sequence mentioned in Table I that belongs to the same combination; and the CDR3 sequence mentioned in Table I that belongs to the same.

In the most preferred in the Nanobodies of the invention, the CDR1, CDR2 and CDR3 sequences present are suitably chosen from the one of the combinations of CDR1, CDR2 and CDR3 sequences, respectively, listed in Table I.

Preferably, when a CDR sequence is suitably chosen from the group of CDR sequences that have at least 80%, preferably at least 90%, more preferably at least 95%, even more preferably at least 99% sequence identity (as defined herein) with one of the CDR sequences listed in Table I; and/or when a CDR sequence is suitably chosen from the group consisting of CDR sequences that have 3, 2 or only 1 amino acid difference(s) with one of the CDR sequences listed in Table I:

i) any amino acid substitution is preferably a conservative amino acid substitution (as defined herein); and/or ii) said amino acid sequence preferably only contains amino acid substitutions, and no amino acid deletions or insertions, compared to the CDR sequence listed in Table I.

According to a non-limiting but preferred embodiment of the invention, the CDR sequences in the Nanobodies of the invention are as defined above and are also such that the Nanobody of the invention binds to TNF-alpha with an dissociation constant ($K_D$) of $10^{-5}$ to $10^{-12}$ moles/liter (M) or less, and preferably $10^{-7}$ to $10^{-12}$ moles/liter (M) or less and more preferably $10^{-8}$ to $10^{-12}$ moles/liter (M), and/or with an association constant ($K_A$) of at least $10^7$ M$^{-1}$, preferably at least $10^8$ M$^{-1}$, more preferably at least $10^9$ M$^{-1}$, such as at least $10^{12}$ M$^{-1}$; and in particular with a $K_D$ less than 500 nM, preferably less than 200 nM, more preferably less than 10 nM, such as less than 500 pM. The $K_D$ and $K_A$ values of the Nanobody of the invention against TNF-alpha can be determined in a manner known per se, for example using the assay described herein.

According to another preferred, but non-limiting embodiment of the invention (a) CDR1 has a length of between 1 and 12 amino acid residues, and usually between 2 and 9 amino acid residues, such as 5, 6 or 7 amino acid residues; and/or (b) CDR2 has a length of between 13 and 24 amino acid residues, and usually between 15 and 21 amino acid residues, such as 16 and 17 amino acid residues; and/or (c) CDR3 has a length of between 2 and 35 amino acid residues, and usually between 3 and 30 amino acid residues, such as between 6 and 23 amino acid residues.

In one aspect, the invention provides Nanobodies against TNF-alpha that are better performing than Nanobody 3E, the best performing Nanobody according to WO 04/041862.

More specifically, some preferred aspects of this embodiment of the invention are:

XXI) A Nanobody against TNF-alpha, which consist of 4 framework regions (FR1 to FR4 respectively) and 3 complementarity determining regions (CDR1 to CDR3 respectively), which has a Koff rate for TNF of better than 2.10-3 (1/s), preferably better than 1.10-3 (1/s); or a humanized variant of such a Nanobody.

XXII) A Nanobody against TNF-alpha, which consist of 4 framework regions (FR1 to FR4 respectively) and 3 complementarity determining regions (CDR1 to CDR3 respectively), which has an EC50 value in the cell-based assay using KYM cells described in Example 1, under 3), of WO 04/041862 that is better than the EC50 value of Nanobody VHH 3E (SEQ ID NO:4) of WO 04/041862 in the same assay; or a humanized variant of such a Nanobody.

XXIII) A Nanobody against TNF-alpha, which has an EC50 value in the cell-based assay using KYM cells described in Example 1, under 3), of WO 04/041862 that is better than 12 nM; or a humanized variant of such a Nanobody.

XXIV) A Nanobody against TNF-alpha, which has an EC50 value in the cell-based assay using KYM cells described in Example 1, under 3), of WO 04/041862 that is better than 5 nM; or a humanized variant of such a Nanobody.

XXV) A Nanobody against TNF-alpha, which has an EC50 value in the cell-based assay using KYM cells described in Example 1, under 3), of WO 04/041862 that is better than 3 nM; or a humanized variant of such a Nanobody;

with some particularly preferred aspects being:

A Nanobody in accordance with any one of XXI) to XXV), which is a GLEW-class Nanobody.

A Nanobody in accordance with any one of XXI) to XXV), which contains an arginine residue (R) at position 103.

A Nanobody in accordance with any one of XXI) to XXV), which is a humanized Nanobody.

A Nanobody in accordance with any one of XXI) to XXV), which contains a leucine residue (L) at position 108.

A Nanobody in accordance with any one of XXI) to XXV), which has at least 80%, preferably at least 90%, more preferably at least 95%, even more preferably at least 99% sequence identity (as defined herein) with one of the amino acid sequences of SEQ ID NO's 52 (TNF1), 76 (TNF13), 77 (TNF14), 95 (TNF29) or 96 (TNF30).

A Nanobody in accordance with any one of XXI) to XXV), in which a) CDR1 comprises:
   the amino acid sequence DYWMY (SEQ ID NO: 164); or
   an amino acid sequence that has at least 80%, preferably at least 90%, more preferably at least 95%, even more preferably at least 99% sequence identity with the amino acid sequence DYWMY (SEQ ID NO: 164); or
   an amino acid sequences that has 2 or only 1 amino acid difference(s) with the amino acid sequence DYWMY (SEQ ID NO: 164);
and
b) CDR2 comprises:
   the amino acid sequence EINTNGLITKYPDSVKG (SEQ ID NO: 233); or
   an amino acid sequence that has at least 80%, preferably at least 90%, more preferably at least 95%, even more preferably at least 99% sequence identity with the amino acid sequence EINTNGLITKYPDSVKG (SEQ ID NO: 233); or
   an amino acid sequences that has 2 or only 1 amino acid difference(s) with the amino acid sequence EINTNGLITKYPDSVKG (SEQ ID NO: 233);
and
c) CDR3 comprises:
   the amino acid sequence SPSGFN (SEQ ID NO: 300); or
   an amino acid sequence that has at least 80%, preferably at least 90%, more preferably at least 95%, even more preferably at least 99% sequence identity with the amino acid sequence SPSGFN (SEQ ID NO: 300); or
   an amino acid sequences that has 2 or only 1 amino acid difference(s) with the amino acid sequence SPSGFN (SEQ ID NO: 300).

A Nanobody in accordance with any one of XXI) to XXV), in which CDR1 comprises the amino acid sequence DYWMY (SEQ ID NO 164).

A Nanobody in accordance with any one of XXI) to XXV), in which CDR2 comprises the amino acid sequence EINTNGLITKYPDSVKG (SEQ ID NO: 233).

A Nanobody in accordance with any one of XXI) to XXV), in which CDR3 comprises the amino acid sequence SPSGFN (SEQ ID NO: 300)

A Nanobody in accordance with any one of XXI) to XXV), in which:
CDR1 comprises the amino acid sequence DYWMY (SEQ ID NO: 164); and CDR3 comprises the amino acid sequence SPSGFN (SEQ ID NO: 300); or
CDR1 comprises the amino acid sequence DYWMY (SEQ ID NO: 164); and CDR2 comprises the amino acid sequence EINTNGLITKYPDSVKG (SEQ ID NO: 233); or
CDR2 comprises the amino acid sequence EINTNGLITKYPDSVKG (SEQ ID NO: 233); and CDR3 comprises the amino acid sequence SPSGFN (SEQ ID NO: 300)

A Nanobody in accordance with any one of XXI) to XXV), in which CDR1 comprises the amino acid sequence DYWMY (SEQ ID NO: 164); and CDR3 comprises the amino acid sequence SPSGFN (SEQ ID NO: 300).

A Nanobody in accordance with any one of XXI) to XXV), in which CDR1 comprises the amino acid sequence DYWMY (SEQ ID NO: 164); CDR2 comprises the amino acid sequence EINTNGLITKYPDSVKG (SEQ ID NO: 233) and CDR3 comprises the amino acid sequence SPSGFN (SEQ ID NO: 300).

A Nanobody in accordance with any one of XXI) to XXV), in which
a) CDR1 is:
the amino acid sequence DYWMY (SEQ ID NO: 164); or
an amino acid sequence that has at least 80%, preferably at least 90%, more preferably at least 95%, even more preferably at least 99% sequence identity with the amino acid sequence DYWMY (SEQ ID NO: 164); or
an amino acid sequences that has 2 or only 1 amino acid difference with the amino acid sequence DYWMY (SEQ ID NO: 164);
and in which:
b) CDR2 is:
the amino acid sequence EINTNGLITKYPDSVKG (SEQ ID NO: 233); or
an amino acid sequence that has at least 80%, preferably at least 90%, more preferably at least 95%, even more preferably at least 99% sequence identity with the amino acid sequence EINTNGLITKYPDSVKG (SEQ ID NO: 233); or
an amino acid sequences that has 2 or only 1 amino acid difference(s) with the amino acid sequence EINTNGLITKYPDSVKG (SEQ ID NO: 233);
and in which
c) CDR3 is:
the amino acid sequence SPSGFN (SEQ ID NO: 300); or
an amino acid sequence that has at least 80%, preferably at least 90%, more preferably at least 95%, even more preferably at least 99% sequence identity with the amino acid sequence SPSGFN (SEQ ID NO: 300); or
an amino acid sequences that has 2 or only 1 amino acid difference with the amino acid sequence SPSGFN (SEQ ID NO: 300).

A Nanobody in accordance with any one of XXI) to XXV), in which CDR1 is the amino acid sequence DYWMY (SEQ ID NO: 164).

A Nanobody in accordance with any one of XXI) to XXV), in which CDR2 is the amino acid sequence EINTNGLITKYPDSVKG (SEQ ID NO: 233).

A Nanobody in accordance with any one of XXI) to XXV), in which CDR3 is the amino acid sequence SPSGFN (SEQ ID NO: 300)

A Nanobody in accordance with any one of XXI) to XXV), in which:
CDR1 is the amino acid sequence DYWMY (SEQ ID NO: 164); and CDR3 is the amino acid sequence SPSGFN (SEQ ID NO: 300); or
CDR1 is the amino acid sequence DYWMY (SEQ ID NO: 164; and CDR2 is the amino acid sequence EINTNGLITKYPDSVKG (SEQ ID NO: 233); or
CDR2 is the amino acid sequence EINTNGLITKYPDSVKG (SEQ ID NO: 233); and CDR3 is the amino acid sequence SPSGFN (SEQ ID NO: 300)

A Nanobody in accordance with any one of XXI) to XXV), in which CDR1 is the amino acid sequence DYWMY (SEQ ID NO: 164); and CDR3 is the amino acid sequence SPSGFN (SEQ ID NO: 300).

A Nanobody in accordance with any one of XXI) to XXV), in which CDR1 is the amino acid sequence DYWMY (SEQ ID NO: 164); CDR2 is the amino acid sequence EINTNGLITKYPDSVKG (SEQ ID NO: 233) and CDR3 is the amino acid sequence SPSGFN (SEQ ID NO: 300).

A Nanobody in accordance with any one of XXI) to XXV), in which
any amino acid substitution is preferably a conservative amino acid substitution; and/or
said amino acid sequence preferably only contains amino acid substitutions, and no amino acid deletions or insertions, compared to the above amino acid sequence(s).

and with some other particularly preferred aspects being:

A Nanobody in accordance with any one of XXI) to XXV), which is a KERE-class Nanobody.

A Nanobody in accordance with any one of XXI) to XXV), which has at least 80%, preferably at least 90%, more preferably at least 95%, even more preferably at least 99% sequence identity (as defined herein) with one of the amino acid sequences of SEQ ID NO's 50 (TNF3), 83 (TNF20), 85 (TNF21), 85 (TNF22), 96 (TNF23) or 98 (TNF33).

A Nanobody in accordance with any one of XXI) to XXV), in which
a) CDR1 comprises:
the amino acid sequence NYYMG (SEQ ID NO: 172); or
an amino acid sequence that has at least 80%, preferably at least 90%, more preferably at least 95%, even more preferably at least 99% sequence identity with the amino acid sequence NYYMG (SEQ ID NO: 172); or an amino acid sequences that has 2 or only 1 amino acid difference with the amino acid sequence NYYMG (SEQ ID NO: 172);

and b) CDR2 comprises:

the amino acid sequence NISWRGYNIYYKDSVKG (SEQ ID NO: 240); or an amino acid sequence that has at least 80%, preferably at least 90%, more preferably at least 95%, even more preferably at least 99% sequence identity with the amino acid sequence NISWRGYNIYYKDSVKG (SEQ ID NO: 240); or an amino acid sequences that has 2 or only 1 amino acid difference(s) with the amino acid sequence NISWRGYNIYYKDSVKG (SEQ ID NO: 240);

and c) CDR3 comprises:

the amino acid sequence SILPLSDDPGWNTY (SEQ ID NO: 308); or an amino acid sequence that has at least 80%, preferably at least 90%, more preferably at least 95%, even more preferably at least 99% sequence identity with the amino acid sequence SILPLSDDPGWNTY (SEQ ID NO: 308); or an amino acid sequences that has 2 or only 1 amino acid difference with the amino acid sequence SILPLSDDPGWNTY (SEQ ID NO: 308).

A Nanobody in accordance with any one of XXI) to XXV), in which CDR1 comprises the amino acid sequence NYYMG (SEQ ID NO: 172).

A Nanobody in accordance with any one of XXI) to XXV), in which CDR2 comprises the amino acid sequence NISWRGYNIYYKDSVKG (SEQ ID NO: 240).

A Nanobody in accordance with any one of XXI) to XXV), in which CDR3 comprises the amino acid sequence SILPLSDDPGWNTY (SEQ ID NO: 308).

A Nanobody in accordance with any one of XXI) to XXV), in which:

CDR1 comprises the amino acid sequence NYYMG (SEQ ID NO: 172); and CDR3 comprises the amino acid sequence SILPLSDDPGWNTY (SEQ ID NO: 308); or CDR1 comprises the amino acid sequence NYYMG (SEQ ID NO: 172); and CDR2 comprises the amino acid sequence NISWRGYNIYYKDSVKG (SEQ ID NO: 240); or CDR2 comprises the amino acid sequence NISWRGYNIYYKDSVKG (SEQ ID NO: 240); and CDR3 comprises the amino acid sequence SILPLSDDPGWNTY (SEQ ID NO: 308).

A Nanobody in accordance with any one of XXI) to XXV), in which CDR1 comprises the amino acid sequence NYYMG (SEQ ID NO: 172); CDR2 comprises the amino acid sequence SILPLSDDPGWNTY (SEQ ID NO: 308) and CDR3 comprises the amino acid sequence ILPLSDDPGWNTY (SEQ ID NO: 436).

A Nanobody in accordance with any one of XXI) to XXV), in which a) CDR1 is:

the amino acid sequence NYYMG (SEQ ID NO: 172); or an amino acid sequence that has at least 80%, preferably at least 90%, more preferably at least 95%, even more preferably at least 99% sequence identity with the amino acid sequence NYYMG (SEQ ID NO: 172); or an amino acid sequences that has 2 or only 1 amino acid difference with the amino acid sequence NYYMG (SEQ ID NO: 172);

and b) CDR2 is:

the amino acid sequence NISWRGYNIYYKDSVKG (SEQ ID NO: 240); or an amino acid sequence that has at least 80%, preferably at least 90%, more preferably at least 95%, even more preferably at least 99% sequence identity with the amino acid sequence NISWRGYNIYYKDSVKG (SEQ ID NO: 240); or an amino acid sequences that has 2 or only 1 amino acid difference(s) with the amino acid sequence NISWRGYNIYYKDSVKG (SEQ ID NO: 240);

and c) CDR3 is:

the amino acid sequence SILPLSDDPGWNTY (SEQ ID NO: 308); or an amino acid sequence that has at least 80%, preferably at least 90%, more preferably at least 95%, even more preferably at least 99% sequence identity with the amino acid sequence SILPLSDDPGWNTY (SEQ ID NO: 308); or an amino acid sequences that has 2 or only 1 amino acid difference with the amino acid sequence SILPLSDDPGWNTY (SEQ ID NO: 308).

A Nanobody in accordance with any one of XXI) to XXV), in which CDR1 is the amino acid sequence NYYMG (SEQ ID NO: 172).

A Nanobody in accordance with any one of XXI) to XXV), in which CDR2 is the amino acid sequence NISWRGYNIYYKDSVKG (SEQ ID NO: 240).

A Nanobody in accordance with any one of XXI) to XXV), in which CDR3 is the amino acid sequence SILPLSDDPGWNTY (SEQ ID NO: 308).

A Nanobody in accordance with any one of XXI) to XXV), in which:

CDR1 is the amino acid sequence NYYMG (SEQ ID NO: 172); and CDR3 is the amino acid sequence SILPLSDDPGWNTY (SEQ ID NO: 308); or CDR1 is the amino acid sequence NYYMG (SEQ ID NO: 172); and CDR2 is the amino acid sequence NISWRGYNIYYKDSVKG (SEQ ID NO: 240); or CDR2 is the amino acid sequence NISWRGYNIYYKDSVKG (SEQ ID NO: 240); and CDR3 is the amino acid sequence SILPLSDDPGWNTY (SEQ ID NO: 308).

A Nanobody in accordance with any one of XXI) to XXV), in which CDR1 is the amino acid sequence NYYMG (SEQ ID NO: 172); CDR2 is the amino acid sequence SILPLSDDPGWNTY (SEQ ID NO: 308) and CDR3 is the amino acid sequence ILPLSDDPGWNTY (SEQ ID NO: 436).

A Nanobody in accordance with any one of XXI) to XXV), in which any amino acid substitution is preferably a conservative amino acid substitution; and/or said amino acid sequence preferably only contains amino acid substitutions, and no amino acid deletions or insertions, compared to the above amino acid sequence(s).

A Nanobody in accordance with any one of XXI) to XXV), which is a humanized Nanobody.

and with yet some other particularly preferred aspects being:

XXVI) A protein or polypeptide, which comprises or essentially consists of at least one Nanobody in accordance with any one of XXI) to XXV).

XXVII) A protein or polypeptide, which comprises two Nanobodies in accordance with any one of XXI) to XXV).

XXVIII) A protein or polypeptide, which comprises two Nanobodies in accordance with any one of XXI) to XXV), and which is such that said protein or polypeptide, upon binding to a TNF trimer, is capable inhibiting or reducing the TNF receptor crosslinking that is mediated by said TNF trimer and/or the signal transduction that is mediated by such receptor crosslinking.

XXIX) A protein or polypeptide, which comprises two Nanobodies in accordance with any one of XXI) to XXV), and which is capable of intramolecular binding to at least two TNF receptor binding sites on a TNF trimer.

XXX) A protein or polypeptide, which comprises two Nanobodies in accordance with any one of XXI) to XXV), linked via a suitable linker.

XXXI) A protein or polypeptide, which comprises two Nanobodies in accordance with any one of XXI) to XXV), linked via a suitable linker, and which is pegylated.

XXXII) A protein or polypeptide which comprises two Nanobodies in accordance with any one of XXI) to XXV), and which further comprises at least one Nanobody directed against human serum albumin.

XXXIII) A protein or polypeptide which comprises two Nanobodies in accordance with any one of XXI) to XXV), and which further comprises at least one Nanobody directed against human serum albumin, and which is such that said protein or polypeptide, upon binding to a TNF trimer, is capable inhibiting or reducing the TNF receptor crosslinking that is mediated by said TNF trimer and/or the signal transduction that is mediated by such receptor crosslinking.

XXXIV) A protein or polypeptide which comprises two Nanobodies in accordance with any one of XXI) to XXV), and which further comprises at least one Nanobody directed against human serum albumin and which is capable of intramolecular binding to at least two TNF receptor binding sites on a TNF trimer.

XXXV) A protein or polypeptide which comprises two Nanobodies in accordance with any one of XXI) to XXV), and which further comprises one Nanobody directed against human serum albumin, in which each of the two Nanobodies in accordance with any one of XXI) to XXV) is linked, optionally via a suitable linker, to the one Nanobody directed against human serum albumin.

XXXVI) A protein or polypeptide which comprises two Nanobodies in accordance with any one of XXI) to XXV), and which further comprises one Nanobody directed against human serum albumin, in which each of the two Nanobodies in accordance with any one of XXI) to XXV) is linked, optionally via a suitable linker, to the one Nanobody directed against human serum albumin, and which is such that said protein or polypeptide, upon binding to a TNF trimer, is capable inhibiting or reducing the TNF receptor crosslinking that is mediated by said TNF trimer and/or the signal transduction that is mediated by such receptor crosslinking.

XXXVII) A protein or polypeptide which comprises two Nanobodies in accordance with any one of XXI) to XXV), and which further comprises one Nanobody directed against human serum albumin, in which each of the two Nanobodies in accordance with any one of XXI) to XXV) is linked, optionally via a suitable linker, to the one Nanobody directed against human serum albumin, and which is capable of intramolecular binding to at least two TNF receptor binding sites on a TNF trimer.

A protein or polypeptide in accordance with any one of XXVI) to XXXVII), in which the at least one Nanobody directed against human serum albumin is a humanized Nanobody.

A protein or polypeptide in accordance with any one of XXVI) to XXXVII), in which the at least one Nanobody directed against human serum albumin is a humanized variant of the Nanobody ALB 1 (SEQ ID NO: 63).

A protein or polypeptide in accordance with any one of XXVI) to XXXVII), in which the at least one Nanobody directed against human serum albumin is a chosen from the group consisting of ALB 3 (SEQ ID NO: 87), ALB 4 (SEQ ID NO: 88), ALB 5 (SEQ ID NO: 89), ALB 6 (SEQ ID NO: 100), ALB 7 (SEQ ID NO: 101), ALB 8 (SEQ ID NO: 102) ALB 9 (SEQ ID NO: 103) and ALB 10 (SEQ ID NO: 104).

A protein or polypeptide in accordance with any one of XXVI) to XXXVII), in which the at least one Nanobody directed against human serum albumin is ALB 8.

A protein or polypeptide in accordance with any one of XXVI) to XXXVII), which comprises or essentially consists of two humanized Nanobodies Nanobodies in accordance with any one of XXI) to XXV), and one humanized variant of the Nanobody ALB 1 (SEQ ID NO: 63).

It should be noted that when a Nanobody is mentioned above as being "in accordance with any one of XXI) to XXV) above", it is at least according to one of XXI) to XXV), may be according to two or more of XXI) to XXV), and may also include any one or more of the other aspects that are indicated as being "in accordance with any one of XXI) to XXV) above. Similarly, when a protein or polypeptide is mentioned above as being "in accordance with any one of XXVI) to XXXVII) above", it is at least according to one of XXVI) to XXXVII), may be according to two or more of XXVI) to XXXVII), and may also include any one or more of the other aspects that are indicated as being "in accordance with any one of XXVI) to XXXVII) above.

A clone that has been found to be particularly useful as an anti-TNF Nanobody is the clone PMP1C2 (TNF1). As can be seen from the comparative data from the KYM-assay in Table 39, TNF1 has an EC50 value that is more then 4 times better than the best monovalent Nanobody described in WO 04/41862 (Nanobody 3E), i.e. 2,466 nM for PMP1C2 vs. 12 nM for 3E (As can be seen from Table 39, all Nanobodies TNF1 to TNF 9 of the invention gave a better EC50 value in this assay than 3E). In this respect, it should also be noted that Nanobody 3E from WO 04/41862 belongs to the "KERE class" (as described herein), and can therefore be humanized to a lesser degree than Nanobody PMP1C2 (which belongs to the "GLEW class"). When Nanobody PMP1C2 is compared to the Nanobody 1A from WO 04/41862, a GLEW-class Nanobody with the highest degree in sequence homology with PMP1C2 (in both the CDR's and the frameworks), the $EC_{50}$ value obtained for PMP1C2 in the KYM assay is more than 50 times better, i.e. 2.466 nM for PMP1C2 compared to 100 nM for 1A.

Accordingly, Nanobodies that comprise one or more, preferably any two and more preferably all three of the CDR's present in the clone PMP1C2 (or CDR sequences that are derived therefrom or correspond thereto) are particularly preferred in the invention. Also, these Nanobodies preferably belong to the "103 P,R,S group" (as defined herein), and most preferably have an R at position 103, and preferably also have GLEW or a GLEW-like sequence at positions 44-47. Also, when these Nanobodies belong to the "103 P, R, S group" (and in particular when they have an R at position 103), one preferred, but non-limiting humanizing substitution is 108Q to 108L. Other preferred, but non-limiting humanizing substitutions in these preferred Nanobodies are one or more of those present in the humanized variants of TNF1 described herein, such as TNF13, TNF14, TNF 29 or TNF30, as will immediately be clear from a comparison between the sequence of TNF1 and these humanized sequences.

Thus, in a particularly preferred Nanobody of the invention, at least one of the CDR1, CDR2 and CDR3 sequences present is suitably chosen from the group consisting of the CDR1 sequence of SEQ ID NO: 164, the CDR2 sequence of SEQ ID NO: 232, and the CDR3 sequence of SEQ ID NO: 300, respectively (i.e. the CDR sequences present in clone TNF1), or from the group of CDR1, CDR2 and CDR3 sequences, respectively, that have at least 80%, preferably at least 90%, more preferably at least 95%, even more preferably at least 99% "sequence identity" (as defined herein) with the CDR1 sequence of SEQ ID NO: 164, the CDR2 sequence of SEQ ID NO: 232, and the CDR3 sequence of SEQ ID NO: 300, respectively; and/or from the group consisting of the CDR1, CDR2 and CDR3 sequences, respectively, that have 3, 2 or only 1 "amino acid difference(s)" (as defined herein) with the CDR1 sequence of SEQ ID NO: 164, the CDR2 sequence of SEQ ID NO: 232, and the CDR3 sequence of SEQ ID NO: 300, respectively.

Preferably, in these preferred Nanobodies of the invention, at least two of the CDR1, CDR2 and CDR3 sequences present are suitably chosen from the group consisting of the CDR1 sequence of SEQ ID NO: 164, the CDR2 sequence of SEQ ID NO: 232, and the CDR3 sequence of SEQ ID NO: 300, respectively (i.e. the CDR sequences present in clone TNF1), or from the group consisting of CDR1, CDR2 and CDR3 sequences, respectively, that have at least 80%, preferably at least 90%, more preferably at least 95%, even more preferably at least 99% sequence identity with the CDR1 sequence of SEQ ID NO: 164, the CDR2 sequence of SEQ ID NO: 232, and the CDR3 sequence of SEQ ID NO: 300, respectively; and/or from the group consisting of the CDR1, CDR2 and CDR3 sequences, respectively, that have 3, 2 or only 1 "amino acid difference(s)" with the CDR1 sequence of SEQ ID NO: 164, the CDR2 sequence of SEQ ID NO: 232, and the CDR3 sequence of SEQ ID NO: 300, respectively.

Most preferably, in these preferred Nanobodies of the invention, all three CDR1, CDR2 and CDR3 sequences present are suitably chosen from the group consisting of the CDR1 sequence of SEQ ID NO: 164, the CDR2 sequence of SEQ ID NO: 232, and the CDR3 sequence of SEQ ID NO: 300, respectively (i.e. the CDR sequences present in clone TNF1), or from the group of CDR1, CDR2 and CDR3 sequences, respectively, that have at least 80%, preferably at least 90%, more preferably at least 95%, even more preferably at least 99% sequence identity with the CDR1 sequence of SEQ ID NO: 164, the CDR2 sequence of SEQ ID NO: 232, and the CDR3 sequence of SEQ ID NO: 300, respectively; and/or from the group consisting of the CDR1, CDR2 and CDR3 sequences, respectively, that have 3, 2 or only 1 amino acid difference(s) with the CDR1 sequence of SEQ ID NO: 164, the CDR2 sequence of SEQ ID NO: 232, and the CDR3 sequence of SEQ ID NO: 300, respectively.

Even more preferably, in these preferred Nanobodies of the invention, at least one of the CDR1, CDR2 and CDR3 sequences present is suitably chosen from the group consisting of the CDR1 sequence of SEQ ID NO: 164, the CDR2 sequence of SEQ ID NO: 232, and the CDR3 sequence of SEQ ID NO: 300, respectively (i.e. the CDR sequences present in clone TNF1). Preferably, in this embodiment, at least one or preferably both of the other two CDR sequences present are suitably suitably chosen from CDR sequences that that have at least 80%, preferably at least 90%, more preferably at least 95%, even more preferably at least 99% sequence identity with the CDR1 sequence of SEQ ID NO: 164, the CDR2 sequence of SEQ ID NO: 232, and the CDR3 sequence of SEQ ID NO: 300, respectively; and/or suitably chosen from the group consisting of the CDR sequences that have 3, 2 or only 1 amino acid difference(s) with the CDR1 sequence of SEQ ID NO: 164, the CDR2 sequence of SEQ ID NO: 232, and the CDR3 sequence of SEQ ID NO: 300, respectively.

Even more preferably, in these preferred Nanobodies of the invention, at least two of the CDR1, CDR2 and CDR3 sequences present are suitably chosen from the group consisting of the CDR1 sequence of SEQ ID NO: 164, the CDR2 sequence of SEQ ID NO: 232, and the CDR3 sequence of SEQ ID NO: 300, respectively (i.e. the CDR sequences present in clone TNF1). Preferably, in this embodiment, the remaining CDR sequence present are suitably chosen from the group of CDR sequences that that have at least 80%, preferably at least 90%, more preferably at least 95%, even more preferably at least 99% sequence identity with the CDR1 sequence of SEQ ID NO: 164, the CDR2 sequence of SEQ ID NO: 232, and the CDR3 sequence of SEQ ID NO: 300, respectively; and/or from the group consisting of CDR sequences that have 3, 2 or only 1 amino acid difference(s) with the CDR1 sequence of SEQ ID NO: 164, the CDR2 sequence of SEQ ID NO: 232, and the CDR3 sequence of SEQ ID NO: 300, respectively.

Particularly preferred Nanobodies of the invention comprise the CDR1 sequence of SEQ ID NO: 164, the CDR2 sequence of SEQ ID NO: 232, and the CDR3 sequence of SEQ ID NO: 300, respectively (i.e. the CDR sequences present in clone TNF1).

Nanobodies with the above CDR sequences preferably have framework sequences that are as further defined herein. Some particularly preferred, but non-limiting combinations of framework sequences can be seen in the above Table I. As will be clear to the skilled person, a combination of FR1, FR2, FR3 and FR4 sequences that occur in the same clone (i.e. FR1, FR2, FR3 and FR4 sequences which are mentioned on the same line in Table I) will usually be preferred (although the invention in its broadest sense is not limited thereto, and also comprises other suitable combinations of the framework sequences mentioned in Table I).

More specifically, some preferred aspects of this embodiment of the invention are:

XXXVIII) A nanobody against TNF-alpha, which consist of 4 framework regions (FR1 to FR4 respectively) and 3 complementarity determining regions (CDR1 to CDR3 respectively), in which:
   a) CDR1 comprises:
      the amino acid sequence DYWMY (SEQ ID NO: 164); or
      an amino acid sequence that has at least 80%, preferably at least 90%, more preferably at least 95%, even more preferably at least 99% sequence identity with the amino acid sequence DYWMY (SEQ ID NO: 164); or an amino acid sequences that has only 1 amino acid difference with the amino acid sequence DYWMY (SEQ ID NO: 164);

and b) CDR2 comprises:

the amino acid sequence EINTNGLITKYPDSVKG (SEQ ID NO: 233); or an amino acid sequence that has at least 80%, preferably at least 90%, more preferably at least 95%, even more preferably at least 99% sequence identity with the amino acid sequence EINTNGLITKYPDSVKG (SEQ ID NO: 233); or an amino acid sequences that has 2 or only 1 amino acid difference(s) with the amino acid sequence EINTNGLITKYPDSVKG (SEQ ID NO: 233);

and c) CDR3 comprises:

the amino acid sequence SPSGFN (SEQ ID NO: 300); or an amino acid sequence that has at least 80%, preferably at least 90%, more preferably at least 95%, even more preferably at least 99% sequence identity with the amino acid sequence SPSGFN (SEQ ID NO: 300); or an amino acid sequences that has only 1 amino acid difference with the amino acid sequence SPSGFN (SEQ ID NO: 300).

A nanobody in accordance with XXXVIII), in which CDR1 comprises the amino acid sequence DYWMY (SEQ ID NO: 164).

A nanobody in accordance with XXXVIII), in which CDR2 comprises the amino acid sequence EINTNGLITKYPDSVKG (SEQ ID NO: 233).

A nanobody in accordance with XXXVIII), in which CDR3 comprises the amino acid sequence SPSGFN (SEQ ID NO: 300).

A nanobody in accordance with XXXVIII), in which:

CDR1 comprises the amino acid sequence DYWMY (SEQ ID NO: 164); and CDR3 comprises the amino acid sequence SPSGFN (SEQ ID NO: 300); or CDR1 comprises the amino acid sequence DYWMY (SEQ ID NO: 164); and CDR2 comprises the amino acid sequence EINTNGLITKYPDSVKG (SEQ ID NO: 233); or CDR2 comprises the amino acid sequence EINTNGLITKYPDSVKG (SEQ ID NO: 233); and CDR3 comprises the amino acid sequence SPSGFN (SEQ ID NO: 300)

A nanobody in accordance with XXXVIII), in which CDR1 comprises the amino acid sequence DYWMY (SEQ ID NO: 164); and CDR3 comprises the amino acid sequence SPSGFN (SEQ ID NO: 300).

A nanobody in accordance with XXXVIII) in which CDR1 comprises the amino acid sequence DYWMY (SEQ ID NO: 164); CDR2 comprises the amino acid sequence EINTNGLITKYPDSVKG (SEQ ID NO: 233) and CDR3 comprises the amino acid sequence SPSGFN (SEQ ID NO: 300).

A Nanobody in accordance with XXXVIII), in which any amino acid substitution is preferably a conservative amino acid substitution; and/or said amino acid sequence preferably only contains amino acid substitutions, and no amino acid deletions or insertions, compared to the above amino acid sequence(s).

A Nanobody in accordance with XXXVIII), which is a GLEW-class Nanobody.

A Nanobody in accordance with XXXVIII), which contains an arginine residue (R) at position 103.

A Nanobody in accordance with XXXVIII), which has at least 80%, preferably at least 90%, more preferably at least 95%, even more preferably at least 99% sequence identity (as defined herein) with one of the amino acid sequences of SEQ ID NO's 52 (TNF1), 76 (TNF13), 77 (TNF14), 95 (TNF29) or 96 (TNF30).

A Nanobody in accordance with XXXVIII), which is a humanized Nanobody.

A Nanobody in accordance with XXXVIII), which contains a leucine residue (L) at position 108.

A Nanobody in accordance with XXXVIII), which has a $K_{off}$ rate for TNF of better than 2.10-3 (1/s), preferably better than 1.10-3 (1/s); or a humanized variant of such a Nanobody;

A Nanobody in accordance with XXXVIII), which has an EC50 value in the cell-based assay using KYM cells described in Example 1, under 3), of WO 04/041862 that is better than the EC50 value of Nanobody VHH 3E (SEQ ID NO:4) of WO 04/041862 in the same assay; or a humanized variant of such a Nanobody.

A Nanobody in accordance with XXXVIII), which has an EC50 value in the cell-based assay using KYM cells described in Example 1, under 3), of WO 04/041862 that is better than 5 nM; or a humanized variant of such a Nanobody.

A Nanobody in accordance with XXXVIII), which has an EC50 value in the cell-based assay using KYM cells described in Example 1, under 3), of WO 04/041862 that is better than 3 nM; or a humanized variant of such a Nanobody.

XXXIX) A Nanobody against TNF-alpha, which consist of 4 framework regions (FR1 to FR4 respectively) and 3 complementarity determining regions (CDR1 to CDR3 respectively), in which a) CDR1 is:

the amino acid sequence DYWMY (SEQ ID NO: 164); or an amino acid sequence that has at least 80%, preferably at least 90%, more preferably at least 95%, even more preferably at least 99% sequence identity with the amino acid sequence DYWMY (SEQ ID NO: 164); or an amino acid sequences that has only 1 amino acid difference with the amino acid sequence DYWMY (SEQ ID NO; 164);

and in which:

b) CDR2 is:

the amino acid sequence EINTNGLITKYPDSVKG (SEQ ID NO: 233); or an amino acid sequence that has at least 80%, preferably at least 90%, more preferably at least 95%, even more preferably at least 99% sequence identity with the amino acid sequence EINTNGLITKYPDSVKG (SEQ ID NO: 233); or an amino acid sequences that has 2 or only 1 amino acid difference(s) with the amino acid sequence EINTNGLITKYPDSVKG (SEQ ID NO: 233);
and in which
c) CDR3 is:
the amino acid sequence SPSGFN (SEQ ID NO: 300); or
an amino acid sequence that has at least 80%, preferably at least 90%, more preferably at least 95%, even more preferably at least 99% sequence identity with the amino acid sequence SPSGFN (SEQ ID NO: 300); or
an amino acid sequences that has only 1 amino acid difference with the amino acid sequence SPSGFN (SEQ ID NO: 300).

A Nanobody in accordance with XXXIX), in which CDR1 is the amino acid sequence DYWMY (SEQ ID NO: 164).

A Nanobody in accordance with XXXIX), in which CDR2 is the amino acid sequence EINTNGLITKYPDSVKG (SEQ ID NO: 233).

A Nanobody in accordance with XXXIX), in which CDR3 is the amino acid sequence SPSGFN (SEQ ID NO: 300)

A Nanobody in accordance with XXXIX), in which:
CDR1 is the amino acid sequence DYWMY (SEQ ID NO: 164); and CDR3 is the amino acid sequence SPSGFN (SEQ ID NO: 300); or
CDR1 is the amino acid sequence DYWMY (SEQ ID NO: 164); and CDR2 is the amino acid sequence EINTNGLITKYPDSVKG (SEQ ID NO: 233); or
CDR2 is the amino acid sequence EINTNGLITKYPDSVKG (SEQ ID NO: 233); and CDR3 is the amino acid sequence SPSGFN (SEQ ID NO: 300)

A Nanobody in accordance with XXXIX), in which CDR1 is the amino acid sequence DYWMY (SEQ ID NO: 164); and CDR3 is the amino acid sequence SPSGFN (SEQ ID NO: 300).

A Nanobody in accordance with XXXIX), in which CDR1 is the amino acid sequence DYWMY (SEQ ID NO: 164); CDR2 is the amino acid sequence EINTNGLITKYPDSVKG (SEQ ID NO: 233) and CDR3 is the amino acid sequence SPSGFN (SEQ ID NO: 300).

A Nanobody in accordance with XXXIX), in which:
any amino acid substitution is preferably a conservative amino acid substitution; and/or
said amino acid sequence preferably only contains amino acid substitutions, and no amino acid deletions or insertions, compared to the above amino acid sequence(s).

A Nanobody in accordance with XXXIX), which is a GLEW-class Nanobody.

A Nanobody in accordance with XXXIX), which contains an arginine residue (R) at position 103.

A Nanobody in accordance with XXXIX), which has at least 80%, preferably at least 90%, more preferably at least 95%, even more preferably at least 99% sequence identity (as defined herein) with one of the amino acid sequences of SEQ ID NO's 52 (TNF1), 76 (TNF13), 77 (TNF14), 95 (TNF29) or 96 (TNF30).

A Nanobody in accordance with XXXIX), which is a humanized Nanobody.

A Nanobody in accordance with XXXIX), which contains a leucine residue (L) at position 108.

A Nanobody in accordance with XXXIX), which has a $K_{off}$ rate for TNF of better than 2.10-3 (1/s), preferably better than 1.10-3 (1/s); or a humanized variant of such a Nanobody.

A Nanobody in accordance with XXXIX), which has an EC50 value in the cell-based assay using KYM cells described in Example 1, under 3), of WO 04/041862 that is better than the EC50 value of Nanobody VHH 3E (SEQ ID NO:4) of WO 04/041862 in the same assay or a humanized variant of such a Nanobody.

A Nanobody in accordance with XXXIX), which has an EC50 value in the cell-based assay using KYM cells described in Example 1, under 3), of WO 04/041862 that is better than 5 nM; or a humanized variant of such a Nanobody.

A Nanobody in accordance with XXXIX), which has an EC50 value in the cell-based assay using KYM cells described in Example 1, under 3), of WO 04/041862 that is better than 3 nM; or a humanized variant of such a Nanobody.

A Nanobody in accordance with XXXIX), which is chosen from the group consisting of TNF 13 (SEQ ID NO: 76), TNF 14 (SEQ ID NO: 77), TNF 29 (SEQ ID NO: 95) and TNF 30 (SEQ ID NO:96).

A Nanobody in accordance with XXXIX), which is TNF 30 (SEQ ID NO: 96);

with some other preferred aspects being:

XL) A protein or polypeptide, which comprises or essentially consists of a Nanobody in accordance with XXXVIII) or XXXIX).

XLI) A protein or polypeptide, which comprises or essentially consists of at least one Nanobody in accordance with XXXVIII) or XXXIX).

A protein or polypeptide in accordance with any one of XL) or XLI), which comprises two Nanobodies in accordance with XXXVIII) or XXXIX).

A protein or polypeptide in accordance with any one of XL) or XLI), which comprises two Nanobodies in accordance with XXXVIII) or XXXIX), and which is such that said protein or polypeptide, upon binding to a TNF trimer, is capable inhibiting or reducing the TNF receptor crosslinking that is mediated by said TNF trimer and/or the signal transduction that is mediated by such receptor crosslinking.

A protein or polypeptide in accordance with any one of XL) or XLI), which comprises two Nanobodies in accordance with XXXVIII) or XXXIX), and which is capable of intramolecular binding to at least two TNF receptor binding sites on a TNF trimer.

A protein or polypeptide in accordance with any one of XL) or XLI), which comprises two Nanobodies in accordance with XXXVIII) or XXXIX), which are directly linked to each other or linked to each other via a linker.

A protein or polypeptide in accordance with any one of XL) or XLI), which comprises two Nanobodies in accordance with XXXVIII) or XXXIX), which are linked to each other via an amino acid sequence.

A protein or polypeptide in accordance with any one of XL) or XLI), which comprises two Nanobodies in accordance with XXXVIII) or XXXIX), which are linked to each other via an amino acid sequence (such as, without limitation, an amino acid sequence that comprises glycine and serine residues) that comprises at least 14 amino acids, more preferably at least 17 amino acids, such as about 20-40 amino acids (such as the linker GS30).

A protein or polypeptide in accordance with any one of XL) or XLI), which comprises or essentially consists of the polypeptide TNF 7 (SEQ ID NO: 73), in which both Nanobodies TNF 1 have been humanized.

A protein or polypeptide in accordance with any one of XL) or XLI), which comprises or essentially consists the polypeptide TNF 55 (SEQ ID NO: 419) or TNF 56 (SEQ ID NO: 420).

A protein or polypeptide in accordance with any one of XL) or XLI), which is pegylated.

A protein or polypeptide in accordance with any one of XL) or XLI), which comprises two Nanobodies in accordance with XXXVIII) or XXXIX), and which is such that said protein or polypeptide, upon binding to a TNF trimer, is capable inhibiting or reducing the TNF receptor crosslinking that is mediated by said TNF trimer and/or the signal transduction that is mediated by such receptor crosslinking; and/or which is such that said protein or polypeptide is capable of intramolecular binding to at least two TNF receptor binding sites on a TNF trimer, and which protein or polypeptide further comprises at least one Nanobody directed against human serum albumin.

A protein or polypeptide in accordance with any one of XL) or XLI), which comprises two Nanobodies in accordance with XXXVIII) or XXXIX), and which protein or polypeptide further comprises at least one Nanobody directed against human serum albumin, in which the two Nanobodies in accordance with XXXVIII) or XXXIX) are linked to each other via the at least one Nanobody directed against human serum albumin, and in which the two Nanobodies in accordance with XXXVIII) or XXXIX) are either linked directly to the at least one Nanobody directed against human serum albumin, or are linked to the at least one Nanobody directed against human serum albumin via a linker.

A protein or polypeptide in accordance with any one of XL) or XLI), which comprises two Nanobodies in accordance with XXXVIII) or XXXIX), and which protein or polypeptide further comprises at least one Nanobody directed against human serum albumin, in which the two Nanobodies in accordance with XXXVIII) or XXXIX) are linked to each other via the at least one Nanobody directed against human serum albumin, and in which the two Nanobodies in accordance with XXXVIII) or XXXIX) are either linked directly to the at least one Nanobody directed against human serum albumin, or are linked to the at least one Nanobody directed against human serum albumin via a linker, in which the linker is an amino acid sequence (such as, without limitation, a linker that comprises glycine and serine residues), and in particular an amino acid sequence that comprises between 3 and 40 amino acid residues, such as between 5 and 15 amino acid residues (such as the linker GS9).

A protein or polypeptide in accordance with any one of XL) or XLI), which comprises two Nanobodies in accordance with XXXVIII) or XXXIX), and which protein or polypeptide further comprises at least one Nanobody directed against human serum albumin, in which the two Nanobodies in accordance with XXXVIII) or XXXIX) are linked to each other via the at least one Nanobody directed against human serum albumin, and in which the two Nanobodies in accordance with XXXVIII) or XXXIX) are either linked directly to the at least one Nanobody directed against human serum albumin, or are linked to the at least one Nanobody directed against human serum albumin via a linker, and which protein or polypeptide is such that said protein or polypeptide, upon binding to a TNF trimer, is capable inhibiting or reducing the TNF receptor crosslinking that is mediated by said TNF trimer and/or the signal transduction that is mediated by such receptor crosslinking; and/or which protein or polypeptide is such that said protein or polypeptide is capable of intramolecular binding to at least two TNF receptor binding sites on a TNF trimer.

A protein or polypeptide in accordance with any one of XL) or XLI), in which the at least one Nanobody directed against human serum albumin is a humanized Nanobody.

A protein or polypeptide in accordance with any one of XL) or XLI), in which the at least one Nanobody directed against human serum albumin is a humanized variant of the Nanobody ALB 1 (SEQ ID NO: 63).

A protein or polypeptide in accordance with any one of XL) or XLI), in which the at least one Nanobody directed against human serum albumin is a chosen from the group consisting of ALB 3 (SEQ ID NO: 87), ALB 4 (SEQ ID NO: 88), ALB 5 (SEQ ID NO: 89), ALB 6 (SEQ ID NO: 100), ALB 7 (SEQ ID NO: 101), ALB 8 (SEQ ID NO: 102) ALB 9 (SEQ ID NO: 103) and ALB 10 (SEQ ID NO: 104).

A protein or polypeptide in accordance with any one of XL) or XLI), in which the at least one Nanobody directed against human serum albumin is ALB 8.

A protein or polypeptide in accordance with any one of XL) or XLI), which comprises or essentially consists of two humanized Nanobodies in accordance with any one of XL) or XLI) and one humanized variant of the Nanobody ALB 1 (SEQ ID NO: 63).

A protein or polypeptide in accordance with any one of XL) or XLI), which comprises or essentially consists of the polypeptide TNF24 (SEQ ID NO: 90), in which both the Nanobody TNF 1 as well as the Nanobody ALB 1 has been humanized.

A protein or polypeptide in accordance with any one of XL) or XLI), which comprises or essentially consists of two Nanobodies TNF 30 and one Nanobody ALB 8.

A protein or polypeptide in accordance with any one of XL) or XLI), which comprises or essentially consists the polypeptide TNF 60 (SEQ ID NO: 417).

It should be noted that when a Nanobody is mentioned above as being "in accordance with XXXVIII" or "in accordance with XXXIX", it is at least according to one of XXXVIII) and/or XXXIX), and may also include any one or more of the other aspects that are indicated as being "in accordance with XXXVIII" or "in accordance with XXXIX" above. Similarly, when a protein or polypeptide is mentioned above as being "in accordance with any one of XL) or XLI)", it is at least according to one of XL) to XLI), may be according to two or more of VI) to XVIII), and may also include any one or more of the other aspects that are indicated as being "in accordance with any one of XL) or XLI) above.

For the Nanobodies based on Nanobody TNF1 above (including but not limited to the humanized Nanobodies), the framework sequences may generally be as described herein, and preferably are as follows:

a) FR1 comprises or is:
the amino acid sequence of SEQ ID NO: 130; or
an amino acid sequence that has at least 80%, preferably at least 90%, more preferably at least 95%, even more preferably at least 99% sequence identity with the amino acid sequence of SEQ ID NO: 130; or an amino acid sequences that has only 1 amino acid difference with the amino acid sequence of SEQ ID NO: 130;

and b) FR2 comprises or is:

the amino acid sequence of SEQ ID NO: 198; or an amino acid sequence that has at least 80%, preferably at least 90%, more preferably at least 95%, even more preferably at least 99% sequence identity with the amino acid sequence of SEQ ID NO: 198; or an amino acid sequences that has 2 or only 1 amino acid difference(s) with the amino acid sequence of SEQ ID NO: 198;

and c) FR3 comprises or is:

the amino acid sequence of SEQ ID NO: 266; or an amino acid sequence that has at least 80%, preferably at least 90%, more preferably at least 95%, even more preferably at least 99% sequence identity with the amino acid sequence of SEQ ID NO: 266; or an amino acid sequences that has only 1 amino acid difference with the amino acid sequence of SEQ ID NO: 266.

and d) FR4 comprises or is:

the amino acid sequence of SEQ ID NO: 334; or an amino acid sequence that has at least 80%, preferably at least 90%, more preferably at least 95%, even more preferably at least 99% sequence identity with the amino acid sequence of SEQ ID NO: 334; or an amino acid sequences that has only 1 amino acid difference with the amino acid sequence of SEQ ID NO: 334;

in which the amino acid differences present in the framework sequences are more preferably as described herein.

Nanobodies against TNF-alpha, which have framework regions as described above (i.e. similar to TNF1), and in which at least one of the framework regions (such as any two, any three or all four framework regions) have been humanized, form a further aspect of the invention. Such Nanobodies may in particular have CDR's that are such that the Nanobody has a Koff rate for TNF of better than 2.10-3 (1/s), preferably better than 1.10-3 (1/s); and/or have CDR's that are such that the Nanobody has an EC50 value in the cell-based assay using KYM cells described in Example 1, under 3), of WO 04/041862 that is better than the EC50 value of Nanobody VHH 3E (SEQ NO:4) of WO 04/041862 in the same assay; and in particular better than 12 nM, more in particular better than 5 nM, even more in particular better than 3 nM. Also, or alternatively, such Nanobodies are preferably directed against the same epitope of TNF (i.e. the TNF trimer) as TNF1.

In particular, the invention relates to a Nanobody against TNF-alpha, which is a humanized variant of a Nanobody against TNF-alpha, which Nanobody against TNF-alpha has the following framework sequences: FR1: SEQ ID NO: 130; FR2: SEQ ID NO: 198; FR3: SEQ ID NO: 266; and FR4: SEQ ID NO: 334. Such a Nanobody may in particular have CDR's that are such that the Nanobody has a Koff rate for TNF of better than 2.10-3 (1/s), preferably better than 1.10-3 (1/s); and/or have CDR's that are such that the Nanobody has an EC50 value in the cell-based assay using KYM cells described in Example 1, under 3), of WO 04/041862 that is better than the EC50 value of Nanobody VHH 3E (SEQ ID NO:4) of WO 04/041862 in the same assay; and in particular better than 12 nM, more in particular better than 5 nM, even more in particular better than 3 nM. Also, or alternatively, such Nanobodies are preferably directed against the same epitope of TNF (i.e. the TNF trimer) as TNF1.

Another clone that has been found to be particularly useful as an anti-TNF Nanobody is the clone PMP5F10 (TNF3, SEQ ID NO: 60). As can be seen from the comparative data from the KYM-assay in Table 39, TNF3 has an EC50 value that is more than 15 times better than the best monovalent Nanobody described in WO 04/41862.

Accordingly, Nanobodies that comprise one or more, preferably any two and more preferably all three of the CDR's present in the clone PMP5F10 (or CDR sequences that are derived therefrom or correspond thereto) are particularly preferred in the invention. Also, these Nanobodies preferably belong to the KERE class.

More specifically, some preferred aspects of this embodiment of the invention are:

XLII) A Nanobody against TNF-alpha, which consist of 4 framework regions (FR1 to FR4 respectively) and 3 complementarity determining regions (CDR1 to CDR3 respectively), in which a) CDR1 comprises:

the amino acid sequence NYYMG (SEQ ID NO: 172); or an amino acid sequence that has at least 80%, preferably at least 90%, more preferably at least 95%, even more preferably at least 99% sequence identity with the amino acid sequence NYYMG (SEQ ID NO: 172); or an amino acid sequences that has 2 or only 1 amino acid difference with the amino acid sequence NYYMG (SEQ ID NO: 172);

and b) CDR2 comprises:

the amino acid sequence NISWRGYNIYYKDSVKG (SEQ ID NO: 240); or an amino acid sequence that has at least 80%, preferably at least 90%, more preferably at least 95%, even more preferably at least 99% sequence identity with the amino acid sequence NISWRGY-NIYYKDSVKG (SEQ ID NO: 240); or an amino acid sequences that has 2 or only 1 amino acid difference(s) with the amino acid sequence NISWRGYNIYYKDSVKG (SEQ ID NO: 240);

and c) CDR3 comprises:

the amino acid sequence SILPLSDDPGWNTY (SEQ ID NO: 308); or an amino acid sequence that has at least 80%, preferably at least 90%, more preferably at least 95%, even more preferably at least 99% sequence identity with the amino acid sequence SILPLSDDPGWNTY (SEQ ID NO: 308); or an amino acid sequences that has 2 or only 1 amino acid difference with the amino acid sequence SIL-PLSDDPGWNTY (SEQ ID NO: 308).

A Nanobody in accordance with XLII), in which CDR1 comprises the amino acid sequence NYYMG (SEQ ID NO: 172).

A Nanobody in accordance with XLII), in which CDR2 comprises the amino acid sequence NISWRGY-NIYYKDSVKG (SEQ ID NO: 240).

A Nanobody in accordance with XLII), in which CDR3 comprises the amino acid sequence SIL-PLSDDPGWNTY (SEQ ID NO: 308).

A Nanobody in accordance with XLII), in which:
  CDR1 comprises the amino acid sequence NYYMG (SEQ ID NO: 172); and CDR3 comprises the amino acid sequence SILPLSDDPGWNTY (SEQ ID NO: 308); or
  CDR1 comprises the amino acid sequence NYYMG (SEQ ID NO: 172); and CDR2 comprises the amino acid sequence NISWRGYNIYYKDSVKG (SEQ ID NO: 240); or
  CDR2 comprises the amino acid sequence NISWRGYNIYYKDSVKG (SEQ ID NO: 240); and CDR3 comprises the amino acid sequence SILPLSDDPGWNTY (SEQ ID NO: 308).
A Nanobody in accordance with XLII), in which CDR1 comprises the amino acid sequence NYYMG (SEQ ID NO: 172); CDR2 comprises the amino acid sequence SILPLSDDPGWNTY (SEQ ID NO: 308) and CDR3 comprises the amino acid sequence ILPLSDDPGWNTY (SEQ ID NO 436).
A Nanobody in accordance with XLII), in which
  any amino acid substitution is preferably a conservative amino acid substitution; and/or
  said amino acid sequence preferably only contains amino acid substitutions, and no amino acid deletions or insertions, compared to the above amino acid sequence(s).
A Nanobody in accordance with XLII), which is a KERE-class Nanobody.
A Nanobody in accordance with XLII), which has at least 80%, preferably at least 90%, more preferably at least 95%, even more preferably at least 99% sequence identity (as defined herein) with one of the amino acid sequences of SEQ ID NO's 50 (TNF3), 83 (TNF20), 85 (TNF21), 85 (TNF22), 96 (TNF23) or 99 (TNF33).
A Nanobody in accordance with XLII), which is a humanized Nanobody.
A Nanobody in accordance with XLII), which has a $K_{off}$ rate for TNF of better than $2.10^{-3}$ (1/s), preferably better than $1.10^{-3}$ (1/s); or a humanized variant of such a Nanobody.
A Nanobody in accordance with XLII), which has an EC50 value in the cell-based assay using KYM cells described in Example 1, under 3), of WO 04/041862 that is better than the EC50 value of Nanobody VHH 3E (SEQ ID NO:4) of WO 04/041862 in the same assay; or a humanized variant of such a Nanobody.
A Nanobody in accordance with XLII), which has an EC50 value in the cell-based assay using KYM cells described in Example 1, under 3), of WO 04/041862 that is better than 5 nM; or a humanized variant of such a Nanobody.
A Nanobody in accordance with XLII), which has an EC50 value in the cell-based assay using KYM cells described in Example 1, under 3), of WO 04/041862 that is better than 3 nM; or a humanized variant of such a Nanobody.
XLIII) A Nanobody against TNF-alpha, which consist of 4 framework regions (FR1 to FR4 respectively) and 3 complementarity determining regions (CDR1 to CDR3 respectively), in which
a) CDR1 is:
  the amino acid sequence NYYMG (SEQ ID NO: 172); or
  an amino acid sequence that has at least 80%, preferably at least 90%, more preferably at least 95%, even more preferably at least 99% sequence identity with the amino acid sequence NYYMG (SEQ ID NO: 172); or
  an amino acid sequences that has 2 or only 1 amino acid difference with the amino acid sequence NYYMG (SEQ ID NO: 172);
and
b) CDR2 is:
  the amino acid sequence NISWRGYNIYYKDSVKG (SEQ ID NO: 240); or
  an amino acid sequence that has at least 80%, preferably at least 90%, more preferably at least 95%, even more preferably at least 99% sequence identity with the amino acid sequence NISWRGYNIYYKDSVKG (SEQ ID NO: 240); or
  an amino acid sequences that has 2 or only 1 amino acid difference(s) with the amino acid sequence NISWRGYNIYYKDSVKG (SEQ ID NO: 240);
and
c) CDR3 is:
  the amino acid sequence SILPLSDDPGWNTY (SEQ ID NO: 308); or
  an amino acid sequence that has at least 80%, preferably at least 90%, more preferably at least 95%, even more preferably at least 99% sequence identity with the amino acid sequence SILPLSDDPGWNTY (SEQ ID NO: 308); or
  an amino acid sequences that has 2 or only 1 amino acid difference with the amino acid sequence SILPLSDDPGWNTY (SEQ ID NO: 308).
A Nanobody in accordance with XLIII), in which CDR1 is the amino acid sequence NYYMG (SEQ ID NO: 172).
A Nanobody in accordance with XLIII), in which CDR2 is the amino acid sequence NISWRGYNIYYKDSVKG (SEQ ID NO: 240).
A Nanobody in accordance with XLIII), in which CDR3 is the amino acid sequence SILPLSDDPGWNTY (SEQ ID NO: 308).
A Nanobody in accordance with XLIII), in which:
  CDR1 is the amino acid sequence NYYMG (SEQ ID NO: 172); and CDR3 is the amino acid sequence SILPLSDDPGWNTY (SEQ ID NO: 308); or
  CDR1 is the amino acid sequence NYYMG (SEQ ID NO: 172); and CDR2 is the amino acid sequence NISWRGYNIYYKDSVKG (SEQ ID NO: 240); or
  CDR2 is the amino acid sequence NISWRGYNIYYKDSVKG (SEQ ID NO: 240); and CDR3 is the amino acid sequence SILPLSDDPGWNTY (SEQ ID NO: 308).
A Nanobody in accordance with XLIII), in which CDR1 is the amino acid sequence NYYMG (SEQ ID NO: 172); CDR2 is the amino acid sequence SILPLSDDPGWNTY (SEQ ID NO: 308) and CDR3 is the amino acid sequence ILPLSDDPGWNTY (SEQ ID NO: 436).
A Nanobody in accordance with XLIII), in which
  any amino acid substitution is preferably a conservative amino acid substitution; and/or
  said amino acid sequence preferably only contains amino acid substitutions, and no amino acid deletions or insertions, compared to the above amino acid sequence(s).
A Nanobody in accordance with XLIII), which is a KERE-class Nanobody.
A Nanobody in accordance with XLIII), which has at least 80%, preferably at least 90%, more preferably at least 95%, even more preferably at least 99% sequence identity (as defined herein) with one of the amino acid sequences of SEQ ID NO's 50 (TNF3), 83 (TNF20), 85 (TNF21), 85 (TNF22), 96 (TNF23) or 99 (TNF33).

A Nanobody in accordance with XLIII), which is a humanized Nanobody.

A Nanobody in accordance with XLIII), which has a $K_{off}$ rate for TNF of better than $2.10^{-3}$ (1/s), preferably better than $2.10^{-3}$ (1/s); or a humanized variant of such a Nanobody.

A Nanobody in accordance with XLIII), which has an EC50 value in the cell-based assay using KYM cells described in Example 1, under 3), of WO 04/041862 that is better than the EC50 value of Nanobody VHH 3E (SEQ ID NO:4) of WO 04/041862 in the same assay; or a humanized variant of such a Nanobody.

A Nanobody in accordance with XLIII), which has an EC50 value in the cell-based assay using KYM cells described in Example 1, under 3), of WO 04/041862 that is better than 5 nM; or a humanized variant of such a Nanobody.

A Nanobody in accordance with XLIII), which has an EC50 value in the cell-based assay using KYM cells described in Example 1, under 3), of WO 04/041862 that is better than 3 nM; or a humanized variant of such a Nanobody.

A Nanobody in accordance with XLIII), which is chosen from the group consisting of SEQ ID NO's, 83 (TNF20), 85 (TNF21), 85 (TNF22), 96 (TNF23) or 98 (TNF33)TNF 13 (SEQ ID NO: 76), TNF 14 (SEQ ID NO: 77), TNF 29 (SEQ ID NO: 95) and TNF 30 (SEQ ID NO:96)

with some other preferred aspects being:

XLIV) A protein or polypeptide, which comprises or essentially consists of a Nanobody in accordance with XLII) or XLIII).

XLV) A protein or polypeptide, which comprises or essentially consists of at least one Nanobody in accordance with XLII) or XLIII).

XLVI) A protein or polypeptide, which comprises two Nanobodies in accordance with XLII) or XLIII).

XLVII) A protein or polypeptide, which comprises two Nanobodies in accordance with XLII) or XLIII), and which is such that said protein or polypeptide, upon binding to a TNF trimer, is capable inhibiting or reducing the TNF receptor crosslinking that is mediated by said TNF trimer and/or the signal transduction that is mediated by such receptor crosslinking.

XLVIII) A protein or polypeptide, which comprises two Nanobodies in accordance with XLII) or XLIII), and which is capable of intramolecular binding to at least two TNF receptor binding sites on a TNF trimer.

A protein or polypeptide in accordance with any one of XLIV) or XLVIII), which comprises or essentially consists of the polypeptide TNF 6 (SEQ ID NO: 72) or TNF 9 (SEQ ID NO: 75, in which both Nanobodies TNF 3 have been humanized A protein or polypeptide in accordance with any one of XLIV) or XLVIII), which is pegylated.

A protein or polypeptide, which comprises two Nanobodies in accordance with XLII) or XLIII), and which is such that said protein or polypeptide, upon binding to a TNF trimer, is capable inhibiting or reducing the TNF receptor crosslinking that is mediated by said TNF trimer and/or the signal transduction that is mediated by such receptor crosslinking; and/or which is such that said protein or polypeptide is capable of intramolecular binding to at least two TNF receptor binding sites on a TNF trimer, and which protein or polypeptide further comprises at least one Nanobody directed against human serum albumin.

A protein or polypeptide in accordance with any one of XLIV) or XLVIII), in which the at least one Nanobody directed against human serum albumin is a humanized Nanobody.

A protein or polypeptide in accordance with any one of XLIV) or XLVIII), in which the at least one Nanobody directed against human serum albumin is a humanized variant of the Nanobody ALB 1 (SEQ ID NO: 63).

A protein or polypeptide in accordance with any one of XLIV) or XLVIII), in which the at least one Nanobody directed against human serum albumin is a chosen from the group consisting of ALB 3 (SEQ ID NO: 87), ALB 4 (SEQ ID NO: 88), ALB 5 (SEQ ID NO: 89), ALB 6 (SEQ ID NO: 100), ALB 7 (SEQ ID NO: 101), ALB 8 (SEQ ID NO: 102) ALB 9 (SEQ ID NO: 103) and ALB 10 (SEQ ID NO: 104).

A protein or polypeptide in accordance with any one of XLIV) or XLVIII), in which the at least one Nanobody directed against human serum albumin is ALB 8.

A protein or polypeptide in accordance with any one of XLIV) or XLVIII), which comprises or essentially consists of two humanized Nanobodies in accordance with any one of XLIV) or XLVIII) and one humanized variant of the Nanobody ALB 1 (SEQ ID NO: 63).

A protein or polypeptide in accordance with any one of XLIV) or XLVIII), which comprises or essentially consists of the polypeptide TNF26 (SEQ ID NO: 92), in which both the Nanobodies TNF 3 as well as the Nanobody ALB 1 has been humanized.

It should be noted that when a Nanobody is mentioned above as being "in accordance with XLII" or "in accordance with XLIII", it is at least according to one of XLII) and/or XLIII), and may also include any one or more of the other aspects that are indicated as being "in accordance with XLII)" or "in accordance with XLIII)" above. Similarly, when a protein or polypeptide is mentioned above as being "in accordance with any one of XLIV) or XLVIII)", it is at least according to one of XL) to XLI), may be according to two or more of XLIV) to XLVIII), and may also include any one or more of the other aspects that are indicated as being "in accordance with any one of XLIV) or XLVIII) above.

For the Nanobodies based on Nanobody TNF3 above (including but not limited to the humanized Nanobodies), the framework sequences may generally be as described herein, and preferably are as follows:

a) FR1 comprises or is:
  the amino acid sequence of SEQ ID NO: 138; or
  an amino acid sequence that has at least 80%, preferably at least 90%, more preferably at least 95%, even more preferably at least 99% sequence identity with the amino acid sequence of SEQ ID NO: 138; or
  an amino acid sequences that has only 1 amino acid difference with the amino acid sequence of SEQ ID NO: 138;
  and b) FR2 comprises or is:
  the amino acid sequence of SEQ ID NO: 206; or
  an amino acid sequence that has at least 80%, preferably at least 90%, more preferably at least 95%, even more preferably at least 99% sequence identity with the amino acid sequence of SEQ ID NO: 206; or an amino acid sequences that has 2 or only 1 amino acid difference(s) with the amino acid sequence of SEQ ID NO: 206;
and c) FR3 comprises or is:
the amino acid sequence of SEQ ID NO: 274; or
an amino acid sequence that has at least 80%, preferably at least 90%, more preferably at least 95%, even more preferably at least 99% sequence identity with the amino acid sequence of SEQ ID NO: 274; or
an amino acid sequences that has only 1 amino acid difference with the amino acid sequence of SEQ ID NO: 274.
and d) FR4 comprises or is:
the amino acid sequence of SEQ ID NO: 342; or
an amino acid sequence that has at least 80%, preferably at least 90%, more preferably at least 95%, even more preferably at least 99% sequence identity with the amino acid sequence of SEQ ID NO: 342; or
an amino acid sequences that has only 1 amino acid difference with the amino acid sequence of SEQ ID NO: 342;
in which the amino acid differences present in the framework sequences are more preferably as described herein.

In another aspect, the invention relates to a Nanobody with an amino acid sequence that is chosen from the group consisting of SEQ ID NO's: 52 to 60, from the group consisting of SEQ ID NO's: 76 to 86, from the group consisting of SEQ ID NO's: 95 to 99, from the group consisting of SEQ ID NO's 105 to 129 or from the group consisting of from amino acid sequences that have more than 80%, preferably more than 90%, more preferably more than 95%, such as 99% or more "sequence identity" (as defined herein) with one or more of the amino acid sequences of SEQ ID NO's: 52 to 60, SEQ ID NO's: 76 to 86, SEQ ID NO's: 95 to 99 or SEQ ID NO's 105 to 129, in which the latter amino acid sequences most preferably have framework sequences that are as further defined below under the general description of the framework sequences of Nanobodies.

According to a specific, but non-limiting embodiment, the latter amino acid sequences are "humanized", as further described herein.

Most preferably, the Nanobodies of the invention are chosen from the group consisting of SEQ ID NO's: 52 to 60, from the group consisting of SEQ ID NO's: 76 to 86, from the group consisting of SEQ ID NO's: 95 to 99, or from the group consisting of SEQ ID NO's 105 to 129, of which the "humanized" Nanobodies of SEQ ID NO's 76 to 86 and SEQ ID NO's: 95 to 99 may be particularly preferred.

As mentioned above, a particularly preferred Nanobody of the invention is the clone PMP1C2 (TNF1; SEQ ID NO: 52). Thus, in a preferred aspect, the invention relates to a Nanobody with an amino acid sequence that is chosen from the group consisting of SEQ ID NO: 52 or from the group consisting of from amino acid sequences that have more than 80%, preferably more than 90%, more preferably more than 95%, such as 99% or more "sequence identity" (as defined herein) with the amino acid sequence of SEQ ID NO:52, in which the latter amino acid sequences most preferably have framework sequences that are as further defined below under the general description of the framework sequences of Nanobodies.

Particularly preferred are humanized variants of the clone PMP1C2 (TNF1; SEQ ID NO: 52). Some preferred, but non-limiting examples of such humanized variants are the clones TNF13 (SEQ ID NO: 76), TNF14 (SEQ ID NO:77), TNF29 (SEQ ID NO: 95) and TNF 30 (SEQ ID NO: 96). Thus, in a preferred aspect, the invention relates to a humanized Nanobody with an amino acid sequence that is chosen from the group consisting of SEQ ID NO's: 76, 77, 95 or 96, or from the group consisting of from amino acid sequences that have more than 80%, preferably more than 90%, more preferably more than 95%, such as 99% or more "sequence identity" (as defined herein) with one of the amino acid sequences of SEQ ID NO's: 76, 77, 95 or 96, in which the latter amino acid sequences most preferably have framework sequences that are as further defined below under the general description of the framework sequences of Nanobodies.

According to one preferred embodiment, the Nanobody of the invention is a humanized variant of the Nanobody TNF 1 (SEQ ID NO: 52).

Some preferred aspects of this embodiment of the invention are:

XLIX) A humanized variant of the Nanobody TNF 1, which has a Koff rate for TNF of better than 2.10-3 (1/s), preferably better than 1.10-3 (1/s).

L) A humanized variant of the Nanobody TNF 1, which has an EC50 value in the cell-based assay using KYM cells described in Example 1, under 3), of WO 04/041862 that is better than the EC50 value of Nanobody VHH 3E (SEQ ID NO:4) of WO 04/041862 in the same assay.

LI) A humanized variant of the Nanobody TNF 1, which has an EC50 value in the cell-based assay using KYM cells described in Example 1, under 3), of WO 04/041862 that is better than 5 nM.

LII) A humanized variant of the Nanobody TNF 1, which has an EC50 value in the cell-based assay using KYM cells described in Example 1, under 3), of WO 04/041862 that is better than 3 nM.

LIII) A protein or polypeptide, which comprises or essentially consists of at least one Nanobody which is a humanized variant of the Nanobody TNF 1 in accordance with any one of XLIX) to LII)

LIV) A protein or polypeptide, which comprises or essentially consists of two Nanobodies which are humanized variants of the Nanobody TNF 1 in accordance with any one of XLIX) to LII) (optionally linked via a linker).

LV) A protein or polypeptide, which comprises or essentially consists of two Nanobodies which are humanized variants of the Nanobody TNF 1 in accordance with any one of XLIX) to LII) (optionally linked via a linker), and which is such that said protein or polypeptide, upon binding to a TNF trimer, is capable inhibiting or reducing the TNF receptor crosslinking that is mediated by said TNF trimer and/or the signal transduction that is mediated by such receptor crosslinking.

LVI) A protein or polypeptide, which comprises or essentially consists of two Nanobodies which are humanized variants of the Nanobody TNF 1 in accordance with any one of XLIX) to LII) and which is capable of intramolecular binding to at least two TNF receptor binding sites on a TNF trimer.

LVII) A protein or polypeptide which comprises or essentially consists of the polypeptide TNF 7 (SEQ ID NO: 73), in which both Nanobodies TNF 1 have been humanized.

LVIII) A protein or polypeptide which comprises or essentially consists of the polypeptide TNF 7 (SEQ ID NO: 73), in which both Nanobodies TNF 1 have been humanized, and which is pegylated.

LIX) A protein or polypeptide, which comprises or essentially consists of two Nanobodies which are humanized variants of the Nanobody TNF 1 in accordance with any one of XLIX) to LII), and which further comprises at least one Nanobody directed against human serum albumin.

LX) A protein or polypeptide, which comprises or essentially consists of two Nanobodies which are humanized variants of the Nanobody TNF 1 in accordance with any one of XLIX) to LII), which are each linked (optionally linked via a linker) to one Nanobody directed against human serum albumin.

A protein or polypeptide in accordance with any one of LIII) to LX), in which the at least one Nanobody directed against human serum albumin is a humanized Nanobody.

A protein or polypeptide in accordance with any one of LIII) to LX), in which the at least one Nanobody directed against human serum albumin is a humanized variant of the Nanobody ALB 1 (SEQ ID NO: 63).

A protein or polypeptide in accordance with any one of LIII) to LX), in which the at least one Nanobody directed against human serum albumin is a chosen from the group consisting of ALB 3 (SEQ ID NO: 87), ALB 4 (SEQ ID NO: 88), ALB 5 (SEQ ID NO: 89), ALB 6 (SEQ ID NO: 100), ALB 7 (SEQ ID NO: 101), ALB 8 (SEQ ID NO: 102) ALB 9 (SEQ ID NO: 103) and ALB 10 (SEQ ID NO: 104).

A protein or polypeptide in accordance with any one of LIII) to LX), in which the at least one Nanobody directed against human serum albumin is ALB 8.

A protein or polypeptide in accordance with any one of LIII) to LX), which comprises or essentially consists of the polypeptide TNF24 (SEQ ID NO: 90), in which both the Nanobody TNF 1 as well as the Nanobody ALB TNF 1 has been humanized.

A protein or polypeptide in accordance with any one of LIII) to LX), which comprises or essentially consists of two Nanobodies TNF 30 and one Nanobody ALB 8.

According to one preferred embodiment, the Nanobody of the invention is a humanized variant of the Nanobody TNF 3 (SEQ ID NO: 60).

Some preferred aspects of this embodiment of the invention are:

LXI) A humanized variant of the Nanobody TNF 3, which has a Koff rate for TNF of better than 2.10-3 (1/s), preferably better than 1.10-3 (1/s).

LXII) A humanized variant of the Nanobody TNF 3, which has an EC50 value in the cell-based assay using KYM cells described in Example 1, under 3), of WO 04/041862 that is better than the EC50 value of Nanobody VHH 3E (SEQ ID NO:4) of WO 04/041862 in the same assay.

LXIII) A humanized variant of the Nanobody TNF 3, which has an EC50 value in the cell-based assay using KYM cells described in Example 1, under 3), of WO 04/041862 that is better than 5 nM.

LXIV) A humanized variant of the Nanobody TNF 3, which has an EC50 value in the cell-based assay using KYM cells described in Example 1, under 3), of WO 04/041862 that is better than 3 nM.

LXV) A protein or polypeptide, which comprises or essentially consists of at least one Nanobody which is a humanized variant of the Nanobody TNF 3 in accordance with any one of LXI) to LXIV)

LXVI) A protein or polypeptide, which comprises or essentially consists of two Nanobodies which are humanized variants of the Nanobody TNF 3 in accordance with any one of LXI) to LXIV) (optionally linked via a linker).

LXVII) A protein or polypeptide, which comprises or essentially consists of two Nanobodies which are humanized variants of the Nanobody TNF 3 in accordance with any one of LXI) to LXIV) (optionally linked via a linker), and which is such that said protein or polypeptide, upon binding to a TNF trimer, is capable inhibiting or reducing the TNF receptor crosslinking that is mediated by said TNF trimer and/or the signal transduction that is mediated by such receptor crosslinking.

LXVIII) A protein or polypeptide, which comprises or essentially consists of two Nanobodies which are humanized variants of the Nanobody TNF 3 in accordance with any one of LXI) to LXIV) and which is capable of intramolecular binding to at least two TNF receptor binding sites on a TNF trimer.

LXIX) A protein or polypeptide which comprises or essentially consists of the polypeptide TNF 6 (SEQ ID NO: 72) or TNF 9 (SEQ ID NO: 75), in which both Nanobodies TNF 3 have been humanized.

LXX) A protein or polypeptide which comprises or essentially consists of the polypeptide TNF 6 (SEQ ID NO: 72) or TNF 9 (SEQ ID NO: 75), in which both Nanobodies TNF 3 have been humanized, and which is pegylated.

LXXI) A protein or polypeptide, which comprises or essentially consists of two Nanobodies which are humanized variants of the Nanobody TNF 3 in accordance with any one of LXI) to LXIV), and which further comprises at least one Nanobody directed against human serum albumin.

LXXII) A protein or polypeptide, which comprises or essentially consists of two Nanobodies which are humanized variants of the Nanobody TNF 3 in accordance with any one of LXI) to LXIV), which are each linked (optionally linked via a linker) to one Nanobody directed against human serum albumin.

A protein or polypeptide in accordance with any one of LXV) to LXXII), in which the at least one Nanobody directed against human serum albumin is a humanized Nanobody.

A protein or polypeptide in accordance with any one of LXV) to LXXII), in which the at least one Nanobody directed against human serum albumin is a humanized variant of the Nanobody ALB 1 (SEQ ID NO: 63).

A protein or polypeptide in accordance with any one of LXV) to LXXII), in which the at least one Nanobody directed against human serum albumin is a chosen from the group consisting of ALB 3 (SEQ ID NO: 87), ALB 4 (SEQ ID NO: 88), ALB 5 (SEQ ID NO: 89), ALB 6 (SEQ ID NO: 100), ALB 7 (SEQ ID NO: 101), ALB 8 (SEQ ID NO: 102) ALB 9 (SEQ ID NO: 103) and ALB 10 (SEQ ID NO: 104).

A protein or polypeptide in accordance with any one of LXV) to LXXII), in which the at least one Nanobody directed against human serum albumin is ALB 8.

A protein or polypeptide in accordance with any one of LXV) to LXXII), which comprises or essentially consists of the polypeptide TNF26 (SEQ ID NO: 92), in which both the Nanobodies TNF 3 as well as the Nanobody ALB 1 has been humanized.

In another aspect, the invention relates to a polypeptide that comprises or essentially consists of at least one Nanobody against TNF-alpha as defined herein. Such polypeptides are also referred to herein as "polypeptides of the invention" and may be as further described hereinbelow and/or as generally described in WO 04/041862 for the Nanobodies disclosed therein, and may for example be multivalent polypeptides or multispecific polypeptides, again as further described hereinbelow.

Preferably, a polypeptide of the invention is either bivalent or trivalent (i.e. comprising two or three Nanobodies of the invention, respectively, optionally linked via one or two linkers as defined below, respectively) or a multispecific polypeptide, comprising one or two, and preferably two, Nanobodies of the invention and at least one Nanobody directed against a serum protein, and in particular against a human serum protein, such as against human serum albumin.

In one preferred, but non-limiting embodiments, the Nanobodies of the invention present in the polypeptides of the invention are chosen from the group consisting of SEQ ID NO's: 52 to 60 and SEQ ID NO's 105-129 or from humanized variants thereof, and in particular from the "humanized" Nanobodies of SEQ ID NO's 76 to 86 and SEQ ID NO's: 95 to 99. The Nanobodies against human serum albumin present in the polypeptides of the invention are preferably as defined below, and are more preferably chosen from the group consisting of SEQ ID NO's: 61 to 67, SEQ ID NO's: 87 to 89 and SEQ ID NO's: 100-104, and in particular from the "humanized" Nanobodies against human serum albumin of SEQ ID NO's 76 to 86 and SEQ ID NO's 100-104.

With respect to the Nanobodies that are present in the polypeptides of the invention, it will be clear to the skilled person that the Nanobodies that are mentioned herein as "preferred" (or as "more preferred", "even more preferred", etc.) are also preferred (or more preferred, or even more preferred, etc.) for use in the polypeptides described herein. Thus, polypeptides that comprise or essentially consist of one or more "preferred" Nanobodies of the invention will generally be preferred, and polypeptides that comprise or essentially consist of one or more "more preferred" Nanobodies of the invention of the invention will generally be more preferred, etc.

Thus, in the invention, polypeptides that comprise one or more Nanobodies that essentially consist of one of the preferred variants of clone PMP1C2 (TNF1; SEQ ID NO: 52), in which said preferred variants are as defined herein, are particularly preferred. Even more preferred are polypeptides that comprise one or more Nanobodies that essentially consist of one of the humanized variants of clone PMP1C2 (TNF1; SEQ ID NO: 52), in which said humanized variants are as defined herein (examples being, without limitation, TNF13, TNF14, TNF29 and TNF30). TNF30 is a particularly preferred humanized "building block" for use in the polypeptides of the invention.

Some preferred, but non-limiting examples of such proteins and polypeptides are PMP1C2 itself, the humanized variants TNF13, TNF14, TNF29 and TNF30; the constructs of SEQ ID NO: 70 (TNF4), SEQ ID NO: 73 (TNF7), SEQ ID NO: 90 (TNF24), SEQ ID NO: 93 (TNF27); and the constructs of SEQ ID NO: 417 (TNF60), SEQ ID NO: 419 (TNF55) and SEQ ID NO: 420 (TNF56), in which the latter three constructs contain the humanized variant TNF 30 as a building block.

As mentioned herein, the Nanobodies and constructs described herein may be pegylated, or contain one or more (additional) amino acid residues that allow for pegylation and/or facilitate pegylation. Two preferred, but non-limiting examples of such polypeptides are TNF55 and TNF56, which both contain an additional cysteine residue for easy attachment of a PEG-group.

Some preferred, but non-limiting examples of polypeptides of the invention are the bivalent polypeptides of the invention of SEQ ID NO's: 70 to 75 and the multispecific polypeptides of the invention of SEQ ID NO's: 90 to 94 and SEQ ID NO's 417 to 420.

As can be seen from the data represented below, and in particular from the data given in the Comparative Example, the Nanobodies and/or polypeptides of the invention have improved properties. In particular, the proteins and polypeptides of the invention may have an improved affinity for human TNF-alpha (expressed as the $EC_{50}$-value in the KYM assay described herein), compared to the commercially available anti-TNF biologicals Enbrel™, Humira™ and Remicade™. Also, the Nanobodies described herein may have an improved affinity for TNF-alpha compared to best performing Nanobody described in the International application WO 04/041862. It can thus be expected that polypeptides of the invention comprising at least one of the Nanobodies of the invention will also have improved properties compared to polypeptides that comprise only the Nanobodies against TNF-alpha described in WO 04/041862.

More in particular, a polypeptide as described herein that comprises two or more (and preferably two) Nanobodies as herein (and optionally for example a Nanobody against human serum albumin), has an an EC50 value in the cell-based assay using KYM cells described in Example 1, under 3), of WO 04/041862 that is better than the EC50 value of Humira® en Remicade®, and preferably also better than Enbrel® in the same assay.

For example, such a protein or polypeptide preferably has an EC50 value in the cell-based assay using KYM cells described in Example 1, under 3), of WO 04/041862 that is better than 0.2 nM, preferably better than 0.1 nM, such as better than 0.7 Nm and in particular better than 0.4 nM.

It has also been shown by applicants that Nanobodies against mouse TNF-alpha and polypeptides comprising Nanobodies against mouse TNF-alpha show a beneficial biological activity in the following disease models (data not shown):

The dextran sulfate sodium ("DSS") model of colitis, using both regular mice as well as IL-10 knock out mice, as described by Okayasu et al. (*Gastroenterol* 1990, 98(3): 694)

The collagen induced arthritis ("CIA") model of arthritis ("RA"), as described by Courtenay et al. (*Nature* 1980, 283(5748): 666), using both regular mice as well as IL-10 knock out mice;

The IL-10 knockout mice model of IBD, as for example described by Rennick et al. (*Clin Immunol Immunopathol* 1995, 76 (3 Pt 2): S174)

The Kollias model of RA as for example described by Keffer et al. (*EMBO J* 1991, 10(13): 4025)

The 2,4,6-trinitrobenzenesulphonic acid ("TNBS") model of IBD, as described by Elson et al. (*J Immunol* 1996, 157(5): 2174)

The CIA model of RA, described by Koppieters et al (manuscript in preparation);

The synovial-derived fibroblast model (described below); and

The murine air pouch model.

Preferably, the Nanobodies described herein are better than Nanobody 1A from WO 04/041862 in at least one of these models, and preferably in all of these models; and more preferably Nanobody 3E from WO 04/041862 in at least one of these models, and preferably in all of these models. Also, the polypeptides described herein are preferably equivalent to or better than Humira® or Remicade® in at least one of these models, and preferably in all of these models; and more preferably also equivalent to or better than Enbrel® in at least one of these models, and preferably in all of these models.

These data confirm that Nanobodies against TNF-alpha and polypeptides containing the same, such as the Nanobodies and polypeptides described in WO 04/041862 and in particular the Nanobodies and polypeptides described herein, should have therapeutic efficacy against TNF mediated diseases and disorders, such as the diseases and disorders mentioned above.

In another aspect, the invention relates to a nucleic acid that encodes a Nanobody of the invention and/or a polypeptide of the invention. Such a nucleic acid will also be referred to below as a "nucleic acid of the invention" and may for example be in the form of a genetic construct, as defined below.

In another aspect, the invention relates to host or host cell that expresses or is capable of expressing a Nanobody of the invention and/or a polypeptide of the invention; and/or that contains a nucleic acid encoding a Nanobody of the invention and/or a polypeptide of the invention. Such a host or a host cell may also be analogous to the hosts and host cells described in WO 04/041862, but expressing or capable of expressing a Nanobody of the invention and/or a polypeptide of the invention and/or containing a nucleic acid as described herein.

The invention further relates to a product or composition containing or comprising a Nanobody of the invention, a polypeptide of the invention; and/or a nucleic acid of the invention. Such a product or composition may for example be a pharmaceutical composition (as described below) or a product or composition for diagnostic use (as also described below). Such a product or composition may also be analogous to the products and compositions described in WO 04/041862, but containing or comprising a Nanobody of the invention, a polypeptide of the invention or a nucleic acid of the invention.

The invention further relates to methods for preparing or generating the Nanobodies, polypeptides, nucleic acids, host cells, products and compositions as described herein, which methods are as further described below. Also, generally, the Nanobodies, polypeptides, nucleic acids, host cells, products and compositions described herein may also be prepared and used in a manner analogous to the manner described in WO 04/041862.

The invention further relates to applications and uses of the above Nanobodies, polypeptides, nucleic acids, host cells, products and compositions described herein, which applications and uses include, but are not limited to, the applications and uses described hereinbelow and/or the further uses and applications for Nanobodies against TNF-alpha and/or for polypeptides containing the same in WO 04/041862.

Other aspects, embodiments, advantages and applications of the invention will become clear from the further description hereinbelow.

DETAILED DESCRIPTION OF THE INVENTION

The above and other aspects and embodiments of the invention will become clear from the further description hereinbelow, in which:

a) Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, U K (2001); and Janeway et al., "Immunobiology" (6th Ed.), Garland Science Publishing/Churchill Livingstone, New York (2005), as well as to the general background art cited herein;

b) Unless indicated otherwise, the term "immunoglobulin sequence"—whether it used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). In addition, the term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acid sequences or nucleotide sequences encoding the same, unless the context requires a more limited interpretation;

c) Unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein;

d) Amino acid residues will be indicated according to the standard three-letter or one-letter amino acid code, as mentioned in Table 1;

TABLE 1 one-letter and three-letter amino acid code

| | | | |
|---|---|---|---|
| Nonpolar, | Alanine | Ala | A |
| uncharged | Valine | Val | V |
| (at pH 6.0-7.0)[3] | Leucine | Leu | L |
| | Isoleucine | Ile | I |
| | Phenylalanine | Phe | F |
| | Methionine[1] | Met | M |
| | Tryptophan | Trp | W |
| | Proline | Pro | P |
| Polar, | Glycine[2] | Gly | G |
| uncharged | Serine | Ser | S |
| (at pH 6.0-7.0) | Threonine | Thr | T |
| | Cysteine | Cys | C |
| | Asparagine | Asn | N |
| | Glutamine | Gln | Q |
| | Tyrosine | Tyr | Y |

TABLE 1-continued one-letter and three-letter amino acid code

| Polar, charged (at pH 6.0-7.0) | Lysine | Lys | K |
| --- | --- | --- | --- |
| | Arginine | Arg | R |
| | Histidine[4] | His | H |
| | Aspartate | Asp | D |
| | Glutamate | Glu | E |

Notes:
[1] Sometimes also considered to be a polar uncharged amino acid.
[2] Sometimes also considered to be a nonpolar uncharged amino acid.
[3] As will be clear to the skilled person, the fact that an amino acid residue is referred to in this Table as being either charged or uncharged at pH 6.0 to 7.0 does not reflect in any way on the charge said amino acid residue may have at a pH lower than 6.0 and/or at a pH higher than 7.0; the amino acid residues mentioned in the Table can be either charged and/or uncharged at such a higher or lower pH, as will be clear to the skilled person.
[4] As is known in the art, the charge of a His residue is greatly dependant upon even small shifts in pH, but a His residu can generally be considered essentially uncharged at a pH of about 6.5.

e) For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position).

Alternatively, the degree of sequence identity between two or more nucleotide sequences may be calculated using a known computer algorithm for sequence alignment such as NCBI Blast v2.0, using standard settings.

Some other techniques, computer algorithms and settings for determining the degree of sequence identity are for example described in WO 04/037999, EP 0 967 284, EP 1 085 089, WO 00/55318, WO 00/78972, WO 98/49185 and GB 2 357 768-A.

Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence;

f) For the purposes of comparing two or more amino acid sequences, the percentage of "sequence identity" between a first amino acid sequence and a second amino acid sequence may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined below.

Alternatively, the degree of sequence identity between two amino acid sequences may be calculated using a known computer algorithm, such as those mentioned above for determining the degree of sequence identity for nucleotide sequences, again using standard settings.

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB-A-2 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Nad. Acad Sci. USA 81: 140-144, 1984; Kyte & Doolittle; J Molec. Biol. 157: 105-132, 1981, and Goldman et al., Ann. Rev. Biophys. Chem. 15: 321-353, 1986, all incorporated herein in their entirety by reference. Information on the primary, secondary and tertiary structure of Nanobodies given in the description herein and in the general background art cited above. Also, for this purpose, the crystal structure of a VHH domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional VH domains form the VH/VL interface and potential camelizing substitutions on these positions can be found in the prior art on Nanobodies cited herein;

g) amino acid sequences and nucleic acid sequences are said to be "exactly the same" if they have 100% sequence identity (as defined herein) over their entire length;

h) when comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences;

i) a nucleic acid sequence or amino acid sequence is considered to be "(in) essentially isolated (form)"—for example, compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatographical technique, such as polyacrylamide-gelelectrophoresis;

j) The term "domain" as used herein generally refers to a globular region of an antibody chain, and in particular to a globular region of a heavy chain antibody, or to a polypeptide that essentially consists of such a globular region. Usually, such a domain will comprise peptide loops (for example 3 or 4 peptide loops) stabilized, for example, as a sheet or by disulfide bonds.

k) The term 'antigenic determinant' refers to the epitope on the antigen recognized by the antigen-binding molecule (such as a Nanobody or a polypeptide of the invention) and more in particular by the antigen-binding site of said molecule. The terms "antigenic determinant" and "epitope' may also be used interchangeably herein.

l) An amino acid sequence (such as a Nanobody, an antibody, a polypeptide of the invention, or generally an antigen binding protein or polypeptide or a fragment thereof) that can bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

m) The term "specificity" refers to the number of different types of antigens or antigenic determinants to which a particular antigen-binding molecule or antigen-binding protein (such as a Nanobody or a polypeptide of the invention) molecule can bind. The specificity of an antigen-binding protein can be determined based on affinity and/or avidity. The affinity, represented by the equilibrium constant for the dissociation of an antigen with an antigen-binding protein (KD), is a measure for the binding strength between an antigenic determinant and an antigen-binding site on the antigen-binding protein: the lesser the value of the KD, the stronger the binding strength between an antigenic determinant and the antigen-binding molecule (alternatively, the affinity can also be expressed as the affinity constant (KA), which is 1/KD). As will be clear to the skilled person (for example on the basis of the further disclosure herein), affinity can be determined in a manner known per se, depending on the specific antigen of interest. Avidity is the measure of the strength of binding between an antigen-binding molecule (such as a Nanobody or polypeptide of the invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as the Nanobodies and/or polypeptides of the invention) will bind with a dissociation constant (KD) of $10^{-5}$ to $10^{-12}$ moles/liter (M) or less, and preferably $10^{-7}$ to $10^{-12}$ moles/liter (M) or less and more preferably $10^{-8}$ to $10^{-12}$ moles/liter, and/or with an association constant ($K_A$) of at least $10^7$ $M^{-1}$, preferably at least $10^8$ $M^{-1}$, more preferably at least $10^9$ $M^{-1}$, such as at least $10^{12}$ M. Any $K_D$ value greater than $10^4$ M is generally considered to indicate non-specific binding. Preferably, a Nanobody or polypeptide of the invention will bind to the desired antigen with an $K_D$ less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art.

n) as further described hereinbelow, the amino acid sequence and structure of a Nanobody can be considered—without however being limited thereto—to be comprised of four framework regions or "FR's", which are referred to in the art and hereinbelow as "Framework region 1" or "FR1"; as "Framework region 2" or"FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively;

o) as also further describe hereinbelow, the total number of amino acid residues in a Nanobody can be in the region of 110-120, is preferably 112-115, and is most preferably 113. It should however be noted that parts, fragments or analogs (as further described hereinbelow) of a Nanobody are not particularly limited as to their length and/or size, as long as such parts, fragments or analogs meet the further requirements outlined hereinbelow and are also preferably suitable for the purposes described herein;

p) the amino acid residues of a Nanobody are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, referred to above (see for example FIG. 2 of said reference). According to this numbering, FR1 of a Nanobody comprises the amino acid residues at positions 1-30, CDR1 of a Nanobody comprises the amino acid residues at positions 31-36, FR2 of a Nanobody comprises the amino acids at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113. [In this respect, it should be noted that—as is well known in the art for $V_H$ domains and for $V_{HH}$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

Alternative methods for numbering the amino acid residues of $V_H$ domains, which methods can also be applied in an analogous manner to $V_{HH}$ domains from Camelids and to Nanobodies, are the method described by Chothia et al. (*Nature* 342, 877-883 (1989)), the so-called "AbM definition" and the so-called "contact definition". However, in the present description, claims and figures, the numbering according to Kabat as applied to $V_{HH}$ domains by Riechmann and Muyldermans will be followed, unless indicated otherwise; and q) the Figures, Sequence Listing and the Experimental Part/Examples are only given to further illustrate the invention and should not be interpreted or construed as limiting the scope of the invention and/or of the appended claims in any way, unless explicitly indicated otherwise herein.

For a general description of heavy chain antibodies and the variable domains thereof, reference is inter alia made to the following references, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and applicant; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551 by applicant and the further published patent applications by applicant;

Hamers-Casterman et al., Nature 1993 June 3; 363 (6428): 446-8; Davies and Riechmann, FEBS Lett. 1994 Feb. 21; 339(3): 285-90; Muyldermans et al., Protein Eng. 1994 September; 7(9): 1129-3; Davies and Riechmann, Biotechnology (NY) 1995 May; 13(5): 475-9; Gharoudi et al., 9th Forum of Applied Biotechnology, Med. Fac. Landbouw Univ. Gent. 1995; 60/4a part I: 2097-2100; Davies and Riechmann, Protein Eng. 1996 June; 9(6): 531-7; Desmyter et al., Nat Struct Biol. 1996 September; 3(9): 803-11; Sheriff et al., Nat Struct Biol. 1996 September; 3(9): 733-6; Spinelli et al., Nat Struct Biol. 1996 September; 3(9): 752-7; Arbabi Ghahroudi et al., FEBS Lett. 1997 Sep. 15; 414(3): 521-6; Vu et al., Mol Immunol. 1997 November-December; 34 (16-17): 1121-31; Atarhouch et al., Journal of Camel Practice and Research 1997; 4: 177-182; Nguyen et al., J. Mol. Biol. 1998 Jan. 23; 275(3): 413-8; Lauwereys et al., EMBO J. 1998 Jul. 1; 17(13): 3512-20; Frenken et al., Res Immunol. 1998 July-August; 149(6):589-99; Transue et al., Proteins 1998 Sep. 1; 32(4): 515-22; Muyldermans and Lauwereys, J. Mol. Recognit. 1999 March-April; 12 (2): 131-40; van der Linden et al., Biochim. Biophys. Acta 1999 Apr. 12; 1431(1): 37-46.; Decanniere et al., Structure Fold. Des. 1999 Apr. 15; 7(4): 361-70; Ngyuen et al., Mol. Immunol. 1999 June; 36(8): 515-24; Woolven et al., Immunogenetics 1999 October; 50 (1-2): 98-101; Riechmann and Muyldermans, J. Immunol. Methods 1999 Dec. 10; 231 (1-2): 25-38; Spinelli et al., Biochemistry 2000 Feb. 15; 39(6): 1217-22; Frenken et al., J. Biotechnol. 2000 Feb. 28; 78(1): 11-21; Nguyen et al., EMBO J. 2000 Mar. 1; 19(5): 921-30; van der Linden et al., J. Immunol. Methods 2000 Jun. 23; 240 (1-2): 185-95; Decanniere et al., J. Mol. Biol. 2000 Jun. 30; 300 (1): 83-91; van der Linden et al., J. Biotechnol. 2000 July 14; 80(3): 261-70; Harmsen et al., Mol. Immunol. 2000 August; 37(10): 579-90; Perez et al., Biochemistry 2001 Jan. 9; 40(1): 74-83; Conrath et al., J. Biol. Chem. 2001 Mar. 9; 276 (10): 7346-50; Muyldermans et al., Trends Biochem Sci. 2001 April; 26(4): 230-5; Muyldermans S., J. Biotechnol. 2001 June; 74 (4): 277-302; Desmyter et al., J. Biol. Chem. 2001 Jul. 13; 276 (28): 26285-90; Spinelli et al., J. Mol. Biol. 2001 Aug. 3; 311 (1): 123-9; Conrath et al., Antimicrob Agents Chemother. 2001 October; 45 (10): 2807-12; Decanniere et al., J. Mol. Biol. 2001 Oct. 26; 313(3): 473-8; Nguyen et al., Adv Immunol. 2001; 79: 261-96; Muruganandam et al., FASEB J. 2002 February; 16 (2): 240-2; Ewert et al., Biochemistry 2002 Mar. 19; 41 (11): 3628-36; Dumoulin et al., Protein Sci. 2002 March; 11 (3): 500-15; Cortez-Retamozo et al., Int. J. Cancer. 2002 Mar. 20; 98 (3): 456-62; Su et al., Mol. Biol. Evol. 2002 March; 19 (3): 205-15; van der Vaart J M., Methods Mol Biol. 2002; 178: 359-66; Vranken et al., Biochemistry 2002 Jul. 9; 41 (27): 8570-9; Nguyen et al., Immunogenetics 2002 April; 54 (1): 39-47; Renisio et al., Proteins 2002 Jun. 1; 47 (4): 546-55; Desmyter et al., J. Biol. Chem. 2002 Jun. 28; 277 (26): 23645-50; Ledeboer et al., J. Dairy Sci. 2002 June; 85 (6): 1376-82; De Genst et al., J. Biol. Chem. 2002 Aug. 16; 277 (33): 29897-907; Ferrat et al., Biochem. J. 2002 Sep. 1; 366 (Pt 2): 415-22; Thomassen et al., Enzyme and Microbial Technol. 2002; 30: 273-8; Harmsen et al., Appl. Microbiol. Biotechnol. 2002 December; 60 (4): 449-54; Jobling et al., Nat Biotechnol. 2003 January; 21 (1): 77-80; Conrath et al., Dev. Comp. Immunol. 2003 February; 27 (2): 87-103; Pleschberger et al., Bioconjug. Chem. 2003 March-April; 14 (2): 440-8; Lah et al., J. Biol. Chem. 2003 April 18; 278 (16): 14101-11; Nguyen et al., Immunology. 2003 May; 109 (1): 93-101; Joosten et al., Microb. Cell Fact. 2003 January 30; 2 (1): 1; Li et al., Proteins 2003 Jul. 1; 52 (1): 47-50; Loris et al., Biol Chem. 2003 Jul. 25; 278 (30): 28252-7; van Koningsbruggen et al., J. Immunol. Methods. 2003 August; 279 (1-2): 149-61; Dumoulin et al., Nature. 2003 Aug. 14; 424 (6950): 783-8; Bond et al., J. Mol. Biol. 2003 Sep. 19; 332 (3): 643-55; Yau et al., J. Immunol. Methods. 2003 Oct. 1; 281 (1-2): 161-75; Dekker et al., J. Virol. 2003 November; 77 (22): 12132-9; Meddeb-Mouelhi et al., Toxicon. 2003 December; 42 (7): 785-91; Verheesen et al., Biochim. Biophys. Acta 2003 Dec. 5; 1624 (1-3): 21-8; Zhang et al., J Mol Biol. 2004 Jan. 2; 335 (1): 49-56; Stijlemans et al., J Biol Chem. 2004 Jan. 9; 279 (2): 1256-61; Cortez-Retamozo et al., Cancer Res. 2004 Apr. 15; 64 (8): 2853-7; Spinelli et al., FEBS Lett. 2004 Apr. 23; 564 (1-2): 35-40; Pleschberger et al., Bioconjug. Chem. 2004 May-June; 15 (3): 664-71; Nicaise et al., Protein Sci. 2004 July; 13 (7): 1882-91; Omidfar et al., Tumour Biol. 2004 July-August; 25 (4): 179-87; Omidfar et al., Tumour Biol. 2004 September-December; 25 (5-6): 296-305; Szynol et al., Antimicrob Agents Chemother. 2004 September; 48(9):3390-5; Saerens et al., J. Biol.

Chem. 2004 Dec. 10; 279 (50): 51965-72; De Genst et al., J. Biol. Chem. 2004 Dec. 17; 279 (51): 53593-601; Dolk et al., Appl. Environ. Microbiol. 2005 January; 71(1): 442-50; Joosten et al., Appl Microbiol Biotechnol. 2005 January; 66(4): 384-92; Dumoulin et al., J. Mol. Biol. 2005 Feb. 25; 346 (3): 773-88; Yau et al., J Immunol Methods. 2005 February; 297 (1-2): 213-24; De Genst et al., J. Biol. Chem. 2005 Apr. 8; 280 (14): 14114-21; Huang et al., Eur. J. Hum. Genet. 2005 Apr. 13; Dolk et al., Proteins. 2005 May 15; 59 (3): 555-64; Bond et al., J. Mol. Biol. 2005 May 6; 348(3):699-709; Zarebski et al., J. Mol. Biol. 2005 Apr. 21; [E-publication ahead of print].

In accordance with the terminology used in the above references, the variable domains present in naturally occurring heavy chain antibodies will also be referred to as "$V_{HH}$ domains", in order to distinguish them from the heavy chain variable domains that are present in conventional 4-chain antibodies (which will be referred to hereinbelow as "$V_H$ domains") and from the light chain variable domains that are present in conventional 4-chain antibodies (which will be referred to hereinbelow as "$V_L$ domains").

As mentioned in the prior art referred to above, $V_{HH}$ domains have a number of unique structural characteristics and functional properties which make isolated $V_{HH}$ domains (as well as Nanobodies based thereon, which share these structural characteristics and functional properties with the naturally occurring $V_{HH}$ domains) and proteins containing the same highly advantageous for use as functional antigen-binding domains or proteins. In particular, and without being limited thereto, $V_{HH}$ domains (which have been "designed" by nature to functionally bind to an antigen without the presence of, and without any interaction with, a light chain variable domain) and Nanobodies can function as a single, relatively small, functional antigen-binding structural unit, domain or protein. This distinguishes the $V_{HH}$ domains from the $V_H$ and $V_L$ domains of conventional 4-chain antibodies, which by themselves are generally not suited for practical application as single antigen-binding proteins or domains, but need to be combined in some form or another to provide a functional antigen-binding unit (as in for example conventional antibody fragments such as Fab fragments; in ScFv's fragments, which consist of a $V_H$ domain covalently linked to a $V_L$ domain).

Because of these unique properties, the use of $V_{HH}$ domains and Nanobodies as single antigen-binding proteins or as antigen-binding domains (i.e. as part of a larger protein or polypeptide) offers a number of significant advantages over the use of conventional $V_H$ and $V_L$ domains, scFv's or conventional antibody fragments (such as Fab- or F(ab')$_2$- fragments):

only a single domain is required to bind an antigen with high affinity and with high selectivity, so that there is no need to have two separate domains present, nor to assure that these two domains are present in the right spacial conformation and configuration (i.e. through the use of especially designed linkers, as with scFv's);

$V_{HH}$ domains and Nanobodies can be expressed from a single gene and require no post-translational folding or modifications;

$V_{HH}$ domains and Nanobodies can easily be engineered into multivalent and multispecific formats (as further discussed herein);

$V_{HH}$ domains and Nanobodies are highly soluble and do not have a tendency to aggregate (as with the mouse-derived antigen-binding domains described by Ward et al., Nature, Vol. 341, 1989, p. 544);

$V_{HH}$ domains and Nanobodies are highly stable to heat, pH, proteases and other denaturing agents or conditions (see for example Ewert et al, supra);

$V_{HH}$ domains and Nanobodies are easy and relatively cheap to prepare, even on a scale required for production. For example, $V_{HH}$ domains, Nanobodies and proteins/polypeptides containing the same can be produced using microbial fermentation (e.g. as further described below) and do not require the use of mammalian expression systems, as with for example conventional antibody fragments;

$V_{HH}$ domains and Nanobodies are relatively small (approximately 15 kDa, or 10 times smaller than a conventional IgG) compared to conventional 4-chain antibodies and antigen-binding fragments thereof, and therefore show high(er) penetration into tissues (including but not limited to solid tumors and other dense tissues) than such conventional 4-chain antibodies and antigen-binding fragments thereof;

$V_{HH}$ domains and Nanobodies can show so-called cavity-binding properties (inter alia due to their extended CDR3 loop, compared to conventional $V_H$ domains) and can therefore also access targets and epitopes not accessible to conventional 4-chain antibodies and antigen-binding fragments thereof. For example, it has been shown that $V_{HH}$ domains and Nanobodies can inhibit enzymes (see for example WO 97/49805; Transue et al., (1998), supra; Lauwereys et al., (1998), supra.

As mentioned above, the invention generally relates to Nanobodies directed against TNF-alpha, as well as to polypeptides comprising or essentially consisting of one or more of such Nanobodies, that can be used for the prophylactic, therapeutic and/or diagnostic purposes described below and in WO 04/041862.

As also mentioned above and further described below, the invention further relates to nucleic acids encoding such Nanobodies and polypeptides, to methods for preparing such Nanobodies and polypeptides, to host cells expressing or capable of expressing such Nanobodies or polypeptides, to uses of such Nanobodies, polypeptides, nucleic acids or host cells, and to compositions comprising such Nanobodies, polypeptides, nucleic acids or host cells.

Generally, it should be noted that the term Nanobody as used herein in its broadest sense is not limited to a specific biological source or to a specific method of preparation. For example, as will be discussed in more detail below, the Nanobodies of the invention can be obtained (1) by isolating the $V_{HH}$ domain of a naturally occurring heavy chain antibody; (2) by expression of a nucleotide sequence encoding a naturally occurring $V_{HH}$ domain; (3) by "humanization" (as described below) of a naturally occurring $V_{HH}$ domain or by expression of a nucleic acid encoding a such humanized $V_{HH}$ domain; (4) by "camelization" (as described below) of a naturally occurring $V_H$ domain from any animal species, in particular a species of mammal, such as from a human being, or by expression of a nucleic acid encoding such a camelized $V_H$ domain; (5) by "camelisation" of a "domain antibody" or "Dab" as described by Ward et al (supra), or by expression of a nucleic acid encoding such a camelized $V_H$ domain; (6) using synthetic or semi-synthetic techniques for preparing proteins, polypeptides or other amino acid sequences; (7) by preparing a nucleic acid encoding a Nanobody using techniques for nucleic acid synthesis, followed by expression of the nucleic acid thus obtained; and/or (8) by any combination of the foregoing. Suitable methods and techniques for performing the foregoing will be clear to the skilled person based on the disclosure herein and for example include the methods and techniques described in more detail hereinbelow.

However, according to a specific embodiment, the Nanobodies of the invention do not have an amino acid sequence that is exactly the same as (i.e. as a degree of sequence identity of 100% with) the amino acid sequence of a naturally occurring $V_H$ domain, such as the amino acid sequence of a naturally occurring $V_H$ domain from a mammal, and in particular from a human being.

One particularly preferred class of Nanobodies of the invention comprises Nanobodies with an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description below and the prior art on humanization referred to herein. Again, it should be noted that such humanized Nanobodies of the invention can be obtained in any suitable manner known per se (i.e. as indicated under points (1)-(8) above) and thus are not strictly limited to polypeptides that have been obtained using a polypeptide that comprises a naturally occurring $V_{HH}$ domain as a starting material.

A preferred, but non-limiting humanizing substitution for Nanobodies belonging to the 103 P,R,S-group and/or the GLEW-group (as defined herein) is 108Q to 108L.

Another particularly preferred class of Nanobodies of the invention comprises Nanobodies with an amino acid sequence that corresponds to the amino acid sequence of a naturally occurring $V_H$ domain that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the further description below. Reference is also made to WO 94/04678. Such camelization may preferentially occur at amino acid positions which are present at the $V_H$-$V_L$ interface and at the so-called Camelidae hallmark residues (see for example also WO 94/04678), as also mentioned below. Preferably, the $V_H$ domain or sequence that is used as a starting material or starting point for generating or designing the camelized Nanobody is preferably a $V_H$ sequence from a mammal, more preferably the $V_H$ sequence of a human being. However, it should be noted that such camelized Nanobodies of the invention can be obtained in any suitable manner known per se (i.e. as indicated under points (1)-(8) above) and thus are not strictly limited to polypeptides that have been obtained using a polypeptide that comprises a naturally occurring $V_H$ domain as a starting material.

For example, again as further described below, both "humanization" and "camelization" can be performed by providing a nucleotide sequence that encodes such a naturally occurring $V_{HH}$ domain or $V_H$ domain, respectively, and then changing, in a manner known per se, one or more codons in said nucleotide sequence such that the new nucleotide sequence encodes a humanized or camelized Nanobody of the invention, respectively, and then expressing the nucleotide sequence thus obtained in a manner known per se so as to provide the desired Nanobody of the invention. Alternatively, based on the amino acid sequence of a naturally occurring $V_{HH}$ domain or $V_H$ domain, respectively, the amino acid sequence of the desired humanized or camelized Nanobody of the invention, respectively, can be designed and then synthesized de novo using techniques for peptide synthesis known per se. Also, based on the amino acid sequence or nucleotide sequence of a naturally occurring $V_{HH}$ domain or $V_H$ domain, respectively, a nucleotide sequence encoding the desired humanized or camelized Nanobody of the invention, respectively, can be designed and then synthesized de novo using techniques for nucleic acid synthesis known per se, after which the nucleotide sequence thus obtained can be expressed in a manner known per se so as to provide the desired Nanobody of the invention.

Other suitable ways and techniques for obtaining Nanobodies of the invention and/or nucleotide sequences and/or nucleic acids encoding the same, starting from (the amino acid sequence of) naturally occurring $V_H$ domains or preferably $V_{HH}$ domains and/or from nucleotide sequences and/or nucleic acid sequences encoding the same will be clear from the skilled person, and may for example comprising combining one or more amino acid sequences and/or nucleotide sequences from naturally occurring $V_H$ domains (such as one or more FR's and/or CDR's) with one or more amino acid sequences and/or nucleotide sequences from naturally occurring $V_{HH}$ domains (such an one or more FR's or CDR's), in a suitable manner so as to provide (a nucleotide sequence or nucleic acid encoding) a Nanobody of the invention.

According to one preferred, but non-limiting aspect of the aspect of the invention, a Nanobody in its broadest sense can be generally defined as a polypeptide comprising:

a) an amino acid sequence that is comprised of four framework regions/sequences interrupted by three complementarity determining regions/sequences, in which the amino acid residue at position 108 according to the Kabat numbering is Q;

and/or:

b) an amino acid sequence that is comprised of four framework regions/sequences interrupted by three complementarity determining regions/sequences, in which the amino acid residue at position 44 according to the Kabat numbering is E and in which the amino acid residue at position 45 according to the Kabat numbering is an R;

and/or:

c) an amino acid sequence that is comprised of four framework regions/sequences interrupted by three complementarity determining regions/sequences, in which the amino acid residue at position 103 according to the Kabat numbering is chosen from the group consisting of P, R and S, and is in particular chosen from the group consisting of R and S.

Thus, in a first preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which i) the amino acid residue at position 108 according to the Kabat numbering is Q;
and/or in which:
ii) the amino acid residue at position 44 according to the Kabat numbering is E and in which the amino acid residue at position 45 according to the Kabat numbering is an R;
and/or in which:
iii) the amino acid residue at position 103 according to the Kabat numbering is chosen from the group consisting of P, R and S, and is in particular chosen from the group consisting of R and S;
and in which
iv) CDR1, CDR2 and CDR3 are as defined above, and are preferably as defined according to one of the preferred definitions above, and are more preferably as defined according to one of the more preferred definitions above. In particular, a Nanobody against TNF-alpha according to the invention may have the structure:

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which
i) the amino acid residue at position 108 according to the Kabat numbering is Q;
and/or in which:
ii) the amino acid residue at position 44 according to the Kabat numbering is E and in which the amino acid residue at position 45 according to the Kabat numbering is an R;
and/or in which:
iii) the amino acid residue at position 103 according to the Kabat numbering is chosen from the group consisting of P, R and S, and is in particular chosen from the group consisting of R and S;
and in which
iv) CDR1, CDR2 and CDR3 are as defined above, and are preferably as defined according to one of the preferred definitions above, and are more preferably as defined according to one of the more preferred definitions above.

In particular, according to one preferred, but non-limiting aspect of the aspect of the invention, a Nanobody can generally be defined as a polypeptide comprising an amino acid sequence that is comprised of four framework regions/sequences interrupted by three complementarity determining regions/sequences, in which;
a-1) the amino acid residue at position 44 according to the Kabat numbering is chosen from the group consisting of G, E, D, G, Q, R, S, L; and is preferably chosen from the group consisting of G, E or Q; and
a-2) the amino acid residue at position 45 according to the Kabat numbering is chosen from the group consisting of L, R or C; and is preferably chosen from the group consisting of L or R; and
a-3) the amino acid residue at position 103 according to the Kabat numbering is chosen from the group consisting of W, R or S; and is preferably W or R, and is most preferably W;
a-4) the amino acid residue at position 108 according to the Kabat numbering is Q;
or in which:
b-1) the amino acid residue at position 44 according to the Kabat numbering is chosen from the group consisting of E and Q; and
b-2) the amino acid residue at position 45 according to the Kabat numbering is R; and
b-3) the amino acid residue at position 103 according to the Kabat numbering is chosen from the group consisting of W, R and S; and is preferably W;
b-4) the amino acid residue at position 108 according to the Kabat numbering is chosen from the group consisting of Q and L; and is preferably Q;
or in which:
c-1) the amino acid residue at position 44 according to the Kabat numbering is chosen from the group consisting of G, E, D, Q, R, S and L; and is preferably chosen from the group consisting of G, E and Q; and
c-2) the amino acid residue at position 45 according to the Kabat numbering is chosen from the group consisting of L, R and C; and is preferably chosen from the group consisting of L and R; and
c-3) the amino acid residue at position 103 according to the Kabat numbering is chosen from the group consisting of P, R and S; and is in particular chosen from the group consisting of R and S; and
c-4) the amino acid residue at position 108 according to the Kabat numbering is chosen from the group consisting of Q and L; is preferably Q.

Thus, in another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
i) the amino acid residue at position 44 according to the Kabat numbering is chosen from the group consisting of G, E, D, G, Q, R, S, L; and is preferably chosen from the group consisting of G, E or Q;
and in which:
ii) the amino acid residue at position 45 according to the Kabat numbering is chosen from the group consisting of L, R or C; and is preferably chosen from the group consisting of L or R;
and in which:
iii) the amino acid residue at position 103 according to the Kabat numbering is chosen from the group consisting of W, R or S; and is preferably W or R, and is most preferably W;
and in which
iv) the amino acid residue at position 108 according to the Kabat numbering is Q;
and in which:
v) CDR1, CDR2 and CDR3 are as defined above, and are preferably as defined according to one of the preferred definitions above, and are more preferably as defined according to one of the more preferred definitions above.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
i) the amino acid residue at position 44 according to the Kabat numbering is chosen from the group consisting of E and Q;

and in which:

ii) the amino acid residue at position 45 according to the Kabat numbering is R;

and in which:

iii) the amino acid residue at position 103 according to the Kabat numbering is chosen from the group consisting of W, R and S; and is preferably W;

and in which:

iv) the amino acid residue at position 108 according to the Kabat numbering is Q;

and in which:

vi) CDR1, CDR2 and CDR3 are as defined above, and are preferably as defined according to one of the preferred definitions above, and are more preferably as defined according to one of the more preferred definitions above.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) the amino acid residue at position 44 according to the Kabat numbering is chosen from the group consisting of G, E, D, Q, R, S and L; and is preferably chosen from the group consisting of G, E and Q;

and in which:

ii) the amino acid residue at position 45 according to the Kabat numbering is chosen from the group consisting of L, R and C; and is preferably chosen from the group consisting of L and R;

and in which:

iii) the amino acid residue at position 103 according to the Kabat numbering is chosen from the group consisting of P, R and S; and is in particular chosen from the group consisting of R and S;

and in which:

iv) the amino acid residue at position 108 according to the Kabat numbering is chosen from the group consisting of Q and L; is preferably Q;

and in which:

v) CDR1, CDR2 and CDR3 are as defined above, and are preferably as defined according to one of the preferred definitions above, and are more preferably as defined according to one of the more preferred definitions above.

Two particularly preferred, but non-limiting groups of the Nanobodies of the invention are those according to a) above; according to I) to a-4) above; according to b) above; according to b-1) to b-4) above; according to c) above; and/or according to c-1) to c-4) above, in which;

a) the amino acid residues at positions 44-47 according to the Kabat numbering form the sequence GLEW (or a GLEW-like sequence as defined below) and the amino acid residue at position 108 is Q;

or in which:

b) the amino acid residues at positions 43-46 according to the Kabat numbering form the sequence KERE (SEQ ID NO: 437) or KQRE (SEQ ID NO: 438) (or a KERE-like sequence) and the amino acid residue at position 108 is Q or L, and is preferably Q.

Thus, in another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) the amino acid residues at positions 44-47 according to the Kabat numbering form the sequence GLEW (or a GLEW-like sequence as defined below) and the amino acid residue at position 108 is Q;

and in which:

ii) CDR1, CDR2 and CDR3 are as defined above, and are preferably as defined according to one of the preferred definitions above, and are more preferably as defined according to one of the more preferred definitions above.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) the amino acid residues at positions 43-46 according to the Kabat numbering form the sequence KERE (SEQ ID NO: 437) or KQRE (SEQ ID NO: 438) (or a KERE-like sequence) and the amino acid residue at position 108 is Q or L, and is preferably Q;

and in which:

ii) CDR1, CDR2 and CDR3 are as defined above, and are preferably as defined according to one of the preferred definitions above, and are more preferably as defined according to one of the more preferred definitions above.

In the Nanobodies of the invention in which the amino acid residues at positions 43-46 according to the Kabat numbering form the sequence KERE (SEQ ID NO: 437) or KQRE (SEQ ID NO: 438), the amino acid residue at position 37 is most preferably F. In the Nanobodies of the invention in which the amino acid residues at positions 44-47 according to the Kabat numbering form the sequence GLEW, the amino acid residue at position 37 is chosen from the group consisting of Y, H, I, V or F, and is most preferably F.

Thus, without being limited hereto in any way, on the basis of the amino acid residues present on the positions mentioned above, the Nanobodies of the invention can generally be classified is on the basis of the following three groups:

a) The "GLEW-group": Nanobodies with the amino acid sequence GLEW at positions 44-47 according to the Kabat numbering and Q at position 108 according to the Kabat numbering. As further described herein, Nanobodies within this group usually have a V at position 37, and can have a W, P, R or S at position 103, and preferably have a W at position 103. The GLEW group also comprises some GLEW-like sequences such as those mentioned in Table 2 below;

b) The "KERE-group": Nanobodies with the amino acid sequence KERE (SEQ ID NO: 437) or KQRE (SEQ ID NO: 438) or at positions 43-46 according to the Kabat numbering and Q or L at position 108 according to the Kabat numbering. As further described herein, Nanobodies within this group usually have a F at position 37, an L or F at position 47; and can have a W, P, R or S at position 103, and preferably have a W at position 103;

c) The "103 P, R, S-group": Nanobodies with a P R or S at position 103. These Nanobodies can have either the amino acid sequence GLEW (SEQ ID NO: 439) at positions 44-47 of the Kabat numbering or the amino acid sequence KERE (SEQ ID NO: 437) or KQRE (SEQ ID NO: 438) at positions 43-46 according to the Kabat numbering, the latter most preferably in combination with an F at position 37 and an L or an F at position 47 (as defined for the KERE-group); and can have Q or L at position 108 according to the Kabat numbering, and preferably have Q.

Thus, in another preferred, but non-limiting aspect, a Nanobody of the invention may be a Nanobody belonging to the GLEW-group (as defined herein), and in which CDR1, CDR2 and CDR3 are as defined above, and are preferably as defined according to one of the preferred definitions above, and are more preferably as defined according to one of the more preferred definitions above.

In another preferred, but non-limiting aspect, a Nanobody of the invention may be a Nanobody belonging to the KERE-group (as defined herein), and in which CDR1, CDR2 and CDR3 are as defined above, and are preferably as defined according to one of the preferred definitions above, and are more preferably as defined according to one of the more preferred definitions above.

Thus, in another preferred, but non-limiting aspect, a Nanobody of the invention may be a Nanobody belonging to the 103 P, R, S-group (as defined herein), and in which CDR1, CDR2 and CDR3 are as defined above, and are preferably as defined according to one of the preferred definitions above, and are more preferably as defined according to one of the more preferred definitions above.

Also, more generally and in addition to the 108Q, 43E/44R and 103P,R,S residues mentioned above, the Nanobodies of the invention can contain, at one or more positions that, in a conventional $V_H$ domain, would form (part of) the $V_H/V_L$ interface, contain one or more amino acid residues that are more highly charged than the amino acid residues that naturally occur at the same position(s) in the corresponding naturally occurring $V_H$ or $V_{HH}$ domain, and in particular one or more charged amino acid residues (as mentioned in Table 1).

Such substitutions include, but are not limited to the GLEW-like sequences mentioned in Table 2 below; as well as the substitutions that are described in the International Application WO 00/29004 for so-called "microbodies", e.g. a Q at position 108 and KLEW at positions 44-47.

In some embodiments of the Nanobodies of the invention, the amino acid residue at position 83 is chosen from the group consisting of L, M, S, V and W; and is preferably L.

Also, in some embodiments of the Nanobodies of the invention, the amino acid residue at position 83 is chosen from the group consisting of R, K, N, E, I and Q; and is most preferably either K or E (for Nanobodies corresponding to naturally occurring $V_{HH}$ domains) or R (for "humanized" Nanobodies, as described below). The amino acid residue at position 84 in some embodiments is chosen from the group consisting of P, A, R, S, D and V, and is most preferably P (for Nanobodies corresponding to naturally occurring $V_{HH}$ domains) or R (for "humanized" Nanobodies, as described below).

Furthermore, in some embodiments of the Nanobodies of the invention, the amino acid residue at position 104 is chosen from the group consisting of G and D; and is most preferably G.

Collectively, the amino acid residues at positions 11, 37, 44, 45, 47, 83, 84, 103, 104 and 108, which in the Nanobodies are as mentioned above, will also be referred to herein as the "Hallmark Residues". The Hallmark Residues and the amino acid residues at the corresponding positions of the most closely related human VH domain, VH3, are summarized in Table 2.

Some especially preferred combinations of these Hallmark Residues as occur in naturally occurring $V_{HH}$ domains are mentioned in Table 3. For comparison, the corresponding amino acid residues of the human $V_H3$ called DP-47 have been indicated in italics.

TABLE 2

Hallmark Residues in Nanobodies

| Position | Human $V_H3$ | Hallmark Residues |
|---|---|---|
| 11 | L, V; predominantly L | L, M, S, V, W; preferably L |
| 37 | V, I, F; usually V | F[1], Y, H, I or V, preferably F[1] or Y |
| 44[8] | G | G[2], E[3], D, Q, R, S, L; preferably G[2], E[3] or Q; most preferably G[2] or E[3]. |
| 45[8] | L | L[2], R[3], C, I, L, P, Q, V; preferably L[2] or R[3] |
| 47[8] | W, Y | W[2], L[1] or F[1], A, G, I, M, R, S or Y; preferably W[2], L[1], F[1] or R |
| 83 | R or K; usually R | R, K[5], N, E[5], I, M or Q; preferably K or R; most preferably K |
| 84 | A, T, D; predominantly A | P[5], A, L, R, S, D, V; preferably P |
| 103 | W | W[4], P[6], R[6], S; preferably W |
| 104 | G | G or D; preferably G |
| 108 | L, M or T; predominantly L | Q, L[7] or R; preferably Q or L[7] |

Notes:
[1]In particular, but not exclusively, in combination with KERE (SEQ ID NO: 437) or KQRE (SEQ ID NO: 438) at positions 43-46.
[2]Usually as GLEW (SEQ ID NO: 439) at positions 44-47.
[3]Usually as KERE or KQRE at positions 43-46, e.g. as KEREL (SEQ ID NO: 440), KEREF (SEQ ID NO: 441), KQREL (SEQ ID NO: 442), KQREF (SEQ ID NO: 443) or KEREG (SEQ ID NO: 444) at positions 43-47. Alternatively, also sequences such as TERE (SEQ ID NO: 445) (for example TEREL (SEQ ID NO: 446)), KECE (SEQ ID NO: 447) (for example KECEL (SEQ ID NO: 448) or KECER (SEQ ID NO: 449)), RERE (SEQ ID NO: 450) (for example REREG (SEQ ID NO: 451)), QERE (SEQ ID NO: 452) (for example QEREG (SEQ ID NO: 453)), KGRE (SEQ ID NO: 454) (for example KGREG (SEQ ID NO: 455)), KDRE (SEQ ID NO: 456) (for example KDREV (SEQ ID NO: 457)) are possible. Some other possible, but less preferred sequences include for example DECKL (SEQ ID NO: 458) and NVCEL (SEQ ID NO: 459).
[4]With both GLEW at positions 44-47 and KERE or KQRE at positions 43-46.
[5]Often as KP or EP at positions 83-84 of naturally occurring $V_{HH}$ domains.
[6]In particular, but not exclusively, in combination with GLEW at positions 44-47.
[7]With the proviso that when positions 44-47 are GLEW, position 108 is always Q.
[8]The GLEW group also contains GLEW-like sequences at positions 44-47, such as for example GVEW (SEQ ID NO: 460), EPEW (SEQ ID NO: 461), GLER (SEQ ID NO: 462), DQEW (SEQ ID NO: 463), DLEW (SEQ ID NO: 464), GIEW (SEQ ID NO: 465), ELEW (SEQ ID NO: 466), GPEW (SEQ ID NO: 467), EWLP (SEQ ID NO: 468), GPER (SEQ ID NO: 469), GLER (SEQ ID NO: 470).

TABLE 3

Some preferred combinations of Hallmark Residues in naturally occurring Nanobodies. For humanization of these combinations, reference is made to the specification.

|  | 11 | 37 | 44 | 45 | 47 | 83 | 84 | 103 | 104 | 108 |
|---|---|---|---|---|---|---|---|---|---|---|
| DP-47 (human) | M | V | G | L | W | R | A | W | G | L |
| "KERE" group | L | F | E | R | L | K | P | W | G | Q |
|  | L | F | E | R | F | E | P | W | G | Q |
|  | L | F | E | R | F | K | P | W | G | Q |
|  | L | Y | Q | R | L | K | P | W | G | Q |
|  | L | F | L | R | V | K | P | Q | G | Q |
|  | L | F | Q | R | L | K | P | W | G | Q |
|  | L | F | E | R | F | K | P | W | G | Q |
| "GLEW" group | L | V | G | L | W | K | S | W | G | Q |
|  | M | V | G | L | W | K | P | R | G | Q |

In the Nanobodies, each amino acid residue at any other position than the Hallmark Residues can be any amino acid residue that naturally occurs at the corresponding position (according to the Kabat numbering) of a naturally occurring $V_{HH}$ domain.

Such amino acid residues will be clear to the skilled person. Tables 4-7 mention some non-limiting residues that can be present at each position (according to the Kabat numbering) of the FR1, FR2, FR3 and FR4 of naturally occurring $V_{HH}$ domains. For each position, the amino acid residue that most frequently occurs at each position of a naturally occurring $V_{HH}$ domain (and which is the most preferred amino acid residue for said position in a Nanobody) is indicated in bold; and other preferred amino acid residues for each position have been underlined (note: the number of amino acid residues that are found at positions 26-30 of naturally occurring $V_{HH}$ domains supports the hypothesis underlying the numbering Chothia (supra) that the residues at these positions already form part of CDR1.)

In Tables 4-7, some of the non-limiting residues that can be present at each position of a human $V_H3$ domain have also been mentioned. Again, for each position, the amino acid residue that most frequently occurs at each position of a naturally occurring human $V_H3$ domain is indicated in bold; and other preferred amino acid residues have been underlined.

TABLE 4

Non-limiting examples of amino acid residues in FR1
(for the footnotes, see the footnotes to Table 2)

Amino acid residue(s):

| Pos. | Human $V_H3$ | Camelid $V_{HH}$'s |
|---|---|---|
| 1 | E, Q | Q, A, E, D, H, R |
| 2 | V | V, A, E, G, L, M, Q |
| 3 | Q | Q, K, E, H, P, R, Y |
| 4 | L | L, F, P, R, V |
| 5 | V, L | Q, E, L, V, M, P, A, I |
| 6 | E | E, D, Q, A, H |
| 7 | S, T | S, F, H |
| 8 | G, R | G, A, R |
| 9 | G | G, E |
| 10 | G, V | G, D, R, A, E, N, T, V |
| 11 | Hallmark residue: L, M, S, V, W, F, N, P, T, Y; preferably L | |
| 12 | V, I | V, A, G, M |
| 13 | Q, K, R | Q, E, K, D, G, A, H, L, N, P, R, T |
| 14 | P | A, Q, A, G, P, T, V, E, F, I, N, S |
| 15 | G | G |
| 16 | G, R | G, A, E, D, N, P, R, S, V, W |
| 17 | S | S, F, T, N, P, A, C |
| 18 | L | L, V, M, Q, R |
| 19 | R, K | R, K, L, N, S, T, A, F, G, I, M, Q |
| 20 | L | L, F, I, V, M, S |
| 21 | S | S, F, T, G, H, P, A |
| 22 | C | C |
| 23 | A, T | A, D, P, S, T, V, E, G, I, L, Q, R |
| 24 | A | A, I, S, T, V, C, E, F, G, L, N, P, Q, Y |
| 25 | S | S, A, F, P, T, L, V |
| 26 | G | G, D, E, R, S, V, A, I, M, P, T |
| 27 | F | S, F, R, L, P, G, N, A, D, E, H, I, K, M, Q, T, V, Y |
| 28 | T | N, T, E, D, S, I, R, A, G, R, F, Y, L, M, P, V |
| 29 | F, V | F, L, D, S, I, G, V, A, E, P, T, Y |
| 30 | S, D, G | N, S, E, G, A, D, M, T, H, I, P, R, V, W |

TABLE 5

Non-limiting examples of amino acid residues in FR2
(for the footnotes, see the footnotes to Table 2)

Amino acid residue(s):

| Pos. | Human $V_H3$ | Camelid $V_{HH}$'s |
|---|---|---|
| 36 | W | W |
| 37 | Hallmark residue: F$^{(1)}$, Y, H, I, A, L, P, S or V preferably F$^{(1)}$ or Y | |
| 38 | R | R |

TABLE 5-continued

Non-limiting examples of amino acid residues in FR2
(for the footnotes, see the footnotes to Table 2)

Amino acid residue(s):

| Pos. | Human $V_H3$ | Camelid $V_{HH}$'s |
|---|---|---|
| 39 | Q | Q, H, P, R, A, D, G, L, E |
| 40 | A | A, F, G, P, T, V, I, L, N, R, S, Y |
| 41 | P, S, T | P, A, L, S, I, Q, T |
| 42 | G | G, E, D, R, T, V |
| 43 | K | K, D, E, N, Q, R, T, V, A, L, M, S |
| 44 | Hallmark residue: G$^{(2)}$, E$^{(3)}$, D, Q, R, S, L, A, F, K, M, N, P, V, W, Y; preferably G$^{(2)}$, E$^{(3)}$ or Q; most preferably G$^{(2)}$ or E$^{(3)}$. | |
| 45 | Hallmark residue: L$^{(2)}$, R$^{(3)}$, C, I, L, P, Q, V, D, E, G, H, K, T; preferably L$^{(2)}$ or R$^{(3)}$ | |
| 46 | E, V | E, D, K, Q, V, A, G, N |
| 47 | Hallmark residue: W$^{(2)}$, L$^{(1)}$ or F$^{(1)}$, A, G, I, M, R, S, D, E, H, K, Q, T, V or Y; preferably W$^{(2)}$, L$^{(1)}$, F$^{(1)}$ or R | |
| 48 | V | V, I, L, A, C, E, F, G, H, M, P, Q, R, S, T, V, W, Y |
| 49 | S, A, G | A, S, A, G, T, V, D, E, I, L, Q, R, Y |

TABLE 6

Non-limiting examples of amino acid residues in FR3
(for the footnotes, see the footnotes to Table 2)

Amino acid residue(s):

| Pos. | Human $V_H3$ | Camelid $V_{HH}$'s |
|---|---|---|
| 66 | R | R |
| 67 | F | F, L, V, A, D, I, S, Y |
| 68 | T | T, A, S, D, F, G, I, K, N |
| 69 | I | I, M, V, A, F, L, R, S, T |
| 70 | S | S, A, F, E, G, K, P, T, V |
| 71 | R | R, G, I, K, Q, S, T, W, A, F, L, M, N |
| 72 | D, E | D, E, G, N, V, A, H, I, L, Q, S, T |
| 73 | N, D, G | N, D, F, I, K, S, T, Y, A, G, H, L, M, R, V |
| 74 | A, S | A, D, G, N, P, S, T, F, H, I, L, R, V, Y |
| 75 | K | K, A, E, K, L, N, Q, R, D, G, I, M, S, T, V, W |
| 76 | N, S | N, D, K, R, S, T, Y, E, G, H, I, Q |
| 77 | S, T, I | T, A, E, I, M, S, K, L, N, R, V |
| 78 | L, A | V, L, A, F, G, I, M, E, N, Q, R, S, T, W |
| 79 | Y, H | Y, A, D, F, H, S, T, C, E, I, L, N, V, W |
| 80 | L | L, F, V, M |
| 81 | Q | Q, E, R, T, G, H, I, K, L, M, N |
| 82 | M | M, I, L, V, G, P, T |
| 82a | N, G | N, D, G, H, S, T, A, E, I, K, R, V |
| 82b | S | S, N, D, G, R, A, C, E, F, I, K, M, P, T, V |
| 82c | L | L, P, M, T, V |
| 83 | Hallmark residue: R, K$^{(5)}$, N, E$^{(5)}$, I, M, A, D, G, L, Q, S, T or Q; preferably K or R; most preferably K | |
| 84 | Hallmark residue: P$^{(5)}$, A, L, R, S, D, V, F, G, H, N, T, Y; preferably P | |
| 85 | E, G | E, D, G, Q, A, N, R, V, Y |
| 86 | D | D, E, F, Y |
| 87 | T, M | T, S, A, C, M |
| 88 | A | A, G, S, D, L, N, P |
| 89 | V, L | V, A, D, I, L, M, N, R, T, E, F, S |
| 90 | Y | Y, F, E, H, N |
| 91 | Y, H | Y, D, F, H, L, S, T, V, C, I, N, R, W |
| 92 | C | C |
| 93 | A, K, T | A, N, G, H, K, R, S, T, V, Y, E, F, I, L, M, Q |
| 94 | K, R, T | A, V, C, F, G, I, L, R, S, D, E, K, M, N, P, Q, T, W, Y T or K; |

TABLE 7

Non-limiting examples of amino acid residues in FR4
(for the footnotes, see the footnotes to Table 2)

| Pos. | Amino acid residue(s): Human V$_H$3 | Camelid V$_{HH}$'s |
|---|---|---|
| 103 | Hallmark residue: W$^{(4)}$, P$^{(6)}$, R$^{(6)}$, S, F, G, K, L, N, Q, V, Y; preferably W | |
| 104 | Hallmark residue: G, A, R, S, T or D; preferably G | |
| 105 | Q, R | Q, E, K, P, R, G, H, L, S, V |
| 106 | G | G |
| 107 | T | T, A, I, N, P |
| 108 | Hallmark residue: Q, L$^{(7)}$, E, H, N, P, T or R; preferably Q or L$^{(7)}$ | |
| 109 | V | V |
| 110 | T | T, I, A |
| 111 | V | V, A, I, G |
| 112 | S | S, F, A, L, P, T, Y |
| 113 | S | S, A, L, P, F, T |

Thus, in another preferred, but not limiting aspect, a Nanobody of the invention can have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
i) the Hallmark residues are as defined above;
and in which:
ii) CDR1, CDR2 and CDR3 are as defined above, and are preferably as defined according to one of the preferred definitions above, and are more preferably as defined according to one of the more preferred definitions above.

In another preferred, but not limiting aspect, a Nanobody of the invention can have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which: and in which
i) FR1 is chosen from the group consisting of the amino acid sequence:

[SEQ ID NO: 1]
[1] QVQLQESGGG<u>X</u>VQAGGSLRLSCAASG [26]

or from the group consisting of amino acid sequences that have at least 80%, preferably at least 90%, more preferably at least 95%, even more preferably at least 99% sequence identity (as defined herein) with the above amino acid sequence; in which
(1) any amino acid substitution at any position other than a Hallmark position is preferably either a conservative amino acid substitution (as defined herein) and/or an amino acid substitution as defined in Table 4; and/or
(2) said amino acid sequence preferably only contains amino acid substitutions, and no amino acid deletions or insertions, compared to the above amino acid sequence(s);
and/or from the group consisting of amino acid sequences that have 3, 2 or only 1 "amino acid difference(s)" (as defined herein) with one of the above amino acid sequences, in which:
(1) any amino acid substitution at any position other than a Hallmark position is preferably either a conservative amino acid substitution (as defined herein) and/or an amino acid substitution as defined in Table 4; and/or
(2) said amino acid sequence preferably only contains amino acid substitutions, and no amino acid deletions or insertions, compared to the above amino acid sequence(s);
and in which:
ii) FR2 is chosen from the group consisting of the amino acid sequence:

[SEQ ID NO: 2]
[36] W<u>X</u>RQAPGK<u>XXE</u>X<u></u>VA [49]

or from the group consisting of amino acid sequences that have at least 80%, preferably at least 90%, more preferably at least 95%, even more preferably at least 99% sequence identity (as defined herein) with the above amino acid sequence; in which
(1) any amino acid substitution at any position other than a Hallmark position is preferably either a conservative amino acid substitution (as defined herein) and/or an amino acid substitution as defined in Table 5; and/or
(2) said amino acid sequence preferably only contains amino acid substitutions, and no amino acid deletions or insertions, compared to the above amino acid sequence(s);
and/or from the group consisting of amino acid sequences that have 3, 2 or only 1 "amino acid difference(s)" (as defined herein) with one of the above amino acid sequences, in which:
(1) any amino acid substitution at any position other than a Hallmark position is preferably either a conservative amino acid substitution (as defined herein) and/or an amino acid substitution as defined in Table 5; and/or
(2) said amino acid sequence preferably only contains amino acid substitutions, and no amino acid deletions or insertions, compared to the above amino acid sequence(s);
and in which:
iii) FR3 is chosen from the group consisting of the amino acid sequence:

[SEQ ID NO: 3]
[66] RFTISRDNAKNTVYLQMNSL<u>XX</u>EDTAVYYCAA [94]

or from the group consisting of amino acid sequences that have at least 80%, preferably at least 90%, more preferably at least 95%, even more preferably at least 99% sequence identity (as defined herein) with the above amino acid sequence; in which
(1) any amino acid substitution at any position other than a Hallmark position is preferably either a conservative amino acid substitution (as defined herein) and/or an amino acid substitution as defined in Table 7; and/or
(2) said amino acid sequence preferably only contains amino acid substitutions, and no amino acid deletions or insertions, compared to the above amino acid sequence(s);
and/or from the group consisting of amino acid sequences that have 3, 2 or only 1 "amino acid difference(s)" (as defined herein) with one of the above amino acid sequences, in which:
(1) any amino acid substitution at any position other than a Hallmark position is preferably either a conservative amino acid substitution (as defined herein) and/or an amino acid substitution as defined in Table 7; and/or (2) said amino acid sequence preferably only contains amino acid substitutions, and no amino acid deletions or insertions, compared to the above amino acid sequence(s);

and in which:

iv) FR4 is chosen from the group consisting of the amino acid sequence:

[SEQ ID NO: 4]
[103] XXQGTXVTVSS [113]

or from the group consisting of amino acid sequences that have at least 80%, preferably at least 90%, more preferably at least 95%, even more preferably at least 99% sequence identity (as defined herein) with the above amino acid sequence; in which (1) any amino acid substitution at any position other than a Hallmark position is preferably either a conservative amino acid substitution (as defined herein) and/or an amino acid substitution as defined in Table 6; and/or (2) said amino acid sequence preferably only contains amino acid substitutions, and no amino acid deletions or insertions, compared to the above amino acid sequence(s);

and/or from the group consisting of amino acid sequences that have 3, 2 or only 1 "amino acid difference(s)" (as defined herein) with one of the above amino acid sequences, in which:

(1) any amino acid substitution at any position other than a Hallmark position is preferably either a conservative amino acid substitution (as defined herein) and/or an amino acid substitution as defined in Table 6; and/or (2) said amino acid sequence preferably only contains amino acid substitutions, and no amino acid deletions or insertions, compared to the above amino acid sequence(s);

and in which:

v) CDR1, CDR2 and CDR3 are as defined above, and are preferably as defined according to one of the preferred definitions above, and are more preferably as defined according to one of the more preferred definitions above; in which the Hallmark Residues are indicated by "X" and are as defined hereinabove and in which the numbers between brackets refer to the amino acid positions according to the Kabat numbering.

In another preferred, but not limiting aspect, a Nanobody of the invention can have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

and in which i) FR1 is chosen from the group consisting of the amino acid sequence:

[SEQ ID NO: 5]
[1] QVQLQESGGGLVQAGGSLRLSCAASG [26]

or from the group consisting of amino acid sequences that have at least 80%, preferably at least 90%, more preferably at least 95%, even more preferably at least 99% sequence identity (as defined herein) with the above amino acid sequence; in which (1) any amino acid substitution at any position other than a Hallmark position is preferably either a conservative amino acid substitution (as defined herein) and/or an amino acid substitution as defined in Table 4; and/or (2) said amino acid sequence preferably only contains amino acid substitutions, and no amino acid deletions or insertions, compared to the above amino acid sequence(s); and (3) the Hallmark residue at position is as indicated in the sequence above;

and/or from the group consisting of amino acid sequences that have 3, 2 or only 1 "amino acid difference(s)" (as defined herein) with one of the above amino acid sequences, in which:

(1) any amino acid substitution at any position other than a Hallmark position is preferably either a conservative amino acid substitution (as defined herein) and/or an amino acid substitution as defined in Table 4; and/or (2) said amino acid sequence preferably only contains amino acid substitutions, and no amino acid deletions or insertions, compared to the above amino acid sequence(s); and (3) the Hallmark residue at position is as indicated in the sequence above;

and in which:

ii) FR2 is chosen from the group consisting of the amino acid sequences:

[SEQ ID NO: 6]
[36] WFRQAPGKERELVA [49]

[SEQ ID NO: 7]
[36] WFRQAPGKEREFVA [49]

[SEQ ID NO: 8]
[36] WFRQAPGKEREGA [49]

[SEQ ID NO: 9]
[36] WFRQAPGKQRELVA [49]

[SEQ ID NO: 10]
[36] WFRQAPGKQREFVA [49]

[SEQ ID NO: 11]
[36] WYRQAPGKGLEWA [49]

or from the group consisting of amino acid sequences that have at least 80%, preferably at least 90%, more preferably at least 95%, even more preferably at least 99% sequence identity (as defined herein) with one of the above amino acid sequences; in which (1) any amino acid substitution at any position other than a Hallmark position is preferably either a conservative amino acid substitution (as defined herein) and/or an amino acid substitution as defined in Table 5; and/or (2) said amino acid sequence preferably only contains amino acid substitutions, and no amino acid deletions or insertions, compared to the above amino acid sequence(s); and (3) the Hallmark residues at positions 37, 44, 45 and 47 are as indicated in each of the sequences above;

and/or from the group consisting of amino acid sequences that have 3, 2 or only 1 "amino acid difference(s)" (as defined herein) with one of the above amino acid sequences, in which:

(1) any amino acid substitution at any position other than a Hallmark position is preferably either a conservative amino acid substitution (as defined herein) and/or an amino acid substitution as defined in Table 5; and/or (2) said amino acid sequence preferably only contains amino acid substitutions, and no amino acid deletions or insertions, compared to the above amino acid sequence(s); and (3) the Hallmark residues at positions 37, 44, 45 and 47 are as indicated in each of the sequences above;

and in which:

iii) FR3 is chosen from the group consisting of the amino acid sequence:

[SEQ ID NO: 12]
[66] RFTISRDNAKNTVYLQMNSLKPEDTAVYYCAA [94]

or from the group consisting of amino acid sequences that have at least 80%, preferably at least 90%, more preferably at least 95%, even more preferably at least 99% sequence identity (as defined herein) with the above amino acid sequence; in which (1) any amino acid substitution at any position other than a Hallmark position is preferably either a conservative amino acid substitution (as defined herein) and/or an amino acid substitution as defined in Table 6; and/or (2) said amino acid sequence preferably only contains amino acid substitutions, and no amino acid deletions or insertions, compared to the above amino acid sequence(s); and (3) the Hallmark residues at positions 83 and 84 are as indicated in each of the sequences above;

and/or from the group consisting of amino acid sequences that have 3, 2 or only 1 "amino acid difference(s)" (as defined herein) with one of the above amino acid sequences, in which:

(1) any amino acid substitution at any position other than a Hallmark position is preferably either a conservative amino acid substitution (as defined herein) and/or an amino acid substitution as defined in Table 6; and/or (2) said amino acid sequence preferably only contains amino acid substitutions, and no amino acid deletions or insertions, compared to the above amino acid sequence(s); and (3) the Hallmark residues at positions 83 and 84 are as indicated in each of the sequences above;

and in which:

iv) FR4 is chosen from the group consisting of the amino acid sequences:

[SEQ ID NO: 13]
[103] WGQGTQVTVSS [113]

[SEQ ID NO: 14]
[103] WGQGTLVTVSS [113]

or from the group consisting of amino acid sequences that have at least 80%, preferably at least 90%, more preferably at least 95%, even more preferably at least 99% sequence identity (as defined herein) with one of the above amino acid sequence;

in which (1) any amino acid substitution at any position other than a Hallmark position is preferably either a conservative amino acid substitution (as defined herein) and/or an amino acid substitution as defined in Table 6; and/or (2) said amino acid sequence preferably only contains amino acid substitutions, and no amino acid deletions or insertions, compared to the above amino acid sequence(s); and (3) the Hallmark residues at positions 103, 104 and 108 are as indicated in each of the sequences above;

and/or from the group consisting of amino acid sequences that have 3, 2 or only 1 "amino acid difference(s)" (as defined herein) with one of the above amino acid sequences, in which:

(1) any amino acid substitution at any position other than a Hallmark position is preferably either a conservative amino acid substitution (as defined herein) and/or an amino acid substitution as defined in Table 6; and/or (2) said amino acid sequence preferably only contains amino acid substitutions, and no amino acid deletions or insertions, compared to the above amino acid sequence(s); and (3) the Hallmark residues at positions 103, 104 and 108 are as indicated in each of the sequences above;

and in which:

v) CDR1, CDR2 and CDR3 are as defined above, and are preferably as defined according to one of the preferred definitions above, and are more preferably as defined according to one of the more preferred definitions above. In another preferred, but not limiting aspect, a Nanobody of the invention can have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

and in which i) FR1 is chosen from the group consisting of the amino acid sequence:

[SEQ ID NO: 5]
[1] QVQLQESGGGLVQAGGSLRLSCAASG [26]

and/or from the group consisting of amino acid sequences that have 3, 2 or only 1 "amino acid difference(s)" (as defined herein) with one of the above amino acid sequences, in which:

(1) any amino acid substitution at any position other than a Hallmark position is preferably either a conservative amino acid substitution (as defined herein) and/or an amino acid substitution as defined in Table 4; and/or (2) said amino acid sequence preferably only contains amino acid substitutions, and no amino acid deletions or insertions, compared to the above amino acid sequence(s); and (3) the Hallmark residue at position is as indicated in the sequence above; and in which:

ii) FR2 is chosen from the group consisting of the amino acid sequences:

[SEQ ID NO: 6]
[36] WFRQAPGKERELVA [49]

[SEQ ID NO: 7]
[36] WFRQAPGKEREFVA [49]

[SEQ ID NO: 8]
[36] WFRQAPGKEREGA [49]

[SEQ ID NO: 9]
[36] WFRQAPGKQRELVA [49]

[SEQ ID NO: 10]
[36] WFRQAPGKQREFVA [49]

and/or from the group consisting of amino acid sequences that have 2 or only 1 "amino acid difference(s)" (as defined herein) with one of the above amino acid sequences, in which:
(1) any amino acid substitution at any position other than a Hallmark position is preferably either a conservative amino acid substitution (as defined herein) and/or an amino acid substitution as defined in Table 5; and/or
(2) said amino acid sequence preferably only contains amino acid substitutions, and no amino acid deletions or insertions, compared to the above amino acid sequence(s); and
(3) the Hallmark residues at positions 37, 44, 45 and 47 are as indicated in each of the sequences above;

and in which:
iii) FR3 is chosen from the group consisting of the amino acid sequence:

[SEQ ID NO: 12]
[66] RFTISRDNAKNTVYLQMNSLKPEDTAVYYCAA [94]

and/or from the group consisting of amino acid sequences that have 3, 2 or only 1 "amino acid difference(s)" (as defined herein) with one of the above amino acid sequences, in which:
(1) any amino acid substitution at any position other than a Hallmark position is preferably either a conservative amino acid substitution (as defined herein) and/or an amino acid substitution as defined in Table 6; and/or
(2) said amino acid sequence preferably only contains amino acid substitutions, and no amino acid deletions or insertions, compared to the above amino acid sequence(s); and
(3) the Hallmark residues at positions 83 and 84 are as indicated in each of the sequences above;

and in which:
iv) FR4 is chosen from the group consisting of the amino acid sequences:

[SEQ ID NO: 13]
[103] WGQGTQVTVSS [113]

[SEQ ID NO: 14]
[103] WGQGTLVTVSS [113]

and/or from the group consisting of amino acid sequences that have 3, 2 or only 1 "amino acid difference(s)" (as defined herein) with one of the above amino acid sequences, in which:
(1) any amino acid substitution at any position other than a Hallmark position is preferably either a conservative amino acid substitution (as defined herein) and/or an amino acid substitution as defined in Table 7; and/or
(2) said amino acid sequence preferably only contains amino acid substitutions, and no amino acid deletions or insertions, compared to the above amino acid sequence(s); and
(3) the Hallmark residues at positions 103, 104 and 108 are as indicated in each of the sequences above;

and in which:
v) CDR1, CDR2 and CDR3 are as defined above, and are preferably as defined according to one of the preferred definitions above, and are more preferably as defined according to one of the more preferred definitions above.

In another preferred, but not limiting aspect, a Nanobody of the invention can have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which: and in which
i) FR1 is chosen from the group consisting of the amino acid sequence:

[SEQ ID NO: 5]
[1] QVQLQESGGGLVQAGGSLRLSCAASG [26]

and/or from the group consisting of amino acid sequences that have 3, 2 or only 1 "amino acid difference(s)" (as defined herein) with one of the above amino acid sequences, in which:
(1) any amino acid substitution at any position other than a Hallmark position is preferably either a conservative amino acid substitution (as defined herein) and/or an amino acid substitution as defined in Table 4; and/or
(2) said amino acid sequence preferably only contains amino acid substitutions, and no amino acid deletions or insertions, compared to the above amino acid sequence(s); and
(3) the Hallmark residue at position is as indicated in the sequence above;

and in which:
ii) FR2 is chosen from the group consisting of the amino acid sequence:

[SEQ ID NO: 11]
[36] WYRQAPGKGLEWA [49]

and/or from the group consisting of amino acid sequences that have 2 or only 1 "amino acid difference(s)" (as defined herein) with one of the above amino acid sequences, in which:
(1) any amino acid substitution at any position other than a Hallmark position is preferably either a conservative amino acid substitution (as defined herein) and/or an amino acid substitution as defined in Table 5; and/or
(2) said amino acid sequence preferably only contains amino acid substitutions, and no amino acid deletions or insertions, compared to the above amino acid sequence(s); and
(3) the Hallmark residues at positions 37, 44, 45 and 47 are as indicated in each of the sequences above;

and in which:
iii) FR3 is chosen from the group consisting of the amino acid sequence:

[SEQ ID NO: 12]
[66] RFTISRDNAKNTVYLQMNSLKPEDTAVYYCAA [94]

and/or from the group consisting of amino acid sequences that have 3, 2 or only 1 "amino acid difference(s)" (as defined herein) with one of the above amino acid sequences, in which:
(1) any amino acid substitution at any position other than a Hallmark position is preferably either a conservative amino acid substitution (as defined herein) and/or an amino acid substitution as defined in Table 6; and/or
(2) said amino acid sequence preferably only contains amino acid substitutions, and no amino acid deletions or insertions, compared to the above amino acid sequence(s); and
(3) the Hallmark residues at positions 83 and 84 are as indicated in each of the sequences above;

and in which:
iv) FR4 is chosen from the group consisting of the amino acid sequence:

[SEQ ID NO: 13]

[103] WGQGTQVTVSS [113]

and/or from the group consisting of amino acid sequences that have 3, 2 or only 1 "amino acid difference(s)" (as defined herein) with one of the above amino acid sequences, in which:
(1) any amino acid substitution at any position other than a Hallmark position is preferably either a conservative amino acid substitution (as defined herein) and/or an amino acid substitution as defined in Table 7; and/or
(2) said amino acid sequence preferably only contains amino acid substitutions, and no amino acid deletions or insertions, compared to the above amino acid sequence(s); and
(3) the Hallmark residues at positions 103, 104 and 108 are as indicated in each of the sequences above;

and in which:
v) CDR1, CDR2 and CDR3 are as defined above, and are preferably as defined according to one of the preferred definitions above, and are more preferably as defined according to one of the more preferred definitions above.

Some other framework sequences that can be present in the Nanobodies of the invention can be found in the European patent EP 656 946 mentioned above (see for example also the granted equivalent U.S. Pat. No. 5,759,808).

In another preferred, but not limiting aspect, a Nanobody of the invention can have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which: and in which
i) FR1 is chosen from the group consisting of the FR1 sequences present in the Nanobodies of SEQ ID NO's 52 to 60, SEQ ID NO's 76 to 86 or SEQ ID NO's 95 to 99, and in particular in the humanized Nanobodies of SEQ ID NO's 76 to 86 or SEQ ID NO's 95 to 99,
or from the group consisting of amino acid sequences that have at least 80%, preferably at least 90%, more preferably at least 95%, even more preferably at least 99% sequence identity (as defined herein) with one of said FR1 sequences; in which
(1) any amino acid substitution at any position other than a Hallmark position is preferably either a conservative amino acid substitution (as defined herein) and/or an amino acid substitution as defined in Table 4; and/or
(2) said amino acid sequence preferably only contains amino acid substitutions, and no amino acid deletions or insertions, compared to said FR1 sequence; and
(3) the Hallmark residue at position is as indicated in said FR1 sequence; and/or from the group consisting of amino acid sequences that have 3, 2 or only 1 "amino acid difference(s)" (as defined herein) with one of said FR1 sequences, in which:
(1) any amino acid substitution at any position other than a Hallmark position is preferably either a conservative amino acid substitution (as defined herein) and/or an amino acid substitution as defined in Table 4; and/or
(2) said amino acid sequence preferably only contains amino acid substitutions, and no amino acid deletions or insertions, compared to said FR1 sequence; and
(3) the Hallmark residue at position is as indicated in said FR1 sequence;

and in which:
ii) FR2 is chosen from the group consisting of the FR2 sequences present in the Nanobodies of SEQ ID NO's 52 to 60, SEQ ID NO's 76 to 86 or SEQ ID NO's 95 to 99, and in particular in the humanized Nanobodies of SEQ ID NO's 76 to 86 or SEQ ID NO's 95 to 99,
or from the group consisting of amino acid sequences that have at least 80%, preferably at least 90%, more preferably at least 95%, even more preferably at least 99% sequence identity (as defined herein) with one of said FR2 sequences; in which
(1) any amino acid substitution at any position other than a Hallmark position is preferably either a conservative amino acid substitution (as defined herein) and/or an amino acid substitution as defined in Table 5; and/or
(2) said amino acid sequence preferably only contains amino acid substitutions, and no amino acid deletions or insertions, compared to said FR2 sequence; and
(3) the Hallmark residues at positions 37, 44, 45 and 47 are as indicated in said FR2 sequence;
and/or from the group consisting of amino acid sequences that have 3, 2 or only 1 "amino acid difference(s)" (as defined herein) with one of said FR2 sequences, in which:
(1) any amino acid substitution at any position other than a Hallmark position is preferably either a conservative amino acid substitution (as defined herein) and/or an amino acid substitution as defined in Table 5; and/or
(2) said amino acid sequence preferably only contains amino acid substitutions, and no amino acid deletions or insertions, compared to said FR2 sequence; and
(3) the Hallmark residues at positions 37, 44, 45 and 47 are as indicated in said FR2 sequence;

and in which:
iii) FR3 is chosen from the group consisting of the FR3 sequences present in the Nanobodies of SEQ ID NO's 52 to 60, SEQ ID NO's 76 to 86 or SEQ ID NO's 95 to 99, and in particular in the humanized Nanobodies of SEQ ID NO's 76 to 86 or SEQ ID NO's 95 to 99,
or from the group consisting of amino acid sequences that have at least 80%, preferably at least 90%, more preferably at least 95%, even more preferably at least 99% sequence identity (as defined herein) with one of said FR3 sequences; in which
(1) any amino acid substitution at any position other than a Hallmark position is preferably either a conservative amino acid substitution (as defined herein) and/or an amino acid substitution as defined in Table 6; and/or
(2) said amino acid sequence preferably only contains amino acid substitutions, and no amino acid deletions or insertions, compared to said FR3 sequence; and
(3) the Hallmark residues at positions 83 and 84 are as indicated in said FR3 sequence;
and/or from the group consisting of amino acid sequences that have 3, 2 or only 1 "amino acid difference(s)" (as defined herein) with one of said FR3 sequences, in which:
(1) any amino acid substitution at any position other than a Hallmark position is preferably either a conservative amino acid substitution (as defined herein) and/or an amino acid substitution as defined in Table 6; and/or
(2) said amino acid sequence preferably only contains amino acid substitutions, and no amino acid deletions or insertions, compared to said FR3 sequence; and (3) the Hallmark residues at positions 83 and 84 are as indicated in said FR3 sequence;

and in which:

iv) FR4 is chosen from the group consisting of the FR4 sequences present in the Nanobodies of SEQ ID NO's 52 to 60, SEQ ID NO's 76 to 86 or SEQ ID NO's 95 to 99, and in particular in the humanized Nanobodies of SEQ ID NO's 76 to 86 or SEQ ID NO's 95 to 99, or from the group consisting of amino acid sequences that have at least 80%, preferably at least 90%, more preferably at least 95%, even more preferably at least 99% sequence identity (as defined herein) with one of said FR4 sequences; in which (1) any amino acid substitution at any position other than a Hallmark position is preferably either a conservative amino acid substitution (as defined herein) and/or an amino acid substitution as defined in Table 6; and/or (2) said amino acid sequence preferably only contains amino acid substitutions, and no amino acid deletions or insertions, compared to said FR4 sequence; and (3) the Hallmark residues at positions 103, 104 and 108 are as indicated in said FR4 sequence;

and/or from the group consisting of amino acid sequences that have 3, 2 or only 1 "amino acid difference(s)" (as defined herein) with one of said FR4 sequences, in which:

(1) any amino acid substitution at any position other than a Hallmark position is preferably either a conservative amino acid substitution (as defined herein) and/or an amino acid substitution as defined in Table 6; and/or (2) said amino acid sequence preferably only contains amino acid substitutions, and no amino acid deletions or insertions, compared to said FR4 sequence; and (3) the Hallmark residues at positions 103, 104 and 108 are as indicated in said FR4 sequence;

and in which:

v) CDR1, CDR2 and CDR3 are as defined above, and are preferably as defined according to one of the preferred definitions above, and are more preferably as defined according to one of the more preferred definitions above.

Some particularly preferred Nanobodies of the invention can be chosen from the group consisting of the amino acid sequences of SEQ ID NO's 52 to 60, SEQ ID NO's 76 to 86 or SEQ ID NO's 95 to 99, and in particular in the humanized Nanobodies of SEQ ID NO's 76 to 86 or SEQ ID NO's 95 to 99 or from the group consisting of amino acid sequences that have at least 80%, preferably at least 90%, more preferably at least 95%, even more preferably at least 99% sequence identity (as defined herein) with one of the amino acid sequences of SEQ ID NO's 52 to 60, SEQ ID NO's 76 to 86 or SEQ ID NO's 95 to 99; in which (1) the Hallmark residues can be as indicated in Table 2 above;

(2) any amino acid substitution at any position other than a Hallmark position is preferably either a conservative amino acid substitution (as defined herein) and/or an amino acid substitution as defined in Tables 4-7; and/or (3) said amino acid sequence preferably only contains amino acid substitutions, and no amino acid deletions or insertions, compared to the above amino acid sequence(s).

Some even more particularly preferred Nanobodies of the invention can be chosen from the group consisting of the amino acid sequences of SEQ ID NO's 52 to 60, SEQ ID NO's 76 to 86 or SEQ ID NO's 95 to 99, and in particular in the humanized Nanobodies of SEQ ID NO's 76 to 86 or SEQ ID NO's 95 to 99 or from the group consisting of amino acid sequences that have at least 80%, preferably at least 90%, more preferably at least 95%, even more preferably at least 99% sequence identity (as defined herein) with one of the amino acid sequences of SEQ ID NO's 52 to 60, SEQ ID NO's 76 to 86 or SEQ ID NO's 95 to 99; in which (1) the Hallmark residues are as indicated in the pertinent sequence chosen from SEQ ID NO's 52 to 60, SEQ ID NO's 76 to 86 or SEQ ID NO's 95 to 99;

(2) any amino acid substitution at any position other than a Hallmark position is preferably either a conservative amino acid substitution (as defined herein) and/or an amino acid substitution as defined in Tables 4-7; and/or (3) said amino acid sequence preferably only contains amino acid substitutions, and no amino acid deletions or insertions, compared to the pertinent sequence chosen from SEQ ID NO's 52 to 60, SEQ ID NO's 76 to 86 or SEQ ID NO's 95 to 99.

Some of the most preferred Nanobodies of the invention can be chosen from the group consisting of the amino acid sequences of SEQ ID NO's 52 to 60, SEQ ID NO's 76 to 86 or SEQ ID NO's 95 to 99, and in particular from the humanized Nanobodies of SEQ ID NO's 76 to 86 or SEQ ID NO's 95 to 99.

As will be clear from the above, the term Nanobodies of the invention as used herein in its broadest sense also comprises natural or synthetic mutants, variants, alleles, analogs and orthologs (hereinbelow collectively referred to as "analogs") of the Nanobodies mentioned in the SEQ ID NO's 52 to 60, SEQ ID NO's 76 to 86 or SEQ ID NO's 95 to 99.

Generally, such analogs can for example comprise homologous sequences, functional portions, or a functional portion of a homologous sequence (as further defined below) of a Nanobody. Generally, in such analogs, each amino acid residue (other than the Hallmark Residue) in each of the framework regions can be replaced by any other amino acid residue, provided that the total degree of sequence identity of the framework regions remains as defined above. Preferably, however, in such analogs:

one or more amino acid residues in the above framework sequences are replaced by one or more amino acid residues that naturally occur at the same position in a naturally occurring $V_{HH}$ domain. Some examples of such substitutions are mentioned in Tables 4-7 above;

and/or:

one or amino acid residues in the above framework sequences are replaced by one or more amino acid residues that can be considered a "conservative" amino acid substitution, as described hereinabove;

and/or:

one or amino acid residues in the above framework sequences are replaced by one or more amino acid residues that naturally occur at the same position in a naturally occurring $V_H$ domain of a human being. This is generally referred to as "humanization" of the naturally occurring $V_{HH}$/Nanobody in general and of said position in particular, and will be discussed in more detail hereinbelow;

and:

positions for which only one amino acid residue is mentioned for both the $V_H$ domain and the $V_{HH}$ domain in Tables 4-7 above are preferably not replaced.

Also, although generally less preferred, in such analogs, one or more amino acid residues may be deleted from the framework regions and/or inserted into the framework regions (optionally in addition to one or more amino acid substitutions as mentioned above), provided that the total degree of sequence identity of the framework regions remains as defined above. The Hallmark residues should not be deleted. Also, most preferably, amino acid residues for which only one amino acid residue is mentioned for both the $V_H$ domain and the $V_{HH}$ domain in Tables 4-7 above are preferably not deleted.

Preferably, such analogs should be such that they still can bind to, have affinity for and/or have specificity for TNF-alpha, i.e. with an affinity and/or a specificity which is at least 10%, preferably at least 50%, more preferably at least 70%, even more preferably at least 80%, such as at least 90%, at least 95%, at least 99% or more, of the affinity and/or specificity of at least one of the Nanobodies of SEQ ID No's SEQ ID NO's 52 to 60, SEQ ID NO's 76 to 86 or SEQ ID NO's 95 to 99, as determined using a suitable assay, for example an assay to determine binding of the analog to TNF, and in particular one of the assays as used in the Examples below.

Generally, such analogs can for example be obtained by providing a nucleic acid that encodes a naturally occurring $V_{HH}$ domain, changing the codons for the one or more amino acid residues that are to be humanized into the codons for the corresponding human amino acid residue(s), expressing the nucleic acid/nucleotide sequence thus obtained in a suitable host or expression system; and optionally isolating and/or purifying the analog thus obtained to provide said analog in essentially isolated form (as defined hereinabove). This can generally be performed using methods and techniques known per se, which will be clear to the skilled person, for example from the handbooks and references cited herein and/or from the further description hereinbelow. Alternatively, and for example, a nucleic acid encoding an analog can be synthesized in a manner known per se (for example using an automated apparatus for synthesizing nucleic acid sequences with a predefined amino acid sequence) and can be expressed in a suitable host or expression system, upon which the analog thus obtained can optionally be isolated and/or purified so as to provide said analog in essentially isolated form (as defined hereinabove). Another way to provide the analogs involves chemical synthesis of the pertinent amino acid sequence using techniques for peptide synthesis known per se, such as those mentioned hereinbelow.

It will be also generally be clear to the skilled person that Nanobodies (including analogs thereof) can also be prepared starting from human $V_H$ sequences (i.e. amino acid sequences or the corresponding nucleotide sequences), such as for example human $V_H3$ sequences such as DP-47, DP-51, DP-54 or DP-29, by changing one or more amino acid residues in the amino acid sequence of said human $V_H$ domain, so as to provide an amino acid sequence that has (a) a Q at position 108; and/or (b) E at position 44 and/or R at position 45, and preferably E at position 44 and R at position 45; and/or (c) P, R or S at position 103, as described above. Again, this can generally be performed using the various methods and techniques referred to in the previous paragraph, using an amino acid sequence and/or nucleotide sequence for a human $V_H$ domain as a starting point.

The term Nanobodies as used herein in its broadest sense also comprises parts or fragments of the Nanobodies (including analogs) of the invention as defined above, which can again be as further described below.

Generally, parts or fragments of the Nanobodies and/or analogs have amino acid sequences in which, compared to the amino acid sequence of the corresponding full length Nanobody or analog, one or more of the amino acid residues at the N-terminal end, one or more amino acid residues at the C-terminal end, one or more contiguous internal amino acid residues, or any combination thereof, have been deleted and/or removed. It is also possible to combine one or more of such parts or fragments to provide a Nanobody of the invention.

Preferably, the amino acid sequence of a Nanobody that comprises one or more parts or fragments of a full length Nanobody and/or analog should have a degree of sequence identity of at least 50%, preferably at least 60%, more preferably at least 70%, such as at least 80%, at least 90% or at least 95%, with the amino acid sequence of the corresponding full length Nanobody.

Also, the amino acid sequence of a Nanobody that comprises one or more parts or fragments of a full length Nanobody and/or analog is preferably such that is comprises at least 10 contiguous amino acid residues, preferably at least 20 contiguous amino acid residues, more preferably at least 30 contiguous amino acid residues, such as at least 40 contiguous amino acid residues, of the amino acid sequence of the corresponding full length Nanobody.

Generally, such parts or fragments of the Nanobodies of the invention will have amino acid sequences in which, compared to the amino acid sequence of the corresponding full length Nanobody of the invention, one or more of the amino acid residues at the N-terminal end, one or more amino acid residues at the C-terminal end, one or more contiguous internal amino acid residues, or any combination thereof, have been deleted and/or removed. It is also possible to combine one or more of such parts or fragments to provide a Nanobody of the invention.

According to one preferred embodiment, a fragment as used herein comprises at least one of the CDR's present in a full-sized Nanobody of the invention, preferably at least two of the CDR's present in a full-sized Nanobody of the invention, more preferably at least CDR2 and CDR3 present in a full-sized Nanobody of the invention, such as for example all three CDR's present in a full-sized Nanobody of the invention.

According to another particularly preferred, but non-limiting embodiment, such a part or fragment comprises at least FR3, CDR3 and FR4 of the corresponding full length Nanobody of the invention, i.e. as for example described in the International application WO 03/050531 (Lasters et al.).

Preferably, such parts or fragments should be such that they still can bind to, have affinity for and/or have specificity for TNF-alpha, i.e. with an affinity and/or a specificity which is at least 10%, preferably at least 50%, more preferably at least 70%, even more preferably at least 80%, such as at least 90%, at least 95%, at least 99% or more, of the affinity and/or specificity of the corresponding full-sized Nanobody of the invention, for example an assay to determine binding of the analog to TNF, and in particular one of the assays as used in the Examples below.

From the description hereinabove, it will be clear that the amino acid sequences of the Nanobodies used herein differ at at least one amino acid position in at least one of the framework regions from the amino acid sequences of naturally occurring $V_H$ domains, such as the amino acid sequences of naturally occurring $V_H$ domains of antibodies from human beings. In particular, it will be clear that the amino acid sequences of the Nanobodies used herein differ at at least one of the Hallmark Residues from amino acid sequences of naturally occurring $V_H$ domains, such as the amino acid sequences of naturally occurring $V_H$ domains from antibodies from Camelids and/or human beings.

Thus, according to one specific embodiment, a Nanobody of the invention has an amino acid sequence that differs at at least one amino acid position in one of the framework regions from the amino acid sequence of a naturally occurring $V_H$ domain. According to a more specific, but non-limiting embodiment of the invention, a Nanobody of the invention has an amino acid sequence that differs at at least one of the Hallmark residues from the amino acid sequence of a naturally occurring $V_H$ domain.

From the description hereinabove, it will also be clear that the amino acid sequences of the some of the Nanobodies of the invention, such as the humanized Nanobodies of the invention, will differ at at least one amino acid position in at least one of the framework regions (i.e. either at the position of a Hallmark residue or at another position) from the amino acid sequences of naturally occurring $V_{HH}$ domains. Thus, according to one specific, but non-limiting embodiment, a Nanobody of the invention has an amino acid sequence that differs at at least one amino acid position in one of the framework regions from the amino acid sequence of a naturally occurring $V_{HH}$ domain. According to a more specific, but non-limiting embodiment of the invention, a Nanobody of the invention has an amino acid sequence that differs at at least one of the Hallmark residues from the amino acid sequence of a naturally occurring $V_{HH}$ domain.

The invention in its broadest sense also comprises derivatives of the Nanobodies of the invention. Such derivatives can generally be obtained by modification, and in particular by chemical and/or biological (e.g. enzymatical) modification, of the Nanobodies of the invention and/or of one or more of the amino acid residues that form the Nanobodies of the invention.

Examples of such modifications, as well as examples of amino acid residues within the Nanobody sequence that can be modified in such a manner (i.e. either on the protein backbone but preferably on a side chain), methods and techniques that can be used to introduce such modifications and the potential uses and advantages of such modifications will be clear to the skilled person.

For example, such a modification may involve the introduction (e.g. by covalent linking or in an other suitable manner) of one or more functional groups, residues or moieties into or onto the Nanobody of the invention, and in particular of one or more functional groups, residues or moieties that confer one or more desired properties or functionalities to the Nanobody of the invention. Example of such functional groups will be clear to the skilled person.

For example, such modification may comprise the introduction (e.g. by covalent binding or in any other suitable manner) of one or more functional groups that that increase the half-life, the solubility and/or the absorption of the Nanobody of the invention, that reduce the immunogenicity and/or the toxicity of the Nanobody of the invention, that eliminate or attenuate any undesirable side effects of the Nanobody of the invention, and/or that confer other advantageous properties to and/or reduce the undesired properties of the Nanobodies and/or polypeptides of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington's Pharmaceutical Sciences, 16th ed., Mack Publishing Co., Easton, Pa. (1980). Such functional groups may for example be linked directly (for example covalently) to a Nanobody of the invention, or optionally via a suitable linker or spacer, as will again be clear to the skilled person.

One of the most widely used techniques for increasing the half-life and/or the reducing immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO 04/060965. Various reagents for pegylation of proteins are also commercially available, for example from Nektar Therapeutics, USA.

Preferably, site-directed pegylation is used, in particular via a cysteine-residue (see for example Yang et al., Protein Engineering, 16, 10, 761-770 (2003). For example, for this purpose, PEG may be attached to a cysteine residue that naturally occurs in a Nanobody of the invention, a Nanobody of the invention may be modified so as to suitably introduce one or more cysteine residues for attachment of PEG, or an amino acid sequence comprising one or more cysteine residues for attachment of PEG may be fused to the N- and/or C-terminus of a Nanobody of the invention, all using techniques of protein engineering known per se to the skilled person.

Preferably, for the Nanobodies and proteins of the invention, a PEG is used with a molecular weight of more than 5000, such as more than 10,000 and less than 200,000, such as less than 100,000; for example in the range of 20,000-80,000.

With regard to pegylation, its should be noted that generally, the invention also encompasses any Nanobody of the invention and/or polypeptide of the invention that has been pegylated at one or more amino acid positions, preferably in such a way that said pegylation either (1) increases the half-life in vivo; (2) reduces immunogenicity; (3) provides one or more further beneficial properties known per se for pegylation; (4) does not essentially affect the affinity of the Nanobody and/or polypeptide for TNF-alpha (e.g. does not reduce said affinity by more than 90%, preferably not by more than 50%, and more preferably not by more than 10%, as determined by a suitable assay, such as those described in the Examples below); and/or (4) does not affect any of the other desired properties of the Nanobodies and/or polypeptides of the invention. Suitable PEG-groups and methods for attaching them, either specifically or non-specifically, will be clear to the skilled person. Suitable kits and reagents for such pegylation can for example be obtained from Nektar (CA, USA).

Another, usually less preferred modification comprises N-linked or O-linked glycosylation, usually as part of co-translational and/or post-translational modification, depending on the host cell used for expressing the Nanobody or polypeptide of the invention.

Yet another modification may comprise the introduction of one or more detectable labels or other signal-generating groups or moieties, depending on the intended use of the labelled Nanobody. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals such as $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes (such as $^{3}$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metals chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{162}$Dy, $^{52}$Cr, and $^{56}$Fe), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, β-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled Nanobodies and polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the Nanobody of the invention to another protein, polypeptide or chemical compound that is bound to the other half of the binding pair, i.e. through formation of the binding pair. For example, a Nanobody of the invention may be conjugated to biotin, and linked to another protein, polypeptide, compound or carrier conjugated to avidin or streptavidin. For example, such a conjugated Nanobody may be used as a reporter, for example in a diagnostic system where a detectable signal-producing agent is conjugated to avidin or streptavidin. Such binding pairs may for example also be used to bind the Nanobody of the invention to a carrier, including carriers suitable for pharmaceutical purposes. One non-limiting example are the liposomal formulations described by Cao and Suresh, Journal of Drug Targetting, 8, 4, 257 (2000). Such binding pairs may also be used to link a therapeutically active agent to the Nanobody of the invention.

For some applications, in particular for those applications in which it is intended to kill a cell that expresses the target against which the Nanobodies of the invention are directed (e.g. in the treatment of cancer), or to reduce or slow the growth and/or proliferation such a cell, the Nanobodies of the invention may also be linked to a toxin or to a toxic residue or moiety. Examples of toxic moieties, compounds or residues which can be linked to a Nanobody of the invention to provide—for example—a cytotoxic compound will be clear to the skilled person and can for example be found in the prior art cited above and/or in the further description herein. One example is the so-called ADEPT™ technology WO 03/055527.

Other potential chemical and enzymatical modifications will be clear to the skilled person. Such modifications may also be introduced for research purposes (e.g. to study function-activity relationships). Reference is for example made to Lundblad and Bradshaw, Biotechnol. Appl. Biochem., 26, 143-151 (1997).

As mentioned above, the invention also relates to proteins or polypeptides comprising at least one $V_{HH}$ domain (i.e. as identified using the methods of the invention) or at least one Nanobody based thereon.

According to one non-limiting embodiment of the invention, such a polypeptide of the invention essentially consists of a Nanobody. By "essentially consist of" is meant that the amino acid sequence of the polypeptide of the invention either is exactly the same as the amino acid sequence of a Nanobody (as mentioned above) or corresponds to the amino acid sequence of a Nanobody in which a limited number of amino acid residues, such as 1-10 amino acid residues and preferably 1-6 amino acid residues, such as 1, 2, 3, 4, 5 or 6 amino acid residues, have been added to the amino terminal end, to the carboxy terminal end, or both to the amino terminal end and to the carboxy terminal end of the amino acid sequence of the Nanobody.

Said amino acid residues may or may not change, alter or otherwise influence the (biological) properties of the Nanobody and may or may not add further functionality to the Nanobody. For example, such amino acid residues:

a) can comprise an N-terminal Met residue, for example as result of expression in a heterologous host cell or host organism.

b) may form a signal sequence or leader sequence that directs secretion of the Nanobody from a host cell upon synthesis. Suitable secretory leader peptides will be clear to the skilled person, and may be as further described herein. Usually, such a leader sequence will be linked to the N-terminus of the Nanobody, although the invention in its broadest sense is not limited thereto;

c) may form a sequence or signal that allows the Nanobody to be directed towards and/or to penetrate or enter into specific organs, tissues, cells, or parts or compartments of cells, and/or that allows the Nanobody to penetrate or cross a biological barrier such as a cell membrane, a cell layer such as a layer of epithelial cells, a tumor including solid tumors, or the blood-brain-barrier. Examples of such amino acid sequences will be clear to the skilled person. Some non-limiting examples are the small peptide vectors ("Pep-trans vectors") described in WO 03/026700 and in Temsamani et al., Expert Opin. Biol. Ther., 1, 773 (2001); Temsamani and Vidal, Drug Discov. Today, 9, 1012 (004) and Rousselle, J. Pharmacol. Exp. Ther., 296, 124-131 (2001), and the membrane translocator sequence described by Zhao et al., Apoptosis, 8, 631-637 (2003). C-terminal and N-terminal amino acid sequences for intracellular targeting of antibody fragments are for example described by Cardinale et al., Methods, 34, 171 (2004). Other suitable techniques for intracellular targeting involve the expression and/or use of so-called "intrabodies" comprising a Nanobody of the invention, as mentioned below;

d) may form a "tag", for example an amino acid sequence or residue that allows or facilitates the purification of the Nanobody, for example using affinity techniques directed against said sequence or residue. Thereafter, said sequence or residue may be removed (e.g. by chemical or enzymatical cleavage) to provide the Nanobody sequence (for this purpose, the tag may optionally be linked to the Nanobody sequence via a cleavable linker sequence or contain a cleavable motif). Some preferred, but non-limiting examples of such residues are multiple histidine residues, glutatione residues and a myc-tag such as AAAEQKLISEEDLNGAA (SEQ ID NO: 476);

e) may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the Nanobodies of the invention.

According to another embodiment, a polypeptide of the invention comprises a Nanobody of the invention, which is fused at its amino terminal end, at its carboxy terminal end, or both at its amino terminal end and at its carboxy terminal end to at least one further amino acid sequence, i.e. so as to provide a fusion protein comprising said Nanobody of the invention and the one or more further amino acid sequences. Such a fusion will also be referred to herein as a "Nanobody fusion".

The one or more further amino acid sequence may be any suitable and/or desired amino acid sequences. The further amino acid sequences may or may not change, alter or otherwise influence the (biological) properties of the Nanobody, and may or may not add further functionality to the Nanobody or the polypeptide of the invention. Preferably, the further amino acid sequence is such that it confers one or more desired properties or functionalities to the Nanobody or the polypeptide of the invention.

Example of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson, Nature Biotechnology, 23, 9, 1126-1136 (2005), For example, such an amino acid sequence may be an amino acid sequence that increases the half-life, the solubility, or the absorption, reduces the immunogenicity or the toxicity, eliminates or attenuates undesirable side effects, and/or confers other advantageous properties to and/or reduces the undesired properties of the polypeptides of the invention, compared to the Nanobody of the invention per se. Some non-limiting examples of such amino acid sequences are serum proteins, such as human serum albumin (see for example WO 00/27435) or haptenic molecules (for example haptens that are recognized by circulating antibodies, see for example WO 98/22141).

The further amino acid sequence may also provide a second binding site, which binding site may be directed against any desired protein, polypeptide, antigen, antigenic determinant or epitope (including but not limited to the same protein, polypeptide, antigen, antigenic determinant or epitope against which the Nanobody of the invention is directed, or a different protein, polypeptide, antigen, antigenic determinant or epitope). For example, the further amino acid sequence may provide a second binding site that is directed against a serum protein (such as, for example, human serum albumin or another serum protein such as IgG), so as to provide increased half-life in serum. Reference is for example made to EP 0 368 684, WO 91/01743, WO 01/45746 and WO 04/003019 (in which various serum proteins are mentioned), the International application by applicant entitled "Nanobodies™ against amyloid-beta and polypeptides comprising the same for the treatment of degenerative neural diseases such as Alzheimer's disease" (in which various other proteins are mentioned), as well as to Harmsen et al., Vaccine, 23 (41); 4926-42.

According to another embodiment, the one or more further amino acid sequences may comprise one or more parts, fragments or domains of conventional 4-chain antibodies (and in particular human antibodies) and/or of heavy chain antibodies. For example, although usually less preferred, a Nanobody of the invention may be linked to a conventional (preferably human) $V_H$ or $V_L$ domain domain or to a natural or synthetic analog of a $V_H$ or $V_L$ domain, again optionally via a linker sequence (including but not limited to other (single) domain antibodies, such as the dAb's described by Ward et al.).

The at least one Nanobody may also be linked to one or more (preferably human) $CH_1$, $CH_2$ and/or $CH_3$ domains, optionally via a linker sequence. For instance, a Nanobody linked to a suitable $CH_1$ domain could for example be used—together with suitable light chains—to generate antibody fragments/structures analogous to conventional Fab fragments or F(ab')2 fragments, but in which one or (in case of an F(ab')2 fragment) one or both of the conventional $V_H$ domains have been replaced by a Nanobody of the invention. Also, two Nanobodies could be linked to a CH3 domain (optionally via a linker) to provide a construct with increased half-life in vivo.

According to one specific embodiment of a polypeptide of the invention, one or more Nanobodies of the invention may linked to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more $CH_2$ and/or $CH_3$ domains of an antibody, such as from a heavy chain antibody (as described herein) and more preferably from a conventional human 4-chain antibody; and/or may form (part of) and Fc region, for example from IgG, from IgE or from another human Ig. For example, WO 94/04678 describes heavy chain antibodies comprising a Camelid $V_{HH}$ domain or a humanized derivative thereof (i.e. a Nanobody), in which the Camelidae $CH_2$ and/or $CH_3$ domain have been replaced by human $CH_2$ and $CH_3$ domains, so as to provide an immunoglobulin that consists of 2 heavy chains each comprising a Nanobody and human CH2 and CH3 domains (but no CH1 domain), which immunoglobulin has the effector function provided by the CH2 and CH3 domains and which immunoglobulin can function without the presence of any light chains. Other amino acid sequences that can be suitably linked to the Nanobodies of the invention so as to provide an effector function will be clear to the skilled person, and may be chosen on the basis of the desired effector function(s). Reference is for example made to WO 04/058820, WO 99/42077 and WO 05/017148, as well as the review by Holliger and Hudson, supra. Coupling of a Nanobody of the invention to an Fc portion may also lead to an increased half-life, compared to the corresponding Nanobody of the invention. For some applications, the use of an Fc portion and/or of constant domains (i.e. $CH_2$ and/or $CH_3$ domains) that confer increased half-life without any biologically significant effector function may also be suitable or even preferred. Other suitable constructs comprising one or more Nanobodies and one or more constant domains with increased half-life in vivo will be clear to the skilled person, and may for example comprise two Nanobodies linked to a CH3 domain, optionally via a linker sequence. Generally, any fusion protein or derivatives with increased half-life will preferably have a molecular weight of more than 50 kD, the cut-off value for renal absorption.

The further amino acid sequences may also form a signal sequence or leader sequence that directs secretion of the Nanobody or the polypeptide of the invention from a host cell upon synthesis (for example to provide a pre-, pro- or prepro-form of the polypeptide of the invention, depending on the host cell used to express the polypeptide of the invention).

The further amino acid sequence may also form a sequence or signal that allows the Nanobody or polypeptide of the invention to be directed towards and/or to penetrate or enter into specific organs, tissues, cells, or parts or compartments of cells, and/or that allows the Nanobody or polypeptide of the invention to penetrate or cross a biological barrier such as a cell membrane, a cell layer such as a layer of epithelial cells, a tumor including solid tumors, or the blood-brain-barrier. Suitable examples of such amino acid sequences will be clear to the skilled person, and for example include, but are not limited to, the "Peptrans" vectors mentioned above, the sequences described by Cardinale et al. and the amino acid sequences and antibody fragments known per se that can be used to express or produce the Nanobodies and polypeptides of the invention as so-called "intrabodies", for example as described in WO 94/02610, WO 95/22618, U.S. Pat. No. 7,004,940, WO 03/014960, WO 99/07414; WO 05/01690; EP 1 512 696; and in Cattaneo, A. & Biocca, S. (1997) Intracellular Antibodies: Development and Applications. Landes and Springer-Verlag; and in Kontermann, Methods 34, (2004), 163-170, and the further references described therein.

For some applications, in particular for those applications in which it is intended to kill a cell that expresses the target against which the Nanobodies of the invention are directed (e.g. in the treatment of cancer), or to reduce or slow the growth and/or proliferation such a cell, the Nanobodies of the invention may also be linked to a (cyto)toxic protein or polypeptide. Examples of such toxic proteins and polypeptides which can be linked to a Nanobody of the invention to provide—for example—a cytotoxic polypeptide of the invention will be clear to the skilled person and can for example be found in the prior art cited above and/or in the further description herein. One example is the so-called ADEPT™ technology WO 03/055527.

According to one non-limiting embodiment, one or more amino acid residues can be added to, inserted in and/or substituted in the amino acid sequence of a Nanobody or polypeptide of the invention, so as to provide one or more specific amino acid residues for attachment of a PEG-group.

The efficacy of protein pharmaceuticals depends on its potency to neutralize the target but also on the intrinsic pharmacokinetics of the potential drug. Because the kidney generally filters out molecules below 60,000 Daltons (Da), efforts to reduce clearance have focused on increasing the molecular weight of the biopharmaceutical through protein fusions (Syed et al., 1997), glycosylations or modification with polyethylene glycol polymers, i.e., PEGylation (Lee et al., 1999; Abuchowski et al., 1977; Nucci et al., 1991; Lecolley, et al. Chem Commun, 2004; Tao et al., J Am Chem Soc, 2004; Mantovani et al., 2005). These methods successfully extend the in vivo exposure of the biopharmaceutical.

Alternatively, the half-life can be extended using another pegylating agent, POLY PEG for conjugation to the bivalent Nanobodies, TNF56 or TNF55. POLY PEG are comb shape polymers with PEG teeth on a methacrylic backbone. POLY PEGs can vary on the length of the PEG chain, on the methacrylic backbone and on the active end-group which determines the method of conjugation of the POLY PEG to the Nanobody. Site-specific conjugation to the C-terminal cysteine present in the Nanobodies can be achieved through the active maleimide end-group in the POLY PEG.

The invention also encompasses any Nanobody of the invention and/or polypeptide of the invention that has been glycosylated at one or more amino acid positions, usually depending upon the host used to express the Nanobody or polypeptide of the invention (as further described below).

According to one non-limiting embodiment, one or more amino acid residues can be added to, inserted in and/or substituted in the amino acid sequence of a Nanobody or polypeptide of the invention, so as to provide one or more specific amino acid residues and/or a site that can be glycosylated by the host organism used. By means of a preferred, but non-limiting example, the N-residue on position 50 within CDR2 of a Nanobody of the invention can for example be replaced by a Q, D or S residue so as to provide a glycosylation site, e.g. for glycosylation by *Pichia*.

According to another embodiment, a polypeptide of the invention can comprise the amino acid sequence of a Nanobody, which is fused at its amino terminal end, at its carboxy terminal end, or both at its amino terminal end and at its carboxy terminal end with at least one further amino acid sequence.

Again, said further amino acid sequence(s) may or may not change, alter or otherwise influence the (biological) properties of the Nanobody and may or may not add further functionality to the Nanobody.

For example, according to one preferred, but non-limiting embodiment, said further amino acid sequence may comprise at least one further Nanobody, so as to provide a polypeptide of the invention that comprises at least two, such as three, four or five, Nanobodies, in which said Nanobodies may optionally be linked via one or more linker sequences (as defined herein).

Polypeptides of the invention comprising two or more Nanobodies will also referred to herein as "multivalent" polypeptides. For example a "bivalent" polypeptide of the Invention comprises two Nanobodies, optionally linked via a linker sequence, whereas a "trivalent" polypeptide of the invention comprises three Nanobodies, optionally linked via two linker sequences; etc.

In a multivalent polypeptide of the invention, the two or more Nanobodies may be the same or different. For example, the two or more Nanobodies in a multivalent polypeptide of the invention:
  may be directed against the same antigen, i.e. against the
    same parts or epitopes of said antigen or against two or
    more different parts or epitopes of said antigen; and/or:
  may be directed against the different antigens;
or a combination thereof.

Thus, a bivalent polypeptide of the invention for example:
  may comprise two identical Nanobodies;
  may comprise a first Nanobody directed against a first part
    or epitope of an antigen and a second Nanobody
    directed against the same part or epitope of said antigen
    or against another part or epitope of said antigen;
  or may comprise a first Nanobody directed against a first
    antigen and a second
  Nanobody directed against a second antigen different
from said first antigen; whereas a trivalent Polypeptide of
the Invention for example:
  may comprises three identical or different Nanobodies
    directed against the same or different parts or epitopes
    of the same antigen;

may comprise two identical or different Nanobodies directed against the same or different parts or epitopes on a first antigen and a third Nanobody directed against a second antigen different from said first antigen; or may comprise a first Nanobody directed against a first antigen, a second Nanobody directed against a second antigen different from said first antigen, and a third Nanobody directed against a third antigen different from said first and second antigen, Polypeptides of the invention that contain at least two Nanobodies, in which at least one Nanobody is directed against a first antigen and at least one Nanobody is directed against a second antigen different from the first antigen, will also be referred to as "multispecific" Nanobodies. Thus, a "bispecific" Nanobody is a Nanobody that comprises at least one Nanobody directed against a first antigen and at least one further Nanobody directed against a second antigen, whereas a "trispecific" Nanobody is a Nanobody that comprises at least one Nanobody directed against a first antigen, at least one further Nanobody directed against a second antigen, and at least one further Nanobody directed against a third antigen; etc.

Accordingly, in their simplest form, a bispecific polypeptide of the invention is a bivalent polypeptide of the invention (as defined herein), comprising a first Nanobody directed against a first antigen and a second Nanobody directed against a second antigen, in which said first and second Nanobody may optionally be linked via a linker sequence (as defined herein); whereas a trispecific polypeptide of the invention in its simplest form is a trivalent polypeptide of the invention (as defined herein), comprising a first Nanobody directed against a first antigen, a second Nanobody directed against a second antigen and a third Nanobody directed against a third antigen, in which said first, second and third Nanobody may optionally be linked via one or more, and in particular one and more in particular two, linker sequences.

However, as will be clear from the description hereinabove, the invention is not limited thereto, in the sense that a multispecific polypeptide of the invention may comprise any number of Nanobodies directed against two or more different antigens.

For multivalent and multispecific polypeptides containing one or more $V_{HH}$ domains and their preparation, reference is also made to Conrath et al., *J. Biol. Chem.*, Vol. 276, 10. 7346-7350, as well as to EP 0 822 985.

In the polypeptides of the invention, the one or more Nanobodies and the one or more polypeptides may be directly linked to each other (as for example described in WO 99/23221) and/or may be linked to each other via one or more suitable spacers or linkers, or any combination thereof.

Suitable spacers or linkers for use in multivalent and multispecific polypeptides will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, its should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each Nanobody by itself forms a complete antigen-binding site).

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is also within the scope of the invention that the linker(s) used confer one or more other favourable properties or functionality to the polypeptides of the invention, and/or provide one or more sites for the formation of derivatives and/or for the attachment of functional groups (e.g. as described herein for the derivatives of the Nanobodies of the invention). For example, linkers containing one or more charged amino acid residues (see Table A-3 above) can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after on some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after on some limited routine experiments.

Linkers for use in multivalent and multispecific polypeptides will be clear to the skilled person, and for example include gly-ser linkers, for example of the type $(gly_x ser_y)_z$, such as (for example $(gly_4 ser)_3$ or $(gly_3 ser_2)_3$, as described in WO 99/42077, hinge like regions such as the hinge regions of naturally occurring heavy chain antibodies or similar sequences. For other suitable linkers, reference is also made to the general background art cited above. Some particularly preferred linkers are given in SEQ ID NO's 68 and 69.

Linkers can also provide some functionality for the multivalent or multispecific polypeptide. For example, linkers containing one or more charged amino acid residues (see Table 1 above) can provide improved hydrophilic properties, whereas linkers that form or contain small epitopes or tags can be used for the purposes of detection, identification and/or purification.

As mentioned herein, in a protein or polypeptide of the invention, the anti-TNF Nanobodies mentioned herein are preferably linked in such a way that said protein or polypeptide, upon binding to a TNF trimer, is capable inhibiting or reducing the TNF receptor crosslinking that is mediated by said TNF trimer and/or the signal transduction that is mediated by such receptor crosslinking; and/or in such a way that the protein or polypeptide is capable of intramolecular binding to at least two TNF receptor binding sites on a TNF trimer. Suitable linkers are as described herein.

As also mentioned herein, whether a protein or polypeptide provides intermolecular binding or extramolecular binding can be assessed (at least initially) by a size exclusion chromatography. By Size Exclusion Chromatography the complexes of TNF-alpha and antibodies can be analyzed for determining the number and the ratio of antibody and TNF-alpha molecules in the complex. From these data it can be deduced if inter- or intramolecular binding occurs, as was done by Santora and colleagues (Santora, L. C., et al, Anal Biochem. 2001) for establishing the stoichiometry of binding of monoclonal antibody D2E7 (Humira) to TNF-alpha☐ at different ratios of antibody and target. From the molecular weight of the complex it was concluded that three antibody molecules complexed with three TNF trimers, thereby indicating that the antibody binds in an intermolecular mode. Similar experiments were performed with bivalent Nanobodies, in which a very short linker induced the formation of large molecular complexes, which were obtained by intermolecular bonds. However, the same bivalent Nanobodies constructs with longer linkers eluted from the gel filtration column as discrete small complexes, thereby demonstrating that intramolecular bonds were formed. Combined with the bioassay data, in which the longer linker containing Nanobody TNF1 had an optimal potency (complete neutralization of amount of TNF used in the assay, i.e. 10 pM), it can be concluded that intramolecular binding of the bivalent Nanobody efficiently prevents cross-linking of two cell bound receptors and the associated receptor activation. Known monoclonal antibodies such as Humira or Remicade can not form such intramolecular bonds, leaving always two receptor bindingsites on the trimeric TNF molecule to a certain degree available for interaction with cell bound receptor, which translates into less potent neutralization as measured in the bioassay.

Alternatively, whether a protein or polypeptide provides intermolecular binding or extramolecular binding can be assessed by crystallography and/or molecular modelling (or other suitable in silico techniques). A model of a trimeric TNF30/TNF-alpha complex was generated based on the crystal structure of the monomeric wild type TNF1/TNF-alpha complex. From this structure the final TNF30-linker-ALB8-linker-TNF30 construct was modeled. The TNF30-linker-ALB8-linker-TNF30 construct was modelled starting from the trimer of TNFα with two TNF30 molecules bound. As the structure of the ALB8 is not known, a third TNF30 molecule was used instead, which was placed in between the other two Nanobodies along the line between the N- and C-termini. The 9 amino acid linkers were then added manually.

The model is shown in FIG. 62. Clearly, the 9 amino acid linkers together with the ALB8 provide ample room to span the about 66 Å between the two TNF30 domains bound to TNFα. ALB8 by itself already spans 40 Å, and each linker can span another ~27 Å in completely extended conformation. As a result, the ALB8 has quite some flexibility of movement, and it is not expected that its binding to albumin would interfere much with the binding to TNFα.

Moreover, it is likely that the linkers can be shortened without affecting avidity, especially in the case of the linker that is C-terminal of ALB8. This may have the beneficial effect of increased binding to the same TNFα trimer versus crosslinking trimers, because the probability that the second TNF30 associates with a different TNFα increases with the length of the linker.

As also further described herein, a multispecific polypeptide of the invention directed against a desired antigen and against at least one serum protein, such as the serum proteins mentioned hereinbelow, and in particular against human serum albumin, may show increased half-life in serum, compared to the corresponding monovalent Nanobody.

As mentioned hereinabove, the methods described herein are particularly suited for generating such multivalent of multispecific polypeptides of the invention.

In a polypeptide of the invention, the at least one Nanobody may also be linked to a conventional $V_H$ domain or to a natural or synthetic analog of a $V_H$ domain, optionally via a linker sequence.

In a polypeptide of the invention, the at least one Nanobody may also be linked to a $V_L$ domain or to a natural or synthetic analog of a $V_L$ domain, optionally via a linker sequence, so as to provide a polypeptide of the invention that is in the form analogous to a conventional scFv fragment, but containing a Nanobody instead of a $V_H$ domain.

In a polypeptide of the invention, the at least one Nanobody may also be linked to one or more of a CH1, CH2 and/or CH3 domain, optionally via a linker sequence. For instance, a Nanobody linked to a suitable CH1 domain could for example be used—together with suitable light chains—to generate antibody fragments/structures analogous to conventional Fab fragments or F(ab')$_2$ fragments, but in which one or (in case of an F(ab')$_2$ fragment) one or both of the conventional $V_H$ domains have been replaced by a Nanobody. Such fragments may also be heterospecific or bispecific, i.e. directed against two or more antigens. A Nanobody linked to suitable CH2 and CH3 domains, for example derived from Camelids, could be used to form a monospecific or bispecific heavy chain antibody. Finally, a Nanobody linked to suitable CH1, CH2 and CH3 domains, for example derived from a human being, could be used—together with suitable light chains—to form an antibody that is analogous to a conventional 4-chain antibody, but in which one or both of the conventional $V_H$ domains have been replaced by a Nanobody.

Also, in addition to the one or more Nanobodies, Polypeptides of the Invention can also contain functional groups, moieties or residues, for example therapeutically active substances, such as those mentioned below, and/or markers or labels, such as fluorescent markers, isotopes, etc., as further described hereinbelow.

The Nanobodies of the invention, the polypeptides of the invention, and nucleic acids encoding the same, can be prepared in a manner known per se, as will be clear to the skilled person from the further description herein. Some preferred, but non-limiting methods for preparing the Nanobodies, polypeptides and nucleic acids include the methods and techniques mentioned above and/or further described hereinbelow.

As will be clear to the skilled person, one particularly useful method for preparing a Nanobody and/or a polypeptide of the invention generally comprises the steps of:

the expression, in a suitable host cell or host organism (also referred to herein as a "host of the invention") or in another suitable expression system of a nucleic acid that encodes said Nanobody or polypeptide of the invention (also referred to herein as a "nucleic acid of the invention"), optionally followed by:

isolating and/or purifying the Nanobody or polypeptide of the invention thus obtained.

In particular, such a method may comprise the steps of:

cultivating and/or maintaining a host of the invention under conditions that are such that said host of the invention expresses and/or produces at least one Nanobody and/or polypeptide of the invention; optionally followed by:

isolating and/or purifying the Nanobody or polypeptide of the invention thus obtained.

A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one embodiment of the invention, the nucleic acid of the invention is in essentially isolated from, as defined hereinabove.

The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the amino acid sequences for the polypeptides of the invention given herein, and/or can be isolated from a suitable natural source. To provide analogs, nucleotide sequences encoding naturally occurring $V_{HH}$ domains can for example be subjected to site-directed mutagenesis, so as to provide a nucleic acid of the invention encoding said analog. Also, as will be clear to the skilled person, to prepare a nucleic acid of the invention, also several nucleotide sequences, such as at least one nucleotide sequence encoding a Nanobody and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers, using for example a sequence of a naturally occurring GPCR as a template. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to hereinbelow. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting embodiment, a genetic construct of the invention comprises
a) at least one nucleic acid of the invention; operably connected to
b) one or more regulatory elements, such as a promoter and optionally a suitable terminator;
c) and optionally also
d) one or more further elements of genetic constructs known per se;
in which the terms "regulatory element", "promoter", "terminator" and "operably connected" have their usual meaning in the art (as further described below); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used, the intended host cell or host organism; the manner in which the nucleotide sequences of the invention of interest are to be expressed (e.g. via constitutive, transient or inducible expression); and/or the transformation technique to be used.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promotor). Generally, when two nucleotide sequences are operably linked, they will be in the same orientation and usually also in the same reading frame. They will usually also be essentially contiguous, although this may also not be required.

Preferably, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence—e.g. a coding sequence—to which it is operably linked (as defined herein).

Some particularly preferred promoters include, but are not limited to, promoters known per se for the expression in bacterial cells, such as those mentioned hereinbelow and/or those used in the Examples.

A selection marker should be such that it allows—i.e. under appropriate selection conditions—host cells and/or host organisms that have been (succesfully) transformed with the nucleotide sequence of the invention to be distinguished from host cells/organisms that have not been (succesfully) transformed. Some preferred, but non-limiting examples of such markers are genes that provide resistance against antibiotics (such as kanamycine or ampicilline), genes that provide for temperature resistance, or genes that allow the host cell or host organism to be maintained in the absence of certain factors, compounds and/or (food) components in the medium that are essential for survival of the non-transformed cells or organisms.

A leader sequence should be such that—in the intended host cell or host organism—it allows for the desired post-translational modifications and/or such that it directs the transcribed mRNA to a desired part or organelle of a cell. A leader sequence may also allow for secretion of the expression product from said cell. As such, the leader sequence may be any pro-, pre-, or prepro-sequence operable in the host cell or host organism. Leader sequences may not be required for expression in a bacterial cell.

An expression marker or reporter gene should be such that—in the host cell or host organism—it allows for detection of the expression of (a gene or nucleotide sequence present on) the genetic construct. An expression marker may optionally also allow for the localisation of the expressed product, e.g. in a specific part or organelle of a cell and/or in (a) specific cell(s), tissue(s), organ(s) or part(s) of a multicellular organism. Such reporter genes may also be expressed as a protein fusion with the amino acid sequence of the invention. Some preferred, but non-limiting examples include fluorescent proteins such as GFP.

Some preferred, but non-limiting examples of suitable promoters, terminator and further elements include those used in the Examples below. For some (further) non-limiting examples of the promoters, selection markers, leader sequences, expression markers and further elements that may be present/used in the genetic constructs of the invention—such as terminators, transcriptional and/or translational enhancers and/or integration factors—reference is made to the general handbooks such as Sambrook et al. and Ausubel et al. mentioned above, as well as to the examples that are given in WO 95/07463, WO 96/23810, WO 95/07463, WO 95/21191, WO 97/11094, WO 97/42320, WO 98/06737, WO 98/21355, U.S. Pat. Nos. 6,207,410, 5,693,492 and EP 1 085 089. Other examples will be clear to the skilled person. Reference is also made to the general background art cited above and the further references cited hereinbelow.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleotide sequence of the invention in a suitable (expression) vector known per se. Some preferred, but non-limiting examples of suitable expression vectors are those used in the Examples below, as well as those mentioned below.

The nucleic acids of the invention and/or the genetic constructs of the invention may be used to transform a host cell or host organism. The host cell or host organism may be any suitable (fungal, prokaryotic or eukaryotic) cell or cell line or any suitable fungal, prokaryotic or eukaryotic organism, for example:

- a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis;*
- a fungal cell, including but not limited to cells from species of *Trichoderma*, for example from *Trichoderma reesei*; of *Neurospora*, for example from *Neurospora crassa*; of *Sordaria*, for example from *Sordaria macrospora*; of *Aspergillus*, for example from *Aspergillus niger* or from *Aspergillus sojae*; or from other filamentous fungi;
- a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for Example of *Arxula Adeninivorans*; of *Yarrowia*, for example of *Yarrowia lipolytica;*
- an amphibian cell or cell line, such as *Xenopus* oocytes;
- an insect-derived cell or cell line, such as cells/cell lines derived from *lepidoptera*, including but not limited to *Spodoptera* SF9 and Sf21 cells or cells/cell lines derived from *Drosophila*, such as Schneider and Kc cells;
- a plant or plant cell, for example in tobacco plants; and/or
- a mammalian cell or cell line, for example derived a cell or cell line derived from a human, from the mammals including but not limited to-cells, BHK-cells (for example BHK-21 cells) and human cells or cell lines such as HeLa, COS (for example COS-7) and PER.C6 cells;

as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al., (1998), supra; Riechmann and Muyldermans, (1999), supra; van der Linden, (2000), supra; Thomassen et al., (2002), supra; Joosten et al., (2003), supra; Joosten et al., (2005), supra; and the further references cited herein.

The Nanobodies and polypeptides of the invention can also be introduced and expressed in one or more cells, tissues or organs of a multicellular organism, for example for prophylactic and/or therapeutic purposes (e.g. as a gene therapy). For this purpose, the nucleotide sequences of the invention may be introduced into the cells or tissues in any suitable way, for example as such (e.g. using liposomes) or after they have been inserted into a suitable gene therapy vector (for example derived from retroviruses such as adenovirus, or parvoviruses such as adeno-associated virus). As will also be clear to the skilled person, such gene therapy may be performed in vivo and/or in situ in the body of a patient by administering a nucleic acid of the invention or a suitable gene therapy vector encoding the same to the patient or to specific cells or a specific tissue or organ of the patient; or suitable cells (often taken from the body of the patient to be treated, such as explanted lymphocytes, bone marrow aspirates or tissue biopsies) may be treated in vitro with a nucleotide sequence of the invention and then be suitably (re-)introduced into the body of the patient. All this can be performed using gene therapy vectors, techniques and delivery systems which are well known to the skilled person, for example, Culver, K. W., "Gene Therapy", 1994, p. xii, Mary Ann Liebert, Inc., Publishers, New York, N.Y.; Giordano, Nature F Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ. Res. 77 (1995), 1077-1086; Onodera, Blood 91; (1998), 30-36; Verma, Gene Ther.

5 (1998), 692-699; Nabel, Ann. N.Y. Acad. Sci.: 811 (1997), 289-292; Verzeletti, Hum. Gene Ther. 9 (1998), 2243-51; Wang, Nature Medicine 2 (1996), 714-716; WO 94/29469; WO 97/00957, U.S. Pat. Nos. 5,580,859; 5,5895,466; or Schaper, Current Opinion in Biotechnology 7 (1996), 635-640. For example, in situ expression of ScFv fragments (Afanasieva et al., Gene Ther., 10, 1850-1859 (2003)) and of diabodies (Blanco et al., J. Immunol, 171, 1070-1077 (2003)) has been described in the art.

For expression of the Nanobodies in a cell, they may also be expressed as so-called "intrabodies", as for example described in WO 94/02610, WO 95/22618 and U.S. Pat. No. 7,004,940; WO 03/014960; in Cattaneo, A. & Biocca, S. (1997) Intracellular Antibodies: Development and Applications. Landes and Springer-Verlag; and in Kontermann, Methods 34, (2004), 163-170.

For production, the Nanobodies and polypeptides of the invention can for example also be produced in the milk of transgenic mammals, for example in the milk of rabbits, cows, goats or sheep (see for example U.S. Pat. Nos. 6,741,957, 6,304,489 and 6,849,992 for general techniques for introducing transgenes into mammals), in plants or parts of plants including but not limited to their leaves, flowers, fruits, seed, roots or tubers (for example in tobacco, maize, soybean or alfalfa) or in for example pupae of the silkworm *Bombyx mori*.

Furthermore, the Nanobodies and polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

As mentioned above, one of the advantages of the use of Nanobodies is that the polypeptides based thereon can be prepared through expression in a suitable bacterial system, and suitable bacterial expression systems, vectors, host cells, regulatory elements, etc., will be clear to the skilled person, for example from the references cited above. It should however be noted that the invention in its broadest sense is not limited to expression in bacterial systems.

Preferably, in the invention, an (in vivo or in vitro) expression system, such as a bacterial expression system, is used that provides the polypeptides of the invention in a form that is suitable for pharmaceutical use, and such expression systems will again be clear to the skilled person. As also will be clear to the skilled person, Polypeptides of the invention suitable for pharmaceutical use can be prepared using techniques for peptide synthesis.

For production on industrial scale, preferred heterologous hosts for the (industrial) production of Nanobodies or Nanobody-containing protein therapeutics include strains of *E. coli, Pichia pastoris, S. cerevisiae* that are suitable for large scale expression/production/fermentation, and in particular for large scale pharmaceutical expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of a Nanobody-containing recombinant protein for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached) will depend on the cell or cell line that is used for the expression. Preferably, either a human cell or cell line is used (i.e. leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast are usually leads to a glycosylation pattern that differs from human glycosylation. Nevertheless, it should be understood that all the foregoing host cells and expression systems can be used in the invention, depending on the desired Nanobody or protein to be obtained.

Thus, according to one non-limiting embodiment of the invention, the Nanobody or polypeptide of the invention is glycosylated. According to another non-limiting embodiment of the invention, the Nanobody or polypeptide of the invention is non-glycosylated.

According to one preferred, but non-limiting embodiment of the invention, the Nanobody or polypeptide of the invention is produced in a bacterial cell, in particular a bacterial cell suitable for large scale pharmaceutical production, such as cells of the strains mentioned above.

According to another preferred, but non-limiting embodiment of the invention, the Nanobody or polypeptide of the invention is produced in a yeast cell, in particular a yeast cell suitable for large scale pharmaceutical production, such as cells of the species mentioned above.

According to yet another preferred, but non-limiting embodiment of the invention, the Nanobody or polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

When expression in a host cell is used to produce the Nanobodies and the proteins of the invention, the Nanobodies and proteins of the invention can be produced either intracellullarly (e.g. in the cytosol, in the periplasma or in inclusion bodies) and then isolated from the host cells and optionally further purified; or can be produced extracellularly (e.g. in the medium in which the host cells are cultured) and then isolated from the culture medium and optionally further purified. When eukaryotic hosts cells are used, extracellular production is usually preferred since this considerably facilitates the further isolation and downstream processing of the Nanobodies and proteins obtained. Bacterial cells such as the strains of *E. coli* mentioned above normally do not secrete proteins extracellularly, except for a few classes of proteins such as toxins and hemolysin, and secretory production in *E. coli* refers to the translocation of proteins across the inner membrane to the periplasmic space. Periplasmic production provides several advantages over cytosolic production. For example, the N-terminal amino acid sequence of the secreted product can be identical to the natural gene product after cleavage of the secretion signal sequence by a specific signal peptidase. Also, there appears to be much less protease activity in the periplasm than in the cytoplasm. In addition, protein purification is simpler due to fewer contaminating proteins in the periplasm. Another advantage is that correct disulfide bonds may form because the periplasm provides a more oxidative environment than the cytoplasm. Proteins overexpressed in *E. coli* are often found in insoluble aggregates, so-called inclusion bodies. These inclusion bodies may be located in the cytosol or in the periplasm; the recovery of biologically active proteins from these inclusion bodies requires a denaturation/refolding process. Many recombinant proteins, including therapeutic proteins, are recovered from inclusion bodies. Alternatively, as will be clear to the skilled person, recombinant strains of bacteria that have been genetically modified so as to secrete a desired protein, and in particular a Nanobody or a polypeptide of the invention, can be used.

Thus, according to one non-limiting embodiment of the invention, the Nanobody or polypeptide of the invention is a Nanobody or polypeptide that has been produced intracellularly and that has been isolated from the host cell, and in particular from a bacterial cell or from an inclusion body in a bacterial cell. According to another non-limiting embodiment of the invention, the Nanobody or polypeptide of the invention is a Nanobody or polypeptide that has been produced extracellularly, and that has been isolated from the medium in which the host cell is cultivated.

Some preferred, but non-limiting promoters for use with these host cells include,
for expression in *E. coli*: lac promoter (and derivatives thereof such as the lacUV5 promoter); arabinose promoter; left- (PL) and rightward (PR) promoter of phage lambda; promoter of the trp operon; hybrid lac/trp promoters (tac and trc); T7-promoter (more specifically that of T7-phage gene 10) and other T-phage promoters; promoter of the Tn10 tetracycline resistance gene; engineered variants of the above promoters that include one or more copies of an extraneous regulatory operator sequence;
for expression in *S. cerevisiae*: constitutive: ADH1 (alcohol dehydrogenase 1), ENO (enolase), CYC1 (cytochrome c iso-1), GAPDH (glyceraldehydes-3-phosphate dehydrogenase); PGK1 (phosphoglycerate kinase), PYK1 (pyruvate kinase); regulated: GAL1, 10,7 (galactose metabolic enzymes), ADH2 (alcohol dehydrogenase 2), PHO5 (acid phosphatase), CUP1 (copper metallothionein); heterologous: CaMV (cauliflower mosaic virus 35S promoter);
for expression in *Pichia pastoris*: the AOX1 promoter (alcohol oxidase I)
for expression in mammalian cells: human cytomegalovirus (hCMV) immediate early enhancer/promoter; human cytomegalovirus (hCMV) immediate early promoter variant that contains two tetracycline operator sequences such that the promoter can be regulated by the Tet repressor; Herpes Simplex Virus thymidine kinase (TK) promoter; Rous Sarcoma Virus long terminal repeat (RSV LTR) enhancer/promoter; elongation factor 1α (hEF-1α) promoter from human, chimpanzee, mouse or rat; the SV40 early promoter; HIV-1 long terminal repeat promoter; β-actin promoter;
Some preferred, but non-limiting vectors for use with these host cells include:
vectors for expression in mammalian cells: pMAMneo (Clontech), pcDNA3 (Invitrogen), pMC1neo (Stratagene), pSG5 (Stratagene), EBO-pSV2-neo (ATCC 37593), pBPV-1 (8-2) (ATCC 37110), pdBPV-MMT-neo (342-12) (ATCC 37224), pRSVgpt (ATCC37199), pRSVneo (ATCC37198), pSV2-dhfr (ATCC 37146), pUCTag (ATCC 37460) and 1ZD35 (ATCC 37565), as well as viral-based expression systems, such as those based on adenovirus;
vectors for expression in bacterials cells: pET vectors (Novagen) and pQE vectors (Qiagen);
vectors for expression in yeast or other fungal cells: pYES2 (Invitrogen) and *Pichia* expression vectors (Invitrogen);
vectors for expression in insect cells: pBlueBacII (Invitrogen) and other baculovirus vectors
vectors for expression in plants or plant cells: for example vectors based on cauliflower mosaic virus or tobacco mosaic virus, suitable strains of *Agrobacterium*, or Ti-plasmid based vectors.
Some preferred, but non-limiting secretory sequences for use with these host cells include:
for use in bacterial cells such as *E. coli*: PelB, Bla, OmpA, OmpC, OmpF, OmpT, StII, PhoA, PhoE, MalE, Lpp, LamB, and the like; TAT signal peptide, hemolysin C-terminal secretion signal for use in yeast: α-mating factor prepro-sequence, phosphatase (pho1), invertase (Suc), etc.,
for use in mammalian cells: indigenous signal in case the target protein is of eukaryotic origin; murine Ig κ-chain V-J2-C signal peptide; etc.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the amino acid sequence of the invention, e.g. using specific antibodies.

The transformed host cell (which may be in the form of a stable cell line) or host organisms (which may be in the form of a stable mutant line or strain) form further aspects of the present invention.

Preferably, these host cells or host organisms are such that they express, or are (at least) capable of expressing (e.g. under suitable conditions), an amino acid sequence of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the amino acid sequences of the invention, the transformed host cell or transformed host organism may generally be kept, maintained and/or cultured under conditions such that the (desired) amino acid sequence of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

It will also be clear to the skilled person that the amino acid sequence of the invention may (first) be generated in an immature form (as mentioned above), which may then be subjected to post-translational modification, depending on the host cell/host organism used. Also, the amino acid sequence of the invention may be glycosylated, again depending on the host cell/host organism used.

The amino acid sequence of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence of the invention) and/or preparative immunological techniques (i.e. using antibodies against the amino acid sequence to be isolated).

Generally, for pharmaceutical use, the polypeptides of the invention of the inventions may be formulated as a pharmaceutical preparation comprising at least one polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such suitable administration forms—which may be solid, semi-solid or liquid, depending on the manner of administration—as well as methods and carriers for use in the preparation thereof, will be clear to the skilled person, and are further described hereinbelow.

Generally, the Nanobodies and polypeptides of the invention can be formulated and administered in any suitable manner known per se, for which reference is for example made to the general background art cited above (and in particular to WO 04/041862, WO 04/041863, WO 04/041865 and WO 04/041867) as well as to the standard handbooks, such as Remington's Pharmaceutical Sciences, 18$^{th}$ Ed., Mack Publishing Company, USA (1990) or Remington, the Science and Practice of Pharmacy, 21th Edition, Lippincott Williams and Wilkins (2005).

For example, the Nanobodies and polypeptides of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (for example intravenous, intraperitoneal, subcutaneous, intramuscular, intraluminal, intra-arterial or intrathecal administration) or for topical (i.e. transdermal or intradermal) administration.

Preparations for parenteral administration may for example be sterile solutions, suspensions, dispersions or emulsions that are suitable for infusion or injection. Suitable carriers or diluents for such preparations for example include, without limitation, sterile water and aqueous buffers and solutions such as physiological phosphate-buffered saline, Ringer's solutions, dextrose solution, and Hank's solution; water oils; glycerol; ethanol; glycols such as propylene glycol or as well as mineral oils, animal oils and vegetable oils, for example peanut oil, soybean oil, as well as suitable mixtures thereof. Usually, aqueous solutions or suspensions will be preferred.

The Nanobodies and polypeptides of the invention can also be administered using gene therapy methods of delivery. See, e.g., U.S. Pat. No. 5,399,346, which is incorporated by reference in its entirety. Using a gene therapy method of delivery, primary cells transfected with the gene encoding a Nanobody or polypeptide of the invention can additionally be transfected with tissue specific promoters to target specific organs, tissue, grafts, tumors, or cells and can additionally be transfected with signal and stabilization sequences for subcellularly localized expression.

Thus, the Nanobodies and polypeptides of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the Nanobodies and polypeptides of the invention may be combined with one or more excipients and used in the form of ingestible tablets, buccal tablets, troches, capsules, elixirs, suspensions, syrups, wafers, and the like. Such compositions and preparations should contain at least 0.1% of the Nanobody or polypeptide of the invention. The percentage of the compositions and preparations may, of course, be varied and may conveniently be between about 2 to about 60% of the weight of a given unit dosage form. The amount of the Nanobody or polypeptide of the invention in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the Nanobodies and polypeptides of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the Nanobodies and polypeptides of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The Nanobodies and polypeptides of the invention may also be administered intravenously or intraperitoneally by infusion or injection. Solutions of the Nanobodies and polypeptides of the invention or their salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the Nanobodies and polypeptides of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the Nanobodies and polypeptides of the invention may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, hydroxyalkyls or glycols or water-alcohol/glycol blends, in which the Nanobodies and polypeptides of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the Nanobodies and polypeptides of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the Nanobodies and polypeptides of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the Nanobodies and polypeptides of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the Nanobodies and polypeptides of the invention required for use in treatment will vary not only with the particular Nanobody or polypeptide selected but also with the route of administration, the nature of the condition being treated and the age and condition of the patient and will be ultimately at the discretion of the attendant physician or clinician. Also the dosage of the Nanobodies and polypeptides of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

In another aspect, the invention relates to a method for the prevention and/or treatment of at least one TNF-relates disease or disorder as mentioned herein, said method comprising administering, to a subject in need thereof, a pharmaceutically active amount of a Nanobody of the invention, of a polypeptide of the invention, and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

The invention also relates to a method for the prevention and/or treatment of at least one disease or disorder that can be prevented and/or treated by administering a Nanobody or polypeptide of the invention to a patient, said method comprising administering, to a subject in need thereof, a pharmaceutically active amount of a Nanobody of the invention, of a polypeptide of the invention, and/or of a pharmaceutical composition comprising the same.

More in particular, the invention relates to a method for the prevention and/or treatment of at least one disease or disorder chosen from the group consisting of the diseases and disorders listed herein, said method comprising administering, to a subject in need thereof, a pharmaceutically active amount of a Nanobody of the invention, of a polypeptide of the invention, and/or of a pharmaceutical composition comprising the same.

In another embodiment, the invention relates to a method for immunotherapy, and in particular for passive immunotherapy, which method comprises administering, to a subject suffering from or at risk of the diseases and disorders mentioned herein, a pharmaceutically active amount of a Nanobody of the invention, of a polypeptide of the invention, and/or of a pharmaceutical composition comprising the same.

In the above methods, the Nanobodies and/or polypeptides of the invention and/or the compositions comprising the same can be administered in any suitable manner, depending on the specific pharmaceutical formulation or composition to be used. Thus, the Nanobodies and/or polypeptides of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

The Nanobodies and/or polypeptides of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific Nanobody or polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more Nanobodies and/or polypeptides of the invention, or of one or more compositions comprising the same, in one or more pharmaceutically effective amounts or doses. The specific amount(s) or doses to administered can be determined by the clinician, again based on the factors cited above.

Generally, for the prevention and/or treatment of the diseases and disorders mentioned herein and depending on the specific disease or disorder to be treated, the potency of the specific Nanobody and polypeptide of the invention to be used, the specific route of administration and the specific pharmaceutical formulation or composition used, the Nanobodies and polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single Nanobody or polypeptide of the invention will be used. It is however within the scope of the invention to use two or more Nanobodies and/or polypeptides of the invention in combination.

The Nanobodies and polypeptides of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

In particular, the Nanobodies and polypeptides of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are administered to be simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

Thus, in a further aspect, the invention relates to a pharmaceutical composition that contains at least one Nanobody of the invention or at least one polypeptide of the invention and at least one suitable carrier (i.e. a carrier suitable for veterinary use), and optionally one or more further active substances.

The invention also relates to the use of a Nanobody of the invention and/or of a polypeptide of the invention in the preparation of a pharmaceutical composition, in particular in the preparation of a pharmaceutical composition for the prevention and/or treatment (including but not limiting to the alleviation of at least one symptom) of a disease or disorder mediated by TNF-alpha and/or associated with TNF-alpha (for example associated with an abnormal activity of TNF-alpha, abnormal levels of TNF-alpha, abnormal expression of TNF-alpha and/or abnormal sensitivity or response to TNF-alpha), or of one of the biological phenomena associated with TNF-alpha, such as one of the diseases or disorders mentioned above.

The invention also relates to a method for preventing and/or treating (including but not limiting to the alleviation of at least one symptom) of a disease or disorder mediated by TNF-alpha and/or associated with TNF-alpha (for example associated with an abnormal activity of TNF-alpha, abnormal levels of TNF-alpha, abnormal expression of TNF-alpha and/or abnormal sensitivity or response to TNF-alpha, or of one of the biological phenomena associated with TNF-alpha), such as one of the diseases or disorders mentioned above, which method comprises administering to a subject in need thereof a therapeutically active amount of a Nanobody of the invention, of polypeptide of the invention, and/or of a pharmaceutical composition as described above.

The present invention provides polypeptides comprising one or more nanobodies directed towards tumor necrosis factor alpha (TNF-alpha). The present invention further relates to their use in diagnosis and therapy. Such antibodies may have a framework sequence with high homology to the human framework sequences. Compositions comprising antibodies to tumor necrosis factor alpha (TNF-alpha) alone or in combination with other drugs are described.

Tumor necrosis factor alpha (TNF-alpha) is believed to play an important role in various disorders, for example in inflammatory disorders such as rheumatoid arthritis, Crohn's disease, ulcerative colitis and multiple sclerosis. Both TNF-alpha and the receptors (CD120a, CD120b) have been studied in great detail. TNF-alpha in its bioactive form is a trimer and the groove formed by neighboring subunits is important for the cytokine-receptor interaction. Several strategies to antagonize the action of the cytokine have been developed and are currently used to treat various disease states.

A TNF-alpha inhibitor which has sufficient specificity and selectivity to TNF-alpha may be an efficient prophylactic or therapeutic pharmaceutical compound for preventing or treating disorders where TNF-alpha has been implicated as causative agent. Methods of treating toxic shock (EP 486526), tumor regression, inhibition of cytotoxicity (U.S. Pat. Nos. 6,448,380, 6,451,983, 6,498,237), autoimmune disease such as RA and Crohn's disease (EP 663836, U.S. Pat. Nos. 5,672,347, 5,656,272), graft versus host reaction (U.S. Pat. No. 5,672,347), bacterial meningitis (EP 585705) by means of an antibody to TNF-alpha have been described.

Yet none of the presently available drugs are completely effective for the treatment of autoimmune disease, and most are limited by severe toxicity. In addition, it is extremely difficult and a lengthy process to develop a new chemical entitiy (NCE) with sufficient potency and selectivity to such target sequence. Antibody-based therapeutics on the other hand have significant potential as drugs because they have exquisite specificity to their target and a low inherent toxicity. In addition, the development time can be reduced considerably when compared to the development of new chemical entities (NCE's). However, conventional antibodies are difficult to raise against multimeric proteins where the receptor-binding domain of the ligand is embedded in a groove, as is the case with TNF-alpha. Heavy chain antibodies described in the invention which are derived from Camelidae, are known to have cavity-binding propensity (WO97/49805; Lauwereys et al, EMBO J. 17, 5312, 1998)). Therefore, such heavy chain antibodies are inherently suited to bind to receptor binding domains of such ligands as TNF. In addition, such antibodies are known to be stable over long periods of time, therefore increasing their shelf-life (Perez et al, Biochemistry, 40, 74, 2001). Furthermore, such heavy chain antibody fragments can be produced 'en-masse' in fermentors using cheap expression systems compared to mammalian cell culture fermentation, such as yeast or other microorganisms (EP 0 698 097).

The use of antibodies derived from sources such as mouse, sheep, goat, rabbit etc., and humanised derivatives thereof as a treatment for conditions which require a modulation of inflammation is problematic for several reasons. Traditional antibodies are not stable at room temperature, and have to be refrigerated for preparation and storage, requiring necessary refrigerated laboratory equipment, storage and transport, which contribute towards time and expense. Refrigeration is sometimes not feasible in developing countries. Furthermore, the manufacture or small-scale production of said antibodies is expensive because the mammalian cellular systems necessary for the expression of intact and active antibodies require high levels of support in terms of time and equipment, and yields are very low. Furthermore the large size of conventional antibodies, would restrict tissue penetration, for example, at the site of inflamed tissue. Furthermore, traditional antibodies have a binding activity which depends upon pH, and hence are unsuitable for use in environments outside the usual physiological pH range such as, for example, in treating gastric bleeding, gastric surgery. Furthermore, traditional antibodies are unstable at low or high pH and hence are not suitable for oral administration. However, it has been demonstrated that camelidae antibodies resist harsh conditions, such as extreme pH, denaturing reagents and high temperatures (Dumoulin et al, Protein Science 11, 500, 2002), so making them suitable for delivery by oral administration. Furthermore, traditional antibodies have a binding activity, which depends upon temperature, and hence are unsuitable for use in assays or kits performed at temperatures outside biologically active-temperature ranges (e.g. 37±20° C.).

Polypeptide therapeutics and in particular antibody-based therapeutics have significant potential as drugs because they have exquisite specificity to their target and a low inherent toxicity. However, it is known by the skilled addressee that an antibody which has been obtained for a therapeutically useful target requires additional modification in order to prepare it for human therapy, so as to avoid an unwanted immunological reaction in a human individual upon administration thereto. The modification process is commonly termed "humanisation". It is known by the skilled artisan that antibodies raised in species, other than in humans, require humanisation to render the antibody therapeutically useful in humans ((1) CDR grafting: Protein Design Labs: U.S. Pat. Nos. 6,180,370, 5,693,761; Genentech U.S. Pat. No. 6,054,297; Celltech: 460167, EP 626390, U.S. Pat. No. 5,859,205; (2) Veneering: Xoma: U.S. Pat. Nos. 5,869,619, 5,766,886, 5,821,123). There is a need for a method for producing antibodies which avoids the requirement for substantial humanisation, or which completely obviates the need for humanisation. There is a need for a new class of antibodies which have defined framework regions or amino acid residues and which can be administered to a human subject without the requirement for substantial humanisation, or the need for humanisation at all.

Another important drawback of conventional antibodies is that they are complex, large molecules and therefore relatively unstable, and they are sensitive to breakdown by proteases. This means that conventional antibody drugs cannot be administered orally, sublingually, topically, nasally, vaginally, rectally or by inhalation because they are not resistant to the low pH at these sites, the action of proteases at these sites and in the blood and/or because of their large size. They have to be administered by injection (intravenously, subcutaneously, etc.) to overcome some of these problems. Administration by injection requires specialist training in order to use a hypodermic syringe or needle correctly and safely. It further requires sterile equipment, a liquid formulation of the therapeutic polypeptide, vial packing of said polypeptide in a sterile and stable form and, of the subject, a suitable site for entry of the needle. Furthermore, subjects commonly experience physical and psychological stress prior to and upon receiving an injection. Therefore, there is need for a method for the delivery of therapeutic polypeptides which avoids the need for injection which is not only cost/time saving, but which would also be more convenient and more comfortable for the subject.

Nanobody-based therapeutics have significant potential as drugs because they have exquisite specificity to their target and a low inherent toxicity. However, improving further their intrinsic and functional affinity can lead to many benefits for a patient such as reduced dose of therapeutic, faster therapy, and reduced side effects.

One embodiment of the present invention is an anti-TNF-alpha nanobody, which nanobody is preferably as further defined above.

One embodiment of the present invention is an anti-TNF-alpha polypeptide comprising at least one anti-TNF-alpha nanobody, which polypeptide is preferably as further defined above.

Another embodiment of the present invention is an anti-TNF-alpha polypeptide as described above further comprising at least one nanobody directed against a serum protein.

Another embodiment of the present invention is an anti-TNF-alpha polypeptide as described above wherein said serum protein is any of serum albumin, serum immunoglobulins, thyroxine-binding protein, transferrin, or fibrinogen.

Another embodiment of the present invention is an anti-TNF-alpha polypeptide as described above further comprising at least one nanobody selected from the group consisting of anti-IFN-gamma nanobody, anti-TNF-alpha receptor nanobody and anti-IFN-gamma receptor nanobody.

Another embodiment of the present invention is an anti-TNF-alpha polypeptide as described above, wherein the number of nanobodies directed against TNF-alpha is at least two.

Another embodiment of the present invention is an anti-TNF-alpha polypeptide as described above, wherein at least one nanobody is a humanized Camelidae $V_{HH}$s.

Another embodiment of the present invention is a composition comprising an anti-TNF-alpha polypeptide as described above and at least one nanobody from the group consisting of anti-IFN-gamma nanobody, anti-TNF-alpha receptor nanobody and anti-IFN-gamma receptor nanobody, for simultaneous, separate or sequential administration to a subject.

Another embodiment of the present invention is an anti-TNF-alpha polypeptide as described above, or a composition as described above, wherein said nanobody is an homologous sequence, a functional portion, or a functional portion of an homologous sequence of the full length nanobody.

Another embodiment of the present invention is an anti-TNF-alpha polypeptide as described above, or a composition as described above, wherein the anti-TNF-alpha polypeptide is an homologous sequence, a functional portion, or a functional portion of an homologous sequence of the full length anti-TNF-alpha polypeptide.

Another embodiment of the present invention is an anti-TNF-alpha polypeptide as described above, or a composition as described above wherein at least one nanobody is a Camelidae $V_{HH}$.

Another embodiment of the present invention is a nucleic acid encoding an anti-TNF-alpha polypeptide as described above.

Another embodiment of the present invention is a method of identifying an agent that modulates the binding of an anti-TNF-alpha polypeptide as described above, to Tumor Necrosis Factor-alpha comprising the steps of:

(a) contacting an anti-TNF-alpha polypeptide as described above with a target that is Tumor Necrosis Factor alpha, in the presence and absence of a candidate modulator under conditions permitting binding between said polypeptide and target, and (b) measuring the binding between the polypeptide and target of step (a), wherein a decrease in binding in the presence of said candidate modulator, relative to the binding in the absence of said candidate modulator identified said candidate modulator as an agent that modulates the binding of an anti-TNF-alpha polypeptide as described above and Tumor Necrosis Factor-alpha.

Another embodiment of the present invention is a method of identifying an agent that modulates Tumor Necrosis Factor-alpha-mediated disorders through the binding of an anti-TNF-alpha polypeptide as described above to Tumor Necrosis Factor-alpha comprising:
(a) contacting an anti-TNF-alpha polypeptide as described above with a target that is Tumor Necrosis Factor alpha, in the presence and absence of a candidate modulator under conditions permitting binding between said polypeptide and target, and
(b) measuring the binding between the polypeptide and target of step (a), wherein a decrease in binding in the presence of said candidate modulator, relative to the binding in the absence of said candidate modulator identified, said candidate modulator as an agent that modulates Tumor Necrosis Factor alpha-mediated disorders.

Another embodiment of the present invention is a method of identifying an agent that modulates the binding of Tumor Necrosis Factor alpha to its receptor through the binding of an anti-TNF-alpha polypeptide as described above to Tumor Necrosis Factor-alpha comprising:
(a) contacting an anti-TNF-alpha polypeptide as described above with a target that is Tumor Necrosis Factor-alpha, in the presence and absence of a candidate modulator under conditions permitting binding between said polypeptide and target, and
(b) measuring the binding between the polypeptide and target of step (a), wherein a decrease in binding in the presence of said candidate modulator, relative to the binding in the absence of said candidate modulator identified said candidate modulator as an agent that modulates the binding of Tumor Necrosis Factor-alpha to its receptor.

Another embodiment of the present invention is a kit for screening for agents that modulate Tumor Necrosis Factor-alpha-mediated disorders comprising an anti-TNF-alpha polypeptide as described above and Tumor Necrosis Factor-alpha.

Another embodiment of the present invention is an unknown agent that modulates the binding of an anti-TNF-alpha polypeptide as described above to Tumor Necrosis Factor-alpha, identified according to the method as described above.

Another embodiment of the present invention is an unknown agent that modulates Tumor Necrosis Factor-alpha-mediated disorders, identified according to the methods as described above.

Another embodiment of the present invention is an unknown agent as described above wherein said disorders are one or more of inflammation, rheumatoid arthritis, Crohn's disease, ulcerative colitis, inflammatory bowel syndrome and multiple sclerosis.

Another embodiment of the present invention is an anti-TNF-alpha polypeptide as described above, or a nucleic acid as described above, or a composition as described above, or an agent as described above for treating and/or preventing and/or alleviating disorders relating to inflammatory processes.

Another embodiment of the present invention is a use of an anti-TNF-alpha polypeptide as described above or a nucleic acid as described above, or a composition as described above, or an agent as described above for the preparation of a medicament for treating and/or preventing and/or alleviating disorders relating to inflammatory reactions.

Another embodiment of the present invention is an anti-TNF-alpha polypeptide as described above or a composition as described above, for treating and/or preventing and/or alleviating disorders susceptible to modulation by a Nanobody or polypeptide of the invention which is able pass through the gastric environment without the substance being inactivated.

Another embodiment of the present invention is an use of an anti-TNF-alpha polypeptide as described above or a composition as described above, for the preparation of a medicament for treating, preventing and/or alleviating the symptoms of disorders susceptible to modulation by a Nanobody or polypeptide of the invention which is able pass through the gastric environment without the substance being inactivated.

Another embodiment of the present invention is an anti-TNF-alpha polypeptide as described above or a composition as described above, for treating and/or preventing and/or alleviating disorders susceptible to modulation by a Nanobody or polypeptide of the invention delivered to the vaginal and/or rectal tract.

Another embodiment of the present invention is a use of an anti-TNF-alpha polypeptide as described above or a composition as described above, for the preparation of a medicament for treating, preventing and/or alleviating the symptoms of disorders susceptible to modulation by a Nanobody or polypeptide of the invention delivered to the vaginal and/or rectal tract.

Another embodiment of the present invention is an anti-TNF-alpha polypeptide as described above or a composition as described above, for treating and/or preventing and/or alleviating disorders susceptible to modulation by a Nanobody or polypeptide of the invention delivered to the nose, upper respiratory tract and/or lung.

Another embodiment of the present invention is a use of an anti-TNF-alpha polypeptide as described above or a composition as described above, for the preparation of a medicament for treating, preventing and/or alleviating the symptoms of disorders susceptible to modulation by a Nanobody or polypeptide of the invention delivered to the nose, upper respiratory tract and/or lung.

Another embodiment of the present invention is an anti-TNF-alpha polypeptide as described above or a composition as described above, for treating and/or preventing and/or alleviating disorders susceptible to modulation by a Nanobody or polypeptide of the invention delivered to the intestinal mucosa, wherein said disorder increases the permeability of the intestinal mucosa.

Another embodiment of the present invention is a use of an anti-TNF-alpha polypeptide as described above or a composition as described above, for the preparation of a medicament for treating, preventing and/or alleviating the symptoms of disorders susceptible to modulation by a Nanobody or polypeptide of the invention delivered to the intestinal mucosa, wherein said disorder increases the permeability of the intestinal mucosa.

Another embodiment of the present invention is an anti-TNF-alpha polypeptide as described above or a composition as described above, for treating and/or preventing and/or alleviating disorders susceptible to modulation by a Nanobody or polypeptide of the invention which is able pass through the tissues beneath the tongue effectively.

Another embodiment of the present invention is a use of an anti-TNF-alpha polypeptide as described above or a composition as described above, for the preparation of a medicament for treating, preventing and/or alleviating the symptoms of disorders susceptible to modulation by a Nanobody or polypeptide of the invention which is able pass through the tissues beneath the tongue effectively.

Another embodiment of the present invention is an anti-TNF-alpha polypeptide as described above or a composition as described above, for treating and/or preventing and/or alleviating disorders susceptible to modulation by a Nanobody or polypeptide of the invention which is able pass through the skin effectively.

Another embodiment of the present invention is a use of an anti-TNF-alpha polypeptide as described above or a composition as described above, for the preparation of a medicament for treating, preventing and/or alleviating the symptoms of disorders susceptible to modulation by a Nanobody or polypeptide of the invention which is able pass through the skin effectively.

Another embodiment of the present invention is a method as described above, a kit as described above, a nucleic acid or agent as described above, use of a nucleic acid or agent as described above, a composition as described above, use of a composition as described above, an anti-TNF-alpha polypeptide as described above, use of an anti-TNF-alpha polypeptide as described above wherein said disorders are any of inflammation, rheumatoid arthritis, COPD, asthma, Crohn's disease, ulcerative colitis, inflammatory bowel syndrome, multiple sclerosis, Addison's disease, Autoimmune hepatitis, Autoimmune parotitis, Diabetes Type I, Epididymitis, Glomerulonephritis, Graves' disease, Guillain-Barre syndrome, Hashimoto's disease, Hemolytic anemia, Systemic lupus erythematosus, Male infertility, Multiple sclerosis, Myasthenia Gravis, Pemphigus, Psoriasis, Rheumatic fever, Rheumatoid arthritis, Sarcoidosis, Scleroderma, Sjogren's syndrome, Spondyloarthropathies, Thyroiditis, and Vasculitis.

Another embodiment of the present invention is a composition comprising a nucleic acid or agent as described above, an anti-TNF-alpha polypeptide as described above, or a composition as described above, and a suitable pharmaceutical vehicle.

Another embodiment of the present invention is a method of diagnosing a disorder characterised by the dysfunction of Tumor Necrosis Factor-alpha comprising:
(a) contacting a sample with an anti-TNF-alpha polypeptide as described above,
(b) detecting binding of said polypeptide to said sample, and
(c) comparing the binding detected in step (b) with a standard, wherein a difference in binding relative to said sample is diagnostic of a disorder characterised by dysfunction of Tumor Necrosis Factor-alpha.

Another embodiment of the present invention is a kit for screening for a disorder as cited above, using a method as described above.

Another embodiment of the present invention is a kit for screening for a disorder as cited above comprising an isolated anti-TNF-alpha polypeptide as described above.

Another embodiment of the present invention is a use of an anti-TNF-alpha polypeptide as described above for the purification of said Tumor Necrosis Factor-alpha.

Another embodiment of the present invention is a use of an anti-TNF-alpha polypeptide as described above for inhibiting the interaction between Tumor Necrosis Factor-alpha and one or more Tumor Necrosis Factor-alpha receptors.

Another embodiment of the present invention is a method for producing an anti-TNF-alpha polypeptide as described above comprising the steps of:
(a) obtaining double stranded DNA encoding a Camelidae $V_{HH}$ directed to Tumor Necrosis Factor alpha,
(b) cloning and expressing the DNA selected in step (b).

Another embodiment of the present invention is a method of producing an anti-TNF-alpha polypeptide as described above comprising:
(a) culturing host cells comprising nucleic acid capable of encoding an anti-TNF-alpha polypeptide as described above, under conditions allowing the expression of the polypeptide, and,
(b) recovering the produced polypeptide from the culture.

Another embodiment of the present invention is a method as described above, wherein said host cells are bacterial or yeast.

Another embodiment of the present invention is a kit for screening for any of inflammation, rheumatoid arthritis, Crohn's disease, ulcerative colitis, inflammatory bowel syndrome or multiple sclerosis comprising an anti-TNF-alpha polypeptide as described above.

$V_{HH}$s, according to the present invention, and as known to the skilled addressee are heavy chain variable domains derived from immunoglobulins naturally devoid of light chains such as those derived from Camelidae as described in WO 94/04678 (and referred to hereinafter as $V_{HH}$ domains or nanobodies). $V_{HH}$ molecules are about 10× smaller than IgG molecules. They are single polypeptides and very stable, resisting extreme pH and temperature conditions. Moreover, they are resistant to the action of proteases which is not the case for conventional antibodies. Furthermore, in vitro expression of $V_{HH}$s produces high yield, properly folded functional $V_{HH}$s. In addition, antibodies generated in Camelids will recognize epitopes other than those recognised by antibodies generated in vitro through the use of antibody libraries or via immunisation of mammals other than Camelids (WO 9749805). As such, anti-TNF-alpha $V_{HH}$'s may interact more efficiently with TNF-alpha than conventional antibodies, thereby blocking its interaction with the TNF-alpha receptor more efficiently.

TNF-alpha is also a fragment of TNF-alpha, capable of eliciting an immune response. TNF-alpha is also a fragment of TNF-alpha, capable of binding to a nanobody raised against the full length TNF-alpha.

A nanobody directed against TNF-alpha means nanobody that it is capable of binding to TNF-alpha with an affinity of better than $10^{-6}$ M.

One embodiment of the present invention is an anti-TNF polypeptide, wherein the nanobodies comprise Camelidae $V_{HH}$ directed against TNF-alpha.

The one or more nanobodies of the anti-TNF polypeptide which are directed against a TNF-alpha may be of the same sequence. Alternatively they may not all have the same sequence. It is within the scope of the invention that an anti-TNF polypeptide comprises anti-TNF-alpha nanobodies which do not all share the same sequence, but which are directed against the same target, one or more antigens thereof.

The present invention further relates to an anti-TNF-alpha polypeptide, wherein said nanobody is a $V_{HH}$ directed against TNF-alpha, wherein the $V_{HH}$ belongs to a class having human-like sequences. The class is characterised in that the $V_{HH}$s carry an amino acid from the group consisting of glycine, alanine, valine, leucine, isoleucine, proline, phenylalanine, tyrosine, tryptophan, methionine, serine, threonine, asparagine, or glutamine at position 45, such as, for example, L45 and a tryptophan at position 103, according to the Kabat numbering. Another human-like class of Camelidae nanobodies have been described in WO03035694 and contain the hydrophobic FR2 residues typically found in conventional antibodies of human origin or from other species, but compensating this loss in hydrophilicity by the charged arginine residue on position 103 that substitutes the conserved tryptophan residue present in VH from double-chain antibodies. As such, peptides belonging to these two classes show a high amino acid sequence homology to human VH framework regions and said peptides might be administered to a human directly without expectation of an unwanted immune response therefrom, and without the burden of further humanisation. The invention also relates to nucleic acids capable of encoding said polypeptides.

Any of the $V_{HH}$s as used by the invention may be of the traditional class or of the classes of human-like Camelidae antibodies. Said antibodies may be directed against whole TNF-alpha or a fragment thereof, or a fragment of a homologous sequence thereof. These polypeptides include the full length Camelidae antibodies, namely Fc and $V_{HH}$ domains, chimeric versions of heavy chain Camelidae antibodies with a human Fc domain or $V_{HH}$'s by themselves or derived fragments.

Anti-serum albumin $V_{HH}$'s may interact in a more efficient way with serum albumin than conventional antibodies which is known to be a carrier protein. As a carrier protein some of the epitopes of serum albumin may be inaccessible by bound proteins, peptides and small chemical compounds. Since $V_{HH}$'s are known to bind into 'unusual' or non-conventional epitopes such as cavities (WO 97/49805), the affinity of such $V_{HH}$'s to circulating albumin may be increased.

The present invention also relates to the finding that an anti-TNF polypeptide as described herein further comprising one or more nanobodies directed against one or more serum proteins of a subject, surprisingly has significantly prolonged half-life in the circulation of said subject compared with the half-life of the anti-TNF-alpha nanobody when not part of said construct. Furthermore, the said polypeptides were found to exhibit the same favourable properties of nanobodies such as high stability remaining intact in mice, extreme pH resistance, high temperature stability and high target affinity.

The serum protein may be any suitable protein found in the serum of subject. In one aspect of the invention, the serum protein is serum albumin, serum immunoglobulins, thyroxine-binding protein, transferrin, or fibrinogen. Depending on the intended use such as the required half-life for effective treatment and/or compartimentalisation of the target antigen, the $V_{HH}$-partner can be directed to one of the above serum proteins.

According to a specific, but non-limiting aspect of the invention, the Nanobody against human serum albumin consists of 4 framework regions (FR1 to FR4 respectively) and 3 complementarity determining regions (CDR1 to CDR3 respectively), in which:
(iv) CDR1 is an amino acid sequence chosen from the group consisting of:

| | |
|---|---|
| SFGMS | [SEQ ID NO: 36] |
| LNLMG | [SEQ ID NO: 37] |
| INLLG | [SEQ ID NO: 38] |
| NYWMY; | [SEQ ID NO: 39] | and/or from the group consisting of amino acid sequences that have 2 or only 1 "amino acid difference(s)" (as defined herein) with one of the above amino acid sequences, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequences;

and in which:
(v) CDR2 is an amino acid sequence chosen from the group consisting of:

| | |
|---|---|
| SISGSGSDTLYADSVKG | [SEQ ID NO: 40] |
| TITVGDSTNYADSVKG | [SEQ ID NO: 41] |
| TITVGDSTSYADSVKG | [SEQ ID NO: 42] |
| SINGRGDDTRYADSVKG | [SEQ ID NO: 43] |
| AISADSSTKNYADSVKG | [SEQ ID NO: 44] |
| AISADSSDKRYADSVKG | [SEQ ID NO: 45] |
| RISTGGGYSYYADSVKG | [SEQ ID NO: 46] | or from the group consisting of amino acid sequences that have at least 80%, preferably at least 90%, more preferably at least 95%, even more preferably at least 99% sequence identity (as defined herein) with one of the above amino acid sequences; in which
(1) any amino acid substitution is preferably a conservative amino acid substitution (as defined herein); and/or
(2) said amino acid sequence preferably only contains amino acid substitutions, and no amino acid deletions or insertions, compared to the above amino acid sequences;
and/or from the group consisting of amino acid sequences that have 3, 2 or only 1 "amino acid difference(s)" (as defined herein) with one of the above amino acid sequences, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequences;
and in which:
(vi) CDR3 is an amino acid sequence chosen from the group consisting of:

| | |
|---|---|
| DREAQVDTLDFDY | [SEQ ID NO: 47] | or from the group consisting of amino acid sequences that have at least 80%, preferably at least 90%, more preferably at least 95%, even more preferably at least 99% sequence identity (as defined herein) with one of the above amino acid sequences; in which
(1) any amino acid substitution is preferably a conservative amino acid substitution (as defined herein); and/or (2) said amino acid sequence preferably only contains amino acid substitutions, and no amino acid deletions or insertions, compared to the above amino acid sequences;

and/or from the group consisting of amino acid sequences that have 3, 2 or only 1 "amino acid difference(s)" (as defined herein) with one of the above amino acid sequences, in which:

(1) any amino acid substitution is preferably a conservative amino acid substitution (as defined herein); and/or (2) said amino acid sequence preferably only contains amino acid substitutions, and no amino acid deletions or insertions, compared to the above amino acid sequences;

or from the group consisting of:

```
                                    [SEQ ID NO: 48]
          GGSLSR

[SEQ ID NO: 49]
          RRTWHSEL

[SEQ ID NO: 50]
          GRSVSRS

[SEQ ID NO: 51]
          GRGSP
``` and/or from the group consisting of amino acid sequences that have 3, 2 or only 1 "amino acid difference(s)" (as defined herein) with one of the above amino acid sequences, in which:

(1) any amino acid substitution is preferably a conservative amino acid substitution (as defined herein); and/or (2) said amino acid sequence preferably only contains amino acid substitutions, and no amino acid deletions or insertions, compared to the above amino acid sequences.

In another aspect, the invention relates to a Nanobody against human serum albumin, which consist of 4 framework regions (FR1 to FR4 respectively) and 3 complementarity determining regions (CDR1 to CDR3 respectively), which is chosen from the group consisting of domain antibodies and/or single domain antibodies with the one of the following combinations of CDR1, CDR2 and CDR3, respectively:

```
CDR1: SFGMS;                   (SEQ ID NO: 36)

CDR2: SISGSGSDTLYADSVKG;       (SEQ ID NO: 40)

CDR3: GGSLSR;                  (SEQ ID NO: 48)

CDR1: LNLMG;                   (SEQ ID NO: 37)

CDR2: TITVGDSTNYADSVKG;        (SEQ ID NO: 41)

CDR3: RRTWHSEL;                (SEQ ID NO: 49)

CDR1: INLLG;                   (SEQ ID NO: 38)

CDR2: TITVGDSTSYADSVKG;        (SEQ ID NO: 42)

CDR3: RRTWHSEL;                (SEQ ID NO: 49)

CDR1: SFGMS;                   (SEQ ID NO: 36)

CDR2: SINGRGDDTRYADSVKG;       (SEQ ID NO: 43)

CDR3: GRSVSRS;                 (SEQ ID NO: 50)
```

-continued

```
CDR1: SFGMS;                   (SEQ ID NO: 36)

CDR2: AISADSSDKRYADSVKG;       (SEQ ID NO: 45)

CDR3: GRGSP;                   (SEQ ID NO: 51)

CDR1: SFGMS;                   (SEQ ID NO: 36)

CDR2: AISADSSDKRYADSVKG;       (SEQ ID NO: 45)

CDR3: GRGSP;                   (SEQ ID NO: 51)

CDR1: NYWMY;                   (SEQ ID NO: 39)

CDR2: RISTGGGYSYYADSVKG;       (SEQ ID NO: 46)

CDR3: DREAQVDTLDFDY.           (SEQ ID NO: 47)
```

In the Nanobodies of the invention that comprise the combinations of CDR's mentioned above, each CDR can be replaced by a CDR chosen from the group consisting of amino acid sequences that have at least 80%, preferably at least 90%, more preferably at least 95%, even more preferably at least 99% sequence identity (as defined herein) with the mentioned CDR's; in which (1) any amino acid substitution is preferably a conservative amino acid substitution (as defined herein); and/or (2) said amino acid sequence preferably only contains amino acid substitutions, and no amino acid deletions or insertions, compared to the above amino acid sequences;

and/or chosen from the group consisting of amino acid sequences that have 3, 2 or only 1 (as indicated in the preceding paragraph) "amino acid difference(s)" (as defined herein) with the mentioned CDR(s) one of the above amino acid sequences, in which:

(1) any amino acid substitution is preferably a conservative amino acid substitution (as defined herein); and/or (2) said amino acid sequence preferably only contains amino acid substitutions, and no amino acid deletions or insertions, compared to the above amino acid sequences.

However, of the Nanobodies of the invention that comprise the combinations of CDR's mentioned above, Nanobodies comprising one or more of the CDR's listed above are particularly preferred; Nanobodies comprising two or more of the CDR's listed above are more particularly preferred; and Nanobodies comprising three of the CDR's listed above are most particularly preferred.

In these Nanobodies against human serum albumin, the Framework regions FR1 to FR4 are preferably as defined hereinabove for the Nanobodies of the invention.

Particularly preferred Nanobodies against human serum albumin are chosen from the group consisting of SEQ ID NO's: 61 to 67, SEQ ID NO's 87 to 89 and SEQ ID NO's 100-104. The preferred combinations of CDR's and framework regions present in these Nanobodies are also listed in Table II

TABLE II

Preferred combination of Framework sequences and CDR's in Nanobodies against human serum albumin.

| Clone | ID FR1 | | ID CDR1 | | ID FR2 | | ID CDR2 | | ID FR3 | | ID CDR3 | | ID FR4 | |
|---|---|---|---|---|---|---|---|---|---|---|---|---|---|---|
| PMP6A8 (ALB2) | 368 | AVQLVES GGGLVQG GGSLRLAC AASERIFD | 375 | LNLMG | 382 | WYRQGPGN ERELVA | 389 | TCITVGDSTNYA DSVKG | 396 | RFTISMDYTKQTVYLHMN SLRPEDTGLYYCKI | 403 | RRTWHSEL | 410 | WGQGTQV TVSS |
| PMP6B4 | 369 | EVQLVES GGGLVQEG GSLRLACA ASERIWD | 376 | INLLG | 383 | WYRQGPGN ERELVA | 390 | TITVGDSTSYAD SVKG | 397 | RFTISRDYDKNTLYLQMN SLRPEDTGLYYCKI | 404 | RRTWHSEL | 411 | WGQGTQV TVSS |
| PMP6A6 (ALB1) | 370 | AVQLVES GGGLVQP GNSLRLSC AASGFTFR | 377 | SFGMS | 384 | WVRQAPGK EPEWVS | 391 | SISGSGSDTLYA DSVKG | 398 | RFTISRDNAKTTLYLQMN SLKPEDTAVYYCTI | 405 | GGSLSR | 412 | SSQGTQV TVSS |
| PMP6C1 | 371 | AVQLVDS GGGLVQPG GSLRLSCA ASGFSFG | 378 | SFGMS | 385 | WVRQYPGK EPEWVS | 392 | SINGRGDDTRYA DSVKG | 399 | RFSISRDNAKNTLYLQMN SLKPEDTAEYYCTI | 406 | GRSVSRS | 413 | RTQGTQV TVSS |
| PMP6G8 | 372 | AVQLVESG GGLVQPGG SLRLTCTA SGFTFR | 379 | SFGMS | 386 | WVRQAPGK DQEWVS | 393 | AISADSSTKNYA DSVKG | 400 | RFTISRDNAKKMLYLEMN SLKPEDTAVYYCVI | 407 | GRGSP | 414 | SSPGTQV TVSS |
| PMP6A5 | 373 | QVQLAES GGGLVQPG GSLRLTCT ASGFTFG | 380 | SFGMS | 387 | WVRQAPGE GLEWVS | 394 | AISADSSDKRYA DSVKG | 401 | RFTISRDNAKKMLYLEMN SLKSEDTAVYYCVI | 408 | GRGSP | 415 | ASQGTQV TVSS |
| PMP6G7 | 374 | QVQLVESG GGLVQPGG SLRLSCA ASGFTFS | 381 | NYWMY | 388 | WVRVAPGK GLERIS | 395 | RDISTGGGYSYY ADSVKG | 402 | RFTISRDNAKNTLYLQMN SLKPEDTALYYCAK | 409 | DREAQVDTLD FDY | 416 | RGQGTQV TVSS |

Another aspect of the invention is an anti-TNF-alpha polypeptide as disclosed herein further comprising at least one polypeptide selected from the group consisting of an anti-IFN-gamma polypeptide, an anti-TNF-alpha receptor polypeptide and anti-IFN-gamma receptor polypeptide.

According to one aspect of the invention, a nanobody is directed against TNF-alpha receptor. Said nanobody may be a Camelidae $V_{HH}$.

According to one aspect of the invention, a nanobody is directed against IFN-gamma receptor. Said nanobody may be a Camelidae $V_{HH}$.

Another aspect of the invention is a method of treating an autoimmune disease or condition as cited herein, comprising administering to a patient an effective amount of an anti-TNF-alpha polypeptide further comprising a least one polypeptide selected from the group consisting of anti-IFN-gamma polypeptide, anti-TNF-alpha receptor polypeptide and anti-IFN-gamma receptor polypeptide, such polypeptides joined to each other as described below.

Such multi-specific constructs may have improved potency as inflammatory therapeutic compound over monospecific constructs.

One aspect of the invention is a composition comprising an anti-TNF-alpha polypeptide as disclosed herein and at least one polypeptide selected from the group consisting of anti-IFN-gamma polypeptide, anti-TNF-alpha receptor polypeptide and anti-IFN-gamma receptor polypeptide, for simultaneous, separate or sequential administration to a subject.

One aspect of the invention is a method for treating autoimmune disease comprising administering to an individual an effective amount of an anti-TNF-alpha polypeptide and a least one polypeptide selected from the group consisting of anti-IFN-gamma polypeptide, anti-TNF-alpha receptor polypeptide and anti-IFN-gamma receptor polypeptide, simultaneously, separately or sequentially.

Another aspect of the invention is a kit containing an anti-TNF-alpha polypeptide and a least one polypeptide selected from the group consisting of anti-IFN-gamma polypeptide, anti-TNF-alpha receptor polypeptide and anti-IFN-gamma receptor polypeptide for simultaneous, separate or sequential administration to a subject. It is an aspect of the invention that the kit may be used according to the invention. It is an aspect of the invention that the kit may be used to treat the diseases as cited herein.

By simultaneous administration means the polypeptides are administered to a subject at the same time. For example, as a mixture of the polypeptides or a composition comprising said polypeptides. Examples include, but are not limited to a solution administered intravenously, a tablet, liquid, topical cream, etc., wherein each preparation comprises the polypeptides of interest.

By separate administration means the polypeptides are administered to a subject at the same time or substantially the same time. The polypeptides are present in the kit as separate, unmixed preparations. For example, the different polypeptides may be present in the kit as individual tablets. The tablets may be administered to the subject by swallowing both tablets at the same time, or one tablet directly following the other.

By sequential administration means the polypeptides are administered to a subject sequentially. The polypeptides are present in the kit as separate, unmixed preparations. There is a time interval between doses. For example, one polypeptide might be administered up to 336, 312, 288, 264, 240, 216, 192, 168, 144, 120, 96, 72, 48, 24, 20, 16, 12, 8, 4, 2, 1, or 0.5 hours after the other component.

In sequential administration, one polypeptide may be administered once, or any number of times and in various doses before and/or after administration of another polypeptide. Sequential administration may be combined with simultaneous or sequential administration.

The medical uses of the anti-TNF-alpha polypeptide described below, also apply to the composition comprising an anti-TNF-alpha polypeptide as disclosed herein and at least one polypeptide selected from the group consisting of anti-IFN-gamma polypeptide, anti-TNF-alpha receptor polypeptide and anti-IFN-gamma receptor polypeptide, for simultaneous, separate or sequential administration to a subject as disclosed here above.

According to one aspect of the invention, an anti-IFN-gamma polypeptide anti-TNF-alpha a nanobody directed against IFN-gamma. Said nanobody may be a Camelidae $V_{HH}$.

According to one aspect of the invention, anti-TNF-alpha a nanobody directed against TNF-alpha receptor. Said nanobody may be a Camelidae $V_{HH}$.

According to one aspect of the invention, an anti-IFN-gamma receptor polypeptide anti-TNF-alpha a nanobody directed against IFN-gamma receptor. Said nanobody may be a Camelidae $V_{HH}$.

Another embodiment of the present invention is an anti-TNF-alpha polypeptide as disclosed herein, wherein the number of nanobodies directed against TNF-alpha is two or more. Such multivalent anti-TNF-alpha polypeptides have the advantage of unusually high functional affinity for the target, displaying much higher than expected inhibitory properties compared to their monovalent counterparts.

The multivalent anti-TNF-alpha polypeptides have functional affinities that are several orders of magnitude higher than the monovalent parent anti-TNF-alpha polypeptides. The inventors have found that the functional affinities of these multivalent polypeptides are much higher than those reported in the prior art for bivalent and multivalent antibodies. Surprisingly, anti-TNF-alpha polypeptides of the present invention linked to each other directly or via a short linker sequence show the high functional affinities expected theoretically with multivalent conventional four-chain antibodies.

The inventors have found that such large increased functional activities can be detected preferably with antigens composed of multidomain and multimeric proteins, either in straight binding assays or in functional assays, e.g. cytotoxicity assays.

The nanobodies may be joined to form any of the polypeptides disclosed herein comprising more than one nanobody using methods known in the art or any future method. For example, they may be fused by chemical cross-linking by reacting amino acid residues with an organic derivatising agent such as described by Blattler et al, Biochemistry 24, 1517-1524; EP294703. Alternatively, the nanobody may be fused genetically at the DNA level i.e. a polynucleotide construct formed which encodes the complete polypeptide construct comprising one or more anti-target nanobodies and one or more anti-serum protein nanobodies. A method for producing bivalent or multivalent $V_{HH}$ polypeptide constructs is disclosed in PCT patent application WO 96/34103. One way of joining multiple nanobodies is via the genetic route by linking nanobody coding sequences either directly or via a peptide linker. For example, the C-terminal end of the first nanobody may be linked to the N-terminal end of the next nanobody. This linking mode can be extended in order to link additional nanobodies for the construction and production of tri-, tetra-, etc. functional constructs.

According to one aspect of the present invention, the nanobodies are linked to each other directly, without use of a linker. Contrary to joining bulky conventional antibodies where a linker sequence is needed to retain binding activity in the two subunits, polypeptides of the invention can be linked directly thereby avoiding potential problems of the linker sequence, such as antigenicity when administered to a human subject, instability of the linker sequence leading to dissociation of the subunits.

According to another aspect of the present invention, the nanobodies are linked to each other via a peptide linker sequence. Such linker sequence may be a naturally occurring sequence or a non-naturally occurring sequence. The linker sequence is expected to be non-immunogenic in the subject to which the anti-TNF-alpha polypeptide is administered. The linker sequence may provide sufficient flexibility to the multivalent anti-TNF-alpha polypeptide, at the same time being resistant to proteolytic degradation. A non-limiting example of a linker sequences is one that can be derived from the hinge region of $V_{HH}$s described in WO 96/34103.

According to another aspect of the invention, multivalent nanobodies comprising more than two nanobodies can be linked to each other either directly or via a linker sequence. Such constructs are difficult to produce with conventional antibodies and due to steric hindrance of the bulky subunits, functionality will be lost or greatly diminished rather than increased considerably as seen with $V_{HH}$'s of the invention compared to the monovalent construct.

The polypeptide constructs disclosed herein may be made by the skilled artisan according to methods known in the art or any future method. For example, $V_{HH}$s may be obtained using methods known in the art such as by immunising a camel and obtaining hybridomas therefrom, or by cloning a library of nanobodies using molecular biology techniques known in the art and subsequent selection by using phage display.

According to an aspect of the invention an anti-TNF-alpha polypeptide may be a homologous sequence of a full-length anti-TNF-alpha polypeptide. According to another aspect of the invention, an anti-TNF-alpha polypeptide may be a functional portion of a full-length anti-TNF-alpha polypeptide. According to another aspect of the invention, an anti-TNF-alpha polypeptide may be a homologous sequence of a full-length anti-TNF-alpha polypeptide. According to another aspect of the invention, an anti-TNF-alpha polypeptide may be a functional portion of a homologous sequence of a full-length anti-TNF-alpha polypeptide. According to an aspect of the invention an anti-TNF-alpha polypeptide may comprise a sequence of an anti-TNF-alpha polypeptide.

According to an aspect of the invention a nanobody used to form an anti-TNF-alpha polypeptide may be a complete nanobody (e.g. a $V_{HH}$) or a homologous sequence thereof. According to another aspect of the invention, a nanobody used to form the polypeptide construct may be a functional portion of a complete nanobody. According to another aspect of the invention, a nanobody used to form the polypeptide construct may be a homologous sequence of a complete nanobody. According to another aspect of the invention, a nanobody used to form the polypeptide construct may be a functional portion of a homologous sequence of a complete nanobody.

As used herein, an homologous sequence of the present invention may comprise additions, deletions or substitutions of one or more amino acids, which do not substantially alter the functional characteristics of the polypeptides of the invention. The number of amino acid deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids.

A homologous sequence according to the present invention may a polypeptide modified by the addition, deletion or substitution of amino acids, said modification not substantially altering the functional characteristics compared with the unmodified polypeptide.

A homologous sequence according to the present invention may be a polypeptide modified by the addition, deletion or substitution of amino acids, said modification not substantially altering the functional characteristics compared with the unmodified polypeptide.

A homologous sequence according to the present invention may be a sequence which exists in other Camelidae species such as, for example, camel, dromedary, llama, alpaca, guanaco etc.

Where homologous sequence indicates sequence identity, it means a sequence which presents a high sequence identity (more than 70%, 75%, 80%, 85%, 90%, 95% or 98% sequence identity) with the parent sequence and is preferably characterised by similar properties of the parent sequence, namely affinity, said identity calculated using known methods.

Alternatively, an homologous sequence may also be any amino acid sequence resulting from allowed substitutions at any number of positions of the parent sequence according to the formula below:
Ser substituted by Ser, Thr, Gly, and Asn;
Arg substituted by one of Arg, His, Gln, Lys, and Glu;
Leu substituted by one of Leu, Ile, Phe, Tyr, Met, and Val;
Pro substituted by one of Pro, Gly, Ala, and Thr;
Thr substituted by one of Thr, Pro, Ser, Ala, Gly, His, and Gln;
Ala substituted by one of Ala, Gly, Thr, and Pro;
Val substituted by one of Val, Met, Tyr, Phe, Ile, and Leu;
Gly substituted by one of Gly, Ala, Thr, Pro, and Ser;
Ile substituted by one of Ile, Met, Tyr, Phe, Val, and Leu;
Phe substituted by one of Phe, Trp, Met, Tyr, Ile, Val, and Leu;
Tyr substituted by one of Tyr, Trp, Met, Phe, Ile, Val, and Leu;
His substituted by one of His, Glu, Lys, Gln, Thr, and Arg;
Gln substituted by one of Gln, Glu, Lys, Asn, His, Thr, and Arg;
Asn substituted by one of Asn, Glu, Asp, Gln, and Ser;
Lys substituted by one of Lys, Glu, Gln, His, and Arg;
Asp substituted by one of Asp, Glu, and Asn;
Glu substituted by one of Glu, Asp, Lys, Asn, Gln, His, and Arg;
Met substituted by one of Met, Phe, Ile, Val, Leu, and Tyr.

A homologous nucleotide sequence according to the present invention may refer to nucleotide sequences of more than 50, 100, 200, 300, 400, 500, 600, 800 or 1000 nucleotides able to hybridize to the reverse-complement of the nucleotide sequence capable of encoding the patent sequence, under stringent hybridisation conditions (such as the ones described by Sambrook et al., Molecular Cloning, Laboratory Manuel, Cold Spring, Harbor Laboratory press, New York).

As used herein, a functional portion refers to a sequence of a nanobody that is of sufficient size such that the interaction of interest is maintained with affinity of $1 \times 10^{-6}$ M or better.

Alternatively, a functional portion comprises a partial deletion of the complete amino acid sequence and still maintains the binding site(s) and protein domain(s) necessary for the binding of and interaction with the target.

As used herein, a functional portion refers to less than 100% of the complete sequence (e.g., 99%, 90%, 80%, 70%, 60% 50%, 40%, 30%, 20%, 10%, 5%, 1% etc.), but comprises 5 or more amino acids or 15 or more nucleotides.

Targets as mentioned herein such as TNF-alpha, TNF-alpha receptor, serum proteins (e.g. serum albumin, serum immunoglobulins, thyroxine-binding protein, transferrin, fibrinogen) and IFN-gamma, IFN-gamma receptor may be fragments of said targets. Thus a target is also a fragment of said target, capable of eliciting an immune response. A target is also a fragment of said target, capable of binding to a nanobody raised against the full length target.

A fragment as used herein refers to less than 100% of the sequence (e.g., 99%, 90%, 80%, 70%, 60%, 50%, 40%, 30%, 20%, 10% etc.), but comprising 5, 6, 7, 8, 9, 10, 12, 13, 14, 15, 16, 17, 18, 19, 20, 21, 22, 23, 24, 25 or more amino acids. A fragment is of sufficient length such that the interaction of interest is maintained with affinity of $1 \times 10^{-6}$ M or better.

A fragment as used herein also refers to optional insertions, deletions and substitutions of one or more amino acids which do not substantially alter the ability of the target to bind to a nanobody raised against the wild-type target. The number of amino acid insertions deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids.

A homologous sequence of the present invention may include an anti-TNF-alpha polypeptide which has been humanised. The humanisation of antibodies of the new class of $V_{HH}$s would further reduce the possibility of unwanted immunological reaction in a human individual upon administration.

One embodiment of the present invention relates to a method for preparing modified polypeptides based upon llama antibodies by determining the amino acid residues of the antibody variable domain ($V_{HH}$) which may be modified without diminishing the native affinity of the domain for antigen and while reducing its immunogenicity with respect to a heterologous species; the use of $V_{HH}$s having modifications at the identified residues which are useful for administration to heterologous species; and to the $V_{HH}$ so modified.

More specifically, the invention relates to the preparation of modified $V_{HH}$s, which are modified for administration to humans, the resulting $V_{HH}$ themselves, and the use of such "humanized" $V_{HH}$s in the treatment of diseases in humans. By humanised is meant mutated so that immunogenicity upon administration in human patients is minor or nonexistent. Humanising a polypeptide, according to the present invention, comprises a step of replacing one or more of the Camelidae amino acids by their human counterpart as found in the human consensus sequence, without that polypeptide losing its typical character, i.e. the humanisation does not significantly affect the antigen binding capacity of the resulting polypeptide. Such methods are known by the skilled addressee.

Humanization of Camelidae nanobodies requires the introduction and mutagenesis of a limited amount of amino acids in a single polypeptide chain. This is in contrast to humanization of scFv, Fab, (Fab)2 and IgG, which requires the introduction of amino acid changes in two chains, the light and the heavy chain and the preservation of the assembly of both chains.

As described in WO 04/041862, an anti-TNF nanobody can be humanized. Humanization may for example involve mutagenesis of residues in FR1 at position 1 and 5 which were introduced by the primer used for repertoire cloning and do not occur naturally in the llama sequence. Mutagenesis of those residues did not result in loss of binding and/or inhibition activity. Humanization may also involve mutagenesis of residues in FR3 at position 74, 76, 83, 84, 93. Mutagenesis of those residues did not result in a dramatic loss of binding and/or inhibition activity. Combining the mutations of FR1 and FR3 therefore did not affect the binding and/or inhibition activity. Humanization may also involve mutagenesis of residues in FR4 at position 108. Mutagenesis of Q108L resulted in lower production level in *Escherichia coli*. Position 108 is solvent exposed in camelid $V_{HH}$, while in human antibodies this position is buried at the VH-VL interface (Spinelli, 1996; Nieba, 1997). In isolated VHs position 108 is solvent exposed. The introduction of a non-polar hydrophobic Leu instead of polar uncharged Gln can have a drastic effect on the intrinsic folding/stability of the molecule. Also, replacement of the hydrophilic residues by human hydrophobic residues at positions 44 and 45 (E44G and R45L), did not have an effect on binding and/or inhibition. However, loss of binding and/or inhibition activity was observed when F37V and F47W were introduced. Modeling data confirmed the critical residue 37 to preserve the integrity of the CDR3 loop conformation and hence on activity (all numbering according to the Kabat).

According to one embodiment of the present invention, humanization involves replacing of any of the following residues either alone or in combination:

FR1 position 1, 5, 28 and 30,
the hallmark amino acid at position 44 and 45 in FR2,
FR3 residues 74, 75, 76, 83, 84, 93 and 94,
and positions 103, 104, 108 and 111 in FR4;
numbering according to the Kabat numbering.

One embodiment of the present invention is an anti-TNF-alpha polypeptide, or a nucleic acid capable of encoding said polypeptide for use in treating, preventing and/or alleviating the symptoms of disorders relating to inflammatory processes. TNF-alpha is involved in inflammatory processes, and the blocking of TNF-alpha action can have an anti-inflammatory effect, which is highly desirable in certain disease states such as, for example, Crohn's disease. The Examples demonstrate $V_{HH}$s according to the invention which bind TNF-alpha and moreover, block its binding to the TNF-alpha receptor.

The anti-TNF-alpha polypeptides of the present invention are applicable to autoimmune diseases, such as Addison's disease (adrenal), Autoimmune diseases of the ear (ear), Autoimmune diseases of the eye (eye), Autoimmune hepatitis (liver), Autoimmune parotitis (parotid glands), Crohn's disease (intestine), Diabetes Type I (pancreas), Epididymitis (epididymis), Glomerulonephritis (kidneys), Graves' disease (thyroid), Guillain-Barre syndrome (nerve cells), Hashimoto's disease (thyroid), Hemolytic anemia (red blood cells), Systemic lupus erythematosus (multiple tissues), Male infertility (sperm), Multiple sclerosis (nerve cells), Myasthenia Gravis (neuromuscular junction), Pemphigus (primarily skin), Psoriasis (skin), Rheumatic fever (heart and joints), Rheumatoid arthritis (joint lining), Sarcoidosis (multiple tissues and organs), Scleroderma (skin and connective tissues), Sjogren's syndrome (exocrine glands, and other tissues), Spondyloarthropathies (axial skeleton, and other tissues), Thyroiditis (thyroid), Vasculitis (blood vessels).

Within parenthesis is the tissue affected by the disease. This listing of autoimmune diseases is intended to be exemplary rather than inclusive.

Autoimmune conditions for which the anti-TNF-alpha polypeptides of the present invention is applicable include, for example, AIDS, atopic allergy, bronchial asthma, eczema, leprosy, schizophrenia, inherited depression, transplantation of tissues and organs, chronic fatigue syndrome, Alzheimer's disease, Parkinson's disease, myocardial infarction, stroke, autism, epilepsy, Arthus's phenomenon, anaphylaxis, and alcohol and drug addiction. In the above-identified autoimmune conditions, the tissue affected is the primary target, in other cases it is the secondary target. These conditions are partly or mostly autoimmune syndromes. Therefore, in treating them, it is possible to use the same methods, or aspects of the same methods that are herein disclosed, sometimes in combination with other methods.

Another embodiment of the present invention is a use of an anti-TNF-alpha polypeptide according to the invention, or a nucleic acid capable of encoding said polypeptide for the preparation of a medicament for treating a disorder relating to inflammatory processes. Examples of disorders include rheumatoid arthritis, Crohn's disease, ulcerative colitis, inflammatory bowel syndrome and multiple sclerosis.

Polypeptides and nucleic acids according to the present invention may be administered to a subject by conventional routes, such as intravenously. However, a special property of the anti-TNF-alpha polypeptides of the invention is that they penetrate barriers such as tissue membranes and/or tumours and act locally thereon, and they are sufficiently stable to withstand extreme environments such as in the stomach. Therefore, another aspect of the present invention relates to the delivery of anti-TNF-alpha polypeptides.

When the Nanobodies and/or polypeptides of the invention are used for, or are intended for use in, the prevention or treatment of diseases and disorders of the gastro-intestinal tract, in particular by means of oral administration or other administration into the gastrointestinal tract, it will usually not be necessary to use polypeptides of the invention that have increased half-life in serum (i.e. that have been pegylated or that contain a Nanobody directed against a serum protein). Thus, for such indications, polypeptides of the invention can be used that only contain Nanobodies of the invention. In particular, it has been found that for oral administration for the prevention and treatment of diseases or disorders of the gastro-intestinal tract associated with and/or mediated by TNF-alpha (such as IBD and the other diseases and disorders of the gastro-intestinal tract mentioned above), the use of a monovalent Nanobody of the invention or of a polypeptide of the invention that essentially consists of a monovalent Nanobody of the invention may be preferred. For other indications, such as the treatment of rheumatoid arthritis (RA), the use of a bivalent Nanobody of the invention may be preferred. When such a Nanobody has to reach its intended site of action via the blood stream, the use of a polypeptide of the invention that has increased half-life in serum may be preferred.

A subject according to the invention can be any mammal susceptible to treatment by therapeutic polypeptides.

Oral delivery of anti-TNF-alpha polypeptides of the invention results in the provision of such molecules in an active form in the colon at local sites that are affected by the disorder. These sites may be highly inflamed and contain TNF-alpha-producing cells. The anti-TNF-alpha polypeptides of the invention which bind to TNF-alpha can neutralise the TNF-alpha locally, avoiding distribution throughout the whole body and thus limiting negative side-effects. Genetically modified microorganisms such as *Micrococcus lactis* are able to secrete antibody or functional portions thereof. Such modified microorganisms can be used as vehicles for local production and delivery of antibodies or functional portions thereof in the intestine. By using a strain which produces an anti-TNF-alpha polypeptide, inflammatory bowel syndrome could be treated.

Another aspect of the invention involves delivering anti-TNF polypeptides by using surface expression on or secretion from non-invasive bacteria, such as Gram-positive host organisms like *Lactococcus* spec. using a vector such as described in WO00/23471.

One embodiment of the present invention is an anti-TNF-alpha polypeptide as disclosed herein for use in treating, preventing and/or alleviating the symptoms of disorders susceptible to modulation by a Nanobody or polypeptide of the invention which is able pass through the gastric environment without the substance being inactivated.

Examples of disorders are any that cause inflammation, including, but not limited to rheumatoid arthritis, Crohn's disease, ulcerative colitis, inflammatory bowel syndrome, and multiple sclerosis. As known by persons skilled in the art, once in possession of said polypeptide construct, formulation technology may be applied to release a maximum amount of polypeptide in the right location (in the stomach, in the colon, etc.). This method of delivery is important for treating, prevent and/or alleviate the symptoms of disorders whose targets are located in the gut system.

An aspect of the invention is a method for treating, preventing and/or alleviating the symptoms of a disorder susceptible to modulation by a Nanobody or polypeptide of the invention which is able pass through the gastric environment without being inactivated, by orally administering to a subject an anti-TNF-alpha polypeptide as disclosed herein.

Another embodiment of the present invention is a use of an anti-TNF-alpha polypeptide as disclosed herein for the preparation of a medicament for treating, preventing and/or alleviating the symptoms of disorders susceptible to modulation by a Nanobody or polypeptide of the invention which is able pass through the gastric environment without being inactivated.

An aspect of the invention is a method for delivering a Nanobody or polypeptide of the invention to the gut system without said substance being inactivated, by orally administering to a subject an anti-TNF-alpha polypeptide as disclosed herein.

An aspect of the invention is a method for delivering a Nanobody or polypeptide of the invention to the bloodstream of a subject without the substance being inactivated, by orally administering to a subject an anti-TNF-alpha polypeptide as disclosed herein.

Another embodiment of the present invention is an anti-TNF-alpha polypeptide as disclosed herein for use in treating, preventing and/or alleviating the symptoms or disorders susceptible to modulation by a Nanobody or polypeptide of the invention delivered to the vaginal and/or rectal tract.

Examples of disorders are any that cause inflammation, including, but not limited to rheumatoid arthritis, Crohn's disease, ulcerative colitis, inflammatory bowel syndrome, and multiple sclerosis. In a non-limiting example, a formulation according to the invention comprises an anti-TNF-alpha polypeptide as disclosed herein, in the form of a gel, cream, suppository, film, or in the form of a sponge or as a vaginal ring that slowly releases the active ingredient over time (such formulations are described in EP 707473, EP 684814, U.S. Pat. No. 5,629,001).

An aspect of the invention is a method for treating, preventing and/or alleviating the symptoms of disorders susceptible to modulation by a Nanobody or polypeptide of the invention delivered to the vaginal and/or rectal tract, by vaginally and/or rectally administering to a subject an anti-TNF-alpha polypeptide as disclosed herein.

Another embodiment of the present invention is a use of an anti-TNF-alpha polypeptide as disclosed herein for the preparation of a medicament for treating, preventing and/or alleviating the symptoms of disorders susceptible to modulation by a Nanobody or polypeptide of the invention delivered to the vaginal and/or rectal tract.

An aspect of the invention is a method for delivering a Nanobody or polypeptide of the invention to the vaginal and/or rectal tract without being said substance being inactivated, by administering to the vaginal and/or rectal tract of a subject an anti-TNF-alpha polypeptide as disclosed herein.

An aspect of the invention is a method for delivering a Nanobody or polypeptide of the invention to the bloodstream of a subject without said substance being inactivated, by administering to the vaginal and/or rectal tract of a subject an anti-TNF-alpha polypeptide as disclosed herein.

Another embodiment of the present invention is an anti-TNF-alpha polypeptide as disclosed herein, for use in treating, preventing and/or alleviating the symptoms of disorders susceptible to modulation by a Nanobody or polypeptide of the invention delivered to the nose, upper respiratory tract and/or lung.

Examples of disorders are any that cause inflammation, including, but not limited to rheumatoid arthritis, Crohn's disease, ulcerative colitis, inflammatory bowel syndrome, and multiple sclerosis. In a non-limiting example, a formulation according to the invention, comprises an anti-TNF-alpha polypeptide as disclosed herein in the form of a nasal spray (e.g. an aerosol) or inhaler. Since the polypeptide construct is small, it can reach its target much more effectively than therapeutic IgG molecules.

An aspect of the invention is a method for treating, preventing and/or alleviating the symptoms of disorders susceptible to modulation by a Nanobody or polypeptide of the invention delivered to the upper respiratory tract and lung, by administering to a subject an anti-TNF-alpha polypeptide as disclosed herein, by inhalation through the mouth or nose.

Another embodiment of the present invention is a use of an anti-TNF-alpha polypeptide as disclosed herein for the preparation of a medicament for treating, preventing and/or alleviating the symptoms of disorders susceptible to modulation by a Nanobody or polypeptide of the invention delivered to the nose, upper respiratory tract and/or lung, without said polypeptide being inactivated.

An aspect of the invention is a method for delivering a Nanobody or polypeptide of the invention to the nose, upper respiratory tract and lung without inactivation, by administering to the nose, upper respiratory tract and/or lung of a subject an anti-TNF-alpha polypeptide as disclosed herein.

An aspect of the invention is a method for delivering a Nanobody or polypeptide of the invention to the bloodstream of a subject without inactivation by administering to the nose, upper respiratory tract and/or lung of a subject an anti-TNF-alpha polypeptide as disclosed herein.

One embodiment of the present invention is an anti-TNF-alpha polypeptide as disclosed herein for use in treating, preventing and/or alleviating the symptoms of disorders susceptible to modulation by a Nanobody or polypeptide of the invention delivered to the intestinal mucosa, wherein said disorder increases the permeability of the intestinal mucosa. Because of their small size, an anti-TNF-alpha polypeptide as disclosed herein can pass through the intestinal mucosa and reach the bloodstream more efficiently in subjects suffering from disorders which cause an increase in the permeability of the intestinal mucosa, for example Crohn's disease.

An aspect of the invention is a method for treating, preventing and/or alleviating the symptoms of disorders susceptible to modulation by a Nanobody or polypeptide of the invention delivered to the intestinal mucosa, wherein said disorder increases the permeability of the intestinal mucosa, by orally administering to a subject an anti-TNF-alpha polypeptide as disclosed herein.

This process can be even further enhanced by an additional aspect of the present invention—the use of active transport carriers. In this aspect of the invention, $V_{HH}$ is fused to a carrier that enhances the transfer through the intestinal wall into the bloodstream. In a non-limiting example, this "carrier" is a second $V_{HH}$ which is fused to the therapeutic $V_{HH}$. Such fusion constructs are made using methods known in the art. The "carrier" $V_{HH}$ binds specifically to a receptor on the intestinal wall which induces an active transfer through the wall.

Another embodiment of the present invention is a use of an anti-TNF-alpha polypeptide as disclosed herein for the preparation of a medicament for treating, preventing and/or alleviating the symptoms of disorders susceptible to modulation by a Nanobody or polypeptide of the invention delivered to the intestinal mucosa, wherein said disorder increases the permeability of the intestinal mucosa.

An aspect of the invention is a method for delivering a Nanobody or polypeptide of the invention to the intestinal mucosa without being inactivated, by administering orally to a subject an anti-TNF-alpha polypeptide of the invention.

An aspect of the invention is a method for delivering a Nanobody or polypeptide of the invention to the bloodstream of a subject without being inactivated, by administering orally to a subject an anti-TNF-alpha polypeptide of the invention.

This process can be even further enhanced by an additional aspect of the present invention—the use of active transport carriers. In this aspect of the invention, an anti-TNF-alpha polypeptide as described herein is fused to a carrier that enhances the transfer through the intestinal wall into the bloodstream. In a non-limiting example, this "carrier" is a $V_{HH}$ which is fused to said polypeptide. Such fusion constructs made using methods known in the art. The "carrier" $V_{HH}$ binds specifically to a receptor on the intestinal wall which induces an active transfer through the wall.

One embodiment of the present invention is an anti-TNF-alpha polypeptide as disclosed herein for use in treating, preventing and/or alleviating the symptoms of disorders susceptible to modulation by a Nanobody or polypeptide of the invention which is able pass through the tissues beneath the tongue effectively.

Examples of disorders are any that cause inflammation, including, but not limited to rheumatoid arthritis, Crohn's disease, ulcerative colitis, inflammatory bowel syndrome, and multiple sclerosis. A formulation of said polypeptide construct as disclosed herein, for example, a tablet, spray, drop is placed under the tongue and adsorbed through the mucus membranes into the capillary network under the tongue.

An aspect of the invention is a method for treating, preventing and/or alleviating the symptoms of disorders susceptible to modulation by a Nanobody or polypeptide of the invention which is able pass through the tissues beneath the tongue effectively, by sublingually administering to a subject an anti-TNF-alpha polypeptide as disclosed herein.

Another embodiment of the present invention is a use of an anti-TNF-alpha polypeptide as disclosed herein for the preparation of a medicament for treating, preventing and/or alleviating the symptoms of disorders susceptible to modulation by a Nanobody or polypeptide of the invention which is able to pass through the tissues beneath the tongue.

An aspect of the invention is a method for delivering a Nanobody or polypeptide of the invention to the tissues beneath the tongue without being inactivated, by administering sublingually to a subject an anti-TNF-alpha polypeptide as disclosed herein.

An aspect of the invention is a method for delivering a Nanobody or polypeptide of the invention to the bloodstream of a subject without being inactivated, by administering orally to a subject an anti-TNF-alpha polypeptide as disclosed herein.

One embodiment of the present invention is an anti-TNF-alpha polypeptide as disclosed herein for use in treating, preventing and/or alleviating the symptoms of disorders susceptible to modulation by a Nanobody or polypeptide of the invention which is able pass through the skin effectively.

Examples of disorders are any that cause inflammation, including, but not limited to rheumatoid arthritis, Crohn's disease, ulcerative colitis, inflammatory bowel syndrome, and multiple sclerosis. A formulation of said polypeptide construct, for example, a cream, film, spray, drop, patch, is placed on the skin and passes through.

An aspect of the invention is a method for treating, preventing and/or alleviating the symptoms of disorders susceptible to modulation by a Nanobody or polypeptide of the invention which is able pass through the skin effectively, by topically administering to a subject an anti-TNF-alpha polypeptide as disclosed herein.

Another embodiment of the present invention is a use of an anti-TNF-alpha polypeptide as disclosed herein for the preparation of a medicament for treating, preventing and/or alleviating the symptoms of disorders susceptible to modulation by a Nanobody or polypeptide of the invention which is able pass through the skin effectively.

An aspect of the invention is a method for delivering a Nanobody or polypeptide of the invention to the skin without being inactivated, by administering topically to a subject an anti-TNF-alpha polypeptide as disclosed herein.

An aspect of the invention is a method for delivering a Nanobody or polypeptide of the invention to the bloodstream of a subject, by administering topically to a subject an anti-TNF-alpha polypeptide as disclosed herein.

In another embodiment of the present invention, an anti-TNF-alpha polypeptide further comprises a carrier nanobody (e.g. $V_{HH}$) which acts as an active transport carrier for transport said anti-TNF-alpha polypeptide, from the lung lumen to the blood.

An anti-TNF-alpha polypeptide further comprising a carrier binds specifically to a receptor present on the mucosal surface (bronchial epithelial cells) resulting in the active transport of the polypeptide from the lung lumen to the blood. The carrier nanobody may be fused to the polypeptide construct. Such fusion constructs may be made using methods known in the art and are describe herein. The "carrier" nanobody binds specifically to a receptor on the mucosal surface which induces an active transfer through the surface.

Another aspect of the present invention is a method to determine which nanobodies (e.g. $V_{HH}s$) are actively transported into the bloodstream upon nasal administration. Similarly, a naïve or immune $V_{HH}$ phage library can be administered nasally, and after different time points after administration, blood or organs can be isolated to rescue phages that have been actively transported to the bloodstream. A non-limiting example of a receptor for active transport from the lung lumen to the bloodstream is the Fc receptor N (FcRn). One aspect of the invention includes the $V_{HH}$ molecules identified by the method. Such $V_{HH}$ can then be used as a carrier $V_{HH}$ for the delivery of a therapeutic $V_{HH}$ to the corresponding target in the bloodstream upon nasal administration.

In one aspect of the invention, one can use an anti-TNF-alpha polypeptide as disclosed herein, in order to screen for agents that modulate the binding of the polypeptide to TNF-alpha. When identified in an assay that measures binding or said polypeptide displacement alone, agents will have to be subjected to functional testing to determine whether they would modulate the action of the antigen in vivo.

In an example of a displacement experiment, phage or cells expressing TNF-alpha or a fragment thereof are incubated in binding buffer with polypeptide of the invention which has been labeled, in the presence or absence of increasing concentrations of a candidate modulator. To validate and calibrate the assay, control competition reactions using increasing concentrations of said polypeptide and which is unlabeled, can be performed. After incubation, cells are washed extensively, and bound, labeled polypeptide is measured as appropriate for the given label (e.g., scintillation counting, fluorescence, etc.). A decrease of at least 10% in the amount of labeled polypeptide bound in the presence of candidate modulator indicates displacement of binding by the candidate modulator. Candidate modulators are considered to bind specifically in this or other assays described herein if they displace 50% of labeled polypeptide (sub-saturating polypeptide dose) at a concentration of 1 μM or less.

Alternatively, binding or displacement of binding can be monitored by surface plasmon resonance (SPR). Surface plasmon resonance assays can be used as a quantitative method to measure binding between two molecules by the change in mass near an immobilized sensor caused by the binding or loss of binding of the polypeptide of the invention from the aqueous phase to TNF-alpha immobilized in a membrane on the sensor. This change in mass is measured as resonance units versus time after injection or removal of the said polypeptide or candidate modulator and is measured using a Biacore Biosensor (Biacore AB). TNF-alpha can be for example immobilized on a sensor chip (for example, research grade CM5 chip; Biacore AB) in a thin film lipid membrane according to methods described by Salamon et al. (Salamon et al., 1996, Biophys J. 71: 283-294; Salamon et al., 2001, Biophys. J. 80: 1557-1567; Salamon et al., 1999, Trends Biochem. Sci. 24: 213-219, each of which is incorporated herein by reference.). Sarrio et al. demonstrated that SPR can be used to detect ligand binding to the GPCR A(1) adenosine receptor immobilized in a lipid layer on the chip (Sarrio et al., 2000, Mol. Cell. Biol. 20: 5164-5174, incorporated herein by reference). Conditions for the binding of a polypeptide of the invention to TNF-alpha in an SPR assay can be fine-tuned by one of skill in the art using the conditions reported by Sarrio et al. as a starting point.

SPR can assay for modulators of binding in at least two ways. First, a polypeptide of the invention can be pre-bound to immobilized TNF-alpha followed by injection of candidate modulator at a concentration ranging from 0.1 nM to 1 μM. Displacement of the bound polypeptide can be quantitated, permitting detection of modulator binding. Alternatively, the membrane-bound TNF-alpha can be pre-incubated with a candidate modulator and challenged with the polypeptide of the invention. A difference in binding affinity between said polypeptide and TNF-alpha pre-incubated with the modulator, compared with that between said polypeptide and TNF-alpha in absence of the modulator will demonstrate binding or displacement of said polypeptide in the presence of modulator. In either assay, a decrease of 10% or more in the amount of said polypeptide bound in the presence of candidate modulator, relative to the amount of said polypeptide bound in the absence of candidate modulator indicates that the candidate modulator inhibits the interaction of TNF-alpha and said polypeptide.

Another method of detecting inhibition of binding of, for example, a polypeptide of the invention, to TNF-alpha uses fluorescence resonance energy transfer (FRET). FRET is a quantum mechanical phenomenon that occurs between a fluorescence donor (D) and a fluorescence acceptor (A) in close proximity to each other (usually <100 Å of separation) if the emission spectrum of D overlaps with the excitation spectrum of A. The molecules to be tested, e.g. a polypeptide polypeptide of the invention and a TNF-alpha are labelled with a complementary pair of donor and acceptor fluorophores. While bound closely together by the TNF-alpha: polypeptide interaction, the fluorescence emitted upon excitation of the donor fluorophore will have a different wavelength from that emitted in response to that excitation wavelength when the said polypeptide and TNF-alpha are not bound, providing for quantitation of bound versus unbound molecules by measurement of emission intensity at each wavelength. Donor fluorophores with which to label the TNF-alpha are well known in the art. Of particular interest are variants of the A. Victoria GFP known as Cyan FP (CFP, Donor (D)) and Yellow FP (YFP, Acceptor (A)). As an example, the YFP variant can be made as a fusion protein with TNF-alpha. Vectors for the expression of GFP variants as fusions (Clontech) as well as fluorophore-labeled reagents (Molecular Probes) are known in the art. The addition of a candidate modulator to the mixture of fluorescently-labelled polypeptide and YFP-TNF-alpha will result in an inhibition of energy transfer evidenced by, for example, a decrease in YFP fluorescence relative to a sample without the candidate modulator. In an assay using FRET for the detection of TNF-alpha: polypeptide interaction, a 10% or greater decrease in the intensity of fluorescent emission at the acceptor wavelength in samples containing a candidate modulator, relative to samples without the candidate modulator, indicates that the candidate modulator inhibits the TNF-alpha:polypeptide interaction.

A sample as used herein may be any biological sample containing TNF-alpha such as clinical (e.g. cell fractions, whole blood, plasma, serum, tissue, cells, etc.), derived from clinical, agricultural, forensic, research, or other possible samples. The clinical samples may be from human or animal origin. The sample analysed can be both solid or liquid in nature. It is evident when solid materials are used, these are first dissolved in a suitable solution.

A variation on FRET uses fluorescence quenching to monitor molecular interactions. One molecule in the interacting pair can be labelled with a fluorophore, and the other with a molecule that quenches the fluorescence of the fluorophore when brought into close apposition with it. A change in fluorescence upon excitation is indicative of a change in the association of the molecules tagged with the fluorophore:quencher pair. Generally, an increase in fluorescence of the labelled TNF-alpha is indicative that anti-TNF-alpha polypeptide bearing the quencher has been displaced. For quenching assays, a 10% or greater increase in the intensity of fluorescent emission in samples containing a candidate modulator, relative to samples without the candidate modulator, indicates that the candidate modulator inhibits TNF-alpha: anti-TNF-alpha polypeptide interaction.

In addition to the surface plasmon resonance and FRET methods, fluorescence polarization measurement is useful to quantitate binding. The fluorescence polarization value for a fluorescently-tagged molecule depends on the rotational correlation time or tumbling rate. Complexes, such as those formed by TNF-alpha associating with a fluorescently labelled anti-TNF-alpha polypeptide, have higher polarization values than uncomplexed, labelled polypeptide. The inclusion of a candidate inhibitor of the TNF-alpha:anti-TNF-alpha polypeptide interaction results in a decrease in fluorescence polarization, relative to a mixture without the candidate inhibitor, if the candidate inhibitor disrupts or inhibits the interaction of TNF-alpha with said polypeptide. Fluorescence polarization is well suited for the identification of small molecules that disrupt the formation of TNF-alpha: anti-TNF-alpha polypeptide complexes. A decrease of 10% or more in fluorescence polarization in samples containing a candidate modulator, relative to fluorescence polarization in a sample lacking the candidate modulator, indicates that the candidate modulator inhibits the TNF-alpha: anti-TNF-alpha polypeptide interaction.

Another alternative for monitoring TNF-alpha: anti-TNF-alpha polypeptide interactions uses a biosensor assay. ICS biosensors have been described in the art (Australian Membrane Biotechnology Research Institute; Cornell B, Braach-Maksvytis V, King L, Osman P, Raguse B, Wieczorek L, and Pace R. "A biosensor that uses ion-channel switches" Nature 1997, 387, 580). In this technology, the association of TNF-alpha and a anti-TNF-alpha polypeptide is coupled to the closing of gramicidine-facilitated ion channels in suspended membrane bilayers and thus to a measurable change in the admittance (similar to impedance) of the biosensor. This approach is linear over six orders of magnitude of admittance change and is ideally suited for large scale, high throughput screening of small molecule combinatorial libraries. A 10% or greater change (increase or decrease) in admittance in a sample containing a candidate modulator, relative to the admittance of a sample lacking the candidate modulator, indicates that the candidate modulator inhibits the interaction of TNF-alpha and said polypeptide. It is important to note that in assays testing the interaction of TNF-alpha with an anti-TNF-alpha polypeptide, it is possible that a modulator of the interaction need not necessarily interact directly with the domain(s) of the proteins that physically interact with said polypeptide. It is also possible that a modulator will interact at a location removed from the site of interaction and cause, for example, a conformational change in the TNF-alpha. Modulators (inhibitors or agonists) that act in this manner are nonetheless of interest as agents to modulate the binding of TNF-alpha to its receptor.

Any of the binding assays described can be used to determine the presence of an agent in a sample, e.g., a tissue sample, that binds to TNF-alpha, or that affects the binding of, for example, a polypeptide polypeptide of the invention to the TNF-alpha. To do so a TNF-alpha is reacted with said polypeptide in the presence or absence of the sample, and polypeptide binding is measured as appropriate for the binding assay being used. A decrease of 10% or more in the binding of said polypeptide indicates that the sample contains an agent that modulates the binding of said polypeptide to the TNF-alpha. Of course, the above-generalized method might easily be applied to screening for candidate modulators which alter the binding between any anti-TNF-alpha polypeptide of the invention, an homologous sequence thereof, a functional portion thereof or a functional portion of an homologous sequence thereof, and TNF-alpha or a fragment thereof.

One embodiment of the present invention is an unknown agent identified by the method disclosed herein.

One embodiment of the present invention is an unknown agent identified by the method disclosed herein for use in treating, preventing and/or alleviating the symptoms of disorders relating to inflammatory processes.

Another embodiment of the present invention is a use of an unknown agent identified by the method disclosed herein for use in treating, preventing and/or alleviating the symptoms of disorders relating to inflammatory processes.

Examples of disorders include rheumatoid arthritis, Crohn's disease, ulcerative colitis, inflammatory bowel syndrome and multiple sclerosis.

A cell that is useful according to the invention is preferably selected from the group consisting of bacterial cells such as, for example, *E. coli*, yeast cells such as, for example, *S. cerevisiae, P. pastoris*, insect cells or mammal cells.

A cell that is useful according to the invention can be any cell into which a nucleic acid sequence encoding a polypeptide comprising an anti-TNF-alpha of the invention, an homologous sequence thereof, a functional portion thereof or a functional portion of an homologous sequence thereof according to the invention can be introduced such that the polypeptide is expressed at natural levels or above natural levels, as defined herein. Preferably a polypeptide of the invention that is expressed in a cell exhibits normal or near normal pharmacology, as defined herein.

According to a preferred embodiment of the present invention, a cell is selected from the group consisting of COS7-cells, a CHO cell, a LM (TK-) cell, a NIH-3T3 cell, HEK-293 cell, K-562 cell or a 1321N1 astrocytoma cell but also other transfectable cell lines.

In general, "therapeutically effective amount", "therapeutically effective dose" and "effective amount" means the amount needed to achieve the desired result or results (modulating TNF-alpha binding; treating or preventing inflammation). One of ordinary skill in the art will recognize that the potency and, therefore, an "effective amount" can vary for the various compounds that modulate TNF-alpha binding used in the invention. One skilled in the art can readily assess the potency of the compound.

As used herein, the term "compound" refers to an anti-TNF-alpha polypeptide of the present invention, a composition, or a nucleic acid capable of encoding said polypeptide or an agent identified according to the screening method described herein or said polypeptide comprising one or more derivatised amino acids.

By "pharmaceutically acceptable" is meant a material that is not biologically or otherwise undesirable, i.e., the material may be administered to an individual along with the compound without causing any undesirable biological effects or interacting in a deleterious manner with any of the other components of the pharmaceutical composition in which it is contained.

Anti-TNF-alpha polypeptides as disclosed herein is useful for treating or preventing conditions in a subject and comprises administering a pharmaceutically effective amount of a compound or composition.

Anti-TNF polypeptides of the present invention are useful for treating or preventing conditions relating to rheumatoid arthritis, Crohn's disease, ulcerative colitis, inflammatory bowel syndrome and multiple sclerosis in a subject and comprises administering a pharmaceutically effective amount of a compound or composition that binds TNF-alpha.

Anti-TNF-alpha polypeptides as disclosed here in are useful for treating or preventing conditions in a subject and comprises administering a pharmaceutically effective amount of a compound combination with another, such as, for example, aspirin.

The anti-TNF-alpha polypeptides as disclosed here in are useful for treating or preventing conditions relating to rheumatoid arthritis, Crohn's disease, ulcerative colitis, inflammatory bowel syndrome and multiple sclerosis in a subject and comprises administering a pharmaceutically effective amount of a compound combination with another, such as, for example, aspirin.

The present invention is not limited to the administration of formulations comprising a single compound of the invention. It is within the scope of the invention to provide combination treatments wherein a formulation is administered to a patient in need thereof that comprises more than one compound of the invention.

Conditions mediated by TNF-alpha include, but are not limited rheumatoid arthritis, Crohn's disease, ulcerative colitis, inflammatory bowel syndrome and multiple sclerosis.

A compound useful in the present invention can be formulated as pharmaceutical compositions and administered to a mammalian host, such as a human patient or a domestic animal in a variety of forms adapted to the chosen route of administration, i.e., orally or parenterally, by intranassally by inhalation, intravenous, intramuscular, topical or subcutaneous routes.

A compound of the present invention can also be administered using gene therapy methods of delivery. See, e.g., U.S. Pat. No. 5,399,346, which is incorporated by reference in its entirety. Using a gene therapy method of delivery, primary cells transfected with the gene for the compound of the present invention can additionally be transfected with tissue specific promoters to target specific organs, tissue, grafts, tumors, or cells.

Thus, the present compound may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compound may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, hydroxyalkyls or glycols or water-alcohol/glycol blends, in which the present compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compound to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compound can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. Also the dosage of the compound varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

The invention provides for an agent that is a modulator of TNF-alpha/TNF-alpha-receptor interactions.

The candidate agent may be a synthetic agent, or a mixture of agents, or may be a natural product (e.g. a plant extract or culture supernatant). A candidate agent according to the invention includes a small molecule that can be synthesized, a natural extract, peptides, proteins, carbohydrates, lipids etc.

Candidate modulator agents from large libraries of synthetic or natural agents can be screened. Numerous means are currently used for random and directed synthesis of saccharide, peptide, and nucleic acid based agents. Synthetic agent libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural agents in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and agents are readily modified through conventional chemical, physical, and biochemical means.

Useful agents may be found within numerous chemical classes. Useful agents may be organic agents, or small organic agents. Small organic agents have a molecular weight of more than 50 yet less than about 2,500 daltons, preferably less than about 750, more preferably less than about 350 daltons. Exemplary classes include heterocycles, peptides, saccharides, steroids, and the like. The agents may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

For primary screening, a useful concentration of a candidate agent according to the invention is from about 10 mM to about 100 µM or more (i.e. 1 mM, 10 mM, 100 mM, 1 M etc.). The primary screening concentration will be used as an upper limit, along with nine additional concentrations, wherein the additional concentrations are determined by reducing the primary screening concentration at half-log intervals (e.g. for 9 more concentrations) for secondary screens or for generating concentration curves.

A high throughput screening kit according to the invention comprises all the necessary means and media for performing the detection of an agent that modulates TNF-alpha/TNF-alpha receptor interactions by interacting with TNF-alpha in the presence of a polypeptide, preferably at a concentration in the range of 1 µM to 1 mM.

The kit comprises the following. Recombinant cells of the invention, comprising and expressing the nucleotide sequence encoding TNF-alpha, which are grown according to the kit on a solid support, such as a microtiter plate, more preferably a 96 well microtiter plate, according to methods well known to the person skilled in the art especially as described in WO 00/02045. Alternatively TNF-alpha is supplied in a purified form to be immobilized on, for example, a 96 well microtiter plate by the person skilled in the art. Alternatively TNF-alpha is supplied in the kit pre-immobilized on, for example, a 96 well microtiter plate. The TNF-alpha may be whole TNF-alpha or a fragment thereof.

Modulator agents according to the invention, at concentrations from about 1 µM to 1 mM or more, are added to defined wells in the presence of an appropriate concentration of anti-TNF-alpha polypeptide, an homologous sequence thereof, a functional portion thereof or a functional portion of an homologous sequence thereof, said concentration of said polypeptide preferably in the range of 1 µM to 1 mM. Kits may contain one or more anti-TNF-alpha polypeptides of the invention.

Binding assays are performed as according to the methods already disclosed herein and the results are compared to the baseline level of, for example TNF-alpha binding to an anti-TNF-alpha polypeptide, an homologous sequence thereof, a functional portion thereof or a functional portion of an homologous sequence thereof, but in the absence of added modulator agent. Wells showing at least 2 fold, preferably 5 fold, more preferably 10 fold and most preferably a 100 fold or more increase or decrease in TNF-alpha-polypeptide binding (for example) as compared to the level of activity in the absence of modulator, are selected for further analysis.

The invention provides for other kits useful for screening for modulators of TNF-alpha/TNF-alpha receptor binding, as well as kits useful for diagnosis of disorders characterised by dysfunction of TNF-alpha. The invention also provides for kits useful for screening for modulators of disorders as well as kits for their diagnosis, said disorders characterised by one or more process involving TNF-alpha. Kits useful according to the invention can include an isolated TNF-alpha. Alternatively, or in addition, a kit can comprise cells transformed to express TNF-alpha. In a further embodiment, a kit according to the invention can comprise a polynucleotide encoding TNF-alpha. In a still further embodiment, a kit according to the invention may comprise the specific primers useful for amplification of TNF-alpha. Kits useful according to the invention can comprise an isolated TNF-alpha polypeptide, a homologue thereof, or a functional portion thereof. A kit according to the invention can comprise cells transformed to express said polypeptide. Kits may contain more than one polypeptide. In a further embodiment, a kit according to the invention can comprise a polynucleotide encoding TNF-alpha. In a still further embodiment, a kit according to the invention may comprise the specific primers useful for amplification of a macromolecule such as, for example, TNF-alpha. All kits according to the invention will comprise the stated items or combinations of items and packaging materials therefore. Kits will also include instructions for use.

Furthermore, it will also be clear to the skilled person that it may be possible to "graft" one or more of the CDR's mentioned above for the Nanobodies of the invention onto other "scaffolds", including but not limited to human scaffolds or non-immunoglobulin scaffolds. Suitable scaffolds and techniques for such CDR grafting will be clear to the skilled person and are well known in the art, see for example U.S. Pat. No. 7,180,370, WO 01/27160, EP 0 605 522, EP 0 460 167, U.S. Pat. No. 7,054,297, Nicaise et al., Protein Science (2004), 13:1882-1891; Ewert et al., Methods, 2004 October; 34(2):184-199; Kettleborough et al., Protein Eng. 1991 October; 4(7): 773-783; O'Brien and Jones, Methods Mol. Biol. 2003: 207: 81-100; and Skerra, J. Mol. Recognit. 2000: 13: 167-187, and Saerens et al., J. Mol. Biol. 2005 Sep. 23; 352(3):597-607, and the further references cited therein. For example, techniques known per se for grafting mouse or rat CDR's onto human frameworks and scaffolds can be used in an analogous manner to provide chimeric proteins comprising one or more of the CDR's of the Nanobodies of the invention and one or human framework regions or sequences.

Thus, in another embodiment, the invention comprises a chimeric polypeptide comprising at least one CDR sequence chosen from the group consisting of CDR1 sequences, CDR2 sequences and CDR3 sequences mentioned herein for the Nanobodies of the invention. Preferably, such a chimeric polypeptide comprises at least one CDR sequence chosen from the group consisting of the CDR3 sequences mentioned herein for the Nanobodies of the invention, and optionally also at least one CDR sequence chosen from the group consisting of the CDR1 sequences and CDR2 sequences mentioned herein for the Nanobodies of the invention. For example, such a chimeric polypeptide may comprise one CDR sequence chosen from the group consisting of the CDR3 sequences mentioned herein for the Nanobodies of the invention, one CDR sequence chosen from the group consisting of the CDR1 sequences mentioned herein for the Nanobodies of the invention and one CDR sequence chosen from the group consisting of the CDR1 sequences and CDR2 sequences mentioned herein for the Nanobodies of the invention. The combinations of CDR's that are mentioned herein as being preferred for the Nanobodies of the invention will usually also be preferred for these chimeric polypeptides.

In said chimeric polypeptides, the CDR's may be linked to further amino acid sequences and/or may be linked to each other via amino acid sequences, in which said amino acid sequences are preferably framework sequences or are amino acid sequences that act as framework sequences, or together form a scaffold for presenting the CDR's. Reference is again made to the prior art mentioned in the last paragraph. According to one preferred embodiment, the amino acid sequences are human framework sequences, for example $V_H3$ framework sequences. However, non-human, synthetic, semi-synthetic or non-immunoglobulin framework sequences may also be used. Preferably, the framework sequences used are such that (1) the chimeric polypeptide is capable of binding TNF-alpha, i.e. with an affinity that is at least 1%, preferably at least 5%, more preferably at least 10%, such as at least 25% and up to 50% or 90% or more of the affinity of the corresponding Nanobody of the invention; (2) the chimeric polypeptide is suitable for pharmaceutical use; and (3) the chimeric polypeptide is preferably essentially non-immunogenic under the intended conditions for pharmaceutical use (i.e. indication, mode of administration, doses and treatment regimen) thereof (which may be essentially analogous to the conditions described herein for the use of the Nanobodies of the invention).

According to one non-limiting embodiment, the chimeric polypeptide comprises at least two CDR sequences (as mentioned above) linked via at least one framework sequence, in which preferably at least one of the two CDR sequences is a CDR3 sequence, with the other CDR sequence being a CDR1 or CDR2 sequence. According to a preferred, but non-limiting embodiment, the chimeric polypeptide comprises at least two CDR sequences (as mentioned above) linked at least two framework sequences, in which preferably at least one of the three CDR sequences is a CDR3 sequence, with the other two CDR sequences being CDR1 or CDR2 sequences, and preferably being one CDR1 sequence and one CDR2 sequence. According to one specifically preferred, but non-limiting embodiment, the chimeric polypeptides have the structure FR1'-CDR1-FR2'-

CDR2-FR3'-CDR3-FR4', in which CDR1, CDR2 and CDR3 are as defined herein for the CDR's of the Nanobodies of the invention, and FR1', FR2', FR3' and FR4' are framework sequences. FR1', FR2', FR3' and FR4' may in particular be Framework 1, Framework 2, Framework 3 and Framework 4 sequences, respectively, of a human antibody (such as $V_H3$ sequences) and/or parts or fragments of such Framework sequences. It is also possible to use parts or fragments of a chimeric polypeptide with the structure FR1'-CDR1-FR2'-CDR2-FR3'-CDR3-FR4. Preferably, such parts or fragments are such that they meet the criteria set out in the preceding paragraph.

The invention also relates to proteins and polypeptides comprising and/or essentially consisting of such chimeric polypeptides, to nucleic acids encoding such proteins or polypeptides; to methods for preparing such proteins and polypeptides; to host cells expressing or capable of expressing such proteins or polypeptides; to compositions, and in particular to pharmaceutical compositions, that comprise such proteins or polypeptides, nucleic acids or host cells; and to uses of such proteins or polypeptides, such nucleic acids, such host cells and/or such compositions, in particular for prophylactic, therapeutic or diagnostic purposes, such as the prophylactic, therapeutic or diagnostic purposes mentioned herein. For example, such proteins, polypeptides, nucleic acids, methods, host cells, compositions and uses may be analogous to the proteins, polypeptides, nucleic acids, methods, host cells, compositions and use described herein for the Nanobodies of the invention.

It should also be noted that, when the Nanobodies of the inventions contain one or more other CDR sequences than the preferred CDR sequences mentioned above, these CDR sequences can be any suitable (i.e. suitable for the purposes described herein) CDR sequences and/or these CDR sequences can be obtained in any manner known per se, for example from Nanobodies (preferred), $V_H$ domains from conventional antibodies (and in particular from human antibodies), heavy chain antibodies, conventional 4-chain antibodies (such as conventional human 4-chain antibodies) or other immunoglobulin sequences directed against TNF. Such immunoglobulin sequences directed against xxxx can be generated in any manner known per se, as will be clear to the skilled person, i.e. by immunization with TNF or by screening a suitable library of immunoglobulin sequences with TNF, or any suitable combination thereof. Optionally, this may be followed by techniques such as random or site-directed mutagenesis and/or other techniques for affinity maturation known per se. Suitable techniques for generating such immunoglobulin sequences will be clear to the skilled person, and for example include the screening techniques reviewed by Hoogenboom, Nature Biotechnology, 23, 9, 1105-1116 (2005). Other techniques for generating immunoglobulins against a specified target include for example the Nanoclone technology (as for example described in the non-prepublished U.S. provisional patent application 60/648,922), so-called SLAM technology (as for example described in the European patent application 0 542 810), the use of transgenic mice expressing human immunoglobulins or the well-known hybridoma techniques (see for example Larrick et al, Biotechnology, Vol. 7, 1989, p. 934). All these techniques can be used to generate immunoglobulins against TNF, and the CDR's of such immunoglobulins can be used in the Nanobodies of the invention, i.e. as outlined above. For example, the sequence of such a CDR can be determined, synthesized and/or isolated, and inserted into the sequence of a Nanobody of the invention (e.g. so as to replace the corresponding native CDR), all using techniques known per se such as those described herein, or Nanobodies of the invention containing such CDR's (or nucleic acids encoding the same) can be synthesized de novo, again using the techniques mentioned herein.

The invention will now be further described by means of the following non-limiting examples and figures, in which the Figures show:

MONOVALENT TNFα NANOBODIES

FIG. 1: Sequence alignment of human TNFα nanobodies

FIG. 2: Sequence alignment of serum albumin specific TNFα nanobodies

FIG. 3: Binding of albumin specific TNFα nanobodies to human serum albumin

Figure 4:
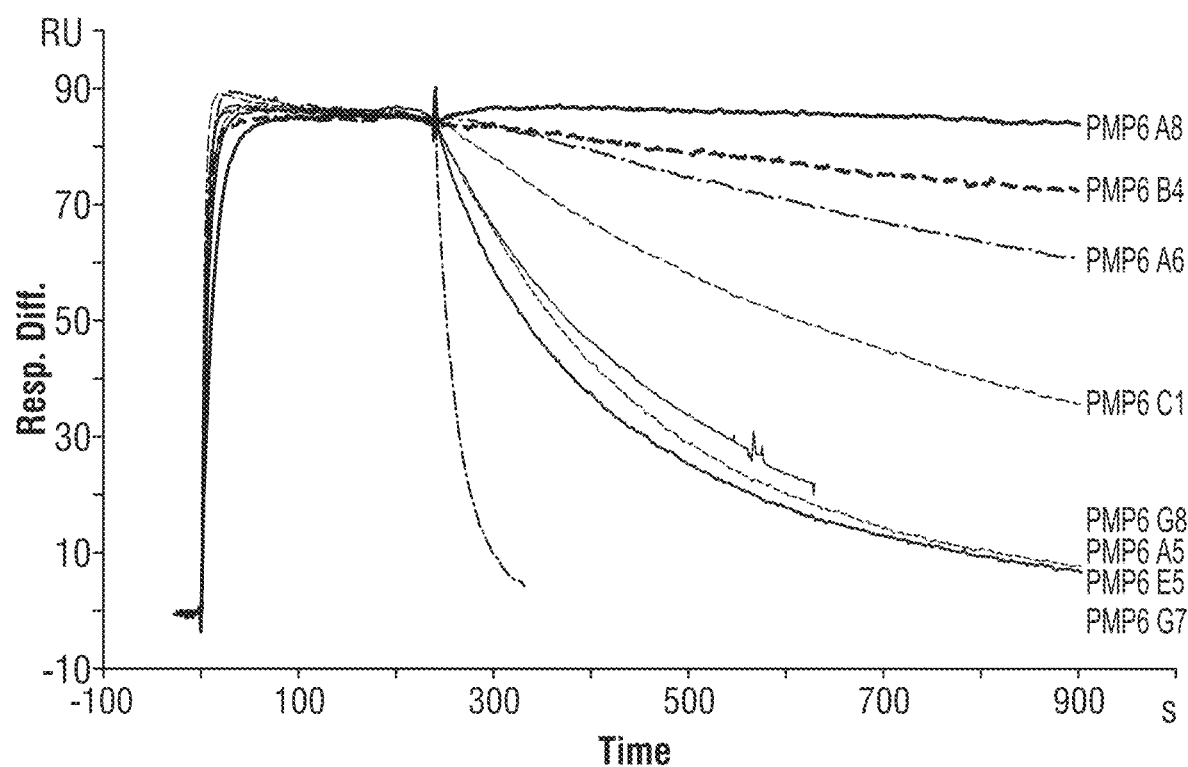

FIG. 4: Binding of albumin specific TNFα nanobodies to rhesus serum albumin

Figure 5:
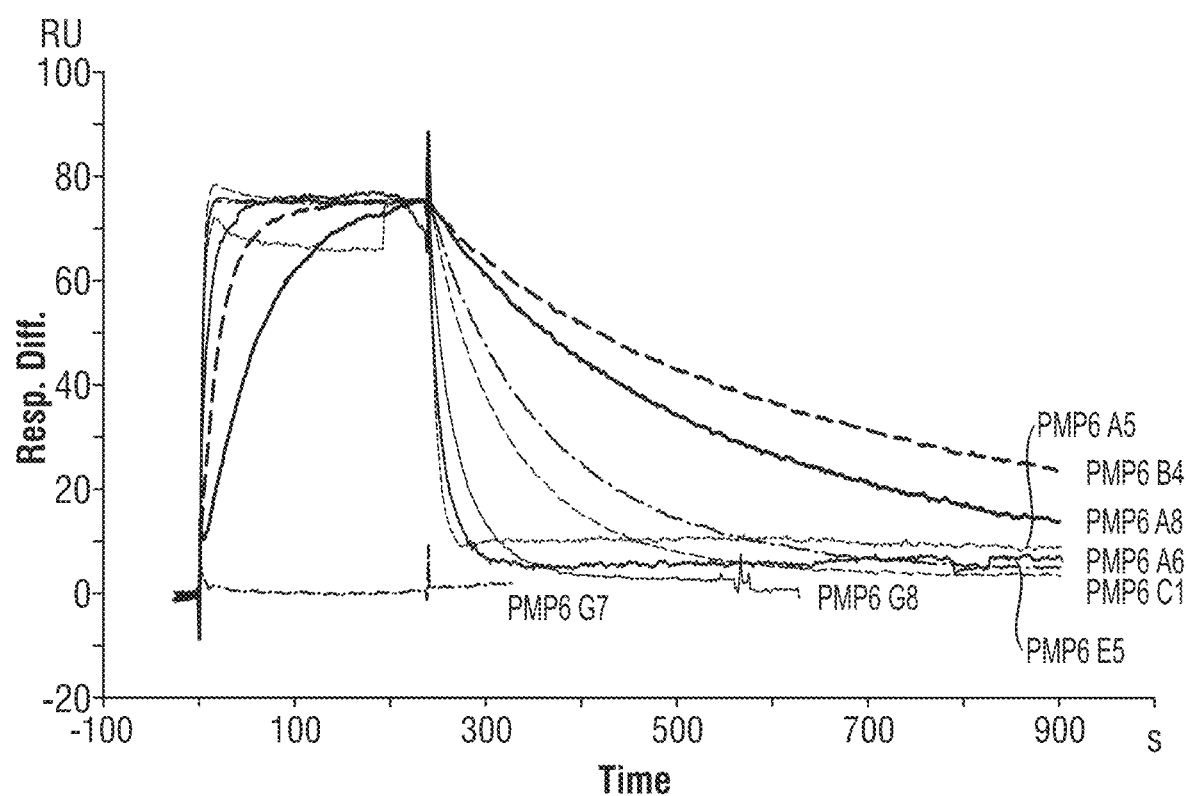

FIG. 5: Binding of albumin specific TNFα nanobodies to mouse serum albumin

Figure 6:
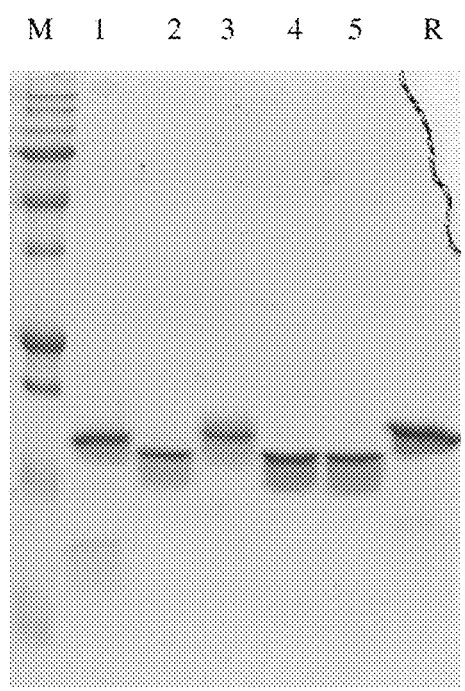

FIG. 6: Purity of TNFα and serum albumin nanobodies (SDS-PAGE)

Figure 7:
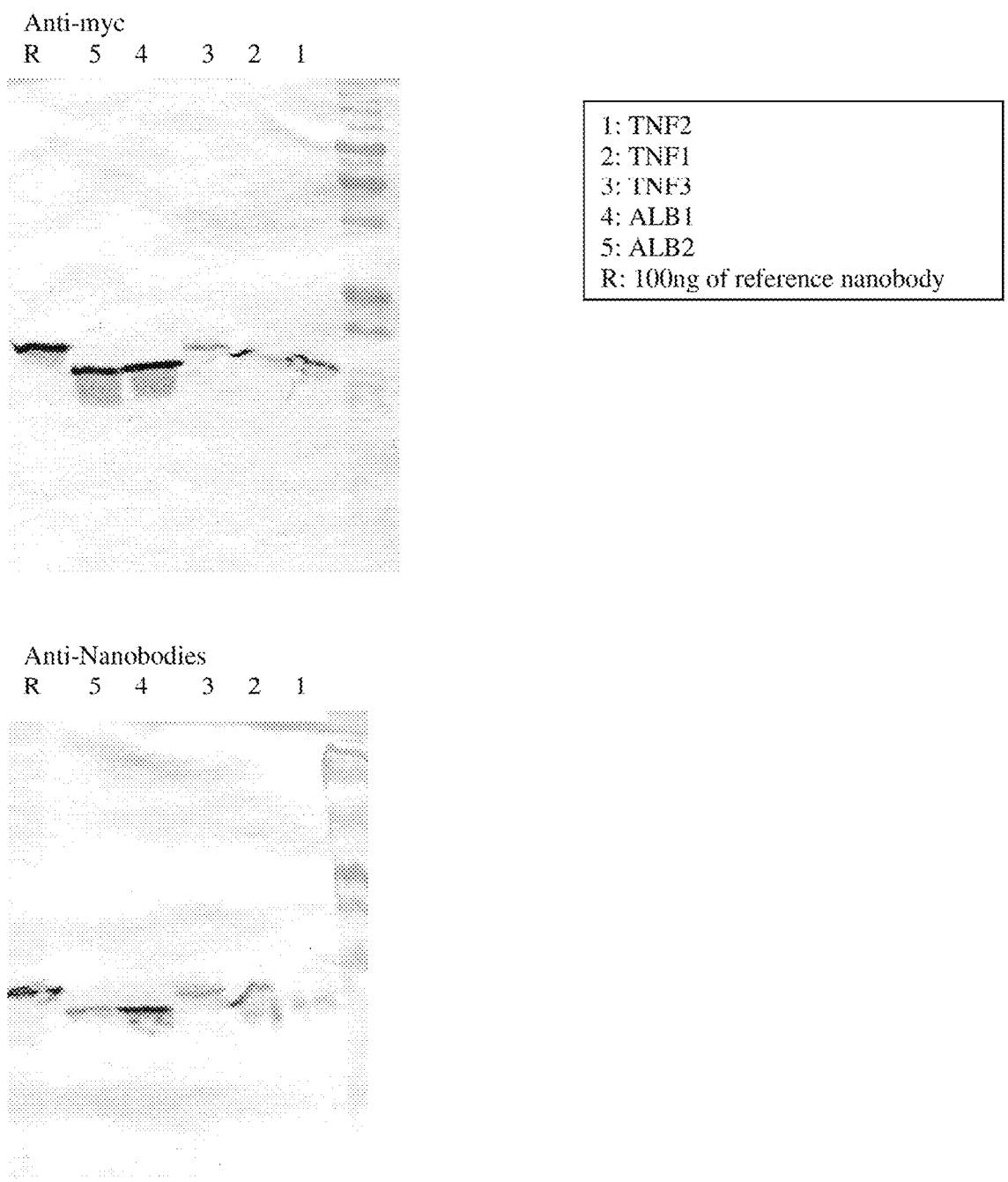

FIG. 7: Western Blot analysis of TNFα and serum albumin nanobodies

Figure 8:
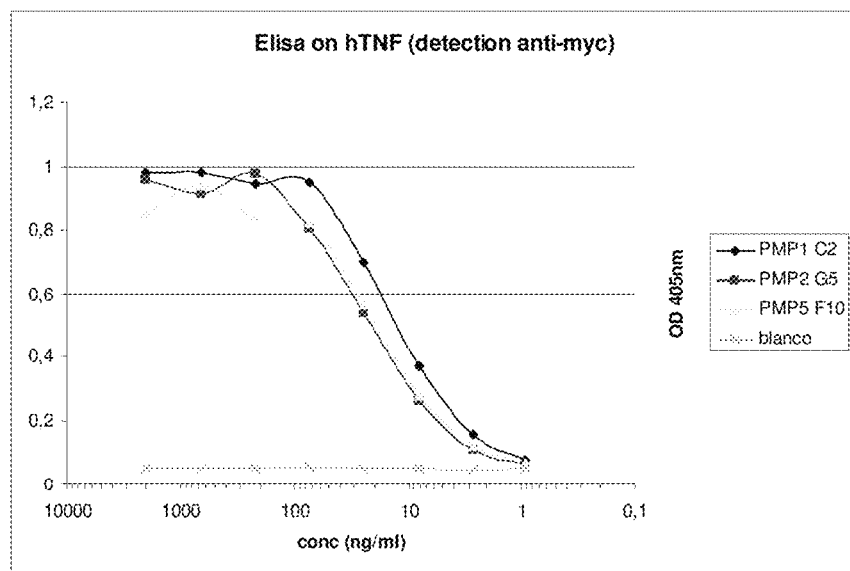

FIG. 8: Binding of TNFα nanobodies to human TNFα (ELISA)

Figure 9:
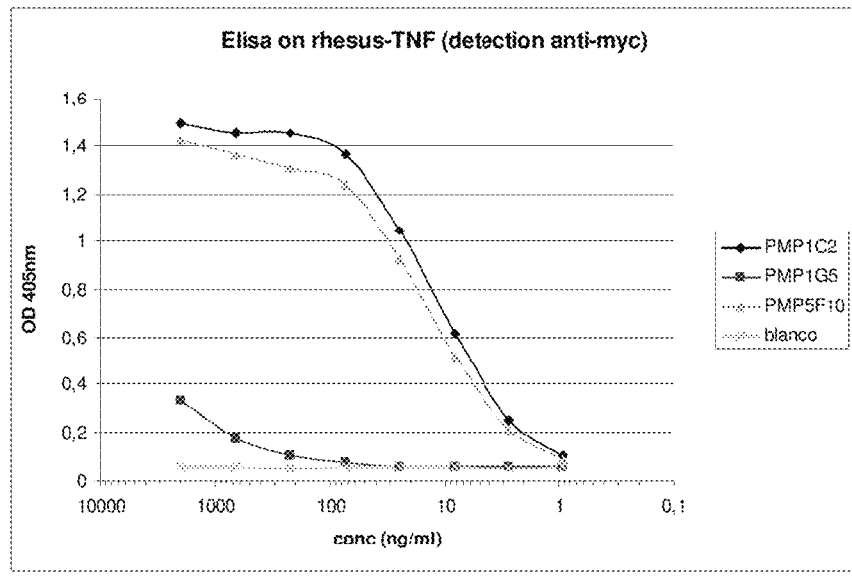

FIG. 9: Binding of TNFα nanobodies to rhesus TNFα (ELISA)

Figure 10:
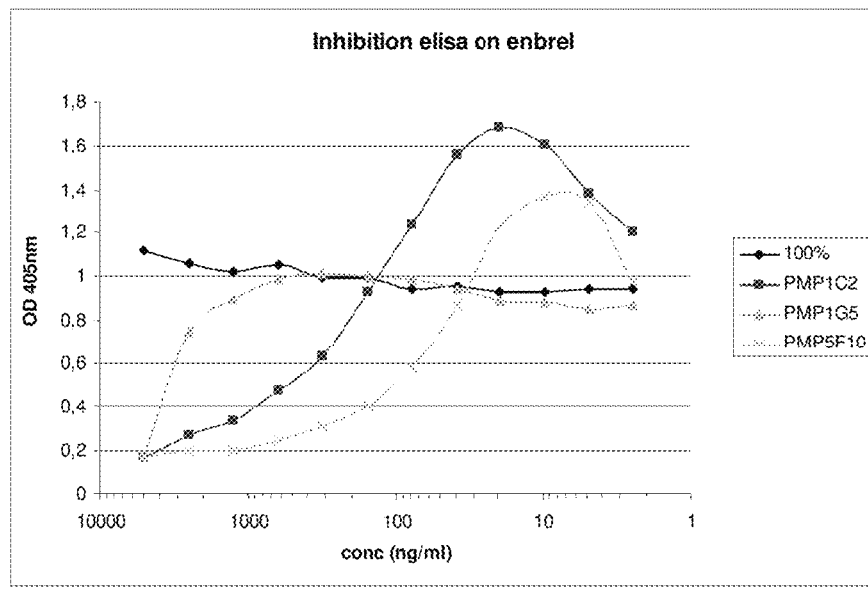

FIG. 10: Receptor-inhibition assay on Enbrel for human TNFα

Figure 11:
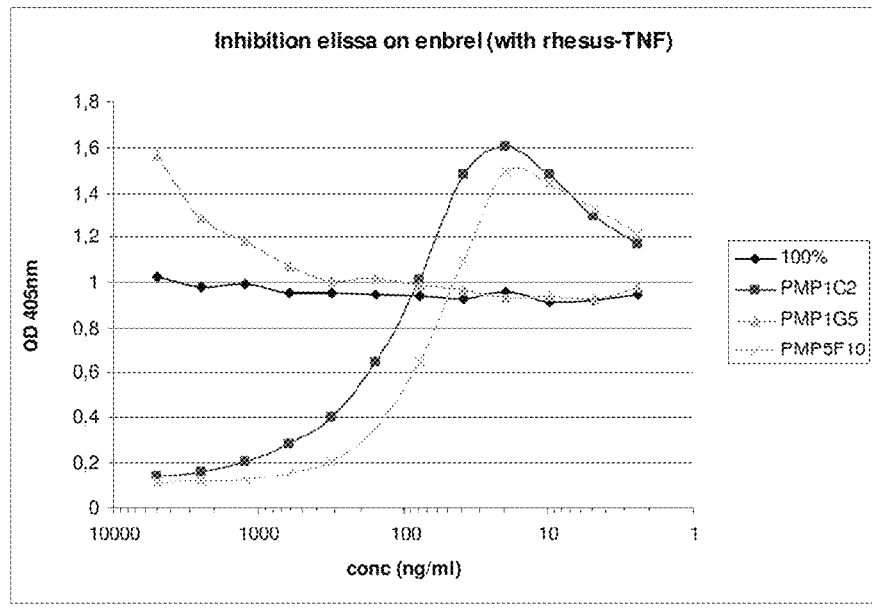

FIG. 11: Receptor-inhibition assay on Enbrel for rhesus TNFα

Figure 12:
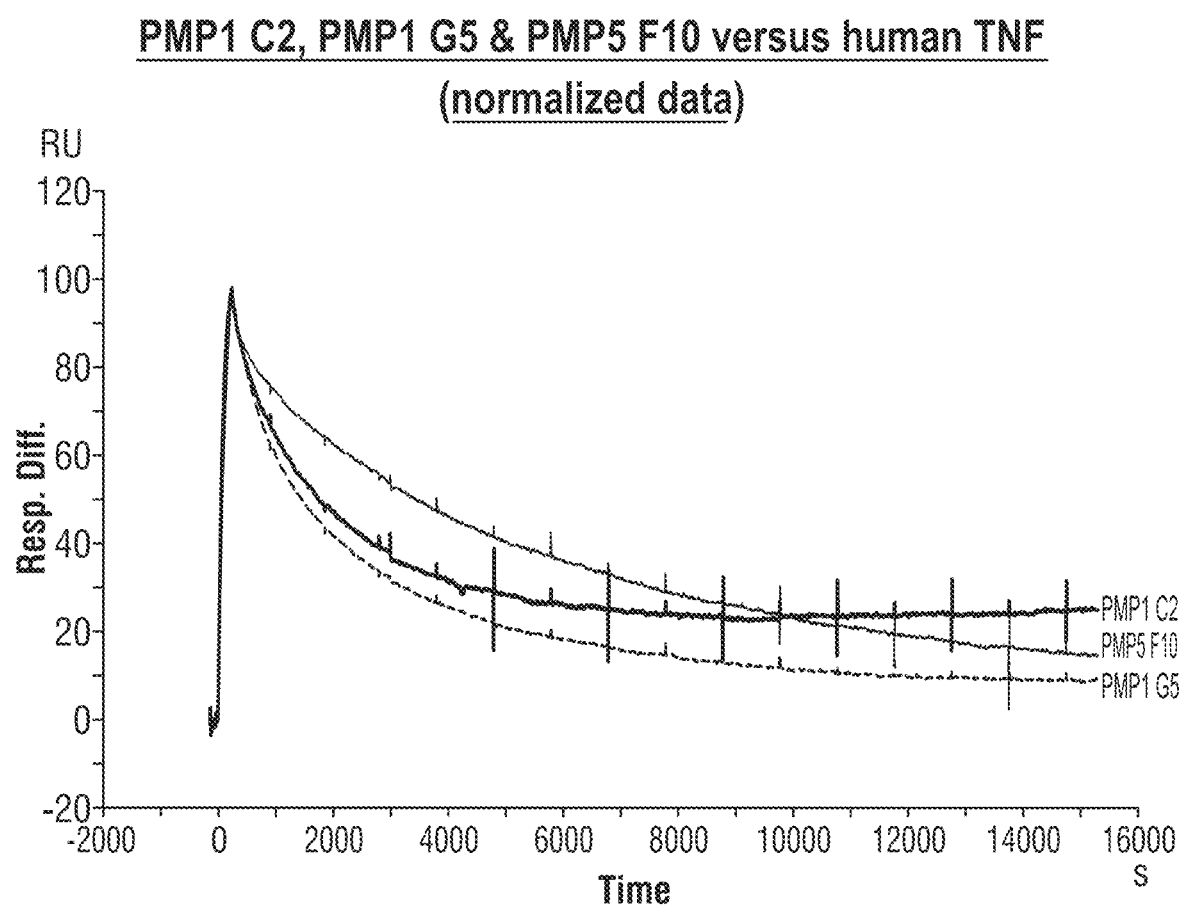

FIG. 12: Binding of TNFα nanobodies to human TNFα (Biacore)

Figure 13:
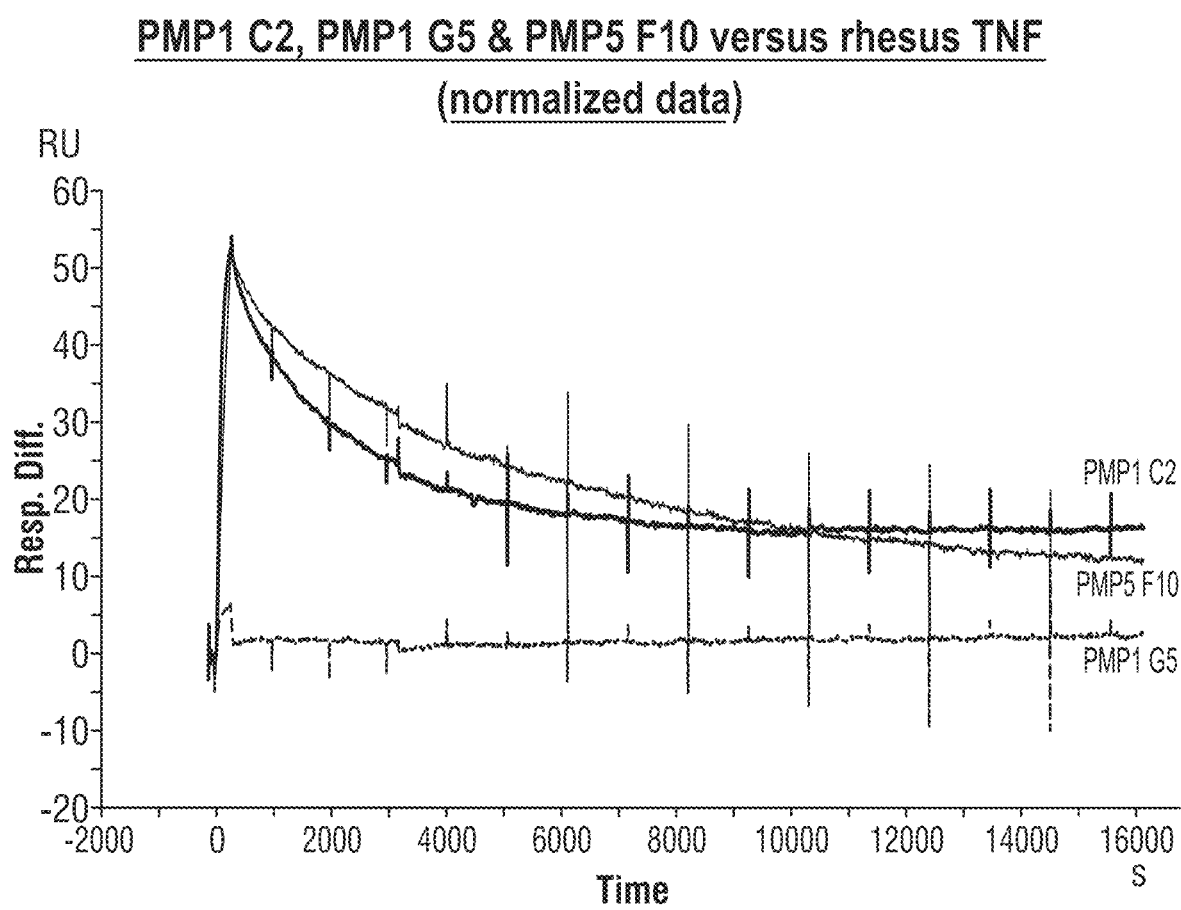

FIG. 13: Binding of TNFα nanobodies to rhesus TNFα (Biacore)

Figure 14:
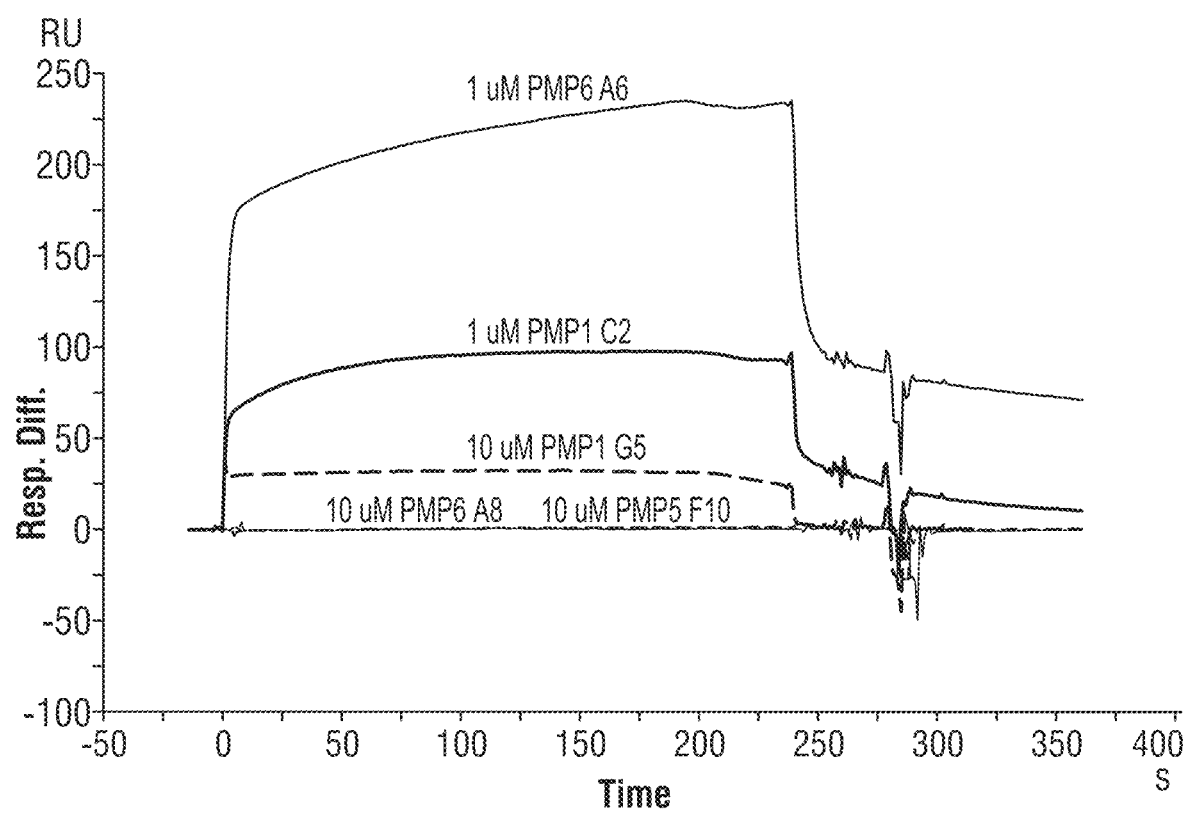

FIG. 14: Binding of TNFα nanobodies to Protein A (Biacore)

FIG. 15: Temperature treatment of TNFα and serum albumin nanobodies (Western Blot)

Figure 16:
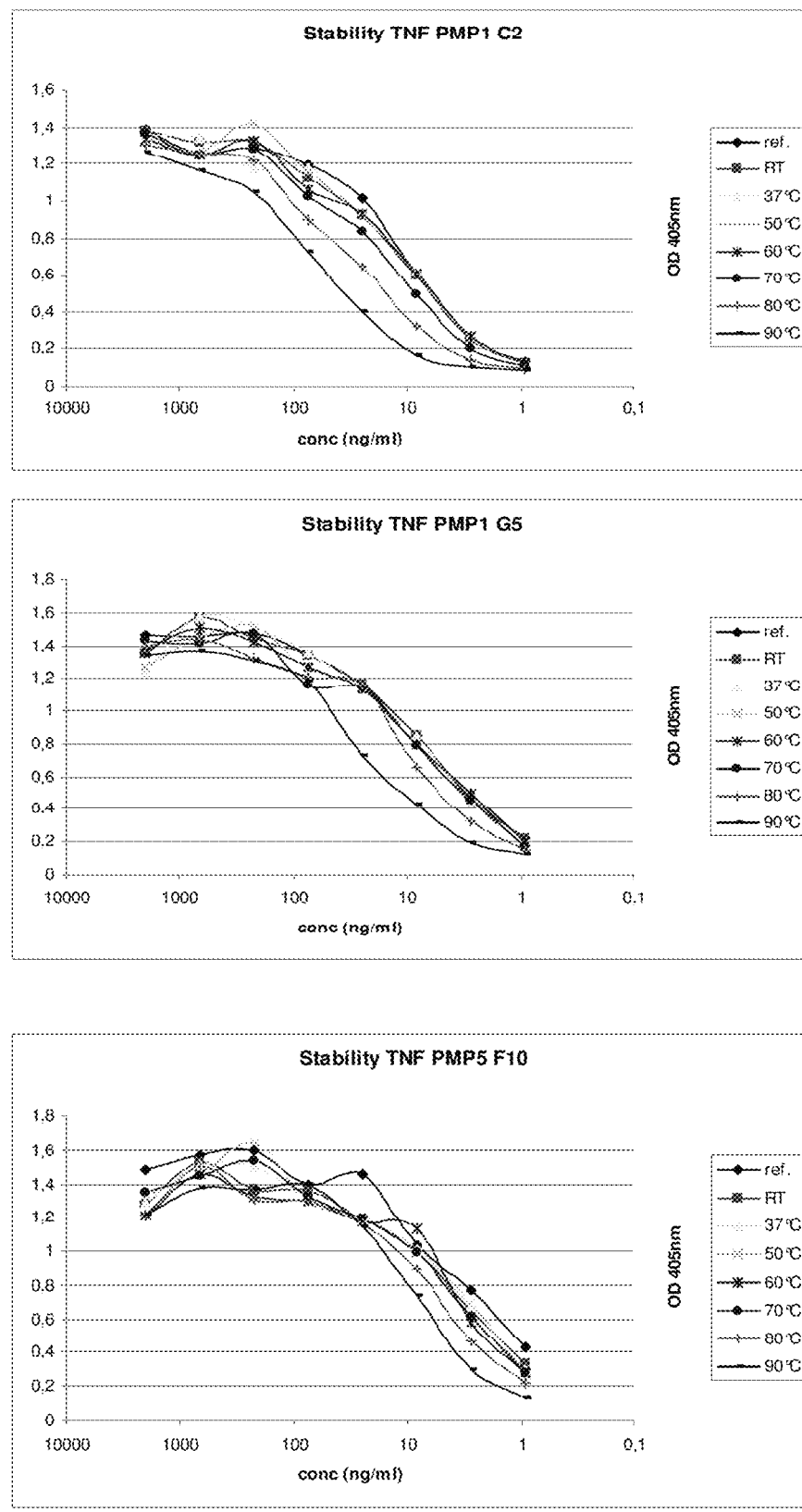

FIG. 16: Stability: temperature treatment of TNFα nanobodies (ELISA)

Figure 17:
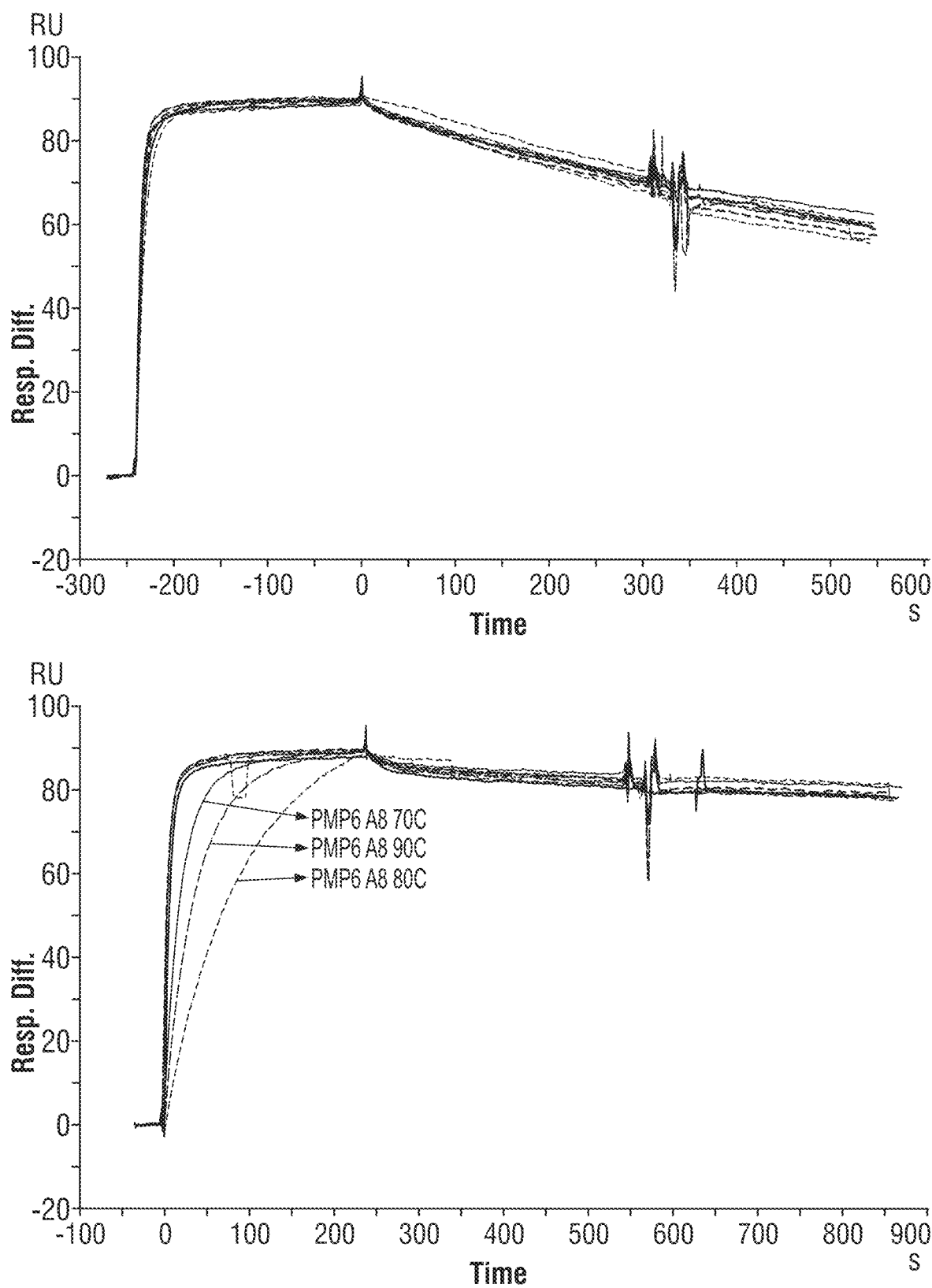

FIG. 17: Temperature treatment of serum albumin nanobodies (Biacore)

Bivalent TNFα nanobodies

Figure 18:

FIG. 18: Purity of bivalent TNFα nanobodies (SDS-PAGE)

FIG. 19: Western Blot analysis of bivalent TNFα nanobodies

Figure 20:
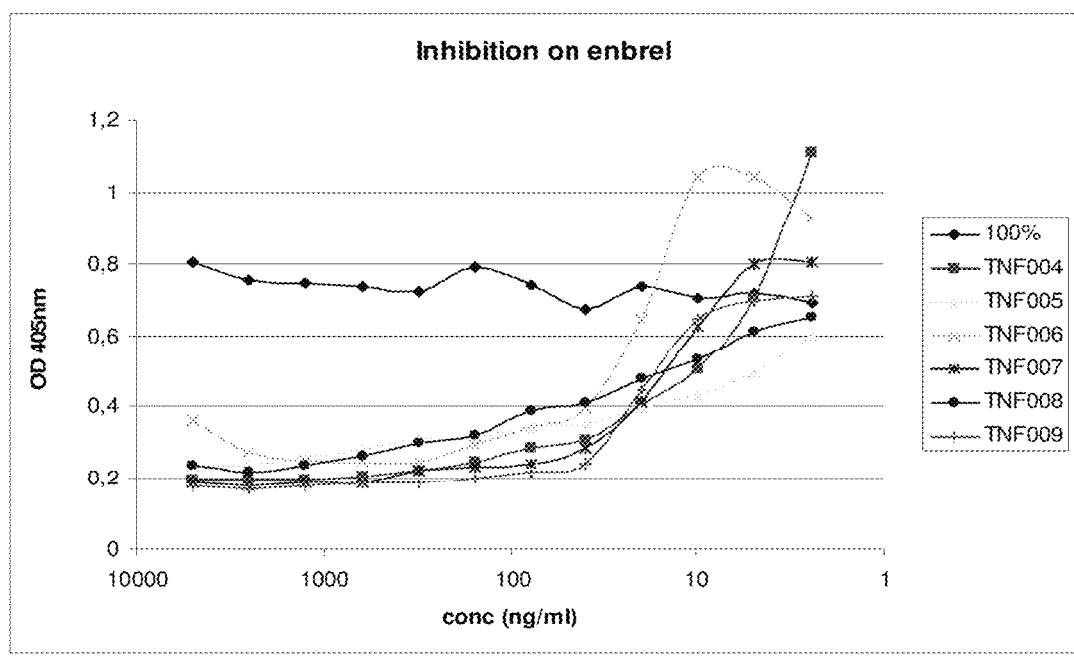

FIG. 20: Receptor-inhibition assay on Enbrel for bivalent TNFα nanobodies

FIG. 21: Stability: temperature treatment of bivalent TNFα nanobodies (ELISA)

Humanised monovalent TNFα nanobodies

FIG. 22: Multiple sequence alignment of TNF1 humanised nanobodies; DP51 is SEQ ID NO: 472, DP53 is SEQ ID NO: 473.

FIG. 23: Multiple sequence alignment of TNF2 humanised nanobodies; DP54 is SEQ ID NO: 474.

FIG. 24: Multiple sequence alignment of TNF3 humanised nanobodies; DP29 is SEQ ID NO: 475.

FIG. 25: Multiple sequence alignment of ALB1 humanised nanobodies

Figure 26:
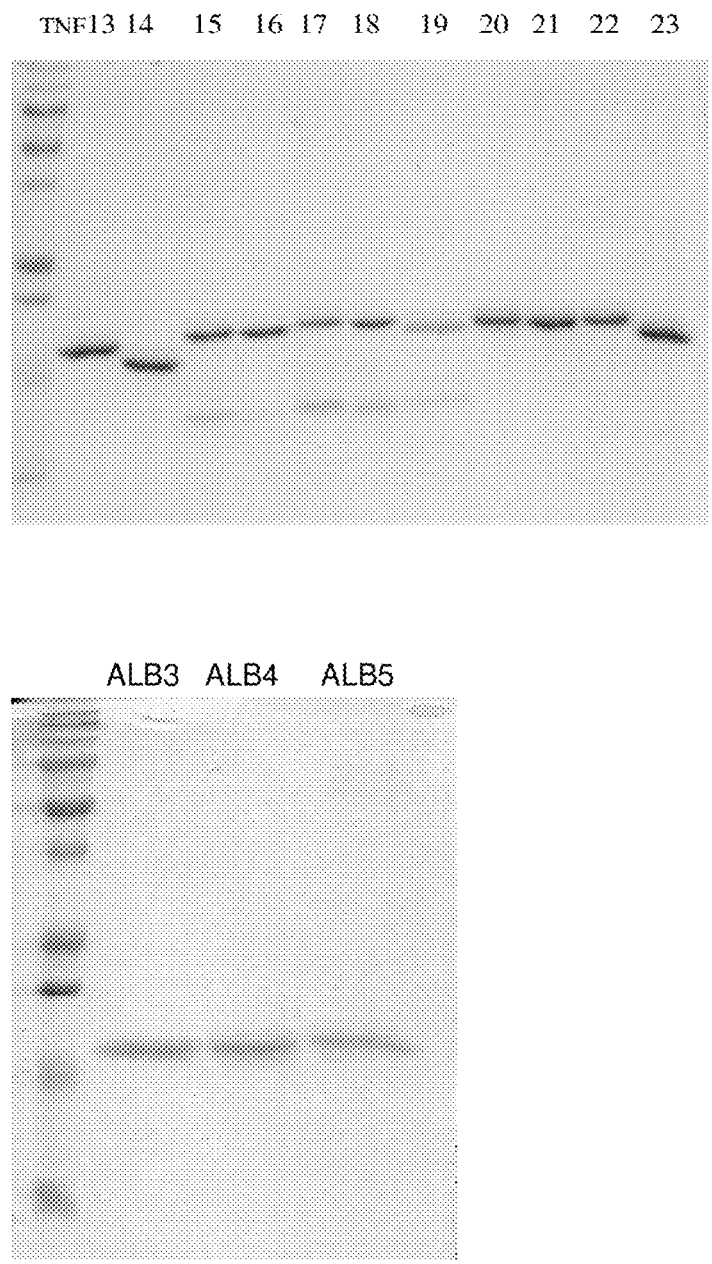

FIG. 26: Purity of humanised TNFα and serum albumin nanobodies (SDS-PAGE)

Figure 27:
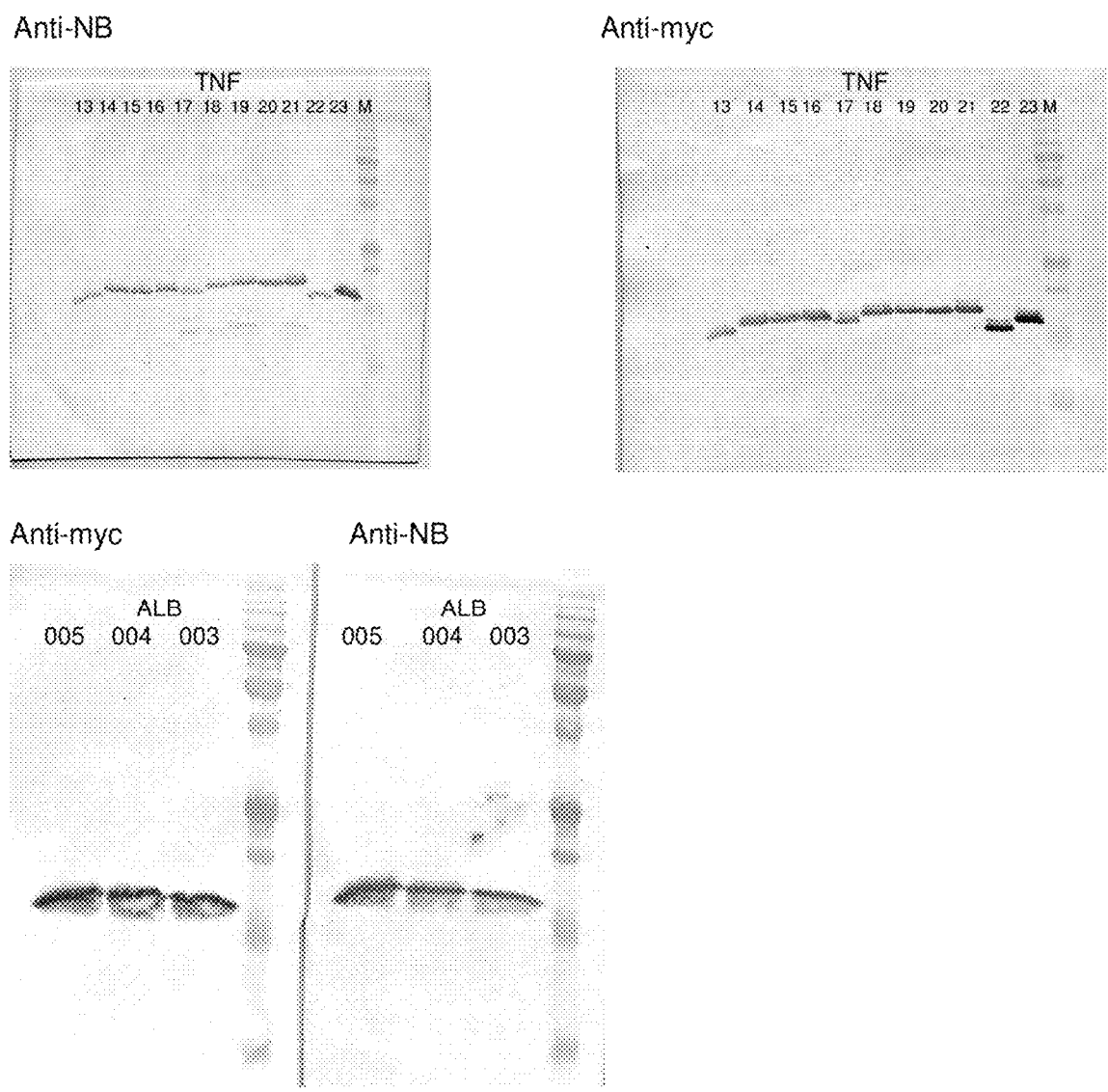

FIG. 27: Western Blot analysis of humanised TNFα and serum albumin nanobodies

Figure 28:
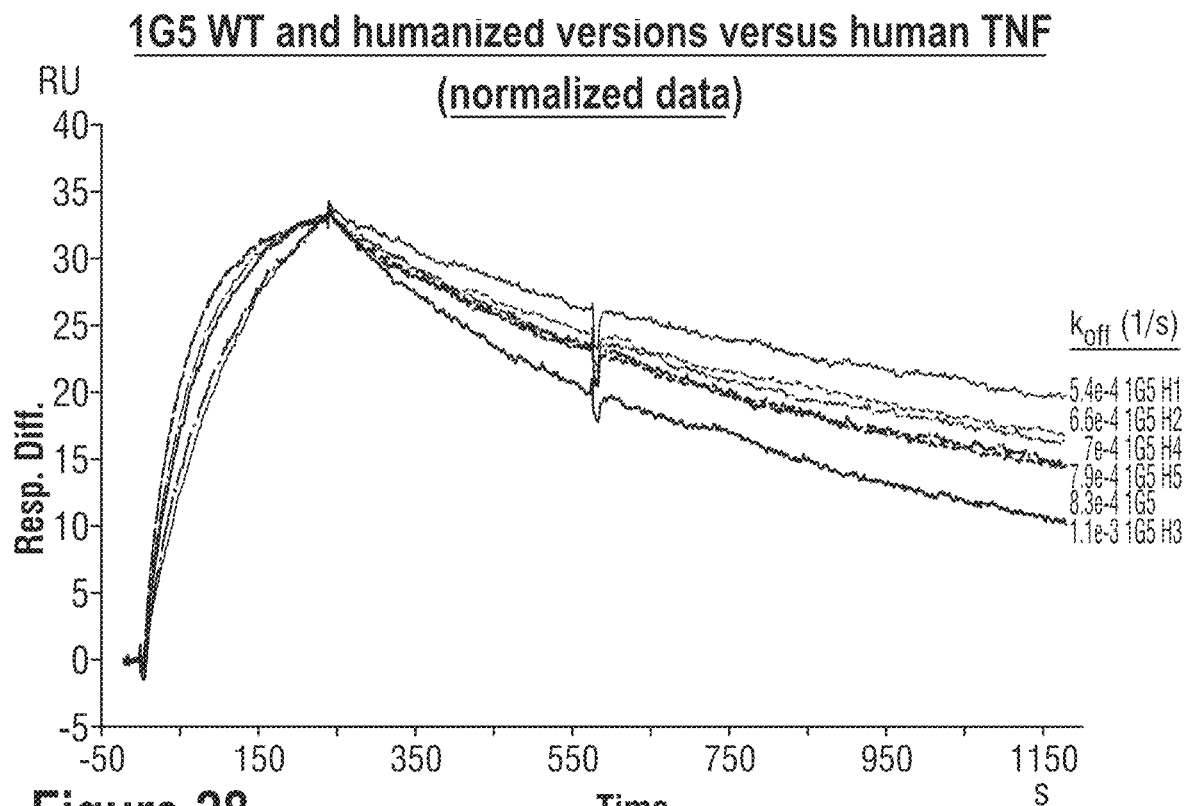

FIG. 28: Binding of humanised TNFα nanobodies to human TNFα

Figure 29:
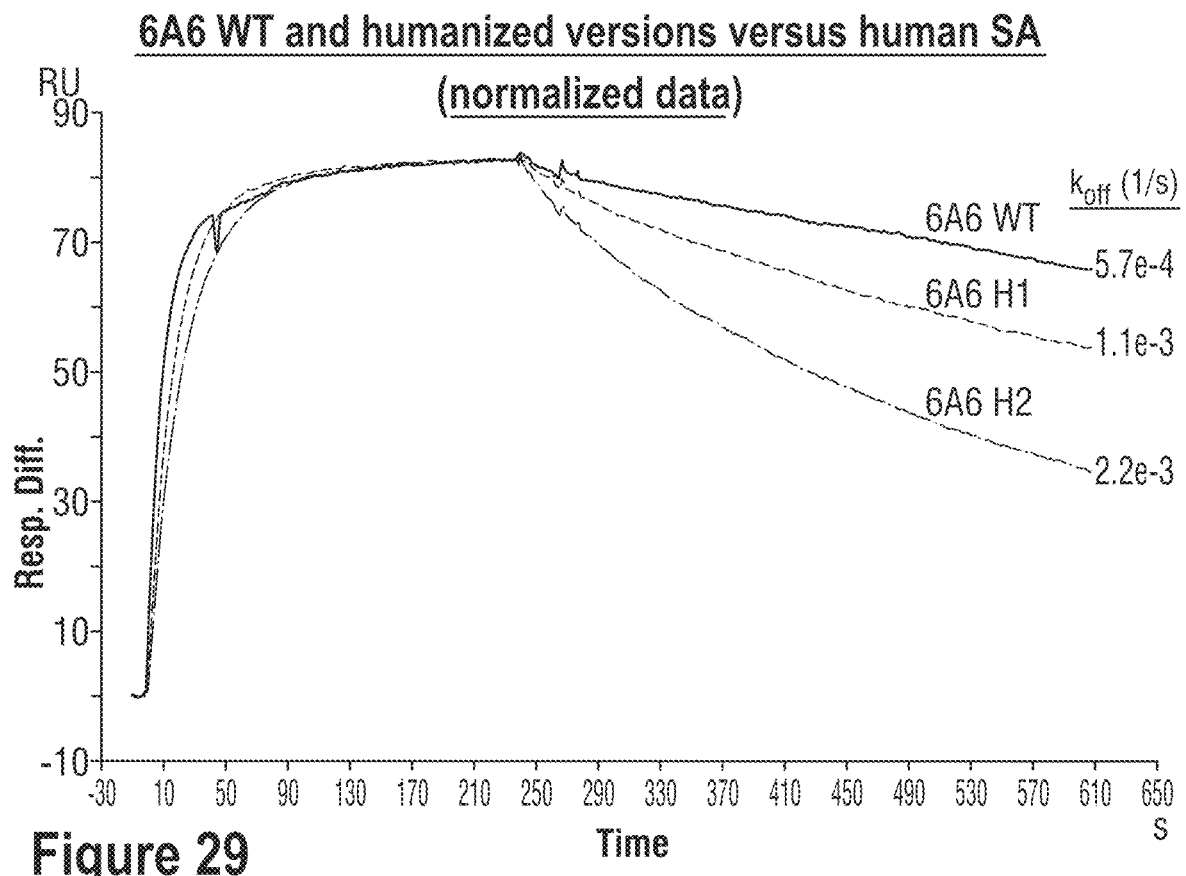

FIG. 29: Binding of humanised serum albumin nanobodies to human serum albumin

FIG. 30: Stability: temperature treatment of humanised TNFα nanobodies (ELISA)

Trivalent TNFα nanobodies

Figure 31:
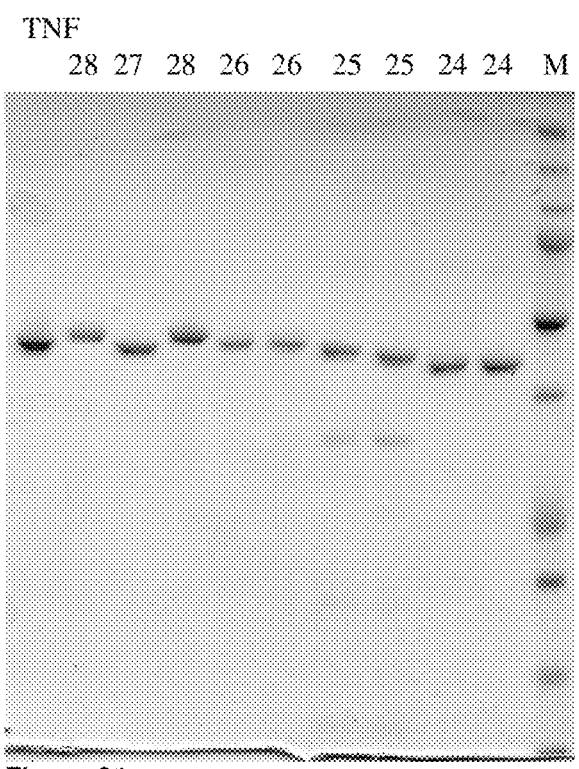

FIG. 31: Purity of trivalent TNFα nanobodies (SDS-PAGE)

FIG. 32: Western Blot analysis of trivalent TNFα nanobodies

Figure 33:
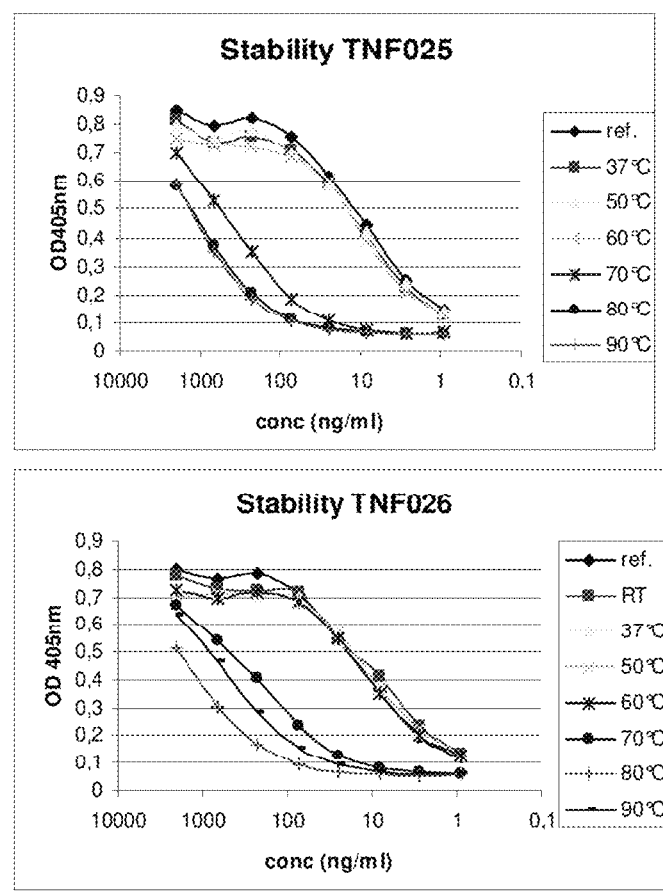

FIG. 33: Stability: temperature treatment of trivalent TNFα nanobodies (ELISA)

Humanised monovalent TNFα nanobodies (second round)

FIG. 34: Multiple sequence alignment of TNF1 humanised nanobodies

FIG. 35: Multiple sequence alignment of TNF2 humanised nanobodies

FIG. 36: Multiple sequence alignment of TNF3 humanised nanobodies

FIG. 37: Multiple sequence alignment of ALB1 humanised nanobodies

Figure 38:

FIG. 38: Purity of humanised TNFα nanobodies (SDS-PAGE)

Figure 39:
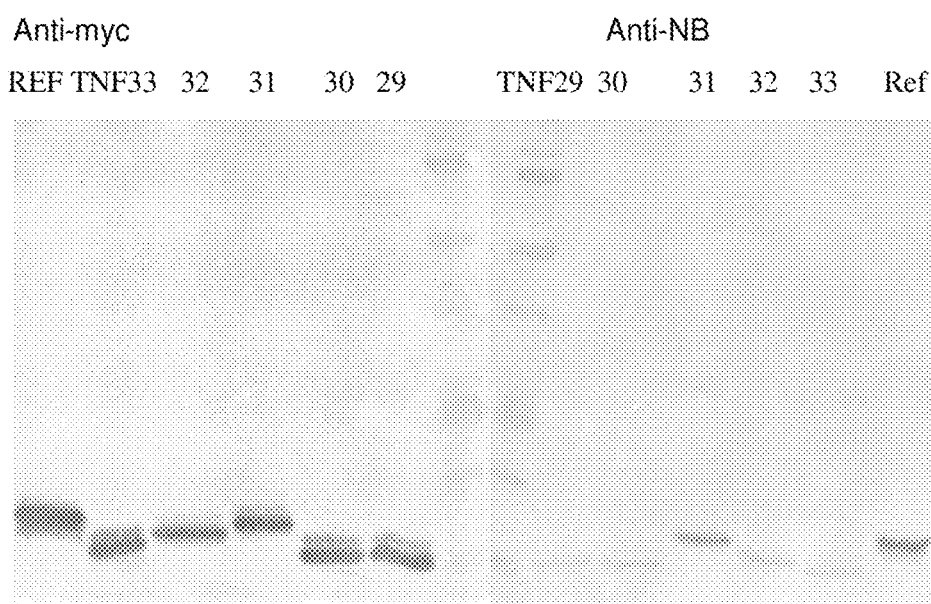

FIG. 39: Western Blot analysis of humanised TNFα nanobodies

FIG. 40: Binding of humanised TNFα nanobodies to human TNFα

Figure 41:
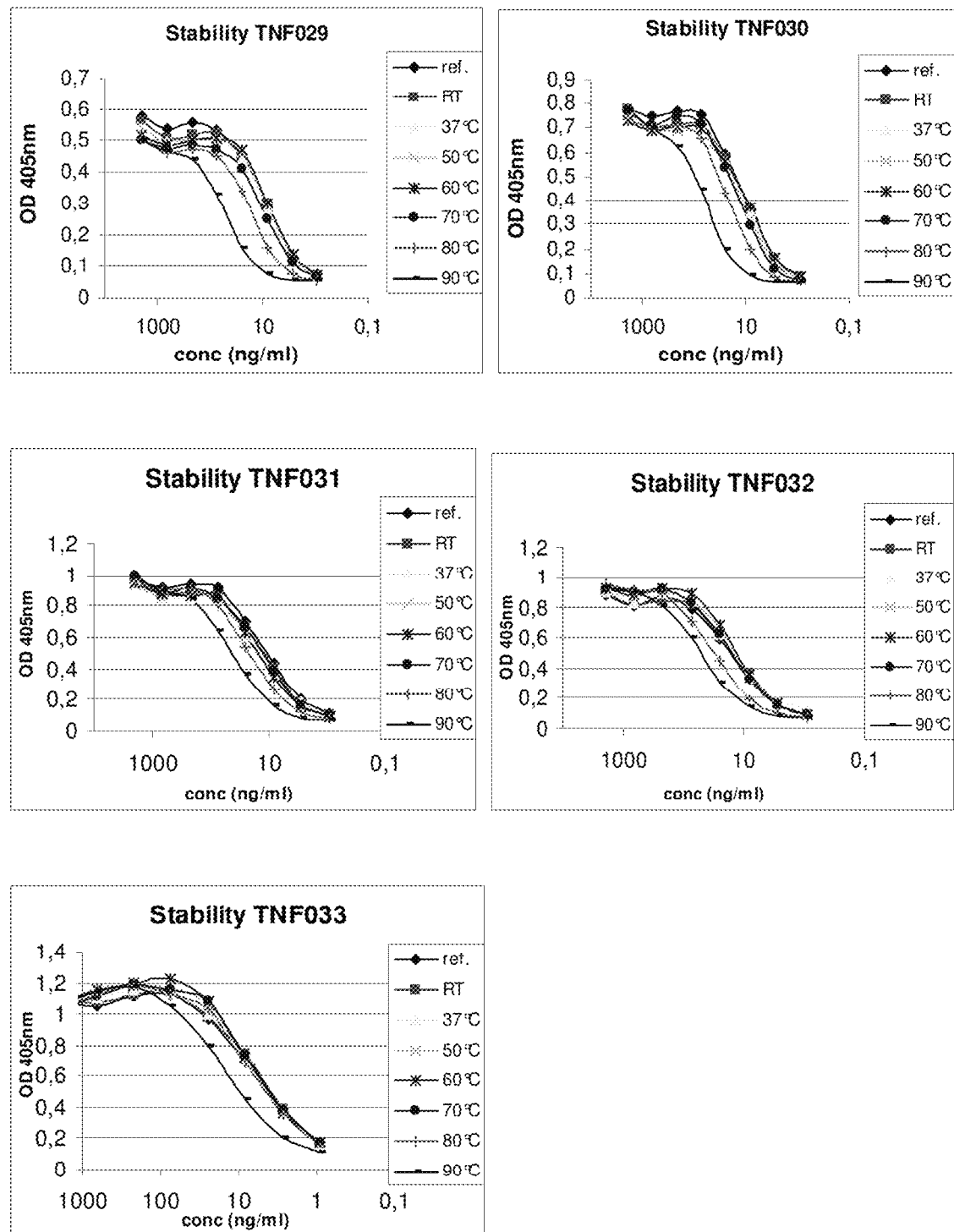

FIG. 41: Stability: temperature treatment of humanised TNFα nanobodies (ELISA)

Figure 42:
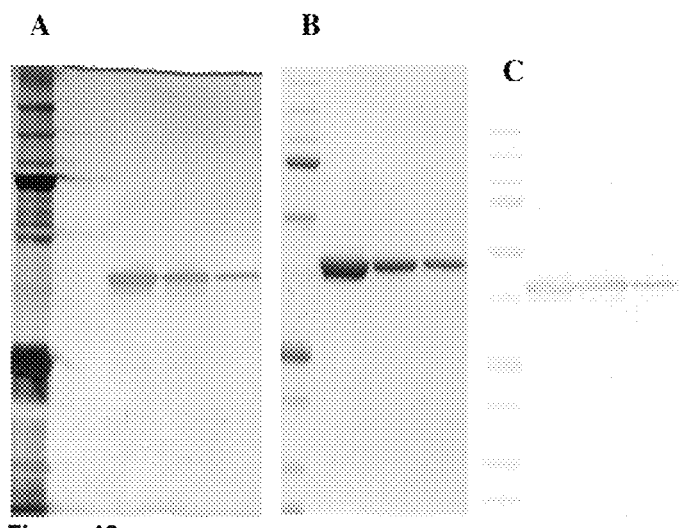

FIG. 42: Analysis of purified TNF60 on Silver stained SDS-PAGE gel (A) Coomassie stained SDS-PAGE gel (B) and in Western blot analysis using anti-NB (C) for detection FIG. 43: Chromatogram of analytical size exclusion of TNF60 on Superdex HR75

Figure 44:
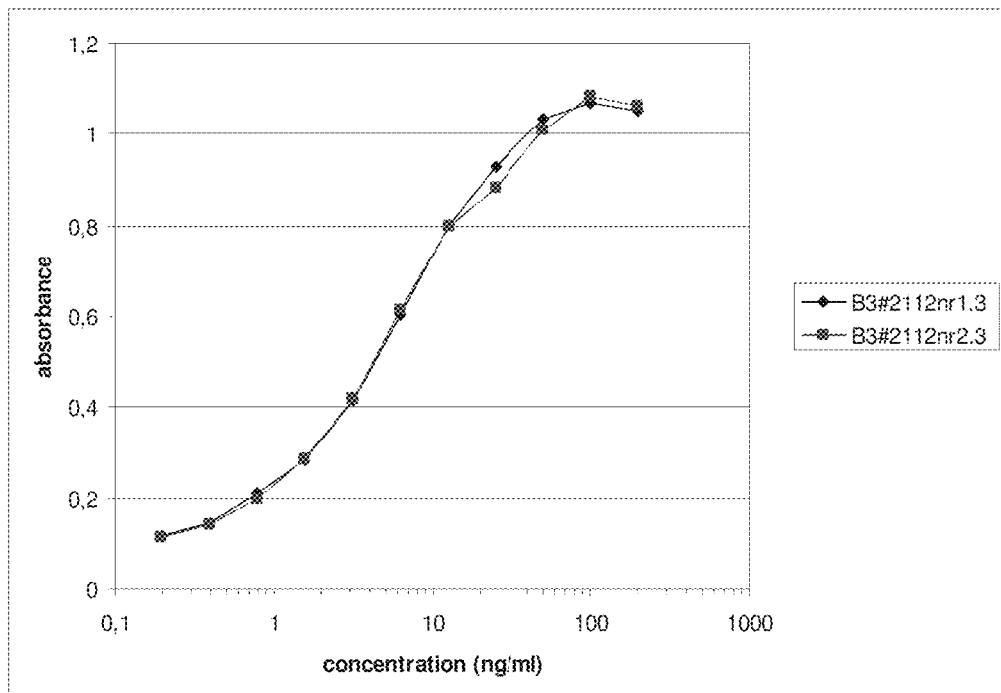

FIG. 44: Binding of TNF60 to human TNF-alpha

Figure 45:
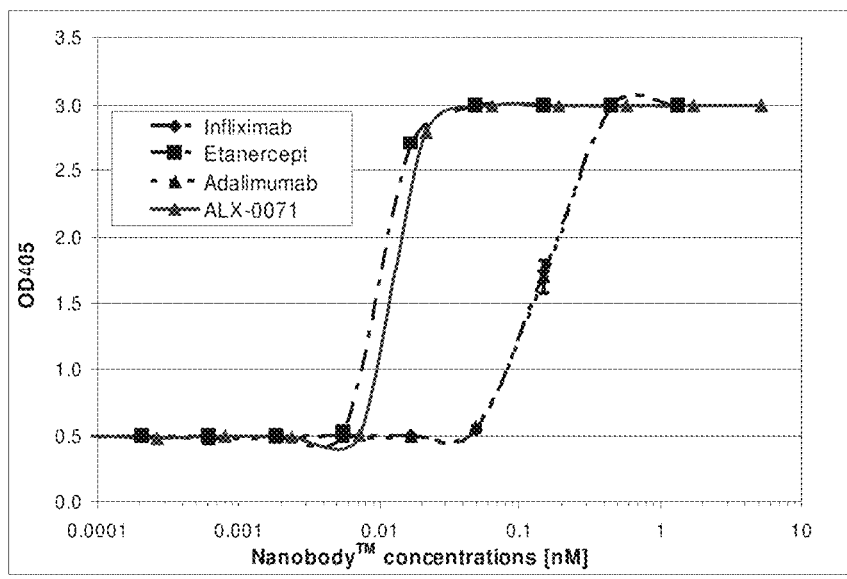

FIG. 45: Dose response curve obtained in cytotoxicity assay with human TNF-alpha using Nanobody™ TNF60 in comparison with Enbrel (Etanercept), Humira (Adalimumab) and Remicade (Infliximab)

Figure 46:
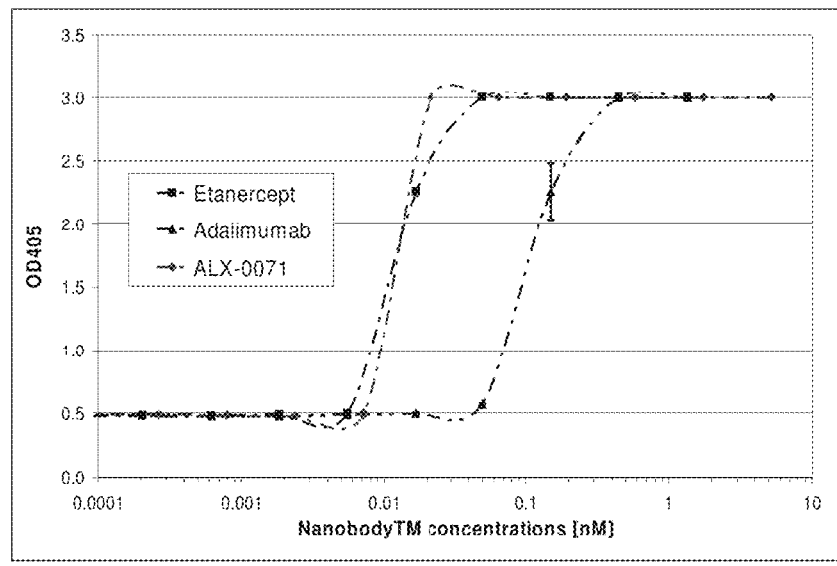

FIG. 46: Dose response curve obtained in cytotoxicity assay with rhesus TNFα using Nanobody™ TNF60 in comparison with Enbrel (Etanercept), Humira (Adalimumab) and Remicade (Infliximab)

Figure 47:
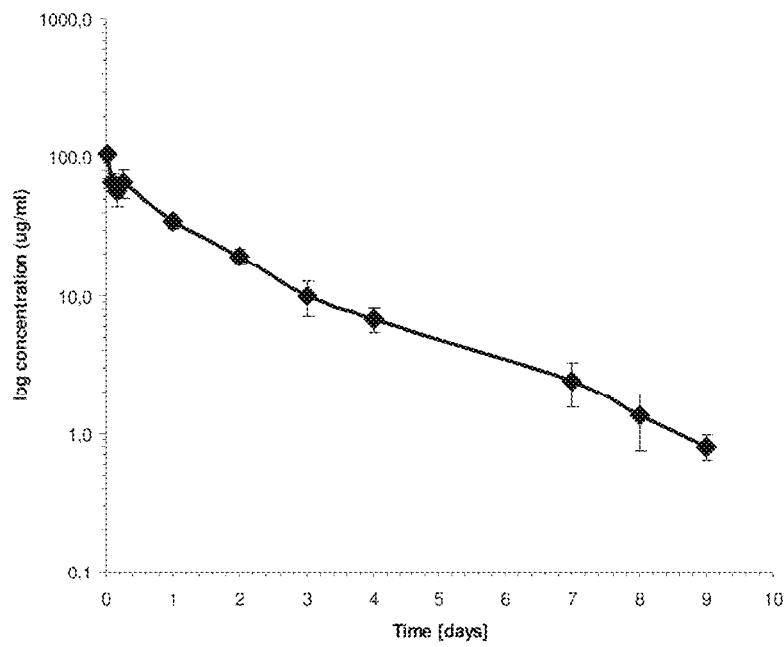

FIG. 47: Pharmacokinetic profile of TNF60 in mice

Figure 48:
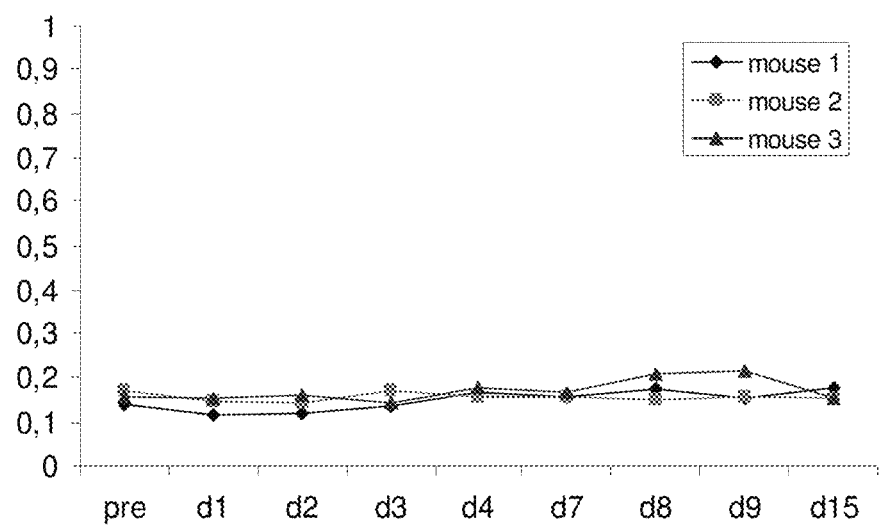

FIG. 48: Immunogenicity profile of TNF60 in mice

Figure 49:
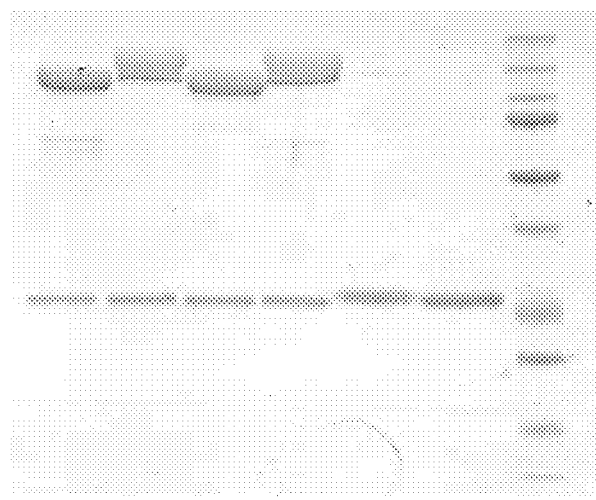
Figure 50:
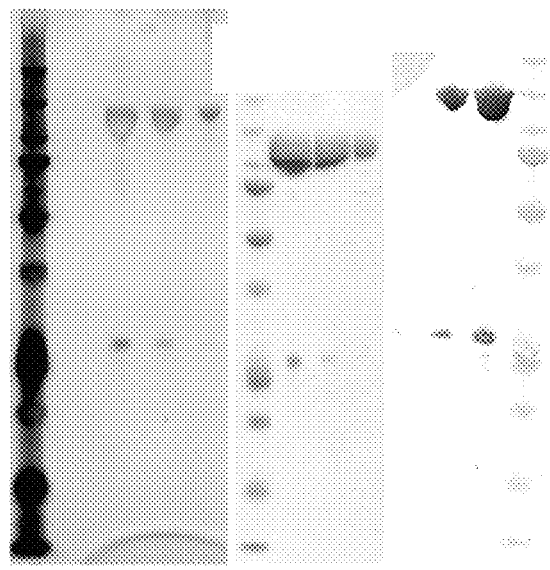

FIG. 49: Analysis of purified TNF56-PEG40, TNF56-PEG60, TNF56-biotine, TNF55-PEG40, TNF55-PEG60 and TNF55-biotine on Coomassie stained SDS-PAGE gel FIG. 50: Analysis of purified TNF56-PEG40 on SDS-PAGE gel using Silver stain (A) Coomassie stain (B) and in Western blot analysis using anti-NB (C) for detection FIG. 51: Chromatogram of analytical size exclusion of TNF56-PEG40 on Superdex HR 75

Figure 52:
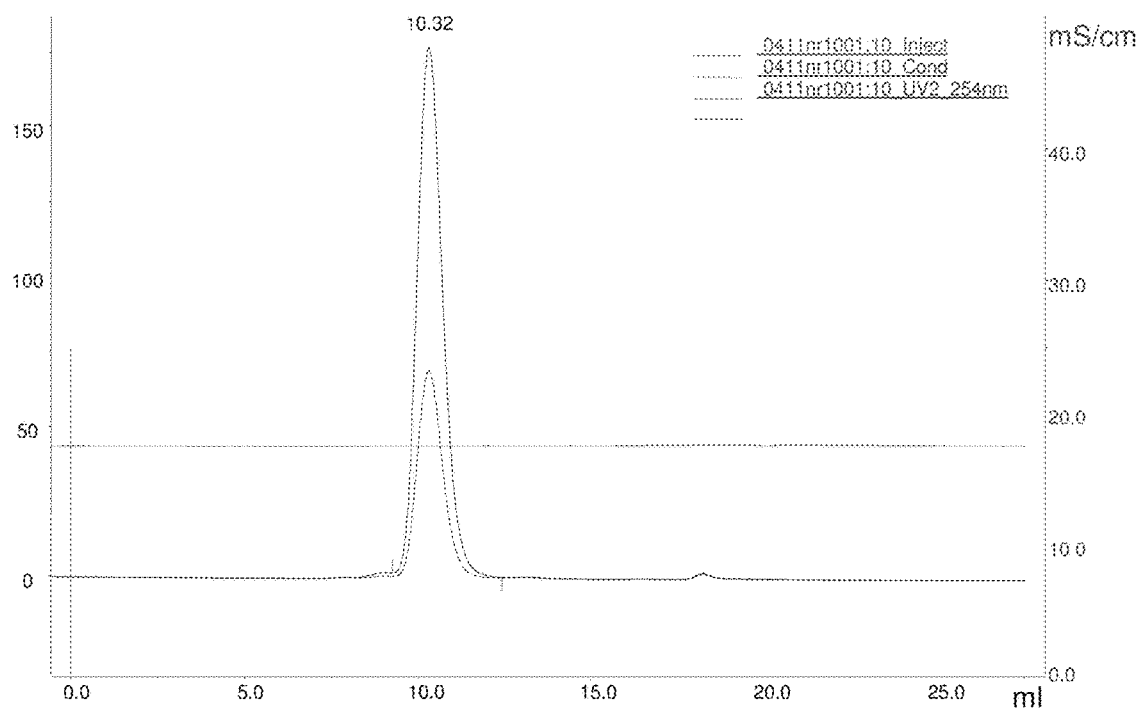

FIG. 52: Chromatogram of analytical size exclusion of TNF56-PEG40 on Superdex HR 200

Figure 53:
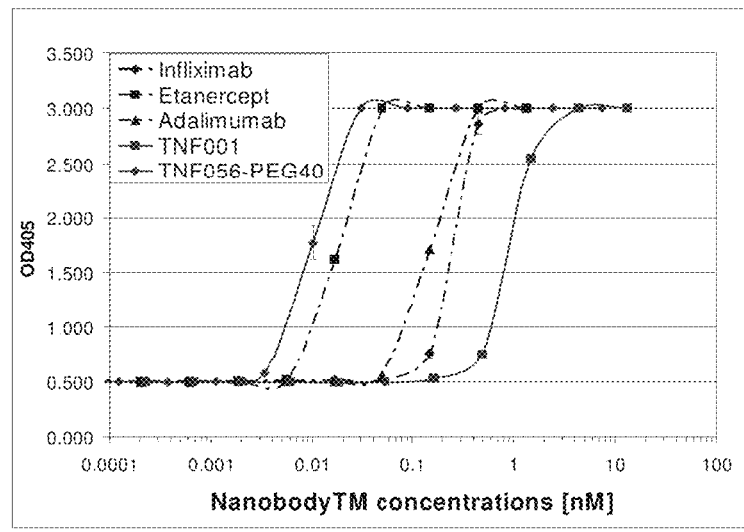

FIG. 53: Dose response curve obtained in cytotoxicity assay with human TNFα using Nanobody™ TNF56-PEG40 and the monovalent wild-type Nanobody™ TNF1 in comparison with Enbrel (Etanercept), Humira (Adalimumab) and Remicade (Infliximab)

Figure 54:
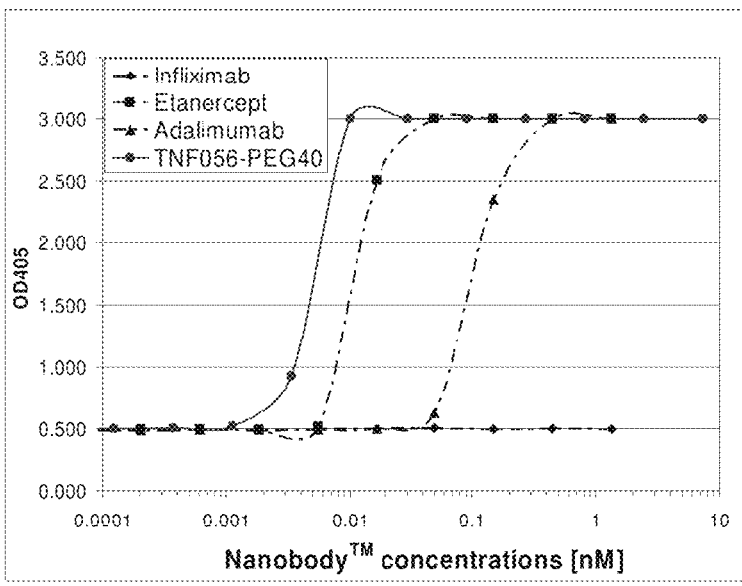

FIG. 54: Dose response curve obtained in cytotoxicity assay with rhesus TNFα using Nanobody™ TNF56-PEG40 in comparison with Enbrel (Etanercept), Humira (Adalimumab) and Remicade (Infliximab)

Figure 55:
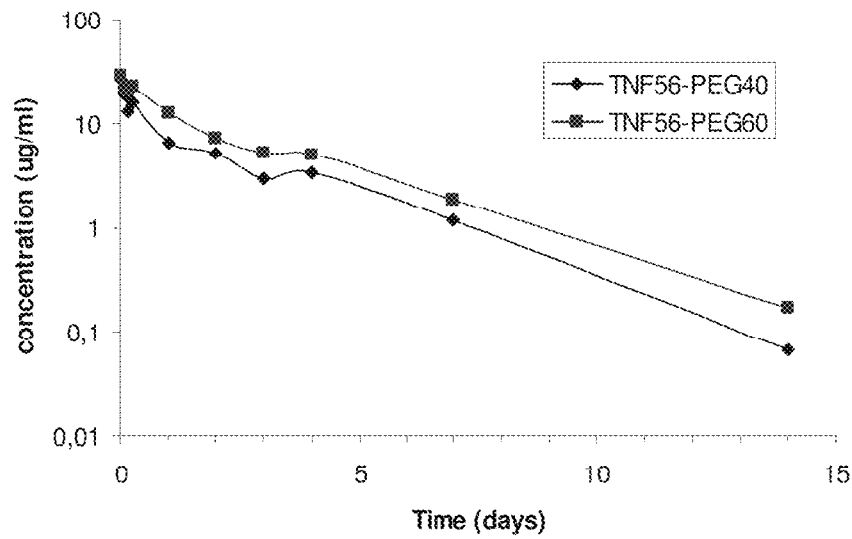
Figure 56:
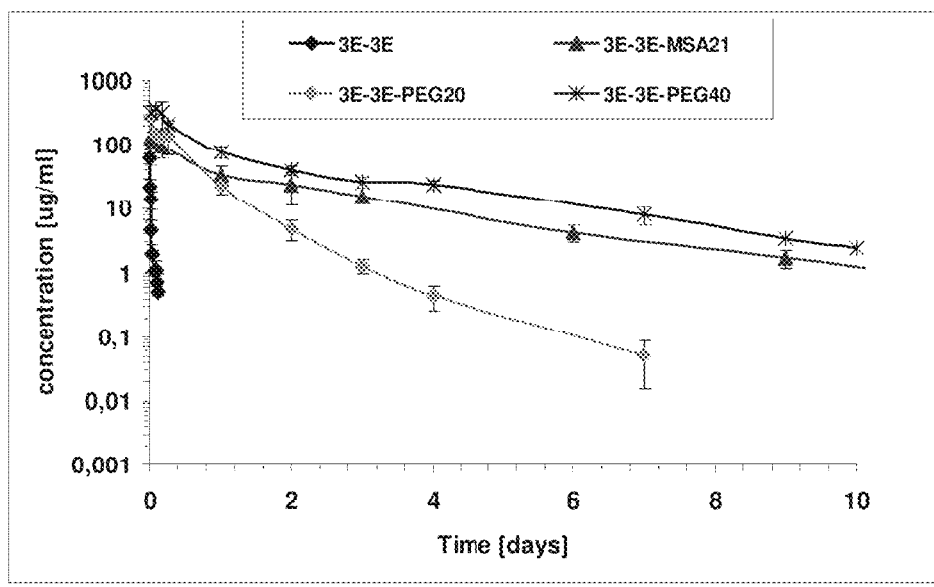
Figure 57:
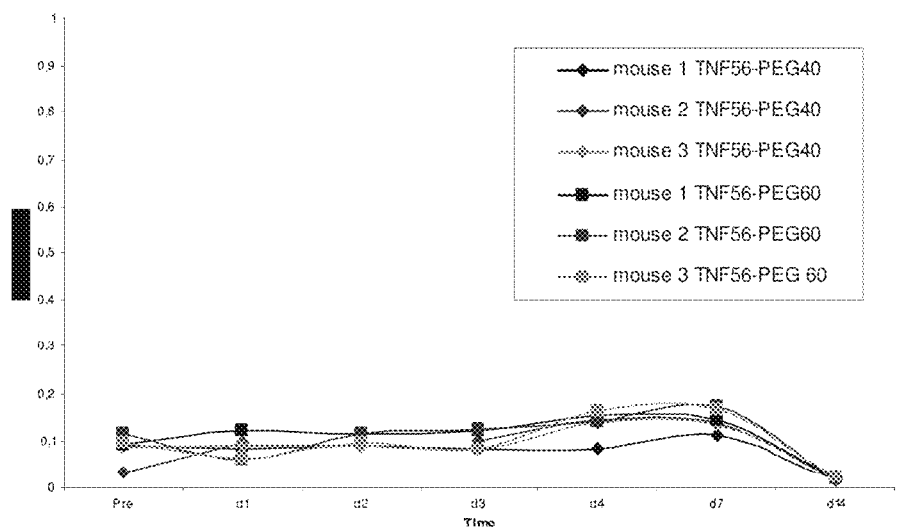

FIG. 55: Pharmacokinetic analysis of pegylated bivalent Nanobody™ TNF56-PEG40 and TNF56-PEG60 after intravenous administration in mice FIG. 56: Pharmacokinetic analysis of pegylated bivalent Nanobody™ 3E-3E-PEG20, pegylated bivalent Nanobody™ 3E-3E-PEG40 and bispecific Nanobody™ 3E-3E-AR1 after intravenous administration in mice FIG. 57: Immunogenicity profile of TNF56-PEG40 and TNF56-PEG60 in mice FIG. 58: Efficacy of TNF60 in the prevention of chronic polyarthritis in mice FIG. 59: Efficacy of TNF60 in therapeutic treatment of chronic polyarthritis in mice FIG. 60: Effect of TNF60 Nanobody™ formatting on efficacy in the prevention of chronic polyarthritis in mice FIG. 61: Sequence alignment of Nanobodies™ PMP1C2, 3E, 1A and 3G FIG. 62: Molecular model of TNF-60

The appended Tables form an integral part of the present specification and are as follows:

Monovalent TNFα nanobodies
  Table 8: Sequence listing of TNFα nanobodies
  Table 9: Koff values of human TNFα nanobodies
  Table 10: Homology of TNFα and serum albumin nanobodies to human germline sequences
  Table 11: Expression levels of TNFα and serum albumin nanobodies
  Table 12: ELISA binding to human and rhesus TNFα
  Table 13: Receptor-inhibition assay of TNFα nanobodies
  Table 14: Biacore analysis of TNFα nanobodies
  Table 15: Binding of TNFα nanobodies to TNFα ($K_D$-values)
  Table 16: Potency of TNFα nanobodies to neutralize human (a) and rhesus (b) TNFα
  Table 17: OD280 nm of TNFα and serum albumin nanobodies after temperature treatment
  Table 18: Potency of TNFα nanobodies after temperature treatment Bivalent TNFα nanobodies
  Table 19: Sequence listing of bivalent TNFα nanobodies and linker sequences
  Table 20: Bivalent TNFα nanobody constructs
  Table 21: Expression levels of bivalent TNFα nanobodies
  Table 22: Receptor-inhibition assay of bivalent TNFα nanobodies
  Table 23: Potency of TNFα nanobodies to neutralize human (a) and rhesus (b) TNFα
  Table 24: OD280 nm of bivalent TNFα nanobodies Humanised monovalent TNFα nanobodies
  Table 25: Sequence listing of humanised monovalent TNFα and serum albumin nanobodies
  Table 26: Expression levels of humanised TNFα and serum albumin nanobodies
  Table 27: Potency of TNFα nanobodies to neutralize human TNFα
  Table 28: OD280 nm of humanised TNFα and serum albumin nanobodies Trivalent TNFα nanobodies
  Table 29: Sequence listing of trivalent TNFα nanobodies
  Table 30: Trivalent TNFα nanobody constructs
  Table 31: Expression levels of trivalent TNFα nanobodies
  Table 32: Potency of trivalent TNFα nanobodies to neutralize human TNFα
  Table 33: Binding of trivalent nanobodies to serum albumin ($K_D$-values)
  Table 34: OD280 nm of trivalent TNFα nanobodies Humanised monovalent TNFα nanobodies (second round)

Table 35: Sequence listing of second round humanised monovalent TNFα nanobodies

Table 36: Expression levels of humanised TNFα nanobodies

Table 37: Potency of TNFα nanobodies to neutralize human TNFα

Table 38: OD280 nm of humanised TNFα nanobodies

Table 39: Comparing bio-activity of nanobodies

Further tables

Table 40: Overview of oligonucleotides used in formatting of trivalent Nanobodies™

Table 41: Overview of oligonucleotides used in cloning of trivalent Nanobodies™

Table 42: EC50 values obtained in cytotoxicity assay using trivalent Nanobody™ TNF60 in comparison with commercial controls (Enbrel, Remicade, Humira)

Table 43: Affinity determination of TNF60 and TNF24 on human serum albumin in Biacore. Nd, not determined.

Table 44: Overview of oligonucleotides used in formatting of bivalent Nanobodies™

Table 45: EC50 values obtained in cytotoxicity assay using bivalent Nanobodies™ in comparison with commercial controls (Enbrel, Remicade, Humira)

Table 46: Results of synovium derived fibroblast studies

Table 47: Results of murine air pouch studies

EXAMPLES

Example 1: Identification of TNFα and Serum Albumin Specific Nanobodies

Antagonistic nanobodies were identified using two llamas (*Llama glama*) immunized with human TNFα by 6 injections of 100 μg of the cytokine at weekly intervals. Screening was performed using a competition based assay, in which individual nanobodies were analyzed for their capability to inhibit binding of labeled TNFα to its receptor. The albumin specific nanobodies were identified from a llama immunized with human serum albumin. Screening of individual nanobodies was performed by ELISA using human, rhesus and mouse albumin, yielding a panel of nanobodies cross-reacting with the serum albumin of various species.

Example 2: Sequence Analysis of Isolated Nanobodies

Different classes of nanobodies were identified based on sequence analysis (FIG. 1) using a BLOSUM62 scoring matrix and a similarity significance value cut-off of ≥60%: Class I (PMP1 C2, PMP1 G11, PMP1 H6), Class II (PMP1 G5, PMP1 H2, PMP3 G2), Class IIb (PMP1 D2), Class III (PMP3 D10, PMP5 F10). Table 8 lists the sequences of these TNFα nanobodies (SEQ ID NOs: 52 to 60).

Based on sequence analysis (FIG. 2) different classes of serum albumin nanobodies were identified using the BLOSUM62 scoring matrix and a similarity significance value cut-off of ≥60%. Table 8 lists the sequences of these serum albumin nanobodies (SEQ ID NOs: 61 to 67).

Example 3: Biacore Analysis

TNFα

Binding of nanobodies to TNFα was characterised by surface plasmon resonance in a Biacore 3000 instrument. TNF from different species was covalently bound to CM5 sensor chips surface via amine coupling until an increase of 250 response units was reached. Remaining reactive groups were inactivated. Nanobody binding was assessed at one concentration (1 in 1,000 diluted). Each nanobody was injected for 4 minutes at a flow rate of 45 μl/min to allow for binding to chip-bound antigen. Binding buffer without nanobody was sent over the chip at the same flow rate to allow spontaneous dissociation of bound nanobody for 4 hours. $K_{off}$-values were calculated from the sensorgrams obtained for the different nanobodies.

Of each class of nanobodies unpurified proteins were analyzed in Biacore. $K_{off}$ data is listed in Table 9.

Representative nanobodies from each class were retained for further analysis based on $k_{off}$ value. For Class I PMP1C2 (TNF1) was selected; PMP1G5 (TNF2) was selected as representative of Class II; PMP5F10 (TNF3) was selected as representative of Class III.

Serum Albumin

Binding was assayed as described above except that 1 in 20 dilutions were used. FIGS. 3, 4 and 5 illustrate screening of albumin specific TNFα nanobodies versus human, rhesus and mouse serum albumin using unpurified protein.

The nanobodies are ranked according to $k_{off}$-values, see Table III below:

TABLE III

| Class | Human | Rhesus | Mouse |
| --- | --- | --- | --- |
| C | PMP6A8 | PMP6A8 | PMP6B4 |
| C | PMP6B4 | PMP6B4 | PMP6A8 |
| B | PMP6A6 | PMP6A6 | PMP6A6 |
| B | PMP6C1 | PMP6C1 | PMP6C1 |
| A | PMP6G8 | PMP6G8 | PMP6G8 |
| A | PMP6A5 | PMP6A5 | PMP6A5 |
| D | PMP6G7 | PMP6G7 | PMP6G7 |

The best $k_{off}$ were obtained for members of family C and family B. Cross-reactivity between mouse, human and rhesus serum albumin was also observed for members of those families. A representative nanobody from class B and C was defined for further analysis: PMP6A6 (ALB1) was selected as representative of Class B and PMP6A8 (ALB2) was selected as representative of Class C.

Example 4: Cloning of Monovalent Nanobodies in pAX051

Description of *Escherichia coli* Expression Vector pAX051 is a derivative of pUC19. It contains the LacZ promoter which enables a controlled induction of expression using IPTG. The vector has a resistance gene for Ampicillin or Carbenicillin. The multicloning sites harbours several restriction sites of which SfiI and BstEII are frequently used for cloning of Nanobodies™. In frame with the NB coding sequence the vector codes for a C-terminal c-myc tag and a (His)6 tag. The signal peptide is the gen3 leader sequence which translocates the expressed Nanobody™ to the periplasm.

The DNA coding for the selected nanobodies TNF1 (PMP1C2), TNF2 (PMP1G5), TNF3 (PMP5F10), ALB1 (PMP6A6) and ALB2 (PMP6A8) was cloned in pAX051 and the construct was transformed to TG1 electrocompetent cells. Clones were analyzed for PCR insert and the nucleotide sequence was determined from 4 positive clones. Glycerol stocks were prepared from clones containing the correct sequence and stored at −80° C.

Example 5: Expression of Monovalent Nanobodies

A preculture was started by inoculating a single colony of the clone expressing the respective nanobodies at 37° C. in Luria Broth, Ampicillin/Carbenicillin (100 µg/ml) and 2% glucose overnight. This preculture was used to inoculate. Inoculum is 1% percent (v/v) of the production culture (TB medium+Ampicillin/Carbenicillin+0.1% Glucose). The production culture is grown at 37° C. until an OD600 nm of 5-10 is reached and nanobody expression is induced by adding IPTG (1 mM final concentration). Protein expression is allowed to continue either for 4 h at 37° C. or overnight at 28° C., at which point cells are collected by centrifugation and stored as wet cell paste at −20° C.

Preparative periplasmic extracts of the −20° C. stored wet cell paste are made by resuspending the pellet in Peri-buffer (50 mM $NaH_2PO_4$, 300 mM NaCl, adjusted pH to 8.0), rotating the mixture for 30 min at 4° C. and centrifuging the mixture using a preparative centrifuge (Sorvall RC-3C Plus with H-6000A rotor) to pellet the cells. Supernatant, representing a rough extract of the periplasmic space, is collected for further purification.

The His(6)-tagged nanobodies are purified on Immobilized Metal Affinity Chromatography (IMAC). The TALON resin (Clontech) is processed according to the manufacturer's instructions. The extracts are incubated with the resin for 30 min at RT on a rotator. The resin is washed with PBS and transferred to a column. The packed resin is washed with 15 mM Imidazole. The nanobodies are eluted from the column using 150 mM Imidazole. The eluated fractions are analyzed by spotting on Hybond Membrane and visualization with Ponceau. Fractions containing protein are pooled and dialysed against PBS. Dialysed proteins are collected, filter sterilized, concentration determined and stored in aliquots at −20° C.

Characterisation of Monovalent TNFα Nanobodies

Example 6: Homology to Human Germline Sequences

The nanobody amino acid sequences were compared to the human germline sequences as represented in Table 10. In order of homology to human sequences the nanobodies rank as follows: TNF1>TNF2>TNF3 for the TNFα nanobodies; ALB1>ALB2 for the serum albumin nanobodies.

Example 7: Expression Level

Expression levels were calculated and represented in Table 11. In order of yield the nanobodies rank as follows: TNF1>TNF2>TNF3 for the TNFα nanobodies; ALB1>ALB2 for the serum albumin nanobodies.

Example 8: SDS-Page Analysis

To determine the purity, protein samples were analyzed on a 15% SDS-PAGE gel. 10 µl Laemmli sample buffer was added to 10 µl (1 ug) purified protein, the sample was heated for 10 minutes at 95° C., cooled and loaded on a 15% SDS-PAGE gel. The gel was processed according to general procedures and stained with Coomassie Brilliant Blue (CBB). FIG. 6 represents the SDS-PAGE for the TNFα-specific and serum albumin-specific nanobodies.

Example 9: Western Blot Analysis 100 ng of purified protein was loaded on the gel. Following SDS-PAGE, proteins were transferred to a nitrocellulose membrane using the Mini Trans-Blot® Electrophoretic Transfer Cell (Biorad). The membrane was blocked overnight in PBS, 1% casein at 4° C. As all constructs were fused to c-myc tag, mouse monoclonal anti-myc antibody was used as a detection tool. In addition, rabbit polyclonal anti-Nanobody (R23) was used as a detection tool. The blot was incubated for 1 h at room temperature with agitation in 1/2000 diluted anti-myc antibody in PBS or 1/2000 anti-Nanobody antibody in PBS, 1% casein. The membrane was washed 5 times in PBS before the secondary antibody was applied (rabbit-anti-mouse IgG alkaline phosphatase conjugate, Sigma, A1902, diluted 1/1000 in PBS or goat anti-rabbit IgG alkaline phosphatase conjugate, Sigma, A8025, 1% casein). After incubation with gentle agitation for 1 h at room temperature, the membrane was washed 5 times in PBS. Blots were developed using BCIP/NBT solutions and the reaction was stopped by washing the blot with milliQ water when bands were clearly visible. FIG. 7 represents the Western Blot analysis.

Example 10: ELISA Binding to Human and Rhesus TNFα

An ELISA was performed to examine binding to human and rhesus TNFα. A 96-well Maxisorp plate was coated with 2 µg/ml Neutravidin in PBS ON at 4° C. Plates were blocked with 1% caseine for 2 hrs at RT. Biotinylated TNFα (400 ng/ml) was added to the wells and incubated for 1 hr at RT. Nanobody samples were diluted starting at 2 µg/ml and using 1 in 3 dilutions. Nanobodies were detected using mouse anti-myc (1/2000 diluted) and rabbit anti-mouse alkaline phosphatase (1/2000 diluted, Sigma, A1902) and pNPP (2 mg/ml) as substrate. FIGS. 9 and 10 represent the binding in ELISA to human and rhesus TNFα.

Results are summarized in Table 12. TNF1 and TNF3 show binding to both human and rhesus TNFα. TNF2 is binding to human TNFα but is only weakly reactive to rhesus TNFα.

Example 11: Receptor-Inhibition Assay

The ability to inhibit receptor-ligand interaction was analyzed for rhesus and human TNFα. A 96-well Maxisorp plate was coated with 2 µg/ml Enbrel in PBS ON at 4° C. Plates were blocked with 1% Caseine for 2 hrs at RT. Nanobody samples were pre-incubated for 30 min at RT with biotinylated TNFα (10 ng/ml) starting at a concentration of 5 µg/ml and using 1 in 2 dilutions. Samples were added to the plates and incubated for 1 hr at RT. Biotinylated TNFα was detected using Extravidin alkaline phosphatase (1/2000 diluted) and pNPP (2 mg/ml) as substrate. FIGS. 11 and 12 represent an inhibition ELISA for human and rhesus TNFα. Results are summarized in Table 13. Inhibition of ligand/receptor binding is observed for TNF1 and TNF3 for both human and rhesus TNF, while TNF2 is only inhibiting human TNFα.

Example 12: Biacore Analysis

TNFα Binding

The analysis was performed as described in Example 3. FIGS. 13 and 14 illustrate the binding to human and rhesus TNFα via Biacore analysis. Results are summarized in Table 14. Binding experiments in Biacore confirm the ELISA results: cross-reactive binding for TNF1 and TNF3, while TNF2 only significantly binds human TNFα.

Serum Albumin

Binding was assayed as described above except that series of different concentrations were used. Each concentration was injected for 4 minutes at a flow rate of 45 µl/min to allow for binding to chip-bound antigen. Binding buffer without analyte was sent over the chip at the same flow rate to allow for dissociation of bound nanobody. After 15 minutes, remaining bound analyte was removed by injection of the regeneration solution (25 mM NaOH).

From the sensorgrams obtained for the different concentrations of each analyte $K_D$-values were calculated via steady state affinity when equilibrium was reached.

Results are summarized in Table 15. Cross-reactivity is observed for both ALB1 and ALB2. The highest affinity is observed for ALB2 on human and rhesus TNFα. However, the difference in affinity for human/rhesus versus mouse serum albumin is more pronounced for ALB2 (factor 400), while for ALB1 a difference of a factor 12 is observed.

Example 13: Bio-Assay

The TNFα sensitive mouse fibroblast cell line L929s was used for measuring the anti-TNFα activity of the selected nanobodies. At a sufficiently high concentration of TNFα in the medium, i.e. cytotoxic dose, L929s cells undergo necrosis. The inhibition of TNFα interaction with its receptor was determined by pre-incubating a series of antibody dilutions with a cytotoxic concentration of TNFα before adding the mixture to the cells. The presence of actinomycin D in the medium sensitises the cells further to TNFα, resulting in increased sensitivity of the bioassay for free TNFα.

The L929 cells were grown to nearly confluency, plated out in 96-well microtiter plates at 5000 cells per well and incubated overnight. Actinomycin D was added to the cells at a final concentration of 1 μg/ml. Serial dilutions of the nanobodies to be tested were mixed with a cytotoxic concentration of TNFα (final assay concentration is 0.5 ng/ml or 15 IU/ml). After at least 30 minutes of incubation at 37° C., this mixture was added to the plated cells. Plates were incubated for 24 hours at 37° C. and 5% $CO_2$. Cell viability was determined by use of the tetrazolium salt WST-1. Dose-response curves and $EC_{50}$ values were calculated with Graphpad Prism.

The results are summarized in Table 16 for human and rhesus TNFα. Based on their potency to neutralize cytotoxic activity, the molecules are ranked as follows: TNF3>TNF1>TNF2 for human TNFα, and TNF1=TNF3>TNF2 for rhesus TNFα.

Example 14: Protein a Binding

FIG. 14 represents Protein A binding analyzed in Biacore as described in Example 12. Positive binding was obtained for TNF1, TNF2, ALB1. No or weak binding was observed for TNF3 and ALB2.

Example 15: Temperature Stability

Samples were diluted at 200 μg/ml and divided in 8 aliquots containing 500 μl. The different vials were incubated each at a given temperature ranging from RT to 90° C. After treatment the samples were cooled down for 2 hrs at RT, they were kept at 4° C. Precipitates were removed by centrifugation for 30 min at 14,000 rpm. SN was carefully removed and further analysed.
OD280 nm
OD at 280 nm was measured and the concentration was calculated. Results are summarized in Table 17. A decrease in protein content was observed for TNF2 and TNF3 starting at 80° C., while for ALB2 a decrease is observed starting from 70° C.

Western Blot

2 μg of treated protein was separated on a 15% SDS-PAGE and transferred to a nitrocellulose membrane and treated as described above. Detection was performed using polyclonal anti-Nanobody (R23, 1/2000 diluted) and anti-rabbit horse radish peroxidase (DAKO, P0448, 1/2000 diluted). FIG. 15 represents the Western Blot analysis. A clear drop in protein concentration was observed for ALB2 treated at 70, 80 and 90° C. Aggregation was still observed for TNF1 treated at 70, 80 and 90° C.; for TNF3 treated at 90° C.; for ALB1 treated at 90° C., meaning that the SN still contains traces of precipitates which result in a higher OD280 nm read-out. This explains why the protein concentration as measured at OD280 nm does not decrease for TNF1, TNF3 and ALB1 treated at these higher T.
ELISA The ELISA to detect binding to human TNFα was essentially performed as described in Example 10. Results are presented in FIG. 16. Human TNFα binding is decreased for TNF1, TNF2, TNF3 starting at 80° C.
Bio-Assay The bio-assay was performed as described in Example 13. The results are summarized in Table 18. Potency of the nanobodies is decreased for TNF1 starting at 70° C.; for TNF2 and TNF3 starting at 80° C.

Biacore

Binding to human serum albumin was determined as described in Example 12. A fixed concentration was used (1 in 50 diluted). Results are presented in FIG. 17. Temperature treatment is not influencing binding to serum albumin for ALB1. The treatment has an effect on the $k_{on}$ for ALB2 starting from T=70° C.

Bivalent Nanobodies

Example 16: Formatting of Bivalent TNFα Specific Nanobodies

TNF1, TNF2 and TNF3 were formatted to bivalent nanobodies. As spacer between the two building blocks either a 9AA GlySer linker (Table 19 SEQ ID No: 68) or a 30 AA GlySer linker (Table 19 SEQ ID No: 69) was used. This generated the constructs represented by Table 20. Table 19 lists the sequences of these bivalent TNFα nanobodies (SEQ ID NOs: 70 to 75).

Example 17: Expression of Bivalent TNFα Specific Nanobodies

Expression was performed as described in Example 5. The His(6)-tagged nanobodies were purified on Immobilized Metal Affinity Chromatography (IMAC). The Ni-NTA resin (Qiagen) was processed according to the manufacturer's instructions. The extracts were incubated with the resin and incubated for 30 min at RT on a rotator. The resin was washed with PBS and transferred to a column. The packed resin was washed with PBS (1 in 10 diluted). The column was pre-eluted with 15 mM Imidazole. The nanobodies were eluted from the column using 25 mM Citric Acid pH=4. The eluated fractions were analyzed by spotting on Hybond Membrane and by visualization with Ponceau. Fractions containing protein were pooled and further purified on Cation exchange followed by size exclusion. Purified proteins were collected, filter sterilized, concentration determined and stored in aliquots at −20° C.
Characterisation of Bivalent TNFα Specific Nanobodies

Example 18: Expression Level

Expression levels of the bivalent TNFα nanobodies were calculated and represented in Table 21. The linker has no significant effect on the expression level of the nanobodies.

Example 19: SDS-PAGE

SDS-Page was performed as described in Example 8. FIG. 18 shows the result of the SDS-Page.

Example 20: Western Blot

Western Blot analysis was performed as described in Example 9. FIG. 19 represents the Western Blot results.

Example 21: Receptor-Inhibition Assay

The assay was performed as described in Example 11. FIG. 20 and Table 22 represent the results. Enhancement of inhibition of ligand/receptor binding was observed for all bivalent nanobodies compared to the monovalent format.

Example 22: Bio-Assay

The assay was performed as described in Example 13. Results are summarized in Table 23. Based on their potency to neutralize cytotoxic activity TNF8, TNF7, TNF9 and TNF5 have a potency in the range of Enbrel.

Example 23: Temperature Stability

Samples were analysed as described in Example 15.
OD280 nm
OD at 280 nm was measured and the concentration was calculated. Results are summarized in Table 24. A decrease in protein content was observed for TNF4 and TNF7 starting at 70° C., while for TNF5, TNF6, TNF8 and TNF9 a decrease was observed starting from 80° C.
Western Blot
Samples were analyzed for the presence of aggregates as described in Example 15.
ELISA
The ELISA to detect binding to human TNFα was essentially performed as described above. Results are presented in FIG. 21. Human TNFα binding was decreased for TNF5, TNF6, TNF8 and TNF9 starting at 80° C., for TNF4 and TNF7 starting from 70° C.
Humanised Monovalent Nanobodies

Example 24: Identification of Non-Human Amino Acid Positions in TNFα and Serum Albumin Specific Nanobodies FIG. 22 (TNF1), FIG. 23 (TNF2), FIG. 24 (TNF3) and FIG. 25 (ALB1) represent multiple sequence alignments (Clustal W 1.7) with DP51, DP53, DP54 and DP29 sequences.
In addition to the amino acid mutations, codon optimization was performed yielding the sequences of Table 25 SEQ ID NOs: 76 to 89 (Nanobodies against TNF-alpha and human serum albumin, respectively).

Example 25: Generation of Codon Optimised Mutants

Oligonucleotides were synthesised spanning the entire sequence of the nanobodies.

Example 26: Expression of Bivalent TNFα Specific Nanobodies

Expression was performed as described in Example 5.
Characterisation of Humanised Nanobody

Example 27: Expression Level

Table 26 represents calculated expression levels. Expression was achieved with yields in the range of 3.5-11.7 mg/ml. Induction time did not influence the yield.

Example 28: SDS-PAGE

SDS-PAGE was performed as described in Example 8. FIG. 26 represents the SDS-PAGE gel.

Example 29: Western Blot

Western Blot analysis was performed as described in Example 9. FIG. 27 represents the Western Blot results.

Example 30: Bio-Assay

The assay was performed as described in Example 13.
The results of the humanised nanobodies are summarized in Table 27. The wildtype nanobodies are included as reference.

Example 31: Biacore

The analysis was performed as described in Example 12. FIGS. 28 and 31 shows Biacore results.

Example 32: Temperature Stability

Samples were analysed as described in Example 15.
OD280 nm
OD at 280 nm was measured and the concentration was calculated. Results are summarized in Table 28.
No significant decrease in protein concentration is observed for the humanised TNF1 nanobodies (TNF13-14). A decrease in protein concentration is observed for humanised TNF2 (TNF15-19) and TNF3 (TNF20-23) starting at 80° C. A decrease in protein concentration is observed for humanized ALB1 (ALB4-5) starting at 70° C. and for ALB3 starting at 60° C.
Western Blot
Samples were analyzed for the presence of aggregates as described in Example 15.
ELISA
The ELISA to detect binding to human TNFα was essentially performed as described in Example 15. Results are presented in FIG. 30.
Human TNFα binding is comparable for temperature treated WT TNF1 and the humanized TNF13 and 14; for temperature treated WT TNF2 and the humanized TNF15-19; human TNFα binding is decreased for TNF21 and 22, and to a less extent for TNF23, while no effect is observed for TNF20 compared to the temperature treated WT TNF3.
Trivalent TNFα Nanobodies

Example 33: Formatting of Trivalent TNFα Specific Nanobodies

TNF1, TNF2, TNF3 and ALB1 were formatted to trivalent nanobodies. As spacer between 2 building blocks either a 9AA GlySer linker (Table 19 SEQ ID No 68) or a 30 AA GlySer linker (Table 19 SEQ ID No 69) was used. This generated the constructs of Table 30. Table 29 lists the sequences of trivalent TNFα nanobodies (SEQ ID NOs: 91 to 94).

Example 34: Expression of Trivalent TNFα Specific Nanobody

Expression was performed as described in Example 5. The His(6)-tagged nanobodies are purified on Immobilized Metal Affinity Chromatography (IMAC). The Ni-NTA resin (Qiagen) is processed according to the manufacturer's instructions. The extracts are incubated with the resin and incubated for 30 min at RT on a rotator. The resin is washed with PBS and transferred to a column. The packed resin is washed with PBS (1 in 10 diluted). Pre-elute with 15 mM Imidazole. The nanobodies are eluted from the column using 25 mM Citirc Acid pH=4. The eluated fractions are analyzed by spotting on Hybond Membrane and visualization with Ponceau. Fractions containing protein are pooled and further purified on Cation exchange followed by size exclusion. Purified proteins are collected, filter sterilized, concentration determined and stored in aliquots at −20° C.
Characterization of Trivalent TNFα/SA Specific Nanobodies

Example 35: Expression Level

Expression levels were calculated and represented in Table 31.

Example 36: SDS-PAGE Analysis

SDS-PAGE was performed as described in Example 8. FIG. 31 represents the SDS-PAGE gel.

Example 37: Western Blot Analysis

Western Blot analysis was performed as described in Example 9. FIG. 32 represents the Western Blot analysis.

Example 38: Bio-Assay

The assay was performed as described in Example 13.
The results of the bivalent nanobodies are summarized in Table 32. Based on their potency to neutralize cytotoxic activity, the molecules are equally potent and comparable to their potency as bivalent molecules.

Example 39: Binding to Human Serum Albumin

Binding was assayed as described above except that series of different concentrations were used. Each concentration was injected for 4 minutes at a flow rate of 45 μl/min to allow for binding to chip-bound antigen. Next, binding buffer without analyte was sent over the chip at the same flow rate to allow for dissociation of bound nanobody. After 15 minutes, remaining bound analyte was removed by injection of the regeneration solution (25 mM NaOH).

From the sensorgrams obtained for the different concentrations of each analyte $K_D$-values were calculated via steady state affinity when equilibrium was reached.

Results are summarized in Table 33. A decrease in affinity was observed for the formatted ALB1 binder compared to the wild type ALB1. The affinity however is still in the range of 7.2-14 nM.

Example 40: Temperature Stability

Samples were analysed as described in Example 15.
OD280 nm
OD at 280 nm was measured and the concentration was calculated. Results are summarized in Table 34. A decrease in protein content is observed for TNF24, TNF27 and TNF28 starting at 60° C., while for TNF25 and TNF26 starting from 70° C.
Western Blot
Samples were analyzed for the presence of aggregates as described in Example 15.
ELISA
The ELISA to detect binding to human TNFα was essentially performed as described above. Results are presented in FIG. 33. Human TNFα binding is decreased for TNF24 and TNF27, starting from 60° C. and for TNF25, TNF26 and TNF28 starting at 70° C.
Humanised Monovalent Nanobodies (Second Round)

Example 41: Identification of Non-Human Amino Acid Positions in TNFα and Serum Albumin Specific Nanobodies FIG. 34 (TNF1), FIG. 35 (TNF2), FIG. 36 (TNF3) and FIG. 37 (ALB1) represent multiple sequence alignments (Clustal W 1.7) with DP51, DP53, DP54 and DP29 sequences. The mutated molecules were expressed and purified as described above, yielding the sequences of Table 35 SEQ ID NOs: 95 to 104 (against TNF-alpha and human serum albumin, respectively).
Characterisation of Humanised Nanobody

Example 42: Expression Level

Table 36 represents calculated expression levels. Expression was achieved with yields in the range of 0.5-2.7 mg/ml.

Example 43: SDS-PAGE

SDS-Page was performed as described in Example 8. FIG. 38 represents the SDS-Page gel.

Example 44: Western Blot

Western Blot analysis was performed as described in Example 9. FIG. 39 represents the Western Blot results.

Example 45: Bio-Assay

The assay was performed as described in Example 13.
The results of the humanised nanobodies are summarized in Table 37. The wildtype nanobodies and first round of humanised nanobodies are included as reference.

Example 46: Biacore

The analysis was performed as described in Example 12. FIG. 40 shows Biacore results.

Example 47: Temperature Stability

Samples were analysed as described in Example 15.
OD280 nm
OD at 280 nm was measured and the concentration was calculated. Results are summarized in Table 38.
No significant decrease in protein concentration is observed for the humanised TNF1 nanobodies (TNF29-30). A decrease in protein concentration is observed for humanised TNF2 (TNF31-32) and TNF3 (TNF33) starting at 80° C.
Western Blot
Samples were analyzed for the presence of aggregates as described in Example 15.
ELISA
The ELISA to detect binding to human TNFα was essentially performed as described in Example 15. Results are presented in FIG. 41.
Human TNFα binding is comparable for WT TNF1 and the humanised TNF29 and TNF30; comparable for WT TNF2 and the humanised TNF31 and TNF32; and also for WT TNF3 and humanised TNF33.

Comparative Example

In this Comparative Example, nine Nanobodies of the invention were compared with three Nanobodies from WO 04/041862, called "$V_{HH}$#1A" or "1A", "$V_{HH}$3E" or "3E" and "$V_{HH}$#3G" or "3G" respectively (SEQ ID NOS:1, 4 and 5 in WO 04/041862). The assay used was the cell based assay using KYM-cells referred to in WO 04/41862 (see for example Example 1, under 3)). The results are mentioned in Table 39 below. As can be seen, the Nanobodies of the invention have an EC50 value in this assay that is 18-fold better than the EC50 value of 3E, the best performing Nanobody according to WO 04/041862.

Example 48: Generation of Trivalent Bispecific Humanized Nanobodies™

Trivalent bispecific Nanobodies were formatted and cloned in the *E. coli* expression vector pAX054 first and then rescued through PCR and cloned in the pPICZαA expression vector.
Description of *Escherichia coli* Expression Vector
pAX54 is a derivative of pUC19. It contains the LacZ promoter which enables a controlled induction of expression using IPTG. The vector has a resistance gene for Ampicillin or Carbenicillin. The multicloning sites harbours several restriction sites of which SfiI and BstEII are frequently used for cloning of Nanobodies™. The signal peptide is the gen3 leader sequence which translocates the expressed Nanobody™ to the periplasm.

Description of *Pichia pastoris* Expression Vector
pPICZαA contains a pUC-derived origin of replication allowing propagation in *E coli*. It contains the promoter of the *Pichia pastoris* AOX1 (alcohol oxidase 1) gene. This 942 bp promoter region (i) allows methanol-inducible, high-level expression of the gene of interest, and (ii) targets plasmid integration to the AOX1 locus following transformation of *Pichia* with vector DNA that is linearized within the 5' AOX1 promoter region. Note that pPICZα vectors do not contain a yeast origin of replication and that, consequently, transformants can only be isolated if recombination occurs between the plasmid and the *Pichia* genome. The vector specifies resistance to the antibiotic Zeocin in both *E. coli* and *Pichia pastoris* host cells. The vector incorporates the secretion signal of the *Saccharomyces cerevisiae* α-mating factor allowing for efficient secretion of most proteins to the culture medium. The initiation ATG in the α-factor signal sequence corresponds to the native initiation ATG of the AOX1 gene. The multicloning site harbours several restriction sites of which Xho1/EcoR1 or Xho1/Not1 are typically used for fusion of the Nanobody™ coding sequences to the secretion signal. The multicloning site is followed by the AOX1 transcription termination region. More details on this expression vector can be found on the website of Invitrogen (http://www.invitrogen.com/content/sfs/manuals/ppiczalpha_man.pdf).
Formatting Trivalent Nanobodies
Three separate PCR reactions were set up to amplify the N-terminal, the middle and the C-terminal Nanobody™ subunit using the oligo combinations indicated in the WPA-0012. The N-terminal Nanobody™ was amplified using M13_rev/Rev_9GlySer_L108; the middle Nanobody™ was amplified using For_GlySer/Short and Rev_15BspEI_L108; the C-terminal Nanobody™ was amplified using For_BspEI/M13_for. A PCR reaction of 1 µl plasmid DNA (50-100 ng), 1.5 µl forward primer (10 µM→300 nM), 1.5 µl reverse primer (10 µM→300 nM), 1 µl dNTPs (10 mM→0.2 mM), 5 µl buffer (10×→1×), 0.75 µl enzyme (3.5 U/µl→2.6 U/µl) and 39.25 µl $H_2O$ with a total volume of 50 µl was prepared. Primer sequences are given in Table 40. A PCR program was started with 2 minutes at 94° C. A cycle of 30 seconds at 94° C., 30 seconds at 50° C. and 1 minute at 72° C. was repeated 30 times and followed by 10 minutes at 72° C. Amplification was checked by separating 5 µl of the PCR reaction on a 2% agarose gel. The PCR product was purified using the QIAquick PCR Purification Kit according to the manufacturer's instructions. One column was used and eluted with 50 µl EB buffer. The N-terminal VHH fragment was prepared by incubating 50 µl DNA and 2 µl BamHI (10 U/µl) in the appropriate buffer recommended by the manufacturer at 37° C. for 2 hours. Subsequently, 2 µl SfiI (10 U/µl) was added and the mixture was incubated at 55° C. for 2 hours. The middle VHH fragment was prepared by incubating 50 µl DNA and 2 µl BamHI (10 U/µl) and 2 µl BspEI (10 U/µl) in the appropriate buffer recommended by the manufacturer at 37° C. for 2 hours. The C-terminal VHH fragment was prepared by incubating 50 µl DNA with 2 µl BspEI (10 U/µl) in the appropriate buffer recommended by the manufacturer at 37° C. for 2 hours. Subsequently, 2 µl BstEII (10 U/µl) was added and the mixture was incubated at 60° C. for 1 hours. The previous digestion reactions were separated on a 2% agarose gel. The VHH bands (350-450 bp) were cut out of the gel and the DNA was purified using the QIAquick Gel Extraction Kit according to the manufacturer's instructions. One column (with a maximum of 400 mg agarose gel per column) was used and the bound DNA was eluted with 50 µl EB buffer. DNA concentration was determined by measuring OD260 (1 OD unit=50 µg/ml). A ligation mixture with a final volume of 10 μl containing 100 ng vector pAX54, 12 ng N-terminal VHH, 12 ng middle VHH fragment, 12 ng C-terminal VHH fragment, 1 μl ligation buffer and 1 μl ligase (3 U) was prepared and incubated for 2 hours at room temperature. Transformation of E. coli, TG1 was performed by using 2 μl of ligation mixture. Colonies are analysed using PCT as described in WPA-0010. Sequence analysis is performed on positive clones. Plasmid preparation was performed using the Qiaprep spin Miniprep kit (Qiagen) according to the manufacturer's instructions and described above. Sequencing was performed at the VIB sequence facility, Antwerp, Belgium.

Amplification of Coding DNA

The Nanobody™ coding region cloned in the pAX054 E. coli expression vector is rescued through PCR using an appropriate primer pair. To ensure that the Nanobody™ is expressed with a native N-terminus, the coding region is cloned in frame with the Kex2 cleavage site of the secretion signal. The forward primer fuses the C-terminal part of the secretion signal, up to the XhoI recognition site, to the Nanobody™ coding region. A PCR reaction of 1 μl plasmid DNA (50-100 ng), 1.5 μl forward primer (10 μM→300 nM), 1.5 μl reverse primer (10 μM→300 nM), 1 μl dNTPs (10 mM→0.2 mM), 5 μl buffer (10×→1×), 0.75 μl enzyme (3.5 U/μl→2.6 U) and 39.25 μl H$_2$O with a total volume of 50 μl was prepared. Primer sequences are given in Table 41. A PCR program was started with 2 minutes at 94° C. A cycle of 30 seconds at 94° C., 30 seconds at 50° C. and 2 minutes at 72° C. was repeated 20 times and followed by 10 minutes at 72° C. Amplification was checked by separating 5 μl of the PCR reaction on a 2% agarose gel. The PCR product was purified using the QIAquick PCR Purification Kit according to the manufacturer's instructions. One column was used and the bound DNA was eluted with 50 μl EB buffer.

Cloning Strategy

The DNA fragment coding for the NB as well as the pPICZαA expression vector is digested with the appropriate restriction enzymes (XhoI+NotI). The insert is obtained by incubating 50 μl PCR product with 2 μl XhoI (10 U/μl) and 2 μl NotI (10 U/μl) in the appropriate buffer recommended by the manufacturer for 3 hrs at 37° C. Vector is obtained similarly, adapting the amount of restriction enzymes to the amount of plasmid. Both the vector and the NB coding fragment are purified and the DNA concentration is quantified using the BioPhotometer (Eppendorf). The fragment and the acceptor vector are ligated in equimolar ratio's using 1 Unit T4 ligase (Promega) for 30 minutes at room temperature or overnight at 16° C. The DNA (20-30 ng) is transformed to TG1 cells. Colonies are analysed through PCR using the 3'AOX1 R and 5'AOX1 F primers. Sequence analysis is performed on positive clones. TNF30, TNF33 and ALB8 were formatted to trivalent bispecific Nanobodies™. As spacer between the building blocks a 9AA GlySer linker was used.

Transformation P. pastoris

To isolate plasmid DNA, a preculture is started by inoculating a single colony of the clone in 50 ml Luria Broth+Ampicillin or Carbenicillin (100 μg/ml)+2% glucose and incubation at 37° C. overnight. Plasmid DNA is prepared using the Plasmid Midi kit (Qiagen) according to the manufacturer's instructions. The DNA is linearized by incubating 30 μg plasmid DNA with 6 μl BstX1 (10 U/μl) in the appropriate buffer according to the manufacturer's instructions for 3 hrs at 45° C. Digested DNA is purified using the PCR Purification kit (Qiagen) according to the manufacturer's instructions. The DNA is concentrated using EtOH precipitation according to standard procedures. X-33 electrocompetent cells are transformed with 10 μg linearized DNA and cells are allowed to grow for 48 hrs on a selective YPD agar plate containing Zeocin (100/250/500 μg/ml). X-33 is a wild type Pichia pastoris strain; the strain itself as well as the derived recombinant strains contain the native AOX1 gene and are able to metabolize methanol (Mut$^+$).

Clones are screened for expression level by incubating single colonies in 1 ml BGCM in a 24-well plate and growing them for 48 hrs at 30° C. at 120 rpm. Cells are centrifuged and fresh BGCM is added to the cells for growth at 30° C. at 120 rpm during 48 hrs. Next, MeOH is added to a final concentration of 0.5% and cells are grown at 30° C. at 120 rpm during 8 hrs, after which MeOH is added again to a final concentration of 0.5%. Cells are grown overnight at 30° C. at 120 rpm. Cells are centrifuged and the supernatant is harvested and analysed in ELISA as described in example 10.

Example 49: Expression and Purification of Trivalent Bispecific Humanized Nanobodies™

Production in Pichia pastoris

Composition of buffers, solutions and others can be found on the website of Invitrogen (http://www.invitrogen.com/content/sfs/manuals/ppiczalpha_man.pdf).

A preculture was started by inoculating a single colony from plate in 5 ml YPD. The culture was grown overnight at 180 rpm and 30° C. The next day, the pre-culture was diluted to 50 ml of YPD and grown overnight at 180 rpm and 30° C. Production cultures were started by inoculating the pre-culture to a final OD600 nm=0.04-0.08. Cultures were grown in BGCM for 24 hrs at 30° C. at 180 rpm and centrifuged at 4,500 rpm for 30 minutes. Cells were resuspended in 1/3 of the original volume in BGCM medium with a final OD600 nm=15-20. Cells were induced with MeOH at regular time points, typically 3 times/day, never exceeding the 1% MeOH content. After 50 hours of induction the supernatant is harvested.

Purification of Nanobody Expressed in Pichia pastoris

Culture supernatant is filtered over a 0.22 μm filtration membrane Micro filtration (Hydrosart, Sartorius). Sample is concentrated using diafiltration on 10 kDa ultra filtration membrane (HydroSart, Sartorius) and concentrated to 0.5-1 L.

Nanobodies™ are purified using Protein A affinity chromatography (MabSelect Xtra, GE Healthcare) using PBS as running buffer and Glycine [100 mM pH=2.5] for elution. Samples are neutralized using 1.5 M Tris pH=8.8. Nanobodies™ are further processed in Anion Exchange Chromatography (Source 30Q, GE Healthcare). Samples are diluted 10-fold with 10 mM Piperazine pH=10.2 and adjusted to pH=10.2 with 1M NaOH and a conductivity of <2 mS/cm with MilliQ water.

Nanobodies are processed in Size Exclusion chromatography (Superdex 75 pg, Hiload XK26/60, GE Healthcare) and LPS is removed via Anion Exchange Chromatography (Source 30Q, GE Healthcare) by passage through 5 ml column, which is sanitized with 1M NaOH and equilibrated in Dulbecco PBS.

To determine the purity, protein samples were analyzed on a 15% SDS-PAGE gel as described in example 8. The gel is processed using the SilverQuest™ according to general procedures described by the manufacturer (Invitrogen). Alternatively, gel is processed using coomassie brilliant blue or in western blot as described in example 8 and 9. Results are given in FIG. 42.

Example 50: Characterization of Trivalent Bispecific Humanized Nanobodies™

TNF60 consists of 363 amino acids. The protein has a molecular weight of 38,441 Da. The pI is 8.71. The extinction coefficient at 280 nm is 1.736.

Mass Spectrophotometry

The mass of the protein was determined in ESI-MS according to standard procedures. The theoretical mass of TNF60 is 38,441 Da. The protein has 2 S-S bridges which should result in a mass of 38,435 Da in ESI-MS. The mass that was experimentally determined for TNF60 derived from 3 different batches ranges from 38,433 Da to 38,435 Da, differing maximally 0.005% with the theoretical mass.

N-Terminal Sequencing

N-terminal sequencing was performed by Edman degradation according to standard procedures. N-terminal sequencing showed that the protein sequence for the first 7 amino acids is as follows: EVQLVES (SEQ ID NO: 487). This is consistent with the theoretical protein sequence, which indicates proper N-terminal processing.

Analytical Sizing

Figure 43:
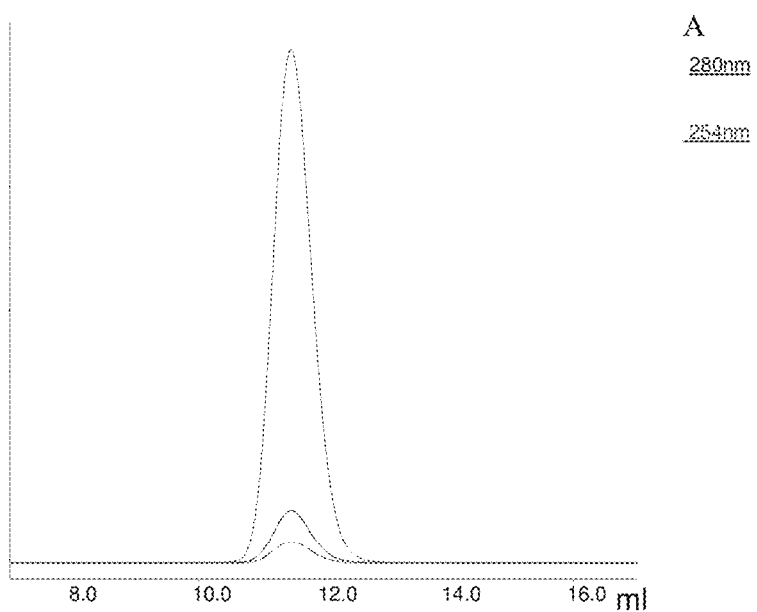

Samples (100 ug) were analysed on the high resolution Superdex75 column, to characterize the different batches of Nanobody™. Size exclusion chromatography of the Nanobody™ typically yields a symmetrical peak, with a retention time of 11.5 min on Superdex75. The absorbance is typically recorded at 280, 254 and 214 nm. The 214 nm measurement permits higher detection sensitivity. Analytical sizing in PBS provides a symmetrical peak. No contaminants were observed. The retention time observed for 3 different batches is 11.5-11.55 min. A representative profile is shown in FIG. 43.

Example 51: Binding of TNF60 to Human TNFα in ELISA

The functionality of TNF60, i.e. binding to human TNFα was analyzed in ELISA as described in example 10. The results are summarized in FIG. 44 and clearly demonstrate a dose-dependent and saturable binding of 2 batches of TNF60 to human TNFα.

Example 52: Functionality in Cell-Based Assay

The potency to neutralize the cytotoxic activity of TNFα was analyzed in a cell-based assay as described in example 13. The results are summarized in Table 42 and in FIGS. 45 and 46.

The data show that TNF60 has potency in the range of Enbrel/Etanercept and a 10-fold better potency than Humira/Adalimumab and Remicade/Infliximab.

Example 53: Binding of TNF60 to Serum Albumin

Binding to human and rhesus serum albumin was analyzed in Biacore as described in example 12. KD, kon and koff values are represented in Table 43. TNF60 is compared to TNF24, which is the trivalent bispecific parent Nanobody™ with wild-type building blocks.

Affinity of TNF60 for human and rhesus serum albumin is similar. Affinity is 2-fold lower as compared to the affinity observed for TNF24 which is the wild type analogue of TNF60. $K_{on}$ is identical for both molecules, but the $k_{off}$ is 2-fold higher for TNF60.

Example 54: Pharmacokinetic and Immunogenicity Analysis of Trivalent Bispecific Humanized Nanobodies in Mice Animals DBA1 or BALBc mice were warmed up under an infrared lamp and 200 μl Nanobody™ (100 μg per mouse) was injected intravenously in the tail. Blood samples were obtained at different time points by making a small incision in the tail and collecting the blood in a microtube. Typically, blood was sampled at t=15 min, 2 hrs, 4 hrs, 6 hrs, 1 day, 2 days, 3 days, 4 days, 7 days, 14 days. Serum was prepared according to standard procedures.

Determination of Nanobody™ Concentration in Mouse Serum

A microtiterplate (NUNC, Maxisorb) was coated with 2 μg/ml neutravidin overnight at 4° C. The plate was washed 5 times with PBS/0.05% Tween-20 and blocked for 2 hours at RT with PBS/1% casein. Biotinylated human TNFα (1/2000 in PBS/0.2% casein; 400 ng/ml) was applied to the wells and incubated for 1 hr at RT. The standard reference Nanobody™ was applied starting at a concentration of 5 μg/ml and using 5-fold dilutions in PBS containing 1% mouse plasma. The Nanobodies™ were allowed to bind for 2 hours at RT. The plate was washed 5 times and rabbit polyclonal anti-Nanobody (R23) was applied at a 2000-fold dilution for one hour at RT. After washing of the plate, binding was detected with goat-polyclonal-anti-rabbit-HRP (DAKO) at a 3000-fold dilution for one hour at RT, and stained with ABTS/$H_2O_2$. The OD405 nm was measured.

This first ELISA was used to determine the linear range of the standard reference. In a second ELISA, the standard reference was used at concentrations in this linear range and typically using 2-fold dilutions. In this second ELISA, serum test samples were diluted 100-fold and further 5-fold dilutions were made in 1% mouse plasma, to determine the dilution at which the serum samples provide a read-out in the linear range of the standard curve. In a third ELISA, serum samples are diluted at an appropriate concentration determined in the second ELISA and using 2-fold dilutions for accurate determination of the Nanobody™ concentration in the serum samples.

Experiments were performed to determine the pharmacokinetic profile of TNF60 in mice (n=3). A Cmax value of 103.84±31 μg/ml was reached 15 minutes after administration. The half-life (t1/2β) was determined to be 1.9 days, similar to the half-life of mouse serum albumin, indicating that TNF60 adopts the half-life of serum albumin. Data are presented in FIG. 47.

Determination of Anti-Nanobody Antibodies in Mice

Nanobody™ was coated at 5 μg/ml in PBS at 4° C. overnight. The plate was washed 5 times with PBS/0.05% Tween-20 and blocked for 2 hours at RT with PBS/1% casein. Serum samples were diluted 100-fold and applied to the wells for incubation during 1 hr at room temperature. Detection was performed using 1000-fold diluted polyclonal rabbit anti-mouse-HRP (DAKO, P0260) and using ABTS as substrate.

Serum samples were diluted 50-fold and analyzed for the presence of mouse anti-TNF60 antibodies. Lack of immunogenicity was demonstrated for TNF60. Data are presented in FIG. 48.

Example 55: Generation of Bivalent Long Half-Lived Humanized Nanobodies™

Description of *Pichia pastoris* Expression Vector
See example 48
Formatting Bivalent Nanobodies™

Two separate PCR reactions were set up to amplify the N-terminal and the C-terminal Nanobody™ subunit using the procedures as indicated in the WPA-0011. For the amplification of the N-terminal Nanobody™ PiForLong and Rev_30GlySer_L108 were used as primer combination; for the amplification of the C-terminal Nanobody™ For_GlySer and PiRevCys1hum were used or alternatively For_GlySer and PiRevCys2hum, introducing the restriction sites required for formatting and free cysteine residues required for C-terminal modifications.

PCR reaction of 1 µl plasmid DNA (50-100 ng), 1.5 µl forward primer (10 µM→300 nM), 1.5 µl reverse primer (10 µM→300 nM), 1 µl dNTPs (10 mM→0.2 mM), 5 µl buffer (10×→1×), 0.75 µl enzyme (3.5 U/µl→2.6 U/µl) and 39.25 µl H$_2$O with a total volume of 50 µl was prepared. Primer sequences are given in Table 44. A PCR program was started with 2 minutes at 94° C. A cycle of 30 seconds at 94° C., 30 seconds at 50° C. and 1 minute at 72° C. was repeated 30 times and followed by 10 minutes at 72° C. Amplification was checked by separating 5 µl of the PCR reaction on a 2% agarose gel. The PCR product was purified using the QIAquick PCR Purification Kit according to the manufacturer's instructions. One column was used and eluted with 50 µl EB buffer. The N-terminal VHH fragment was prepared by incubating 50 µl DNA and 2 µl BamHI (10 U/µl) and 2 µl XhoI (10 U/µl) in the appropriate buffer recommended by the manufacturer at 37° C. for 1.5 hours. The C-terminal VHH fragment was prepared by incubating 50 µl DNA and 2 µl BamHI (10 U/µl) and 2 µl EcoRI (10 U/µl) in the appropriate buffer recommended by the manufacturer at 37° C. for 1 hour. The previous digestion reactions were separated on a 2% agarose gel. The VHH bands (350-450 bp) were cut out of the gel and the DNA was purified using the QIAquick Gel Extraction Kit according to the manufacturer's instructions. One column (with a maximum of 400 mg agarose gel per column) was used and the bound DNA was eluted with 50 µl EB buffer. DNA concentration was determined by measuring OD260 (1 OD unit=50 µg/ml). A ligation mixture with a final volume of 10 µl containing 100 ng vector pPICZαA, linearized with XhoI/EcoRI, 30 ng N-terminal VHH, 30 ng C-terminal VHH fragment, 1 µl ligation buffer and 1 µl ligase (3 U) was prepared and incubated for 1 hour at RT. Transformation of *E. coli*, TG1 was performed by using 2 µl of ligation mixture. Colonies are analysed using PCR as described in WPA-0010 but using the AOXIFor/AOXIRev primer combination. Sequence analysis is performed on positive clones. Plasmid preparation was performed using the Qiaprep spin Miniprep kit (Qiagen) according to the manufacturer's instructions and described above. Sequencing was performed at the VIB sequence facility, Antwerp, Belgium.

Transformation of *P. pastoris*
See example 48.

TNF30 was formatted to bivalent Nanobodies™. As spacer between the 2 building blocks a 30 AA GlySer linker was used. To allow for C-terminal site-specific modifications a free cysteine was introduced, either as the last AA of the Nanobody™ or with an extra spacer consisting of GlyGlyGlyCys (SEQ ID NO: 471).

Example 56: Expression and Purification of Bivalent Long Half-Lived Humanized Nanobodies™

Production in *Pichia pastoris*
See example 49
Purification of Bivalent Nanobodies The culture medium was made cell-free via centrifugation and 0.22 µm filtration. The sterile medium was stored at 4° C. until further processed. Low molecular weight contaminants were reduced via ultra filtration on a 10 kDa ultra filtration (UF) membrane (HydroSart Sartocon Slice Cassette, Sartorius) as follows: four liter medium was concentrated to 0.5-1 lit, then diluted with 5 lit PBS and again concentrated to 0.5 lit. This action was carried out twice. The retentate of the UF was filtered through nylon 47 mm membranes 0.45 µm (Alltech #2024).

In a next step bivalent Nanobody™ was captured from the concentrated medium via Protein A affinity purification (using MabSelectXtra™, GE Healthcare). The column [35× 100 mm] was equilibrated in PBS and after sample application washed extensively with PBS. TNF56 was eluted with Glycine [100 mM, pH=2.5].

The eluted fractions of MabSelectXtra™ were neutralized with Tris [1.5M, pH 8,8] and stored at 4° C. TNF56 was concentrated and purified via AEX (A=10 mM piperazin, pH 10.8 and B=1M NaCl in 50 mM Tris, pH 7.5) using Source 30Q (GE Healthcare). To this end the Nanobody™ fractions were diluted with A buffer (10 mM piperazin, pH 10.8) to a conductivity of 5 mS/cm and the pH was adjusted to 10.8. The column [25×100 mm] was equilibrated in A buffer before loading the sample onto the column. TNF56 was eluted with a 5 Column Volume (CV) gradient. The pH of the collected fractions was adjusted to 7.8 using 1M Tris pH=7.8.

Pegylation of Bivalent Nanobodies™ Expressed in *Pichia pastoris*
Reduction of C-Terminal Cysteines Dithiotreitol (DTT, Aldrich Cat 15,046-0) was added to the neutralized fractions to reduce potential disulfide bridges that formed between the carboxy terminal cysteines of the Nanobodies™ (usually around 20%). A final concentration of 10 mM DTT and incubation overnight at 4° C. was found to be optimal. The reduction was evaluated by analytical size exclusion chromatography (SEC). Therefore 25 µl of the reduced Nanobody™ was added to 75 µl D-PBS and injected on a Sup75 10/300 GL column equilibrated in Dulbecco's PBS (D-PBS, Gibco™ REF 14190-094).

Non reduced Nanobody™ and DTT was removed by preparative SEC on a Hiload 26/60 Superdex75 prep grade column equilibrated in D-PBS.

The concentration of the reduced Nanobody™ was measured by measuring the Absorbance at 280 nm. A Uvikon 943 Double Beam UV/VIS Spectrophotometer (method: see SOP ABL-0038) was used. The absorption was measured in a wavelength scan 245-330 nm. Two Precision cells made of Quartz Suprasil® cells were used (Hellma type No.: 104-QS; light path: 10 mm). First the absorption of the blank was measured at 280 nm by placing two cells filled by 900 µl D-PBS. The sample was diluted (1/10) by adding 100 µl of the sample to the first cell. The absorption of the sample was measured at 280 nm.

The concentration was calculated with following formula:

$$\frac{OD_{280} Sample - OD_{280} blank}{\varepsilon \times 1} \times 10 \quad \begin{array}{l} \text{For } TNF55: \varepsilon = 1.85 \\ \text{For } TNF56: \varepsilon = 1.83. \end{array}$$

PEGylation

To PEGylate Nanobody™ a 5× molar excess of freshly made 1 mM PEG40 solution was added to the reduced Nanobody™ solution. (MPEG2-MAL-40K of NEKTAR™ Transforming Therapeutics (2D3YOTO1) Mw=40,000 g/mol; MPEG2-MAL-60K of NEKTAR™ Transforming Therapeutics (2D3YOVO1) Mw=60,000 g/mol).

The Nanobody™-PEG mixture was incubated for 1 h at room temperature (RT) with gentle agitation and then transferred to 4° C. The PEGylation was evaluated via analytical SEC. Therefore 250 of the Nanobody™ was added to 750 D-PBS and injected on a Sup75HR 10/300 column equilibrated in D-PBS. Pegylated Nanobody™ eluted in the range of the exclusion volume of the column (>75 kDa).

The PEGylated and non PEGylated Nanobody™ were separated via cation exchange chromatography (CEX, using Source30S, GE Healthcare; A buffer=25 mM citric acid pH=4 and B=1M NaCl in PBS). The sample was diluted to a conductivity of <5 mS/cm and the pH was adjusted to 4.0. The column [25×100 mm] was equilibrated and after sample application washed extensively with A-buffer. Pegylated Nanobody™ was eluted with a 3 CV gradient. The collected Nanobody™ was buffer exchanged to D-PBS by SEC on a Hiload 26/60 Superdex 75 prep grade column equilibrated in D-PBS.

Finally the Nanobody™ was made LPS-free via passage over an anion exchange column (Source30Q). The column (10×100 mm) was sanitized overnight in NaOH [1M] and afterwards equilibrated in endotoxin free D-PBS.

Biotinylation

To biotinylate Nanobody™ a 5× Molar excess of biotin (EZ-Link® Maleimide-PO2-Biotin, Pierce #21901) from a 10 mM stock solution was added to the reduced Nanobody™ (see 5.5.1). The biotin-Nanobody™ mixture was incubated for 1 h at RT with gentle agitation and then stored at 4° C.

The purity of biotinylated Nanobody™ was controlled via analytical SEC. Therefore 25 µl of biotinylated Nanobody™ was added to 75 µl D-PBS and injected on a Sup75HR 10/300 column equilibrated in D-PBS. From the obtained chromatogram could be concluded that the Nanobody™-biotin needs no further purification: no dimerization of Nanobody™ via an oxidation of free sulfidrils could be detected. A buffer change to D-PBS was done by a passage over a desalting column Sephadex G25 fine (90 ml) column.

Finally the Nanobody™-biotin was made LPS-free by passage over an anion exchange column (Source30Q, GE Healthcare). The column (1×10 cm) was sanitized overnight in 1M NaOH and then equilibrated in D-PBS.

To determine the purity, protein samples were analyzed on a 15% SDS-PAGE gel as described in example 8 and 49. Results are presented in FIGS. 49 and 50.

Example 57: Characterization of Bivalent Long Half-Lived Humanized Nanobodies™

Biochemical Characterization

TNF55 consists of 260 amino acids. The protein has a molecular weight of 27,106 Da. The pI is 8.67. The extinction coefficient at 280 nm is 1.850.

TNF56 consists of 264 amino acids. The protein has a molecular weight of 27,365 Da. The pI is 8.67. The extinction coefficient at 280 nm is 1.830.

Mass Spectrophotometry

The theoretical mass of TNF55 is 27,106 Da. The TNF55-Biotine protein has 2 S-S bridges and a biotine modification which should result in a mass of 27,627 Da in ESI-MS. The mass that was experimentally determined for TNF55-biotine is 27,627 Da.

The theoretical mass of TNF56 is 27,365 Da. The TNF55-Biotine protein has 2 S-S bridges and a biotine modification which should result in a mass of 27,886 Da in ESI-MS. The mass that was experimentally determined for TNF55-biotine is 27,886 Da.

N-Terminal Sequencing

N-terminal sequencing of TNF56-PEG40 showed that the protein sequence for the first 7 amino acids is as follows: EVQLVES (SEQ ID NO: 487). This is consistent with the theoretical protein sequence, which indicates proper N-terminal processing.

Analytical Sizing

Figure 51:
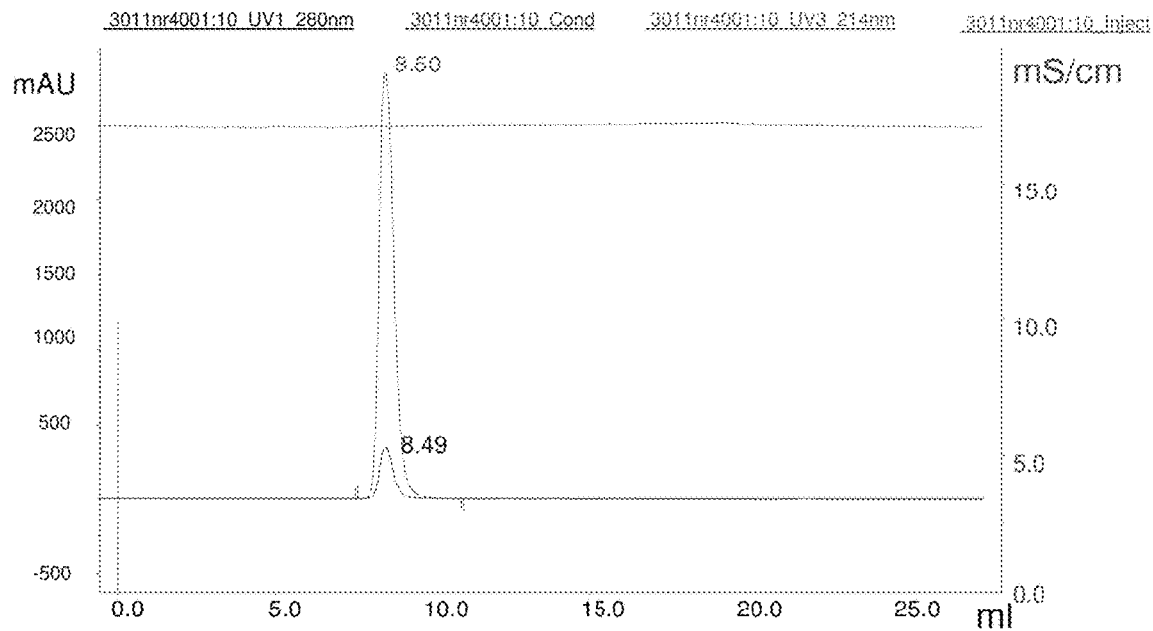

Analytical sizing of TNF56-PEG40 in PBS provides a symmetrical peak. No contaminants were observed. The retention time observed is 8.5 ml on Superdex HR 75 and 10.32 ml on Superdex HR 200. A representative profile is shown in FIGS. 51 and 52.

Example 58: Functionality in Cell-Based Assay

The potency to neutralize the cytotoxic activity of TNFα was analyzed in a cell-based assay. Potency was examined at different concentrations of Nanobody™ as well as of the commercially available Enbrel, Humira and Remicade on a molar base. The higher the EC50 observed the lower the activity of the compound to neutralize TNFα.

The results are summarized in Table 45 and FIGS. 53 and 54.

The data show an increase in potency for the bivalent Nanobodies™ when compared to the monovalent Nanobody™ TNF1. Potency of TNF55 derivatives is similar to TNF56 derivatives, which is in the range of Enbrel and 10-fold better than Humira and Remicade.

Example 59: Pharmacokinetic and Immunogenicity Analysis of Bivalent Long Half-Lived Humanized Nanobodies in Mice See example 54

Experiments were performed in order to examine the half-life of pegylated Nanobodies™ in mice. The half-life of bivalent TNF56-PEG40 was compared to the half-life of TNF56-PEG60. Both Nanobodies™ have comparable half-life of ~2 days. The results are presented in FIG. 55.

In addition, the half-life of pegylated bivalent 3E-3E was explored. The half-life of 3E-3E-PEG20 was compared to the half-life of 3E-3E-PEG40 after intravenous administration of 100 µg of the Nanobodies™. 3E-3E-PEG20 has a half-life of 17 hrs, while 3E-3E-PEG40 has a half-life of 2.1 days, comparable to the half-life of 3E-3E-MSA21. The results are presented in FIG. 56.

Serum samples were diluted 100-fold and analyzed for the presence of mouse anti-TNF56-PEG40 or anti-TNF56-PEG60 antibodies. Lack of immunogenicity was demonstrated for both molecules. Data are presented in FIG. 57.

Example 60: Efficacy of Anti-TNF-α Nanobody TNF60 (TNF60) in Prevention of Chronic Polyarthritis Transgenic mouse lines carrying and expressing a 3'-modified human tumour necrosis factor (hTNF-alpha, cachectin) transgene were used as a model to study the efficacy of TNF60 (TNF60) in preventing the development of arthritis (EMBO J. 10, 4025-4031). These mice have been shown to develop chronic polyarthritis with 100% incidence at four to seven weeks of age.

From the third week of age, litters of transgenic mice were divided into groups of eight animals. Before initializing the study, the average body weight was calculated for each group. From then on, during the whole study animal weights were recorded once a week for each group.

To test the efficacy of TNF60 in the prevention of chronic polyarthritis, intraperitoneal injections were given twice a week to each animal of a particular group according to the following scheme:

Group 1 (negative control): phosphate buffered saline (PBS) (formulation buffer)
Group 2 (Nanobody treatment): TNF60 at a final dose of 30 mg/kg
Group 3 (Nanobody treatment): TNF60 at a final dose of 10 mg/kg
Group 4 (Nanobody treatment): TNF60 at a final dose of 3 mg/kg
Group 5 ($1^{st}$ positive control): Enbrel at a final dose of 30 mg/kg
Group 6 ($1^{st}$ positive control): Enbrel at a final dose of 10 mg/kg
Group 7 ($2^{nd}$ positive control): Remicade at a final dose of 30 mg/kg
Group 8 ($2^{nd}$ positive control): Remicade at a final dose of 10 mg/kg
Group 9 ($2^{nd}$ positive control): Remicade at a final dose of 3 mg/kg For each group, dates of injection and injection volumes were noted.

Injections continued for seven weeks. During this period, clinical scores were recorded by observing macroscopic changes in joint morphology for each animal.

At 10 weeks of age, all mice were sacrificed and sera and joints were collected. Sera were stored at −70° C. and ankle joints were conserved in formalin.

For selected groups, ankle joints were embedded in paraffin and sectioned. Ankle joint sections were subsequently used for histopathological evaluation of disease progression.

Figure 58:
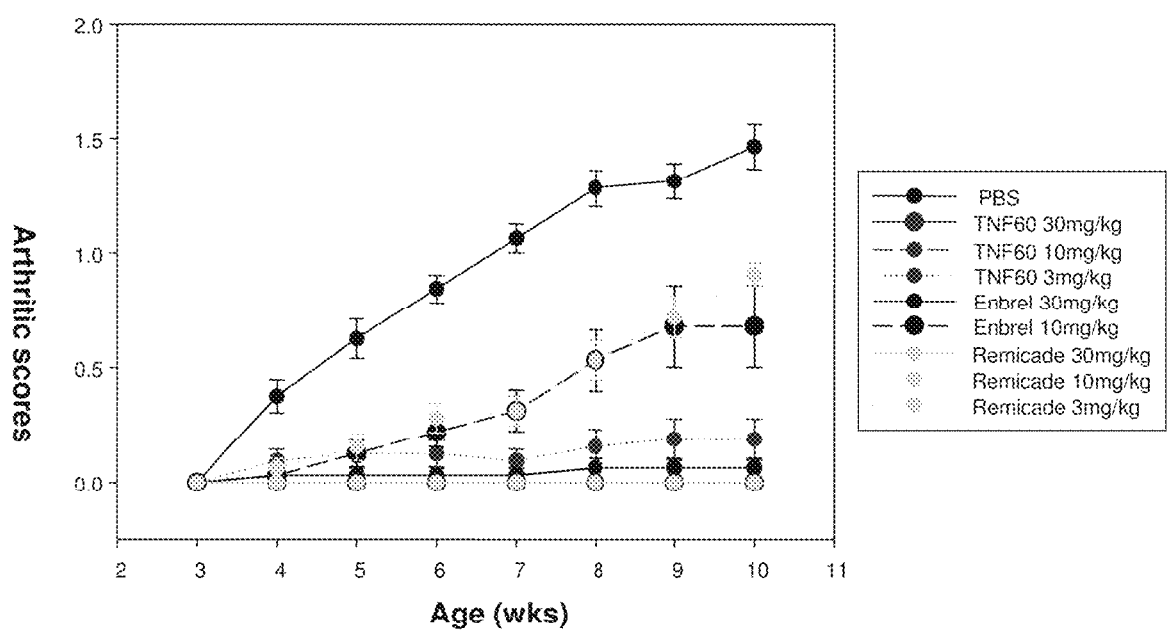

Results are depicted in FIG. 58.

Example 61: Efficacy of Anti-TNF-α Nanobody TNF60 (TNF60) in Therapeutic Treatment of Chronic Polyarthritis Transgenic mouse lines carrying and expressing a 3'-modified human tumour necrosis factor (hTNF-alpha, cachectin) transgene were used as a model to study the efficacy of TNF60 (TNF60) in therapeutic treatment of arthritis (EMBO J. 10, 4025-4031). These mice have been shown to develop chronic polyarthritis with 100% incidence at four to seven weeks of age.

From the sixth week of age, litters of transgenic mice were divided into groups of eight animals. Before initializing the study, the average body weight was calculated for each group. From then on, during the whole study animal weights were recorded once a week for each group.

To test the efficacy of TNF60 in the therapeutic treatment of chronic polyarthritis, intraperitoneal injections were given twice a week to each animal of a particular group according to the following scheme:

Group 1 (negative control): phosphate buffered saline (PBS) (formulation buffer)
Group 2 (Nanobody treatment): TNF60 at a final dose of 30 mg/kg
Group 3 (Nanobody treatment): TNF60 at a final dose of 10 mg/kg
Group 4 ($1^{st}$ positive control): Enbrel at a final dose of 30 mg/kg
Group 5 ($2^{nd}$ positive control): Remicade at a final dose of 30 mg/kg For each group, dates of injection and injection volumes were noted.

Injections continued for seven weeks. During this period, clinical scores were recorded by observing macroscopic changes in joint morphology for each animal.

At 13 weeks of age, all mice were sacrificed and sera and joints were collected. Sera were stored at −70° C. and ankle joints were conserved in formalin.

For selected groups, ankle joints were embedded in paraffin and sectioned. Ankle joint sections were subsequently used for histopathological evaluation of disease progression.

Figure 59:
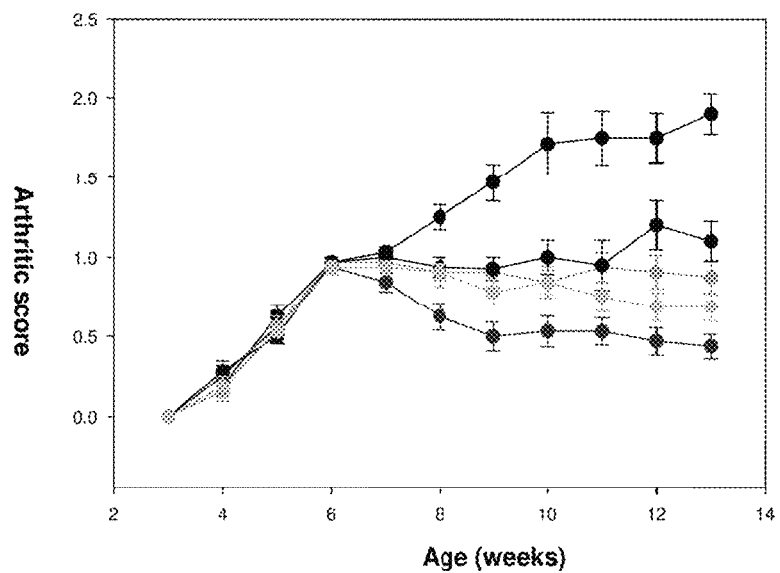

Results are depicted in FIG. 59.

Example 62: Effect of Formatting on Efficacy of an Anti-TNF-α Nanobody in Prevention of Chronic Polyarthritis Transgenic mouse lines carrying and expressing a 3'-modified human tumour necrosis factor (hTNF-alpha, cachectin) transgene were used as a model to study the efficacy of an anti-TNF-α Nanobody formatted in different ways in the prevention of chronic polyarthritis (EMBO J. 10, 4025-4031). These mice have been shown to develop chronic polyarthritis with 100% incidence at four to seven weeks of age.

From the third week of age, litters of transgenic mice were divided into groups of eight animals. Before initializing the study, the average body weight was calculated for each group. From then on, during the whole study animal weights were recorded once a week for each group.

To study the efficacy of an anti-TNF-α Nanobody in different formats for prevention of chronic polyarthritis, intraperitoneal injections were given twice a week to each animal of a particular group according to the following scheme:

Group 1 (negative control): phosphate buffered saline (PBS) (formulation buffer)
Group 2 (Nanobody format 1): TNF60 at a final dose of 10 mg/kg
Group 3 (Nanobody format 1): TNF60 at a final dose of 2.5 mg/kg
Group 4 (Nanobody format 1): TNF60 at a final dose of 1 mg/kg
Group 5 (Nanobody format 2): TNF56-PEG40 at a final dose of 10 mg/kg
Group 6 (Nanobody format 2): TNF56-PEG40 at a final dose of 1.8 mg/kg
Group 7 (Nanobody format 2): TNF56-PEG40 at a final dose of 0.7 mg/kg
Group 8 (Nanobody format 3): TNF56-biot at a final dose of 1.8 mg/kg
Group 9 (Nanobody format 4): TNF30 at a final dose of 1 mg/kg
Group 10 (Nanobody format 5): TNF1 at a final dose of 1 mg/kg
Group 11 ($1^{st}$ positive control): Enbrel at a final dose of 10 mg/kg
Group 12 ($2^{nd}$ positive control): Remicade at a final dose of 10 mg/kg For each group, dates of injection and injection volumes were noted.

Injections continued for seven weeks. During this period, clinical scores were recorded by observing macroscopic changes in joint morphology for each animal.

At 10 weeks of age, all mice were sacrificed and sera and joints were collected. Sera were stored at −70° C. and ankle joints were conserved in formalin.

For selected groups, ankle joints were embedded in paraffin and sectioned. Ankle joint sections were subsequently used for histopathological evaluation of disease progression.

Figure 60:
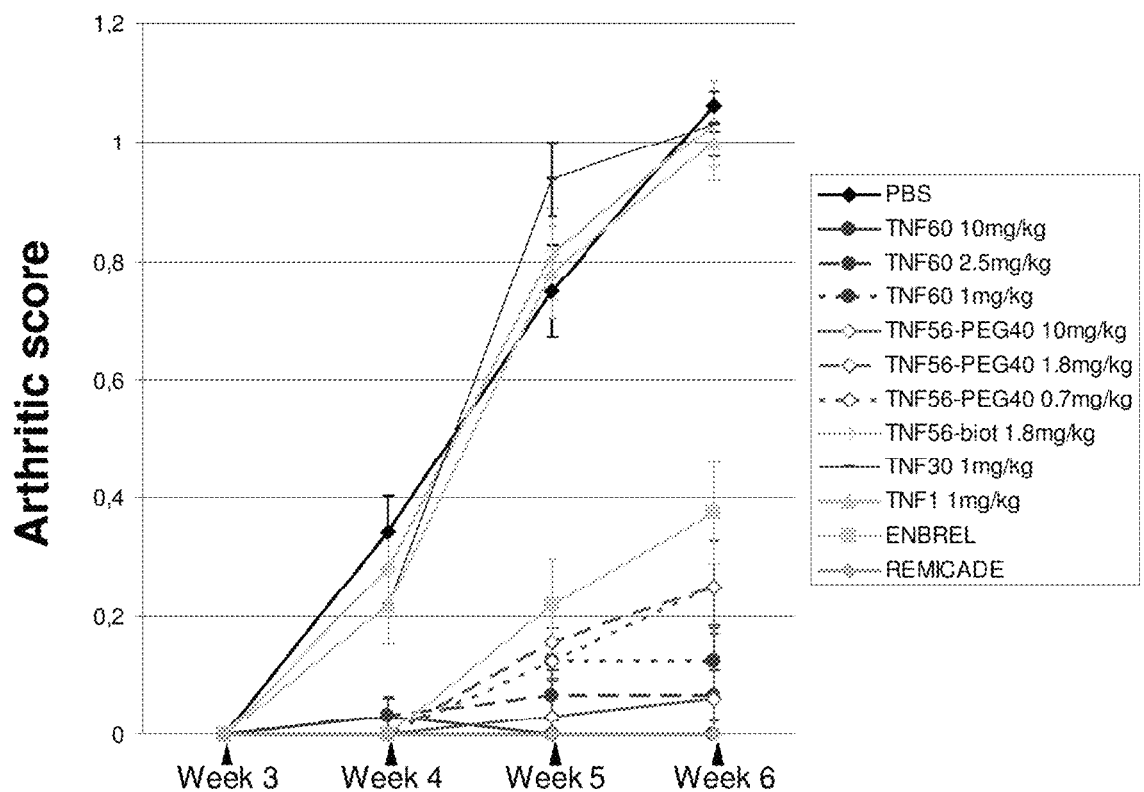

Results are depicted in FIG. 60.

Example 63: Pharmacokinetic Study of Anti-TNF-α Nanobodies TNF60 (TNF60) and TNF56-PEG40 in Rhesus Monkey Captive-bred rhesus monkeys (*Macaca mulatta*) are used to determine the pharmacokinetic profile of TNF60 and TNF56-PEG40.

Sixteen animals are used in this study (eight males and eight females) and are divided into four groups (two males and two females per group). All animals weighed approximately 5 kg and are disease-free for at least six weeks prior to use. Sniff® Pri vegetarisch V3994 serves as food. Sixty g/kg b.w. are offered to each monkey. The residue is removed. At regular intervals (at least twice a year) the food is analyzed based on EPA/USA for contaminants by LUFA-ITL. Tap water is offered ad libitum. The animals in each treatment group are housed in a block of several adjacent cages within the monkey unit. The monkeys are kept singly in $V_2A$ steel cages with a size of 90 cm×82 cm×96 cm. The room temperature is maintained at 23° C.±3° C. (maximum range) and the relative humidity at 60%±20% (maximum range). Deviations from the maximum range caused for example during cleaning procedure are dealt with in SOPs. The rooms are lit and darkened for periods of 12 hours each.

Two groups are infused with TNF60 and two groups are infused with TNF56-PEG40. Intravenous infusions of TNF60 and TNF56-PEG40 (dissolved in PBS) into the vena cephalica of the right or the left arm using indwelling catheters and a TSE infusion pump (see below) are given at a fixed dose of 2 mg/kg.

Four single administrations are performed, separated by a wash-out period of at least fourteen days. After the last administration the follow-up period is at least eight weeks. Two out of the four groups are treated with TNF60 or TNF56-PEG40 in combination with methotrexate (MTX) (dissolved in PBS). Group 2 is treated with TNF60 and MTX; group 4 is treated with TNF56-PEG40 and MTX. MTX is dosed weekly intramuscularly at 0.2 mg/kg. On the administration days, MTX is given approximately 30 minutes prior to administration. Dosing starts at the first Nanobody administration and will continue throughout the eight week wash-out after the fourth dose. There are fourteen single MTX administrations, separated by a wash-out period of at least one week starting at the first test item administration.

Example 64: Synovium-Derived Fibroblast Studies

In this study the ability of the anti-TNF biologicals, ALX0071 and Etanercept, to attenuate TNFα-induced IL-6 production by RA-synovium derived fibroblasts was assessed.

Isolation of Synovial Fibroblasts

Synovial joint tissue from consenting RA patients was stored in DMEM-based medium with antibiotics at 4° C. for up to 96 hours after joint replacement surgery. Synovial cells were isolated from dissected synovium by collagenase digestion at 37° C. for 2 hours. The resultant cell suspension was then washed by a series of centrifugation and resuspension steps and the resultant cells then cultured at 37° C. in DMEM-based culture medium supplemented with 10% FCS (v/v). The resultant fibroblasts were used for the following experiment at either the second or third passage. Cells from four donors were used in individual experiments. Fibroblasts were seeded into 96-well flat bottom polystyrene plates at $1.5 \times 10^4$ cells in a final volume of 250 μL of DMEM-based culture medium supplemented with 10% FCS (v/v) per well and cultured overnight.

Stimulation of Synovial Fibroblasts

Cells were then incubated for 72 hours in DMEM-based culture medium supplemented with TNFα at 50 ng per mL (3 nM (R&D Systems 210-TA/CF) alone or in the presence of increasing doses of ALX0071 (0.575 to 1920 ng per mL; 0.015 to 50 nM) or Etanercept (Wyeth Labs; 3.75 to 11250 ng per mL; 0.025 to 75 nM). The final volume in each well was 250 μL and each assessment was performed in triplicate. After 72 hours, the supernatant media was removed and stored at −40° C. prior to analysis by IL-6 ELISA (R&D Systems). The inhibition of TNFα-induced IL-6 production was determined and $IC_{50}$ values were calculated for both ALX0071 and Etanercept.

Summary of Results

Both ALX10071 and Etanercept dose-dependently reduced TNF□-induced IL-6 production by RA synovium derived fibroblasts from all four donors. There was a similar potency between the two reagents under these assay conditions.

Example 65: Murine Air Pouch Studies

In this study the ability of the anti-TNF biologicals, ALX0071 and Etanercept, to attenuate TNFα-induced cell infiltration in to a murine air pouch was assessed.

Creation of Air Pouch

Air pouches were formed by the sub-cutaneous (s.c.) injection of 2.5 mL of sterile air in to the dorsal surface of anaesthetised male C57B1/6/J mice (25-30 g, Harlan). The pouch was re-inflated by injecting 2.5 ml of sterile air 3 days later.

TNFα Stimulation

Six days after the initial creation of the air pouch, the animals were anaesthetised and the pouch injected with 1 ml of 0.5% CarboxyMethylCellulose (CMC) vehicle containing 0.1 μg recombinant human TNFα (R & D Systems, 210-TA-050/CF). In three other groups of animals, ALX0071 (0.0625, 0.125 and 0.25 mg/kg) was injected s.c. 19 hours prior to the injection of TNFα. A second three groups of animals were injected (s.c.) with Etanercept (Wyeth Labs, 0.125, 0.25 and 0.5 mg/kg) immediately prior to the injection of TNFα.

24 hours following TNFα □ injection, mice were culled with a rising concentration of $CO_2$. Pouches were lavaged with 2 ml of ice cold endotoxin free sterile PBS containing 5 IU/ml heparin. Volumes were recorded and 0.5 ml aliquots were separated for counting of the total white blood cell (WBC) population on a Sysmex XT-Vet cell counter. The mean and standard error of the mean (SEM) total WBC counts for each group were calculated per ml of lavage fluid withdrawn. Statistical analysis was by ANOVA with Kruskal-Wallis post-test on untransformed data.

Summary of Results

Both ALX0071 and Etanercept attenuated the TNFα-induced WBC infiltration in to the air pouches (Table).

While this attenuation reached statistical significance at both the 0.125 (P<0.01) and 0.25 mg/kg (P<0.05) ALX0071 dose groups, statistical significance was not observed with any Etanercept dose group.

TABLE 8

| Name | SEQ ID NO | Sequence |
|---|---|---|
| PMP1C2(TNF1) | 52 | QVQLVESGGGLVQPGGSLRLSCAASGFTFSDYWMYWVRQAPGKGLE WVSEINTNGLITKYPDSVKGRFTISRDNAKNTLYLQMNSLKPEDTA LYYCARSPSGFNRGQGTQVTVSS |
| PMP1G11 | 53 | QVQLQESGGGMVQPGGSLRLSCAASGFDFGVSWMYWVRQAPGKGLE WVSEINTNGLITKYPDSVKGRFTISRDNAKTTLYLQMNSLKPEDTA LYYCARSPSGSFRGQGTQVTVSS |
| PMP1H6 | 54 | EVQLVESGGGLVQPGGSLRLSCATSGFDFSVSWMYWVRQAPGKGLE WVSEINTNGLITKYVDSVKGRFTISRDNAKNTLYLQMDSLIPEDTA LYYCARSPSGSFRGQGTQVTVSS |
| PMP1G5(TNF2) | 55 | QVQLVESGGGLVQAGGSLRLSCAASGRTFSEPSGYTYTIGWFRQAP GKEREFVARIYWSSGLTYYADSVKGRFTISRDIAKNTVDLLMNSLK PEDTAVYYCAARDGIPTSRSVGSYNYWGQGTQVTVSS |
| PMP1H2 | 56 | QVKLEESGGGLVQPGDSLRLSCAASGRTFSDYSGYTYTVGWFRQAP GKEREFVARIYWSSGNTYYADSVKGRFTISRDIAKNTVDLLMNNLE PEDTAVYYCAARDGIPTSRSVESYNYWGQGTQVTVSS |
| PMP3G2 | 57 | AVQLVESGGGLVQPGDSLRLSCAASGRTFSDYSGYTYTVGWFRQAP GKEREFVARIYWSSGNTYYADSVKGRFTISRDIAKNTVDLLMNNLE PEDTAVYYCAARDGIPTSRSVESYNYWGQGTQVTVSS |
| PMP1D2 | 58 | AVQLVDSGGGLVQAGGSLRLSCAASGRTFSAHSVYTMGWFRQAPGK EREFVARIYWSSANTYYADSVKGRFTISRDNAKNTVDLLMNCLKPE DTAVYYCAARDGIPTSRSVEAYNYWGQGTQVTVSS |
| PMP3D10 | 59 | QVQLVESGGGLVQAGGSLSLSCAASGRSFTGYYMGWFRQAPGKERQ LLASISWRGDNTYYKESVKGRFTISRDDAKNTIYLQMNSLKPEDTA VYYCAASILPLSDDPGWNTNWGQGTQVTVSS |
| PMP5F10(TNF3) | 60 | EVQLVESGGGLVQAGGSLSLSCSASGRSLSNYYMGWFRQAPGKERE LLGNISWRGYNIYYKDSVKGRFTISRDDAKNTIYLQMNRLKPEDTA VYYCAASILPLSDDPGWNTYWGQGTQVTVSS |
| PMP6A8(ALB2) | 61 | AVQLVESGGGLVQGGGSLRLACAASERIFDLNLMGWYRQGPGNERE LVATCITVG.DSTNYADSVKGRFTISMDYTKQTVYLHMNSLRPEDT GLYYCKIRRTWHSELWGQGTQVTVSS |
| PMP6B4 | 62 | EVQLVESGGGLVQEGGSLRLACAASERIWDINLLGWYRQGPGNERE LVATITVG.DSTSYADSVKGRFTISRDYDKNTLYLQMNSLRPEDTG LYYCKIRRTWHSELWGQGTQVTVSS |
| PMP6A6(ALB1) | 63 | AVQLVESGGGLVQPGNSLRLSCAASGFTFRSFGMSWVRQAPGKEPE WVSSISGSGSDTLYADSVKGRFTISRDNAKTTLYLQMNSLKPEDTA VYYCTIGGSLSRSSQGTQVTVSS |
| PMP6C1 | 64 | AVQLVDSGGGLVQPGGSLRLSCAASGFSFGSFGMSWVRQYPGKEPE WVSSINGRGDDTRYADSVKGRFSISRDNAKNTLYLQMNSLKPEDTA EYYCTIGRSVSRSRTQGTQVTVSS |
| PMP6G8 | 65 | AVQLVESGGGLVQPGGSLRLTCTASGFTFRSFGMSWVRQAPGKDQE WVSAISADSSTKNYADSVKGRFTISRDNAKKMLYLEMNSLKPEDTA VYYCVIGRGSPSSPGTQVTVSS |
| PMP6A5 | 66 | QVQLAESGGGLVQPGGSLRLTCTASGFTFGSFGMSWVRQAPGEGLE WVSAISADSSDKRYADSVKGRFTISRDNAKKMLYLEMNSLKSEDTA VYYCVIGRGSPASQGTQVTVSS |
| PMP6G7 | 67 | QVQLVESGGGLVQPGGSLRLSCAASGFTFSNYWMYWVRVAPGKGLE RISRDISTGGGYSYYADSVKGRFTISRDNAKNTLYLQMNSLKPEDT ALYYCAKDREAQVDTLDFDYRGQGTQVTVSS |
| NC55TNF_S1C4 | 105 | EVQLVESGGGLVQAGDSLRLSCAASQIIFGSHVAAWFRQAPGRERE FVAEIRPSGDFGPEGEFEHVTASLKGRFTIAKNSVDNTVYLQMNSL KPEDTAVYYCAAAPYRGGRDYRWEYEYEYWGQGTQVTV |
| NC55TNF_S1C3 | 106 | EVQLVESGGGLVQPGGSLRLSCKNAGSTSNAYATGWFRRAPGKERE FVAGIQWSGGDAFYRNSVKGRFRITRDPDNTVYLQMNDLKPEDTAI YYCAQKLSPYYNDFDSSNYEYWGQGTQVTV |

TABLE 8-continued

| Name | SEQ ID NO | Sequence |
|---|---|---|
| NC55TNF_S2C1 | 107 | EVQLVESGGDLVQPGGSLRLSCAVSGQLFSTNDVGWYRRAPGKQRE<br>LVATITDDGTTDYGDDVKGRFVISREGEMVYLEMNSLKPEDTAVYY<br>CNINRLRSTWGIRYDVWGQGTQVTVSS |
| NC55TNF_S2C5 | 108 | EVQLVESGGGLVQPGGSLRLSCVVSGFTFSTTSMTWVRQAPGKFEE<br>WVSFINSDGSSTTYADSVKGRFTISRDNAKNTLYLQMNSLKPEDTA<br>MYYCGRRGYGRDRSKGIQVTVAS |
| NC55TNF_S3C7 | 109 | EVQLVESGGGTVQAGDSLRLSCAASGRSFSSVAMGWFRQAPGKQRE<br>FLAGVGYDGSSIRYAESVKGRFTIARGNRESTVFLQMENLKPEDTA<br>VYFCTAEPIGAYEGLWTYWGQGTQVTVSS |
| NC55TNF_S3C1 | 110 | XXXXVESGGGLMQPGGSLKLSCAASGFMFSDSAMGWFRQAPGKERE<br>FVATISWNGGSSSYADFVKGRFTISRDNAKNTVYLQMNGLTPQDTA<br>IYYCAGSYSNGNPHRFSQYQYWGQGTQVTVSS |
| NC55TNF_BMP1B2 | 111 | EVQLVESGGGLVQAGGSLRLSCAASGRTFGTYAMGWFRQAPGKERE<br>FVAAISWGGGSIVYAESAKGRFTISRDNAKXTMYLQMDSLKPEDTA<br>VYYCAAANNIATLRQGSWGQGTQVTVSS |
| NC55TNF_BMP1D2 | 112 | EVQLVESGGELVQAGGSLKLSCTASGRNFVTYAMSWFRRAPGKERE<br>FVASISWSGDTTYYSNSVKGRFTVSRDNGKNTAYLRMNSLKPEDTA<br>DYYCAVVQVIDPSWSGVNLDDYDYLGSGTQVTVSS |
| NC55TNF_BMP1E2 | 113 | EVQLVESGGRLVQPGGSLRLSCKNAGSTSNAYATGWFRRAPGKERE<br>FVAGIQWSGGDAFYRNSVKGRFRITRDPDNTVYLQMNDLKPEDTAI<br>YYCAQKLSPYYNDFDSSNYEYWGQGTQVTVSS |
| NC55TNF_BMP1G2 | 114 | EVQLVESGGGLVQPGGSLRLSCAASATISSIVMLGWYRQAPGKQRE<br>WVASITIGSRTNYADSVKGRFTISRDNAKNTVYLQMNSLKPEDTAV<br>YFCNAVPPRDDYWGQGTQVTVSS |
| NC55TNF_BMP2A2 | 115 | EVQLVESGGGLVQAGGSLRLSCAASGQTSSSYDMGWFRQAPGEGRE<br>FVARISGSDGSTYYSDRAKDRFTISRDNTKNMVYLQMDRLKPDDTA<br>VYYCRVPRYENQWSSYDYWGQGTQVTVSS |
| NC55TNF_BMP2C2 | 116 | EVQLVESGGGLVQPGGSLRLSCAASGSTFSTYDMSWVRQAPGKGLE<br>WVSGIDSGGGSPMYVDSVKGRFTVSRDNAKNTLYLQMNSLKPEDTA<br>VYYCAKFSTGADGGSWYWSYGMDSWGKGTQVTVSS |
| NC55TNF_BMP2F2 | 117 | EVQLVESGGGLVQAGDSLRLSCEASERSSNRYNMAWFRQAPGKERE<br>FLARVDVSGGNTLYGDSVKDRFTVSRINGKNAMYLQMNNLKPEDTA<br>IYYCAAGGWGTTQYDYDYWGQGTQVTVSS |
| NC55TNF_NC10 | 118 | EVQLVESGGGLVQPGGSLRLSCVCVSSGCTFSAYSMTWVRQAPGKA<br>EEWVSFINSDGSSTTYADSVNGRFKISRDNAKKTLYLQMNSLGPED<br>TAMYYCQRRGYALDRGQGTQVTVSS |
| NC55TNF_NC11 | 119 | EVQLVESGGGLVQAGDSLTLSCASSGRGFYKNAMGWFRQPPGKERE<br>FVASIKWNGNNTYYADSVRGRFTISRGNAKNTENTVSLQMNSLKPE<br>DTADYYCAADSSHYSYVYSKAYEYDYWGQGTQVTVSS |
| NC55TNF_NC1 | 120 | EVQLVESGGGLVQPGGSLRLSCVFSGFAFSASSMAWVRQAPGKYEE<br>WVSFINSDGSSTTYADSVQGRFTISRDNAKNTLYLQMNSLKSEDTA<br>MYYCGRRGYGRDRSQGIQVTVSS |
| NC55TNF_NC2 | 121 | EVQLVESGGGLVQAGGSLRLSCAASGRTFSSYAMGWFRQAPGKERE<br>FVAAISWSGTITNYADSVKGRFTISRDNGKNTVHLQMNSLKPEDTA<br>VYHCAVVQPYSGGDYYTGVEEYDYWGXGTQVTVSS |
| NC55TNF_NC3 | 122 | EVQLVESGGGLVQPGGSLRLSCVVSGFTFSATSMTWVRQAPGKAEE<br>WVSFINSDGSSTTYADSVKGRFTISRDNAKNTLYLQMDDLQSEDTA<br>MYYCGRRGYGRDRSRGIQVTVSS |
| NC55TNF_NC5 | 123 | EVQLVESGGGLVQAGGSLRLSCAASGGAFSNYDVGWFRQAPGEGRE<br>IVARISGSGDSTYSSNRAKGRFTISRDNAKNTVYLQMNSLKREDTA<br>VYYCRAARYNGTWSSNDYWGQGTQVTVSS |
| NC55TNF_NC6 | 124 | EVQLVESGGGLVQPGGSLRLSCECVSSGCTFSAYSMTWVRQAPGKA<br>EEFVSFINSDGSSTTYANSVNGRFKISRDNAKKTLYLQMNSLGPED<br>TAMYYCQRRGYALDRGQGTQVTVSS |
| NC55TNF_NC7 | 125 | QVQLVESGGGLVQAGGSLRLSCTASGQTSSTADMGWFRQPPGKGRE<br>FVARISGIDGTTYYDEPVKGRFTISRDKAQNTVYLQMDSLKPEDTA<br>VYYCRSPRYADQWSAYDYWGQGTQVTVSS |

TABLE 8-continued

| Name | SEQ ID NO | Sequence |
|---|---|---|
| NC55TNF_NC8 | 126 | EVQLVESGGGLVQPGGSLRLSCVVSGFTFSTTSMTWVRQAPGKFEEWVSFINSDGSSTTYADSVKGRFTISRDNAKNTLYLQMNSLKPEDTAMYYCGRRGYGRDRSKGIQVTVSS |
| NC55TNF_S2C2 | 127 | EVQLVESGGGLVQPGGSLRLSCVASASGVKVNDMGWYRQAPGKERELVATITDDGRTNYEDFAKGRFTISRDNAKNTVYLQMNSLLPEDTAVYYCNARTYWAHLPTYWGQGTQVTVSS |
| NC55TNF_S1C6 | 128 | EVQLVESGGGLVQAGGSLRLSCAASGRSFGSVAMGWFRQAPGKEREFVAAIGYDGNSIRYGDSVKGRFTISRDNIKNTMYLEMENLNADDTARYLCAAEPLARYEGLWTYWGQGTQVTVSS |
| NC55TNF_S3C2 | 129 | EVQLVESGGGLVQAGASLRLSCTTSTRTNDRFNMAWFHQAPGKDREFVSRIDVAGYNTAYGDFVKGRFTVSRDSAENTVVLQMNSLRPEDTGVYYCAAGGWGISQSDYDLWGQGTQVTVSS |

TABLE 9

| nanobody | Class | Estimated koff (1/s) |
|---|---|---|
| PMP5 F10 | III | 2.63E−04 |
| PMP1 G5 | II | 3.59E−04 |
| PMP1 C2 | I | 4.39E−04 |
| PMP1 G11 | I | 1.15E−03 |
| PMP1 H6 | I | 2.14E−03 |
| PMP1 H2 | II | 3.65E−03 |
| PMP3 G2 | II | 1.09E−02 |

TABLE 10

| Nanobody | Germline sequence | #AA differences/total #AA | % AA identity |
|---|---|---|---|
| ALB1 | DP51/DP53 | 13/87 | 85.1 |
| ALB2 | DP54 | 26/87 | 70.2 |
| TNF1 | DP51/DP53 | 6/87 | 93.2 |
| TNF2 | DP54 | 16/87 | 81.7 |
| TNF3 | DP29 | 18/87 | 79.4 |

TABLE 11

| Nanobody | Induction time | Yield (mg/L) |
|---|---|---|
| ALB1 | short/37° C. | 18 |
| ALB2 | short/37° C. | 4 |
| TNF1 | short/37° C. | 8.3 |
| TNF2 | short/37° C. | 5 |
| TNF3 | short/37° C. | 0.8 |

TABLE 12

| | 50% binding (ng/ml) | |
|---|---|---|
| ID | Human TNFα | Rhesus TNFα |
| TNF1 | 12 | 12 |
| TNF2 | 20 | >3000 |
| TNF3 | 18 | 16 |

TABLE 13

| | 50% inhibition (ng/ml) | |
|---|---|---|
| ID | Human TNFα | Rhesus TNFα |
| TNF1 | 530 | 220 |
| TNF2 | 3500 | >5000 |
| TNF3 | 100 | 100 |

TABLE 14

| Human TNFα | Kd (1/s) |
|---|---|
| TNF1 | 1.05E−03 |
| TNF2 | 1.33E−03 |
| TNF3 | 3.02E−04 |

TABLE 15

| | | Human albumin | Rhesus albumin | Mouse albumin |
|---|---|---|---|---|
| ALB1 | KD (nM) | 0.57 | 0.52 | 6.5 |
| | ka (1/Ms) | 1.11E+06 | 1.05E+06 | 1.11E+06 |
| | kd (1/s) | 6.30E−04 | 5.46E−04 | 7.25E−03 |
| ALB2 | KD (nM) | 0.092 | 0.036 | 15.7 |
| | ka (1/Ms) | 8.15E+05 | 1.94E+06 | 1.95E+05 |
| | kd (1/s) | 7.52E−05 | 7.12E−05 | 3.07E−03 |

TABLE 16 assay: L929s + Act D (5000 c/w)
TNF: human TNFα @ 0.5 ng/ml

| Nanobody | | EC$_{50}$ in nM | | | relative potency | |
|---|---|---|---|---|---|---|
| | | mean | stdev | # | mean | stdev |
| TNF1 | 1C2 | 0.707 | 0.265 | 14 | 0.015 | 0.007 |
| TNF2 | 1G5 | 1.412 | 0.622 | 14 | 0.007 | 0.002 |
| TNF3 | 5F10 | 0.224 | 0.133 | 14 | 0.048 | 0.019 |
| Enbrel | | 0.009 | 0.005 | 45 | 1.002 | 0.011 |
| Humira | | 0.079 | 0.043 | 39 | 0.097 | 0.069 |
| Remicade | | 0.083 | 0.037 | 45 | 0.103 | 0.058 |

TABLE 16-continued assay: L929s + Act D (5000 c/w)
TNF: rhesus TNFα @ 0.5 ng/ml

| Nanobody | | EC₅₀ in nM | | | relative potency | |
|---|---|---|---|---|---|---|
| | | mean | stdev | # | mean | stdev |
| TNF1 | 1C2 | 0.693 | 0.305 | 9 | 0.015 | 0.009 |
| TNF2 | 1G5 | >50 | | 9 | | |
| TNF3 | 5F10 | 0.602 | 0.283 | 9 | 0.017 | 0.010 |
| Enbrel | | 0.009 | 0.003 | 7 | 1 | 0.000 |
| Humira | | 0.071 | 0.025 | 8 | 0.103 | 0.059 |
| Remicade | | >6.7 | | 7 | | |

TABLE 17

| % | Untreated | RT | 37° C. | 50° C. | 60° C. | 70° C. | 80° C. | 90° C. |
|---|---|---|---|---|---|---|---|---|
| TNF1 | 100 | 98 | 98 | 98 | 98 | 95 | 92 | 90 |
| TNF2 | 100 | 99 | 100 | 99 | 97 | 96 | 63 | 50 |
| TNF3 | 100 | 96 | 97 | 98 | 96 | 94 | 75 | 70 |
| ALB1 | 100 | 101 | 102 | 101 | 100 | 64 | 94 | 90 |
| ALB2 | 100 | 100 | 102 | 100 | 100 | 28 | 8 | 17 |

TABLE 18

| nanobody | temp in ° C. | EC₅₀ in nM | # | relative potency |
|---|---|---|---|---|
| TNF1 92#2302nr1.TNF1 | control | 0.916 | 1 | 0.013 |
| | RT | 0.873 | 1 | 0.014 |
| | 37 | 0.901 | 1 | 0.013 |
| | 50 | 0.908 | 1 | 0.013 |
| | 60 | 0.891 | 1 | 0.013 |
| | 70 | 1.218 | 1 | 0.010 |
| | 80 | 2.655 | 1 | 0.004 |
| | 90 | 5.797 | 1 | 0.002 |
| TNF2 92#2302nr2.TNF2 | control | 2.500 | 1 | 0.005 |
| | RT | 2.165 | 1 | 0.005 |
| | 37 | 2.212 | 1 | 0.005 |
| | 50 | 2.241 | 1 | 0.005 |
| | 60 | 1.782 | 1 | 0.007 |
| | 70 | 2.487 | 1 | 0.005 |
| | 80 | 2.818 | 1 | 0.004 |
| | 90 | 6.135 | 1 | 0.002 |
| TNF3 92#2302nr3.TNF3 | control | 0.278 | 1 | 0.043 |
| | RT | 0.289 | 1 | 0.041 |
| | 37 | 0.295 | 1 | 0.040 |
| | 50 | 0.290 | 1 | 0.041 |
| | 60 | 0.281 | 1 | 0.042 |
| | 70 | 0.293 | 1 | 0.040 |
| | 80 | 0.576 | 1 | 0.021 |
| | 90 | 0.861 | 1 | 0.014 |

TABLE 19

| Name | SEQ ID NO | Sequence |
|---|---|---|
| GS9 | 68 | GGGGSGGGS |
| GS30 | 69 | GGGGSGGGGSGGGGSGGGGSGGGGSGGGGS |
| TNF1-GS9-TNF1(TNF4) | 70 | QVQLVESGGGLVQPGGSLRLSCAASGFTFSDYWMYWVRQAPGKGLEWVSEINTNGLITKYPDSVKGRFTISRDNAKNTLYLQMNSLKPEDTALYYCARSPSGFNRGQGTQVTVSSGGGGSGGGSQVQLVESGGGLVQPGGSLRLSCAASGFTFSDYWMYWVRQAPGKGLEWVSEINTNGLITKYPDSVKGRFTISRDNAKNTLYLQMNSLKPEDTALYYCARSPSGFNRGQGTQVTVSS |
| TNF2-GS9-TNF2(TNF5) | 71 | QVQLVESGGGLVQAGGSLRLSCAASGRTFSEPSGYTYTIGWFRQAPGKEREFVARIYWSSGLTYYADSVKGRFTISRDIAKNTVDLLMNSLKPEDTAVYYCAARDGIPTSRSVGSYNYWGQGTQVTVSSGGGGSGGGSQVQLVESGGGLVQAGGSLRLSCAASGRTFSEPSGYTYTIGWFRQAPGKEREFVARIYWSSGLTYYADSVKGRFTISRDIAKNTVDLLMNSLKPEDTAVYYCAARDGIPTSRSVGSYNYWGQGTQVTVSS |
| TNF3-GS9-TNF3(TNF6) | 72 | EVQLVESGGGLVQAGGSLSLSCSASGRSLSNYYMGWFRQAPGKERELLGNISWRGYNIYYKDSVKGRFTISRDDAKNTIYLQMNRLKPEDTAVYYCAASILPLSDDPGWNTYWGQGTQVTVSSGGGGSGGGSEVQLVESGGGLVQAGGSLSLSCSASGRSLSNYYMGWFRQAPGKERELLGNISWRGYNIYYKDSVKGRFTISRDDAKNTIYLQMNRLKPEDTAVYYCAASILPLSDDPGWNTYWGQGTQVTVSS |

TABLE 19-continued

| Name | SEQ ID NO | Sequence |
|---|---|---|
| TNF1-GS30-TNF1(TNF7) | 73 | QVQLVESGGGLVQPGGSLRLSCAASGFTFSDYWMYWVRQAPGKGLE WVSEINTNGLITKYPDSVKGRFTISRDNAKNTLYLQMNSLKPEDTA LYYCARSPSGFNRGQGTQVTVSSGGGGSGGGGSGGGGSGGGGSGGG GSGGGGSQVQLVESGGGLVQPGGSLRLSCAASGFTFSDYWMYWVRQ APGKGLEWVSEINTNGLITKYPDSVKGRFTISRDNAKNTLYLQMNS LKPEDTALYYCARSPSGFNRGQGTQVTVSS |
| TNF2-GS30-TNF2(TNF8) | 74 | QVQLVESGGGLVQAGGSLRLSCAASGRTFSEPSGYTYTIGWFRQAP GKEREFVARIYWSSGLTYYADSVKGRFTISRDIAKNTVDLLMNSLK PEDTAVYYCAARDGIPTSRSVGSYNYWGQGTQVTVSSGGGGSGGGG SGGGGSGGGGSGGGGSGGGGSQVQLVESGGGLVQAGGSLRLSCAAS GRTFSEPSGYTYTIGWFRQAPGKEREFVARIYWSSGLTYYADSVKG RFTISRDIAKNTVDLLMNSLKPEDTAVYYCAARDGIPTSRSVGSYN YWGQGTQVTVSS |
| TNF3-GS30-TNF3(TNF9) | 75 | EVQLVESGGGLVQAGGSLSLSCSASGRSLSNYYMGWFRQAPGKERE LLGNISWRGYNIYYKDSVKGRFTISRDDAKNTIYLQMNRLKPEDTA VYYCAASILPLSDDPGWNTYWGQGTQVTVSSGGGGSGGGGSGGGGS GGGGSGGGGSGGGGSEVQLVESGGGLVQAGGSLSLSCSASGRSLSN YYMGWFRQAPGKERELLGNISWRGYNIYYKDSVKGRFTISRDDAKN TIYLQMNRLKPEDTAVYYCAASILPLSDDPGWNTYWGQGTQVTVSS |
| TNF30-30GS-TNF30-C (TNF55) | 419 | EVQLVESGGGLVQPGGSLRLSCAASGFTFSDYWMYWVRQAPGKGLE WVSEINTNGLITKYPDSVKGRFTISRDNAKNTLYLQMNSLRPEDTA VYYCARSPSGFNRGQGTLVTVSSggggsggggsggggsggggsggg gsggggsEVQLVESGGGLVQPGGSLRLSCAASGFTFSDYWMYWVRQ APGKGLEWVSEINTNGLITKYPDSVKGRFTISRDNAKNTLYLQMNS LRPEDTAVYYCARSPSGFNRGQGTLVTVSC |
| TNF30-30GS-TNF30-gggC (TNF56) | 420 | EVQLVESGGGLVQPGGSLRLSCAASGFTFSDYWMYWVRQAPGKGLE WVSEINTNGLITKYPDSVKGRFTISRDNAKNTLYLQMNSLRPEDTA VYYCARSPSGFNRGQGTLVTVSSggggsggggsggggsggggsggg gsggggsEVQLVESGGGLVQPGGSLRLSCAASGFTFSDYWMYWVRQ APGKGLEWVSEINTNGLITKYPDSVKGRFTISRDNAKNTLYLQMNS LRPEDTAVYYCARSPSGFNRGQGTLVTVSSgggC |

TABLE 20

| ID | Format | Linker |
|---|---|---|
| TNF4 | TNF1-TNF1 | 9 AA GlySer |
| TNF5 | TNF2-TNF2 | 9 AA GlySer |
| TNF6 | TNF3-TNF3 | 9 AA GlySer |
| TNF7 | TNF1-TNF1 | 30 AA GlySer |
| TNF8 | TNF2-TNF2 | 30 AA GlySer |
| TNF9 | TNF3-TNF3 | 30 AA GlySer |

TABLE 21

| Nanobody ™ | Induction time | Yield (mg/L) |
|---|---|---|
| TNF4 | ON/28° C. | 3.2 |
| TNF5 | short/37° C. | 5.5 |
| TNF6 | short/37° C. | 1.19 |
| TNF7 | ON/28° C. | 2.7 |
| TNF8 | short/37° C. | 6.6 |
| TNF9 | ON/28° C. | 1.3 |

TABLE 22

| ID | 50% inhibition (ng/ml) Human TNFα |
|---|---|
| TNF4 | 13 |
| TNF5 | 6.3 |
| TNF6 | 30 |
| TNF7 | 16 |
| TNF8 | 23 |
| TNF9 | 18 |

TABLE 23

| Nanobody | $EC_{50}$ in nM | | | relative potency | |
|---|---|---|---|---|---|
| | mean | stdev | # | mean | stdev |
| assay: L929s + Act D (5000 c/w) TNF: human TNFa @ 0.5 ng/ml | | | | | |
| TNF4 | 0.236 | 0.049 | 4 | 0.033 | 0.012 |
| TNF5 | 0.020 | 0.010 | 9 | 0.566 | 0.275 |
| TNF6 | 0.078 | 0.047 | 8 | 0.179 | 0.168 |
| TNF7 | 0.013 | 0.005 | 8 | 0.673 | 0.211 |
| TNF8 | 0.007 | 0.002 | 2 | 1.240 | 0.137 |
| TNF9 | 0.012 | 0.005 | 6 | 0.729 | 0.242 |
| Enbrel | 0.009 | 0.005 | 45 | 1.002 | 0.011 |
| Humira | 0.079 | 0.043 | 39 | 0.097 | 0.069 |
| Remicade | 0.083 | 0.037 | 45 | 0.103 | 0.058 |
| assay: L929s + Act D (5000 c/w) TNF: rhesus TNFa @ 0.5 ng/ml | | | | | |
| TNF4 | 0.141 | 0.025 | 4 | 0.065 | 0.015 |
| TNF5 | 35.000 | 16.000 | 5 | 0.000 | 0.000 |
| TNF6 | 0.398 | 0.074 | 6 | 0.024 | 0.003 |
| TNF7 | 0.011 | 0.005 | 4 | 0.860 | 0.142 |
| TNF8 | 1.026 | 0.444 | 2 | 0.010 | 0.001 |
| TNF9 | 0.038 | 0.012 | 4 | 0.249 | 0.032 |
| Enbrel | 0.009 | 0.003 | 7 | 1.000 | 0.000 |
| Humira | 0.071 | 0.025 | 8 | 0.103 | 0.059 |
| Remicade | >6.7 | | 7 | | |

TABLE 24

| % | untreated | RT | 37° C. | 50° C. | 60° C. | 70° C. | 80° C. | 90° C. |
|---|---|---|---|---|---|---|---|---|
| TNF4 | 100 | 99 | 99 | 99 | 98 | 55 | 34 | 17 |
| TNF5 | 100 | 99 | 101 | 99 | 98 | 92 | 26 | 22 |
| TNF6 | 100 | 103 | 104 | 103 | 105 | 99 | 7 | 7 |
| TNF7 | 100 | 100 | 100 | 98 | 96 | 66 | 33 | 40 |
| TNF8 | 100 | 99 | 100 | 99 | 100 | 89 | 11 | 8 |
| TNF9 | 100 | 101 | 101 | 101 | 101 | 99 | 17 | 18 |

TABLE 25

| Name | SEQ ID NO | Sequence |
|---|---|---|
| TNF13(TNF1 HUM1) | 76 | EVQLVESGGGLVQPGGSLRLSCAASGFTFSDYWMYWVRQAPGKGLE WVSEINTNGLITKYPDSVKGRFTISRDNAKNTLYLQMNSLKPEDTA VYYCARSPSGFNRGQGTQVTVSS |
| TNF14(TNF1 HUM2) | 77 | EVQLVESGGGLVQPGGSLRLSCAASGFTFSDYWMYWVRQAPGKGLE WVSEINTNGLITKYPDSVKGRFTISRDNAKNTLYLQMNSLKPEDTA LYYCARSPSGFNRGQGTLVTVSS |
| TNF15(TNF2 HUM1) | 78 | EVQLVESGGGLVQPGGSLRLSCAASGRTFSEPSGYTYTIGWFRQAP GKGREFVARIYWSSGLTYYADSVKGRFTISRDIAKNTVDLQMNSLK PEDTAVYYCAARDGIPTSRSVGSYNYWGQGTQVTVSS |
| TNF16(TNF2 HUM2) | 79 | EVQLVESGGGLVQPGGSLRLSCAASGFTFSEPSGYTYTIGWFRQAP GKGREFVARIYWSSGLTYYADSVKGRFTISRDIAKNTVDLQMNSLK PEDTAVYYCAARDGIPTSRSVGSYNYWGQGTQVTVSS |
| TNF17(TNF2 HUM3) | 80 | EVQLVESGGGLVQPGGSLRLSCAASGRTFSEPSGYTYTIGWFRQAP GKGREFVARIYWSSGLTYYADSVKGRFTISRDNAKNTVDLQMNSLK PEDTAVYYCAARDGIPTSRSVGSYNYWGQGTQVTVSS |
| TNF18(TNF2 HUM4) | 81 | EVQLVESGGGLVQPGGSLRLSCAASGRTFSEPSGYTYTIGWFRQAP GKGREFVARIYWSSGLTYYADSVKGRFTISRDIAKNTVDLQMNSLR PEDTAVYYCAARDGIPTSRSVGSYNYWGQGTQVTVSS |
| TNF19(TNF2 HUM5) | 82 | EVQLVESGGGLVQPGGSLRLSCAASGRTFSEPSGYTYTIGWFRQAP GKGREFVARIYWSSGLTYYADSVKGRFTISRDIAKNTVDLQMNSLK PEDTAVYYCAARDGIPTSRSVGSYNYWGQGTLVTVSS |
| TNF20(TNF3 HUM1) | 83 | EVQLVESGGGLVQPGGSLRLSCAASGRSLSNYYMGWFRQAPGKGRE LLGNISWRGYNIYYKDSVKGRFTISRDDSKNTIYLQMNSLKPEDTA VYYCAASILPLSDDPGWNTYWGQGTQVTVSS |
| TNF21(TNF3 HUM2) | 84 | EVQLVESGGGLVQPGGSLRLSCAASGFTFSNYYMGWFRQAPGKGRE LLGNISWRGYNIYYKDSVKGRFTISRDDSKNTIYLQMNSLKPEDTA VYYCAASILPLSDDPGWNTYWGQGTQVTVSS |
| TNF22(TNF3 HUM3) | 85 | EVQLVESGGGLVQPGGSLRLSCAASGRSLSNYYMGWFRQAPGKGRE LLGNISWRGYNIYYKDSVKGRFTISRDDSKNTIYLQMNSLKTEDTA VYYCAASILPLSDDPGWNTYWGQGTQVTVSS |
| TNF23(TNF3 HUM4) | 86 | EVQLVESGGGLVQPGGSLRLSCAASGRSLSNYYMGWFRQAPGKGRE LLGNISWRGYNIYYKDSVKGRFTISRDDSKNTIYLQMNSLKPEDTA VYYCAASILPLSDDPGWNTYWGQGTLVTVSS |
| ALB3(ALB1 HUM1) | 87 | EVQLVESGGGLVQPGGSLRLSCAASGFTFRSFGMSWVRQAPGKEPE WVSSISGSGSDTLYADSVKGRFTISRDNAKTTLYLQMNSLKPEDTA VYYCTIGGSLSRSSQGTQVTVSS |
| ALB4(ALB1 HUM2) | 88 | EVQLVESGGGLVQPGGSLRLSCAASGFTFSSFGMSWVRQAPGKEPE WVSSISGSGSDTLYADSVKGRFTISRDNAKTTLYLQMNSLKPEDTA VYYCTIGGSLSRSSQGTQVTVSS |
| ALB5(ALB1 HUM3) | 89 | EVQLVESGGGLVQPGGSLRLSCAASGFTFRSFGMSWVRQAPGKGLE WVSSISGSGSDTLYADSVKGRFTISRDNAKTTLYLQMNSLKPEDTA VYYCTIGGSLSRSSQGTQVTVSS |

TABLE 26

| Nanobody | Induction time | Yield (mg/L) |
|---|---|---|
| TNF13 | ON/28° C. | 8.8 |
| TNF14 | ON/28° C. | 7 |

TABLE 26-continued

| Nanobody | Induction time | Yield (mg/L) |
|---|---|---|
| TNF15 | Short/37° C. | 7.6 |
| TNF16 | Short/37° C. | 8.7 |

TABLE 26-continued

| Nanobody | Induction time | Yield (mg/L) |
|---|---|---|
| TNF17 | Short/37° C. | 7.2 |
| TNF18 | Short/37° C. | 4.8 |
| TNF19 | Short/37° C. | 8 |
| TNF20 | ON/28° C. | 3.5 |
| TNF21 | ON/28° C. | 7.5 |
| TNF22 | ON/28° C. | 6 |
| TNF23 | ON/28° C. | 2.8 |
| ALB3 | ON/28° C. | 11.8 |
| ALB4 | ON/28° C. | 9 |
| ALB5 | ON/28° C. | 11.7 |

TABLE 27 assay: L929s + Act D (5000 c/w)
TNF: human TNFa @ 0.5 ng/ml

| | $EC_{50}$ in nM | | | relative potency | |
|---|---|---|---|---|---|
| Nanobody | mean | stdev | # | mean | stdev |
| TNF1 | 0.707 | 0.265 | 14 | 0.015 | 0.007 |
| TNF13 | 0.988 | 0.014 | 3 | 0.014 | 0.003 |
| TNF14 | 0.981 | 0.007 | 3 | 0.014 | 0.003 |
| TNF2 | 1.412 | 0.622 | 14 | 0.007 | 0.002 |
| TNF15 | 1.669 | 1.253 | 4 | 0.002 | 0.000 |
| TNF16 | 1.898 | 0.192 | 4 | 0.005 | 0.001 |
| TNF17 | 3.023 | 0.562 | 4 | 0.001 | 0.001 |
| TNF18 | 1.508 | 0.481 | 4 | 0.004 | 0.001 |
| TNF19 | 2.191 | 0.941 | 4 | 0.001 | 0.001 |
| TNF3 | 0.224 | 0.133 | 14 | 0.048 | 0.019 |
| TNF20 | 0.380 | 0.080 | 3 | 0.035 | 0.005 |
| TNF21 | 0.889 | 0.019 | 3 | 0.015 | 0.003 |
| TNF22 | 0.303 | 0.005 | 3 | 0.044 | 0.011 |
| TNF23 | 0.3 | 0.011 | 3 | 0.044 | 0.011 |
| Enbrel | 0.009 | 0.005 | 45 | 1.002 | 0.011 |
| Humira | 0.079 | 0.043 | 39 | 0.097 | 0.069 |
| Remicade | 0.083 | 0.037 | 45 | 0.103 | 0.058 |

TABLE 28

| % | Untreated | RT | 37° C. | 50° C. | 60° C. | 70° C. | 80° C. | 90° C. |
|---|---|---|---|---|---|---|---|---|
| TNF13 | 100 | 104 | 99 | 98 | 99 | 84 | 93 | 93 |
| TNF14 | 100 | 98 | 101 | 95 | 99 | 96 | 99 | 90 |
| TNF15 | 100 | 100 | 91 | 99 | 95 | 90 | 59 | 46 |
| TNF16 | 100 | 97 | 102 | 101 | 94 | 101 | 58 | 48 |
| TNF17 | 100 | 102 | 98 | 100 | 90 | 90 | 69 | 59 |
| TNF18 | 100 | 100 | 101 | 97 | 91 | 93 | 63 | 50 |
| TNF19 | 100 | 102 | 111 | 98 | 92 | 91 | 60 | 49 |
| TNF20 | 100 | 94 | 93 | 93 | 93 | 92 | 85 | 67 |
| TNF21 | 100 | 98 | 99 | 101 | 98 | 96 | 36 | 40 |
| TNF22 | 100 | 102 | 101 | 105 | 99 | 93 | 25 | 31 |
| TNF23 | 100 | 98 | 97 | 99 | 97 | 98 | 87 | 55 |
| ALB3 | 100 | 100 | 99 | 98 | 25 | 18 | 60 | 62 |
| ALB4 | 100 | 100 | 100 | 100 | 99 | 29 | 61 | 55 |
| ALB5 | 100 | 100 | 100 | 99 | 94 | 32 | 61 | 48 |

TABLE 29

| Name | SEQ ID NO | Sequence |
|---|---|---|
| TNF1-9GS-ALB1-9GS-TNF1 (TNF24) | 90 | QVQLVESGGGLVQPGGSLRLSCAASGFTFSDYWMYWVRQAPGKGLE WVSEINTNGLITKYPDSVKGRFTISRDNAKNTLYLQMNSLKPEDTA LYYCARSPSGFNRGQGTQVTVSSGGGGSGGGSEVQLVESGGGLVQP GNSLRLSCAASGFTFRSFGMSWVRQAPGKEPEWVSSISGSGSDTLY ADSVKGRFTISRDNAKTTLYLQMNSLKPEDTAVYYCTIGGSLSRSS QGTQVTVSSGGGGSGGGSEVQLVESGGGLVQPGGSLRLSCAASGFT FSDYWMYWVRQAPGKGLEWVSEINTNGLITKYPDSVKGRFTISRDN AKNTLYLQMNSLKPEDTALYYCARSPSGFNRGQGTQVTVSS |
| TNF2-9GS-TNF2-9GS-ALB1 (TNF25) | 91 | QVQLVESGGGLVQAGGSLRLSCAASGRTFSEPSGYTYTIGWFRQAP GKEREFVARIYWSSGLTYYADSVKGRFTISRDIAKNTVDLLMNSLK PEDTAVYYCAARDGIPTSRSVGSYNYWGQGTQVTVSSGGGGSGGGS EVQLVESGGGLVQAGGSLRLSCAASGRTFSEPSGYTYTIGWFRQAP GKEREFVARIYWSSGLTYYADSVKGRFTISRDIAKNTVDLLMNSLK PEDTAVYYCAARDGIPTSRSVGSYNYWGQGTQVTVSSGGGGSGGGS EVQLVESGGGLVQPGNSLRLSCAASGFTFRSFGMSWVRQAPGKEPE WVSSISGSGSDTLYADSVKGRFTISRDNAKTTLYLQMNSLKPEDTA VYYCTIGGSLSRSSQGTQVTVSS |
| TNF3-9GS-ALB1-9GS-TNF3 (TNF26) | 92 | EVQLVESGGGLVQAGGSLSLSCSASGRSLSNYYMGWFRQAPGKERE LLGNISWRGYNIYYKDSVKGRFTISRDDAKNTIYLQMNRLKPEDTA VYYCAASILPLSDDPGWNTYWGQGTQVTVSSGGGGSGGGSEVQLVE SGGGLVQPGNSLRLSCAASGFTFRSFGMSWVRQAPGKEPEWVSSIS GSGSDTLYADSVKGRFTISRDNAKTTLYLQMNSLKPEDTAVYYCTI GGSLSRSSQGTQVTVSSGGGGSGGGSEVQLVESGGGLVQAGGSLSL SCSASGRSLSNYYMGWFRQAPGKERELLGNISWRGYNIYYKDSVKG |

TABLE 29-continued

| Name | SEQ ID NO | Sequence |
|---|---|---|
| | | RFTISRDDAKNTIYLQMNRLKPEDTAVYYCAASILPLSDDPGWNTY WGQGTQVTVSS |
| TNF1-30GS-TNF1-9GS-ALB1(TNF27) | 93 | QVQLVESGGGLVQPGGSLRLSCAASGFTFSDYWMWVRQAPGKGLE WVSEINTNGLITKYPDSVKGRFTISRDNAKNTLYLQMNSLKPEDTA LYYCARSPSGFNRGQGTQVTVSSGGGGSGGGGSGGGGSGGGGSGGG GSGGGGSEVQLVESGGGLVQPGGSLRLSCAASGFTFSDYWMYWVRQ APGKGLEWVSEINTNGLITKYPDSVKGRFTISRDNAKNTLYLQMNS LKPEDTALYYCARSPSGFNRGQGTQVTVSSGGGGSGGGGSEVQLVES GGGLVQPGNSLRLSCAASGFTFRSFGMSWVRQAPGKEPEWVSSISG SGSDTLYADSVKGRFTISRDNAKTTLYLQMNSLKPEDTAVYYCTIG GSLSRSSQGTQVTVSS |
| TNF3-30GS-TNF3-9GS-ALB1(TNF28) | 94 | EVQLVESGGGLVQAGGSLSLSCSASGRSLSNYYMGWFRQAPGKERE LLGNISWRGYNIYYKDSVKGRFTISRDDAKNTIYLQMNRLKPEDTA VYYCAASILPLSDDPGWNTYWGQGTQVTVSSGGGGSGGGGSGGGGS GGGGSGGGSSGGGGSEVQVVESGGGLVQAGGSLSLSCSASGRSLSN YYMGWFRQAPGKERELLGNISWRGYNIYYKDSVKGRFTISRDDAKN TIYLQMNRLKPEDTAVYYCAASILPLSDDPGWNTYWGQGTQVTVSS GGGGSGGGSEVQLVESGGGLVQPGNSLRLSCAASGFTFRSFGMSWV RQAPGKEPEWVSSISGSGSDTLYADSVKGRFTISRDNAKTTLYLQM NSLKPEDTAVYYCTIGGSLSRSSQGTQVTVSS |
| TNF30-9GS-ALB8-9GS-TNF30 (TNF60) | 417 | EVQLVESGGGLVQPGGSLRLSCAASGFTFSDYWMYWVRQAPGKGLE WVSEINTNGLITKYPDSVKGRFTISRDNAKNTLYLQMNSLRPEDTA VYYCARSPSGFNRGQGTLVTVSSggggsgggsEVQLVESGGGLVQP GNSLRLSCAASGFTFSSFGMSWVRQAPGKGLEWVSSISGSGSDTLY ADSVKGRFTISRDNAKTTLYLQMNSLRPEDTAVYYCTIGGSLSRSS QGTLVTVSSggggsgggsEVQLVESGGGLVQPGGSLRLSCAASGFT FSDYWMYWVRQAPGKGLEWVSEINTNGLITKYPDSVKGRFTISRDN AKNTLYLQMNSLRPEDTAVYYCARSPSGFNRGQGTLVTVSS |
| TNF33-9GS-ALB8-9GS-TNF33 (TNF62) | 418 | EVQLVESGGGLVQPGGSLRLSCAASGRSLSNYYMGWFRQAPGKGRE LLGNISWRGYNIYYKDSVKGRFTISRDDSKNTIYLQMNSLRPEDTA VYYCAASILPLSDDPGWNTYWGQGTLVTVSSggggsgggsEVQLVE SGGGLVQPGNSLRLSCAASGFTFSSFGMSWVRQAPGKGLEWVSSIS GSGSDTLYADSVKGRFTISRDNAKTTLYLQMNSLRPEDTAVYYCTI GGSLSRSSQGTLVTVSSggggsgggsEVQLVESGGGLVQPGGSLRL SCAASGRSLSNYYMGWFRQAPGKGRELLGNISWRGYNIYYKDSVKG RFTISRDDSKNTIYLQMNSLRPEDTAVYYCAASILPLSDDPGWNTY WGQGTLVTVSS |

TABLE 30

| ID | Format |
|---|---|
| TNF24 | TNF1-9GS-ALB1-9GS-TNF1 |
| TNF25 | TNF2-9GS-TNF2-9GS-ALB1 |
| TNF26 | TNF3-9GS-ALB1-9GS-TNF3 |
| TNF27 | TNF1-30GS-TNF1-9GS-ALB1 |
| TNF28 | TNF3-30GS-TNF3-9GS-ALB1 |

TABLE 31

| Nanobody | Induction time | Yield (mg/L) |
|---|---|---|
| TNF24 | ON/28° C. | 1.7 |
| TNF25 | short/37° C. | 0.445 |
| TNF26 | short/37° C. | 0.167 |
| TNF27 | ON/28° C. | 2.2 |
| TNF28 | short/37° C. | 1 |

TABLE 32 assay: L929s + Act D (5000 c/w)
TNF: human TNFa @ 0.5 ng/ml

| | $EC_{50}$ in nM | | | relative potency | |
|---|---|---|---|---|---|
| Nanobody | mean | stdev | # | mean | stdev |
| TNF24 | 0.011 | 0.003 | 11 | 0.878 | 0.248 |
| TNF25 | 0.018 | 0.008 | 14 | 0.603 | 0.243 |
| TNF26 | 0.020 | 0.009 | 14 | 0.583 | 0.210 |
| TNF27 | 0.012 | 0.003 | 3 | 0.810 | 0.037 |
| TNF28 | 0.021 | 0.008 | 6 | 0.548 | 0.360 |
| Enbrel | 0.009 | 0.005 | 45 | 1.002 | 0.011 |
| Humira | 0.079 | 0.043 | 39 | 0.097 | 0.069 |
| Remicade | 0.083 | 0.037 | 45 | 0.103 | 0.058 |

TABLE 33

| Human albumin | KD (nM) | ka (1/Ms) | kd (1/s) |
|---|---|---|---|
| 6A6 (ALB1) | 0.57 | 1.11E+6 | 6.30E−4 |
| 1C2-GS-6A6-GS-1C2 (TNF24) | 11 | 2.26E+05 | 2.48E−03 |
| 1G5-GS-1G5-GS-6A6 (TNF25) | 7.2 | 2.91E+05 | 2.10E−03 |
| 5F10-GS-6A6-GS-5F10 (TNF26) | 7.3 | 2.81E+05 | 2.05E−03 |

TABLE 33-continued

| Human albumin | KD (nM) | ka (1/Ms) | kd (1/s) |
|---|---|---|---|
| 1C2-GS6-1C2-GS-6A6 (TNF27) | 8.9 | 3.19E+05 | 2.84E-03 |
| 5F10-GS6-5F10-GS-6A6 (TNF28) | 14 | 1.55E+05 | 2.13E-03 |

TABLE 34

| % | untreated | RT | 37° C. | 50° C. | 60° C. | 70° C. | 80° C. | 90° C. |
|---|---|---|---|---|---|---|---|---|
| TNF24 | 100 | 100 | 99 | 98 | 5 | 3 | 8 | 18 |
| TNF25 | 100 | nd | 103 | 102 | 95 | 5 | 4 | 6 |
| TNF26 | 100 | 109 | 115 | 112 | 107 | 10 | 8 | 10 |
| TNF27 | 100 | 102 | 103 | 102 | 22 | 9 | 26 | 34 |
| TNF28 | 100 | 97 | 99 | 99 | 66 | 3 | 6 | 10 |

TABLE 35

| Name | SEQ ID NO | Sequence |
|---|---|---|
| TNF29(TNF1 HUM1) | 95 | EVQLVESGGGLVQPGGSLRLSCAASGFTFSDYWMYWVRQAPGKGLEWVSEINTNGLITKYPDSVKGRFTISRDNAKNTLYLQMNSLKPEDTAVYYCARSPSGFNRGQGTLVTVSS |
| TNF30(TNF1 HUM2) | 96 | EVQLVESGGGLVQPGGSLRLSCAASGFTFSDYWMYWVRQAPGKGLEWVSEINTNGLITKYPDSVKGRFTISRDNAKNTLYLQMNSLRPEDTAVYYCARSPSGFNRGQGTLVTVSS |
| TNF31(TNF2 HUM1) | 97 | EVQLVESGGGLVQPGGSLRLSCAASGFTFSEPSGYTYTIGWFRQAPGKGREFVARIYWSSGLTYYADSVKGRFTISRDIAKNTVDLQMNSLRPEDTAVYYCAARDGIPTSRSVGSYNYWGQGTQVTVSS |
| TNF32(TNF2 HUM2) | 98 | EVQLVESGGGLVQPGGSLRLSCAASGFTFSEPSGYTYTIGWFRQAPGKGREFVARIYWSSGLTYYADSVKGRFTISRDIAKNTVDLQMNSLRPEDTAVYYCAARDGIPTSRSVGSYNYWGQGTLVTVSS |
| TNF33(TNF3 HUM1) | 99 | EVQLVESGGGLVQPGGSLRLSCAASGRSLSNYYMGWFRQAPGKGRELLGNISWRGYNIYYKDSVKGRFTISRDDSKNTIYLQMNSLRPEDTAVYYCAASILPLSDDPGWNTYWGQGTLVTVSS |
| ALB6(ALB1 HUM1) | 100 | EVQLVESGGGLVQPGNSLRLSCAASGFTFRSFGMSWVRQAPGKGLEWVSSISGSGSDTLYADSVKGRFTISRDNAKTTLYLQMNSLKPEDTAVYYCTIGGSLSRSSQGTLVTVSS |
| ALB7(ALB1 HUM2) | 101 | EVQLVESGGGLVQPGNSLRLSCAASGFTFRSFGMSWVRQAPGKGLEWVSSISGSGSDTLYADSVKGRFTISRDNAKTTLYLQMNSLRPEDTAVYYCTIGGSLSRSSQGTLVTVSS |
| ALB8(ALB1 HUM3) | 102 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| ALB9(ALB1 HUM4) | 103 | EVQLVESGGGLVQPGNSLRLSCAASGFTFSSFGMSWVRQAPGKGLEWVSSISGSGSDTLYADSVKGRFTISRDNAKNTLYLQMNSLRPEDTAVYYCTIGGSLSRSSQGTLVTVSS |
| ALB10(ALB1 HUM5) | 104 | EVQLVESGGGLVQPGNSLRLSCAASGFTFSSFGMSWVRQAPGKGLEWVSSISGSGSDTLYADSVKGRFTISRDNAKNTLYLQMNSLRPEDTAVYYCTIGGSLSRSGQGTLVTVSS |

TABLE 36

| Nanobody ™ | Induction time | yield |
|---|---|---|
| TNF29 | ON/28° C. | 2.1 mg/L |
| TNF30 | ON/28° C. | 2.7 mg/L |
| TNF31 | ON/28° C. | 2 mg/L |
| TNF32 | ON/28° C. | 1.5 mg/L |
| TNF33 | ON/28° C. | 0.5 mg/L |

TABLE 37 assay: L929s + Act D (5000 c/w)
TNF: human TNFa @ 0.5 ng/ml

| | $EC_{50}$ in nM | | | relative potency | |
|---|---|---|---|---|---|
| $V_{HH}$ | mean | stdev | # | mean | stdev |
| TNF1 | 0.707 | 0.265 | 14 | 0.015 | 0.007 |
| TNF13 | 0.988 | 0.014 | 3 | 0.014 | 0.003 |
| TNF14 | 0.981 | 0.007 | 3 | 0.014 | 0.003 |

TABLE 37-continued assay: L929s + Act D (5000 c/w)
TNF: human TNFa @ 0.5 ng/ml

| | EC$_{50}$ in nM | | | relative potency | |
|---|---|---|---|---|---|
| V$_{HH}$ | mean | stdev | # | mean | stdev |
| TNF29 | 1.336 | | 1 | 0.013 | |
| TNF30 | 0.985 | | 1 | 0.017 | |
| TNF2 | 1.412 | 0.622 | 14 | 0.007 | 0.002 |
| TNF15 | 5.896 | 1.253 | 4 | 0.002 | 0.000 |
| TNF16 | 2.422 | 0.192 | 4 | 0.005 | 0.001 |
| TNF17 | 7.555 | 0.562 | 4 | 0.001 | 0.001 |
| TNF18 | 3.134 | 0.481 | 4 | 0.004 | 0.001 |
| TNF19 | 7.372 | 0.941 | 4 | 0.001 | 0.001 |
| TNF31 | 2.195 | | 1 | 0.008 | |
| TNF32 | 2.506 | | 1 | 0.007 | |
| TNF3 | 0.224 | 0.133 | 14 | 0.048 | 0.019 |
| TNF20 | 0.380 | 0.080 | 3 | 0.035 | 0.005 |
| TNF21 | 0.889 | 0.019 | 3 | 0.015 | 0.003 |
| TNF22 | 0.303 | 0.005 | 3 | 0.004 | 0.011 |
| TNF23 | 0.3 | 0.011 | 3 | 0.04 | 0.011 |
| TNF33 | 0.3 | | 1 | 0.057 | |
| Enbrel | 0.009 | 0.005 | 45 | 1.002 | 0.011 |
| Humira | 0.079 | 0.043 | 39 | 0.097 | 0.069 |
| Remicade | 0.083 | 0.037 | 45 | 0.103 | 0.058 |

TABLE 38

| | untreated | RT | 37° C. | 50° C. | 60° C. | 70° C. | 80° C. | 90° C. |
|---|---|---|---|---|---|---|---|---|
| TNF29 | 100 | 100 | 100 | 100 | 100 | 96 | 91 | 89 |
| TNF30 | 100 | 100 | 100 | 99 | 100 | 96 | 92 | 89 |
| TNF31 | 100 | 100 | 100 | 98 | 91 | 84 | 56 | 43 |
| TNF32 | 100 | 99 | 98 | 97 | 87 | 78 | 45 | 39 |
| TNF33 | 100 | 98 | 97 | 97 | 94 | 91 | 79 | 49 |

TABLE 39 assay: alphaKYM (10000 c/w)
TNF: human TNFa @ 1 ng/ml

| Nanobody | EC$_{50}$ in nM |
|---|---|
| TNF1 | 2.466 |
| TNF2 | 4.236 |
| TNF3 | 0.655 |
| TNF4 | 0.069 |
| TNF5 | 0.008 |
| TNF6 | 0.121 |
| TNF7 | 0.009 |
| TNF8 | 0.013 |
| TNF9 | 0.020 |
| Enbrel | 0.040 |
| Humira | 0.103 |
| Remicade | 0.100 |

Results from WO 04/41862

| Nanobody | SEQ ID No | EC$_{50}$ in nM |
|---|---|---|
| 1A | 1 | 100 |
| 3E | 4 | 12 |
| 3G | 5 | 20 |
| Remicade | | 0.080 |

TABLE 40

| M13_rev | SEQ ID NO: 421 | GGATAACAATTTCACACAGG |
|---|---|---|
| Rev_9GlySer_L108 | SEQ ID NO: 422 | TCAGTAACCTGGATCCGCCACCGCT GCCTCCACCGCCTGAGGAGACGGTG ACCAG |
| For_GS/Short | SEQ ID NO: 423 | AGGTTACTGAGGATCCGAGGTGCAGC TGGTGGAGTCTGG |
| Rev_15BspEI_L108 | SEQ ID NO: 424 | TCAGTAACCTTCCGGAACCGCCACC GCCTGAGGAGACGGTGACAAG |
| For_BspEI | SEQ ID NO: 425 | AGGTTACTGATCCGGAGGCGGTAGC GAGGTGCAGCTGGTGGAGTCTGG |
| M13_for | SEQ ID NO: 426 | CACGACGTTGTAAAACGAC |

TABLE 41

| | | Sequence |
|---|---|---|
| Reverse primer | | |
| PiRevhumNot/ a40c (Not1) | SEQ ID NO: 427 | ATGGTGGTGTGCGGCCGCCTATTATGA GGAGACGGTGACCAGG |
| Forward primer | | |
| Pi2for (Xho1) | SEQ ID NO: 428 | AGGGGTATCTCTCGAGAAAAGAGAGGT GCAGCTGGTGGAGTCTGG |

TABLE 42

| | Human TNFα | | |
|---|---|---|---|
| | EC$_{50}$ in nM | | |
| VHH | mean | stdev | Number of assays |
| TNF60 | 0.010 | 0.002 | 6 |
| Enbrel | 0.014 | 0.009 | 33 |
| Humira | 0.141 | 0.074 | 33 |
| Remicade | 0.120 | 0.037 | 33 |

TABLE 43

| | | human albumin | rhesus albumin |
|---|---|---|---|
| TNF60 | K$_D$ (nM) | 24.4 | 24.1 |
| | k$_{on}$ (1/Ms) | 2.05E+05 | 2.09E+05 |
| | k$_{off}$ (1/s) | 5.02E−03 | 5.04E−03 |

TABLE 43-continued

|  |  | human albumin | rhesus albumin |
|---|---|---|---|
| TNF24 | $K_D$ (nM) | 11 | Nd |
|  | $k_{on}$ (1/Ms) | 2.26E+05 | Nd |
|  | $k_{off}$ (1/s) | 2.48E-03 | Nd |

TABLE 44

| | | |
|---|---|---|
| PiForLong | SEQ ID NO: 429 | GCTAAAGAAGAAGGGGTATCTCTC GAGAAAAGAGAGGTGCAGCTGGTG GAGTCTGG |
| Rev_30GlySer_L108 | SEQ ID NO: 430 | TCAGTAACCTGGATCCCCCGCCA CCGCTGCCTCCACCGCCGCTACCC CCGCCACCGCTGCCTCCACCGCCT GAGGAGACGGTGACAAG |
| For_GlySer | SEQ ID NO: 431 | AGGTTACTGAGGATCCGGCGGTG GAGGCAGCGGTGGCGGGGGTAGC GAGGTGCAGCTGGTGGAGTCTGG |
| PiRevCys1hum | SEQ ID NO: 432 | ATGGTGGTGTGAATTCTTATTAGC AGGAGACGGTGACAAGG |
| PiRevCys2hum | SEQ ID NO: 433 | ATGGTGGTGTGAATTCTTATTAGC AACCTCCACCTGAGGAGACG GTGACAAGG |
| AOXIFor | SEQ ID NO: 434 | GACTGGTTCCAATTGACAAGC |
| AOXIRev | SEQ ID NO: 435 | GCAAATGGCATTCTGACATCC |

TABLE 45

| | Human TNFα | | |
|---|---|---|---|
| | $EC_{50}$ in nM | | |
| VHH | mean | stdev | Number of assays |
| TNF1 | 0.748 | 0.153 | 27 |
| TNF55-PEG40 | 0.004 | 0.001 | 8 |
| TNF55-PEG60 | 0.004 | 0.002 | 6 |
| TNF55-Biotine | 0.012 | 0.003 | 5 |
| TNF56-PEG40 | 0.006 | 0.003 | 57 |
| TNF56-PEG60 | 0.005 | 0.003 | 7 |
| TNF56-Biotine | 0.017 | 0.009 | 13 |
| Enbrel | 0.013 | 0.006 | 71 |
| Humira | 0.127 | 0.058 | 67 |
| Remicade | 0.144 | 0.061 | 67 |

TABLE 46

|  | DS534 P4 | DS592 P4 | DS605 P3 | KM05-179 P4 |
|---|---|---|---|---|
| p[IC]50 | | | | |
| Etanercept | 9.55 | 9.49 | 9.51 | 9.51 |
| Accipiter | 9.88 | 9.44 | 9.37 | 9.27 |
| pM | | | | |
| Etanercept | 282 | 324 | 309 | 309 |
| Accipiter | 132 | 363 | 427 | 537 |

TABLE 47

| | Total WBC count (×10⁶/mL) | |
|---|---|---|
| Dose Group | ALX0071 | Etanercept |
| CMC vehicle | 0.86 ± 0.09 | |
| 0.1 µg human TNFα | 3.72 ± 0.21 | |
| 0.0625 mg/kg | 3.03 ± 0.6 | — |
| 0.125 mg/kg | 1.23 ± 0.3** | 2.40 ± 0.39 |
| 0.25 mg/kg | 1.37 ± 0.17* | 2.47 ± 0.54 |
| 0.5 mg/kg | — | 2.19 ± 0.10 |

*$P < 0.05$,
**$P < 0.01$ vs 0.1 µg human TNFα

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

The invention claimed is:

1. A polypeptide comprising the amino acid sequence of: DVQLVESGGGLVQPGGSLKLSCAASGFDFSX$^{31}$X$^{32}$WMYWVRQAPGKELEWLSEINTNGLITX$^{59}$YX$^{61}$DSVKGRFTVSRNNAANKMYLELTRLEPEDTALYYCARX$^{99}$X$^{100}$X$^{101}$GX$^{103}$N KGQGTQVTVSS (SEQ ID NO: 478), wherein:

the amino acid of X$^{31}$ is a polar amino acid selected from the group consisting of G, T, C, N, Q, Y, K, R, H, D and E;

the amino acid of X$^{32}$ is a polar amino acid selected from the group consisting of G, S, T, C, N, Q, Y, K, R, H, D and E;

the amino acid of X$^{59}$ is a polar, positively charged amino acid selected from the group consisting of K, R, and H;

the amino acid of X$^{61}$ is a small aliphatic, nonpolar or slightly polar residue selected from the group consisting of A, S, T, P, and G;

the amino acid of X$^{99}$ is a polar, uncharged amino acid selected from the group consisting of G, S, T, C, N, Q, and Y;

the amino acid of X$^{100}$ is any amino acid;

the amino acid of X$^{101}$ is a polar amino acid selected from the group consisting of G, S, T, C, N, Q, Y, K, R, H, D, and E; and the amino acid of X$^{103}$ is a nonpolar, uncharged amino acid selected from the group consisting of A, V, L, I, F, M, W, and P.

2. The polypeptide of claim 1, wherein the polypeptide binds human TNFα.

3. A pharmaceutical composition comprising the polypeptide of 1.

4. The pharmaceutical composition of claim 3, further comprising one or more excipients.

5

UNITED STATES PATENT AND TRADEMARK OFFICE
CERTIFICATE OF CORRECTION

PATENT NO. : 11,472,871 B2
APPLICATION NO. : 16/423596
DATED : October 18, 2022
INVENTOR(S) : Els Anna Alice Beirnaert It is certified that error appears in the above-identified patent and that said Letters Patent is hereby corrected as shown below:

In the Claims

Claim 1, beginning at Column 449, Line 25, should read:
1. A polypeptide comprising the amino acid sequence of:
DVQLVESGGGLVQPGGSLKLSCAASGFDFSX$^{31}$X$^{32}$WMYWVRQAPGKELEWLSEIN
 TNGLITX$^{59}$YX$^{61}$DSVKGRFTVSRNNAANKMYLELTRLEPEDTALYYCARX$^{99}$X$^{100}$
 X$^{101}$GX$^{103}$NKGQGTQVTVSS (SEQ ID NO: 478), wherein:
the amino acid of X$^{31}$ is a polar amino acid selected from the group consisting of G, T, C,
 N, Q, Y, K, R, H, D and E;
the amino acid of X$^{32}$ is a polar amino acid selected from the group consisting of G, S, T,
 C, N, Q, Y, K, R, H, D and E;
the amino acid of X$^{59}$ is a polar, positively charged amino acid selected from the group
 consisting of K, R, and H; the amino acid of X$^{61}$ is a small aliphatic, nonpolar or slightly
 polar residue selected from the group consisting of A, S, T, P, and G;
the amino acid of X$^{99}$ is a polar, uncharged amino acid selected from the group consisting
 of G, S, T, C, N, Q, and Y;
the amino acid of X$^{100}$ is any amino acid;
the amino acid of X$^{101}$ is a polar amino acid selected from the group consisting of G, S, T,
 C, N, Q, Y, K, R, H, D, and E; and
the amino acid of X$^{103}$ is a nonpolar, uncharged amino acid selected from the group
 consisting of A, V, L, I, F, M, W, and P.

Signed and Sealed this
Seventeenth Day of January, 2023

Katherine Kelly Vidal
*Director of the United States Patent and Trademark Office*

SEQUENCE LISTING

<160> NUMBER OF SEQ ID NOS: 487

<210> SEQ ID NO 1
<211> LENGTH: 26
<212> TYPE: PRT
<213> ORGANISM: Artificial
<220> FEATURE:
<223> OTHER INFORMATION: FR1 element
<220> FEATURE:
<221> NAME/KEY: MISC_FEATURE
<222> LOCATION: (11)..(11)
<223> OTHER INFORMATION: Xaa may be Leu, Met, Ser, Val, Trp, Phe, Asn,
      Pro, Thr, or Tyr

<400> SEQUENCE: 1

Gln Val Gln Leu Gln Glu Ser Gly Gly Gly Xaa Val Gln Ala Gly Gly
1               5                   10                  15

Ser Leu Arg Leu Ser Cys Ala Ala Ser Gly
            20                  25

```
<210> SEQ ID NO 2
<211> LENGTH: 14
<212> TYPE: PRT
<213> ORGANISM: Artificial
<220> FEATURE:
<223> OTHER INFORMATION: FR2 element
<220> FEATURE:
<221> NAME/KEY: MISC_FEATURE
<222> LOCATION: (2)..(2)
<223> OTHER INFORMATION: Xaa may be Phe, Tyr, His, Ile, Ala, Leu, Pro,
      Ser, or Val
<220> FEATURE:
<221> NAME/KEY: MISC_FEATURE
<222> LOCATION: (9)..(9)
<223> OTHER INFORMATION: Xaa may be Gly, Glu, Asp, Gln, Arg, Ser, Leu,
      Ala, Phe, Lys, Met, Asn, Pro, Val, Trp, or Tyr
<220> FEATURE:
<221> NAME/KEY: MISC_FEATURE
<222> LOCATION: (10)..(10)
<223> OTHER INFORMATION: Xaa may be Leu, Arg, Cys, Ile, Pro, Gln, Val,
      Asp, Glu, Gly, His, Lys, or Thr
<220> FEATURE:
<221> NAME/KEY: MISC_FEATURE
<222> LOCATION: (12)..(12)
<223> OTHER INFORMATION: Xaa may be Trp, Leu, Phe, Ala, Gly, Ile, Met,
      Arg, Ser, Asp, Glu, His, Lys, Gln, Thr, Val, or Tyr

<400> SEQUENCE: 2

Trp Xaa Arg Gln Ala Pro Gly Lys Xaa Xaa Glu Xaa Val Ala
1               5                   10

<210> SEQ ID NO 3
<211> LENGTH: 32
<212> TYPE: PRT
<213> ORGANISM: Artificial
<220> FEATURE:
<223> OTHER INFORMATION: FR3 element
<220> FEATURE:
<221> NAME/KEY: MISC_FEATURE
<222> LOCATION: (21)..(21)
<223> OTHER INFORMATION: Xaa may be Arg, Lys, Asn, Glu, Ile, Met, Ala,
      Asp, Gly, Leu, Gln, Ser, Thr, or Gln
<220> FEATURE:
<221> NAME/KEY: MISC_FEATURE
<222> LOCATION: (22)..(22)
<223> OTHER INFORMATION: Xaa may be Pro, Ala, Leu, Arg, Ser, Asp, Val,
      Phe, Gly, His, Asn, Thr, or Tyr

<400> SEQUENCE: 3

Arg Phe Thr Ile Ser Arg Asp Asn Ala Lys Asn Thr Val Tyr Leu Gln
1               5                   10                  15

Met Asn Ser Leu Xaa Xaa Glu Asp Thr Ala Val Tyr Tyr Cys Ala Ala
            20                  25                  30

<210> SEQ ID NO 4
<211> LENGTH: 11
<212> TYPE: PRT
<213> ORGANISM: Artificial
<220> FEATURE:
<223> OTHER INFORMATION: FR4 element
<220> FEATURE:
<221> NAME/KEY: MISC_FEATURE
<222> LOCATION: (1)..(1)
<223> OTHER INFORMATION: Xaa may be Trp, Pro, Arg, Ser, Phe, Gly, Lys,
      Leu, Asn, Gln, Val, or Tyr
<220> FEATURE:
<221> NAME/KEY: MISC_FEATURE
<222> LOCATION: (2)..(2)
<223> OTHER INFORMATION: Xaa may be Gly, Ala, Arg, Ser, Thr, or Asp
<220> FEATURE:
<221> NAME/KEY: MISC_FEATURE
<222> LOCATION: (6)..(6)
<223> OTHER INFORMATION: Xaa may be Gln, Leu, Glu, His, Asn, Pro, Thr,
``` or Arg

<400> SEQUENCE: 4

Xaa Xaa Gln Gly Thr Xaa Val Thr Val Ser Ser
1               5                  10

<210> SEQ ID NO 5
<211> LENGTH: 26
<212> TYPE: PRT
<213> ORGANISM: Artificial
<220> FEATURE:
<223> OTHER INFORMATION: FR1 element

<400> SEQUENCE: 5

Gln Val Gln Leu Gln Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 6
<211> LENGTH: 14
<212> TYPE: PRT
<213> ORGANISM: Artificial
<220> FEATURE:
<223> OTHER INFORMATION: FR2 element

<400> SEQUENCE: 6

Trp Phe Arg Gln Ala Pro Gly Lys Glu Arg Glu Leu Val Ala
1               5                   10

<210> SEQ ID NO 7
<211> LENGTH: 14
<212> TYPE: PRT
<213> ORGANISM: Artificial
<220> FEATURE:
<223> OTHER INFORMATION: FR2 element

<400> SEQUENCE: 7

Trp Phe Arg Gln Ala Pro Gly Lys Glu Arg Glu Phe Val Ala
1               5                   10

<210> SEQ ID NO 8
<211> LENGTH: 13
<212> TYPE: PRT
<213> ORGANISM: Artificial
<220> FEATURE:
<223> OTHER INFORMATION: FR2 element

<400> SEQUENCE: 8

Trp Phe Arg Gln Ala Pro Gly Lys Glu Arg Glu Gly Ala
1               5                   10

<210> SEQ ID NO 9
<211> LENGTH: 14
<212> TYPE: PRT
<213> ORGANISM: Artificial
<220> FEATURE:
<223> OTHER INFORMATION: FR2 element

<400> SEQUENCE: 9

Trp Phe Arg Gln Ala Pro Gly Lys Gln Arg Glu Leu Val Ala
1               5                   10

<210> SEQ ID NO 10
<211> LENGTH: 14
<212> TYPE: PRT

```
<213> ORGANISM: Artificial
<220> FEATURE:
<223> OTHER INFORMATION: FR2 element

<400> SEQUENCE: 10

Trp Phe Arg Gln Ala Pro Gly Lys Gln Arg Glu Phe Val Ala
1               5                   10

<210> SEQ ID NO 11
<211> LENGTH: 13
<212> TYPE: PRT
<213> ORGANISM: Artificial
<220> FEATURE:
<223> OTHER INFORMATION: FR2 element

<400> SEQUENCE: 11

Trp Tyr Arg Gln Ala Pro Gly Lys Gly Leu Glu Trp Ala
1               5                   10

<210> SEQ ID NO 12
<211> LENGTH: 32
<212> TYPE: PRT
<213> ORGANISM: Artificial
<220> FEATURE:
<223> OTHER INFORMATION: FR3 element

<400> SEQUENCE: 12

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 13
<211> LENGTH: 11
<212> TYPE: PRT
<213> ORGANISM: Artificial
<220> FEATURE:
<223> OTHER INFORMATION: FR4 element

<400> SEQUENCE: 13

Trp Gly Gln Gly Thr Gln Val Thr Val Ser Ser
1               5                   10

<210> SEQ ID NO 14
<211> LENGTH: 11
<212> TYPE: PRT
<213> ORGANISM: Artificial
<220> FEATURE:
<223> OTHER INFORMATION: FR4 element

<400> SEQUENCE: 14

Trp Gly Gln Gly Thr Leu Val Thr Val Ser Ser
1               5                   10

<210> SEQ ID NO 15
<211> LENGTH: 5
<212> TYPE: PRT
<213> ORGANISM: Artificial
<220> FEATURE:
<223> OTHER INFORMATION: CDR1 element

<400> SEQUENCE: 15

Asp Tyr Trp Met Tyr
1               5

<210> SEQ ID NO 16
```

```
<211> LENGTH: 10
<212> TYPE: PRT
<213> ORGANISM: Artificial
<220> FEATURE:
<223> OTHER INFORMATION: CDR1 element

<400> SEQUENCE: 16

Glu Pro Ser Gly Tyr Thr Tyr Thr Ile Gly
1               5                   10

<210> SEQ ID NO 17
<211> LENGTH: 5
<212> TYPE: PRT
<213> ORGANISM: Artificial
<220> FEATURE:
<223> OTHER INFORMATION: CDR1 element

<400> SEQUENCE: 17

Asn Tyr Tyr Met Gly
1               5

<210> SEQ ID NO 18
<211> LENGTH: 5
<212> TYPE: PRT
<213> ORGANISM: Artificial
<220> FEATURE:
<223> OTHER INFORMATION: CDR1 element

<400> SEQUENCE: 18

Val Ser Trp Met Tyr
1               5

<210> SEQ ID NO 19
<211> LENGTH: 8
<212> TYPE: PRT
<213> ORGANISM: Artificial
<220> FEATURE:
<223> OTHER INFORMATION: CDR1 element

<400> SEQUENCE: 19

Ala His Ser Val Tyr Thr Met Gly
1               5

<210> SEQ ID NO 20
<211> LENGTH: 5
<212> TYPE: PRT
<213> ORGANISM: Artificial
<220> FEATURE:
<223> OTHER INFORMATION: CDR1 element

<400> SEQUENCE: 20

Gly Tyr Tyr Met Gly
1               5

<210> SEQ ID NO 21
<211> LENGTH: 10
<212> TYPE: PRT
<213> ORGANISM: Artificial
<220> FEATURE:
<223> OTHER INFORMATION: CDR1 element

<400> SEQUENCE: 21

Asp Tyr Ser Gly Tyr Thr Tyr Thr Val Gly
1               5                   10

<210> SEQ ID NO 22
<211> LENGTH: 17
```

```
<212> TYPE: PRT
<213> ORGANISM: Artificial
<220> FEATURE:
<223> OTHER INFORMATION: CDR2 element

<400> SEQUENCE: 22

Glu Ile Asn Thr Asn Gly Leu Ile Thr Lys Tyr Pro Asp Ser Val Lys
1               5                   10                  15
Gly

<210> SEQ ID NO 23
<211> LENGTH: 17
<212> TYPE: PRT
<213> ORGANISM: Artificial
<220> FEATURE:
<223> OTHER INFORMATION: CDR2 element

<400> SEQUENCE: 23

Arg Ile Tyr Trp Ser Ser Gly Leu Thr Tyr Tyr Ala Asp Ser Val Lys
1               5                   10                  15
Gly

<210> SEQ ID NO 24
<211> LENGTH: 17
<212> TYPE: PRT
<213> ORGANISM: Artificial
<220> FEATURE:
<223> OTHER INFORMATION: CDR2 element

<400> SEQUENCE: 24

Asn Ile Ser Trp Arg Gly Tyr Asn Ile Tyr Tyr Lys Asp Ser Val Lys
1               5                   10                  15
Gly

<210> SEQ ID NO 25
<211> LENGTH: 17
<212> TYPE: PRT
<213> ORGANISM: Artificial
<220> FEATURE:
<223> OTHER INFORMATION: CDR2 element

<400> SEQUENCE: 25

Glu Ile Asn Thr Asn Gly Leu Ile Thr Lys Tyr Val Asp Ser Val Lys
1               5                   10                  15
Gly

<210> SEQ ID NO 26
<211> LENGTH: 17
<212> TYPE: PRT
<213> ORGANISM: Artificial
<220> FEATURE:
<223> OTHER INFORMATION: CDR2 element

<400> SEQUENCE: 26

Arg Ile Tyr Trp Ser Ser Gly Asn Thr Tyr Tyr Ala Asp Ser Val Lys
1               5                   10                  15
Gly

<210> SEQ ID NO 27
<211> LENGTH: 17
<212> TYPE: PRT
<213> ORGANISM: Artificial
<220> FEATURE:
<223> OTHER INFORMATION: CDR2 element
```

```
<400> SEQUENCE: 27

Arg Ile Tyr Trp Ser Ser Ala Asn Thr Tyr Tyr Ala Asp Ser Val Lys
1               5                   10                  15
Gly

<210> SEQ ID NO 28
<211> LENGTH: 17
<212> TYPE: PRT
<213> ORGANISM: Artificial
<220> FEATURE:
<223> OTHER INFORMATION: CDR2 element

<400> SEQUENCE: 28

Ser Ile Ser Trp Arg Gly Asp Asn Thr Tyr Tyr Lys Glu Ser Val Lys
1               5                   10                  15
Gly

<210> SEQ ID NO 29
<211> LENGTH: 15
<212> TYPE: PRT
<213> ORGANISM: Artificial
<220> FEATURE:
<223> OTHER INFORMATION: CDR3 element

<400> SEQUENCE: 29

Arg Asp Gly Ile Pro Thr Ser Arg Ser Val Gly Ser Tyr Asn Tyr
1               5                   10                  15

<210> SEQ ID NO 30
<211> LENGTH: 14
<212> TYPE: PRT
<213> ORGANISM: Artificial
<220> FEATURE:
<223> OTHER INFORMATION: CDR3 element

<400> SEQUENCE: 30

Ser Ile Leu Pro Leu Ser Asp Asp Pro Gly Trp Asn Thr Tyr
1               5                   10

<210> SEQ ID NO 31
<211> LENGTH: 15
<212> TYPE: PRT
<213> ORGANISM: Artificial
<220> FEATURE:
<223> OTHER INFORMATION: CDR3 element

<400> SEQUENCE: 31

Arg Asp Gly Ile Pro Thr Ser Arg Ser Val Glu Ala Tyr Asn Tyr
1               5                   10                  15

<210> SEQ ID NO 32
<211> LENGTH: 14
<212> TYPE: PRT
<213> ORGANISM: Artificial
<220> FEATURE:
<223> OTHER INFORMATION: CDR3 element

<400> SEQUENCE: 32

Ser Ile Leu Pro Leu Ser Asp Asp Pro Gly Trp Asn Thr Asn
1               5                   10

<210> SEQ ID NO 33
<211> LENGTH: 15
<212> TYPE: PRT
```

```
<213> ORGANISM: Artificial
<220> FEATURE:
<223> OTHER INFORMATION: CDR3 element

<400> SEQUENCE: 33

Arg Asp Gly Ile Pro Thr Ser Arg Ser Val Glu Ser Tyr Asn Tyr
1               5                   10                  15

<210> SEQ ID NO 34
<211> LENGTH: 6
<212> TYPE: PRT
<213> ORGANISM: Artificial
<220> FEATURE:
<223> OTHER INFORMATION: CDR3 element

<400> SEQUENCE: 34

Ser Pro Ser Gly Phe Asn
1               5

<210> SEQ ID NO 35
<211> LENGTH: 6
<212> TYPE: PRT
<213> ORGANISM: Artificial
<220> FEATURE:
<223> OTHER INFORMATION: CDR3 element

<400> SEQUENCE: 35

Ser Pro Ser Gly Ser Phe
1               5

<210> SEQ ID NO 36
<211> LENGTH: 5
<212> TYPE: PRT
<213> ORGANISM: Artificial
<220> FEATURE:
<223> OTHER INFORMATION: CDR1 element

<400> SEQUENCE: 36

Ser Phe Gly Met Ser
1               5

<210> SEQ ID NO 37
<211> LENGTH: 5
<212> TYPE: PRT
<213> ORGANISM: Artificial
<220> FEATURE:
<223> OTHER INFORMATION: CDR1 element

<400> SEQUENCE: 37

Leu Asn Leu Met Gly
1               5

<210> SEQ ID NO 38
<211> LENGTH: 5
<212> TYPE: PRT
<213> ORGANISM: Artificial
<220> FEATURE:
<223> OTHER INFORMATION: CDR1 element

<400> SEQUENCE: 38

Ile Asn Leu Leu Gly
1               5

<210> SEQ ID NO 39
<211> LENGTH: 5
<212> TYPE: PRT
<213> ORGANISM: Artificial
```

```
<220> FEATURE:
<223> OTHER INFORMATION: CDR1 element

<400> SEQUENCE: 39

Asn Tyr Trp Met Tyr
1               5

<210> SEQ ID NO 40
<211> LENGTH: 17
<212> TYPE: PRT
<213> ORGANISM: Artificial
<220> FEATURE:
<223> OTHER INFORMATION: CDR2 element

<400> SEQUENCE: 40

Ser Ile Ser Gly Ser Gly Ser Asp Thr Leu Tyr Ala Asp Ser Val Lys
1               5                   10                  15
Gly

<210> SEQ ID NO 41
<211> LENGTH: 16
<212> TYPE: PRT
<213> ORGANISM: Artificial
<220> FEATURE:
<223> OTHER INFORMATION: CDR2 element

<400> SEQUENCE: 41

Thr Ile Thr Val Gly Asp Ser Thr Asn Tyr Ala Asp Ser Val Lys Gly
1               5                   10                  15

<210> SEQ ID NO 42
<211> LENGTH: 16
<212> TYPE: PRT
<213> ORGANISM: Artificial
<220> FEATURE:
<223> OTHER INFORMATION: CDR2 element

<400> SEQUENCE: 42

Thr Ile Thr Val Gly Asp Ser Ser Tyr Ala Asp Ser Val Lys Gly
1               5                   10                  15

<210> SEQ ID NO 43
<211> LENGTH: 17
<212> TYPE: PRT
<213> ORGANISM: Artificial
<220> FEATURE:
<223> OTHER INFORMATION: CDR2 element

<400> SEQUENCE: 43

Ser Ile Asn Gly Arg Gly Asp Asp Thr Arg Tyr Ala Asp Ser Val Lys
1               5                   10                  15
Gly

<210> SEQ ID NO 44
<211> LENGTH: 17
<212> TYPE: PRT
<213> ORGANISM: Artificial
<220> FEATURE:
<223> OTHER INFORMATION: CDR2 element

<400> SEQUENCE: 44

Ala Ile Ser Ala Asp Ser Ser Thr Lys Asn Tyr Ala Asp Ser Val Lys
1               5                   10                  15
Gly
```

```
<210> SEQ ID NO 45
<211> LENGTH: 17
<212> TYPE: PRT
<213> ORGANISM: Artificial
<220> FEATURE:
<223> OTHER INFORMATION: CDR2 element

<400> SEQUENCE: 45

Ala Ile Ser Ala Asp Ser Ser Asp Lys Arg Tyr Ala Asp Ser Val Lys
1               5                   10                  15

Gly

<210> SEQ ID NO 46
<211> LENGTH: 17
<212> TYPE: PRT
<213> ORGANISM: Artificial
<220> FEATURE:
<223> OTHER INFORMATION: CDR2 element

<400> SEQUENCE: 46

Arg Ile Ser Thr Gly Gly Gly Tyr Ser Tyr Tyr Ala Asp Ser Val Lys
1               5                   10                  15

Gly

<210> SEQ ID NO 47
<211> LENGTH: 13
<212> TYPE: PRT
<213> ORGANISM: Artificial
<220> FEATURE:
<223> OTHER INFORMATION: CDR3 element

<400> SEQUENCE: 47

Asp Arg Glu Ala Gln Val Asp Thr Leu Asp Phe Asp Tyr
1               5                   10

<210> SEQ ID NO 48
<211> LENGTH: 6
<212> TYPE: PRT
<213> ORGANISM: Artificial
<220> FEATURE:
<223> OTHER INFORMATION: CDR3 element

<400> SEQUENCE: 48

Gly Gly Ser Leu Ser Arg
1               5

<210> SEQ ID NO 49
<211> LENGTH: 8
<212> TYPE: PRT
<213> ORGANISM: Artificial
<220> FEATURE:
<223> OTHER INFORMATION: CDR3 element

<400> SEQUENCE: 49

Arg Arg Thr Trp His Ser Glu Leu
1               5

<210> SEQ ID NO 50
<211> LENGTH: 7
<212> TYPE: PRT
<213> ORGANISM: Artificial
<220> FEATURE:
<223> OTHER INFORMATION: CDR3 element

<400> SEQUENCE: 50
```

Gly Arg Ser Val Ser Arg Ser
1               5

<210> SEQ ID NO 51
<211> LENGTH: 5
<212> TYPE: PRT
<213> ORGANISM: Artificial
<220> FEATURE:
<223> OTHER INFORMATION: CDR3 element

<400> SEQUENCE: 51

Gly Arg Gly Ser Pro
1               5

<210> SEQ ID NO 52
<211> LENGTH: 115
<212> TYPE: PRT
<213> ORGANISM: Artificial
<220> FEATURE:
<223> OTHER INFORMATION: nanobody

<400> SEQUENCE: 52

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Trp Met Tyr Trp Val Arg Gln Ala Pro Gly Lys Gly Leu Glu Trp Val
            35                  40                  45

Ser Glu Ile Asn Thr Asn Gly Leu Ile Thr Lys Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Arg Ser Pro Ser Gly Phe Asn Arg Gly Gln Gly Thr Gln Val Thr
            100                 105                 110

Val Ser Ser
        115

<210> SEQ ID NO 53
<211> LENGTH: 115
<212> TYPE: PRT
<213> ORGANISM: Artificial
<220> FEATURE:
<223> OTHER INFORMATION: nanobody

<400> SEQUENCE: 53

Gln Val Gln Leu Gln Glu Ser Gly Gly Gly Met Val Gln Pro Gly Gly
1               5                   10                  15

Ser Leu Arg Leu Ser Cys Ala Ala Ser Gly Phe Asp Phe Gly Val Ser
                20                  25                  30

Trp Met Tyr Trp Val Arg Gln Ala Pro Gly Lys Gly Leu Glu Trp Val
            35                  40                  45

Ser Glu Ile Asn Thr Asn Gly Leu Ile Thr Lys Tyr Pro Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Leu Tyr Tyr Cys
                85                  90                  95

Ala Arg Ser Pro Ser Gly Ser Phe Arg Gly Gln Gly Thr Gln Val Thr

Val Ser Ser
    115

<210> SEQ ID NO 54
<211> LENGTH: 115
<212> TYPE: PRT
<213> ORGANISM: Artificial
<220> FEATURE:
<223> OTHER INFORMATION: nanobody

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Asp Phe Ser Val Ser
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Ile Pro Glu Asp Thr Ala Leu Tyr Tyr Cys
                85                  90                  95

Ala Arg Ser Pro Ser Gly Ser Phe Arg Gly Gln Gly Thr Gln Val Thr
            100                 105                 110

Val Ser Ser
    115

<210> SEQ ID NO 55
<211> LENGTH: 129
<212> TYPE: PRT
<213> ORGANISM: Artificial
<220> FEATURE:
<223> OTHER INFORMATION: nanobody

<400> SEQUENCE: 55

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Glu Pro
            20                  25                  30

Ser Gly Tyr Thr Tyr Thr Ile Gly Trp Phe Arg Gln Ala Pro Gly Lys
        35                  40                  45

Glu Arg Glu Phe Val Ala Arg Ile Tyr Trp Ser Ser Gly Leu Thr Tyr
    50                  55                  60

Tyr Ala Asp Ser Val Lys Gly Arg Phe Thr Ile Ser Arg Asp Ile Ala
65                  70                  75                  80

Lys Asn Thr Val Asp Leu Leu Met Asn Ser Leu Lys Pro Glu Asp Thr
                85                  90                  95

Ala Val Tyr Tyr Cys Ala Ala Arg Asp Gly Ile Pro Thr Ser Arg Ser
            100                 105                 110

Val Gly Ser Tyr Asn Tyr Trp Gly Gln Gly Thr Gln Val Thr Val Ser
        115                 120                 125

Ser

<210> SEQ ID NO 56
<211> LENGTH: 129
<212> TYPE: PRT

<213> ORGANISM: Artificial
<220> FEATURE:
<223> OTHER INFORMATION: nanobody

<400> SEQUENCE: 56

Gln Val Lys Leu Glu Glu Ser Gly Gly Gly Leu Val Gln Pro Gly Asp
1               5                   10                  15

Ser Leu Arg Leu Ser Cys Ala Ala Ser Gly Arg Thr Phe Ser Asp Tyr
            20                  25                  30

Ser Gly Tyr Thr Tyr Thr Val Gly Trp Phe Arg Gln Ala Pro Gly Lys
        35                  40                  45

Glu Arg Glu Phe Val Ala Arg Ile Tyr Trp Ser Ser Gly Asn Thr Tyr
    50                  55                  60

Tyr Ala Asp Ser Val Lys Gly Arg Phe Thr Ile Ser Arg Asp Ile Ala
65                  70                  75                  80

Lys Asn Thr Val Asp Leu Leu Met Asn Asn Leu Glu Pro Glu Asp Thr
                85                  90                  95

Ala Val Tyr Tyr Cys Ala Ala Arg Asp Gly Ile Pro Thr Ser Arg Ser
            100                 105                 110

Val Glu Ser Tyr Asn Tyr Trp Gly Gln Gly Thr Gln Val Thr Val Ser
        115                 120                 125

Ser

<210> SEQ ID NO 57
<211> LENGTH: 129
<212> TYPE: PRT
<213> ORGANISM: Artificial
<220> FEATURE:
<223> OTHER INFORMATION: nanobody

<400> SEQUENCE: 57

Ala Val Gln Leu Val Glu Ser Gly Gly Gly Leu Val Gln Pro Gly Asp
1               5                   10                  15

Ser Leu Arg Leu Ser Cys Ala Ala Ser Gly Arg Thr Phe Ser Asp Tyr
            20                  25                  30

Ser Gly Tyr Thr Tyr Thr Val Gly Trp Phe Arg Gln Ala Pro Gly Lys
        35                  40                  45

Glu Arg Glu Phe Val Ala Arg Ile Tyr Trp Ser Ser Gly Asn Thr Tyr
    50                  55                  60

Tyr Ala Asp Ser Val Lys Gly Arg Phe Thr Ile Ser Arg Asp Ile Ala
65                  70                  75                  80

Lys Asn Thr Val Asp Leu Leu Met Asn Asn Leu Glu Pro Glu Asp Thr
                85                  90                  95

Ala Val Tyr Tyr Cys Ala Ala Arg Asp Gly Ile Pro Thr Ser Arg Ser
            100                 105                 110

Val Glu Ser Tyr Asn Tyr Trp Gly Gln Gly Thr Gln Val Thr Val Ser
        115                 120                 125

Ser

<210> SEQ ID NO 58
<211> LENGTH: 127
<212> TYPE: PRT
<213> ORGANISM: Artificial
<220> FEATURE:
<223> OTHER INFORMATION: nanobody

<400> SEQUENCE: 58

Ala Val Gln Leu Val Asp Ser Gly Gly Gly Leu Val Gln Ala Gly Gly

-continued

```
                1               5                  10                  15
            Ser Leu Arg Leu Ser Cys Ala Ala Ser Gly Arg Thr Phe Ser Ala His
                           20                  25                  30

Ser Val Tyr Thr Met Gly Trp Phe Arg Gln Ala Pro Gly Lys Glu Arg
                           35                  40                  45

Glu Phe Val Ala Arg Ile Tyr Trp Ser Ser Ala Asn Thr Tyr Tyr Ala
                           50                  55                  60

Asp Ser Val Lys Gly Arg Phe Thr Ile Ser Arg Asp Asn Ala Lys Asn
             65                  70                  75                  80

Thr Val Asp Leu Leu Met Asn Cys Leu Lys Pro Glu Asp Thr Ala Val
                              85                  90                  95

Tyr Tyr Cys Ala Ala Arg Asp Gly Ile Pro Thr Ser Arg Ser Val Glu
                             100                 105                 110

Ala Tyr Asn Tyr Trp Gly Gln Gly Thr Gln Val Thr Val Ser Ser
                             115                 120                 125
```

<210> SEQ ID NO 59
<211> LENGTH: 123
<212> TYPE: PRT
<213> ORGANISM: Artificial
<220> FEATURE:
<223> OTHER INFORMATION: nanobody

<400> SEQUENCE: 59

```
            Gln Val Gln Leu Val Glu Ser Gly Gly Gly Leu Val Gln Ala Gly Gly
             1               5                  10                  15

Ser Leu Ser Leu Ser Cys Ala Ala Ser Gly Arg Ser Phe Thr Gly Tyr
                           20                  25                  30

Tyr Met Gly Trp Phe Arg Gln Ala Pro Gly Lys Glu Arg Gln Leu Leu
                           35                  40                  45

Ala Ser Ile Ser Trp Arg Gly Asp Asn Thr Tyr Tyr Lys Glu Ser Val
                           50                  55                  60

Lys Gly Arg Phe Thr Ile Ser Arg Asp Asp Ala Lys Asn Thr Ile Tyr
             65                  70                  75                  80

Leu Gln Met Asn Ser Leu Lys Pro Glu Asp Thr Ala Val Tyr Tyr Cys
                              85                  90                  95

Ala Ala Ser Ile Leu Pro Leu Ser Asp Asp Pro Gly Trp Asn Thr Asn
                             100                 105                 110

Trp Gly Gln Gly Thr Gln Val Thr Val Ser Ser
                             115                 120
```

<210> SEQ ID NO 60
<211> LENGTH: 123
<212> TYPE: PRT
<213> ORGANISM: Artificial
<220> FEATURE:
<223> OTHER INFORMATION: nanobody

<400> SEQUENCE: 60

```
            Glu Val Gln Leu Val Glu Ser Gly Gly Gly Leu Val Gln Ala Gly Gly
             1               5                  10                  15

Ser Leu Ser Leu Ser Cys Ser Ala Ser Gly Arg Ser Leu Ser Asn Tyr
                           20                  25                  30

Tyr Met Gly Trp Phe Arg Gln Ala Pro Gly Lys Glu Arg Glu Leu Leu
                           35                  40                  45

Gly Asn Ile Ser Trp Arg Gly Tyr Asn Ile Tyr Tyr Lys Asp Ser Val
                           50                  55                  60
```

```
Lys Gly Arg Phe Thr Ile Ser Arg Asp Asp Ala Lys Asn Thr Ile Tyr
 65                  70                  75                  80

Leu Gln Met Asn Arg Leu Lys Pro Glu Asp Thr Ala Val Tyr Tyr Cys
                 85                  90                  95

Ala Ala Ser Ile Leu Pro Leu Ser Asp Asp Pro Gly Trp Asn Thr Tyr
            100                 105                 110

Trp Gly Gln Gly Thr Gln Val Thr Val Ser Ser
            115                 120
```

<210> SEQ ID NO 61
<211> LENGTH: 117
<212> TYPE: PRT
<213> ORGANISM: Artificial
<220> FEATURE:
<223> OTHER INFORMATION: nanobody

<400> SEQUENCE: 61

```
Ala Val Gln Leu Val Glu Ser Gly Gly Gly Leu Val Gln Gly Gly
 1               5                   10                  15

Ser Leu Arg Leu Ala Cys Ala Ala Ser Glu Arg Ile Phe Asp Leu Asn
                 20                  25                  30

Leu Met Gly Trp Tyr Arg Gln Gly Pro Gly Asn Glu Arg Glu Leu Val
             35                  40                  45

Ala Thr Cys Ile Thr Val Gly Asp Ser Thr Asn Tyr Ala Asp Ser Val
         50                  55                  60

Lys Gly Arg Phe Thr Ile Ser Met Asp Tyr Thr Lys Gln Thr Val Tyr
 65                  70                  75                  80

Leu His Met Asn Ser Leu Arg Pro Glu Asp Thr Gly Leu Tyr Tyr Cys
                 85                  90                  95

Lys Ile Arg Arg Thr Trp His Ser Glu Leu Trp Gly Gln Gly Thr Gln
            100                 105                 110

Val Thr Val Ser Ser
            115
```

<210> SEQ ID NO 62
<211> LENGTH: 116
<212> TYPE: PRT
<213> ORGANISM: Artificial
<220> FEATURE:
<223> OTHER INFORMATION: nanobody

<400> SEQUENCE: 62

```
Glu Val Gln Leu Val Glu Ser Gly Gly Gly Leu Val Gln Gly Gly
 1               5                   10                  15

Ser Leu Arg Leu Ala Cys Ala Ala Ser Glu Arg Ile Trp Asp Ile Asn
                 20                  25                  30

Leu Leu Gly Trp Tyr Arg Gln Gly Pro Gly Asn Glu Arg Glu Leu Val
             35                  40                  45

Ala Thr Ile Thr Val Gly Asp Ser Thr Ser Tyr Ala Asp Ser Val Lys
         50                  55                  60

Gly Arg Phe Thr Ile Ser Arg Asp Tyr Asp Lys Asn Thr Leu Tyr Leu
 65                  70                  75                  80

Gln Met Asn Ser Leu Arg Pro Glu Asp Thr Gly Leu Tyr Tyr Cys Lys
                 85                  90                  95

Ile Arg Arg Thr Trp His Ser Glu Leu Trp Gly Gln Gly Thr Gln Val
            100                 105                 110

Thr Val Ser Ser
            115
```

```
<210> SEQ ID NO 63
<211> LENGTH: 115
<212> TYPE: PRT
<213> ORGANISM: Artificial
<220> FEATURE:
<223> OTHER INFORMATION: nanobody

<400> SEQUENCE: 63

Ala Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 64
<211> LENGTH: 116
<212> TYPE: PRT
<213> ORGANISM: Artificial
<220> FEATURE:
<223> OTHER INFORMATION: nanobody

<400> SEQUENCE: 64

Ala Val Gln Leu Val Asp Ser Gly Gly Gly Leu Val Gln Pro Gly Gly
1               5                   10                  15

Ser Leu Arg Leu Ser Cys Ala Ala Ser Gly Phe Ser Phe Gly Ser Phe
            20                  25                  30

Gly Met Ser Trp Val Arg Gln Tyr Pro Gly Lys Glu Pro Glu Trp Val
        35                  40                  45

Ser Ser Ile Asn Gly Arg Gly Asp Asp Thr Arg Tyr Ala Asp Ser Val
    50                  55                  60

Lys Gly Arg Phe Ser Ile Ser Arg Asp Asn Ala Lys Asn Thr Leu Tyr
65                  70                  75                  80

Leu Gln Met Asn Ser Leu Lys Pro Glu Asp Thr Ala Glu Tyr Tyr Cys
                85                  90                  95

Thr Ile Gly Arg Ser Val Ser Arg Ser Arg Thr Gln Gly Thr Gln Val
            100                 105                 110

Thr Val Ser Ser
        115

<210> SEQ ID NO 65
<211> LENGTH: 114
<212> TYPE: PRT
<213> ORGANISM: Artificial
<220> FEATURE:
<223> OTHER INFORMATION: nanobody

<400> SEQUENCE: 65
```

Ala Val Gln Leu Val Glu Ser Gly Gly Gly Leu Val Gln Pro Gly Gly
1               5                   10                  15

Ser Leu Arg Leu Thr Cys Thr Ala Ser Gly Phe Thr Phe Arg Ser Phe
            20                  25                  30

Gly Met Ser Trp Val Arg Gln Ala Pro Gly Lys Asp Gln Glu Trp Val
        35                  40                  45

Ser Ala Ile Ser Ala Asp Ser Ser Thr Lys Asn Tyr Ala Asp Ser Val
    50                  55                  60

Lys Gly Arg Phe Thr Ile Ser Arg Asp Asn Ala Lys Lys Met Leu Tyr
65                  70                  75                  80

Leu Glu Met Asn Ser Leu Lys Pro Glu Asp Thr Ala Val Tyr Tyr Cys
                85                  90                  95

Val Ile Gly Arg Gly Ser Pro Ser Ser Pro Gly Thr Gln Val Thr Val
            100                 105                 110

Ser Ser

<210> SEQ ID NO 66
<211> LENGTH: 114
<212> TYPE: PRT
<213> ORGANISM: Artificial
<220> FEATURE:
<223> OTHER INFORMATION: nanobody

<400> SEQUENCE: 66

Gln Val Gln Leu Ala Glu Ser Gly Gly Gly Leu Val Gln Pro Gly Gly
1               5                   10                  15

Ser Leu Arg Leu Thr Cys Thr Ala Ser Gly Phe Thr Phe Gly Ser Phe
            20                  25                  30

Gly Met Ser Trp Val Arg Gln Ala Pro Gly Glu Gly Leu Glu Trp Val
        35                  40                  45

Ser Ala Ile Ser Ala Asp Ser Ser Asp Lys Arg Tyr Ala Asp Ser Val
    50                  55                  60

Lys Gly Arg Phe Thr Ile Ser Arg Asp Asn Ala Lys Lys Met Leu Tyr
65                  70                  75                  80

Leu Glu Met Asn Ser Leu Lys Ser Glu Asp Thr Ala Val Tyr Tyr Cys
                85                  90                  95

Val Ile Gly Arg Gly Ser Pro Ala Ser Gln Gly Thr Gln Val Thr Val
            100                 105                 110

Ser Ser

<210> SEQ ID NO 67
<211> LENGTH: 123
<212> TYPE: PRT
<213> ORGANISM: Artificial
<220> FEATURE:
<223> OTHER INFORMATION: nanobody

<400> SEQUENCE: 67

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Val Ala Pro Gly Lys Gly Leu Glu Arg Ile
        35                  40                  45

Ser Arg Asp Ile Ser Thr Gly Gly Tyr Ser Tyr Tyr Ala Asp Ser
    50                  55                  60

Val Lys Gly Arg Phe Thr Ile Ser Arg Asp Asn Ala Lys Asn Thr Leu

```
            65                  70                  75                  80
Tyr Leu Gln Met Asn Ser Leu Lys Pro Glu Asp Thr Ala Leu Tyr Tyr
                85                  90                  95

Cys Ala Lys Asp Arg Glu Ala Gln Val Asp Thr Leu Asp Phe Asp Tyr
            100                 105                 110

Arg Gly Gln Gly Thr Gln Val Thr Val Ser Ser
        115                 120

<210> SEQ ID NO 68
<211> LENGTH: 9
<212> TYPE: PRT
<213> ORGANISM: Artificial
<220> FEATURE:
<223> OTHER INFORMATION: linker

<400> SEQUENCE: 68

Gly Gly Gly Gly Ser Gly Gly Gly Ser
1               5

<210> SEQ ID NO 69
<211> LENGTH: 30
<212> TYPE: PRT
<213> ORGANISM: Artificial
<220> FEATURE:
<223> OTHER INFORMATION: linker

<400> SEQUENCE: 69

Gly Gly Gly Gly Ser Gly Gly Gly Ser Gly Gly Gly Ser Gly
1               5                   10                  15

Gly Gly Ser Gly Gly Gly Ser Gly Gly Gly Gly Ser
        20                  25                  30

<210> SEQ ID NO 70
<211> LENGTH: 239
<212> TYPE: PRT
<213> ORGANISM: Artificial
<220> FEATURE:
<223> OTHER INFORMATION: nanobody construct

<400> SEQUENCE: 70

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Arg Ser Pro Ser Gly Phe Asn Arg Gly Gln Gly Thr Gln Val Thr
            100                 105                 110

Val Ser Ser Gly Gly Gly Ser Gly Gly Gly Ser Gln Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Phe Ser Asp Tyr Trp Met Tyr Trp
145                 150                 155                 160
```

Val Arg Gln Ala Pro Gly Lys Gly Leu Glu Trp Val Ser Glu Ile Asn
            165                 170                 175

Thr Asn Gly Leu Ile Thr Lys Tyr Pro Asp Ser Val Lys Gly Arg Phe
            180                 185                 190

Thr Ile Ser Arg Asp Asn Ala Lys Asn Thr Leu Tyr Leu Gln Met Asn
            195                 200                 205

Ser Leu Lys Pro Glu Asp Thr Ala Leu Tyr Tyr Cys Ala Arg Ser Pro
            210                 215                 220

Ser Gly Phe Asn Arg Gly Gln Gly Thr Gln Val Thr Val Ser Ser
225                 230                 235

<210> SEQ ID NO 71
<211> LENGTH: 267
<212> TYPE: PRT
<213> ORGANISM: Artificial
<220> FEATURE:
<223> OTHER INFORMATION: nanobody construct

<400> SEQUENCE: 71

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Glu Pro
            20                  25                  30

Ser Gly Tyr Thr Tyr Thr Ile Gly Trp Phe Arg Gln Ala Pro Gly Lys
            35                  40                  45

Glu Arg Glu Phe Val Ala Arg Ile Tyr Trp Ser Ser Gly Leu Thr Tyr
50                  55                  60

Tyr Ala Asp Ser Val Lys Gly Arg Phe Thr Ile Ser Arg Asp Ile Ala
65                  70                  75                  80

Lys Asn Thr Val Asp Leu Leu Met Asn Ser Leu Lys Pro Glu Asp Thr
            85                  90                  95

Ala Val Tyr Tyr Cys Ala Ala Arg Asp Gly Ile Pro Thr Ser Arg Ser
            100                 105                 110

Val Gly Ser Tyr Asn Tyr Trp Gly Gln Gly Thr Gln Val Thr Val Ser
            115                 120                 125

Ser Gly Gly Gly Gly Ser Gly Gly Gly Ser Gln Val Gln Leu Val Glu
            130                 135                 140

Ser Gly Gly Gly Leu Val Gln Ala Gly Gly Ser Leu Arg Leu Ser Cys
145                 150                 155                 160

Ala Ala Ser Gly Arg Thr Phe Ser Glu Pro Ser Gly Tyr Thr Tyr Thr
            165                 170                 175

Ile Gly Trp Phe Arg Gln Ala Pro Gly Lys Glu Arg Glu Phe Val Ala
            180                 185                 190

Arg Ile Tyr Trp Ser Ser Gly Leu Thr Tyr Tyr Ala Asp Ser Val Lys
            195                 200                 205

Gly Arg Phe Thr Ile Ser Arg Asp Ile Ala Lys Asn Thr Val Asp Leu
            210                 215                 220

Leu Met Asn Ser Leu Lys Pro Glu Asp Thr Ala Val Tyr Tyr Cys Ala
225                 230                 235                 240

Ala Arg Asp Gly Ile Pro Thr Ser Arg Ser Val Gly Ser Tyr Asn Tyr
            245                 250                 255

Trp Gly Gln Gly Thr Gln Val Thr Val Ser Ser
            260                 265

<210> SEQ ID NO 72

```
<211> LENGTH: 255
<212> TYPE: PRT
<213> ORGANISM: Artificial
<220> FEATURE:
<223> OTHER INFORMATION: nanobody construct

<400> SEQUENCE: 72

Glu Val Gln Leu Val Glu Ser Gly Gly Gly Leu Val Gln Ala Gly Gly
1               5                   10                  15

Ser Leu Ser Leu Ser Cys Ser Ala Ser Gly Arg Ser Leu Ser Asn Tyr
            20                  25                  30

Tyr Met Gly Trp Phe Arg Gln Ala Pro Gly Lys Glu Arg Glu Leu Leu
        35                  40                  45

Gly Asn Ile Ser Trp Arg Gly Tyr Asn Ile Tyr Tyr Lys Asp Ser Val
    50                  55                  60

Lys Gly Arg Phe Thr Ile Ser Arg Asp Asp Ala Lys Asn Thr Ile Tyr
65                  70                  75                  80

Leu Gln Met Asn Arg Leu Lys Pro Glu Asp Thr Ala Val Tyr Tyr Cys
                85                  90                  95

Ala Ala Ser Ile Leu Pro Leu Ser Asp Asp Pro Gly Trp Asn Thr Tyr
            100                 105                 110

Trp Gly Gln Gly Thr Gln Val Thr Val Ser Ser Gly Gly Gly Gly Ser
        115                 120                 125

Gly Gly Gly Ser Glu Val Gln Leu Val Glu Ser Gly Gly Gly Leu Val
    130                 135                 140

Gln Ala Gly Gly Ser Leu Ser Leu Ser Cys Ser Ala Ser Gly Arg Ser
145                 150                 155                 160

Leu Ser Asn Tyr Tyr Met Gly Trp Phe Arg Gln Ala Pro Gly Lys Glu
                165                 170                 175

Arg Glu Leu Leu Gly Asn Ile Ser Trp Arg Gly Tyr Asn Ile Tyr Tyr
            180                 185                 190

Lys Asp Ser Val Lys Gly Arg Phe Thr Ile Ser Arg Asp Asp Ala Lys
        195                 200                 205

Asn Thr Ile Tyr Leu Gln Met Asn Arg Leu Lys Pro Glu Asp Thr Ala
    210                 215                 220

Val Tyr Tyr Cys Ala Ala Ser Ile Leu Pro Leu Ser Asp Asp Pro Gly
225                 230                 235                 240

Trp Asn Thr Tyr Trp Gly Gln Gly Thr Gln Val Thr Val Ser Ser
                245                 250                 255

<210> SEQ ID NO 73
<211> LENGTH: 260
<212> TYPE: PRT
<213> ORGANISM: Artificial
<220> FEATURE:
<223> OTHER INFORMATION: nanobody construct

<400> SEQUENCE: 73

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Pro Asp Ser Val
    50                  55                  60

Lys Gly Arg Phe Thr Ile Ser Arg Asp Asn Ala Lys Asn Thr Leu Tyr
```

```
               65                  70                  75                  80
Leu Gln Met Asn Ser Leu Lys Pro Glu Asp Thr Ala Leu Tyr Tyr Cys
                85                  90                  95

Ala Arg Ser Pro Ser Gly Phe Asn Arg Gly Gln Gly Thr Gln Val Thr
            100                 105                 110

Val Ser Ser Gly Gly Gly Gly Ser Gly Gly Gly Ser Gly Gly Gly Gly
            115                 120                 125

Gly Ser Gly Gly Gly Gly Ser Gly Gly Gly Ser Gly Gly Gly Gly
130                 135                 140

Ser Gln Val Gln Leu Val Glu Ser Gly Gly Leu Val Gln Pro Gly
145                 150                 155                 160

Gly Ser Leu Arg Leu Ser Cys Ala Ala Ser Gly Phe Thr Phe Ser Asp
                165                 170                 175

Tyr Trp Met Tyr Trp Val Arg Gln Ala Pro Gly Lys Gly Leu Glu Trp
            180                 185                 190

Val Ser Glu Ile Asn Thr Asn Gly Leu Ile Thr Lys Tyr Pro Asp Ser
            195                 200                 205

Val Lys Gly Arg Phe Thr Ile Ser Arg Asp Asn Ala Lys Asn Thr Leu
            210                 215                 220

Tyr Leu Gln Met Asn Ser Leu Lys Pro Glu Asp Thr Ala Leu Tyr Tyr
225                 230                 235                 240

Cys Ala Arg Ser Pro Ser Gly Phe Asn Arg Gly Gln Gly Thr Gln Val
                245                 250                 255

Thr Val Ser Ser
            260

<210> SEQ ID NO 74
<211> LENGTH: 288
<212> TYPE: PRT
<213> ORGANISM: Artificial
<220> FEATURE:
<223> OTHER INFORMATION: nanobody construct

<400> SEQUENCE: 74

Gln Val Gln Leu Val Glu Ser Gly Gly Gly Leu Val Gln Ala Gly Gly
1               5                  10                  15

Ser Leu Arg Leu Ser Cys Ala Ala Ser Gly Arg Thr Phe Ser Glu Pro
            20                  25                  30

Ser Gly Tyr Thr Tyr Thr Ile Gly Trp Phe Arg Gln Ala Pro Gly Lys
            35                  40                  45

Glu Arg Glu Phe Val Ala Arg Ile Tyr Trp Ser Ser Gly Leu Thr Tyr
        50                  55                  60

Tyr Ala Asp Ser Val Lys Gly Arg Phe Thr Ile Ser Arg Asp Ile Ala
65                  70                  75                  80

Lys Asn Thr Val Asp Leu Leu Met Asn Ser Leu Lys Pro Glu Asp Thr
                85                  90                  95

Ala Val Tyr Tyr Cys Ala Ala Arg Asp Gly Ile Pro Thr Ser Arg Ser
            100                 105                 110

Val Gly Ser Tyr Asn Tyr Trp Gly Gln Gly Thr Gln Val Thr Val Ser
            115                 120                 125

Ser Gly Gly Gly Gly Ser Gly Gly Gly Ser Gly Gly Gly Gly Ser
            130                 135                 140

Gly Gly Gly Gly Ser Gly Gly Gly Ser Gly Gly Gly Gly Ser Gln
145                 150                 155                 160

Val Gln Leu Val Glu Ser Gly Gly Gly Leu Val Gln Ala Gly Gly Ser
```

```
                165                 170                 175
Leu Arg Leu Ser Cys Ala Ala Ser Gly Arg Thr Phe Ser Glu Pro Ser
            180                 185                 190
Gly Tyr Thr Tyr Thr Ile Gly Trp Phe Arg Gln Ala Pro Gly Lys Glu
            195                 200                 205
Arg Glu Phe Val Ala Arg Ile Tyr Trp Ser Ser Gly Leu Thr Tyr Tyr
            210                 215                 220
Ala Asp Ser Val Lys Gly Arg Phe Thr Ile Ser Arg Asp Ile Ala Lys
225                 230                 235                 240
Asn Thr Val Asp Leu Leu Met Asn Ser Leu Lys Pro Glu Asp Thr Ala
            245                 250                 255
Val Tyr Tyr Cys Ala Ala Arg Asp Gly Ile Pro Thr Ser Arg Ser Val
            260                 265                 270
Gly Ser Tyr Asn Tyr Trp Gly Gln Gly Thr Gln Val Thr Val Ser Ser
            275                 280                 285

<210> SEQ ID NO 75
<211> LENGTH: 276
<212> TYPE: PRT
<213> ORGANISM: Artificial
<220> FEATURE:
<223> OTHER INFORMATION: nanobody construct

<400> SEQUENCE: 75

Glu Val Gln Leu Val Glu Ser Gly Gly Gly Leu Val Gln Ala Gly Gly
1               5                   10                  15
Ser Leu Ser Leu Ser Cys Ser Ala Ser Gly Arg Ser Leu Ser Asn Tyr
            20                  25                  30
Tyr Met Gly Trp Phe Arg Gln Ala Pro Gly Lys Glu Arg Glu Leu Leu
            35                  40                  45
Gly Asn Ile Ser Trp Arg Gly Tyr Asn Ile Tyr Tyr Lys Asp Ser Val
            50                  55                  60
Lys Gly Arg Phe Thr Ile Ser Arg Asp Asp Ala Lys Asn Thr Ile Tyr
65                  70                  75                  80
Leu Gln Met Asn Arg Leu Lys Pro Glu Asp Thr Ala Val Tyr Tyr Cys
            85                  90                  95
Ala Ala Ser Ile Leu Pro Leu Ser Asp Asp Pro Gly Trp Asn Thr Tyr
            100                 105                 110
Trp Gly Gln Gly Thr Gln Val Thr Val Ser Ser Gly Gly Gly Gly Ser
            115                 120                 125
Gly Gly Gly Gly Ser Gly Gly Gly Ser Gly Gly Gly Gly Ser Gly
130                 135                 140
Gly Gly Ser Gly Gly Gly Gly Ser Glu Val Gln Leu Val Glu Ser
145                 150                 155                 160
Gly Gly Gly Leu Val Gln Ala Gly Gly Ser Leu Ser Leu Ser Cys Ser
            165                 170                 175
Ala Ser Gly Arg Ser Leu Ser Asn Tyr Tyr Met Gly Trp Phe Arg Gln
            180                 185                 190
Ala Pro Gly Lys Glu Arg Glu Leu Leu Gly Asn Ile Ser Trp Arg Gly
            195                 200                 205
Tyr Asn Ile Tyr Tyr Lys Asp Ser Val Lys Gly Arg Phe Thr Ile Ser
            210                 215                 220
Arg Asp Asp Ala Lys Asn Thr Ile Tyr Leu Gln Met Asn Arg Leu Lys
225                 230                 235                 240
Pro Glu Asp Thr Ala Val Tyr Tyr Cys Ala Ala Ser Ile Leu Pro Leu
```

```
                    245                 250                 255

Ser Asp Asp Pro Gly Trp Asn Thr Tyr Trp Gly Gln Gly Thr Gln Val
            260                 265                 270

Thr Val Ser Ser
        275

<210> SEQ ID NO 76
<211> LENGTH: 115
<212> TYPE: PRT
<213> ORGANISM: Artificial
<220> FEATURE:
<223> OTHER INFORMATION: nanobody construct

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Arg Ser Pro Ser Gly Phe Asn Arg Gly Gln Gly Thr Gln Val Thr
            100                 105                 110

Val Ser Ser
        115

<210> SEQ ID NO 77
<211> LENGTH: 115
<212> TYPE: PRT
<213> ORGANISM: Artificial
<220> FEATURE:
<223> OTHER INFORMATION: nanobody construct

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Arg Ser Pro Ser Gly Phe Asn Arg Gly Gln Gly Thr Leu Val Thr
            100                 105                 110

Val Ser Ser
        115

<210> SEQ ID NO 78
<211> LENGTH: 129
```

<212> TYPE: PRT
<213> ORGANISM: Artificial
<220> FEATURE:
<223> OTHER INFORMATION: nanobody construct

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Glu Pro
            20                  25                  30

Ser Gly Tyr Thr Tyr Thr Ile Gly Trp Phe Arg Gln Ala Pro Gly Lys
        35                  40                  45

Gly Arg Glu Phe Val Ala Arg Ile Tyr Trp Ser Ser Gly Leu Thr Tyr
    50                  55                  60

Tyr Ala Asp Ser Val Lys Gly Arg Phe Thr Ile Ser Arg Asp Ile Ala
65                  70                  75                  80

Lys Asn Thr Val Asp Leu Gln Met Asn Ser Leu Lys Pro Glu Asp Thr
                85                  90                  95

Ala Val Tyr Tyr Cys Ala Ala Arg Asp Gly Ile Pro Thr Ser Arg Ser
            100                 105                 110

Val Gly Ser Tyr Asn Tyr Trp Gly Gln Gly Thr Gln Val Thr Val Ser
        115                 120                 125

Ser

<210> SEQ ID NO 79
<211> LENGTH: 129
<212> TYPE: PRT
<213> ORGANISM: Artificial
<220> FEATURE:
<223> OTHER INFORMATION: nanobody construct

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Glu Pro
            20                  25                  30

Ser Gly Tyr Thr Tyr Thr Ile Gly Trp Phe Arg Gln Ala Pro Gly Lys
        35                  40                  45

Gly Arg Glu Phe Val Ala Arg Ile Tyr Trp Ser Ser Gly Leu Thr Tyr
    50                  55                  60

Tyr Ala Asp Ser Val Lys Gly Arg Phe Thr Ile Ser Arg Asp Ile Ala
65                  70                  75                  80

Lys Asn Thr Val Asp Leu Gln Met Asn Ser Leu Lys Pro Glu Asp Thr
                85                  90                  95

Ala Val Tyr Tyr Cys Ala Ala Arg Asp Gly Ile Pro Thr Ser Arg Ser
            100                 105                 110

Val Gly Ser Tyr Asn Tyr Trp Gly Gln Gly Thr Gln Val Thr Val Ser
        115                 120                 125

Ser

<210> SEQ ID NO 80
<211> LENGTH: 129
<212> TYPE: PRT
<213> ORGANISM: Artificial
<220> FEATURE:
<223> OTHER INFORMATION: nanobody construct

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Glu Pro
            20                  25                  30

Ser Gly Tyr Thr Tyr Thr Ile Gly Trp Phe Arg Gln Ala Pro Gly Lys
        35                  40                  45

Gly Arg Glu Phe Val Ala Arg Ile Tyr Trp Ser Ser Gly Leu Thr Tyr
    50                  55                  60

Tyr Ala Asp Ser Val Lys Gly Arg Phe Thr Ile Ser Arg Asp Asn Ala
65                  70                  75                  80

Lys Asn Thr Val Asp Leu Gln Met Asn Ser Leu Lys Pro Glu Asp Thr
                85                  90                  95

Ala Val Tyr Tyr Cys Ala Ala Arg Asp Gly Ile Pro Thr Ser Arg Ser
                100                 105                 110

Val Gly Ser Tyr Asn Tyr Trp Gly Gln Gly Thr Gln Val Thr Val Ser
            115                 120                 125

Ser

<210> SEQ ID NO 81
<211> LENGTH: 129
<212> TYPE: PRT
<213> ORGANISM: Artificial
<220> FEATURE:
<223> OTHER INFORMATION: nanobody construct

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Glu Pro
            20                  25                  30

Ser Gly Tyr Thr Tyr Thr Ile Gly Trp Phe Arg Gln Ala Pro Gly Lys
        35                  40                  45

Gly Arg Glu Phe Val Ala Arg Ile Tyr Trp Ser Ser Gly Leu Thr Tyr
    50                  55                  60

Tyr Ala Asp Ser Val Lys Gly Arg Phe Thr Ile Ser Arg Asp Ile Ala
65                  70                  75                  80

Lys Asn Thr Val Asp Leu Gln Met Asn Ser Leu Arg Pro Glu Asp Thr
                85                  90                  95

Ala Val Tyr Tyr Cys Ala Ala Arg Asp Gly Ile Pro Thr Ser Arg Ser
                100                 105                 110

Val Gly Ser Tyr Asn Tyr Trp Gly Gln Gly Thr Gln Val Thr Val Ser
            115                 120                 125

Ser

<210> SEQ ID NO 82
<211> LENGTH: 129
<212> TYPE: PRT
<213> ORGANISM: Artificial
<220> FEATURE:
<223> OTHER INFORMATION: nanobody construct

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Glu Pro
            20                  25                  30

Ser Gly Tyr Thr Tyr Thr Ile Gly Trp Phe Arg Gln Ala Pro Gly Lys

```
                    35                  40                  45
Gly Arg Glu Phe Val Ala Arg Ile Tyr Trp Ser Ser Gly Leu Thr Tyr
         50                  55                  60
Tyr Ala Asp Ser Val Lys Gly Arg Phe Thr Ile Ser Arg Asp Ile Ala
 65                  70                  75                  80
Lys Asn Thr Val Asp Leu Gln Met Asn Ser Leu Lys Pro Glu Asp Thr
                 85                  90                  95
Ala Val Tyr Tyr Cys Ala Ala Arg Asp Gly Ile Pro Thr Ser Arg Ser
                100                 105                 110
Val Gly Ser Tyr Asn Tyr Trp Gly Gln Gly Thr Leu Val Thr Val Ser
            115                 120                 125
Ser
```

<210> SEQ ID NO 83
<211> LENGTH: 123
<212> TYPE: PRT
<213> ORGANISM: Artificial
<220> FEATURE:
<223> OTHER INFORMATION: nanobody construct

<400> SEQUENCE: 83

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Arg Ser Leu Ser Asn Tyr
             20                  25                  30
Tyr Met Gly Trp Phe Arg Gln Ala Pro Gly Lys Gly Arg Glu Leu Leu
         35                  40                  45
Gly Asn Ile Ser Trp Arg Gly Tyr Asn Ile Tyr Tyr Lys Asp Ser Val
     50                  55                  60
Lys Gly Arg Phe Thr Ile Ser Arg Asp Ser Lys Asn Thr Ile Tyr
 65                  70                  75                  80
Leu Gln Met Asn Ser Leu Lys Pro Glu Asp Thr Ala Val Tyr Tyr Cys
                 85                  90                  95
Ala Ala Ser Ile Leu Pro Leu Ser Asp Asp Pro Gly Trp Asn Thr Tyr
                100                 105                 110
Trp Gly Gln Gly Thr Gln Val Thr Val Ser Ser
            115                 120
```

<210> SEQ ID NO 84
<211> LENGTH: 123
<212> TYPE: PRT
<213> ORGANISM: Artificial
<220> FEATURE:
<223> OTHER INFORMATION: nanobody construct

<400> SEQUENCE: 84

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Asn Tyr
             20                  25                  30
Tyr Met Gly Trp Phe Arg Gln Ala Pro Gly Lys Gly Arg Glu Leu Leu
         35                  40                  45
Gly Asn Ile Ser Trp Arg Gly Tyr Asn Ile Tyr Tyr Lys Asp Ser Val
     50                  55                  60
Lys Gly Arg Phe Thr Ile Ser Arg Asp Asp Ser Lys Asn Thr Ile Tyr
 65                  70                  75                  80
Leu Gln Met Asn Ser Leu Lys Pro Glu Asp Thr Ala Val Tyr Tyr Cys
```

85                  90                  95

Ala Ala Ser Ile Leu Pro Leu Ser Asp Asp Pro Gly Trp Asn Thr Tyr
            100                 105                 110

Trp Gly Gln Gly Thr Gln Val Thr Val Ser Ser
        115                 120

<210> SEQ ID NO 85
<211> LENGTH: 123
<212> TYPE: PRT
<213> ORGANISM: Artificial
<220> FEATURE:
<223> OTHER INFORMATION: nanobody construct

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ser Leu Ser Asn Tyr
            20                  25                  30

Tyr Met Gly Trp Phe Arg Gln Ala Pro Gly Lys Gly Arg Glu Leu Leu
        35                  40                  45

Gly Asn Ile Ser Trp Arg Gly Tyr Asn Ile Tyr Tyr Lys Asp Ser Val
50                  55                  60

Lys Gly Arg Phe Thr Ile Ser Arg Asp Asp Ser Lys Asn Thr Ile Tyr
65                  70                  75                  80

Leu Gln Met Asn Ser Leu Lys Thr Glu Asp Thr Ala Val Tyr Tyr Cys
                85                  90                  95

Ala Ala Ser Ile Leu Pro Leu Ser Asp Asp Pro Gly Trp Asn Thr Tyr
            100                 105                 110

Trp Gly Gln Gly Thr Gln Val Thr Val Ser Ser
        115                 120

<210> SEQ ID NO 86
<211> LENGTH: 123
<212> TYPE: PRT
<213> ORGANISM: Artificial
<220> FEATURE:
<223> OTHER INFORMATION: nanobody construct

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ser Leu Ser Asn Tyr
            20                  25                  30

Tyr Met Gly Trp Phe Arg Gln Ala Pro Gly Lys Gly Arg Glu Leu Leu
        35                  40                  45

Gly Asn Ile Ser Trp Arg Gly Tyr Asn Ile Tyr Tyr Lys Asp Ser Val
50                  55                  60

Lys Gly Arg Phe Thr Ile Ser Arg Asp Asp Ser Lys Asn Thr Ile Tyr
65                  70                  75                  80

Leu Gln Met Asn Ser Leu Lys Pro Glu Asp Thr Ala Val Tyr Tyr Cys
                85                  90                  95

Ala Ala Ser Ile Leu Pro Leu Ser Asp Asp Pro Gly Trp Asn Thr Tyr
            100                 105                 110

Trp Gly Gln Gly Thr Leu Val Thr Val Ser Ser
        115                 120

<210> SEQ ID NO 87
<211> LENGTH: 115

```
<212> TYPE: PRT
<213> ORGANISM: Artificial
<220> FEATURE:
<223> OTHER INFORMATION: nanobody construct

<400> SEQUENCE: 87
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

```
<210> SEQ ID NO 88
<211> LENGTH: 115
<212> TYPE: PRT
<213> ORGANISM: Artificial
<220> FEATURE:
<223> OTHER INFORMATION: nanobody construct

<400> SEQUENCE: 88
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

```
<210> SEQ ID NO 89
<211> LENGTH: 115
<212> TYPE: PRT
<213> ORGANISM: Artificial
<220> FEATURE:
<223> OTHER INFORMATION: nanobody construct

<400> SEQUENCE: 89
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe

```
                20                  25                  30
Gly Met Ser Trp Val Arg Gln Ala Pro Gly Lys Gly Leu Glu Trp Val
            35                  40                  45

Ser Ser Ile Ser Gly Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 90
<211> LENGTH: 363
<212> TYPE: PRT
<213> ORGANISM: Artificial
<220> FEATURE:
<223> OTHER INFORMATION: nanobody construct

<400> SEQUENCE: 90

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Pro Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Arg Ser Pro Ser Gly Phe Asn Arg Gly Gln Gly Thr Gln Val Thr
            100                 105                 110

Val Ser Ser Gly Gly Gly Gly Ser Gly Gly Gly Ser Glu Val Gln Leu
        115                 120                 125

Val Glu Ser Gly Gly Gly Leu Val Gln Pro Gly Asn Ser Leu Arg Leu
    130                 135                 140

Ser Cys Ala Ala Ser Gly Phe Thr Phe Arg Ser Phe Gly Met Ser Trp
145                 150                 155                 160

Val Arg Gln Ala Pro Gly Lys Glu Pro Glu Trp Val Ser Ser Ile Ser
                165                 170                 175

Gly Ser Gly Ser Asp Thr Leu Tyr Ala Asp Ser Val Lys Gly Arg Phe
            180                 185                 190

Thr Ile Ser Arg Asp Asn Ala Lys Thr Thr Leu Tyr Leu Gln Met Asn
        195                 200                 205

Ser Leu Lys Pro Glu Asp Thr Ala Val Tyr Tyr Cys Thr Ile Gly Gly
    210                 215                 220

Ser Leu Ser Arg Ser Ser Gln Gly Thr Gln Val Thr Val Ser Ser Gly
225                 230                 235                 240

Gly Gly Gly Ser Gly Gly Gly Ser Glu Val Gln Leu Val Glu Ser Gly
                245                 250                 255

Gly Gly Leu Val Gln Pro Gly Gly Ser Leu Arg Leu Ser Cys Ala Ala
```

```
                    260                 265                 270
Ser Gly Phe Thr Phe Ser Asp Tyr Trp Met Tyr Trp Val Arg Gln Ala
            275                 280                 285

Pro Gly Lys Gly Leu Glu Trp Val Ser Glu Ile Asn Thr Asn Gly Leu
            290                 295                 300

Ile Thr Lys Tyr Pro Asp Ser Val Lys Gly Arg Phe Thr Ile Ser Arg
305                 310                 315                 320

Asp Asn Ala Lys Asn Thr Leu Tyr Leu Gln Met Asn Ser Leu Lys Pro
                325                 330                 335

Glu Asp Thr Ala Leu Tyr Tyr Cys Ala Arg Ser Pro Ser Gly Phe Asn
            340                 345                 350

Arg Gly Gln Gly Thr Gln Val Thr Val Ser Ser
            355                 360

<210> SEQ ID NO 91
<211> LENGTH: 391
<212> TYPE: PRT
<213> ORGANISM: Artificial
<220> FEATURE:
<223> OTHER INFORMATION: nanobody construct

<400> SEQUENCE: 91

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Glu Pro
            20                  25                  30

Ser Gly Tyr Thr Tyr Thr Ile Gly Trp Phe Arg Gln Ala Pro Gly Lys
        35                  40                  45

Glu Arg Glu Phe Val Ala Arg Ile Tyr Trp Ser Ser Gly Leu Thr Tyr
50                  55                  60

Tyr Ala Asp Ser Val Lys Gly Arg Phe Thr Ile Ser Arg Asp Ile Ala
65                  70                  75                  80

Lys Asn Thr Val Asp Leu Leu Met Asn Ser Leu Lys Pro Glu Asp Thr
                85                  90                  95

Ala Val Tyr Tyr Cys Ala Ala Arg Asp Gly Ile Pro Thr Ser Arg Ser
            100                 105                 110

Val Gly Ser Tyr Asn Tyr Trp Gly Gln Gly Thr Gln Val Thr Val Ser
        115                 120                 125

Ser Gly Gly Gly Gly Ser Gly Gly Gly Ser Glu Val Gln Leu Val Glu
    130                 135                 140

Ser Gly Gly Gly Leu Val Gln Ala Gly Ser Leu Arg Leu Ser Cys
145                 150                 155                 160

Ala Ala Ser Gly Arg Thr Phe Ser Glu Pro Ser Gly Tyr Thr Tyr Thr
                165                 170                 175

Ile Gly Trp Phe Arg Gln Ala Pro Gly Lys Glu Arg Glu Phe Val Ala
            180                 185                 190

Arg Ile Tyr Trp Ser Ser Gly Leu Thr Tyr Tyr Ala Asp Ser Val Lys
        195                 200                 205

Gly Arg Phe Thr Ile Ser Arg Asp Ile Ala Lys Asn Thr Val Asp Leu
    210                 215                 220

Leu Met Asn Ser Leu Lys Pro Glu Asp Thr Ala Val Tyr Tyr Cys Ala
225                 230                 235                 240

Ala Arg Asp Gly Ile Pro Thr Ser Arg Ser Val Gly Ser Tyr Asn Tyr
                245                 250                 255

Trp Gly Gln Gly Thr Gln Val Thr Val Ser Ser Gly Gly Gly Gly Ser
```

Gly Gly Gly Ser Glu Val Gln Leu Val Glu Ser Gly Gly Leu Val
          260                 265                 270

Gln Pro Gly Asn Ser Leu Arg Leu Ser Cys Ala Ala Ser Gly Phe Thr
        275                 280                 285

Phe Arg Ser Phe Gly Met Ser Trp Val Arg Gln Ala Pro Gly Lys Glu
290                 295                 300

Pro Glu Trp Val Ser Ser Ile Ser Gly Ser Gly Ser Asp Thr Leu Tyr
305                 310                 315                 320

Ala Asp Ser Val Lys Gly Arg Phe Thr Ile Ser Arg Asp Asn Ala Lys
        325                 330                 335

Thr Thr Leu Tyr Leu Gln Met Asn Ser Leu Lys Pro Glu Asp Thr Ala
        340                 345                 350

Val Tyr Tyr Cys Thr Ile Gly Gly Ser Leu Ser Arg Ser Ser Gln Gly
        355                 360                 365

Thr Gln Val Thr Val Ser Ser
        370                 375

385         390

<210> SEQ ID NO 92
<211> LENGTH: 379
<212> TYPE: PRT
<213> ORGANISM: Artificial
<220> FEATURE:
<223> OTHER INFORMATION: nanobody construct

<400> SEQUENCE: 92

Glu Val Gln Leu Val Glu Ser Gly Gly Gly Leu Val Gln Ala Gly Gly
1               5                   10                  15

Ser Leu Ser Leu Ser Cys Ser Ala Ser Gly Arg Ser Leu Ser Asn Tyr
            20                  25                  30

Tyr Met Gly Trp Phe Arg Gln Ala Pro Gly Lys Glu Arg Glu Leu Leu
        35                  40                  45

Gly Asn Ile Ser Trp Arg Gly Tyr Asn Ile Tyr Tyr Lys Asp Ser Val
    50                  55                  60

Lys Gly Arg Phe Thr Ile Ser Arg Asp Asp Ala Lys Asn Thr Ile Tyr
65                  70                  75                  80

Leu Gln Met Asn Arg Leu Lys Pro Glu Asp Thr Ala Val Tyr Tyr Cys
                85                  90                  95

Ala Ala Ser Ile Leu Pro Leu Ser Asp Asp Pro Gly Trp Asn Thr Tyr
            100                 105                 110

Trp Gly Gln Gly Thr Gln Val Thr Val Ser Ser Gly Gly Gly Gly Ser
        115                 120                 125

Gly Gly Gly Ser Glu Val Gln Leu Val Glu Ser Gly Gly Gly Leu Val
    130                 135                 140

Gln Pro Gly Asn Ser Leu Arg Leu Ser Cys Ala Ala Ser Gly Phe Thr
145                 150                 155                 160

Phe Arg Ser Phe Gly Met Ser Trp Val Arg Gln Ala Pro Gly Lys Glu
                165                 170                 175

Pro Glu Trp Val Ser Ser Ile Ser Gly Ser Gly Ser Asp Thr Leu Tyr
            180                 185                 190

Ala Asp Ser Val Lys Gly Arg Phe Thr Ile Ser Arg Asp Asn Ala Lys
        195                 200                 205

Thr Thr Leu Tyr Leu Gln Met Asn Ser Leu Lys Pro Glu Asp Thr Ala
    210                 215                 220

Val Tyr Tyr Cys Thr Ile Gly Gly Ser Leu Ser Arg Ser Ser Gln Gly

```
                    225                 230                 235                 240
            Thr Gln Val Thr Val Ser Ser Gly Gly Gly Ser Gly Gly Gly Ser
                            245                 250                 255

Glu Val Gln Leu Val Glu Ser Gly Gly Gly Leu Val Gln Ala Gly Gly
                        260                 265                 270

Ser Leu Ser Leu Ser Cys Ser Ala Ser Gly Arg Ser Leu Ser Asn Tyr
                        275                 280                 285

Tyr Met Gly Trp Phe Arg Gln Ala Pro Gly Lys Glu Arg Glu Leu Leu
                        290                 295                 300

Gly Asn Ile Ser Trp Arg Gly Tyr Asn Ile Tyr Tyr Lys Asp Ser Val
            305                 310                 315                 320

Lys Gly Arg Phe Thr Ile Ser Arg Asp Asp Ala Lys Asn Thr Ile Tyr
                            325                 330                 335

Leu Gln Met Asn Arg Leu Lys Pro Glu Asp Thr Ala Val Tyr Tyr Cys
                        340                 345                 350

Ala Ala Ser Ile Leu Pro Leu Ser Asp Asp Pro Gly Trp Asn Thr Tyr
                        355                 360                 365

Trp Gly Gln Gly Thr Gln Val Thr Val Ser Ser
                        370                 375

<210> SEQ ID NO 93
<211> LENGTH: 384
<212> TYPE: PRT
<213> ORGANISM: Artificial
<220> FEATURE:
<223> OTHER INFORMATION: nanobody construct

<400> SEQUENCE: 93

Gln Val Gln Leu Val Glu Ser Gly Gly Gly Leu Val Gln Pro Gly Gly
            1               5                   10                  15

Ser Leu Arg Leu Ser Cys Ala Ala Ser Gly Phe Thr Phe Ser Asp Tyr
                        20                  25                  30

Trp Met Tyr Trp Val Arg Gln Ala Pro Gly Lys Gly Leu Glu Trp Val
                        35                  40                  45

Ser Glu Ile Asn Thr Asn Gly Leu Ile Thr Lys Tyr Pro Asp Ser Val
                50                  55                  60

Lys Gly Arg Phe Thr Ile Ser Arg Asp Asn Ala Lys Asn Thr Leu Tyr
            65                  70                  75                  80

Leu Gln Met Asn Ser Leu Lys Pro Glu Asp Thr Ala Leu Tyr Tyr Cys
                            85                  90                  95

Ala Arg Ser Pro Ser Gly Phe Asn Arg Gly Gln Gly Thr Gln Val Thr
                        100                 105                 110

Val Ser Ser Gly Gly Gly Gly Ser Gly Gly Gly Gly Ser Gly Gly Gly
                        115                 120                 125

Gly Ser Gly Gly Gly Gly Ser Gly Gly Gly Gly Ser Gly Gly Gly Gly
                        130                 135                 140

Ser Glu Val Gln Leu Val Glu Ser Gly Gly Gly Leu Val Gln Pro Gly
            145                 150                 155                 160

Gly Ser Leu Arg Leu Ser Cys Ala Ala Ser Gly Phe Thr Phe Ser Asp
                            165                 170                 175

Tyr Trp Met Tyr Trp Val Arg Gln Ala Pro Gly Lys Gly Leu Glu Trp
                        180                 185                 190

Val Ser Glu Ile Asn Thr Asn Gly Leu Ile Thr Lys Tyr Pro Asp Ser
                        195                 200                 205

Val Lys Gly Arg Phe Thr Ile Ser Arg Asp Asn Ala Lys Asn Thr Leu
```

```
            210                 215                 220
Tyr Leu Gln Met Asn Ser Leu Lys Pro Glu Asp Thr Ala Leu Tyr Tyr
225                 230                 235                 240

Cys Ala Arg Ser Pro Ser Gly Phe Asn Arg Gly Gln Gly Thr Gln Val
                245                 250                 255

Thr Val Ser Ser Gly Gly Gly Gly Ser Gly Gly Gly Ser Glu Val Gln
            260                 265                 270

Leu Val Glu Ser Gly Gly Leu Val Gln Pro Gly Asn Ser Leu Arg
            275                 280                 285

Leu Ser Cys Ala Ala Ser Gly Phe Thr Phe Arg Ser Phe Gly Met Ser
            290                 295                 300

Trp Val Arg Gln Ala Pro Gly Lys Glu Pro Glu Trp Val Ser Ser Ile
305                 310                 315                 320

Ser Gly Ser Gly Ser Asp Thr Leu Tyr Ala Asp Ser Val Lys Gly Arg
                325                 330                 335

Phe Thr Ile Ser Arg Asp Asn Ala Lys Thr Thr Leu Tyr Leu Gln Met
                340                 345                 350

Asn Ser Leu Lys Pro Glu Asp Thr Ala Val Tyr Tyr Cys Thr Ile Gly
            355                 360                 365

Gly Ser Leu Ser Arg Ser Ser Gln Gly Thr Gln Val Thr Val Ser Ser
            370                 375                 380

<210> SEQ ID NO 94
<211> LENGTH: 400
<212> TYPE: PRT
<213> ORGANISM: Artificial
<220> FEATURE:
<223> OTHER INFORMATION: nanobody construct

<400> SEQUENCE: 94

Glu Val Gln Leu Val Glu Ser Gly Gly Gly Leu Val Gln Ala Gly Gly
1               5                   10                  15

Ser Leu Ser Leu Ser Cys Ser Ala Ser Gly Arg Ser Leu Ser Asn Tyr
                20                  25                  30

Tyr Met Gly Trp Phe Arg Gln Ala Pro Gly Lys Glu Arg Glu Leu Leu
            35                  40                  45

Gly Asn Ile Ser Trp Arg Gly Tyr Asn Ile Tyr Tyr Lys Asp Ser Val
        50                  55                  60

Lys Gly Arg Phe Thr Ile Ser Arg Asp Asp Ala Lys Asn Thr Ile Tyr
65                  70                  75                  80

Leu Gln Met Asn Arg Leu Lys Pro Glu Asp Thr Ala Val Tyr Tyr Cys
                85                  90                  95

Ala Ala Ser Ile Leu Pro Leu Ser Asp Asp Pro Gly Trp Asn Thr Tyr
                100                 105                 110

Trp Gly Gln Gly Thr Gln Val Thr Val Ser Ser Gly Gly Gly Gly Ser
            115                 120                 125

Gly Gly Gly Gly Ser Gly Gly Gly Ser Gly Gly Gly Gly Ser Gly
            130                 135                 140

Gly Gly Ser Ser Gly Gly Gly Ser Glu Val Gln Val Val Glu Ser
145                 150                 155                 160

Gly Gly Gly Leu Val Gln Ala Gly Gly Ser Leu Ser Leu Ser Cys Ser
                165                 170                 175

Ala Ser Gly Arg Ser Leu Ser Asn Tyr Tyr Met Gly Trp Phe Arg Gln
            180                 185                 190

Ala Pro Gly Lys Glu Arg Glu Leu Leu Gly Asn Ile Ser Trp Arg Gly
```

-continued

```
                195                 200                 205
Tyr Asn Ile Tyr Tyr Lys Asp Ser Val Lys Gly Arg Phe Thr Ile Ser
    210                 215                 220
Arg Asp Asp Ala Lys Asn Thr Ile Tyr Leu Gln Met Asn Arg Leu Lys
225                 230                 235                 240
Pro Glu Asp Thr Ala Val Tyr Tyr Cys Ala Ala Ser Ile Leu Pro Leu
                245                 250                 255
Ser Asp Asp Pro Gly Trp Asn Thr Tyr Trp Gly Gln Gly Thr Gln Val
            260                 265                 270
Thr Val Ser Ser Gly Gly Gly Gly Ser Gly Gly Gly Ser Glu Val Gln
            275                 280                 285
Leu Val Glu Ser Gly Gly Gly Leu Val Gln Pro Gly Asn Ser Leu Arg
    290                 295                 300
Leu Ser Cys Ala Ala Ser Gly Phe Thr Phe Arg Ser Phe Gly Met Ser
305                 310                 315                 320
Trp Val Arg Gln Ala Pro Gly Lys Glu Pro Glu Trp Val Ser Ser Ile
                325                 330                 335
Ser Gly Ser Gly Ser Asp Thr Leu Tyr Ala Asp Ser Val Lys Gly Arg
            340                 345                 350
Phe Thr Ile Ser Arg Asp Asn Ala Lys Thr Thr Leu Tyr Leu Gln Met
                355                 360                 365
Asn Ser Leu Lys Pro Glu Asp Thr Ala Val Tyr Tyr Cys Thr Ile Gly
    370                 375                 380
Gly Ser Leu Ser Arg Ser Ser Gln Gly Thr Gln Val Thr Val Ser Ser
385                 390                 395                 400

<210> SEQ ID NO 95
<211> LENGTH: 115
<212> TYPE: PRT
<213> ORGANISM: Artificial
<220> FEATURE:
<223> OTHER INFORMATION: nanobody construct

<400> SEQUENCE: 95

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Tyr
            20                  25                  30
Trp Met Tyr Trp Val Arg Gln Ala Pro Gly Lys Gly Leu Glu Trp Val
        35                  40                  45
Ser Glu Ile Asn Thr Asn Gly Leu Ile Thr Lys Tyr Pro Asp Ser Val
    50                  55                  60
Lys Gly Arg Phe Thr Ile Ser Arg Asp Asn Ala Lys Asn Thr Leu Tyr
65                  70                  75                  80
Leu Gln Met Asn Ser Leu Lys Pro Glu Asp Thr Ala Val Tyr Tyr Cys
                85                  90                  95
Ala Arg Ser Pro Ser Gly Phe Asn Arg Gly Gln Gly Thr Leu Val Thr
            100                 105                 110
Val Ser Ser
        115

<210> SEQ ID NO 96
<211> LENGTH: 115
<212> TYPE: PRT
<213> ORGANISM: Artificial
<220> FEATURE:
<223> OTHER INFORMATION: nanobody construct
```

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Pro Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Ser Pro Ser Gly Phe Asn Arg Gly Gln Gly Thr Leu Val Thr
            100                 105                 110

Val Ser Ser
        115

<210> SEQ ID NO 97
<211> LENGTH: 129
<212> TYPE: PRT
<213> ORGANISM: Artificial
<220> FEATURE:
<223> OTHER INFORMATION: nanobody construct

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Glu Pro
            20                  25                  30

Ser Gly Tyr Thr Tyr Thr Ile Gly Trp Phe Arg Gln Ala Pro Gly Lys
        35                  40                  45

Gly Arg Glu Phe Val Ala Arg Ile Tyr Trp Ser Ser Gly Leu Thr Tyr
50                  55                  60

Tyr Ala Asp Ser Val Lys Gly Arg Phe Thr Ile Ser Arg Asp Ile Ala
65                  70                  75                  80

Lys Asn Thr Val Asp Leu Gln Met Asn Ser Leu Arg Pro Glu Asp Thr
                85                  90                  95

Ala Val Tyr Tyr Cys Ala Ala Arg Asp Gly Ile Pro Thr Ser Arg Ser
            100                 105                 110

Val Gly Ser Tyr Asn Tyr Trp Gly Gln Gly Thr Gln Val Thr Val Ser
            115                 120                 125

Ser

<210> SEQ ID NO 98
<211> LENGTH: 129
<212> TYPE: PRT
<213> ORGANISM: Artificial
<220> FEATURE:
<223> OTHER INFORMATION: nanobody construct

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Glu Pro
            20                  25                  30

Ser Gly Tyr Thr Tyr Thr Ile Gly Trp Phe Arg Gln Ala Pro Gly Lys
            35                  40                  45

Gly Arg Glu Phe Val Ala Arg Ile Tyr Trp Ser Gly Leu Thr Tyr
 50                  55                  60

Tyr Ala Asp Ser Val Lys Gly Arg Phe Thr Ile Ser Arg Asp Ile Ala
 65                  70                  75                  80

Lys Asn Thr Val Asp Leu Gln Met Asn Ser Leu Arg Pro Glu Asp Thr
                 85                  90                  95

Ala Val Tyr Tyr Cys Ala Ala Arg Asp Gly Ile Pro Thr Ser Arg Ser
                100                 105                 110

Val Gly Ser Tyr Asn Tyr Trp Gly Gln Gly Thr Leu Val Thr Val Ser
            115                 120                 125

Ser

<210> SEQ ID NO 99
<211> LENGTH: 123
<212> TYPE: PRT
<213> ORGANISM: Artificial
<220> FEATURE:
<223> OTHER INFORMATION: nanobody construct

<400> SEQUENCE: 99

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Ser Leu Ser Asn Tyr
                 20                  25                  30

Tyr Met Gly Trp Phe Arg Gln Ala Pro Gly Lys Gly Arg Glu Leu Leu
            35                  40                  45

Gly Asn Ile Ser Trp Arg Gly Tyr Asn Ile Tyr Tyr Lys Asp Ser Val
 50                  55                  60

Lys Gly Arg Phe Thr Ile Ser Arg Asp Asp Ser Lys Asn Thr Ile Tyr
 65                  70                  75                  80

Leu Gln Met Asn Ser Leu Arg Pro Glu Asp Thr Ala Val Tyr Tyr Cys
                 85                  90                  95

Ala Ala Ser Ile Leu Pro Leu Ser Asp Asp Pro Gly Trp Asn Thr Tyr
                100                 105                 110

Trp Gly Gln Gly Thr Leu Val Thr Val Ser Ser
            115                 120

<210> SEQ ID NO 100
<211> LENGTH: 115
<212> TYPE: PRT
<213> ORGANISM: Artificial
<220> FEATURE:
<223> OTHER INFORMATION: nanobody construct

<400> SEQUENCE: 100

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Arg Ser Phe
                 20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

```
Leu Gln Met Asn Ser Leu Lys Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 101
<211> LENGTH: 115
<212> TYPE: PRT
<213> ORGANISM: Artificial
<220> FEATURE:
<223> OTHER INFORMATION: nanobody construct

<400> SEQUENCE: 101

Glu Val Gln Leu Val Glu Ser Gly Gly Gly Leu Val Gln Pro Gly Asn
1               5                  10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 102
<211> LENGTH: 115
<212> TYPE: PRT
<213> ORGANISM: Artificial
<220> FEATURE:
<223> OTHER INFORMATION: nanobody construct

<400> SEQUENCE: 102

Glu Val Gln Leu Val Glu Ser Gly Gly Gly Leu Val Gln Pro Gly Asn
1               5                  10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 103
```

<211> LENGTH: 115
<212> TYPE: PRT
<213> ORGANISM: Artificial
<220> FEATURE:
<223> OTHER INFORMATION: nanobody construct

<400> SEQUENCE: 103

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 104
<211> LENGTH: 115
<212> TYPE: PRT
<213> ORGANISM: Artificial
<220> FEATURE:
<223> OTHER INFORMATION: nanobody construct

<400> SEQUENCE: 104

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Gly Gln Gly Thr Leu Val Thr
            100                 105                 110

Val Ser Ser
        115

<210> SEQ ID NO 105
<211> LENGTH: 130
<212> TYPE: PRT
<213> ORGANISM: Artificial
<220> FEATURE:
<223> OTHER INFORMATION: nanobody

<400> SEQUENCE: 105

Glu Val Gln Leu Val Glu Ser Gly Gly Gly Leu Val Gln Ala Gly Asp
1               5                   10                  15

-continued

Ser Leu Arg Leu Ser Cys Ala Ala Ser Gln Ile Ile Phe Gly Ser His
        20                  25                  30

Val Ala Ala Trp Phe Arg Gln Ala Pro Gly Arg Glu Arg Glu Phe Val
        35                  40                  45

Ala Glu Ile Arg Pro Ser Gly Asp Phe Gly Pro Glu Gly Glu Phe Glu
50                  55                  60

His Val Thr Ala Ser Leu Lys Gly Arg Phe Thr Ile Ala Lys Asn Ser
65                  70                  75                  80

Val Asp Asn Thr Val Tyr Leu Gln Met Asn Ser Leu Lys Pro Glu Asp
                85                  90                  95

Thr Ala Val Tyr Tyr Cys Ala Ala Pro Tyr Arg Gly Gly Arg Asp
            100                 105                 110

Tyr Arg Trp Glu Tyr Glu Tyr Glu Tyr Trp Gly Gln Gly Thr Gln Val
        115                 120                 125

Thr Val
    130

<210> SEQ ID NO 106
<211> LENGTH: 122
<212> TYPE: PRT
<213> ORGANISM: Artificial
<220> FEATURE:
<223> OTHER INFORMATION: nanobody

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Lys Asn Ala Gly Ser Thr Ser Asn Ala Tyr
        20                  25                  30

Ala Thr Gly Trp Phe Arg Arg Ala Pro Gly Lys Glu Arg Glu Phe Val
        35                  40                  45

Ala Gly Ile Gln Trp Ser Gly Gly Asp Ala Phe Tyr Arg Asn Ser Val
50                  55                  60

Lys Gly Arg Phe Arg Ile Thr Arg Asp Pro Asp Asn Thr Val Tyr Leu
65                  70                  75                  80

Gln Met Asn Asp Leu Lys Pro Glu Asp Thr Ala Ile Tyr Tyr Cys Ala
                85                  90                  95

Gln Lys Leu Ser Pro Tyr Tyr Asp Phe Asp Ser Ser Asn Tyr Glu
            100                 105                 110

Tyr Trp Gly Gln Gly Thr Gln Val Thr Val
        115                 120

<210> SEQ ID NO 107
<211> LENGTH: 119
<212> TYPE: PRT
<213> ORGANISM: Artificial
<220> FEATURE:
<223> OTHER INFORMATION: nanobody

<400> SEQUENCE: 107

Glu Val Gln Leu Val Glu Ser Gly Gly Asp Leu Val Gln Pro Gly Gly
1               5                   10                  15

Ser Leu Arg Leu Ser Cys Ala Val Ser Gly Gln Leu Phe Ser Thr Asn
        20                  25                  30

Asp Val Gly Trp Tyr Arg Arg Ala Pro Gly Lys Gln Arg Glu Leu Val
        35                  40                  45

Ala Thr Ile Thr Asp Asp Gly Thr Asp Tyr Gly Asp Asp Val Lys
50                  55                  60

Gly Arg Phe Val Ile Ser Arg Glu Gly Glu Met Val Tyr Leu Glu Met
65                  70                  75                  80

Asn Ser Leu Lys Pro Glu Asp Thr Ala Val Tyr Tyr Cys Asn Ile Asn
                85                  90                  95

Arg Leu Arg Ser Thr Trp Gly Ile Arg Tyr Asp Val Trp Gly Gln Gly
            100                 105                 110

Thr Gln Val Thr Val Ser Ser
            115

<210> SEQ ID NO 108
<211> LENGTH: 115
<212> TYPE: PRT
<213> ORGANISM: Artificial
<220> FEATURE:
<223> OTHER INFORMATION: nanobody

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Ser Thr Thr
            20                  25                  30

Ser Met Thr Trp Val Arg Gln Ala Pro Gly Lys Phe Glu Glu Trp Val
        35                  40                  45

Ser Phe Ile Asn Ser Asp Gly Ser Ser Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Gly Arg Arg Gly Tyr Gly Arg Asp Arg Ser Lys Gly Ile Gln Val Thr
            100                 105                 110

Val Ala Ser
        115

<210> SEQ ID NO 109
<211> LENGTH: 121
<212> TYPE: PRT
<213> ORGANISM: Artificial
<220> FEATURE:
<223> OTHER INFORMATION: nanobody

<400> SEQUENCE: 109

Glu Val Gln Leu Val Glu Ser Gly Gly Gly Thr Val Gln Ala Gly Asp
1               5                   10                  15

Ser Leu Arg Leu Ser Cys Ala Ala Ser Gly Arg Ser Phe Ser Ser Val
            20                  25                  30

Ala Met Gly Trp Phe Arg Gln Ala Pro Gly Lys Gln Arg Glu Phe Leu
        35                  40                  45

Ala Gly Val Gly Tyr Asp Gly Ser Ser Ile Arg Tyr Ala Glu Ser Val
    50                  55                  60

Lys Gly Arg Phe Thr Ile Ala Arg Gly Asn Arg Glu Ser Thr Val Phe
65                  70                  75                  80

Leu Gln Met Glu Asn Leu Lys Pro Glu Asp Thr Ala Val Tyr Phe Cys
                85                  90                  95

Thr Ala Glu Pro Ile Gly Ala Tyr Glu Gly Leu Trp Thr Tyr Trp Gly
            100                 105                 110

Gln Gly Thr Gln Val Thr Val Ser Ser

```
<210> SEQ ID NO 110
<211> LENGTH: 124
<212> TYPE: PRT
<213> ORGANISM: Artificial
<220> FEATURE:
<223> OTHER INFORMATION: nanobody
<220> FEATURE:
<221> NAME/KEY: misc_feature
<222> LOCATION: (1)..(4)
<223> OTHER INFORMATION: unknown amino acid residues, probably EVQL,
      QVQL or a similar sequence

<400> SEQUENCE: 110

Xaa Xaa Xaa Xaa Val Glu Ser Gly Gly Gly Leu Met Gln Pro Gly Gly
1               5                   10                  15

Ser Leu Lys Leu Ser Cys Ala Ala Ser Gly Phe Met Phe Ser Asp Ser
            20                  25                  30

Ala Met Gly Trp Phe Arg Gln Ala Pro Gly Lys Glu Arg Glu Phe Val
        35                  40                  45

Ala Thr Ile Ser Trp Asn Gly Gly Ser Ser Tyr Ala Asp Phe Val
    50                  55                  60

Lys Gly Arg Phe Thr Ile Ser Arg Asp Asn Ala Lys Asn Thr Val Tyr
65                  70                  75                  80

Leu Gln Met Asn Gly Leu Thr Pro Gln Asp Thr Ala Ile Tyr Tyr Cys
                85                  90                  95

Ala Gly Ser Tyr Ser Asn Gly Asn Pro His Arg Phe Ser Gln Tyr Gln
            100                 105                 110

Tyr Trp Gly Gln Gly Thr Gln Val Thr Val Ser Ser
        115                 120

<210> SEQ ID NO 111
<211> LENGTH: 120
<212> TYPE: PRT
<213> ORGANISM: Artificial
<220> FEATURE:
<223> OTHER INFORMATION: nanobody
<220> FEATURE:
<221> NAME/KEY: MISC_FEATURE
<222> LOCATION: (77)..(77)
<223> OTHER INFORMATION: Unknown amino acid residue

<400> SEQUENCE: 111

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Gly Thr Tyr
            20                  25                  30

Ala Met Gly Trp Phe Arg Gln Ala Pro Gly Lys Glu Arg Glu Phe Val
        35                  40                  45

Ala Ala Ile Ser Trp Gly Gly Gly Ser Ile Val Tyr Ala Glu Ser Ala
    50                  55                  60

Lys Gly Arg Phe Thr Ile Ser Arg Asp Asn Ala Lys Xaa Thr Met Tyr
65                  70                  75                  80

Leu Gln Met Asp Ser Leu Lys Pro Glu Asp Thr Ala Val Tyr Tyr Cys
                85                  90                  95

Ala Ala Ala Asn Asn Ile Ala Thr Leu Arg Gln Gly Ser Trp Gly Gln
            100                 105                 110

Gly Thr Gln Val Thr Val Ser Ser
        115                 120
```

```
<210> SEQ ID NO 112
<211> LENGTH: 127
<212> TYPE: PRT
<213> ORGANISM: Artificial
<220> FEATURE:
<223> OTHER INFORMATION: nanobody

<400> SEQUENCE: 112

Glu Val Gln Leu Val Glu Ser Gly Gly Glu Leu Val Gln Ala Gly Gly
1               5                   10                  15

Ser Leu Lys Leu Ser Cys Thr Ala Ser Gly Arg Asn Phe Val Thr Tyr
            20                  25                  30

Ala Met Ser Trp Phe Arg Arg Ala Pro Gly Lys Glu Arg Glu Phe Val
        35                  40                  45

Ala Ser Ile Ser Trp Ser Gly Asp Thr Thr Tyr Tyr Ser Asn Ser Val
    50                  55                  60

Lys Gly Arg Phe Thr Val Ser Arg Asp Asn Gly Lys Asn Thr Ala Tyr
65                  70                  75                  80

Leu Arg Met Asn Ser Leu Lys Pro Glu Asp Thr Ala Asp Tyr Tyr Cys
                85                  90                  95

Ala Val Val Gln Val Ile Asp Pro Ser Trp Ser Gly Val Asn Leu Asp
            100                 105                 110

Asp Tyr Asp Tyr Leu Gly Ser Gly Thr Gln Val Thr Val Ser Ser
        115                 120                 125

<210> SEQ ID NO 113
<211> LENGTH: 124
<212> TYPE: PRT
<213> ORGANISM: Artificial
<220> FEATURE:
<223> OTHER INFORMATION: nanobody

<400> SEQUENCE: 113

Glu Val Gln Leu Val Glu Ser Gly Gly Arg Leu Val Gln Pro Gly Gly
1               5                   10                  15

Ser Leu Arg Leu Ser Cys Lys Asn Ala Gly Ser Thr Ser Asn Ala Tyr
            20                  25                  30

Ala Thr Gly Trp Phe Arg Arg Ala Pro Gly Lys Glu Arg Glu Phe Val
        35                  40                  45

Ala Gly Ile Gln Trp Ser Gly Gly Asp Ala Phe Tyr Arg Asn Ser Val
    50                  55                  60

Lys Gly Arg Phe Arg Ile Thr Arg Asp Pro Asp Asn Thr Val Tyr Leu
65                  70                  75                  80

Gln Met Asn Asp Leu Lys Pro Glu Asp Thr Ala Ile Tyr Tyr Cys Ala
                85                  90                  95

Gln Lys Leu Ser Pro Tyr Tyr Asn Asp Phe Asp Ser Ser Asn Tyr Glu
            100                 105                 110

Tyr Trp Gly Gln Gly Thr Gln Val Thr Val Ser Ser
        115                 120

<210> SEQ ID NO 114
<211> LENGTH: 115
<212> TYPE: PRT
<213> ORGANISM: Artificial
<220> FEATURE:
<223> OTHER INFORMATION: nanobody

<400> SEQUENCE: 114

Glu Val Gln Leu Val Glu Ser Gly Gly Gly Leu Val Gln Pro Gly Gly
```

```
              1               5                  10                 15
Ser Leu Arg Leu Ser Cys Ala Ala Ser Ala Thr Ile Ser Ser Ile Val
                20                  25                 30

Met Leu Gly Trp Tyr Arg Gln Ala Pro Gly Lys Gln Arg Glu Trp Val
                35                  40                 45

Ala Ser Ile Thr Ile Gly Ser Arg Thr Asn Tyr Ala Asp Ser Val Lys
                50                  55                 60

Gly Arg Phe Thr Ile Ser Arg Asp Asn Ala Lys Asn Thr Val Tyr Leu
 65              70                  75                 80

Gln Met Asn Ser Leu Lys Pro Glu Asp Thr Ala Val Tyr Phe Cys Asn
                85                  90                 95

Ala Val Pro Pro Arg Asp Asp Tyr Trp Gly Gln Gly Thr Gln Val Thr
               100                 105                110

Val Ser Ser
       115
```

<210> SEQ ID NO 115
<211> LENGTH: 121
<212> TYPE: PRT
<213> ORGANISM: Artificial
<220> FEATURE:
<223> OTHER INFORMATION: nanobody

<400> SEQUENCE: 115

```
Glu Val Gln Leu Val Glu Ser Gly Gly Gly Leu Val Gln Ala Gly Gly
 1               5                  10                 15

Ser Leu Arg Leu Ser Cys Ala Ala Ser Gly Gln Thr Ser Ser Ser Tyr
                20                  25                 30

Asp Met Gly Trp Phe Arg Gln Ala Pro Gly Glu Gly Arg Glu Phe Val
                35                  40                 45

Ala Arg Ile Ser Gly Ser Asp Gly Ser Thr Tyr Tyr Ser Asp Arg Ala
                50                  55                 60

Lys Asp Arg Phe Thr Ile Ser Arg Asp Asn Thr Lys Asn Met Val Tyr
 65              70                  75                 80

Leu Gln Met Asp Arg Leu Lys Pro Asp Thr Ala Val Tyr Tyr Cys
                85                  90                 95

Arg Val Pro Arg Tyr Glu Asn Gln Trp Ser Tyr Asp Tyr Trp Gly
               100                 105                110

Gln Gly Thr Gln Val Thr Val Ser Ser
       115                 120
```

<210> SEQ ID NO 116
<211> LENGTH: 127
<212> TYPE: PRT
<213> ORGANISM: Artificial
<220> FEATURE:
<223> OTHER INFORMATION: nanobody

<400> SEQUENCE: 116

```
Glu Val Gln Leu Val Glu Ser Gly Gly Gly Leu Val Gln Pro Gly Gly
 1               5                  10                 15

Ser Leu Arg Leu Ser Cys Ala Ala Ser Gly Ser Thr Phe Ser Thr Tyr
                20                  25                 30

Asp Met Ser Trp Val Arg Gln Ala Pro Gly Lys Gly Leu Glu Trp Val
                35                  40                 45

Ser Gly Ile Asp Ser Gly Gly Gly Ser Pro Met Tyr Val Asp Ser Val
                50                  55                 60
```

```
Lys Gly Arg Phe Thr Val Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Lys Phe Ser Thr Gly Ala Asp Gly Gly Ser Trp Tyr Trp Ser Tyr
            100                 105                 110

Gly Met Asp Ser Trp Gly Lys Gly Thr Gln Val Thr Val Ser Ser
            115                 120                 125
```

<210> SEQ ID NO 117
<211> LENGTH: 121
<212> TYPE: PRT
<213> ORGANISM: Artificial
<220> FEATURE:
<223> OTHER INFORMATION: nanobody

<400> SEQUENCE: 117

```
Glu Val Gln Leu Val Glu Ser Gly Gly Gly Leu Val Gln Ala Gly Asp
 1               5                  10                  15

Ser Leu Arg Leu Ser Cys Glu Ala Ser Glu Arg Ser Ser Asn Arg Tyr
                 20                  25                  30

Asn Met Ala Trp Phe Arg Gln Ala Pro Gly Lys Glu Arg Glu Phe Leu
             35                  40                  45

Ala Arg Val Asp Val Ser Gly Gly Asn Thr Leu Tyr Gly Asp Ser Val
         50                  55                  60

Lys Asp Arg Phe Thr Val Ser Arg Ile Asn Gly Lys Asn Ala Met Tyr
 65                  70                  75                  80

Leu Gln Met Asn Asn Leu Lys Pro Glu Asp Thr Ala Ile Tyr Tyr Cys
                 85                  90                  95

Ala Ala Gly Gly Trp Gly Thr Thr Gln Tyr Asp Tyr Asp Tyr Trp Gly
            100                 105                 110

Gln Gly Thr Gln Val Thr Val Ser Ser
            115                 120
```

<210> SEQ ID NO 118
<211> LENGTH: 117
<212> TYPE: PRT
<213> ORGANISM: Artificial
<220> FEATURE:
<223> OTHER INFORMATION: nanobody

<400> SEQUENCE: 118

```
Glu Val Gln Leu Val Glu Ser Gly Gly Gly Leu Val Gln Pro Gly Gly
 1               5                  10                  15

Ser Leu Arg Leu Ser Cys Val Cys Val Ser Ser Gly Cys Thr Phe Ser
                 20                  25                  30

Ala Tyr Ser Met Thr Trp Val Arg Gln Ala Pro Gly Lys Ala Glu Glu
             35                  40                  45

Trp Val Ser Phe Ile Asn Ser Asp Gly Ser Ser Thr Thr Tyr Ala Asp
         50                  55                  60

Ser Val Asn Gly Arg Phe Lys Ile Ser Arg Asp Asn Ala Lys Lys Thr
 65                  70                  75                  80

Leu Tyr Leu Gln Met Asn Ser Leu Gly Pro Glu Asp Thr Ala Met Tyr
                 85                  90                  95

Tyr Cys Gln Arg Arg Gly Tyr Ala Leu Asp Arg Gly Gln Gly Thr Gln
            100                 105                 110

Val Thr Val Ser Ser
            115
```

<210> SEQ ID NO 119
<211> LENGTH: 129
<212> TYPE: PRT
<213> ORGANISM: Artificial
<220> FEATURE:
<223> OTHER INFORMATION: nanobody

<400> SEQUENCE: 119

Glu Val Gln Leu Val Glu Ser Gly Gly Gly Leu Val Gln Ala Gly Asp
1               5                   10                  15

Ser Leu Thr Leu Ser Cys Ala Ser Ser Gly Arg Gly Phe Tyr Lys Asn
            20                  25                  30

Ala Met Gly Trp Phe Arg Gln Pro Pro Gly Lys Glu Arg Glu Phe Val
        35                  40                  45

Ala Ser Ile Lys Trp Asn Gly Asn Asn Thr Tyr Tyr Ala Asp Ser Val
    50                  55                  60

Arg Gly Arg Phe Thr Ile Ser Arg Gly Asn Ala Lys Asn Thr Glu Asn
65                  70                  75                  80

Thr Val Ser Leu Gln Met Asn Ser Leu Lys Pro Glu Asp Thr Ala Asp
                85                  90                  95

Tyr Tyr Cys Ala Ala Asp Ser Ser His Tyr Ser Tyr Val Tyr Ser Lys
            100                 105                 110

Ala Tyr Glu Tyr Asp Tyr Trp Gly Gln Gly Thr Gln Val Thr Val Ser
        115                 120                 125

Ser

<210> SEQ ID NO 120
<211> LENGTH: 115
<212> TYPE: PRT
<213> ORGANISM: Artificial
<220> FEATURE:
<223> OTHER INFORMATION: nanobody

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Val Phe Ser Gly Phe Ala Phe Ser Ala Ser
            20                  25                  30

Ser Met Ala Trp Val Arg Gln Ala Pro Gly Lys Tyr Glu Glu Trp Val
        35                  40                  45

Ser Phe Ile Asn Ser Asp Gly Ser Ser Thr Thr Tyr Ala Asp Ser Val
    50                  55                  60

Gln Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Met Tyr Tyr Cys
                85                  90                  95

Gly Arg Arg Gly Tyr Gly Arg Asp Arg Ser Gln Gly Ile Gln Val Thr
            100                 105                 110

Val Ser Ser
        115

<210> SEQ ID NO 121
<211> LENGTH: 127
<212> TYPE: PRT
<213> ORGANISM: Artificial
<220> FEATURE:
<223> OTHER INFORMATION: nanobody
<220> FEATURE:

<221> NAME/KEY: MISC_FEATURE
<222> LOCATION: (119)..(119)
<223> OTHER INFORMATION: Unknown amino acid residue

<400> SEQUENCE: 121

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Thr Ile Thr Asn Tyr Ala Asp Ser Val
50                  55                  60

Lys Gly Arg Phe Thr Ile Ser Arg Asp Asn Gly Lys Asn Thr Val His
65                  70                  75                  80

Leu Gln Met Asn Ser Leu Lys Pro Glu Asp Thr Ala Val Tyr His Cys
                85                  90                  95

Ala Val Val Gln Pro Tyr Ser Gly Gly Asp Tyr Tyr Thr Gly Val Glu
            100                 105                 110

Glu Tyr Asp Tyr Trp Gly Xaa Gly Thr Gln Val Thr Val Ser Ser
        115                 120                 125

<210> SEQ ID NO 122
<211> LENGTH: 115
<212> TYPE: PRT
<213> ORGANISM: Artificial
<220> FEATURE:
<223> OTHER INFORMATION: nanobody

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Ser Ala Thr
            20                  25                  30

Ser Met Thr Trp Val Arg Gln Ala Pro Gly Lys Ala Glu Glu Trp Val
        35                  40                  45

Ser Phe Ile Asn Ser Asp Gly Ser Ser Thr Thr Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asp Asp Leu Gln Ser Glu Asp Thr Ala Met Tyr Tyr Cys
                85                  90                  95

Gly Arg Arg Gly Tyr Gly Arg Asp Arg Ser Arg Gly Ile Gln Val Thr
            100                 105                 110

Val Ser Ser
        115

<210> SEQ ID NO 123
<211> LENGTH: 121
<212> TYPE: PRT
<213> ORGANISM: Artificial
<220> FEATURE:
<223> OTHER INFORMATION: nanobody

<400> SEQUENCE: 123

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Ala Phe Ser Asn Tyr
            20                  25                  30

```
Asp Val Gly Trp Phe Arg Gln Ala Pro Gly Glu Gly Arg Glu Ile Val
            35                  40                  45

Ala Arg Ile Ser Gly Ser Gly Asp Ser Thr Tyr Ser Ser Asn Arg Ala
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Arg Glu Asp Thr Ala Val Tyr Tyr Cys
                85                  90                  95

Arg Ala Ala Arg Tyr Asn Gly Thr Trp Ser Ser Asn Asp Tyr Trp Gly
            100                 105                 110

Gln Gly Thr Gln Val Thr Val Ser Ser
            115                 120

<210> SEQ ID NO 124
<211> LENGTH: 117
<212> TYPE: PRT
<213> ORGANISM: Artificial
<220> FEATURE:
<223> OTHER INFORMATION: nanobody

<400> SEQUENCE: 124

Glu Val Gln Leu Val Glu Ser Gly Gly Gly Leu Val Gln Pro Gly Gly
 1               5                  10                  15

Ser Leu Arg Leu Ser Cys Glu Cys Val Ser Ser Gly Cys Thr Phe Ser
            20                  25                  30

Ala Tyr Ser Met Thr Trp Val Arg Gln Ala Pro Gly Lys Ala Glu Glu
            35                  40                  45

Phe Val Ser Phe Ile Asn Ser Asp Gly Ser Ser Thr Thr Tyr Ala Asn
 50                  55                  60

Ser Val Asn Gly Arg Phe Lys Ile Ser Arg Asp Asn Ala Lys Lys Thr
 65                  70                  75                  80

Leu Tyr Leu Gln Met Asn Ser Leu Gly Pro Glu Asp Thr Ala Met Tyr
                85                  90                  95

Tyr Cys Gln Arg Arg Gly Tyr Ala Leu Asp Arg Gly Gln Gly Thr Gln
            100                 105                 110

Val Thr Val Ser Ser
            115

<210> SEQ ID NO 125
<211> LENGTH: 121
<212> TYPE: PRT
<213> ORGANISM: Artificial
<220> FEATURE:
<223> OTHER INFORMATION: nanobody

<400> SEQUENCE: 125

Gln Val Gln Leu Val Glu Ser Gly Gly Gly Leu Val Gln Ala Gly Gly
 1               5                  10                  15

Ser Leu Arg Leu Ser Cys Thr Ala Ser Gly Gln Thr Ser Ser Thr Ala
            20                  25                  30

Asp Met Gly Trp Phe Arg Gln Pro Gly Lys Gly Arg Glu Phe Val
            35                  40                  45

Ala Arg Ile Ser Gly Ile Asp Gly Thr Thr Tyr Tyr Asp Glu Pro Val
 50                  55                  60

Lys Gly Arg Phe Thr Ile Ser Arg Asp Lys Ala Gln Asn Thr Val Tyr
 65                  70                  75                  80

Leu Gln Met Asp Ser Leu Lys Pro Glu Asp Thr Ala Val Tyr Tyr Cys
```

85                  90                  95

Arg Ser Pro Arg Tyr Ala Asp Gln Trp Ser Ala Tyr Asp Tyr Trp Gly
            100                 105                 110

Gln Gly Thr Gln Val Thr Val Ser Ser
            115                 120

<210> SEQ ID NO 126
<211> LENGTH: 115
<212> TYPE: PRT
<213> ORGANISM: Artificial
<220> FEATURE:
<223> OTHER INFORMATION: nanobody

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Ser Thr Thr
            20                  25                  30

Ser Met Thr Trp Val Arg Gln Ala Pro Gly Lys Phe Glu Glu Trp Val
            35                  40                  45

Ser Phe Ile Asn Ser Asp Gly Ser Ser Thr Thr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Met Tyr Tyr Cys
            85                  90                  95

Gly Arg Arg Gly Tyr Gly Arg Asp Arg Ser Lys Gly Ile Gln Val Thr
            100                 105                 110

Val Ser Ser
        115

<210> SEQ ID NO 127
<211> LENGTH: 118
<212> TYPE: PRT
<213> ORGANISM: Artificial
<220> FEATURE:
<223> OTHER INFORMATION: nanobody

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Val Ala Ser Ala Ser Gly Val Lys Val Asn
            20                  25                  30

Asp Met Gly Trp Tyr Arg Gln Ala Pro Gly Lys Glu Arg Glu Leu Val
            35                  40                  45

Ala Thr Ile Thr Asp Asp Gly Arg Thr Asn Tyr Glu Asp Phe Ala Lys
        50                  55                  60

Gly Arg Phe Thr Ile Ser Arg Asp Asn Ala Lys Asn Thr Val Tyr Leu
65                  70                  75                  80

Gln Met Asn Ser Leu Leu Pro Glu Asp Thr Ala Val Tyr Tyr Cys Asn
            85                  90                  95

Ala Arg Thr Tyr Trp Ala His Leu Pro Thr Tyr Trp Gly Gln Gly Thr
            100                 105                 110

Gln Val Thr Val Ser Ser
        115

<210> SEQ ID NO 128
<211> LENGTH: 121

```
<212> TYPE: PRT
<213> ORGANISM: Artificial
<220> FEATURE:
<223> OTHER INFORMATION: nanobody

<400> SEQUENCE: 128

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Gly Ser Val
            20                  25                  30

Ala Met Gly Trp Phe Arg Gln Ala Pro Gly Lys Glu Arg Glu Phe Val
        35                  40                  45

Ala Ala Ile Gly Tyr Asp Gly Asn Ser Ile Arg Tyr Gly Asp Ser Val
    50                  55                  60

Lys Gly Arg Phe Thr Ile Ser Arg Asp Asn Ile Lys Asn Thr Met Tyr
65                  70                  75                  80

Leu Glu Met Glu Asn Leu Asn Ala Asp Thr Ala Arg Tyr Leu Cys
                85                  90                  95

Ala Ala Glu Pro Leu Ala Arg Tyr Glu Gly Leu Trp Thr Tyr Trp Gly
            100                 105                 110

Gln Gly Thr Gln Val Thr Val Ser Ser
        115                 120

<210> SEQ ID NO 129
<211> LENGTH: 121
<212> TYPE: PRT
<213> ORGANISM: Artificial
<220> FEATURE:
<223> OTHER INFORMATION: nanobody

<400> SEQUENCE: 129

Glu Val Gln Leu Val Glu Ser Gly Gly Gly Leu Val Gln Ala Gly Ala
1               5                   10                  15

Ser Leu Arg Leu Ser Cys Thr Thr Ser Thr Arg Thr Asn Asp Arg Phe
            20                  25                  30

Asn Met Ala Trp Phe His Gln Ala Pro Gly Lys Asp Arg Glu Phe Val
        35                  40                  45

Ser Arg Ile Asp Val Ala Gly Tyr Asn Thr Ala Tyr Gly Asp Phe Val
    50                  55                  60

Lys Gly Arg Phe Thr Val Ser Arg Asp Ser Ala Glu Asn Thr Val Val
65                  70                  75                  80

Leu Gln Met Asn Ser Leu Arg Pro Glu Asp Thr Gly Val Tyr Tyr Cys
                85                  90                  95

Ala Ala Gly Gly Trp Gly Ile Ser Gln Ser Asp Tyr Asp Leu Trp Gly
            100                 105                 110

Gln Gly Thr Gln Val Thr Val Ser Ser
        115                 120

<210> SEQ ID NO 130
<211> LENGTH: 30
<212> TYPE: PRT
<213> ORGANISM: Artificial
<220> FEATURE:
<223> OTHER INFORMATION: FR1 element

<400> SEQUENCE: 130

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
```

```
            20                  25                  30

<210> SEQ ID NO 131
<211> LENGTH: 30
<212> TYPE: PRT
<213> ORGANISM: Artificial
<220> FEATURE:
<223> OTHER INFORMATION: FR1 element

<400> SEQUENCE: 131

Gln Val Gln Leu Gln Glu Ser Gly Gly Gly Met Val Gln Pro Gly Gly
1               5                   10                  15

Ser Leu Arg Leu Ser Cys Ala Ala Ser Gly Phe Asp Phe Gly
            20                  25                  30

<210> SEQ ID NO 132
<211> LENGTH: 30
<212> TYPE: PRT
<213> ORGANISM: Artificial
<220> FEATURE:
<223> OTHER INFORMATION: FR1 element

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Asp Phe Ser
            20                  25                  30

<210> SEQ ID NO 133
<211> LENGTH: 30
<212> TYPE: PRT
<213> ORGANISM: Artificial
<220> FEATURE:
<223> OTHER INFORMATION: FR1 element

<400> SEQUENCE: 133

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 134
<211> LENGTH: 30
<212> TYPE: PRT
<213> ORGANISM: Artificial
<220> FEATURE:
<223> OTHER INFORMATION: FR1 element

<400> SEQUENCE: 134

Gln Val Lys Leu Glu Glu Ser Gly Gly Gly Leu Val Gln Pro Gly Asp
1               5                   10                  15

Ser Leu Arg Leu Ser Cys Ala Ala Ser Gly Arg Thr Phe Ser
            20                  25                  30

<210> SEQ ID NO 135
<211> LENGTH: 30
<212> TYPE: PRT
<213> ORGANISM: Artificial
<220> FEATURE:
<223> OTHER INFORMATION: FR1 element

<400> SEQUENCE: 135

Ala Val Gln Leu Val Glu Ser Gly Gly Gly Leu Val Gln Pro Gly Asp
1               5                   10                  15
```

```
Ser Leu Arg Leu Ser Cys Ala Ala Ser Gly Arg Thr Phe Ser
            20                  25                  30
```

<210> SEQ ID NO 136
<211> LENGTH: 30
<212> TYPE: PRT
<213> ORGANISM: Artificial
<220> FEATURE:
<223> OTHER INFORMATION: FR1 element

<400> SEQUENCE: 136

```
Ala Val Gln Leu Val Asp Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30
```

<210> SEQ ID NO 137
<211> LENGTH: 30
<212> TYPE: PRT
<213> ORGANISM: Artificial
<220> FEATURE:
<223> OTHER INFORMATION: FR1 element

<400> SEQUENCE: 137

```
Gln Val Gln Leu Val Glu Ser Gly Gly Gly Leu Val Gln Ala Gly Gly
1               5                   10                  15

Ser Leu Ser Leu Ser Cys Ala Ala Ser Gly Arg Ser Phe Thr
            20                  25                  30
```

<210> SEQ ID NO 138
<211> LENGTH: 30
<212> TYPE: PRT
<213> ORGANISM: Artificial
<220> FEATURE:
<223> OTHER INFORMATION: FR1 element

<400> SEQUENCE: 138

```
Glu Val Gln Leu Val Glu Ser Gly Gly Gly Leu Val Gln Ala Gly Gly
1               5                   10                  15

Ser Leu Ser Leu Ser Cys Ser Ala Ser Gly Arg Ser Leu Ser
            20                  25                  30
```

<210> SEQ ID NO 139
<211> LENGTH: 30
<212> TYPE: PRT
<213> ORGANISM: Artificial
<220> FEATURE:
<223> OTHER INFORMATION: FR1 element

<400> SEQUENCE: 139

```
Glu Val Gln Leu Val Glu Ser Gly Gly Gly Leu Val Gln Ala Gly Asp
1               5                   10                  15

Ser Leu Arg Leu Ser Cys Ala Ala Ser Gln Ile Ile Phe Gly
            20                  25                  30
```

<210> SEQ ID NO 140
<211> LENGTH: 30
<212> TYPE: PRT
<213> ORGANISM: Artificial
<220> FEATURE:
<223> OTHER INFORMATION: FR1 element

<400> SEQUENCE: 140

```
Glu Val Gln Leu Val Glu Ser Gly Gly Gly Leu Val Gln Pro Gly Gly
1               5                   10                  15
```

Ser Leu Arg Leu Ser Cys Lys Asn Ala Gly Ser Thr Ser Asn
            20                  25                  30

<210> SEQ ID NO 141
<211> LENGTH: 30
<212> TYPE: PRT
<213> ORGANISM: Artificial
<220> FEATURE:
<223> OTHER INFORMATION: FR1 element

<400> SEQUENCE: 141

Glu Val Gln Leu Val Glu Ser Gly Gly Asp Leu Val Gln Pro Gly Gly
1               5                   10                  15

Ser Leu Arg Leu Ser Cys Ala Val Ser Gly Gln Leu Phe Ser
            20                  25                  30

<210> SEQ ID NO 142
<211> LENGTH: 30
<212> TYPE: PRT
<213> ORGANISM: Artificial
<220> FEATURE:
<223> OTHER INFORMATION: FR1 element

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Ser
            20                  25                  30

<210> SEQ ID NO 143
<211> LENGTH: 30
<212> TYPE: PRT
<213> ORGANISM: Artificial
<220> FEATURE:
<223> OTHER INFORMATION: FR1 element

<400> SEQUENCE: 143

Glu Val Gln Leu Val Glu Ser Gly Gly Gly Thr Val Gln Ala Gly Asp
1               5                   10                  15

Ser Leu Arg Leu Ser Cys Ala Ala Ser Gly Arg Ser Phe Ser
            20                  25                  30

<210> SEQ ID NO 144
<211> LENGTH: 30
<212> TYPE: PRT
<213> ORGANISM: Artificial
<220> FEATURE:
<223> OTHER INFORMATION: FR1 element
<220> FEATURE:
<221> NAME/KEY: MISC_FEATURE
<222> LOCATION: (1)..(4)
<223> OTHER INFORMATION: Unknown amino acid residues, probably EVQL,
      QVQL or a similar sequence

<400> SEQUENCE: 144

Xaa Xaa Xaa Xaa Val Glu Ser Gly Gly Gly Leu Met Gln Pro Gly Gly
1               5                   10                  15

Ser Leu Lys Leu Ser Cys Ala Ala Ser Gly Phe Met Phe Ser
            20                  25                  30

<210> SEQ ID NO 145
<211> LENGTH: 30
<212> TYPE: PRT
<213> ORGANISM: Artificial
<220> FEATURE:

<223> OTHER INFORMATION: FR1 element

<400> SEQUENCE: 145

Glu Val Gln Leu Val Glu Ser Gly Gly Gly Leu Val Gln Ala Gly Gly
1               5                   10                  15
Ser Leu Arg Leu Ser Cys Ala Ala Ser Gly Arg Thr Phe Gly
            20                  25                  30

<210> SEQ ID NO 146
<211> LENGTH: 30
<212> TYPE: PRT
<213> ORGANISM: Artificial
<220> FEATURE:
<223> OTHER INFORMATION: FR1 element

<400> SEQUENCE: 146

Glu Val Gln Leu Val Glu Ser Gly Gly Glu Leu Val Gln Ala Gly Gly
1               5                   10                  15
Ser Leu Lys Leu Ser Cys Thr Ala Ser Gly Arg Asn Phe Val
            20                  25                  30

<210> SEQ ID NO 147
<211> LENGTH: 30
<212> TYPE: PRT
<213> ORGANISM: Artificial
<220> FEATURE:
<223> OTHER INFORMATION: FR1 element

<400> SEQUENCE: 147

Glu Val Gln Leu Val Glu Ser Gly Gly Arg Leu Val Gln Pro Gly Gly
1               5                   10                  15
Ser Leu Arg Leu Ser Cys Lys Asn Ala Gly Ser Thr Ser Asn
            20                  25                  30

<210> SEQ ID NO 148
<211> LENGTH: 30
<212> TYPE: PRT
<213> ORGANISM: Artificial
<220> FEATURE:
<223> OTHER INFORMATION: FR1 element

<400> SEQUENCE: 148

Glu Val Gln Leu Val Glu Ser Gly Gly Gly Leu Val Gln Pro Gly Gly
1               5                   10                  15
Ser Leu Arg Leu Ser Cys Ala Ala Ser Ala Thr Ile Ser Ser
            20                  25                  30

<210> SEQ ID NO 149
<211> LENGTH: 30
<212> TYPE: PRT
<213> ORGANISM: Artificial
<220> FEATURE:
<223> OTHER INFORMATION: FR1 element

<400> SEQUENCE: 149

Glu Val Gln Leu Val Glu Ser Gly Gly Gly Leu Val Gln Ala Gly Gly
1               5                   10                  15
Ser Leu Arg Leu Ser Cys Ala Ala Ser Gly Gln Thr Ser Ser
            20                  25                  30

<210> SEQ ID NO 150
<211> LENGTH: 30
<212> TYPE: PRT
<213> ORGANISM: Artificial

-continued

```
<220> FEATURE:
<223> OTHER INFORMATION: FR1 element

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Ser
            20                  25                  30

<210> SEQ ID NO 151
<211> LENGTH: 30
<212> TYPE: PRT
<213> ORGANISM: Artificial
<220> FEATURE:
<223> OTHER INFORMATION: FR1 element

<400> SEQUENCE: 151

Glu Val Gln Leu Val Glu Ser Gly Gly Gly Leu Val Gln Ala Gly Asp
1               5                   10                  15

Ser Leu Arg Leu Ser Cys Glu Ala Ser Glu Arg Ser Ser Asn
            20                  25                  30

<210> SEQ ID NO 152
<211> LENGTH: 30
<212> TYPE: PRT
<213> ORGANISM: Artificial
<220> FEATURE:
<223> OTHER INFORMATION: FR1 element

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr
            20                  25                  30

<210> SEQ ID NO 153
<211> LENGTH: 30
<212> TYPE: PRT
<213> ORGANISM: Artificial
<220> FEATURE:
<223> OTHER INFORMATION: FR1 element

<400> SEQUENCE: 153

Glu Val Gln Leu Val Glu Ser Gly Gly Gly Leu Val Gln Ala Gly Asp
1               5                   10                  15

Ser Leu Thr Leu Ser Cys Ala Ser Ser Gly Arg Gly Phe Tyr
            20                  25                  30

<210> SEQ ID NO 154
<211> LENGTH: 30
<212> TYPE: PRT
<213> ORGANISM: Artificial
<220> FEATURE:
<223> OTHER INFORMATION: FR1 element

<400> SEQUENCE: 154

Glu Val Gln Leu Val Glu Ser Gly Gly Gly Leu Val Gln Pro Gly Gly
1               5                   10                  15

Ser Leu Arg Leu Ser Cys Val Phe Ser Gly Phe Ala Phe Ser
            20                  25                  30

<210> SEQ ID NO 155
<211> LENGTH: 30
<212> TYPE: PRT
```

```
<213> ORGANISM: Artificial
<220> FEATURE:
<223> OTHER INFORMATION: FR1 element

<400> SEQUENCE: 155

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 156
<211> LENGTH: 30
<212> TYPE: PRT
<213> ORGANISM: Artificial
<220> FEATURE:
<223> OTHER INFORMATION: FR1 element

<400> SEQUENCE: 156

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Ser
            20                  25                  30

<210> SEQ ID NO 157
<211> LENGTH: 30
<212> TYPE: PRT
<213> ORGANISM: Artificial
<220> FEATURE:
<223> OTHER INFORMATION: FR1 element

<400> SEQUENCE: 157

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Ala Phe Ser
            20                  25                  30

<210> SEQ ID NO 158
<211> LENGTH: 30
<212> TYPE: PRT
<213> ORGANISM: Artificial
<220> FEATURE:
<223> OTHER INFORMATION: FR1 element

<400> SEQUENCE: 158

Glu Val Gln Leu Val Glu Ser Gly Gly Gly Leu Val Gln Pro Gly Gly
1               5                   10                  15

Ser Leu Arg Leu Ser Cys Glu Cys Val Ser Ser Gly Cys Thr
            20                  25                  30

<210> SEQ ID NO 159
<211> LENGTH: 30
<212> TYPE: PRT
<213> ORGANISM: Artificial
<220> FEATURE:
<223> OTHER INFORMATION: FR1 element

<400> SEQUENCE: 159

Gln Val Gln Leu Val Glu Ser Gly Gly Gly Leu Val Gln Ala Gly Gly
1               5                   10                  15

Ser Leu Arg Leu Ser Cys Thr Ala Ser Gly Gln Thr Ser Ser
            20                  25                  30

<210> SEQ ID NO 160
<211> LENGTH: 30
```

```
<212> TYPE: PRT
<213> ORGANISM: Artificial
<220> FEATURE:
<223> OTHER INFORMATION: FR1 element

<400> SEQUENCE: 160

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Ser
            20                  25                  30

<210> SEQ ID NO 161
<211> LENGTH: 30
<212> TYPE: PRT
<213> ORGANISM: Artificial
<220> FEATURE:
<223> OTHER INFORMATION: FR1 element

<400> SEQUENCE: 161

Glu Val Gln Leu Val Glu Ser Gly Gly Gly Leu Val Gln Pro Gly Gly
1               5                   10                  15

Ser Leu Arg Leu Ser Cys Val Ala Ser Ala Ser Gly Val Lys
            20                  25                  30

<210> SEQ ID NO 162
<211> LENGTH: 30
<212> TYPE: PRT
<213> ORGANISM: Artificial
<220> FEATURE:
<223> OTHER INFORMATION: FR1 element

<400> SEQUENCE: 162

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Gly
            20                  25                  30

<210> SEQ ID NO 163
<211> LENGTH: 29
<212> TYPE: PRT
<213> ORGANISM: Artificial
<220> FEATURE:
<223> OTHER INFORMATION: FR1 element

<400> SEQUENCE: 163

Glu Val Gln Leu Val Glu Ser Gly Gly Gly Leu Val Gln Ala Gly Ala
1               5                   10                  15

Ser Leu Arg Leu Ser Cys Thr Thr Ser Thr Arg Thr Asn
            20                  25

<210> SEQ ID NO 164
<211> LENGTH: 5
<212> TYPE: PRT
<213> ORGANISM: Artificial
<220> FEATURE:
<223> OTHER INFORMATION: CDR1 element

<400> SEQUENCE: 164

Asp Tyr Trp Met Tyr
1               5

<210> SEQ ID NO 165
<211> LENGTH: 5
<212> TYPE: PRT
<213> ORGANISM: Artificial
```

```
<220> FEATURE:
<223> OTHER INFORMATION: CDR1 element

<400> SEQUENCE: 165

Val Ser Trp Met Tyr
1               5

<210> SEQ ID NO 166
<211> LENGTH: 5
<212> TYPE: PRT
<213> ORGANISM: Artificial
<220> FEATURE:
<223> OTHER INFORMATION: CDR1 element

<400> SEQUENCE: 166

Val Ser Trp Met Tyr
1               5

<210> SEQ ID NO 167
<211> LENGTH: 10
<212> TYPE: PRT
<213> ORGANISM: Artificial
<220> FEATURE:
<223> OTHER INFORMATION: CDR1 element

<400> SEQUENCE: 167

Glu Pro Ser Gly Tyr Thr Tyr Thr Ile Gly
1               5                   10

<210> SEQ ID NO 168
<211> LENGTH: 10
<212> TYPE: PRT
<213> ORGANISM: Artificial
<220> FEATURE:
<223> OTHER INFORMATION: CDR1 element

<400> SEQUENCE: 168

Asp Tyr Ser Gly Tyr Thr Tyr Thr Val Gly
1               5                   10

<210> SEQ ID NO 169
<211> LENGTH: 10
<212> TYPE: PRT
<213> ORGANISM: Artificial
<220> FEATURE:
<223> OTHER INFORMATION: CDR1 element

<400> SEQUENCE: 169

Asp Tyr Ser Gly Tyr Thr Tyr Thr Val Gly
1               5                   10

<210> SEQ ID NO 170
<211> LENGTH: 8
<212> TYPE: PRT
<213> ORGANISM: Artificial
<220> FEATURE:
<223> OTHER INFORMATION: CDR1 element

<400> SEQUENCE: 170

Ala His Ser Val Tyr Thr Met Gly
1               5

<210> SEQ ID NO 171
<211> LENGTH: 5
<212> TYPE: PRT
<213> ORGANISM: Artificial
<220> FEATURE:
```

<223> OTHER INFORMATION: CDR1 element

<400> SEQUENCE: 171

Gly Tyr Tyr Met Gly
1               5

<210> SEQ ID NO 172
<211> LENGTH: 5
<212> TYPE: PRT
<213> ORGANISM: Artificial
<220> FEATURE:
<223> OTHER INFORMATION: CDR1 element

<400> SEQUENCE: 172

Asn Tyr Tyr Met Gly
1               5

<210> SEQ ID NO 173
<211> LENGTH: 5
<212> TYPE: PRT
<213> ORGANISM: Artificial
<220> FEATURE:
<223> OTHER INFORMATION: CDR1 element

<400> SEQUENCE: 173

Ser His Val Ala Ala
1               5

<210> SEQ ID NO 174
<211> LENGTH: 5
<212> TYPE: PRT
<213> ORGANISM: Artificial
<220> FEATURE:
<223> OTHER INFORMATION: CDR1 element

<400> SEQUENCE: 174

Ala Tyr Ala Thr Gly
1               5

<210> SEQ ID NO 175
<211> LENGTH: 5
<212> TYPE: PRT
<213> ORGANISM: Artificial
<220> FEATURE:
<223> OTHER INFORMATION: CDR1 element

<400> SEQUENCE: 175

Thr Asn Asp Val Gly
1               5

<210> SEQ ID NO 176
<211> LENGTH: 5
<212> TYPE: PRT
<213> ORGANISM: Artificial
<220> FEATURE:
<223> OTHER INFORMATION: CDR1 element

<400> SEQUENCE: 176

Thr Thr Ser Met Thr
1               5

<210> SEQ ID NO 177
<211> LENGTH: 5
<212> TYPE: PRT
<213> ORGANISM: Artificial
<220> FEATURE:
<223> OTHER INFORMATION: CDR1 element

```
<400> SEQUENCE: 177

Ser Val Ala Met Gly
1               5

<210> SEQ ID NO 178
<211> LENGTH: 5
<212> TYPE: PRT
<213> ORGANISM: Artificial
<220> FEATURE:
<223> OTHER INFORMATION: CDR1 element

<400> SEQUENCE: 178

Asp Ser Ala Met Gly
1               5

<210> SEQ ID NO 179
<211> LENGTH: 5
<212> TYPE: PRT
<213> ORGANISM: Artificial
<220> FEATURE:
<223> OTHER INFORMATION: CDR1 element

<400> SEQUENCE: 179

Thr Tyr Ala Met Gly
1               5

<210> SEQ ID NO 180
<211> LENGTH: 5
<212> TYPE: PRT
<213> ORGANISM: Artificial
<220> FEATURE:
<223> OTHER INFORMATION: CDR1 element

<400> SEQUENCE: 180

Thr Tyr Ala Met Ser
1               5

<210> SEQ ID NO 181
<211> LENGTH: 5
<212> TYPE: PRT
<213> ORGANISM: Artificial
<220> FEATURE:
<223> OTHER INFORMATION: CDR1 element

<400> SEQUENCE: 181

Ala Tyr Ala Thr Gly
1               5

<210> SEQ ID NO 182
<211> LENGTH: 5
<212> TYPE: PRT
<213> ORGANISM: Artificial
<220> FEATURE:
<223> OTHER INFORMATION: CDR1 element

<400> SEQUENCE: 182

Ile Val Met Leu Gly
1               5

<210> SEQ ID NO 183
<211> LENGTH: 5
<212> TYPE: PRT
<213> ORGANISM: Artificial
<220> FEATURE:
<223> OTHER INFORMATION: CDR1 element
```

<400> SEQUENCE: 183

Ser Tyr Asp Met Gly
1               5

<210> SEQ ID NO 184
<211> LENGTH: 5
<212> TYPE: PRT
<213> ORGANISM: Artificial
<220> FEATURE:
<223> OTHER INFORMATION: CDR1 element

<400> SEQUENCE: 184

Thr Tyr Asp Met Ser
1               5

<210> SEQ ID NO 185
<211> LENGTH: 5
<212> TYPE: PRT
<213> ORGANISM: Artificial
<220> FEATURE:
<223> OTHER INFORMATION: CDR1 element

<400> SEQUENCE: 185

Arg Tyr Asn Met Ala
1               5

<210> SEQ ID NO 186
<211> LENGTH: 7
<212> TYPE: PRT
<213> ORGANISM: Artificial
<220> FEATURE:
<223> OTHER INFORMATION: CDR1 element

<400> SEQUENCE: 186

Phe Ser Ala Tyr Ser Met Thr
1               5

<210> SEQ ID NO 187
<211> LENGTH: 5
<212> TYPE: PRT
<213> ORGANISM: Artificial
<220> FEATURE:
<223> OTHER INFORMATION: CDR1 element

<400> SEQUENCE: 187

Lys Asn Ala Met Gly
1               5

<210> SEQ ID NO 188
<211> LENGTH: 5
<212> TYPE: PRT
<213> ORGANISM: Artificial
<220> FEATURE:
<223> OTHER INFORMATION: CDR1 element

<400> SEQUENCE: 188

Ala Ser Ser Met Ala
1               5

<210> SEQ ID NO 189
<211> LENGTH: 5
<212> TYPE: PRT
<213> ORGANISM: Artificial
<220> FEATURE:
<223> OTHER INFORMATION: CDR1 element

<400> SEQUENCE: 189

```
Ser Tyr Ala Met Gly
1               5

<210> SEQ ID NO 190
<211> LENGTH: 5
<212> TYPE: PRT
<213> ORGANISM: Artificial
<220> FEATURE:
<223> OTHER INFORMATION: CDR1 element

<400> SEQUENCE: 190

Ala Thr Ser Met Thr
1               5

<210> SEQ ID NO 191
<211> LENGTH: 5
<212> TYPE: PRT
<213> ORGANISM: Artificial
<220> FEATURE:
<223> OTHER INFORMATION: CDR1 element

<400> SEQUENCE: 191

Asn Tyr Asp Val Gly
1               5

<210> SEQ ID NO 192
<211> LENGTH: 7
<212> TYPE: PRT
<213> ORGANISM: Artificial
<220> FEATURE:
<223> OTHER INFORMATION: CDR1 element

<400> SEQUENCE: 192

Phe Ser Ala Tyr Ser Met Thr
1               5

<210> SEQ ID NO 193
<211> LENGTH: 5
<212> TYPE: PRT
<213> ORGANISM: Artificial
<220> FEATURE:
<223> OTHER INFORMATION: CDR1 element

<400> SEQUENCE: 193

Thr Ala Asp Met Gly
1               5

<210> SEQ ID NO 194
<211> LENGTH: 5
<212> TYPE: PRT
<213> ORGANISM: Artificial
<220> FEATURE:
<223> OTHER INFORMATION: CDR1 element

<400> SEQUENCE: 194

Thr Thr Ser Met Thr
1               5

<210> SEQ ID NO 195
<211> LENGTH: 5
<212> TYPE: PRT
<213> ORGANISM: Artificial
<220> FEATURE:
<223> OTHER INFORMATION: CDR1 element

<400> SEQUENCE: 195
```

```
Val Asn Asp Met Gly
1               5

<210> SEQ ID NO 196
<211> LENGTH: 5
<212> TYPE: PRT
<213> ORGANISM: Artificial
<220> FEATURE:
<223> OTHER INFORMATION: CDR1 element

<400> SEQUENCE: 196

Ser Val Ala Met Gly
1               5

<210> SEQ ID NO 197
<211> LENGTH: 6
<212> TYPE: PRT
<213> ORGANISM: Artificial
<220> FEATURE:
<223> OTHER INFORMATION: CDR1 element

<400> SEQUENCE: 197

Asp Arg Phe Asn Met Ala
1               5

<210> SEQ ID NO 198
<211> LENGTH: 14
<212> TYPE: PRT
<213> ORGANISM: Artificial
<220> FEATURE:
<223> OTHER INFORMATION: FR2 element

<400> SEQUENCE: 198

Trp Val Arg Gln Ala Pro Gly Lys Gly Leu Glu Trp Val Ser
1               5                   10

<210> SEQ ID NO 199
<211> LENGTH: 14
<212> TYPE: PRT
<213> ORGANISM: Artificial
<220> FEATURE:
<223> OTHER INFORMATION: FR2 element

<400> SEQUENCE: 199

Trp Val Arg Gln Ala Pro Gly Lys Gly Leu Glu Trp Val Ser
1               5                   10

<210> SEQ ID NO 200
<211> LENGTH: 14
<212> TYPE: PRT
<213> ORGANISM: Artificial
<220> FEATURE:
<223> OTHER INFORMATION: FR2 element

<400> SEQUENCE: 200

Trp Val Arg Gln Ala Pro Gly Lys Gly Leu Glu Trp Val Ser
1               5                   10

<210> SEQ ID NO 201
<211> LENGTH: 14
<212> TYPE: PRT
<213> ORGANISM: Artificial
<220> FEATURE:
<223> OTHER INFORMATION: FR2 element

<400> SEQUENCE: 201

Trp Phe Arg Gln Ala Pro Gly Lys Glu Arg Glu Phe Val Ala
```

```
<210> SEQ ID NO 202
<211> LENGTH: 14
<212> TYPE: PRT
<213> ORGANISM: Artificial
<220> FEATURE:
<223> OTHER INFORMATION: FR2 element

<400> SEQUENCE: 202

Trp Phe Arg Gln Ala Pro Gly Lys Glu Arg Glu Phe Val Ala
1               5                   10

<210> SEQ ID NO 203
<211> LENGTH: 14
<212> TYPE: PRT
<213> ORGANISM: Artificial
<220> FEATURE:
<223> OTHER INFORMATION: FR2 element

<400> SEQUENCE: 203

Trp Phe Arg Gln Ala Pro Gly Lys Glu Arg Glu Phe Val Ala
1               5                   10

<210> SEQ ID NO 204
<211> LENGTH: 14
<212> TYPE: PRT
<213> ORGANISM: Artificial
<220> FEATURE:
<223> OTHER INFORMATION: FR2 element

<400> SEQUENCE: 204

Trp Phe Arg Gln Ala Pro Gly Lys Glu Arg Glu Phe Val Ala
1               5                   10

<210> SEQ ID NO 205
<211> LENGTH: 14
<212> TYPE: PRT
<213> ORGANISM: Artificial
<220> FEATURE:
<223> OTHER INFORMATION: FR2 element

<400> SEQUENCE: 205

Trp Phe Arg Gln Ala Pro Gly Lys Glu Arg Gln Leu Leu Ala
1               5                   10

<210> SEQ ID NO 206
<211> LENGTH: 14
<212> TYPE: PRT
<213> ORGANISM: Artificial
<220> FEATURE:
<223> OTHER INFORMATION: FR2 element

<400> SEQUENCE: 206

Trp Phe Arg Gln Ala Pro Gly Lys Glu Arg Glu Leu Leu Gly
1               5                   10

<210> SEQ ID NO 207
<211> LENGTH: 14
<212> TYPE: PRT
<213> ORGANISM: Artificial
<220> FEATURE:
<223> OTHER INFORMATION: FR2 element

<400> SEQUENCE: 207

Trp Phe Arg Gln Ala Pro Gly Arg Glu Arg Glu Phe Val Ala
1               5                   10
```

```
<210> SEQ ID NO 208
<211> LENGTH: 14
<212> TYPE: PRT
<213> ORGANISM: Artificial
<220> FEATURE:
<223> OTHER INFORMATION: FR2 element

<400> SEQUENCE: 208

Trp Phe Arg Arg Ala Pro Gly Lys Glu Arg Glu Phe Val Ala
1               5                   10

<210> SEQ ID NO 209
<211> LENGTH: 14
<212> TYPE: PRT
<213> ORGANISM: Artificial
<220> FEATURE:
<223> OTHER INFORMATION: FR2 element

<400> SEQUENCE: 209

Trp Tyr Arg Arg Ala Pro Gly Lys Gln Arg Glu Leu Val Ala
1               5                   10

<210> SEQ ID NO 210
<211> LENGTH: 14
<212> TYPE: PRT
<213> ORGANISM: Artificial
<220> FEATURE:
<223> OTHER INFORMATION: FR2 element

<400> SEQUENCE: 210

Trp Val Arg Gln Ala Pro Gly Lys Phe Glu Glu Trp Val Ser
1               5                   10

<210> SEQ ID NO 211
<211> LENGTH: 14
<212> TYPE: PRT
<213> ORGANISM: Artificial
<220> FEATURE:
<223> OTHER INFORMATION: FR2 element

<400> SEQUENCE: 211

Trp Phe Arg Gln Ala Pro Gly Lys Gln Arg Glu Phe Leu Ala
1               5                   10

<210> SEQ ID NO 212
<211> LENGTH: 14
<212> TYPE: PRT
<213> ORGANISM: Artificial
<220> FEATURE:
<223> OTHER INFORMATION: FR2 element

<400> SEQUENCE: 212

Trp Phe Arg Gln Ala Pro Gly Lys Glu Arg Glu Phe Val Ala
1               5                   10

<210> SEQ ID NO 213
<211> LENGTH: 14
<212> TYPE: PRT
<213> ORGANISM: Artificial
<220> FEATURE:
<223> OTHER INFORMATION: FR2 element

<400> SEQUENCE: 213

Trp Phe Arg Gln Ala Pro Gly Lys Glu Arg Glu Phe Val Ala
1               5                   10
```

<210> SEQ ID NO 214
<211> LENGTH: 14
<212> TYPE: PRT
<213> ORGANISM: Artificial
<220> FEATURE:
<223> OTHER INFORMATION: FR2 element

<400> SEQUENCE: 214

Trp Phe Arg Arg Ala Pro Gly Lys Glu Arg Glu Phe Val Ala
1               5                   10

<210> SEQ ID NO 215
<211> LENGTH: 14
<212> TYPE: PRT
<213> ORGANISM: Artificial
<220> FEATURE:
<223> OTHER INFORMATION: FR2 element

<400> SEQUENCE: 215

Trp Phe Arg Arg Ala Pro Gly Lys Glu Arg Glu Phe Val Ala
1               5                   10

<210> SEQ ID NO 216
<211> LENGTH: 14
<212> TYPE: PRT
<213> ORGANISM: Artificial
<220> FEATURE:
<223> OTHER INFORMATION: FR2 element

<400> SEQUENCE: 216

Trp Tyr Arg Gln Ala Pro Gly Lys Gln Arg Glu Trp Val Ala
1               5                   10

<210> SEQ ID NO 217
<211> LENGTH: 14
<212> TYPE: PRT
<213> ORGANISM: Artificial
<220> FEATURE:
<223> OTHER INFORMATION: FR2 element

<400> SEQUENCE: 217

Trp Phe Arg Gln Ala Pro Gly Glu Gly Arg Glu Phe Val Ala
1               5                   10

<210> SEQ ID NO 218
<211> LENGTH: 14
<212> TYPE: PRT
<213> ORGANISM: Artificial
<220> FEATURE:
<223> OTHER INFORMATION: FR2 element

<400> SEQUENCE: 218

Trp Val Arg Gln Ala Pro Gly Lys Gly Leu Glu Trp Val Ser
1               5                   10

<210> SEQ ID NO 219
<211> LENGTH: 14
<212> TYPE: PRT
<213> ORGANISM: Artificial
<220> FEATURE:
<223> OTHER INFORMATION: FR2 element

<400> SEQUENCE: 219

Trp Phe Arg Gln Ala Pro Gly Lys Glu Arg Glu Phe Leu Ala
1               5                   10

```
<210> SEQ ID NO 220
<211> LENGTH: 14
<212> TYPE: PRT
<213> ORGANISM: Artificial
<220> FEATURE:
<223> OTHER INFORMATION: FR2 element

<400> SEQUENCE: 220

Trp Val Arg Gln Ala Pro Gly Lys Ala Glu Glu Trp Val Ser
1               5                   10

<210> SEQ ID NO 221
<211> LENGTH: 14
<212> TYPE: PRT
<213> ORGANISM: Artificial
<220> FEATURE:
<223> OTHER INFORMATION: FR2 element

<400> SEQUENCE: 221

Trp Phe Arg Gln Pro Pro Gly Lys Glu Arg Glu Phe Val Ala
1               5                   10

<210> SEQ ID NO 222
<211> LENGTH: 14
<212> TYPE: PRT
<213> ORGANISM: Artificial
<220> FEATURE:
<223> OTHER INFORMATION: FR2 element

<400> SEQUENCE: 222

Trp Val Arg Gln Ala Pro Gly Lys Tyr Glu Glu Trp Val Ser
1               5                   10

<210> SEQ ID NO 223
<211> LENGTH: 14
<212> TYPE: PRT
<213> ORGANISM: Artificial
<220> FEATURE:
<223> OTHER INFORMATION: FR2 element

<400> SEQUENCE: 223

Trp Phe Arg Gln Ala Pro Gly Lys Glu Arg Glu Phe Val Ala
1               5                   10

<210> SEQ ID NO 224
<211> LENGTH: 14
<212> TYPE: PRT
<213> ORGANISM: Artificial
<220> FEATURE:
<223> OTHER INFORMATION: FR2 element

<400> SEQUENCE: 224

Trp Val Arg Gln Ala Pro Gly Lys Ala Glu Glu Trp Val Ser
1               5                   10

<210> SEQ ID NO 225
<211> LENGTH: 14
<212> TYPE: PRT
<213> ORGANISM: Artificial
<220> FEATURE:
<223> OTHER INFORMATION: FR2 element

<400> SEQUENCE: 225

Trp Phe Arg Gln Ala Pro Gly Glu Gly Arg Glu Ile Val Ala
1               5                   10

<210> SEQ ID NO 226
```

```
<211> LENGTH: 14
<212> TYPE: PRT
<213> ORGANISM: Artificial
<220> FEATURE:
<223> OTHER INFORMATION: FR2 element

<400> SEQUENCE: 226

Trp Val Arg Gln Ala Pro Gly Lys Ala Glu Glu Phe Val Ser
1               5                   10

<210> SEQ ID NO 227
<211> LENGTH: 14
<212> TYPE: PRT
<213> ORGANISM: Artificial
<220> FEATURE:
<223> OTHER INFORMATION: FR2 element

<400> SEQUENCE: 227

Trp Phe Arg Gln Pro Pro Gly Lys Gly Arg Glu Phe Val Ala
1               5                   10

<210> SEQ ID NO 228
<211> LENGTH: 14
<212> TYPE: PRT
<213> ORGANISM: Artificial
<220> FEATURE:
<223> OTHER INFORMATION: FR2 element

<400> SEQUENCE: 228

Trp Val Arg Gln Ala Pro Gly Lys Phe Glu Glu Trp Val Ser
1               5                   10

<210> SEQ ID NO 229
<211> LENGTH: 14
<212> TYPE: PRT
<213> ORGANISM: Artificial
<220> FEATURE:
<223> OTHER INFORMATION: FR2 element

<400> SEQUENCE: 229

Trp Tyr Arg Gln Ala Pro Gly Lys Glu Arg Glu Leu Val Ala
1               5                   10

<210> SEQ ID NO 230
<211> LENGTH: 14
<212> TYPE: PRT
<213> ORGANISM: Artificial
<220> FEATURE:
<223> OTHER INFORMATION: FR2 element

<400> SEQUENCE: 230

Trp Phe Arg Gln Ala Pro Gly Lys Glu Arg Glu Phe Val Ala
1               5                   10

<210> SEQ ID NO 231
<211> LENGTH: 14
<212> TYPE: PRT
<213> ORGANISM: Artificial
<220> FEATURE:
<223> OTHER INFORMATION: FR2 element

<400> SEQUENCE: 231

Trp Phe His Gln Ala Pro Gly Lys Asp Arg Glu Phe Val Ser
1               5                   10

<210> SEQ ID NO 232
<211> LENGTH: 17
```

```
<212> TYPE: PRT
<213> ORGANISM: Artificial
<220> FEATURE:
<223> OTHER INFORMATION: CDR2 element

<400> SEQUENCE: 232

Glu Ile Asn Thr Asn Gly Leu Ile Thr Lys Tyr Pro Asp Ser Val Lys
1               5                   10                  15

Gly

<210> SEQ ID NO 233
<211> LENGTH: 17
<212> TYPE: PRT
<213> ORGANISM: Artificial
<220> FEATURE:
<223> OTHER INFORMATION: CDR2 element

<400> SEQUENCE: 233

Glu Ile Asn Thr Asn Gly Leu Ile Thr Lys Tyr Pro Asp Ser Val Lys
1               5                   10                  15

Gly

<210> SEQ ID NO 234
<211> LENGTH: 17
<212> TYPE: PRT
<213> ORGANISM: Artificial
<220> FEATURE:
<223> OTHER INFORMATION: CDR2 element

<400> SEQUENCE: 234

Glu Ile Asn Thr Asn Gly Leu Ile Thr Lys Tyr Val Asp Ser Val Lys
1               5                   10                  15

Gly

<210> SEQ ID NO 235
<211> LENGTH: 17
<212> TYPE: PRT
<213> ORGANISM: Artificial
<220> FEATURE:
<223> OTHER INFORMATION: CDR2 element

<400> SEQUENCE: 235

Arg Ile Tyr Trp Ser Ser Gly Leu Thr Tyr Tyr Ala Asp Ser Val Lys
1               5                   10                  15

Gly

<210> SEQ ID NO 236
<211> LENGTH: 17
<212> TYPE: PRT
<213> ORGANISM: Artificial
<220> FEATURE:
<223> OTHER INFORMATION: CDR2 element

<400> SEQUENCE: 236

Arg Ile Tyr Trp Ser Ser Gly Asn Thr Tyr Tyr Ala Asp Ser Val Lys
1               5                   10                  15

Gly

<210> SEQ ID NO 237
<211> LENGTH: 17
<212> TYPE: PRT
<213> ORGANISM: Artificial
<220> FEATURE:
<223> OTHER INFORMATION: CDR2 element
```

```
<400> SEQUENCE: 237

Arg Ile Tyr Trp Ser Ser Gly Asn Thr Tyr Tyr Ala Asp Ser Val Lys
1               5                   10                  15

Gly

<210> SEQ ID NO 238
<211> LENGTH: 17
<212> TYPE: PRT
<213> ORGANISM: Artificial
<220> FEATURE:
<223> OTHER INFORMATION: CDR2 element

<400> SEQUENCE: 238

Arg Ile Tyr Trp Ser Ser Ala Asn Thr Tyr Tyr Ala Asp Ser Val Lys
1               5                   10                  15

Gly

<210> SEQ ID NO 239
<211> LENGTH: 17
<212> TYPE: PRT
<213> ORGANISM: Artificial
<220> FEATURE:
<223> OTHER INFORMATION: CDR2 element

<400> SEQUENCE: 239

Ser Ile Ser Trp Arg Gly Asp Asn Thr Tyr Tyr Lys Glu Ser Val Lys
1               5                   10                  15

Gly

<210> SEQ ID NO 240
<211> LENGTH: 17
<212> TYPE: PRT
<213> ORGANISM: Artificial
<220> FEATURE:
<223> OTHER INFORMATION: CDR2 element

<400> SEQUENCE: 240

Asn Ile Ser Trp Arg Gly Tyr Asn Ile Tyr Tyr Lys Asp Ser Val Lys
1               5                   10                  15

Gly

<210> SEQ ID NO 241
<211> LENGTH: 23
<212> TYPE: PRT
<213> ORGANISM: Artificial
<220> FEATURE:
<223> OTHER INFORMATION: CDR2 element

<400> SEQUENCE: 241

Glu Ile Arg Pro Ser Gly Asp Phe Gly Pro Glu Gly Glu Phe Glu His
1               5                   10                  15

Val Thr Ala Ser Leu Lys Gly
            20

<210> SEQ ID NO 242
<211> LENGTH: 17
<212> TYPE: PRT
<213> ORGANISM: Artificial
<220> FEATURE:
<223> OTHER INFORMATION: CDR2 element

<400> SEQUENCE: 242
```

```
Gly Ile Gln Trp Ser Gly Gly Asp Ala Phe Tyr Arg Asn Ser Val Lys
1               5                   10                  15
Gly
```

<210> SEQ ID NO 243
<211> LENGTH: 16
<212> TYPE: PRT
<213> ORGANISM: Artificial
<220> FEATURE:
<223> OTHER INFORMATION: CDR2 element

<400> SEQUENCE: 243

```
Thr Ile Thr Asp Asp Gly Thr Thr Asp Tyr Gly Asp Asp Val Lys Gly
1               5                   10                  15
```

<210> SEQ ID NO 244
<211> LENGTH: 17
<212> TYPE: PRT
<213> ORGANISM: Artificial
<220> FEATURE:
<223> OTHER INFORMATION: CDR2 element

<400> SEQUENCE: 244

```
Phe Ile Asn Ser Asp Gly Ser Ser Thr Thr Tyr Ala Asp Ser Val Lys
1               5                   10                  15
Gly
```

<210> SEQ ID NO 245
<211> LENGTH: 17
<212> TYPE: PRT
<213> ORGANISM: Artificial
<220> FEATURE:
<223> OTHER INFORMATION: CDR2 element

<400> SEQUENCE: 245

```
Gly Val Gly Tyr Asp Gly Ser Ser Ile Arg Tyr Ala Glu Ser Val Lys
1               5                   10                  15
Gly
```

<210> SEQ ID NO 246
<211> LENGTH: 17
<212> TYPE: PRT
<213> ORGANISM: Artificial
<220> FEATURE:
<223> OTHER INFORMATION: CDR2 element

<400> SEQUENCE: 246

```
Thr Ile Ser Trp Asn Gly Gly Ser Ser Tyr Ala Asp Phe Val Lys
1               5                   10                  15
Gly
```

<210> SEQ ID NO 247
<211> LENGTH: 17
<212> TYPE: PRT
<213> ORGANISM: Artificial
<220> FEATURE:
<223> OTHER INFORMATION: CDR2 element

<400> SEQUENCE: 247

```
Ala Ile Ser Trp Gly Gly Gly Ser Ile Val Tyr Ala Glu Ser Ala Lys
1               5                   10                  15
Gly
```

```
<210> SEQ ID NO 248
<211> LENGTH: 17
<212> TYPE: PRT
<213> ORGANISM: Artificial
<220> FEATURE:
<223> OTHER INFORMATION: CDR2 element

<400> SEQUENCE: 248

Ser Ile Ser Trp Ser Gly Asp Thr Thr Tyr Tyr Ser Asn Ser Val Lys
1               5                   10                  15
Gly

<210> SEQ ID NO 249
<211> LENGTH: 17
<212> TYPE: PRT
<213> ORGANISM: Artificial
<220> FEATURE:
<223> OTHER INFORMATION: CDR2 element

<400> SEQUENCE: 249

Gly Ile Gln Trp Ser Gly Gly Asp Ala Phe Tyr Arg Asn Ser Val Lys
1               5                   10                  15
Gly

<210> SEQ ID NO 250
<211> LENGTH: 16
<212> TYPE: PRT
<213> ORGANISM: Artificial
<220> FEATURE:
<223> OTHER INFORMATION: CDR2 element

<400> SEQUENCE: 250

Ser Ile Thr Ile Gly Ser Arg Thr Asn Tyr Ala Asp Ser Val Lys Gly
1               5                   10                  15

<210> SEQ ID NO 251
<211> LENGTH: 17
<212> TYPE: PRT
<213> ORGANISM: Artificial
<220> FEATURE:
<223> OTHER INFORMATION: CDR2 element

<400> SEQUENCE: 251

Arg Ile Ser Gly Ser Asp Gly Ser Thr Tyr Tyr Ser Asp Arg Ala Lys
1               5                   10                  15
Asp

<210> SEQ ID NO 252
<211> LENGTH: 17
<212> TYPE: PRT
<213> ORGANISM: Artificial
<220> FEATURE:
<223> OTHER INFORMATION: CDR2 element

<400> SEQUENCE: 252

Gly Ile Asp Ser Gly Gly Gly Ser Pro Met Tyr Val Asp Ser Val Lys
1               5                   10                  15
Gly

<210> SEQ ID NO 253
<211> LENGTH: 17
<212> TYPE: PRT
<213> ORGANISM: Artificial
<220> FEATURE:
<223> OTHER INFORMATION: CDR2 element
```

```
-continued

<400> SEQUENCE: 253

Arg Val Asp Val Ser Gly Gly Asn Thr Leu Tyr Gly Asp Ser Val Lys
1               5                   10                  15

Asp

<210> SEQ ID NO 254
<211> LENGTH: 17
<212> TYPE: PRT
<213> ORGANISM: Artificial
<220> FEATURE:
<223> OTHER INFORMATION: CDR2 element

<400> SEQUENCE: 254

Phe Ile Asn Ser Asp Gly Ser Ser Thr Thr Tyr Ala Asp Ser Val Asn
1               5                   10                  15

Gly

<210> SEQ ID NO 255
<211> LENGTH: 17
<212> TYPE: PRT
<213> ORGANISM: Artificial
<220> FEATURE:
<223> OTHER INFORMATION: CDR2 element

<400> SEQUENCE: 255

Ser Ile Lys Trp Asn Gly Asn Asn Thr Tyr Tyr Ala Asp Ser Val Arg
1               5                   10                  15

Gly

<210> SEQ ID NO 256
<211> LENGTH: 17
<212> TYPE: PRT
<213> ORGANISM: Artificial
<220> FEATURE:
<223> OTHER INFORMATION: CDR2 element

<400> SEQUENCE: 256

Phe Ile Asn Ser Asp Gly Ser Ser Thr Thr Tyr Ala Asp Ser Val Gln
1               5                   10                  15

Gly

<210> SEQ ID NO 257
<211> LENGTH: 17
<212> TYPE: PRT
<213> ORGANISM: Artificial
<220> FEATURE:
<223> OTHER INFORMATION: CDR2 element

<400> SEQUENCE: 257

Ala Ile Ser Trp Ser Gly Thr Ile Thr Asn Tyr Ala Asp Ser Val Lys
1               5                   10                  15

Gly

<210> SEQ ID NO 258
<211> LENGTH: 17
<212> TYPE: PRT
<213> ORGANISM: Artificial
<220> FEATURE:
<223> OTHER INFORMATION: CDR2 element

<400> SEQUENCE: 258

Phe Ile Asn Ser Asp Gly Ser Ser Thr Thr Tyr Ala Asp Ser Val Lys
```

```
1               5                   10                  15

Gly

<210> SEQ ID NO 259
<211> LENGTH: 17
<212> TYPE: PRT
<213> ORGANISM: Artificial
<220> FEATURE:
<223> OTHER INFORMATION: CDR2 element

<400> SEQUENCE: 259

Arg Ile Ser Gly Ser Gly Asp Ser Thr Tyr Ser Ser Asn Arg Ala Lys
1               5                   10                  15

Gly

<210> SEQ ID NO 260
<211> LENGTH: 17
<212> TYPE: PRT
<213> ORGANISM: Artificial
<220> FEATURE:
<223> OTHER INFORMATION: CDR2 element

<400> SEQUENCE: 260

Phe Ile Asn Ser Asp Gly Ser Ser Thr Thr Tyr Ala Asn Ser Val Asn
1               5                   10                  15

Gly

<210> SEQ ID NO 261
<211> LENGTH: 17
<212> TYPE: PRT
<213> ORGANISM: Artificial
<220> FEATURE:
<223> OTHER INFORMATION: CDR2 element

<400> SEQUENCE: 261

Arg Ile Ser Gly Ile Asp Gly Thr Thr Tyr Tyr Asp Glu Pro Val Lys
1               5                   10                  15

Gly

<210> SEQ ID NO 262
<211> LENGTH: 17
<212> TYPE: PRT
<213> ORGANISM: Artificial
<220> FEATURE:
<223> OTHER INFORMATION: CDR2 element

<400> SEQUENCE: 262

Phe Ile Asn Ser Asp Gly Ser Ser Thr Thr Tyr Ala Asp Ser Val Lys
1               5                   10                  15

Gly

<210> SEQ ID NO 263
<211> LENGTH: 16
<212> TYPE: PRT
<213> ORGANISM: Artificial
<220> FEATURE:
<223> OTHER INFORMATION: CDR2 element

<400> SEQUENCE: 263

Thr Ile Thr Asp Asp Gly Arg Thr Asn Tyr Glu Asp Phe Ala Lys Gly
1               5                   10                  15

<210> SEQ ID NO 264
```

```
<211> LENGTH: 17
<212> TYPE: PRT
<213> ORGANISM: Artificial
<220> FEATURE:
<223> OTHER INFORMATION: CDR2 element

<400> SEQUENCE: 264

Ala Ile Gly Tyr Asp Gly Asn Ser Ile Arg Tyr Gly Asp Ser Val Lys
1               5                   10                  15

Gly

<210> SEQ ID NO 265
<211> LENGTH: 17
<212> TYPE: PRT
<213> ORGANISM: Artificial
<220> FEATURE:
<223> OTHER INFORMATION: CDR2 element

<400> SEQUENCE: 265

Arg Ile Asp Val Ala Gly Tyr Asn Thr Ala Tyr Gly Asp Phe Val Lys
1               5                   10                  15

Gly

<210> SEQ ID NO 266
<211> LENGTH: 32
<212> TYPE: PRT
<213> ORGANISM: Artificial
<220> FEATURE:
<223> OTHER INFORMATION: FR3 element

<400> SEQUENCE: 266

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Leu Tyr Tyr Cys Ala Arg
            20                  25                  30

<210> SEQ ID NO 267
<211> LENGTH: 32
<212> TYPE: PRT
<213> ORGANISM: Artificial
<220> FEATURE:
<223> OTHER INFORMATION: FR3 element

<400> SEQUENCE: 267

Arg Phe Thr Ile Ser Arg Asp Asn Ala Lys Thr Thr Leu Tyr Leu Gln
1               5                   10                  15

Met Asn Ser Leu Lys Pro Glu Asp Thr Ala Leu Tyr Tyr Cys Ala Arg
            20                  25                  30

<210> SEQ ID NO 268
<211> LENGTH: 32
<212> TYPE: PRT
<213> ORGANISM: Artificial
<220> FEATURE:
<223> OTHER INFORMATION: FR3 element

<400> SEQUENCE: 268

Arg Phe Thr Ile Ser Arg Asp Asn Ala Lys Asn Thr Leu Tyr Leu Gln
1               5                   10                  15

Met Asp Ser Leu Ile Pro Glu Asp Thr Ala Leu Tyr Tyr Cys Ala Arg
            20                  25                  30

<210> SEQ ID NO 269
<211> LENGTH: 32
```

<212> TYPE: PRT
<213> ORGANISM: Artificial
<220> FEATURE:
<223> OTHER INFORMATION: FR3 element

<400> SEQUENCE: 269

Arg Phe Thr Ile Ser Arg Asp Ile Ala Lys Asn Thr Val Asp Leu Leu
1               5                   10                  15

Met Asn Ser Leu Lys Pro Glu Asp Thr Ala Val Tyr Tyr Cys Ala Ala
            20                  25                  30

<210> SEQ ID NO 270
<211> LENGTH: 32
<212> TYPE: PRT
<213> ORGANISM: Artificial
<220> FEATURE:
<223> OTHER INFORMATION: FR3 element

<400> SEQUENCE: 270

Arg Phe Thr Ile Ser Arg Asp Ile Ala Lys Asn Thr Val Asp Leu Leu
1               5                   10                  15

Met Asn Asn Leu Glu Pro Glu Asp Thr Ala Val Tyr Tyr Cys Ala Ala
            20                  25                  30

<210> SEQ ID NO 271
<211> LENGTH: 32
<212> TYPE: PRT
<213> ORGANISM: Artificial
<220> FEATURE:
<223> OTHER INFORMATION: FR3 element

<400> SEQUENCE: 271

Arg Phe Thr Ile Ser Arg Asp Ile Ala Lys Asn Thr Val Asp Leu Leu
1               5                   10                  15

Met Asn Asn Leu Glu Pro Glu Asp Thr Ala Val Tyr Tyr Cys Ala Ala
            20                  25                  30

<210> SEQ ID NO 272
<211> LENGTH: 32
<212> TYPE: PRT
<213> ORGANISM: Artificial
<220> FEATURE:
<223> OTHER INFORMATION: FR3 element

<400> SEQUENCE: 272

Arg Phe Thr Ile Ser Arg Asp Asn Ala Lys Asn Thr Val Asp Leu Leu
1               5                   10                  15

Met Asn Cys Leu Lys Pro Glu Asp Thr Ala Val Tyr Tyr Cys Ala Ala
            20                  25                  30

<210> SEQ ID NO 273
<211> LENGTH: 32
<212> TYPE: PRT
<213> ORGANISM: Artificial
<220> FEATURE:
<223> OTHER INFORMATION: FR3 element

<400> SEQUENCE: 273

Arg Phe Thr Ile Ser Arg Asp Asp Ala Lys Asn Thr Ile Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 274

```
<211> LENGTH: 32
<212> TYPE: PRT
<213> ORGANISM: Artificial
<220> FEATURE:
<223> OTHER INFORMATION: FR3 element

<400> SEQUENCE: 274

Arg Phe Thr Ile Ser Arg Asp Asp Ala Lys Asn Thr Ile Tyr Leu Gln
1               5                   10                  15

Met Asn Arg Leu Lys Pro Glu Asp Thr Ala Val Tyr Tyr Cys Ala Ala
            20                  25                  30

<210> SEQ ID NO 275
<211> LENGTH: 32
<212> TYPE: PRT
<213> ORGANISM: Artificial
<220> FEATURE:
<223> OTHER INFORMATION: FR3 element

<400> SEQUENCE: 275

Arg Phe Thr Ile Ala Lys Asn Ser Val Asp Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 276
<211> LENGTH: 31
<212> TYPE: PRT
<213> ORGANISM: Artificial
<220> FEATURE:
<223> OTHER INFORMATION: FR3 element

<400> SEQUENCE: 276

Arg Phe Arg Ile Thr Arg Asp Pro Asp Asn Thr Val Tyr Leu Gln Met
1               5                   10                  15

Asn Asp Leu Lys Pro Glu Asp Thr Ala Ile Tyr Tyr Cys Ala Gln
            20                  25                  30

<210> SEQ ID NO 277
<211> LENGTH: 30
<212> TYPE: PRT
<213> ORGANISM: Artificial
<220> FEATURE:
<223> OTHER INFORMATION: FR3 element

<400> SEQUENCE: 277

Arg Phe Val Ile Ser Arg Glu Gly Glu Met Val Tyr Leu Glu Met Asn
1               5                   10                  15

Ser Leu Lys Pro Glu Asp Thr Ala Val Tyr Tyr Cys Asn Ile
            20                  25                  30

<210> SEQ ID NO 278
<211> LENGTH: 32
<212> TYPE: PRT
<213> ORGANISM: Artificial
<220> FEATURE:
<223> OTHER INFORMATION: FR3 element

<400> SEQUENCE: 278

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Met Tyr Tyr Cys Gly Arg
            20                  25                  30
```

```
<210> SEQ ID NO 279
<211> LENGTH: 32
<212> TYPE: PRT
<213> ORGANISM: Artificial
<220> FEATURE:
<223> OTHER INFORMATION: FR3 element

<400> SEQUENCE: 279

Arg Phe Thr Ile Ala Arg Gly Asn Arg Glu Ser Thr Val Phe Leu Gln
1               5                   10                  15

Met Glu Asn Leu Lys Pro Glu Asp Thr Ala Val Tyr Phe Cys Thr Ala
            20                  25                  30

<210> SEQ ID NO 280
<211> LENGTH: 32
<212> TYPE: PRT
<213> ORGANISM: Artificial
<220> FEATURE:
<223> OTHER INFORMATION: FR3 element

<400> SEQUENCE: 280

Arg Phe Thr Ile Ser Arg Asp Asn Ala Lys Asn Thr Val Tyr Leu Gln
1               5                   10                  15

Met Asn Gly Leu Thr Pro Gln Asp Thr Ala Ile Tyr Tyr Cys Ala Gly
            20                  25                  30

<210> SEQ ID NO 281
<211> LENGTH: 32
<212> TYPE: PRT
<213> ORGANISM: Artificial
<220> FEATURE:
<223> OTHER INFORMATION: FR3 element
<220> FEATURE:
<221> NAME/KEY: MISC_FEATURE
<222> LOCATION: (11)..(11)
<223> OTHER INFORMATION: unknown amino acid residue

<400> SEQUENCE: 281

Arg Phe Thr Ile Ser Arg Asp Asn Ala Lys Xaa Thr Met Tyr Leu Gln
1               5                   10                  15

Met Asp Ser Leu Lys Pro Glu Asp Thr Ala Val Tyr Tyr Cys Ala Ala
            20                  25                  30

<210> SEQ ID NO 282
<211> LENGTH: 32
<212> TYPE: PRT
<213> ORGANISM: Artificial
<220> FEATURE:
<223> OTHER INFORMATION: FR3 element

<400> SEQUENCE: 282

Arg Phe Thr Val Ser Arg Asp Asn Gly Lys Asn Thr Ala Tyr Leu Arg
1               5                   10                  15

Met Asn Ser Leu Lys Pro Glu Asp Thr Ala Asp Tyr Tyr Cys Ala Val
            20                  25                  30

<210> SEQ ID NO 283
<211> LENGTH: 31
<212> TYPE: PRT
<213> ORGANISM: Artificial
<220> FEATURE:
<223> OTHER INFORMATION: FR3 element

<400> SEQUENCE: 283

Arg Phe Arg Ile Thr Arg Asp Pro Asp Asn Thr Val Tyr Leu Gln Met
1               5                   10                  15
```

Asn Asp Leu Lys Pro Glu Asp Thr Ala Ile Tyr Tyr Cys Ala Gln
            20                  25                  30

<210> SEQ ID NO 284
<211> LENGTH: 32
<212> TYPE: PRT
<213> ORGANISM: Artificial
<220> FEATURE:
<223> OTHER INFORMATION: FR3 element

<400> SEQUENCE: 284

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Phe Cys Asn Ala
            20                  25                  30

<210> SEQ ID NO 285
<211> LENGTH: 32
<212> TYPE: PRT
<213> ORGANISM: Artificial
<220> FEATURE:
<223> OTHER INFORMATION: FR3 element

<400> SEQUENCE: 285

Arg Phe Thr Ile Ser Arg Asp Asn Thr Lys Asn Met Val Tyr Leu Gln
1               5                   10                  15

Met Asp Arg Leu Lys Pro Asp Asp Thr Ala Val Tyr Tyr Cys Arg Val
            20                  25                  30

<210> SEQ ID NO 286
<211> LENGTH: 32
<212> TYPE: PRT
<213> ORGANISM: Artificial
<220> FEATURE:
<223> OTHER INFORMATION: FR3 element

<400> SEQUENCE: 286

Arg Phe Thr Val Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Ala Lys
            20                  25                  30

<210> SEQ ID NO 287
<211> LENGTH: 32
<212> TYPE: PRT
<213> ORGANISM: Artificial
<220> FEATURE:
<223> OTHER INFORMATION: FR3 element

<400> SEQUENCE: 287

Arg Phe Thr Val Ser Arg Ile Asn Gly Lys Asn Ala Met Tyr Leu Gln
1               5                   10                  15

Met Asn Asn Leu Lys Pro Glu Asp Thr Ala Ile Tyr Tyr Cys Ala Ala
            20                  25                  30

<210> SEQ ID NO 288
<211> LENGTH: 32
<212> TYPE: PRT
<213> ORGANISM: Artificial
<220> FEATURE:
<223> OTHER INFORMATION: FR3 element

<400> SEQUENCE: 288

Arg Phe Lys Ile Ser Arg Asp Asn Ala Lys Lys Thr Leu Tyr Leu Gln

-continued

```
                1               5                  10                  15
Met Asn Ser Leu Gly Pro Glu Asp Thr Ala Met Tyr Tyr Cys Gln Arg
                20                  25                  30

<210> SEQ ID NO 289
<211> LENGTH: 35
<212> TYPE: PRT
<213> ORGANISM: Artificial
<220> FEATURE:
<223> OTHER INFORMATION: FR3 element

<400> SEQUENCE: 289

Arg Phe Thr Ile Ser Arg Gly Asn Ala Lys Asn Thr Glu Asn Thr Val
1               5                   10                  15

Ser Leu Gln Met Asn Ser Leu Lys Pro Glu Asp Thr Ala Asp Tyr Tyr
                20                  25                  30

Cys Ala Ala
        35

<210> SEQ ID NO 290
<211> LENGTH: 32
<212> TYPE: PRT
<213> ORGANISM: Artificial
<220> FEATURE:
<223> OTHER INFORMATION: FR3 element

<400> SEQUENCE: 290

Arg Phe Thr Ile Ser Arg Asp Asn Ala Lys Asn Thr Leu Tyr Leu Gln
1               5                   10                  15

Met Asn Ser Leu Lys Ser Glu Asp Thr Ala Met Tyr Tyr Cys Gly Arg
                20                  25                  30

<210> SEQ ID NO 291
<211> LENGTH: 32
<212> TYPE: PRT
<213> ORGANISM: Artificial
<220> FEATURE:
<223> OTHER INFORMATION: FR3 element

<400> SEQUENCE: 291

Arg Phe Thr Ile Ser Arg Asp Asn Gly Lys Asn Thr Val His Leu Gln
1               5                   10                  15

Met Asn Ser Leu Lys Pro Glu Asp Thr Ala Val Tyr His Cys Ala Val
                20                  25                  30

<210> SEQ ID NO 292
<211> LENGTH: 32
<212> TYPE: PRT
<213> ORGANISM: Artificial
<220> FEATURE:
<223> OTHER INFORMATION: FR3 element

<400> SEQUENCE: 292

Arg Phe Thr Ile Ser Arg Asp Asn Ala Lys Asn Thr Leu Tyr Leu Gln
1               5                   10                  15

Met Asp Asp Leu Gln Ser Glu Asp Thr Ala Met Tyr Tyr Cys Gly Arg
                20                  25                  30

<210> SEQ ID NO 293
<211> LENGTH: 32
<212> TYPE: PRT
<213> ORGANISM: Artificial
<220> FEATURE:
<223> OTHER INFORMATION: FR3 element
```

<400> SEQUENCE: 293

Arg Phe Thr Ile Ser Arg Asp Asn Ala Lys Asn Thr Val Tyr Leu Gln
1               5                   10                  15

Met Asn Ser Leu Lys Arg Glu Asp Thr Ala Val Tyr Tyr Cys Arg Ala
            20                  25                  30

<210> SEQ ID NO 294
<211> LENGTH: 32
<212> TYPE: PRT
<213> ORGANISM: Artificial
<220> FEATURE:
<223> OTHER INFORMATION: FR3 element

<400> SEQUENCE: 294

Arg Phe Lys Ile Ser Arg Asp Asn Ala Lys Lys Thr Leu Tyr Leu Gln
1               5                   10                  15

Met Asn Ser Leu Gly Pro Glu Asp Thr Ala Met Tyr Tyr Cys Gln Arg
            20                  25                  30

<210> SEQ ID NO 295
<211> LENGTH: 32
<212> TYPE: PRT
<213> ORGANISM: Artificial
<220> FEATURE:
<223> OTHER INFORMATION: FR3 element

<400> SEQUENCE: 295

Arg Phe Thr Ile Ser Arg Asp Lys Ala Gln Asn Thr Val Tyr Leu Gln
1               5                   10                  15

Met Asp Ser Leu Lys Pro Glu Asp Thr Ala Val Tyr Tyr Cys Arg Ser
            20                  25                  30

<210> SEQ ID NO 296
<211> LENGTH: 32
<212> TYPE: PRT
<213> ORGANISM: Artificial
<220> FEATURE:
<223> OTHER INFORMATION: FR3 element

<400> SEQUENCE: 296

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Met Tyr Tyr Cys Gly Arg
            20                  25                  30

<210> SEQ ID NO 297
<211> LENGTH: 32
<212> TYPE: PRT
<213> ORGANISM: Artificial
<220> FEATURE:
<223> OTHER INFORMATION: FR3 element

<400> SEQUENCE: 297

Arg Phe Thr Ile Ser Arg Asp Asn Ala Lys Asn Thr Val Tyr Leu Gln
1               5                   10                  15

Met Asn Ser Leu Leu Pro Glu Asp Thr Ala Val Tyr Tyr Cys Asn Ala
            20                  25                  30

<210> SEQ ID NO 298
<211> LENGTH: 32
<212> TYPE: PRT
<213> ORGANISM: Artificial
<220> FEATURE:

<223> OTHER INFORMATION: FR3 element

<400> SEQUENCE: 298

Arg Phe Thr Ile Ser Arg Asp Asn Ile Lys Asn Thr Met Tyr Leu Glu
1               5                   10                  15
Met Glu Asn Leu Asn Ala Asp Asp Thr Ala Arg Tyr Leu Cys Ala Ala
            20                  25                  30

<210> SEQ ID NO 299
<211> LENGTH: 32
<212> TYPE: PRT
<213> ORGANISM: Artificial
<220> FEATURE:
<223> OTHER INFORMATION: FR3 element

<400> SEQUENCE: 299

Arg Phe Thr Val Ser Arg Asp Ser Ala Glu Asn Thr Val Val Leu Gln
1               5                   10                  15
Met Asn Ser Leu Arg Pro Glu Asp Thr Gly Val Tyr Tyr Cys Ala Ala
            20                  25                  30

<210> SEQ ID NO 300
<211> LENGTH: 6
<212> TYPE: PRT
<213> ORGANISM: Artificial
<220> FEATURE:
<223> OTHER INFORMATION: CDR3 element

<400> SEQUENCE: 300

Ser Pro Ser Gly Phe Asn
1               5

<210> SEQ ID NO 301
<211> LENGTH: 6
<212> TYPE: PRT
<213> ORGANISM: Artificial
<220> FEATURE:
<223> OTHER INFORMATION: CDR3 element

<400> SEQUENCE: 301

Ser Pro Ser Gly Ser Phe
1               5

<210> SEQ ID NO 302
<211> LENGTH: 6
<212> TYPE: PRT
<213> ORGANISM: Artificial
<220> FEATURE:
<223> OTHER INFORMATION: CDR3 element

<400> SEQUENCE: 302

Ser Pro Ser Gly Ser Phe
1               5

<210> SEQ ID NO 303
<211> LENGTH: 15
<212> TYPE: PRT
<213> ORGANISM: Artificial
<220> FEATURE:
<223> OTHER INFORMATION: CDR3 element

<400> SEQUENCE: 303

Arg Asp Gly Ile Pro Thr Ser Arg Ser Val Gly Ser Tyr Asn Tyr
1               5                   10                  15

```
<210> SEQ ID NO 304
<211> LENGTH: 15
<212> TYPE: PRT
<213> ORGANISM: Artificial
<220> FEATURE:
<223> OTHER INFORMATION: CDR3 element

<400> SEQUENCE: 304

Arg Asp Gly Ile Pro Thr Ser Arg Ser Val Glu Ser Tyr Asn Tyr
1               5                   10                  15

<210> SEQ ID NO 305
<211> LENGTH: 15
<212> TYPE: PRT
<213> ORGANISM: Artificial
<220> FEATURE:
<223> OTHER INFORMATION: CDR3 element

<400> SEQUENCE: 305

Arg Asp Gly Ile Pro Thr Ser Arg Ser Val Glu Ser Tyr Asn Tyr
1               5                   10                  15

<210> SEQ ID NO 306
<211> LENGTH: 15
<212> TYPE: PRT
<213> ORGANISM: Artificial
<220> FEATURE:
<223> OTHER INFORMATION: CDR3 element

<400> SEQUENCE: 306

Arg Asp Gly Ile Pro Thr Ser Arg Ser Val Glu Ala Tyr Asn Tyr
1               5                   10                  15

<210> SEQ ID NO 307
<211> LENGTH: 14
<212> TYPE: PRT
<213> ORGANISM: Artificial
<220> FEATURE:
<223> OTHER INFORMATION: CDR3 element

<400> SEQUENCE: 307

Ser Ile Leu Pro Leu Ser Asp Asp Pro Gly Trp Asn Thr Asn
1               5                   10

<210> SEQ ID NO 308
<211> LENGTH: 14
<212> TYPE: PRT
<213> ORGANISM: Artificial
<220> FEATURE:
<223> OTHER INFORMATION: CDR3 element

<400> SEQUENCE: 308

Ser Ile Leu Pro Leu Ser Asp Asp Pro Gly Trp Asn Thr Tyr
1               5                   10

<210> SEQ ID NO 309
<211> LENGTH: 17
<212> TYPE: PRT
<213> ORGANISM: Artificial
<220> FEATURE:
<223> OTHER INFORMATION: CDR3 element

<400> SEQUENCE: 309

Ala Pro Tyr Arg Gly Gly Arg Asp Tyr Arg Trp Glu Tyr Glu Tyr Glu
1               5                   10                  15

Tyr
```

<210> SEQ ID NO 310
<211> LENGTH: 16
<212> TYPE: PRT
<213> ORGANISM: Artificial
<220> FEATURE:
<223> OTHER INFORMATION: CDR3 element

<400> SEQUENCE: 310

Lys Leu Ser Pro Tyr Tyr Asn Asp Phe Asp Ser Ser Asn Tyr Glu Tyr
1               5                   10                  15

<210> SEQ ID NO 311
<211> LENGTH: 13
<212> TYPE: PRT
<213> ORGANISM: Artificial
<220> FEATURE:
<223> OTHER INFORMATION: CDR3 element

<400> SEQUENCE: 311

Asn Arg Leu Arg Ser Thr Trp Gly Ile Arg Tyr Asp Val
1               5                   10

<210> SEQ ID NO 312
<211> LENGTH: 6
<212> TYPE: PRT
<213> ORGANISM: Artificial
<220> FEATURE:
<223> OTHER INFORMATION: CDR3 element

<400> SEQUENCE: 312

Arg Gly Tyr Gly Arg Asp
1               5

<210> SEQ ID NO 313
<211> LENGTH: 12
<212> TYPE: PRT
<213> ORGANISM: Artificial
<220> FEATURE:
<223> OTHER INFORMATION: CDR3 element

<400> SEQUENCE: 313

Glu Pro Ile Gly Ala Tyr Glu Gly Leu Trp Thr Tyr
1               5                   10

<210> SEQ ID NO 314
<211> LENGTH: 15
<212> TYPE: PRT
<213> ORGANISM: Artificial
<220> FEATURE:
<223> OTHER INFORMATION: CDR3 element

<400> SEQUENCE: 314

Ser Tyr Ser Asn Gly Asn Pro His Arg Phe Ser Gln Tyr Gln Tyr
1               5                   10                  15

<210> SEQ ID NO 315
<211> LENGTH: 11
<212> TYPE: PRT
<213> ORGANISM: Artificial
<220> FEATURE:
<223> OTHER INFORMATION: CDR3 element

<400> SEQUENCE: 315

Ala Asn Asn Ile Ala Thr Leu Arg Gln Gly Ser
1               5                   10

```
<210> SEQ ID NO 316
<211> LENGTH: 18
<212> TYPE: PRT
<213> ORGANISM: Artificial
<220> FEATURE:
<223> OTHER INFORMATION: CDR3 element

<400> SEQUENCE: 316

Val Gln Val Ile Asp Pro Ser Trp Ser Gly Val Asn Leu Asp Asp Tyr
1               5                   10                  15

Asp Tyr

<210> SEQ ID NO 317
<211> LENGTH: 16
<212> TYPE: PRT
<213> ORGANISM: Artificial
<220> FEATURE:
<223> OTHER INFORMATION: CDR3 element

<400> SEQUENCE: 317

Lys Leu Ser Pro Tyr Tyr Asn Asp Phe Asp Ser Ser Asn Tyr Glu Tyr
1               5                   10                  15

<210> SEQ ID NO 318
<211> LENGTH: 7
<212> TYPE: PRT
<213> ORGANISM: Artificial
<220> FEATURE:
<223> OTHER INFORMATION: CDR3 element

<400> SEQUENCE: 318

Val Pro Pro Arg Asp Asp Tyr
1               5

<210> SEQ ID NO 319
<211> LENGTH: 12
<212> TYPE: PRT
<213> ORGANISM: Artificial
<220> FEATURE:
<223> OTHER INFORMATION: CDR3 element

<400> SEQUENCE: 319

Pro Arg Tyr Glu Asn Gln Trp Ser Ser Tyr Asp Tyr
1               5                   10

<210> SEQ ID NO 320
<211> LENGTH: 18
<212> TYPE: PRT
<213> ORGANISM: Artificial
<220> FEATURE:
<223> OTHER INFORMATION: CDR3 element

<400> SEQUENCE: 320

Phe Ser Thr Gly Ala Asp Gly Ser Trp Tyr Trp Ser Tyr Gly Met
1               5                   10                  15

Asp Ser

<210> SEQ ID NO 321
<211> LENGTH: 12
<212> TYPE: PRT
<213> ORGANISM: Artificial
<220> FEATURE:
<223> OTHER INFORMATION: CDR3 element

<400> SEQUENCE: 321

Gly Gly Trp Gly Thr Thr Gln Tyr Asp Tyr Asp Tyr
```

<210> SEQ ID NO 322
<211> LENGTH: 6
<212> TYPE: PRT
<213> ORGANISM: Artificial
<220> FEATURE:
<223> OTHER INFORMATION: CDR3 element

<400> SEQUENCE: 322

Arg Gly Tyr Ala Leu Asp
1               5

<210> SEQ ID NO 323
<211> LENGTH: 17
<212> TYPE: PRT
<213> ORGANISM: Artificial
<220> FEATURE:
<223> OTHER INFORMATION: CDR3 element

<400> SEQUENCE: 323

Asp Ser Ser His Tyr Ser Tyr Val Tyr Ser Lys Ala Tyr Glu Tyr Asp
1               5                   10                  15
Tyr

<210> SEQ ID NO 324
<211> LENGTH: 6
<212> TYPE: PRT
<213> ORGANISM: Artificial
<220> FEATURE:
<223> OTHER INFORMATION: CDR3 element

<400> SEQUENCE: 324

Arg Gly Tyr Gly Arg Asp
1               5

<210> SEQ ID NO 325
<211> LENGTH: 18
<212> TYPE: PRT
<213> ORGANISM: Artificial
<220> FEATURE:
<223> OTHER INFORMATION: CDR3 element

<400> SEQUENCE: 325

Val Gln Pro Tyr Ser Gly Gly Asp Tyr Tyr Thr Gly Val Glu Glu Tyr
1               5                   10                  15
Asp Tyr

<210> SEQ ID NO 326
<211> LENGTH: 6
<212> TYPE: PRT
<213> ORGANISM: Artificial
<220> FEATURE:
<223> OTHER INFORMATION: CDR3 element

<400> SEQUENCE: 326

Arg Gly Tyr Gly Arg Asp
1               5

<210> SEQ ID NO 327
<211> LENGTH: 12
<212> TYPE: PRT
<213> ORGANISM: Artificial
<220> FEATURE:
<223> OTHER INFORMATION: CDR3 element

```
<400> SEQUENCE: 327

Ala Arg Tyr Asn Gly Thr Trp Ser Ser Asn Asp Tyr
1               5                   10

<210> SEQ ID NO 328
<211> LENGTH: 6
<212> TYPE: PRT
<213> ORGANISM: Artificial
<220> FEATURE:
<223> OTHER INFORMATION: CDR3 element

<400> SEQUENCE: 328

Arg Gly Tyr Ala Leu Asp
1               5

<210> SEQ ID NO 329
<211> LENGTH: 12
<212> TYPE: PRT
<213> ORGANISM: Artificial
<220> FEATURE:
<223> OTHER INFORMATION: CDR3 element

<400> SEQUENCE: 329

Pro Arg Tyr Ala Asp Gln Trp Ser Ala Tyr Asp Tyr
1               5                   10

<210> SEQ ID NO 330
<211> LENGTH: 6
<212> TYPE: PRT
<213> ORGANISM: Artificial
<220> FEATURE:
<223> OTHER INFORMATION: CDR3 element

<400> SEQUENCE: 330

Arg Gly Tyr Gly Arg Asp
1               5

<210> SEQ ID NO 331
<211> LENGTH: 10
<212> TYPE: PRT
<213> ORGANISM: Artificial
<220> FEATURE:
<223> OTHER INFORMATION: CDR3 element

<400> SEQUENCE: 331

Arg Thr Tyr Trp Ala His Leu Pro Thr Tyr
1               5                   10

<210> SEQ ID NO 332
<211> LENGTH: 12
<212> TYPE: PRT
<213> ORGANISM: Artificial
<220> FEATURE:
<223> OTHER INFORMATION: CDR3 element

<400> SEQUENCE: 332

Glu Pro Leu Ala Arg Tyr Glu Gly Leu Trp Thr Tyr
1               5                   10

<210> SEQ ID NO 333
<211> LENGTH: 12
<212> TYPE: PRT
<213> ORGANISM: Artificial
<220> FEATURE:
<223> OTHER INFORMATION: CDR3 element

<400> SEQUENCE: 333
```

Gly Gly Trp Gly Ile Ser Gln Ser Asp Tyr Asp Leu
1               5                   10

<210> SEQ ID NO 334
<211> LENGTH: 11
<212> TYPE: PRT
<213> ORGANISM: Artificial
<220> FEATURE:
<223> OTHER INFORMATION: FR4 element

<400> SEQUENCE: 334

Arg Gly Gln Gly Thr Gln Val Thr Val Ser Ser
1               5                   10

<210> SEQ ID NO 335
<211> LENGTH: 11
<212> TYPE: PRT
<213> ORGANISM: Artificial
<220> FEATURE:
<223> OTHER INFORMATION: FR4 element

<400> SEQUENCE: 335

Arg Gly Gln Gly Thr Gln Val Thr Val Ser Ser
1               5                   10

<210> SEQ ID NO 336
<211> LENGTH: 11
<212> TYPE: PRT
<213> ORGANISM: Artificial
<220> FEATURE:
<223> OTHER INFORMATION: FR4 element

<400> SEQUENCE: 336

Arg Gly Gln Gly Thr Gln Val Thr Val Ser Ser
1               5                   10

<210> SEQ ID NO 337
<211> LENGTH: 11
<212> TYPE: PRT
<213> ORGANISM: Artificial
<220> FEATURE:
<223> OTHER INFORMATION: FR4 element

<400> SEQUENCE: 337

Trp Gly Gln Gly Thr Gln Val Thr Val Ser Ser
1               5                   10

<210> SEQ ID NO 338
<211> LENGTH: 11
<212> TYPE: PRT
<213> ORGANISM: Artificial
<220> FEATURE:
<223> OTHER INFORMATION: FR4 element

<400> SEQUENCE: 338

Trp Gly Gln Gly Thr Gln Val Thr Val Ser Ser
1               5                   10

<210> SEQ ID NO 339
<211> LENGTH: 11
<212> TYPE: PRT
<213> ORGANISM: Artificial
<220> FEATURE:
<223> OTHER INFORMATION: FR4 element

<400> SEQUENCE: 339

Trp Gly Gln Gly Thr Gln Val Thr Val Ser Ser
1               5                   10

<210> SEQ ID NO 340
<211> LENGTH: 11
<212> TYPE: PRT
<213> ORGANISM: Artificial
<220> FEATURE:
<223> OTHER INFORMATION: FR4 element

<400> SEQUENCE: 340

Trp Gly Gln Gly Thr Gln Val Thr Val Ser Ser
1               5                   10

<210> SEQ ID NO 341
<211> LENGTH: 11
<212> TYPE: PRT
<213> ORGANISM: Artificial
<220> FEATURE:
<223> OTHER INFORMATION: FR4 element

<400> SEQUENCE: 341

Trp Gly Gln Gly Thr Gln Val Thr Val Ser Ser
1               5                   10

<210> SEQ ID NO 342
<211> LENGTH: 11
<212> TYPE: PRT
<213> ORGANISM: Artificial
<220> FEATURE:
<223> OTHER INFORMATION: FR4 element

<400> SEQUENCE: 342

Trp Gly Gln Gly Thr Gln Val Thr Val Ser Ser
1               5                   10

<210> SEQ ID NO 343
<211> LENGTH: 11
<212> TYPE: PRT
<213> ORGANISM: Artificial
<220> FEATURE:
<223> OTHER INFORMATION: FR4 element

<400> SEQUENCE: 343

Trp Gly Gln Gly Thr Gln Val Thr Val Ser Ser
1               5                   10

<210> SEQ ID NO 344
<211> LENGTH: 11
<212> TYPE: PRT
<213> ORGANISM: Artificial
<220> FEATURE:
<223> OTHER INFORMATION: FR4 element

<400> SEQUENCE: 344

Trp Gly Gln Gly Thr Gln Val Thr Val Ser Ser
1               5                   10

<210> SEQ ID NO 345
<211> LENGTH: 11
<212> TYPE: PRT
<213> ORGANISM: Artificial
<220> FEATURE:
<223> OTHER INFORMATION: FR4 element

<400> SEQUENCE: 345

Trp Gly Gln Gly Thr Gln Val Thr Val Ser Ser

```
1               5                   10

<210> SEQ ID NO 346
<211> LENGTH: 11
<212> TYPE: PRT
<213> ORGANISM: Artificial
<220> FEATURE:
<223> OTHER INFORMATION: FR4 element

<400> SEQUENCE: 346

Arg Ser Lys Gly Ile Gln Val Thr Val Ala Ser
1               5                   10

<210> SEQ ID NO 347
<211> LENGTH: 11
<212> TYPE: PRT
<213> ORGANISM: Artificial
<220> FEATURE:
<223> OTHER INFORMATION: FR4 element

<400> SEQUENCE: 347

Trp Gly Gln Gly Thr Gln Val Thr Val Ser Ser
1               5                   10

<210> SEQ ID NO 348
<211> LENGTH: 11
<212> TYPE: PRT
<213> ORGANISM: Artificial
<220> FEATURE:
<223> OTHER INFORMATION: FR4 element

<400> SEQUENCE: 348

Trp Gly Gln Gly Thr Gln Val Thr Val Ser Ser
1               5                   10

<210> SEQ ID NO 349
<211> LENGTH: 11
<212> TYPE: PRT
<213> ORGANISM: Artificial
<220> FEATURE:
<223> OTHER INFORMATION: FR4 element

<400> SEQUENCE: 349

Trp Gly Gln Gly Thr Gln Val Thr Val Ser Ser
1               5                   10

<210> SEQ ID NO 350
<211> LENGTH: 11
<212> TYPE: PRT
<213> ORGANISM: Artificial
<220> FEATURE:
<223> OTHER INFORMATION: FR4 element

<400> SEQUENCE: 350

Leu Gly Ser Gly Thr Gln Val Thr Val Ser Ser
1               5                   10

<210> SEQ ID NO 351
<211> LENGTH: 11
<212> TYPE: PRT
<213> ORGANISM: Artificial
<220> FEATURE:
<223> OTHER INFORMATION: FR4 element

<400> SEQUENCE: 351

Trp Gly Gln Gly Thr Gln Val Thr Val Ser Ser
1               5                   10
```

```
<210> SEQ ID NO 352
<211> LENGTH: 11
<212> TYPE: PRT
<213> ORGANISM: Artificial
<220> FEATURE:
<223> OTHER INFORMATION: FR4 element

<400> SEQUENCE: 352

Trp Gly Gln Gly Thr Gln Val Thr Val Ser Ser
1               5                   10

<210> SEQ ID NO 353
<211> LENGTH: 11
<212> TYPE: PRT
<213> ORGANISM: Artificial
<220> FEATURE:
<223> OTHER INFORMATION: FR4 element

<400> SEQUENCE: 353

Trp Gly Gln Gly Thr Gln Val Thr Val Ser Ser
1               5                   10

<210> SEQ ID NO 354
<211> LENGTH: 11
<212> TYPE: PRT
<213> ORGANISM: Artificial
<220> FEATURE:
<223> OTHER INFORMATION: FR4 element

<400> SEQUENCE: 354

Trp Gly Lys Gly Thr Gln Val Thr Val Ser Ser
1               5                   10

<210> SEQ ID NO 355
<211> LENGTH: 11
<212> TYPE: PRT
<213> ORGANISM: Artificial
<220> FEATURE:
<223> OTHER INFORMATION: FR4 element

<400> SEQUENCE: 355

Trp Gly Gln Gly Thr Gln Val Thr Val Ser Ser
1               5                   10

<210> SEQ ID NO 356
<211> LENGTH: 11
<212> TYPE: PRT
<213> ORGANISM: Artificial
<220> FEATURE:
<223> OTHER INFORMATION: FR4 element

<400> SEQUENCE: 356

Arg Gly Gln Gly Thr Gln Val Thr Val Ser Ser
1               5                   10

<210> SEQ ID NO 357
<211> LENGTH: 11
<212> TYPE: PRT
<213> ORGANISM: Artificial
<220> FEATURE:
<223> OTHER INFORMATION: FR4 element

<400> SEQUENCE: 357

Trp Gly Gln Gly Thr Gln Val Thr Val Ser Ser
1               5                   10
```

```
<210> SEQ ID NO 358
<211> LENGTH: 11
<212> TYPE: PRT
<213> ORGANISM: Artificial
<220> FEATURE:
<223> OTHER INFORMATION: FR4 element

<400> SEQUENCE: 358

Arg Ser Gln Gly Ile Gln Val Thr Val Ser Ser
1               5                   10

<210> SEQ ID NO 359
<211> LENGTH: 11
<212> TYPE: PRT
<213> ORGANISM: Artificial
<220> FEATURE:
<223> OTHER INFORMATION: FR4 element
<220> FEATURE:
<221> NAME/KEY: MISC_FEATURE
<222> LOCATION: (3)..(3)
<223> OTHER INFORMATION: Unknown amino acid residue

<400> SEQUENCE: 359

Trp Gly Xaa Gly Thr Gln Val Thr Val Ser Ser
1               5                   10

<210> SEQ ID NO 360
<211> LENGTH: 11
<212> TYPE: PRT
<213> ORGANISM: Artificial
<220> FEATURE:
<223> OTHER INFORMATION: FR4 element

<400> SEQUENCE: 360

Arg Ser Arg Gly Ile Gln Val Thr Val Ser Ser
1               5                   10

<210> SEQ ID NO 361
<211> LENGTH: 11
<212> TYPE: PRT
<213> ORGANISM: Artificial
<220> FEATURE:
<223> OTHER INFORMATION: FR4 element

<400> SEQUENCE: 361

Trp Gly Gln Gly Thr Gln Val Thr Val Ser Ser
1               5                   10

<210> SEQ ID NO 362
<211> LENGTH: 11
<212> TYPE: PRT
<213> ORGANISM: Artificial
<220> FEATURE:
<223> OTHER INFORMATION: FR4 element

<400> SEQUENCE: 362

Arg Gly Gln Gly Thr Gln Val Thr Val Ser Ser
1               5                   10

<210> SEQ ID NO 363
<211> LENGTH: 11
<212> TYPE: PRT
<213> ORGANISM: Artificial
<220> FEATURE:
<223> OTHER INFORMATION: FR4 element

<400> SEQUENCE: 363
```

Trp Gly Gln Gly Thr Gln Val Thr Val Ser Ser
1               5                   10

<210> SEQ ID NO 364
<211> LENGTH: 11
<212> TYPE: PRT
<213> ORGANISM: Artificial
<220> FEATURE:
<223> OTHER INFORMATION: FR4 element

<400> SEQUENCE: 364

Arg Ser Lys Gly Ile Gln Val Thr Val Ser Ser
1               5                   10

<210> SEQ ID NO 365
<211> LENGTH: 11
<212> TYPE: PRT
<213> ORGANISM: Artificial
<220> FEATURE:
<223> OTHER INFORMATION: FR4 element

<400> SEQUENCE: 365

Trp Gly Gln Gly Thr Gln Val Thr Val Ser Ser
1               5                   10

<210> SEQ ID NO 366
<211> LENGTH: 11
<212> TYPE: PRT
<213> ORGANISM: Artificial
<220> FEATURE:
<223> OTHER INFORMATION: FR4 element

<400> SEQUENCE: 366

Trp Gly Gln Gly Thr Gln Val Thr Val Ser Ser
1               5                   10

<210> SEQ ID NO 367
<211> LENGTH: 11
<212> TYPE: PRT
<213> ORGANISM: Artificial
<220> FEATURE:
<223> OTHER INFORMATION: FR4 element

<400> SEQUENCE: 367

Trp Gly Gln Gly Thr Gln Val Thr Val Ser Ser
1               5                   10

<210> SEQ ID NO 368
<211> LENGTH: 30
<212> TYPE: PRT
<213> ORGANISM: Artificial
<220> FEATURE:
<223> OTHER INFORMATION: FR1 element

<400> SEQUENCE: 368

Ala Val Gln Leu Val Glu Ser Gly Gly Gly Leu Val Gln Gly Gly
1               5                   10                  15

Ser Leu Arg Leu Ala Cys Ala Ala Ser Glu Arg Ile Phe Asp
                20                  25                  30

<210> SEQ ID NO 369
<211> LENGTH: 30
<212> TYPE: PRT
<213> ORGANISM: Artificial
<220> FEATURE:
<223> OTHER INFORMATION: FR1 element -continued

```
<400> SEQUENCE: 369

Glu Val Gln Leu Val Glu Ser Gly Gly Gly Leu Val Gln Gly Gly
1               5                   10                  15

Ser Leu Arg Leu Ala Cys Ala Ala Ser Glu Arg Ile Trp Asp
            20                  25                  30

<210> SEQ ID NO 370
<211> LENGTH: 30
<212> TYPE: PRT
<213> ORGANISM: Artificial
<220> FEATURE:
<223> OTHER INFORMATION: FR1 element

<400> SEQUENCE: 370

Ala Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg
            20                  25                  30

<210> SEQ ID NO 371
<211> LENGTH: 30
<212> TYPE: PRT
<213> ORGANISM: Artificial
<220> FEATURE:
<223> OTHER INFORMATION: FR1 element

<400> SEQUENCE: 371

Ala Val Gln Leu Val Asp Ser Gly Gly Gly Leu Val Gln Pro Gly Gly
1               5                   10                  15

Ser Leu Arg Leu Ser Cys Ala Ala Ser Gly Phe Ser Phe Gly
            20                  25                  30

<210> SEQ ID NO 372
<211> LENGTH: 30
<212> TYPE: PRT
<213> ORGANISM: Artificial
<220> FEATURE:
<223> OTHER INFORMATION: FR1 element

<400> SEQUENCE: 372

Ala Val Gln Leu Val Glu Ser Gly Gly Gly Leu Val Gln Pro Gly Gly
1               5                   10                  15

Ser Leu Arg Leu Thr Cys Thr Ala Ser Gly Phe Thr Phe Arg
            20                  25                  30

<210> SEQ ID NO 373
<211> LENGTH: 30
<212> TYPE: PRT
<213> ORGANISM: Artificial
<220> FEATURE:
<223> OTHER INFORMATION: FR1 element

<400> SEQUENCE: 373

Gln Val Gln Leu Ala Glu Ser Gly Gly Gly Leu Val Gln Pro Gly Gly
1               5                   10                  15

Ser Leu Arg Leu Thr Cys Thr Ala Ser Gly Phe Thr Phe Gly
            20                  25                  30

<210> SEQ ID NO 374
<211> LENGTH: 30
<212> TYPE: PRT
<213> ORGANISM: Artificial
<220> FEATURE:
<223> OTHER INFORMATION: FR1 element
```

<400> SEQUENCE: 374

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 375
<211> LENGTH: 5
<212> TYPE: PRT
<213> ORGANISM: Artificial
<220> FEATURE:
<223> OTHER INFORMATION: CDR1 element

<400> SEQUENCE: 375

Leu Asn Leu Met Gly
1               5

<210> SEQ ID NO 376
<211> LENGTH: 5
<212> TYPE: PRT
<213> ORGANISM: Artificial
<220> FEATURE:
<223> OTHER INFORMATION: CDR1 element

<400> SEQUENCE: 376

Ile Asn Leu Leu Gly
1               5

<210> SEQ ID NO 377
<211> LENGTH: 5
<212> TYPE: PRT
<213> ORGANISM: Artificial
<220> FEATURE:
<223> OTHER INFORMATION: CDR1 element

<400> SEQUENCE: 377

Ser Phe Gly Met Ser
1               5

<210> SEQ ID NO 378
<211> LENGTH: 5
<212> TYPE: PRT
<213> ORGANISM: Artificial
<220> FEATURE:
<223> OTHER INFORMATION: CDR1 element

<400> SEQUENCE: 378

Ser Phe Gly Met Ser
1               5

<210> SEQ ID NO 379
<211> LENGTH: 5
<212> TYPE: PRT
<213> ORGANISM: Artificial
<220> FEATURE:
<223> OTHER INFORMATION: CDR1 element

<400> SEQUENCE: 379

Ser Phe Gly Met Ser
1               5

<210> SEQ ID NO 380
<211> LENGTH: 5
<212> TYPE: PRT
<213> ORGANISM: Artificial

```
<220> FEATURE:
<223> OTHER INFORMATION: CDR1 element

<400> SEQUENCE: 380

Ser Phe Gly Met Ser
1               5

<210> SEQ ID NO 381
<211> LENGTH: 5
<212> TYPE: PRT
<213> ORGANISM: Artificial
<220> FEATURE:
<223> OTHER INFORMATION: CDR1 element

<400> SEQUENCE: 381

Asn Tyr Trp Met Tyr
1               5

<210> SEQ ID NO 382
<211> LENGTH: 14
<212> TYPE: PRT
<213> ORGANISM: Artificial
<220> FEATURE:
<223> OTHER INFORMATION: FR2 element

<400> SEQUENCE: 382

Trp Tyr Arg Gln Gly Pro Gly Asn Glu Arg Glu Leu Val Ala
1               5                   10

<210> SEQ ID NO 383
<211> LENGTH: 14
<212> TYPE: PRT
<213> ORGANISM: Artificial
<220> FEATURE:
<223> OTHER INFORMATION: FR2 element

<400> SEQUENCE: 383

Trp Tyr Arg Gln Gly Pro Gly Asn Glu Arg Glu Leu Val Ala
1               5                   10

<210> SEQ ID NO 384
<211> LENGTH: 14
<212> TYPE: PRT
<213> ORGANISM: Artificial
<220> FEATURE:
<223> OTHER INFORMATION: FR2 element

<400> SEQUENCE: 384

Trp Val Arg Gln Ala Pro Gly Lys Glu Pro Glu Trp Val Ser
1               5                   10

<210> SEQ ID NO 385
<211> LENGTH: 14
<212> TYPE: PRT
<213> ORGANISM: Artificial
<220> FEATURE:
<223> OTHER INFORMATION: FR2 element

<400> SEQUENCE: 385

Trp Val Arg Gln Tyr Pro Gly Lys Glu Pro Glu Trp Val Ser
1               5                   10

<210> SEQ ID NO 386
<211> LENGTH: 14
<212> TYPE: PRT
<213> ORGANISM: Artificial
<220> FEATURE:
```

```
<223> OTHER INFORMATION: FR2 element

<400> SEQUENCE: 386

Trp Val Arg Gln Ala Pro Gly Lys Asp Gln Glu Trp Val Ser
1               5                   10

<210> SEQ ID NO 387
<211> LENGTH: 14
<212> TYPE: PRT
<213> ORGANISM: Artificial
<220> FEATURE:
<223> OTHER INFORMATION: FR2 element

<400> SEQUENCE: 387

Trp Val Arg Gln Ala Pro Gly Glu Gly Leu Glu Trp Val Ser
1               5                   10

<210> SEQ ID NO 388
<211> LENGTH: 14
<212> TYPE: PRT
<213> ORGANISM: Artificial
<220> FEATURE:
<223> OTHER INFORMATION: FR2 element

<400> SEQUENCE: 388

Trp Val Arg Val Ala Pro Gly Lys Gly Leu Glu Arg Ile Ser
1               5                   10

<210> SEQ ID NO 389
<211> LENGTH: 17
<212> TYPE: PRT
<213> ORGANISM: Artificial
<220> FEATURE:
<223> OTHER INFORMATION: CDR2 element

<400> SEQUENCE: 389

Thr Cys Ile Thr Val Gly Asp Ser Thr Asn Tyr Ala Asp Ser Val Lys
1               5                   10                  15
Gly

<210> SEQ ID NO 390
<211> LENGTH: 16
<212> TYPE: PRT
<213> ORGANISM: Artificial
<220> FEATURE:
<223> OTHER INFORMATION: CDR2 element

<400> SEQUENCE: 390

Thr Ile Thr Val Gly Asp Ser Thr Ser Tyr Ala Asp Ser Val Lys Gly
1               5                   10                  15

<210> SEQ ID NO 391
<211> LENGTH: 17
<212> TYPE: PRT
<213> ORGANISM: Artificial
<220> FEATURE:
<223> OTHER INFORMATION: CDR2 element

<400> SEQUENCE: 391

Ser Ile Ser Gly Ser Gly Ser Asp Thr Leu Tyr Ala Asp Ser Val Lys
1               5                   10                  15
Gly

<210> SEQ ID NO 392
<211> LENGTH: 17
```

```
<212> TYPE: PRT
<213> ORGANISM: Artificial
<220> FEATURE:
<223> OTHER INFORMATION: CDR2 element

<400> SEQUENCE: 392

Ser Ile Asn Gly Arg Gly Asp Asp Thr Arg Tyr Ala Asp Ser Val Lys
1               5                   10                  15

Gly

<210> SEQ ID NO 393
<211> LENGTH: 17
<212> TYPE: PRT
<213> ORGANISM: Artificial
<220> FEATURE:
<223> OTHER INFORMATION: CDR2 element

<400> SEQUENCE: 393

Ala Ile Ser Ala Asp Ser Ser Thr Lys Asn Tyr Ala Asp Ser Val Lys
1               5                   10                  15

Gly

<210> SEQ ID NO 394
<211> LENGTH: 17
<212> TYPE: PRT
<213> ORGANISM: Artificial
<220> FEATURE:
<223> OTHER INFORMATION: CDR2 element

<400> SEQUENCE: 394

Ala Ile Ser Ala Asp Ser Ser Asp Lys Arg Tyr Ala Asp Ser Val Lys
1               5                   10                  15

Gly

<210> SEQ ID NO 395
<211> LENGTH: 18
<212> TYPE: PRT
<213> ORGANISM: Artificial
<220> FEATURE:
<223> OTHER INFORMATION: CDR2 element

<400> SEQUENCE: 395

Arg Asp Ile Ser Thr Gly Gly Gly Tyr Ser Tyr Tyr Ala Asp Ser Val
1               5                   10                  15

Lys Gly

<210> SEQ ID NO 396
<211> LENGTH: 32
<212> TYPE: PRT
<213> ORGANISM: Artificial
<220> FEATURE:
<223> OTHER INFORMATION: FR3 element

<400> SEQUENCE: 396

Arg Phe Thr Ile Ser Met Asp Tyr Thr Lys Gln Thr Val Tyr Leu His
1               5                   10                  15

Met Asn Ser Leu Arg Pro Glu Asp Thr Gly Leu Tyr Tyr Cys Lys Ile
                20                  25                  30

<210> SEQ ID NO 397
<211> LENGTH: 32
<212> TYPE: PRT
<213> ORGANISM: Artificial
<220> FEATURE:
```

<223> OTHER INFORMATION: FR3 element

<400> SEQUENCE: 397

Arg Phe Thr Ile Ser Arg Asp Tyr Asp Lys Asn Thr Leu Tyr Leu Gln
1               5                   10                  15

Met Asn Ser Leu Arg Pro Glu Asp Thr Gly Leu Tyr Tyr Cys Lys Ile
            20                  25                  30

<210> SEQ ID NO 398
<211> LENGTH: 32
<212> TYPE: PRT
<213> ORGANISM: Artificial
<220> FEATURE:
<223> OTHER INFORMATION: FR3 element

<400> SEQUENCE: 398

Arg Phe Thr Ile Ser Arg Asp Asn Ala Lys Thr Thr Leu Tyr Leu Gln
1               5                   10                  15

Met Asn Ser Leu Lys Pro Glu Asp Thr Ala Val Tyr Tyr Cys Thr Ile
            20                  25                  30

<210> SEQ ID NO 399
<211> LENGTH: 32
<212> TYPE: PRT
<213> ORGANISM: Artificial
<220> FEATURE:
<223> OTHER INFORMATION: FR3 element

<400> SEQUENCE: 399

Arg Phe Ser Ile Ser Arg Asp Asn Ala Lys Asn Thr Leu Tyr Leu Gln
1               5                   10                  15

Met Asn Ser Leu Lys Pro Glu Asp Thr Ala Glu Tyr Tyr Cys Thr Ile
            20                  25                  30

<210> SEQ ID NO 400
<211> LENGTH: 32
<212> TYPE: PRT
<213> ORGANISM: Artificial
<220> FEATURE:
<223> OTHER INFORMATION: FR3 element

<400> SEQUENCE: 400

Arg Phe Thr Ile Ser Arg Asp Asn Ala Lys Lys Met Leu Tyr Leu Glu
1               5                   10                  15

Met Asn Ser Leu Lys Pro Glu Asp Thr Ala Val Tyr Tyr Cys Val Ile
            20                  25                  30

<210> SEQ ID NO 401
<211> LENGTH: 32
<212> TYPE: PRT
<213> ORGANISM: Artificial
<220> FEATURE:
<223> OTHER INFORMATION: FR3 element

<400> SEQUENCE: 401

Arg Phe Thr Ile Ser Arg Asp Asn Ala Lys Lys Met Leu Tyr Leu Glu
1               5                   10                  15

Met Asn Ser Leu Lys Ser Glu Asp Thr Ala Val Tyr Tyr Cys Val Ile
            20                  25                  30

<210> SEQ ID NO 402
<211> LENGTH: 32
<212> TYPE: PRT
<213> ORGANISM: Artificial

```
<220> FEATURE:
<223> OTHER INFORMATION: FR3 element

<400> SEQUENCE: 402

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Leu Tyr Tyr Cys Ala Lys
                20                  25                  30

<210> SEQ ID NO 403
<211> LENGTH: 8
<212> TYPE: PRT
<213> ORGANISM: Artificial
<220> FEATURE:
<223> OTHER INFORMATION: CDR3 element

<400> SEQUENCE: 403

Arg Arg Thr Trp His Ser Glu Leu
1               5

<210> SEQ ID NO 404
<211> LENGTH: 8
<212> TYPE: PRT
<213> ORGANISM: Artificial
<220> FEATURE:
<223> OTHER INFORMATION: CDR3 element

<400> SEQUENCE: 404

Arg Arg Thr Trp His Ser Glu Leu
1               5

<210> SEQ ID NO 405
<211> LENGTH: 6
<212> TYPE: PRT
<213> ORGANISM: Artificial
<220> FEATURE:
<223> OTHER INFORMATION: CDR3 element

<400> SEQUENCE: 405

Gly Gly Ser Leu Ser Arg
1               5

<210> SEQ ID NO 406
<211> LENGTH: 7
<212> TYPE: PRT
<213> ORGANISM: Artificial
<220> FEATURE:
<223> OTHER INFORMATION: CDR3 element

<400> SEQUENCE: 406

Gly Arg Ser Val Ser Arg Ser
1               5

<210> SEQ ID NO 407
<211> LENGTH: 5
<212> TYPE: PRT
<213> ORGANISM: Artificial
<220> FEATURE:
<223> OTHER INFORMATION: CDR3 element

<400> SEQUENCE: 407

Gly Arg Gly Ser Pro
1               5

<210> SEQ ID NO 408
<211> LENGTH: 5
```

```
<212> TYPE: PRT
<213> ORGANISM: Artificial
<220> FEATURE:
<223> OTHER INFORMATION: CDR3 element

<400> SEQUENCE: 408

Gly Arg Gly Ser Pro
1               5

<210> SEQ ID NO 409
<211> LENGTH: 13
<212> TYPE: PRT
<213> ORGANISM: Artificial
<220> FEATURE:
<223> OTHER INFORMATION: CDR3 element

<400> SEQUENCE: 409

Asp Arg Glu Ala Gln Val Asp Thr Leu Asp Phe Asp Tyr
1               5                   10

<210> SEQ ID NO 410
<211> LENGTH: 11
<212> TYPE: PRT
<213> ORGANISM: Artificial
<220> FEATURE:
<223> OTHER INFORMATION: FR4 element

<400> SEQUENCE: 410

Trp Gly Gln Gly Thr Gln Val Thr Val Ser Ser
1               5                   10

<210> SEQ ID NO 411
<211> LENGTH: 11
<212> TYPE: PRT
<213> ORGANISM: Artificial
<220> FEATURE:
<223> OTHER INFORMATION: FR4 element

<400> SEQUENCE: 411

Trp Gly Gln Gly Thr Gln Val Thr Val Ser Ser
1               5                   10

<210> SEQ ID NO 412
<211> LENGTH: 11
<212> TYPE: PRT
<213> ORGANISM: Artificial
<220> FEATURE:
<223> OTHER INFORMATION: FR4 element

<400> SEQUENCE: 412

Ser Ser Gln Gly Thr Gln Val Thr Val Ser Ser
1               5                   10

<210> SEQ ID NO 413
<211> LENGTH: 11
<212> TYPE: PRT
<213> ORGANISM: Artificial
<220> FEATURE:
<223> OTHER INFORMATION: FR4 element

<400> SEQUENCE: 413

Arg Thr Gln Gly Thr Gln Val Thr Val Ser Ser
1               5                   10

<210> SEQ ID NO 414
<211> LENGTH: 11
<212> TYPE: PRT
```

<213> ORGANISM: Artificial
<220> FEATURE:
<223> OTHER INFORMATION: FR4 element

<400> SEQUENCE: 414

```
Ser Ser Pro Gly Thr Gln Val Thr Val Ser Ser
1               5                   10
```

<210> SEQ ID NO 415
<211> LENGTH: 11
<212> TYPE: PRT
<213> ORGANISM: Artificial
<220> FEATURE:
<223> OTHER INFORMATION: FR4 element

<400> SEQUENCE: 415

```
Ala Ser Gln Gly Thr Gln Val Thr Val Ser Ser
1               5                   10
```

<210> SEQ ID NO 416
<211> LENGTH: 11
<212> TYPE: PRT
<213> ORGANISM: Artificial
<220> FEATURE:
<223> OTHER INFORMATION: FR4 element

<400> SEQUENCE: 416

```
Arg Gly Gln Gly Thr Gln Val Thr Val Ser Ser
1               5                   10
```

<210> SEQ ID NO 417
<211> LENGTH: 363
<212> TYPE: PRT
<213> ORGANISM: Artificial
<220> FEATURE:
<223> OTHER INFORMATION: nanobody construct

<400> SEQUENCE: 417

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Ser Pro Ser Gly Phe Asn Arg Gly Gln Gly Thr Leu Val Thr
            100                 105                 110

Val Ser Ser Gly Gly Gly Gly Ser Gly Gly Gly Ser Glu Val Gln Leu
        115                 120                 125

Val Glu Ser Gly Gly Gly Leu Val Gln Pro Gly Asn Ser Leu Arg Leu
    130                 135                 140

Ser Cys Ala Ala Ser Gly Phe Thr Phe Ser Ser Phe Gly Met Ser Trp
145                 150                 155                 160

Val Arg Gln Ala Pro Gly Lys Gly Leu Glu Trp Val Ser Ser Ile Ser
                165                 170                 175

Gly Ser Gly Ser Asp Thr Leu Tyr Ala Asp Ser Val Lys Gly Arg Phe
```

```
            180                185                190
Thr Ile Ser Arg Asp Asn Ala Lys Thr Thr Leu Tyr Leu Gln Met Asn
            195                200                205
Ser Leu Arg Pro Glu Asp Thr Ala Val Tyr Tyr Cys Thr Ile Gly Gly
            210                215                220
Ser Leu Ser Arg Ser Ser Gln Gly Thr Leu Val Thr Val Ser Ser Gly
225                230                235                240
Gly Gly Gly Ser Gly Gly Gly Ser Glu Val Gln Leu Val Glu Ser Gly
            245                250                255
Gly Gly Leu Val Gln Pro Gly Gly Ser Leu Arg Leu Ser Cys Ala Ala
            260                265                270
Ser Gly Phe Thr Phe Ser Asp Tyr Trp Met Tyr Trp Val Arg Gln Ala
            275                280                285
Pro Gly Lys Gly Leu Glu Trp Val Ser Glu Ile Asn Thr Asn Gly Leu
            290                295                300
Ile Thr Lys Tyr Pro Asp Ser Val Lys Gly Arg Phe Thr Ile Ser Arg
305                310                315                320
Asp Asn Ala Lys Asn Thr Leu Tyr Leu Gln Met Asn Ser Leu Arg Pro
            325                330                335
Glu Asp Thr Ala Val Tyr Tyr Cys Ala Arg Ser Pro Ser Gly Phe Asn
            340                345                350
Arg Gly Gln Gly Thr Leu Val Thr Val Ser Ser
            355                360
```

<210> SEQ ID NO 418
<211> LENGTH: 379
<212> TYPE: PRT
<213> ORGANISM: Artificial
<220> FEATURE:
<223> OTHER INFORMATION: nanobody construct

<400> SEQUENCE: 418

```
Glu Val Gln Leu Val Glu Ser Gly Gly Gly Leu Val Gln Pro Gly Gly
1               5                  10                 15
Ser Leu Arg Leu Ser Cys Ala Ala Ser Gly Arg Ser Leu Ser Asn Tyr
            20                 25                 30
Tyr Met Gly Trp Phe Arg Gln Ala Pro Gly Lys Gly Arg Glu Leu Leu
            35                 40                 45
Gly Asn Ile Ser Trp Arg Gly Tyr Asn Ile Tyr Tyr Lys Asp Ser Val
            50                 55                 60
Lys Gly Arg Phe Thr Ile Ser Arg Asp Ser Lys Asn Thr Ile Tyr
65                70                 75                 80
Leu Gln Met Asn Ser Leu Arg Pro Glu Asp Thr Ala Val Tyr Tyr Cys
            85                 90                 95
Ala Ala Ser Ile Leu Pro Leu Ser Asp Asp Pro Gly Trp Asn Thr Tyr
            100                105                110
Trp Gly Gln Gly Thr Leu Val Thr Val Ser Ser Gly Gly Gly Ser
            115                120                125
Gly Gly Gly Ser Glu Val Gln Leu Val Glu Ser Gly Gly Gly Leu Val
130                135                140
Gln Pro Gly Asn Ser Leu Arg Leu Ser Cys Ala Ala Ser Gly Phe Thr
145                150                155                160
Phe Ser Ser Phe Gly Met Ser Trp Val Arg Gln Ala Pro Gly Lys Gly
            165                170                175
Leu Glu Trp Val Ser Ser Ile Ser Gly Ser Gly Ser Asp Thr Leu Tyr
```

```
            180                 185                 190
Ala Asp Ser Val Lys Gly Arg Phe Thr Ile Ser Arg Asp Asn Ala Lys
        195                 200                 205

Thr Thr Leu Tyr Leu Gln Met Asn Ser Leu Arg Pro Glu Asp Thr Ala
        210                 215                 220

Val Tyr Tyr Cys Thr Ile Gly Gly Ser Leu Ser Arg Ser Ser Gln Gly
225                 230                 235                 240

Thr Leu Val Thr Val Ser Ser Gly Gly Gly Ser Gly Gly Gly Ser
                245                 250                 255

Glu Val Gln Leu Val Glu Ser Gly Gly Gly Leu Val Gln Pro Gly Gly
            260                 265                 270

Ser Leu Arg Leu Ser Cys Ala Ala Ser Gly Arg Ser Leu Ser Asn Tyr
        275                 280                 285

Tyr Met Gly Trp Phe Arg Gln Ala Pro Gly Lys Gly Arg Glu Leu Leu
        290                 295                 300

Gly Asn Ile Ser Trp Arg Gly Tyr Asn Ile Tyr Tyr Lys Asp Ser Val
305                 310                 315                 320

Lys Gly Arg Phe Thr Ile Ser Arg Asp Asp Ser Lys Asn Thr Ile Tyr
                325                 330                 335

Leu Gln Met Asn Ser Leu Arg Pro Glu Asp Thr Ala Val Tyr Tyr Cys
                340                 345                 350

Ala Ala Ser Ile Leu Pro Leu Ser Asp Asp Pro Gly Trp Asn Thr Tyr
            355                 360                 365

Trp Gly Gln Gly Thr Leu Val Thr Val Ser Ser
        370                 375

<210> SEQ ID NO 419
<211> LENGTH: 260
<212> TYPE: PRT
<213> ORGANISM: Artificial
<220> FEATURE:
<223> OTHER INFORMATION: nanobody construct

<400> SEQUENCE: 419

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Ser Pro Ser Gly Phe Asn Arg Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Glu Val Gln Leu Val Glu Ser Gly Gly Gly Leu Val Gln Pro Gly
145                 150                 155                 160

Gly Ser Leu Arg Leu Ser Cys Ala Ala Ser Gly Phe Thr Phe Ser Asp
```

```
                    165                 170                 175
Tyr Trp Met Tyr Trp Val Arg Gln Ala Pro Gly Lys Gly Leu Glu Trp
                180                 185                 190

Val Ser Glu Ile Asn Thr Asn Gly Leu Ile Thr Lys Tyr Pro Asp Ser
            195                 200                 205

Val Lys Gly Arg Phe Thr Ile Ser Arg Asp Asn Ala Lys Asn Thr Leu
        210                 215                 220

Tyr Leu Gln Met Asn Ser Leu Arg Pro Glu Asp Thr Ala Val Tyr Tyr
225                 230                 235                 240

Cys Ala Arg Ser Pro Ser Gly Phe Asn Arg Gly Gln Gly Thr Leu Val
                245                 250                 255

Thr Val Ser Cys
            260

<210> SEQ ID NO 420
<211> LENGTH: 264
<212> TYPE: PRT
<213> ORGANISM: Artificial
<220> FEATURE:
<223> OTHER INFORMATION: nanobody construct

<400> SEQUENCE: 420

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Ser Pro Ser Gly Phe Asn Arg Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Glu Val Gln Leu Val Glu Ser Gly Gly Gly Leu Val Gln Pro Gly
145                 150                 155                 160

Gly Ser Leu Arg Leu Ser Cys Ala Ala Ser Gly Phe Thr Phe Ser Asp
                165                 170                 175

Tyr Trp Met Tyr Trp Val Arg Gln Ala Pro Gly Lys Gly Leu Glu Trp
            180                 185                 190

Val Ser Glu Ile Asn Thr Asn Gly Leu Ile Thr Lys Tyr Pro Asp Ser
        195                 200                 205

Val Lys Gly Arg Phe Thr Ile Ser Arg Asp Asn Ala Lys Asn Thr Leu
    210                 215                 220

Tyr Leu Gln Met Asn Ser Leu Arg Pro Glu Asp Thr Ala Val Tyr Tyr
225                 230                 235                 240

Cys Ala Arg Ser Pro Ser Gly Phe Asn Arg Gly Gln Gly Thr Leu Val
                245                 250                 255

Thr Val Ser Ser Gly Gly Gly Cys
```

```
                    260

<210> SEQ ID NO 421
<211> LENGTH: 20
<212> TYPE: DNA
<213> ORGANISM: Artificial
<220> FEATURE:
<223> OTHER INFORMATION: oligonucleotide primer

<400> SEQUENCE: 421
ggataacaat ttcacacagg                                             20

<210> SEQ ID NO 422
<211> LENGTH: 55
<212> TYPE: DNA
<213> ORGANISM: Artificial
<220> FEATURE:
<223> OTHER INFORMATION: oligonucleotide primer

<400> SEQUENCE: 422
tcagtaacct ggatccgcca ccgctgcctc caccgcctga ggagacggtg accag       55

<210> SEQ ID NO 423
<211> LENGTH: 39
<212> TYPE: DNA
<213> ORGANISM: Artificial
<220> FEATURE:
<223> OTHER INFORMATION: oligonucleotide primer

<400> SEQUENCE: 423
aggttactga ggatccgagg tgcagctggt ggagtctgg                        39

<210> SEQ ID NO 424
<211> LENGTH: 46
<212> TYPE: DNA
<213> ORGANISM: Artificial
<220> FEATURE:
<223> OTHER INFORMATION: oligonucleotide primer

<400> SEQUENCE: 424
tcagtaacct tccggaaccg ccaccgcctg aggagacggt gacaag                46

<210> SEQ ID NO 425
<211> LENGTH: 48
<212> TYPE: DNA
<213> ORGANISM: Artificial
<220> FEATURE:
<223> OTHER INFORMATION: oligonucleotide primer

<400> SEQUENCE: 425
aggttactga tccggaggcg gtagcgaggt gcagctggtg gagtctgg              48

<210> SEQ ID NO 426
<211> LENGTH: 19
<212> TYPE: DNA
<213> ORGANISM: Artificial
<220> FEATURE:
<223> OTHER INFORMATION: oligonucleotide primer

<400> SEQUENCE: 426
cacgacgttg taaaacgac                                              19

<210> SEQ ID NO 427
<211> LENGTH: 43
<212> TYPE: DNA
<213> ORGANISM: Artificial
```

<220> FEATURE:
<223> OTHER INFORMATION: oligonucleotide primer

<400> SEQUENCE: 427
atggtggtgt gcggccgcct attatgagga gacggtgacc agg    43

<210> SEQ ID NO 428
<211> LENGTH: 45
<212> TYPE: DNA
<213> ORGANISM: Artificial
<220> FEATURE:
<223> OTHER INFORMATION: oligonucleotide primer

<400> SEQUENCE: 428
aggggtatct ctcgagaaaa gagaggtgca gctggtggag tctgg    45

<210> SEQ ID NO 429
<211> LENGTH: 56
<212> TYPE: DNA
<213> ORGANISM: Artificial
<220> FEATURE:
<223> OTHER INFORMATION: oligonucleotide primer

<400> SEQUENCE: 429
gctaaagaag aagggtatc tctcgagaaa agagaggtgc agctggtgga gtctgg    56

<210> SEQ ID NO 430
<211> LENGTH: 88
<212> TYPE: DNA
<213> ORGANISM: Artificial
<220> FEATURE:
<223> OTHER INFORMATION: oligonucleotide primer

<400> SEQUENCE: 430
tcagtaacct ggatcccccg ccaccgctgc ctccaccgcc gctaccccg ccaccgctgc    60 ctccaccgcc tgaggagacg gtgacaag    88

<210> SEQ ID NO 431
<211> LENGTH: 69
<212> TYPE: DNA
<213> ORGANISM: Artificial
<220> FEATURE:
<223> OTHER INFORMATION: oligonucleotide primer

<400> SEQUENCE: 431
aggttactga ggatccggcg gtggaggcag cggtggcggg ggtagcgagg tgcagctggt    60
ggagtctgg    69

<210> SEQ ID NO 432
<211> LENGTH: 41
<212> TYPE: DNA
<213> ORGANISM: Artificial
<220> FEATURE:
<223> OTHER INFORMATION: oligonucleotide primer

<400> SEQUENCE: 432
atggtggtgt gaattcttat tagcaggaga cggtgacaag g    41

<210> SEQ ID NO 433
<211> LENGTH: 53
<212> TYPE: DNA
<213> ORGANISM: Artificial
<220> FEATURE:
<223> OTHER INFORMATION: oligonucleotide primer

```
<400> SEQUENCE: 433
atggtggtgt gaattcttat tagcaacctc cacctgagga gacggtgaca agg          53

<210> SEQ ID NO 434
<211> LENGTH: 21
<212> TYPE: DNA
<213> ORGANISM: Artificial
<220> FEATURE:
<223> OTHER INFORMATION: oligonucleotide primer

<400> SEQUENCE: 434
gactggttcc aattgacaag c                                            21

<210> SEQ ID NO 435
<211> LENGTH: 21
<212> TYPE: DNA
<213> ORGANISM: Artificial
<220> FEATURE:
<223> OTHER INFORMATION: oligonucleotide primer

<400> SEQUENCE: 435
gcaaatggca ttctgacatc c                                            21

<210> SEQ ID NO 436
<211> LENGTH: 13
<212> TYPE: PRT
<213> ORGANISM: Artificial
<220> FEATURE:
<223> OTHER INFORMATION: CDR3 element

<400> SEQUENCE: 436

Ile Leu Pro Leu Ser Asp Asp Pro Gly Trp Asn Thr Tyr
1               5                   10

<210> SEQ ID NO 437
<211> LENGTH: 4
<212> TYPE: PRT
<213> ORGANISM: Artificial
<220> FEATURE:
<223> OTHER INFORMATION: nanobody element

<400> SEQUENCE: 437

Lys Glu Arg Glu
1

<210> SEQ ID NO 438
<211> LENGTH: 4
<212> TYPE: PRT
<213> ORGANISM: Artificial
<220> FEATURE:
<223> OTHER INFORMATION: nanobody element

<400> SEQUENCE: 438

Lys Gln Arg Glu
1

<210> SEQ ID NO 439
<211> LENGTH: 4
<212> TYPE: PRT
<213> ORGANISM: Artificial
<220> FEATURE:
<223> OTHER INFORMATION: nanobody element

<400> SEQUENCE: 439

Gly Leu Glu Trp
1
```

```
<210> SEQ ID NO 440
<211> LENGTH: 5
<212> TYPE: PRT
<213> ORGANISM: Artificial
<220> FEATURE:
<223> OTHER INFORMATION: nanobody element

<400> SEQUENCE: 440

Lys Glu Arg Glu Leu
1               5

<210> SEQ ID NO 441
<211> LENGTH: 5
<212> TYPE: PRT
<213> ORGANISM: Artificial
<220> FEATURE:
<223> OTHER INFORMATION: nanobody element

<400> SEQUENCE: 441

Lys Glu Arg Glu Phe
1               5

<210> SEQ ID NO 442
<211> LENGTH: 5
<212> TYPE: PRT
<213> ORGANISM: Artificial
<220> FEATURE:
<223> OTHER INFORMATION: nanobody element

<400> SEQUENCE: 442

Lys Gln Arg Glu Leu
1               5

<210> SEQ ID NO 443
<211> LENGTH: 5
<212> TYPE: PRT
<213> ORGANISM: Artificial
<220> FEATURE:
<223> OTHER INFORMATION: nanobody element

<400> SEQUENCE: 443

Lys Gln Arg Glu Phe
1               5

<210> SEQ ID NO 444
<211> LENGTH: 5
<212> TYPE: PRT
<213> ORGANISM: Artificial
<220> FEATURE:
<223> OTHER INFORMATION: nanobody element

<400> SEQUENCE: 444

Lys Glu Arg Glu Gly
1               5

<210> SEQ ID NO 445
<211> LENGTH: 4
<212> TYPE: PRT
<213> ORGANISM: Artificial
<220> FEATURE:
<223> OTHER INFORMATION: nanobody element

<400> SEQUENCE: 445

Thr Glu Arg Glu
1
```

<210> SEQ ID NO 446
<211> LENGTH: 5
<212> TYPE: PRT
<213> ORGANISM: Artificial
<220> FEATURE:
<223> OTHER INFORMATION: nanobody element

<400> SEQUENCE: 446

Thr Glu Arg Glu Leu
1               5

<210> SEQ ID NO 447
<211> LENGTH: 4
<212> TYPE: PRT
<213> ORGANISM: Artificial
<220> FEATURE:
<223> OTHER INFORMATION: nanobody element

<400> SEQUENCE: 447

Lys Glu Cys Glu
1

<210> SEQ ID NO 448
<211> LENGTH: 5
<212> TYPE: PRT
<213> ORGANISM: Artificial
<220> FEATURE:
<223> OTHER INFORMATION: nanobody element

<400> SEQUENCE: 448

Lys Glu Cys Glu Leu
1               5

<210> SEQ ID NO 449
<211> LENGTH: 5
<212> TYPE: PRT
<213> ORGANISM: Artificial
<220> FEATURE:
<223> OTHER INFORMATION: nanobody element

<400> SEQUENCE: 449

Lys Glu Cys Glu Arg
1               5

<210> SEQ ID NO 450
<211> LENGTH: 4
<212> TYPE: PRT
<213> ORGANISM: Artificial
<220> FEATURE:
<223> OTHER INFORMATION: nanobody element

<400> SEQUENCE: 450

Arg Glu Arg Glu
1

<210> SEQ ID NO 451
<211> LENGTH: 5
<212> TYPE: PRT
<213> ORGANISM: Artificial
<220> FEATURE:
<223> OTHER INFORMATION: nanobody element

<400> SEQUENCE: 451

Arg Glu Arg Glu Gly
1               5

```
<210> SEQ ID NO 452
<211> LENGTH: 4
<212> TYPE: PRT
<213> ORGANISM: Artificial
<220> FEATURE:
<223> OTHER INFORMATION: nanobody element

<400> SEQUENCE: 452

Gln Glu Arg Glu
1

<210> SEQ ID NO 453
<211> LENGTH: 5
<212> TYPE: PRT
<213> ORGANISM: Artificial
<220> FEATURE:
<223> OTHER INFORMATION: nanobody element

<400> SEQUENCE: 453

Gln Glu Arg Glu Gly
1               5

<210> SEQ ID NO 454
<211> LENGTH: 4
<212> TYPE: PRT
<213> ORGANISM: Artificial
<220> FEATURE:
<223> OTHER INFORMATION: nanobody element

<400> SEQUENCE: 454

Lys Gly Arg Glu
1

<210> SEQ ID NO 455
<211> LENGTH: 5
<212> TYPE: PRT
<213> ORGANISM: Artificial
<220> FEATURE:
<223> OTHER INFORMATION: nanobody element

<400> SEQUENCE: 455

Lys Gly Arg Glu Gly
1               5

<210> SEQ ID NO 456
<211> LENGTH: 4
<212> TYPE: PRT
<213> ORGANISM: Artificial
<220> FEATURE:
<223> OTHER INFORMATION: nanobody element

<400> SEQUENCE: 456

Lys Asp Arg Glu
1

<210> SEQ ID NO 457
<211> LENGTH: 5
<212> TYPE: PRT
<213> ORGANISM: Artificial
<220> FEATURE:
<223> OTHER INFORMATION: nanobody element

<400> SEQUENCE: 457

Lys Asp Arg Glu Val
1               5

<210> SEQ ID NO 458
```

```
<211> LENGTH: 5
<212> TYPE: PRT
<213> ORGANISM: Artificial
<220> FEATURE:
<223> OTHER INFORMATION: nanobody element

<400> SEQUENCE: 458

Asp Glu Cys Lys Leu
1               5

<210> SEQ ID NO 459
<211> LENGTH: 5
<212> TYPE: PRT
<213> ORGANISM: Artificial
<220> FEATURE:
<223> OTHER INFORMATION: nanobody element

<400> SEQUENCE: 459

Asn Val Cys Glu Leu
1               5

<210> SEQ ID NO 460
<211> LENGTH: 4
<212> TYPE: PRT
<213> ORGANISM: Artificial
<220> FEATURE:
<223> OTHER INFORMATION: nanobody element

<400> SEQUENCE: 460

Gly Val Glu Trp
1

<210> SEQ ID NO 461
<211> LENGTH: 4
<212> TYPE: PRT
<213> ORGANISM: Artificial
<220> FEATURE:
<223> OTHER INFORMATION: nanobody element

<400> SEQUENCE: 461

Glu Pro Glu Trp
1

<210> SEQ ID NO 462
<211> LENGTH: 4
<212> TYPE: PRT
<213> ORGANISM: Artificial
<220> FEATURE:
<223> OTHER INFORMATION: nanobody element

<400> SEQUENCE: 462

Gly Leu Glu Arg
1

<210> SEQ ID NO 463
<211> LENGTH: 4
<212> TYPE: PRT
<213> ORGANISM: Artificial
<220> FEATURE:
<223> OTHER INFORMATION: nanobody element

<400> SEQUENCE: 463

Asp Gln Glu Trp
1

<210> SEQ ID NO 464
<211> LENGTH: 4
```

```
<212> TYPE: PRT
<213> ORGANISM: Artificial
<220> FEATURE:
<223> OTHER INFORMATION: nanobody element

<400> SEQUENCE: 464

Asp Leu Glu Trp
1

<210> SEQ ID NO 465
<211> LENGTH: 4
<212> TYPE: PRT
<213> ORGANISM: Artificial
<220> FEATURE:
<223> OTHER INFORMATION: nanobody element

<400> SEQUENCE: 465

Gly Ile Glu Trp
1

<210> SEQ ID NO 466
<211> LENGTH: 4
<212> TYPE: PRT
<213> ORGANISM: Artificial
<220> FEATURE:
<223> OTHER INFORMATION: nanobody element

<400> SEQUENCE: 466

Glu Leu Glu Trp
1

<210> SEQ ID NO 467
<211> LENGTH: 4
<212> TYPE: PRT
<213> ORGANISM: Artificial
<220> FEATURE:
<223> OTHER INFORMATION: nanobody element

<400> SEQUENCE: 467

Gly Pro Glu Trp
1

<210> SEQ ID NO 468
<211> LENGTH: 4
<212> TYPE: PRT
<213> ORGANISM: Artificial
<220> FEATURE:
<223> OTHER INFORMATION: nanobody element

<400> SEQUENCE: 468

Glu Trp Leu Pro
1

<210> SEQ ID NO 469
<211> LENGTH: 4
<212> TYPE: PRT
<213> ORGANISM: Artificial
<220> FEATURE:
<223> OTHER INFORMATION: nanobody element

<400> SEQUENCE: 469

Gly Pro Glu Arg
1

<210> SEQ ID NO 470
<211> LENGTH: 4
<212> TYPE: PRT
```

<213> ORGANISM: Artificial
<220> FEATURE:
<223> OTHER INFORMATION: nanobody element

<400> SEQUENCE: 470

Gly Leu Glu Arg
1

<210> SEQ ID NO 471
<211> LENGTH: 4
<212> TYPE: PRT
<213> ORGANISM: Artificial
<220> FEATURE:
<223> OTHER INFORMATION: spacer

<400> SEQUENCE: 471

Gly Gly Gly Cys
1

<210> SEQ ID NO 472
<211> LENGTH: 109
<212> TYPE: PRT
<213> ORGANISM: Artificial
<220> FEATURE:
<223> OTHER INFORMATION: immunoglobulin construct

<400> SEQUENCE: 472

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Trp Gly Gln Gly Thr Leu Val Thr Val Ser Ser
            100                 105

<210> SEQ ID NO 473
<211> LENGTH: 109
<212> TYPE: PRT
<213> ORGANISM: Artificial
<220> FEATURE:
<223> OTHER INFORMATION: immunoglobulin construct

<400> SEQUENCE: 473

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys

```
                85                  90                  95

Ala Arg Trp Gly Gln Gly Thr Leu Val Thr Val Ser Ser
            100                 105

<210> SEQ ID NO 474
<211> LENGTH: 109
<212> TYPE: PRT
<213> ORGANISM: Artificial
<220> FEATURE:
<223> OTHER INFORMATION: immunoglobulin construct

<400> SEQUENCE: 474

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser
            100                 105

<210> SEQ ID NO 475
<211> LENGTH: 111
<212> TYPE: PRT
<213> ORGANISM: Artificial
<220> FEATURE:
<223> OTHER INFORMATION: immunoglobulin construct

<400> SEQUENCE: 475

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Trp Gly Gln Gly Thr Leu Val Thr Val Ser Ser
            100                 105                 110

<210> SEQ ID NO 476
<211> LENGTH: 17
<212> TYPE: PRT
<213> ORGANISM: Artificial
<220> FEATURE:
<223> OTHER INFORMATION: linker

<400> SEQUENCE: 476

Ala Ala Ala Glu Gln Lys Leu Ile Ser Glu Glu Asp Leu Asn Gly Ala
1               5                   10                  15
```

Ala

```
<210> SEQ ID NO 477
<211> LENGTH: 115
<212> TYPE: PRT
<213> ORGANISM: Artificial
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa may be Gln, Glu, or Asp
<220> FEATURE:
<221> NAME/KEY: MISC_FEATURE
<222> LOCATION: (19)..(19)
<223> OTHER INFORMATION: Xaa may be Arg or Lys
<220> FEATURE:
<221> NAME/KEY: MISC_FEATURE
<222> LOCATION: (28)..(28)
<223> OTHER INFORMATION: Xaa may be Asn, Thr, Glu, Asp, Ser, Arg, or Tyr
<220> FEATURE:
<221> NAME/KEY: MISC_FEATURE
<222> LOCATION: (31)..(31)
<223> OTHER INFORMATION: Xaa may be Gly, Ser, Thr, Cys, Asn, Gln, Tyr,
      Lys, Arg, His, Asp, or Glu
<220> FEATURE:
<221> NAME/KEY: MISC_FEATURE
<222> LOCATION: (32)..(32)
<223> OTHER INFORMATION: Xaa may be Gly, Ser, Thr, Cys, Asn, Gln, Tyr,
      Lys, Arg, His, Asp, or Glu
<220> FEATURE:
<221> NAME/KEY: MISC_FEATURE
<222> LOCATION: (44)..(44)
<223> OTHER INFORMATION: Xaa may be Gly, Glu, or Gln
<220> FEATURE:
<221> NAME/KEY: MISC_FEATURE
<222> LOCATION: (48)..(48)
<223> OTHER INFORMATION: Xaa may be Val, Ile, or Leu
<220> FEATURE:
<221> NAME/KEY: MISC_FEATURE
<222> LOCATION: (59)..(59)
<223> OTHER INFORMATION: Xaa may be Lys, Arg, or His
<220> FEATURE:
<221> NAME/KEY: MISC_FEATURE
<222> LOCATION: (61)..(61)
<223> OTHER INFORMATION: Xaa may be Ala, Ser, Thr, Pro, or Gly
<220> FEATURE:
<221> NAME/KEY: MISC_FEATURE
<222> LOCATION: (70)..(70)
<223> OTHER INFORMATION: Xaa may be Val, Ile, or Leu
<220> FEATURE:
<221> NAME/KEY: MISC_FEATURE
<222> LOCATION: (73)..(73)
<223> OTHER INFORMATION: Xaa may be Asp or Asn
<220> FEATURE:
<221> NAME/KEY: MISC_FEATURE
<222> LOCATION: (78)..(78)
<223> OTHER INFORMATION: Xaa may be Thr, Glu, Ser, Lys, Asn, or Arg
<220> FEATURE:
<221> NAME/KEY: MISC_FEATURE
<222> LOCATION: (79)..(79)
<223> OTHER INFORMATION: Xaa may be Val, Leu, Ile, or Met
<220> FEATURE:
<221> NAME/KEY: MISC_FEATURE
<222> LOCATION: (82)..(82)
<223> OTHER INFORMATION: Xaa may be Gln or Glu
<220> FEATURE:
<221> NAME/KEY: MISC_FEATURE
<222> LOCATION: (83)..(83)
<223> OTHER INFORMATION: Xaa may be Met or Leu
<220> FEATURE:
<221> NAME/KEY: MISC_FEATURE
<222> LOCATION: (84)..(84)
<223> OTHER INFORMATION: Xaa may be Asn, Ser, or Thr
<220> FEATURE:
<221> NAME/KEY: MISC_FEATURE
<222> LOCATION: (85)..(85)
```

```
<223> OTHER INFORMATION: Xaa may be Ser, Asn, Asp, Gly, Arg, Cys, Glu,
      Lys, or Thr
<220> FEATURE:
<221> NAME/KEY: MISC_FEATURE
<222> LOCATION: (87)..(87)
<223> OTHER INFORMATION: Xaa may be Arg, Lys, or Glu
<220> FEATURE:
<221> NAME/KEY: MISC_FEATURE
<222> LOCATION: (93)..(93)
<223> OTHER INFORMATION: Xaa may be Val, Ile, or Leu
<220> FEATURE:
<221> NAME/KEY: MISC_FEATURE
<222> LOCATION: (99)..(99)
<223> OTHER INFORMATION: Xaa may be Gly, Ser, Thr, Cys, Asn, Gln, or Tyr
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: MISC_FEATURE
<222> LOCATION: (101)..(101)
<223> OTHER INFORMATION: Xaa may be Gly, Ser, Thr, Cys, Asn, Gln, Tyr,
      Lys, Arg, His, Asp, or Glu
<220> FEATURE:
<221> NAME/KEY: MISC_FEATURE
<222> LOCATION: (103)..(103)
<223> OTHER INFORMATION: Xaa may be Ala, Val, Leu, Ile, Phe, Met, Trp,
      or Pro
<220> FEATURE:
<221> NAME/KEY: MISC_FEATURE
<222> LOCATION: (105)..(105)
<223> OTHER INFORMATION: Xaa may be Arg or Lys
<220> FEATURE:
<221> NAME/KEY: MISC_FEATURE
<222> LOCATION: (110)..(110)
<223> OTHER INFORMATION: Xaa may be Gln or Leu

<400> SEQUENCE: 477

Xaa Val Gln Leu Val Glu Ser Gly Gly Gly Leu Val Gln Pro Gly Gly
1               5                   10                  15

Ser Leu Xaa Leu Ser Cys Ala Ala Ser Gly Phe Xaa Phe Ser Xaa Xaa
            20                  25                  30

Trp Met Tyr Trp Val Arg Gln Ala Pro Gly Lys Xaa Leu Glu Trp Xaa
        35                  40                  45

Ser Glu Ile Asn Thr Asn Gly Leu Ile Thr Xaa Tyr Xaa Asp Ser Val
50                  55                  60

Lys Gly Arg Phe Thr Xaa Ser Arg Xaa Asn Ala Ala Asn Xaa Xaa Tyr
65                  70                  75                  80

Leu Xaa Xaa Xaa Xaa Leu Xaa Pro Glu Asp Thr Ala Xaa Tyr Tyr Cys
                85                  90                  95

Ala Arg Xaa Xaa Xaa Gly Xaa Asn Xaa Gly Gln Gly Thr Xaa Val Thr
            100                 105                 110

Val Ser Ser
        115

<210> SEQ ID NO 478
<211> LENGTH: 115
<212> TYPE: PRT
<213> ORGANISM: Artificial
<220> FEATURE:
<223> OTHER INFORMATION: Synthetic Polypeptide
<220> FEATURE:
<221> NAME/KEY: MISC_FEATURE
<222> LOCATION: (31)..(31)
<223> OTHER INFORMATION: Xaa may be Gly, Ser, Thr, Cys, Asn, Gln, Tyr,
      Lys, Arg, His, Asp, or Glu
<220> FEATURE:
<221> NAME/KEY: MISC_FEATURE
<222> LOCATION: (32)..(32)
<223> OTHER INFORMATION: Xaa may be Gly, Ser, Thr, Cys, Asn, Gln, Tyr,
```

```
                Lys, Arg, His, Asp, or Glu
<220> FEATURE:
<221> NAME/KEY: MISC_FEATURE
<222> LOCATION: (59)..(59)
<223> OTHER INFORMATION: Xaa may be Lys, Arg, or His
<220> FEATURE:
<221> NAME/KEY: MISC_FEATURE
<222> LOCATION: (61)..(61)
<223> OTHER INFORMATION: Xaa may be Ala, Ser, Thr, Pro, or Gly
<220> FEATURE:
<221> NAME/KEY: MISC_FEATURE
<222> LOCATION: (99)..(99)
<223> OTHER INFORMATION: Xaa may be Gly, Ser, Thr, Cys, Asn, Gln, or Tyr
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: MISC_FEATURE
<222> LOCATION: (101)..(101)
<223> OTHER INFORMATION: Xaa may be Gly, Ser, Thr, Cys, Asn, Gln, Tyr,
                Lys, Arg, His, Asp, or Glu
<220> FEATURE:
<221> NAME/KEY: MISC_FEATURE
<222> LOCATION: (103)..(103)
<223> OTHER INFORMATION: Xaa may be Ala, Val, Leu, Ile, Phe, Met, Trp,
                or Pro

<400> SEQUENCE: 478

Asp Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Xaa Xaa
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr Xaa Tyr Xaa Asp Ser Val
    50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Xaa Xaa Xaa Gly Xaa Asn Lys Gly Gln Gly Thr Gln Val Thr
            100                 105                 110

Val Ser Ser
        115

<210> SEQ ID NO 479
<211> LENGTH: 30
<212> TYPE: PRT
<213> ORGANISM: Artificial
<220> FEATURE:
<223> OTHER INFORMATION: Synthetic Polypeptide

<400> SEQUENCE: 479

Asp Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser
            20                  25                  30

<210> SEQ ID NO 480
<211> LENGTH: 14
<212> TYPE: PRT
<213> ORGANISM: Artificial
<220> FEATURE:
<223> OTHER INFORMATION: Synthetic Polypeptide

<400> SEQUENCE: 480
```

```
Trp Val Arg Gln Ala Pro Gly Lys Glu Leu Glu Trp Leu Ser
1               5                   10
```

```
<210> SEQ ID NO 481
<211> LENGTH: 32
<212> TYPE: PRT
<213> ORGANISM: Artificial
<220> FEATURE:
<223> OTHER INFORMATION: Synthetic Polypeptide

<400> SEQUENCE: 481

Arg Phe Thr Ile Ser Arg Asp Asp Ala Lys Asn Thr Ile Tyr Leu Gln
1               5                   10                  15

Met Asn Arg Leu Lys Pro Glu Asp Thr Ala Val Tyr Tyr Cys Ala Ala
            20                  25                  30
```

```
<210> SEQ ID NO 482
<211> LENGTH: 11
<212> TYPE: PRT
<213> ORGANISM: Artificial
<220> FEATURE:
<223> OTHER INFORMATION: Synthetic Polypeptide

<400> SEQUENCE: 482

Lys Gly Gln Gly Thr Gln Val Thr Val Ser Ser
1               5                   10
```

```
<210> SEQ ID NO 483
<211> LENGTH: 115
<212> TYPE: PRT
<213> ORGANISM: Artificial Sequence
<220> FEATURE:
<223> OTHER INFORMATION: Synthetic

<400> SEQUENCE: 483

Gln Val Gln Leu Gln Glu Ser Gly Gly Gly Leu Val Gln Pro Gly Gly
1               5                   10                  15

Ser Leu Arg Leu Ser Cys Ala Thr Ser Gly Phe Asp Phe Ser Val Ser
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Ile Pro Glu Asp Thr Ala Leu Tyr Tyr Cys
                85                  90                  95

Ala Arg Ser Pro Ser Gly Ser Phe Arg Gly Gln Gly Thr Gln Val Thr
            100                 105                 110

Val Ser Ser
        115
```

```
<210> SEQ ID NO 484
<211> LENGTH: 128
<212> TYPE: PRT
<213> ORGANISM: Artificial Sequence
<220> FEATURE:
<223> OTHER INFORMATION: Synthetic

<400> SEQUENCE: 484

Gln Val Gln Leu Gln Glu Ser Gly Gly Gly Leu Val Gln Pro Gly Gly
1               5                   10                  15
```

```
Ser Leu Arg Leu Ser Cys Ala Ala Ser Gly Arg Thr Phe Ser Asp His
            20                  25                  30

Ser Gly Tyr Thr Tyr Ile Gly Trp Phe Arg Gln Ala Pro Gly Lys Glu
        35                  40                  45

Arg Glu Phe Val Ala Arg Ile Tyr Trp Ser Ser Gly Asn Thr Tyr Tyr
 50                  55                  60

Ala Asp Ser Val Lys Gly Arg Phe Ala Ile Ser Arg Asp Ile Ala Lys
 65                  70                  75                  80

Asn Thr Val Asp Leu Thr Met Asn Asn Leu Glu Pro Glu Asp Thr Ala
                85                  90                  95

Val Tyr Tyr Cys Ala Ala Arg Asp Gly Ile Pro Thr Ser Arg Ser Val
                100                 105                 110

Glu Ser Tyr Asn Tyr Trp Gly Gln Gly Thr Gln Val Thr Val Ser Ser
            115                 120                 125

<210> SEQ ID NO 485
<211> LENGTH: 127
<212> TYPE: PRT
<213> ORGANISM: Artificial Sequence
<220> FEATURE:
<223> OTHER INFORMATION: Synthetic

<400> SEQUENCE: 485

Gln Val Gln Leu Gln Asp Ser Gly Gly Gly Leu Val Gln Ala Gly Gly
1               5                   10                  15

Ser Leu Arg Leu Ser Cys Ala Val Ser Gly Arg Thr Phe Ser Ala His
            20                  25                  30

Ser Val Tyr Thr Met Gly Trp Phe Arg Gln Ala Pro Gly Lys Glu Arg
        35                  40                  45

Glu Phe Val Ala Arg Ile Tyr Trp Ser Ser Ala Asn Thr Tyr Tyr Ala
 50                  55                  60

Asp Ser Val Lys Gly Arg Phe Thr Ile Ser Arg Asp Asn Ala Lys Asn
 65                  70                  75                  80

Thr Val Asp Leu Leu Met Asn Ser Leu Lys Pro Glu Asp Thr Ala Val
                85                  90                  95

Tyr Tyr Cys Ala Ala Arg Asp Gly Ile Pro Thr Ser Arg Thr Val Gly
            100                 105                 110

Ser Tyr Asn Tyr Trp Gly Gln Gly Thr Gln Val Thr Val Ser Ser
        115                 120                 125

<210> SEQ ID NO 486
<211> LENGTH: 126
<212> TYPE: PRT
<213> ORGANISM: Artificial Sequence
<220> FEATURE:
<223> OTHER INFORMATION: Synthetic

<400> SEQUENCE: 486

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Phe Ser Asp His
            20                  25                  30

Trp Tyr Thr Met Tyr Trp Val Arg Gln Ala Pro Gly Lys Gly Arg Glu
        35                  40                  45

Phe Val Ala Arg Ile Tyr Trp Ser Ser Leu Asn Thr Tyr Tyr Ala Asp
 50                  55                  60

Ser Val Lys Gly Arg Phe Thr Ile Ser Arg Asp Asn Ala Lys Asn Thr
```

```
65                  70                  75                  80
Leu Tyr Leu Gln Met Asn Ser Leu Lys Pro Glu Asp Thr Ala Leu Tyr
                85                  90                  95

Tyr Cys Ala Arg Arg Asp Gly Ile Pro Thr Ser Arg Ser Val Ser Ser
            100                 105                 110

Tyr Asn Tyr Trp Gly Gln Gly Thr Gln Val Thr Val Ser Ser
            115                 120                 125

<210> SEQ ID NO 487
<211> LENGTH: 7
<212> TYPE: PRT
<213> ORGANISM: Artificial
<220> FEATURE:
<223> OTHER INFORMATION: Synthetic

<400> SEQUENCE: 487

Glu Val Gln Leu Val Glu Ser
1               5
```